US007097917B1

(12) United States Patent
Fujita et al.

(10) Patent No.: US 7,097,917 B1
(45) Date of Patent: Aug. 29, 2006

(54) COMPOUNDS FOR USE IN ORGANIC EL DEVICES AND ORGANIC EL DEVICES

(75) Inventors: Tetsuji Fujita, Tokyo (JP); Sumiko Kitagawa, Tokyo (JP); Tetsushi Inoue, Tokyo (JP)

(73) Assignee: TDK Corporation, Tokyo (JP)

( * ) Notice: Subject to any disclaimer, the term of this patent is extended or adjusted under 35 U.S.C. 154(b) by 281 days.

(21) Appl. No.: 10/125,480

(22) Filed: Apr. 19, 2002

(30) Foreign Application Priority Data

Apr. 19, 2001 (JP) ............................ 2001-121788

(51) Int. Cl.
*H05B 33/14* (2006.01)

(52) U.S. Cl. ...................... 428/690; 428/917; 428/704; 313/504; 313/506; 564/426; 252/301.16; 252/301.35; 257/40; 257/103

(58) Field of Classification Search ................ 428/690, 428/704, 917; 313/504, 506; 564/426; 252/301.16, 252/301.35; 257/40, 103
See application file for complete search history.

(56) References Cited

U.S. PATENT DOCUMENTS 6,613,454 B1 * 9/2003 Ara et al. .................. 428/690

FOREIGN PATENT DOCUMENTS

| | | |
|---|---|---|
| EP | 1148109 A2 * | 10/2001 |
| JP | 11-12205 | 1/1999 |
| JP | 2000-178212 | 6/2000 |
| JP | 2000-186054 | 7/2000 |
| JP | 2001-250688 | 9/2001 |
| JP | 2001-257075 | 9/2001 |
| JP | 2001-319785 | 11/2001 |

OTHER PUBLICATIONS

J. D. Debad, et al., J. Org. Chem., vol. 62, No. 3, pp. 530-537, "Anodic Coupling of Diphenylbenzo[k] Fluoranthene: Mechanistic and Kinetic Studies Utilizing Cyclic Voltammetry and Electrogenerated Chemiluminescence," 1997.

S. E. Mallakpour, et al., Organic Preparations and Procedures Int., vol. 28, No. 6, pp. 691-693, "A Convenient One-Step Synthesis of Dialkylbenzo[k]Fluoranthenes and Tetraethyl bis-Benzo[k][k']Fluoranthenes," 1996.

(Continued)

*Primary Examiner*—Ling Xu
(74) *Attorney, Agent, or Firm*—Oblon, Spivak, McClelland, Maier & Neustadt, P.C.

(57) ABSTRACT

A compound for use in organic EL devices comprising $X_n$—Y wherein X is a compound of the formula and Y is a linking group

X =

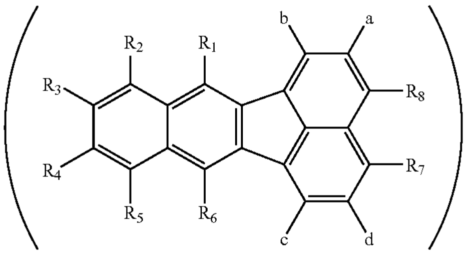

and $R_1$ to $R_8$ and a to d are hydrogen, an alkyl group, an aryl group which may be substituted, an allyl group which may be substituted, a heterocyclic group which may be substituted, an amino group, or an arylamino group which may be substituted.

31 Claims, 8 Drawing Sheets

OTHER PUBLICATIONS

R. Taylor, et al., Nature, vol. 366, No. 6457, pp. 728-731, "Formation of $C_{60}$ by Pyrolysis of Naphthalene," Dec. 23-30, 1993.

U.S. Appl. No. 10/189,428, filed Jul. 5, 2002, Fujita, et al.

Mallakpour, S. E., et al., "Reaction of 3, 4, 3', 4'-Tetrahydrobiphenyl (Bisbenzyne) With Tetracyclone and Acecyclon," Indian Journal of Chemisry, Sect. B, vol. 39, No. 3, 2000, pp. 173-176.

Korean Office Action dated Jan. 15, 2005. Reference cited in the Office Action were filed on Jul. 30, 2002, and entered by the Examiner on Oct. 20, 2003.

Korean Office Action dated Jun. 14, 2005. Reference cited in the Office Action were filed on Sep. 3, 2004, and entered by the Examiner on Jan. 3, 2005.

* cited by examiner

COMPOUNDS FOR USE IN ORGANIC EL DEVICES AND ORGANIC EL DEVICES

BACKGROUND OF THE INVENTION

1. Field of the Invention

This invention relates to an organic electroluminescent (EL) device, and more particularly, to a compound for use in a device of the type wherein an electric field is applied across a thin film of an organic compound to emit light.

2. Background Art

Organic electroluminescent (EL) devices include a thin film containing a luminescent organic compound interleaved between an electron injecting electrode and a hole injecting electrode. Electrons and holes are injected into the thin film where they are recombined to create excitons. Light is emitted by utilizing luminescence (phosphorescence or fluorescence) upon deactivation of excitons.

The organic EL devices are characterized by plane light emission at a high luminance of about 100 to 10,000 cd/$m^2$ with a voltage of about 10 volts and light emission in a spectrum from blue to red color by a simple choice of the type of fluorescent material.

Doping is one technique for producing light emission of any desired color from organic EL devices. It was reported in Jpn. J. Appl. Phys., 10, 527 (1971) to change emission color from blue to green by doping anthracene crystals with a minor level of tetracene. With respect to organic thin film EL devices having a multilayer structure, it was reported in JP-A 63-264692 to incorporate in a host material having a light emitting function a minor amount of a fluorescent dye capable of emitting light different from that of the host material in response to light emission from the host material as a dopant to form a light emitting layer, thereby changing the color of light emission from green to orange or red.

With respect to long wavelength light emission of yellow to red, known light emitting materials or dopant materials include laser dyes capable of red oscillation (EPO 281381), compounds capable of exciplex emission (JP-A 2-255788), perylene compounds (JP-A 3-791), coumarin compounds (JP-A 3-792), dicyanomethylene compounds (JP-A 3-162481), thioxanthene compounds (JP-A 3-177486), mixtures of a conjugated polymer and an electron transporting compound (JP-A 6-73374), squalirium compounds (JP-A 6-93257), oxadiazole compounds (JP-A 6-136359), oxynate derivatives (JP-A 6-145146), and pyrene compounds (JP-A 6-240246).

It is reported in J. Am. Chem. Soc., 118, 2374–2379, 1996, that benzofluoranthene derivatives have a very high fluorescent quantum yield. JP-A 10-330295 and JP-A 11-233261 disclose organic EL devices having a light emitting layer in which a variety of host materials are doped with dibenzo[f,f']diindeno[1,2,3-cd:1',2',3'-lm]perylene derivatives derived from benzofluoranthene.

Other light emitting materials disclosed heretofore include condensed polycyclic aromatic compounds (JP-A 5-32966 and 5-214334). Also dopant materials proposed heretofore include various condensed polycyclic aromatic compounds (JP-A 5-258859).

However, few of the prior art fluorescent materials could produce light emission of a color close to pure blue. From the standpoint of achieving full color displays of high quality, it would be desirable to have a high efficiency pure blue fluorescent material.

SUMMARY OF THE INVENTION

An object of the invention is to provide a compound for use in organic EL devices capable of light emission to a satisfactory luminance, especially at a long wavelength, and with a high color purity, especially a color purity sufficient for use in full color displays, and having a sufficient durability to sustain such improved light emission performance over a long time as well as an organic EL device using the same.

The above objects are achieved by the invention which is defined below.

(1) A compound for use in organic EL devices having a basic skeleton of the following formula (1):

$$X_n—Y \quad (1)$$

wherein X is a compound of the following formula (2) and may be the same or different, Y is a linking group selected from among a single bond, a substituted or unsubstituted aryl group, and a heterocyclic group, and n is an integer of 2 or 3, (2)

C19

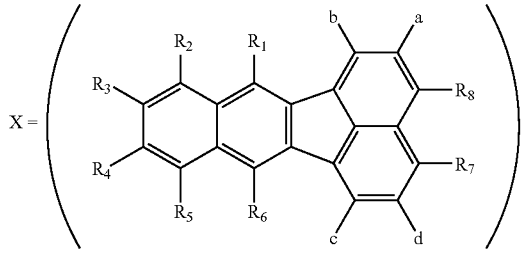

wherein $R_1$ to $R_8$ and a to d each are selected from among hydrogen, an alkyl group, an aryl group which may be substituted, an allyl group which may be substituted, a heterocyclic group which may be substituted, an amino group, and an arylamino group which may be substituted.

(2) The compound for use in organic EL devices of (1) wherein Y is at least one group selected from the following compounds:

C20

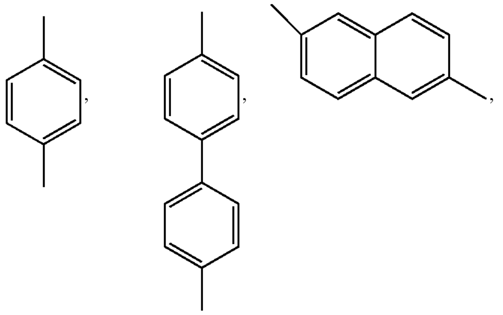

-continued

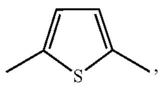,
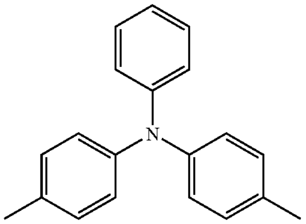
and
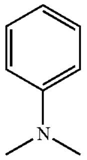

(3) The compound for use in organic EL devices of (1) or (2) wherein n is 2.

(4) The compound for use in organic EL devices of any one of (1) to (3) which is used as a dopant.

(5) The compound for use in organic EL devices of any one of (1) to (4) which is an electron transporting material.

(6) The compound for use in organic EL devices of any one of (1) to (4) which is a hole injecting or transporting material.

(7) The compound for use in organic EL devices of any one of (1) to (6) having a basic skeleton of the following formula (3a):

(3a)

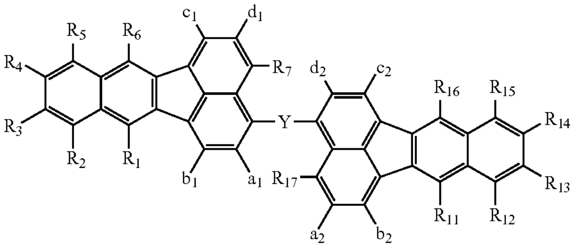

wherein $R_1$ to $R_7$, $a_1$ to $d_1$, $R_{11}$ to $R_{17}$ and $a_2$ to $d_2$ each are selected from among hydrogen, an alkyl group, an aryl group which may be substituted, an allyl group which may be substituted, a heterocyclic group which may be substituted, an amino group, and an arylamino group which may be substituted; Y is a linking group selected from the class consisting of substituted or unsubstituted phenylene, biphenylene, naphthacene, perylene, pyrene, phenanthrene, thiophene, pyridine, pyrazine, triazine, amine, triarylamine, pyrrole derivatives, thiazole, thiadiazole, phenanthroline, quinoline and quinoxaline.

(8) The compound for use in organic EL devices of any one of (1) to (6) having a basic skeleton of the following formula (3b):

(3b)

C22

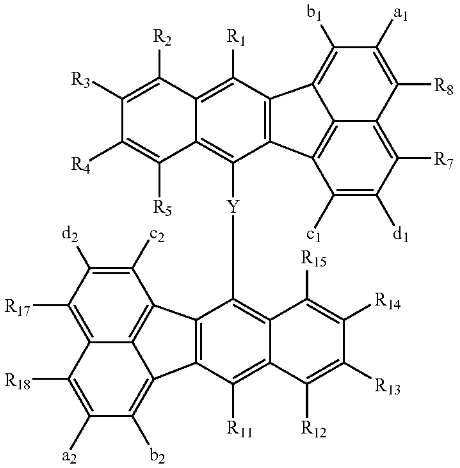

wherein $R_1$ to $R_8$, $a_1$ to $d_1$, $R_{11}$ to $R_{18}$ and $a_2$ to $d_2$ each are selected from among hydrogen, an alkyl group, an aryl group which may be substituted, an allyl group which may be substituted, a heterocyclic group which may be substituted, an amino group, and an arylamino group which may be substituted; Y is a linking group selected from among a single bond, a substituted or unsubstituted aryl group, and a heterocyclic group.

(9) The compound for use in organic EL devices of any one of (1) to (6) having a basic skeleton of the following formula (3c):

(3c)

C23

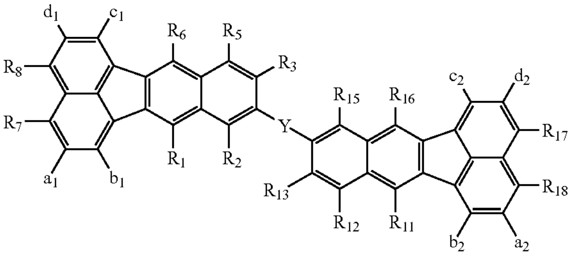

wherein $R_1$ to $R_8$, $a_1$ to $d_1$, $R_{11}$ to $R_{18}$ and $a_2$ to $d_2$ each are selected from among hydrogen, an alkyl group, an aryl group which may be substituted, an allyl group which may be substituted, a heterocyclic group which may be substituted, an amino group, and an arylamino group which may be substituted; Y is a linking group selected from among a single bond, a substituted or unsubstituted aryl group, and a heterocyclic group.

(10) The compound for use in organic EL devices of any one of (1) to (6) having a basic skeleton of the following formula (A):

(A)

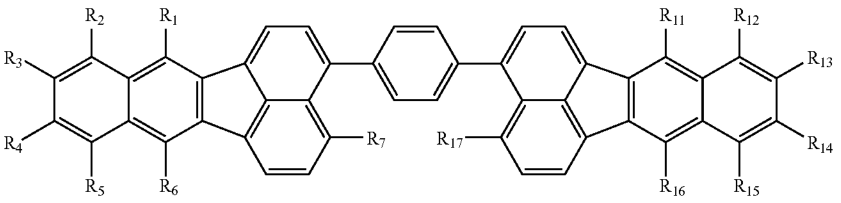

C24 wherein $R_1$ to $R_7$ and $R_{11}$ to $R_{17}$ each are hydrogen, an alkyl group, a substituted or unsubstituted aryl group, or a heterocyclic group.

(11) The compound for use in organic EL devices of any one of (1) to (6) having a basic skeleton of the following formula (B):

(B)

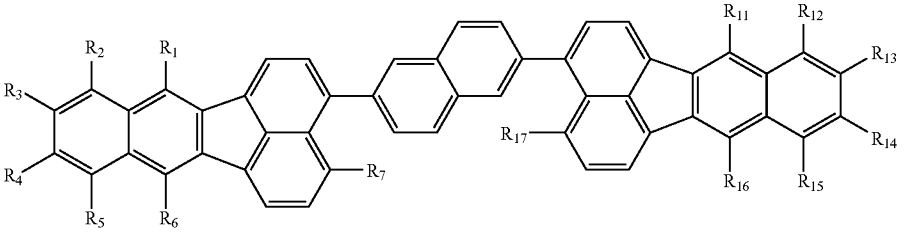

C25 wherein $R_1$ to $R_7$ and $R_{11}$ to $R_{17}$ each are hydrogen, an alkyl group, a substituted or unsubstituted aryl group, or a heterocyclic group.

(12) The compound for use in organic EL devices of any one of (1) to (6) having a basic skeleton of the following formula (E):

(E)

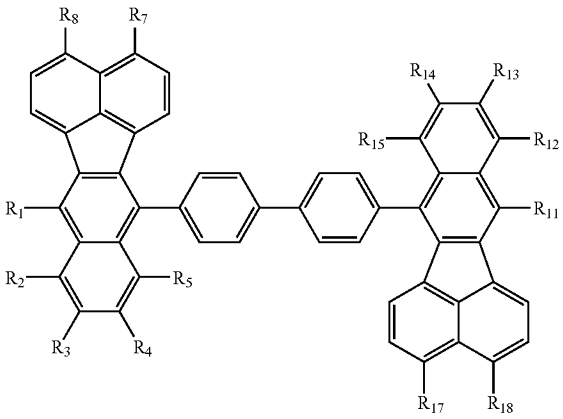

C26 wherein $R_1$ to $R_8$ and $R_{11}$ to $R_{18}$ each are hydrogen, an alkyl group, a substituted or unsubstituted aryl group, or a heterocyclic group.

(13) The compound for use in organic EL devices of any one of (1) to (6) having a basic skeleton of the following formula (H):

(H)

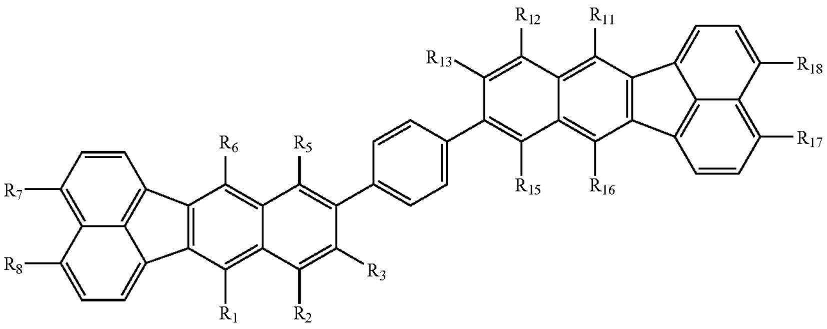

C27 wherein $R_1$ to $R_8$ and $R_{11}$ to $R_{18}$ each are hydrogen, an alkyl group, a substituted or unsubstituted aryl group, or a hetero cyclic group.

(14) The compound for use in organic EL devices of any one of (1) to (6) having a basic skeleton of the following formula (X):

(X)

C28

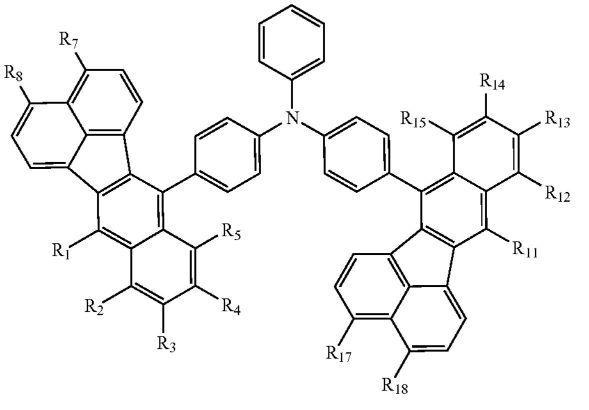

wherein $R_1$ to $R_8$ and $R_{11}$ to $R_{18}$ each are hydrogen, an alkyl group, a substituted or unsubstituted aryl group, or a heterocyclic group.

(15) The compound for use in organic EL devices of any one of (1) to (6) having a basic skeleton of the following formula (Z):

(Z)

C29

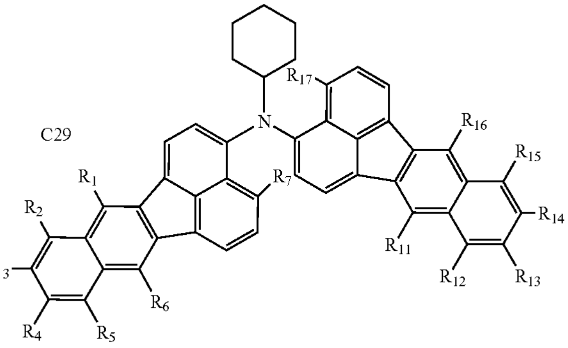

wherein $R_1$ to $R_7$ and $R_{11}$ to $R_{17}$, each are hydrogen, an alkyl group, a substituted or unsubstituted aryl group, or a heterocyclic group.

(16) The compound for use in organic EL devices of any one of (1) to (6) having a basic skeleton of the following formula (AAA'):

(AAA')

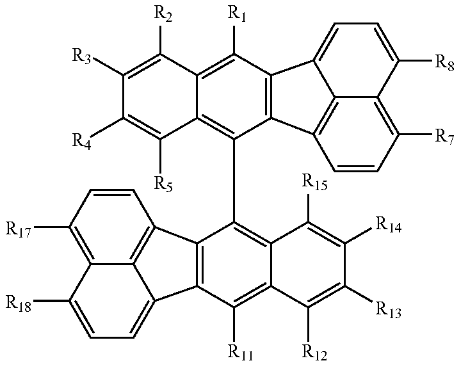

C30 wherein $R_1$ to $R_8$ and $R_{11}$ to $R_{18}$ each are selected from among hydrogen, an alkyl group, an aryl group which may be substituted, an allyl group which may be substituted, a heterocyclic group which may be substituted, an amino group, and an arylamino group which may be substituted.

(17) The compound for use in organic EL devices of any one of (1) to (6) having a basic skeleton of the following formula (BBB'):

(BBB')

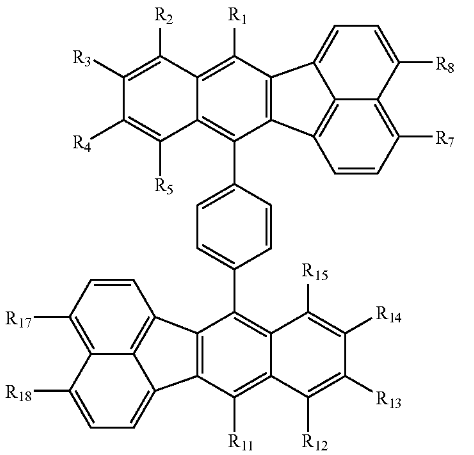

C31 wherein $R_1$ to $R_8$ and $R_{11}$ to $R_{18}$ each are selected from among hydrogen, an alkyl group, an aryl group which may be substituted, an allyl group which may be substituted, a heterocyclic group which may be substituted, an amino group, and an arylamino group which may be substituted.

(18) The compound for use in organic EL devices of any one of (1) to (6) having a basic skeleton of the following formula (CCC'):

(CCC')

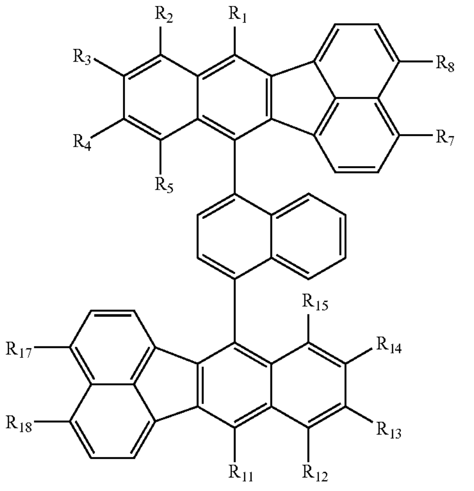

C32 wherein $R_1$ to $R_8$ and $R_{11}$ to $R_{18}$ each are selected from among hydrogen, an alkyl group, an aryl group which may be substituted, an allyl group which may be substituted, a heterocyclic group which may be substituted, an amino group, and an arylamino group which may be substituted.

(19) The compound for use in organic EL devices of any one of (1) to (6) having a basic skeleton of the following formula (DDD'):

(DDD')

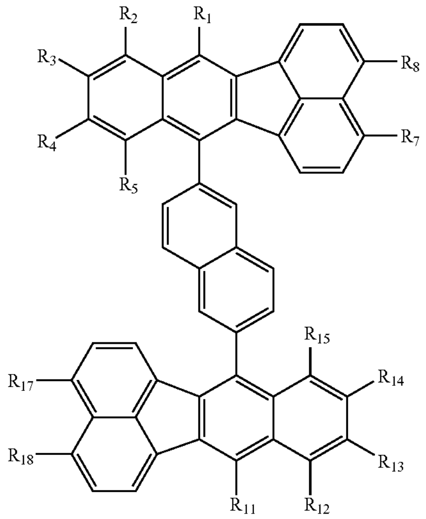

C33 wherein $R_1$ to $R_8$ and $R_{11}$ to $R_{18}$ each are selected from among hydrogen, an alkyl group, an aryl group which may be substituted, an allyl group which may be substituted, a heterocyclic group which may be substituted, an amino group, and an arylamino group which may be substituted.

(20) The compound for use in organic EL devices of any one of (1) to (6) having a basic skeleton of the following formula (EEE'):

(EEE')

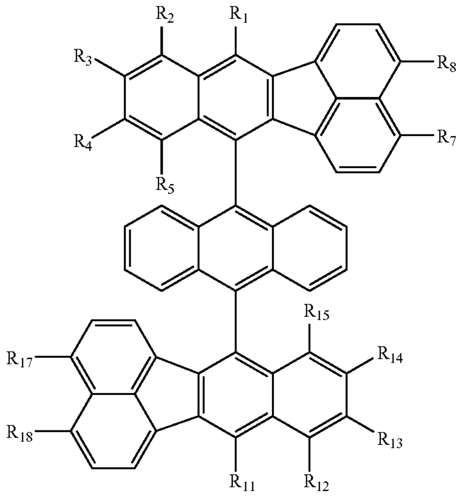

C34 wherein $R_1$ to $R_8$ and $R_{11}$ to $R_{18}$ each are selected from among hydrogen, an alkyl group, an aryl group which may be substituted, an allyl group which may be substituted, a heterocyclic group which may be substituted, an amino group, and an arylamino group which may be substituted.

(21) The compound for use in organic EL devices of any one of (1) to (6) having a basic skeleton of the following formula (RRR'):

(28) The organic EL device of any one of (23) to (25) wherein the compound for use in organic EL devices is contained in an electron transporting layer.

C35

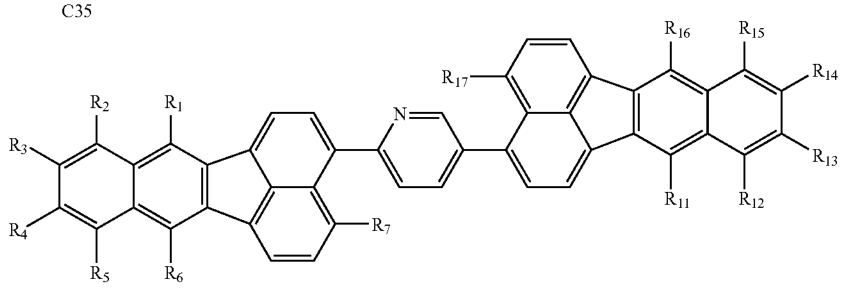

(RRR')

wherein $R_1$ to $R_7$ and $R_{11}$ to $R_{17}$ each are selected from among hydrogen, an alkyl group, an aryl group which may be substituted, an allyl group which may be substituted, a heterocyclic group which may be substituted, an amino group, and an arylamino group which may be substituted.

(22) The compound for use in organic EL devices of any one of (1) to (6) having a basic skeleton of the following formula (SSS'):

(29) The organic EL device of any one of (23) to (28) wherein the compound for use in organic EL devices is contained in a hole injecting and transporting layer.

(30) The organic EL device of any one of (23) to (29) exhibiting at least two maximum wavelengths of light emission ascribable to at least two light-emitting materials.

C36

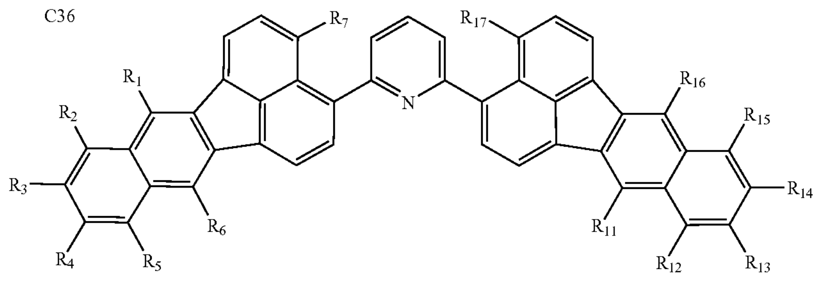

(SSS')

wherein $R_1$ to $R_7$ and $R_{11}$ to $R_{17}$ each are selected from among hydrogen, an alkyl group, an aryl group which may be substituted, an allyl group which may be substituted, a heterocyclic group which may be substituted, an amino group, and an arylamino group which may be substituted.

(23) An organic EL device comprising one or more organic layers between a pair of electrodes participating in at least a light emitting function, at least one of the organic layers containing one or more compound for use in organic EL devices according to any one of (1) to (22).

(24) The organic EL device of (23), further comprising one or more anthracene compound in addition to the compound for use in organic EL devices.

(25) The organic EL device of (24) wherein the anthracene compound is contained as a host material for a light emitting layer.

(26) The organic EL device of any one of (23) to (25) wherein the compound for use in organic EL devices is contained as a dopant.

(27) The organic EL device of any one of (23) to (26) wherein the compound for use in organic EL devices is contained in a light emitting layer.

DESCRIPTION OF THE PREFERRED EMBODIMENT

Figure 1:
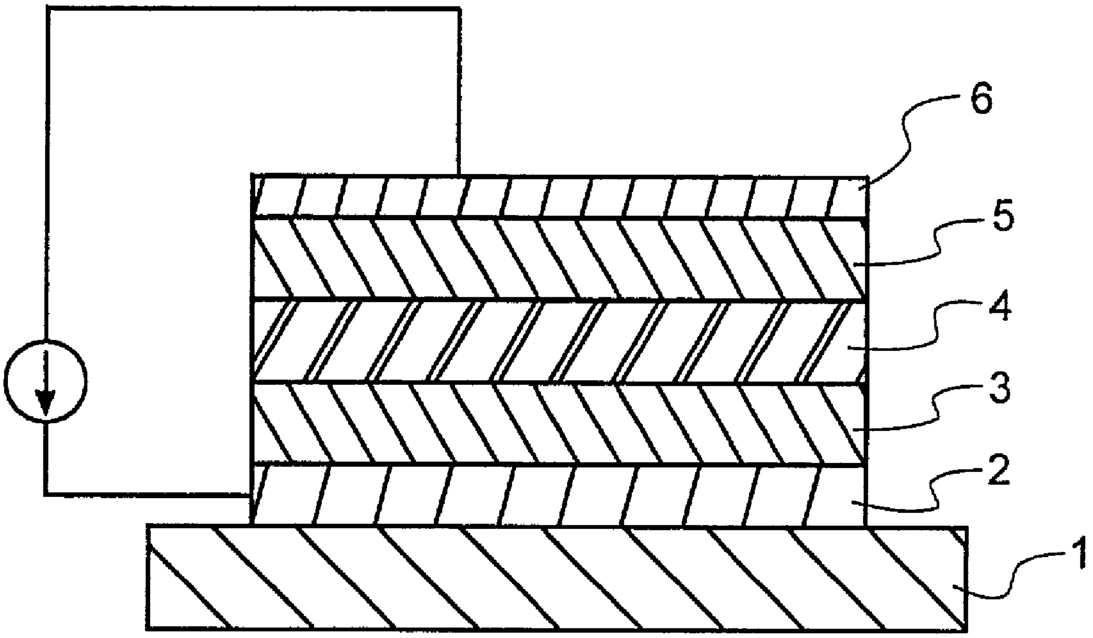
FIG. 1 is a schematic cross-sectional view showing the basic construction of an organic EL device according to the invention.

The compounds for use in organic EL devices according to the invention have a basic skeleton of the following formula (1).

$X_n$—Y (1)

In formula (1), X is a compound of the following formula (2) and may be the same or different, Y is a linking group selected from among a single bond, a substituted or unsubstituted aryl group, and a heterocyclic group, and n is an integer of 2 or 3.

(2)

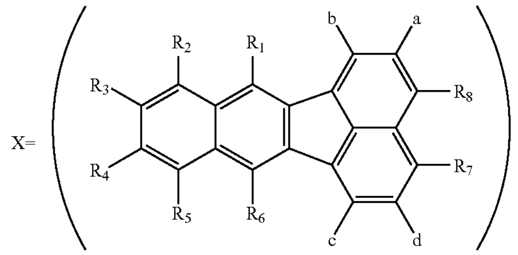

C37

In formula (2), $R_1$ to $R_8$ and a to d each are hydrogen, an alkyl group, an aryl group which may be substituted, an allyl group which may be substituted, a heterocyclic group which may be substituted, an amino group, or an arylamino group which may be substituted.

The compounds having the formula (1) are described in more detail.

In formula (1), X is a compound of the formula (2) and each may be the same or different. Namely, X's may be an identical compound or different compounds as long as they are compounds of the formula (2). It is preferred that X's be an identical compound. Where n=3, three X's may be different from each other.

In formula (2), $R_1$ to $R_8$ and a to d each are hydrogen, an alkyl group, an aryl group which may be substituted, an allyl group which may be substituted, a heterocyclic group which may be substituted, an amino group, or an arylamino group which may be substituted. They are preferably selected from among methyl, ethyl, propyl, phenyl, tolyl, biphenyl, naphthyl, thiophenyl, pyridyl, pyrrole, styryl, triphenylamino, and phenylamino groups, and especially from among methyl, phenyl, tolyl, biphenyl, naphthyl, triphenylamino, and phenylamino groups.

$R_1$ to $R_8$ and a to d may be the same or different. Also, adjoining ones of $R_1$ to $R_8$ and a to d may form a fused ring.

In particular, $R_7$ and $R_8$ preferably have substituents because the structure allows for a high reactivity to these sites. By masking the sites of $R_7$ and $R_8$ with substituents, the compounds can be made chemically stable and prevented from degradation during EL light emission. It is preferred that at least either one of $R_7$ and $R_8$ have a substituent, and especially both have substituents.

The substituents on $R_7$ and $R_8$ include those enumerated above, with alkyl, aryl, allyl and heterocyclic groups being especially preferred.

Depending on the type of substituents introduced into $R_7$ and $R_8$, the wavelength of light emission is sensitively altered. For this reason, a choice of the substituents introduced into $R_7$ and $R_8$ can control the wavelength of light emission.

The letter n representative of the number of X's is an integer of 2 or 3, preferably n=2. If n=3, sublimation ability lowers so that pyrolysis can occur during sublimation, and the stability of the compound somewhat lowers. On the other hand, if n=1, the compound tends to crystallize and emit blue-ultraviolet light and becomes difficult to induce EL light emission.

In formula (1), Y is a linking group selected from among a single bond, a substituted or unsubstituted aryl group, and a heterocyclic group. Preferably, when Y bonds X's together in a positional combination of $R_7$ with $R_7$, $R_8$ with $R_8$ or $R_7$ with $R_8$, a single bond and naphthalene and anthracene compounds having bond positions as shown by the following formulae (11) and (12) are excluded.

(11)

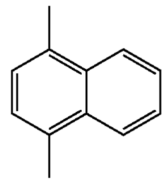

C38

(12)

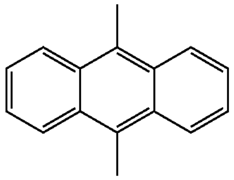

The link positions between X's are not critical. X's may be linked at any position on X or by any carbon on the linking group. Namely, in the basic skeleton represented by the formula (2), the link position may be any position of $R_1$ to $R_8$ and a to d, preferably any site selected from among $R_1$ to $R_8$, and especially any site selected from among $R_1$, $R_6$, $R_7$ and $R_8$.

Also preferably, when Y bonds at the position of $R_7$ or $R_8$, a single bond, that is, the event where X's are directly bonded together, and naphthalene and anthracene linking groups at the above-illustrated bond sites are excluded. If X's are directly bonded together at the position of $R_7$ or $R_8$, the compound loses thermal stability during sublimation purification and electrochemical stability during EL light emission, or bonding at the two positions of $R_7$ and $R_8$ (symmetric positions) can occur.

In particular, Y is preferably a linking group selected from among substituted or unsubstituted phenylene, biphenylene, naphthacene, perylene, pyrene, phenanthrene, thiophene, pyridine, pyrazine, triazine, amine, triarylamine, pyrrole derivatives, thiazole, thiadiazole, phenanthroline, quinoline, and quinoxaline, and more preferably from among substituted or unsubstituted benzene, tetracene, perylene, pyrene and heterocyclic groups. More preferably, Y is a linking group of one type selected from the following compounds.

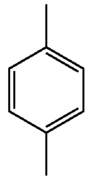 , 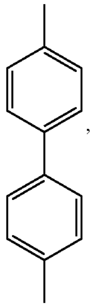 , 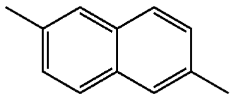 ,

C39

-continued

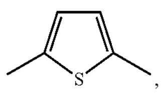
,
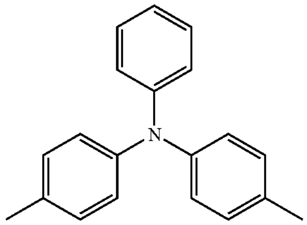
,
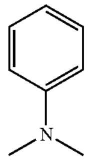

X is preferably selected from compounds of the following formulae (3a), (3b) and (3c).

C40

(3a)

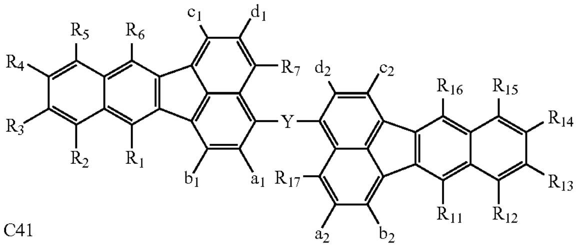

C41

(3b)

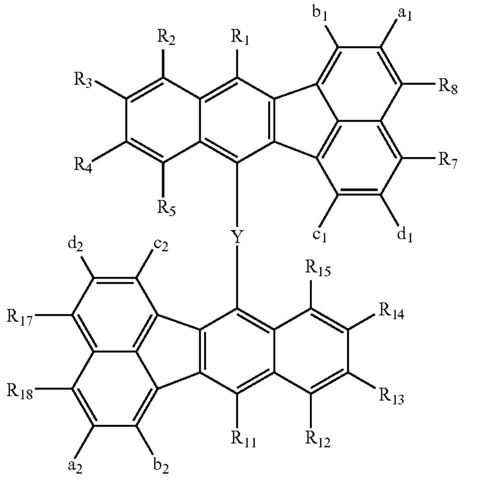

-continued

C42

(3c)

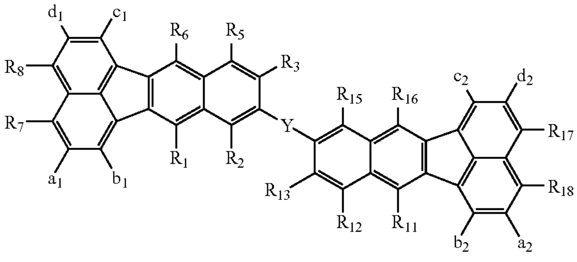

In formulae (3a), (3b) and (3c), $R_1$ to $R_8$, $a_1$ to $d_1$, $R_{11}$ to $R_{18}$, and $a_2$ to $d_2$ are as defined for $R_1$ to $R_8$ and a to d in formula (2). Of the formulae (3a) to (3c), the compounds of formula (3a) are most preferred, and the compounds of formula (3b) are preferred next.

The compounds of the invention should preferably have an absolute value of ionization potential of less than 5.9 eV, more preferably up to 5.8 eV, and even more preferably up to 5.7 eV. Compounds with an absolute value of ionization potential of less than 5.9 eV provide satisfactory light emission when combined with those compounds having an absolute value of ionization potential of about 5.9 eV, especially anthracene dimers. The lower limit of ionization potential is not critical and is usually about 5.2 eV.

The compounds of the invention should preferably have a half-wave oxidation potential of up to 1.5 V, more preferably up to 1.4 V, and even more preferably up to 1.3 V, as measured with a platinum electrode in a methylene chloride solution. Compounds with an oxidation potential up to the above-specified value are more stable, providing a longer device life. The same effects as the ionization potential are also obtained. The lower limit of oxidation potential is not critical and is usually about 0.4 V.

Preferred examples of the compounds of the invention are given below.

C43

(A)

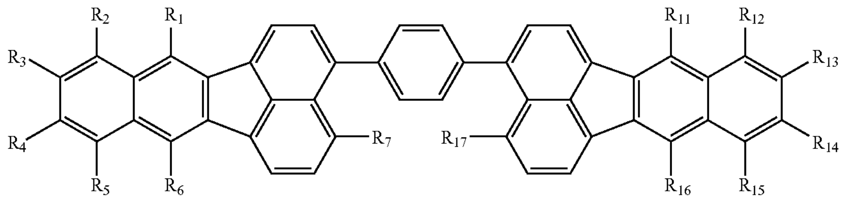

-continued
(B)
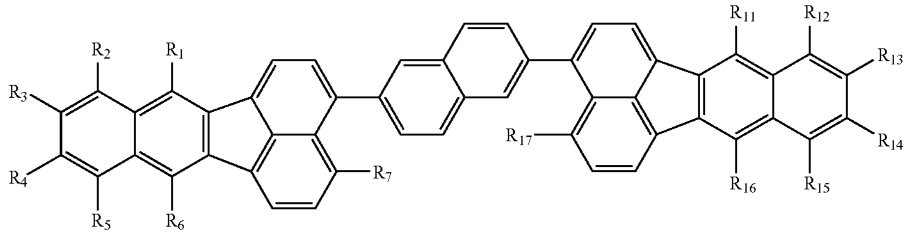
(C)
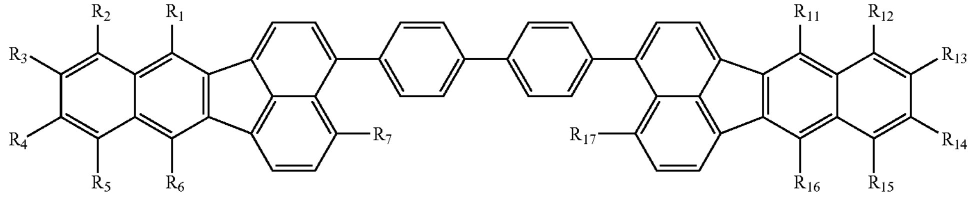
(D)
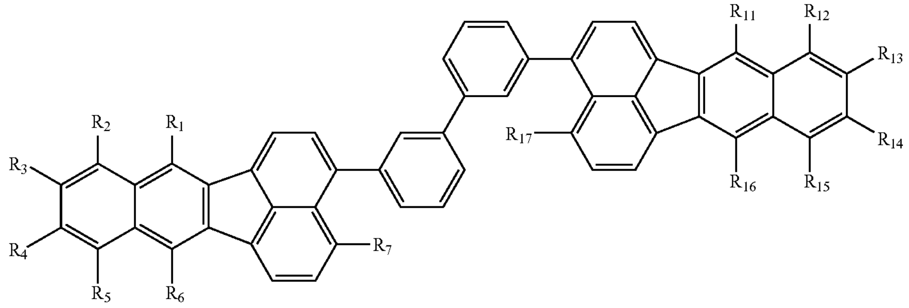
(E)
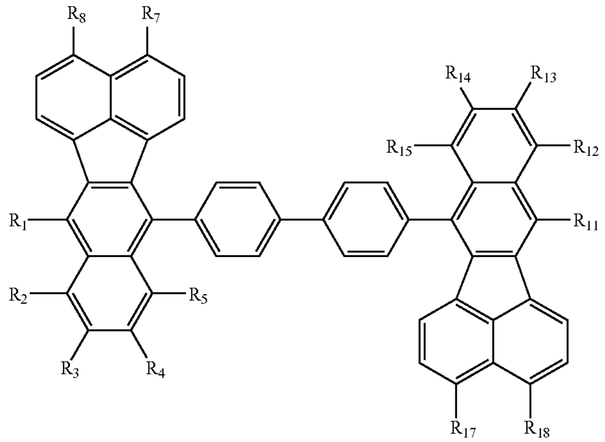
(F)
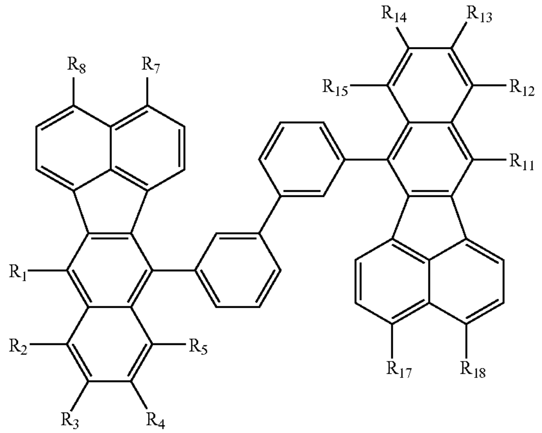

-continued
(G)
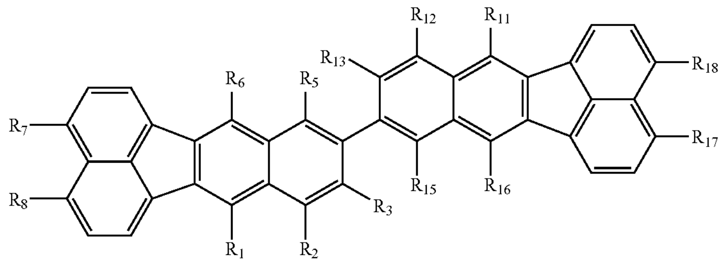
(H)
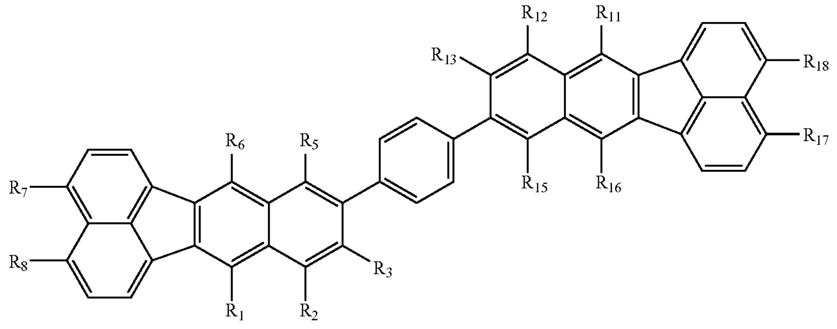
(I)
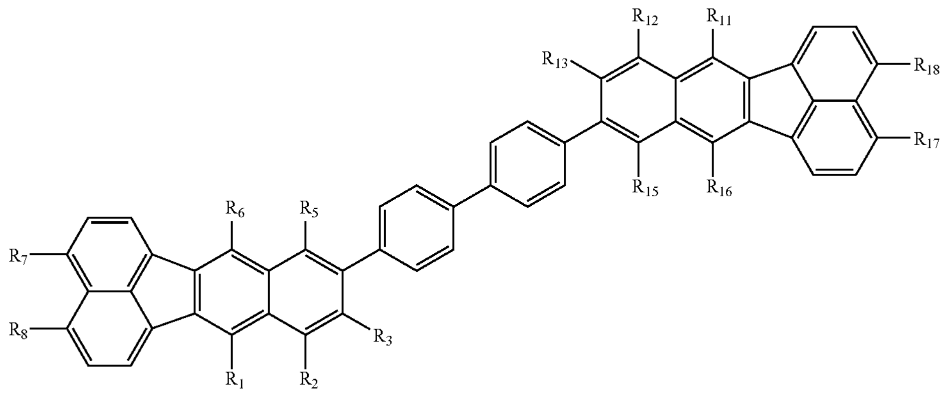
(J)
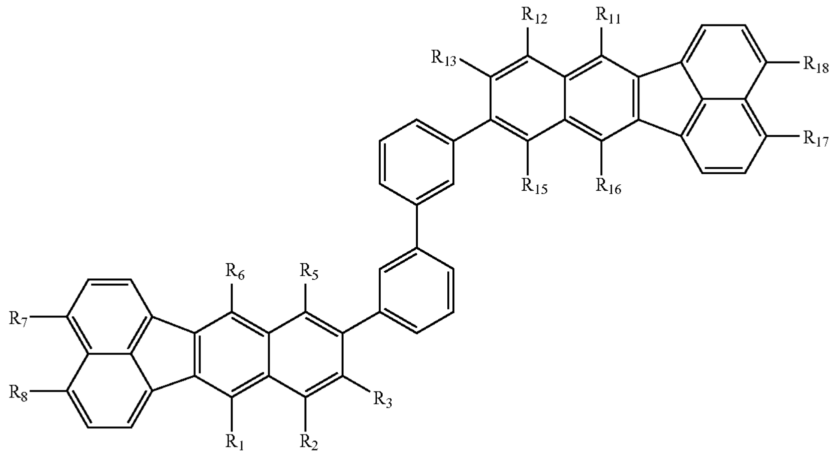

-continued
(K)
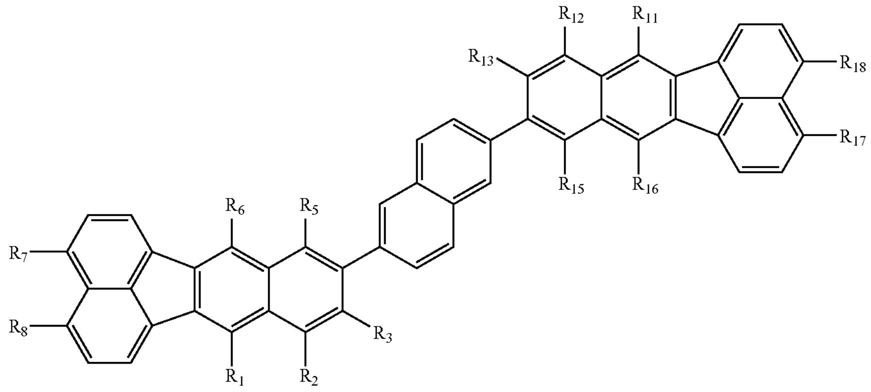
C44
(L)
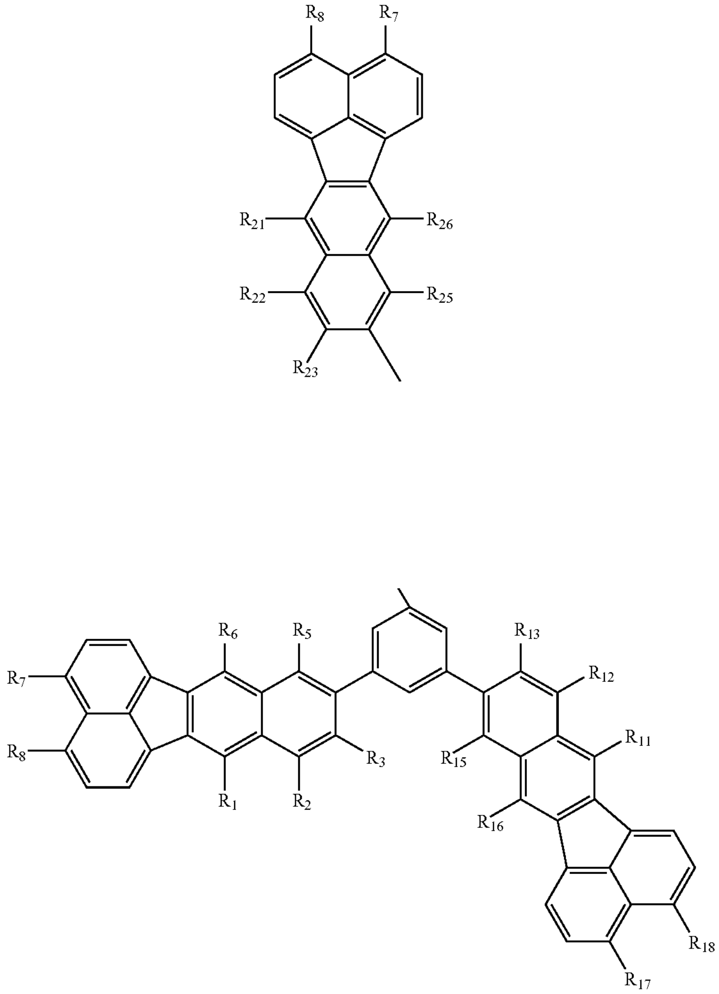

-continued
(M)
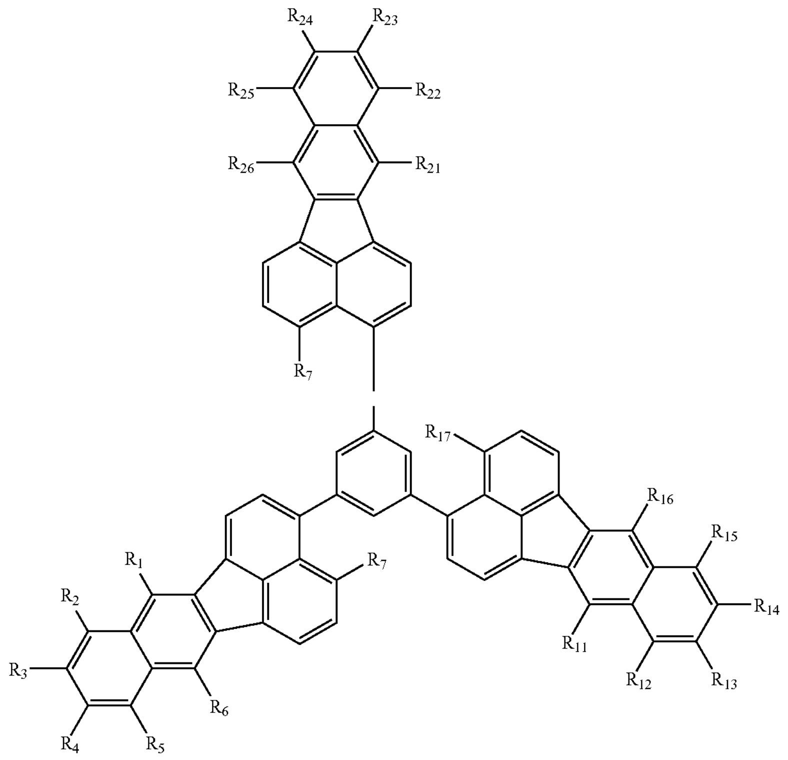
(N)
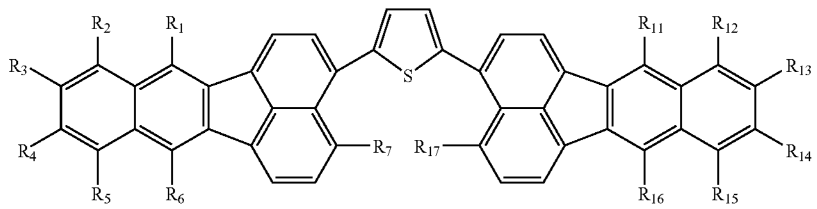
(O)
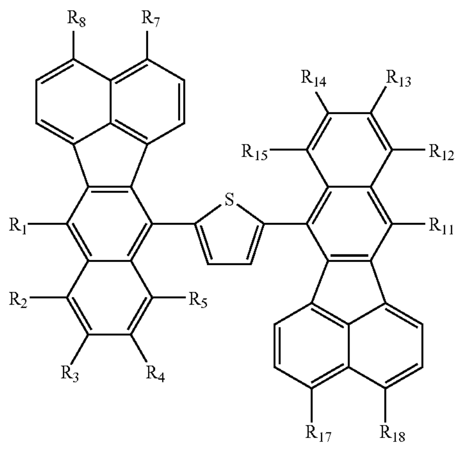

-continued
(P)
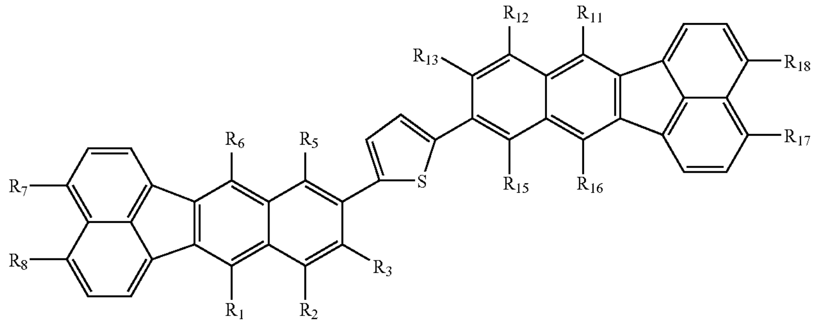
(Q)
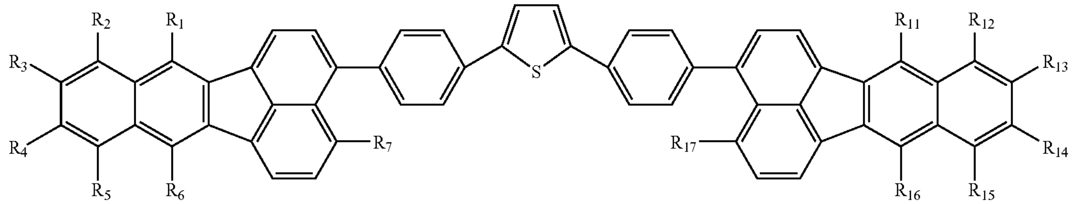
(R)
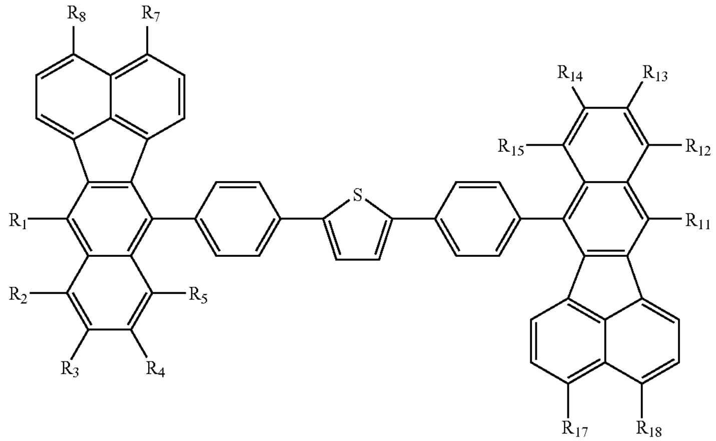
(S)
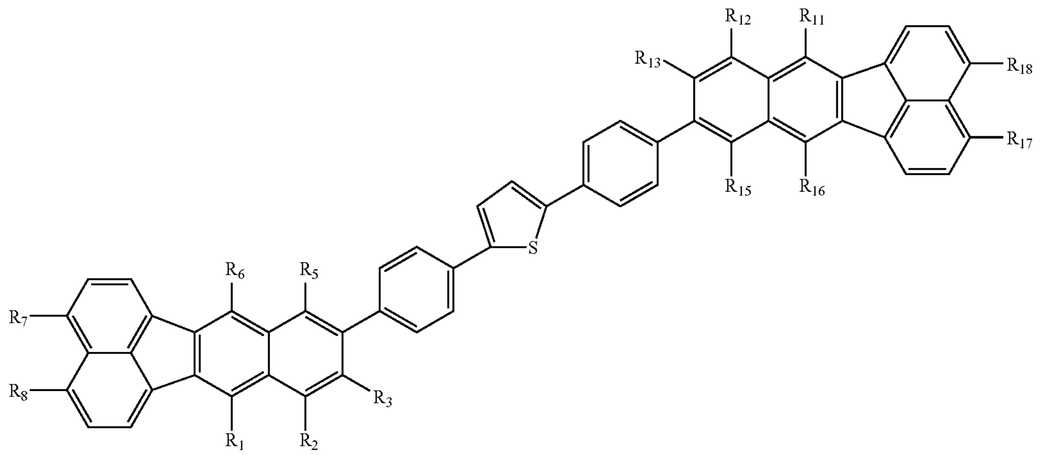

-continued
(T)
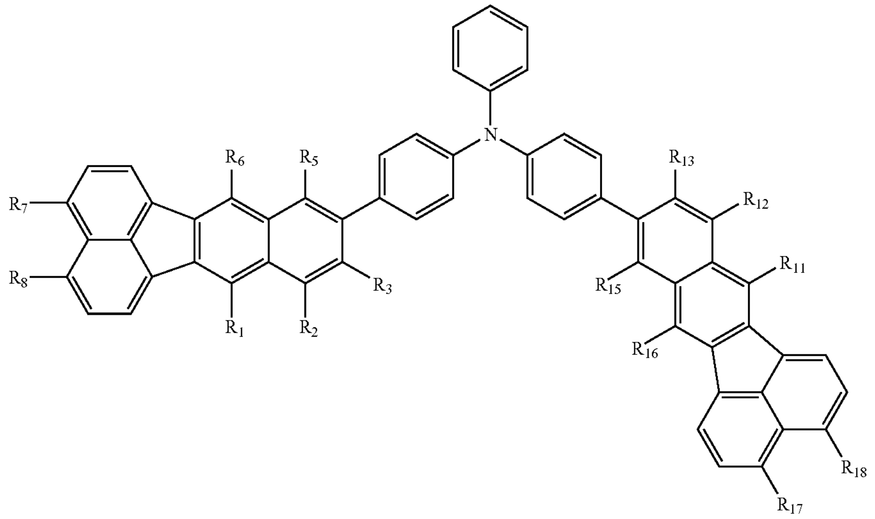
C45
(U)
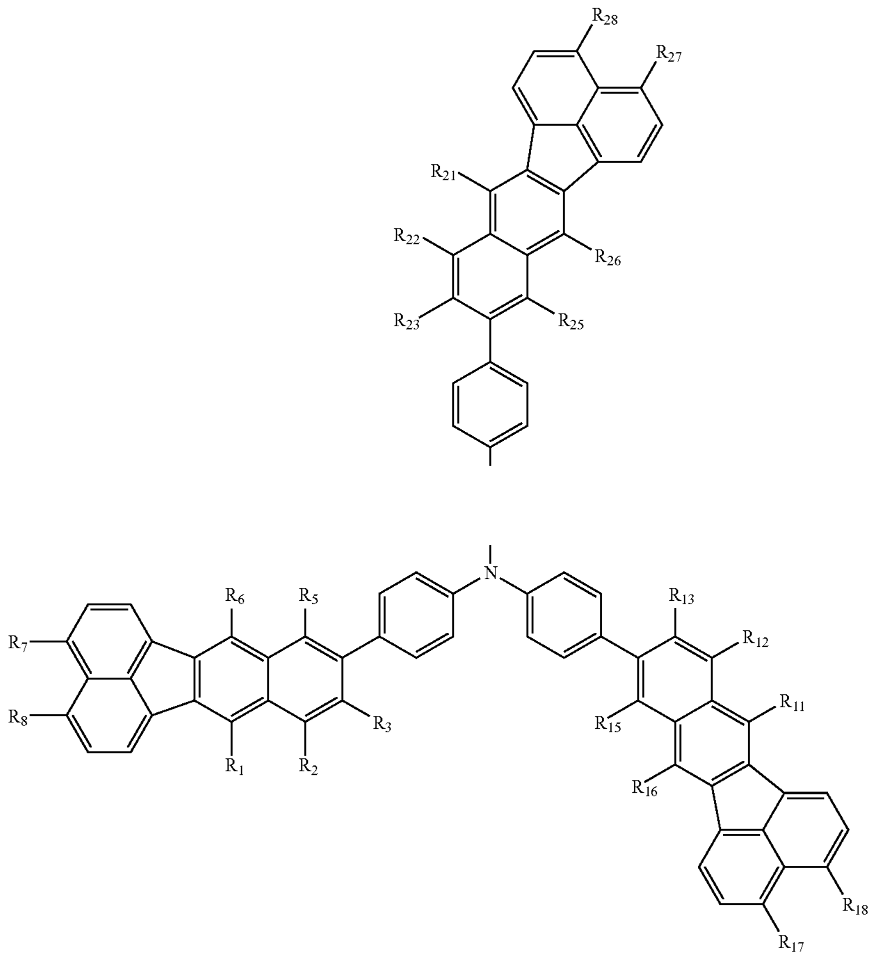

-continued
(V)
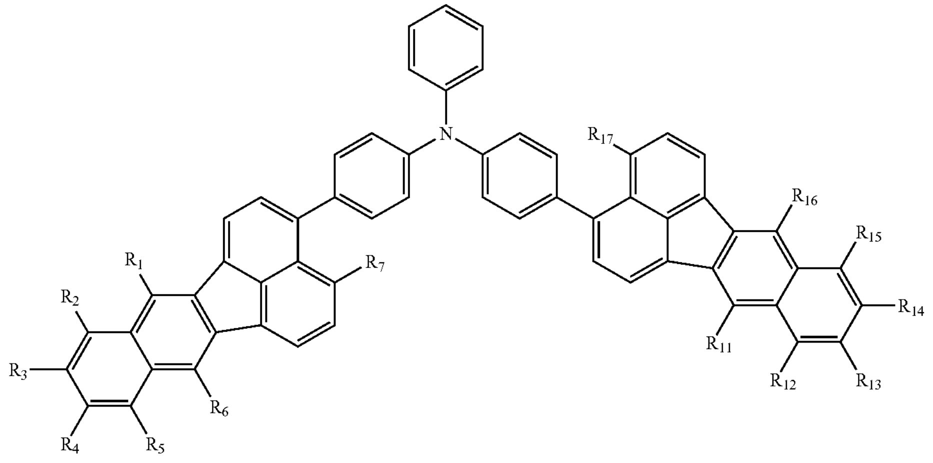
(W)
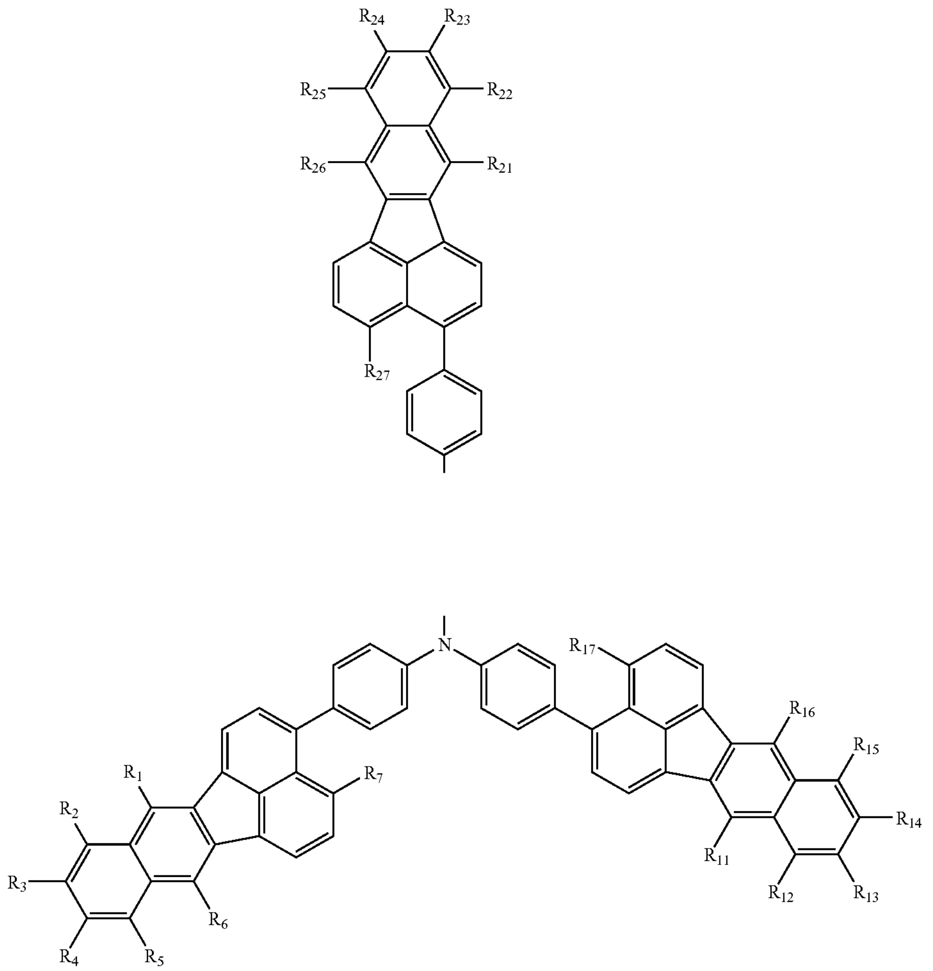

-continued
(X)
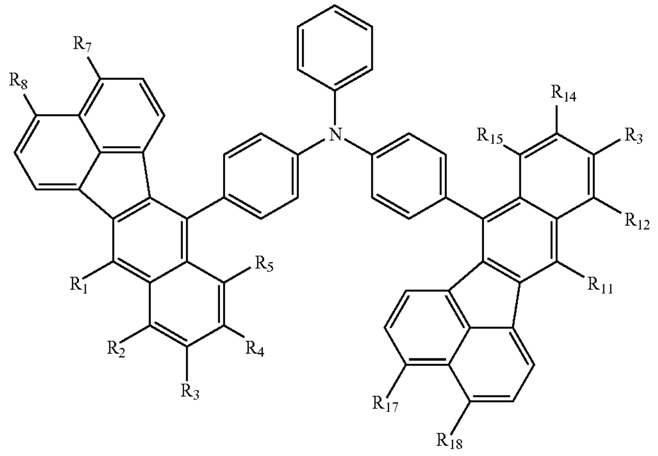
(X')
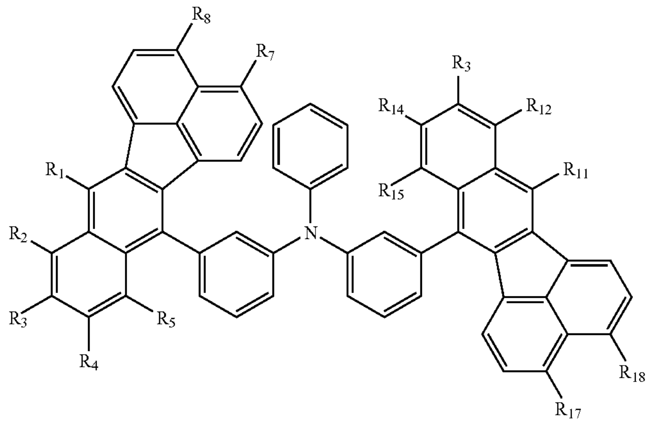
(Y)
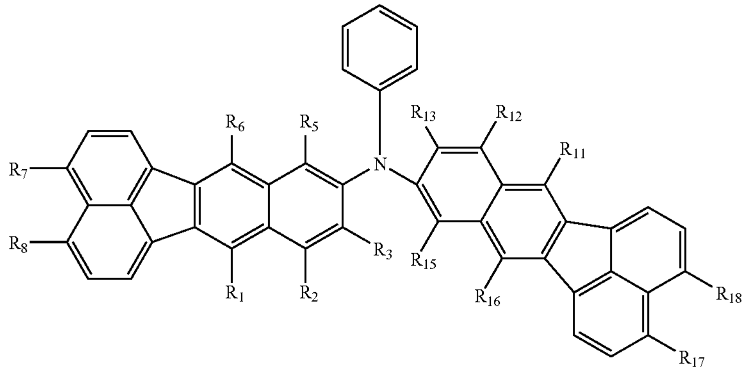

-continued
(Z)
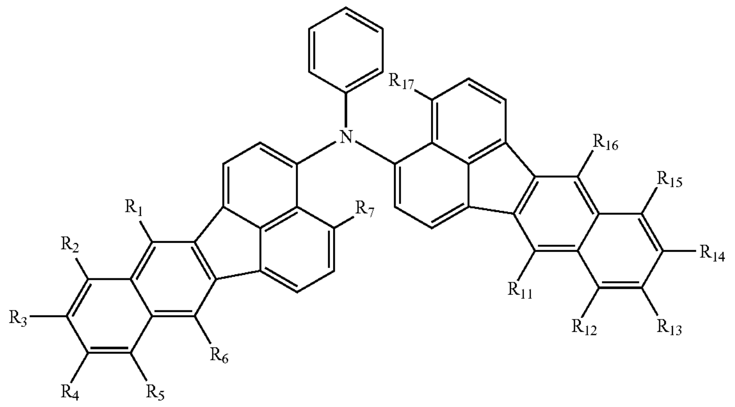
C46
(AA)
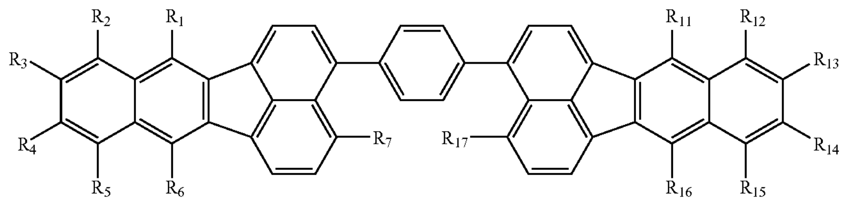
(BB)
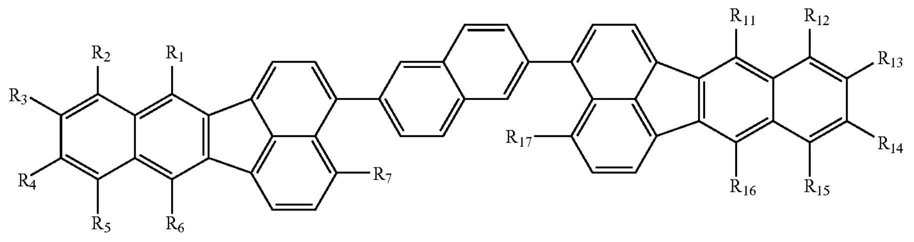
(CC)
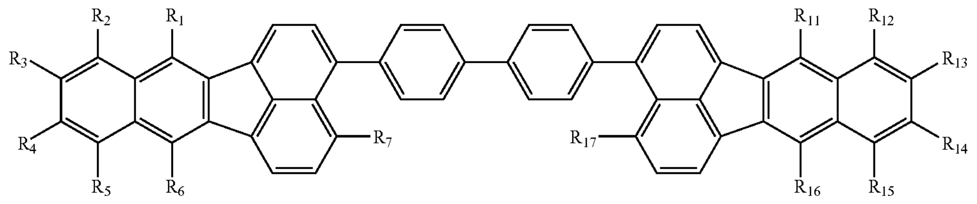
(DD)
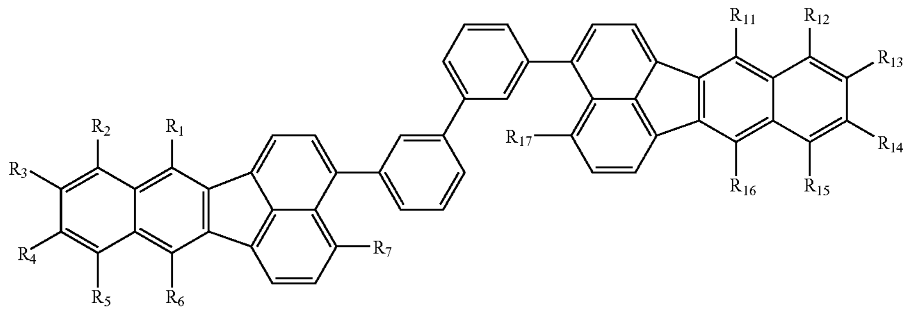

-continued
(EE)
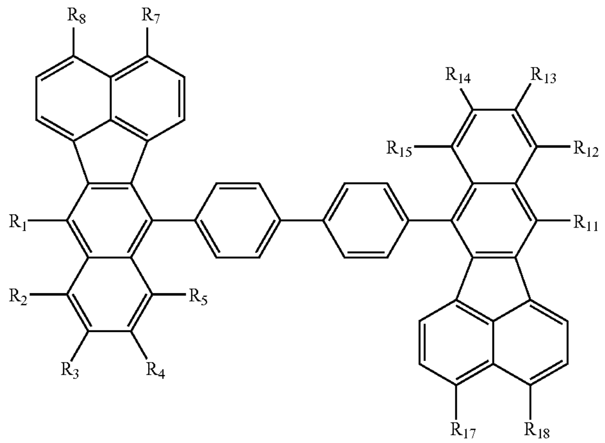
(FF)
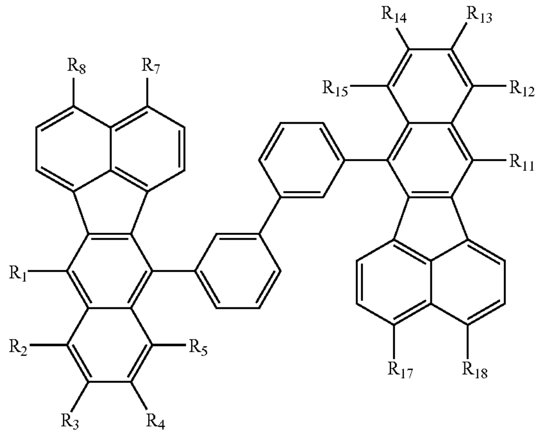
(GG)
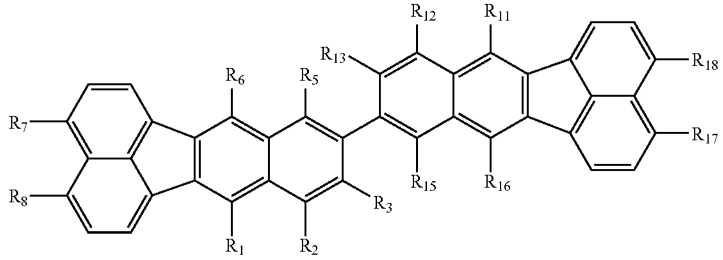
C47
(HH)
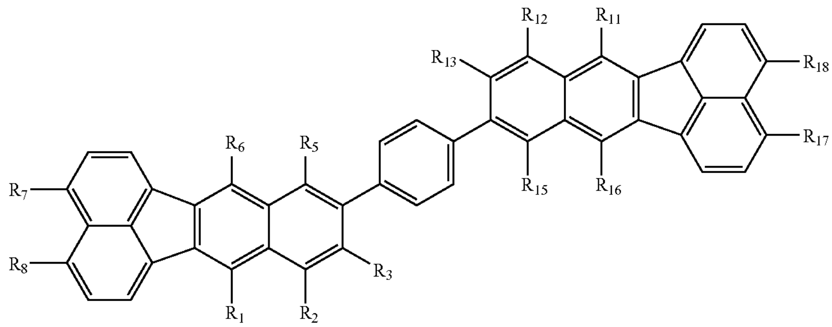

-continued
(II)
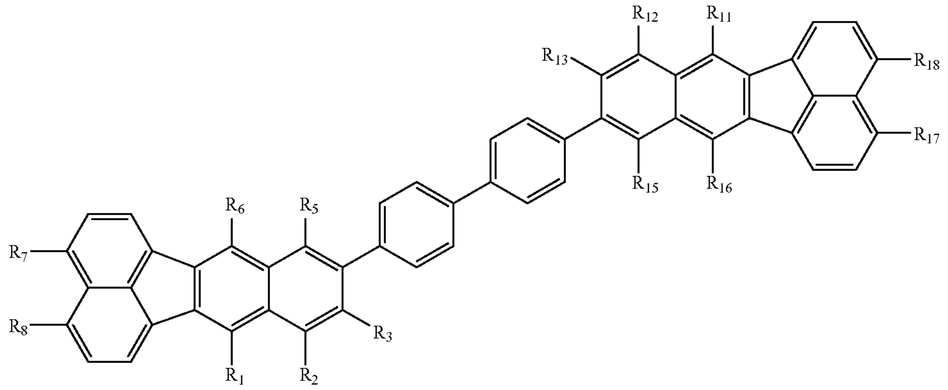
(JJ)
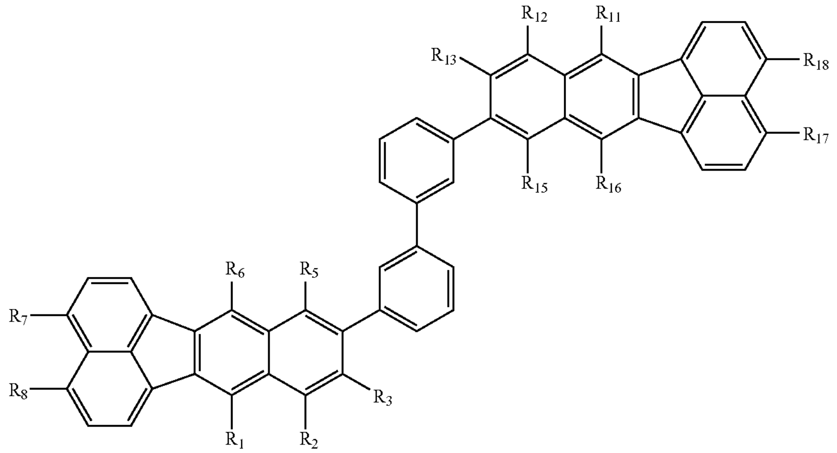
(KK)
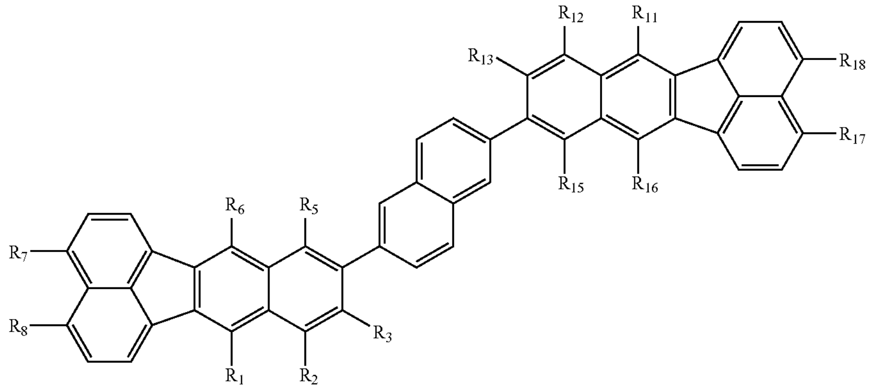
(LL)
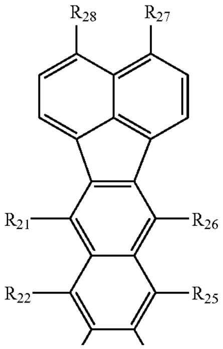

-continued
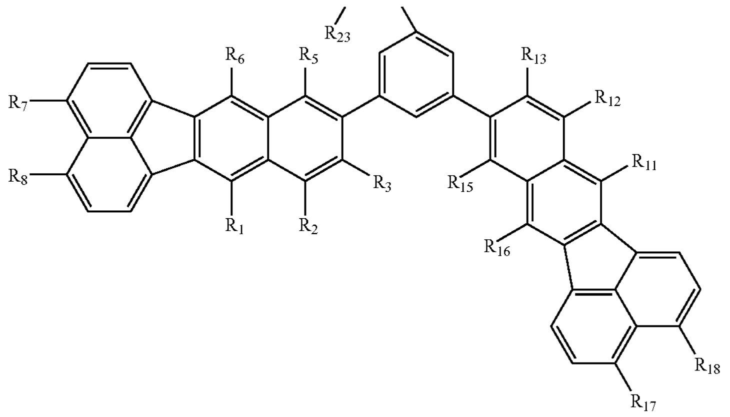
(MM)
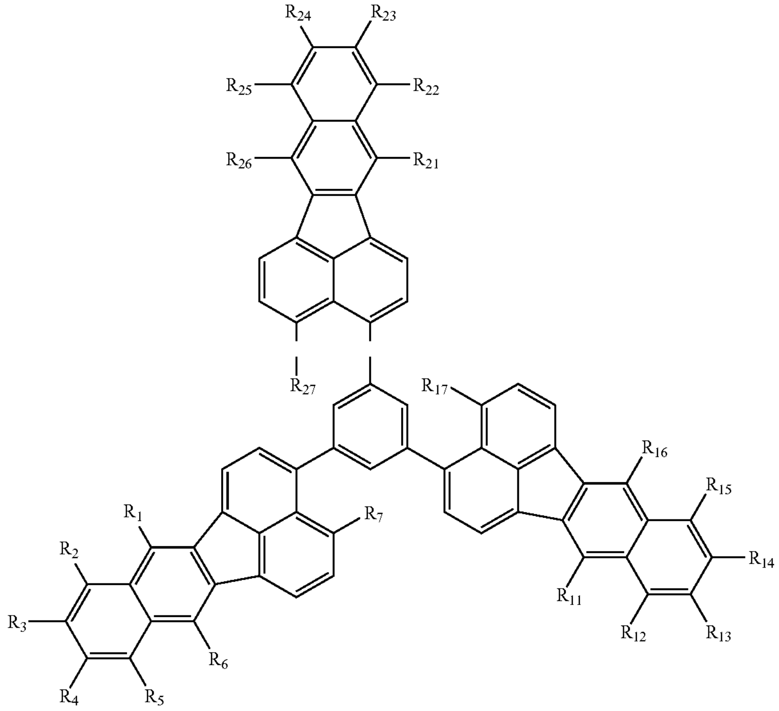
C48
(NN)
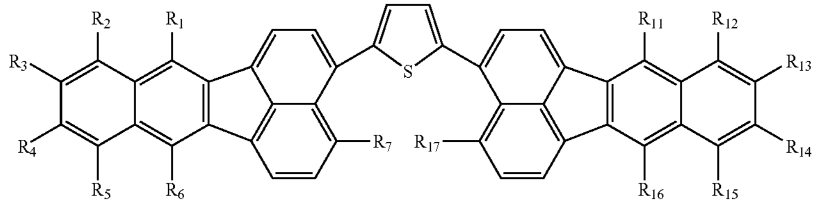

-continued
(OO)
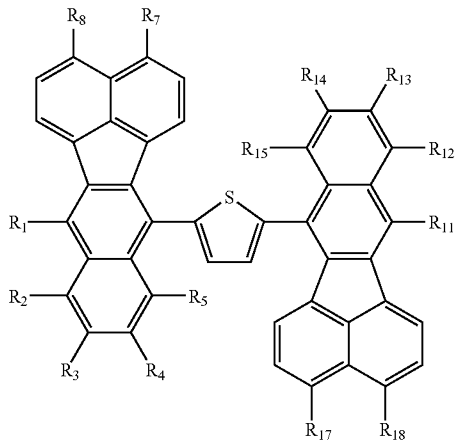
(PP)
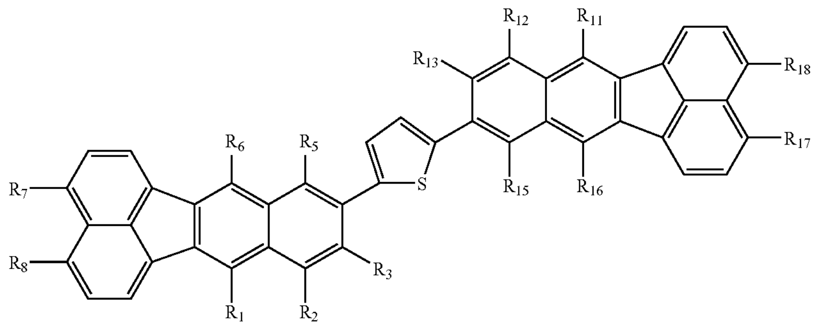
(QQ)
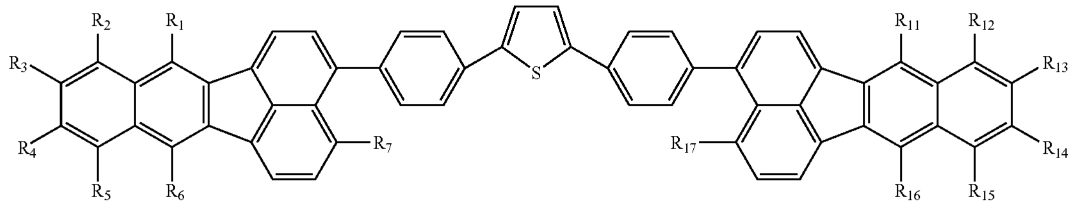
(RR)
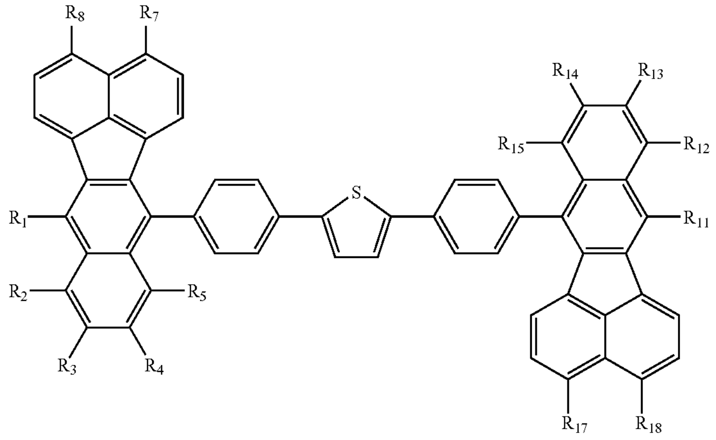

-continued
(SS)
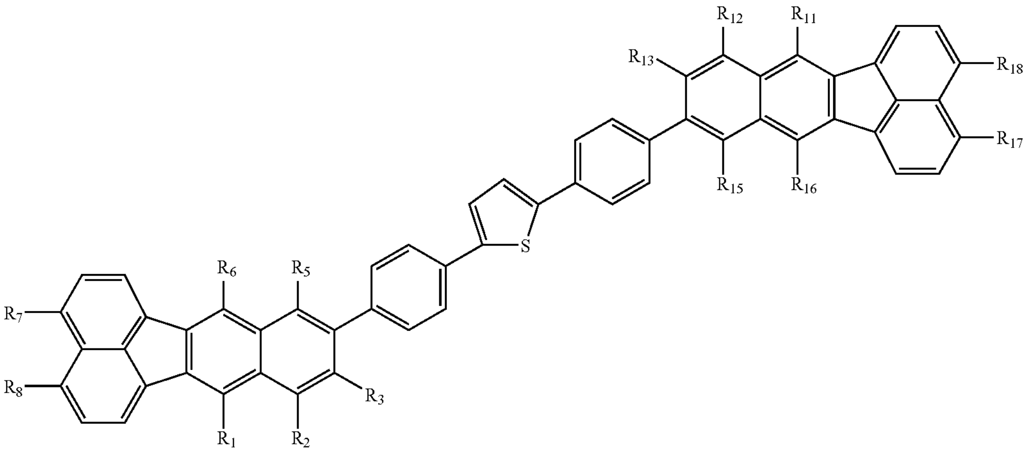
C49
(TT)
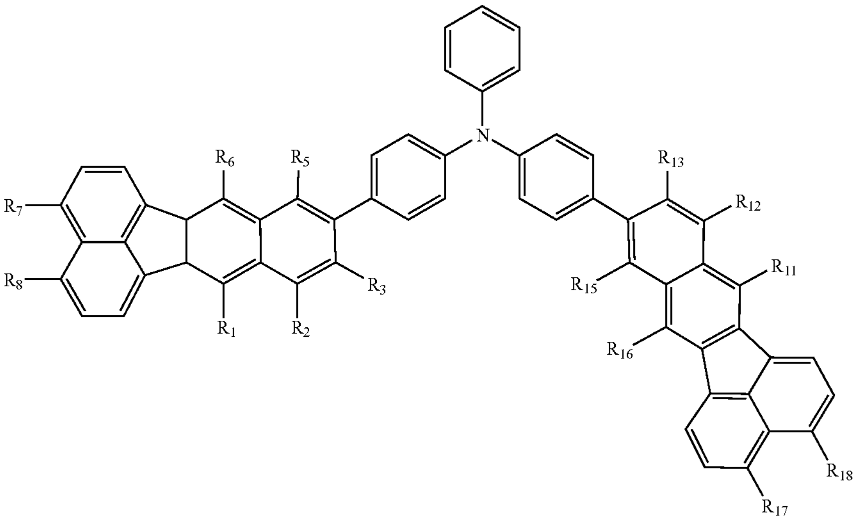
(UU)
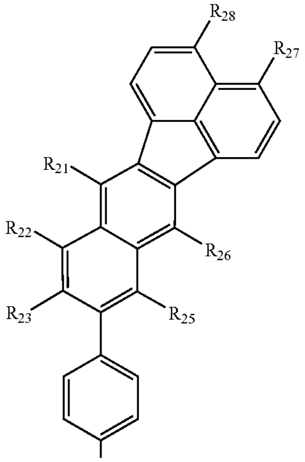

-continued
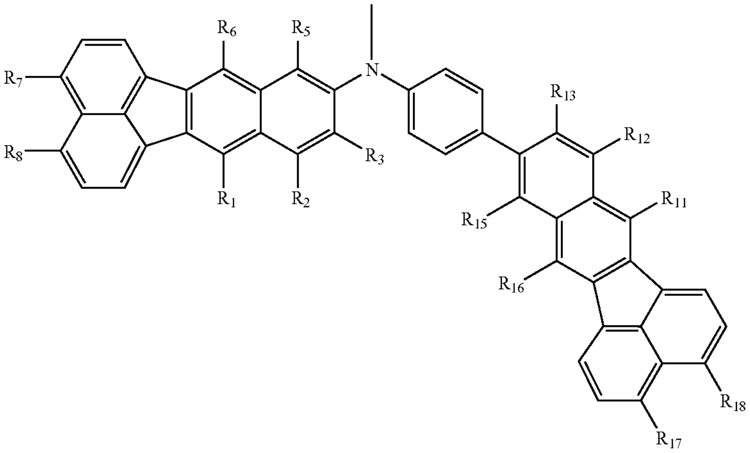
(VV)
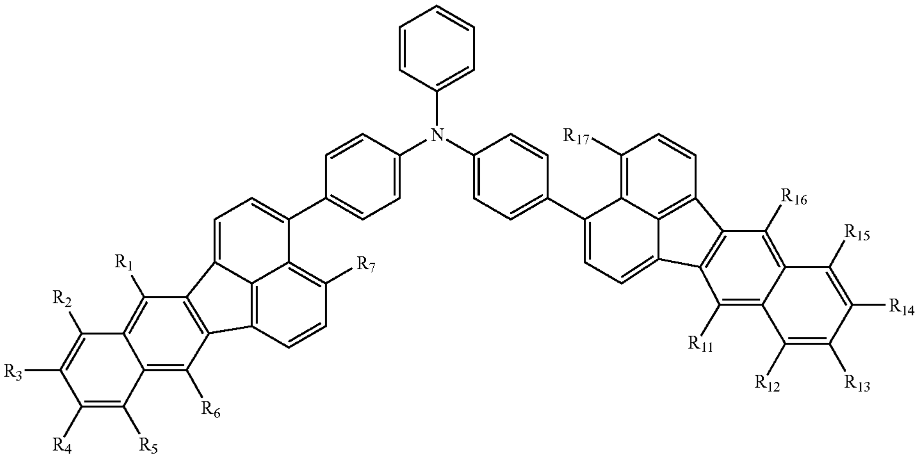
(WW)
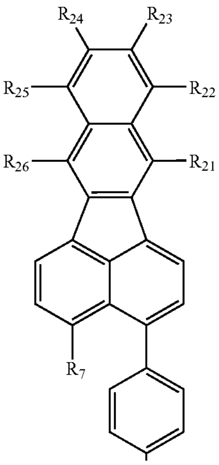

-continued
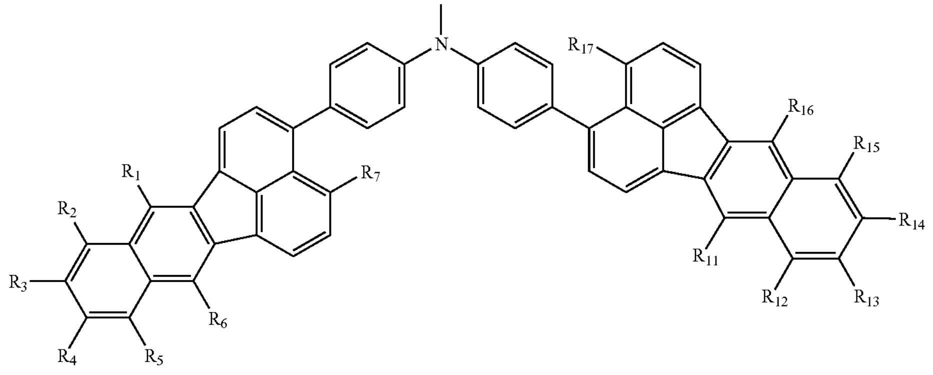
(XX)
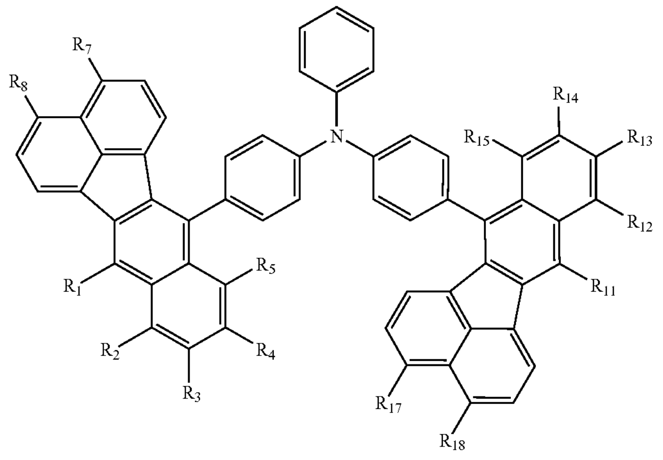
(X'X')
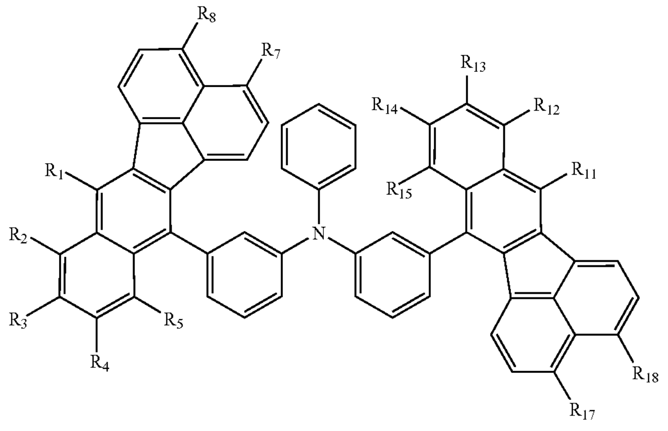

-continued
(YY)
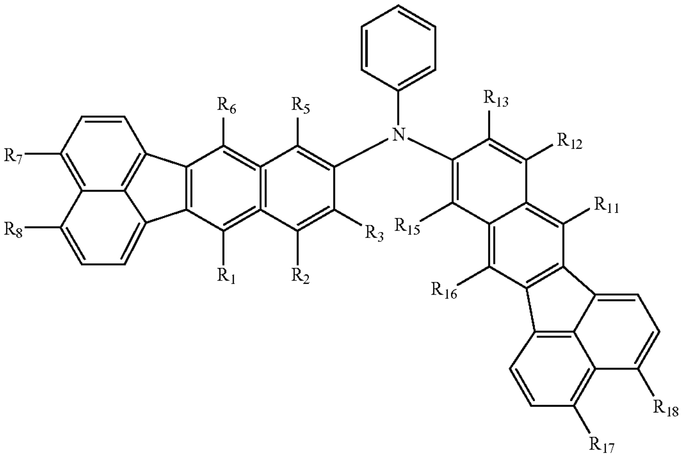
(ZZ)
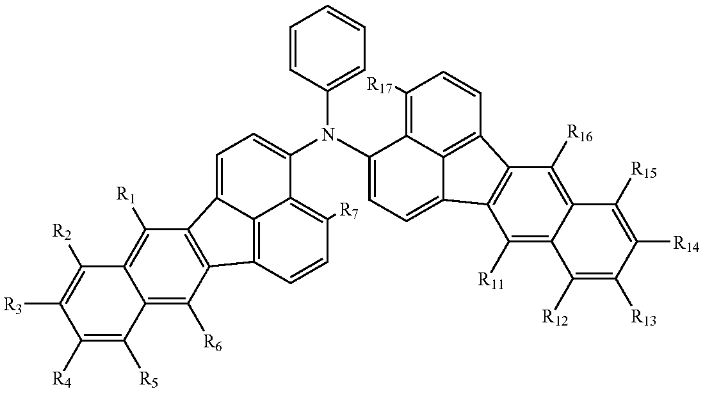
C50
(AAA)
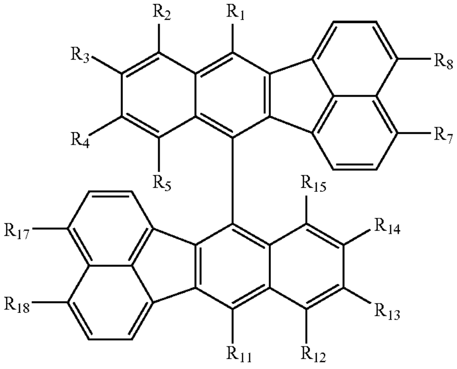
-continued
(BBB)
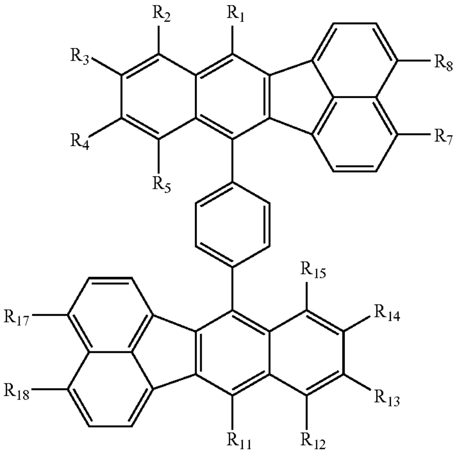

-continued
(CCC)
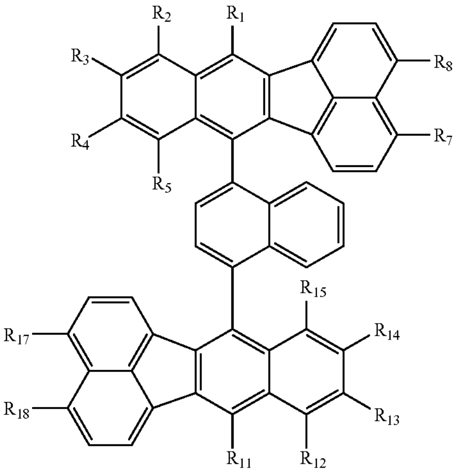
(DDD)
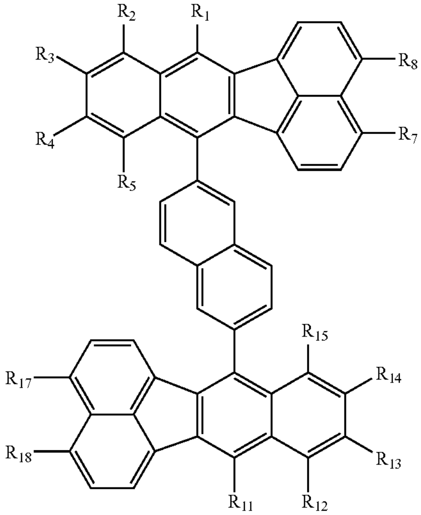
(EEE)
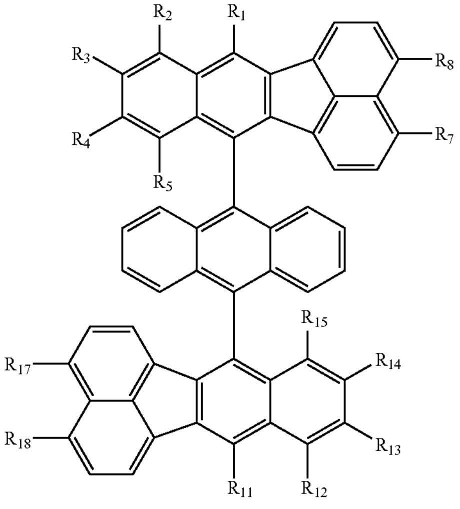
-continued
(FFF)
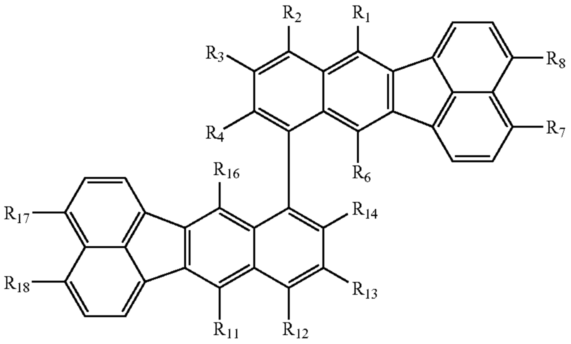
(GGG)
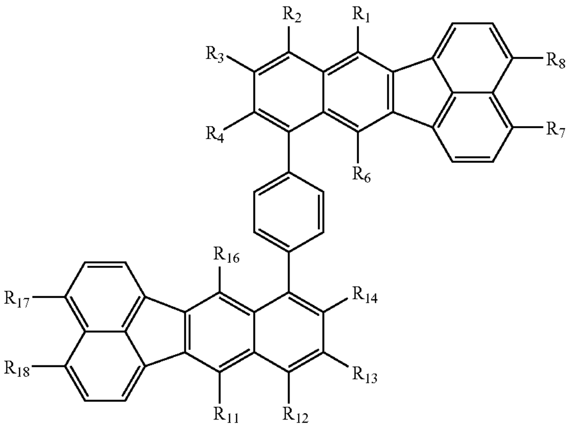
(HHH)
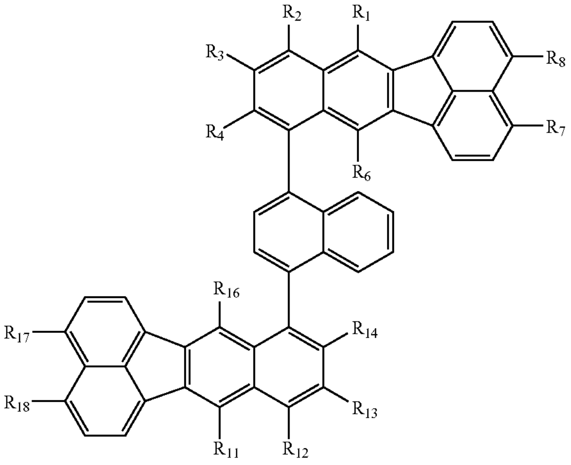

-continued
(JJJ)
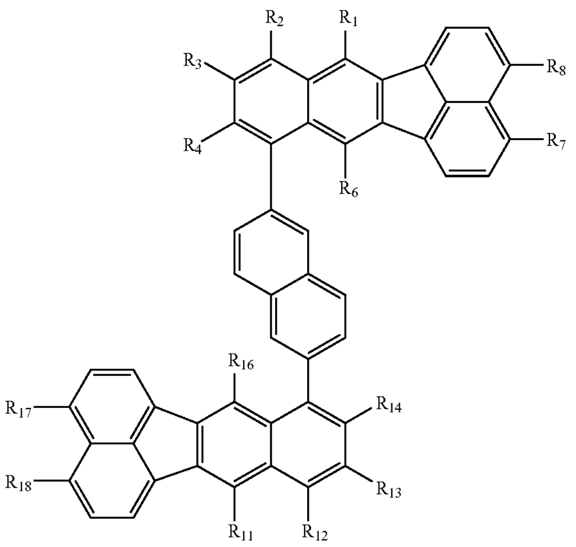
(KKK)
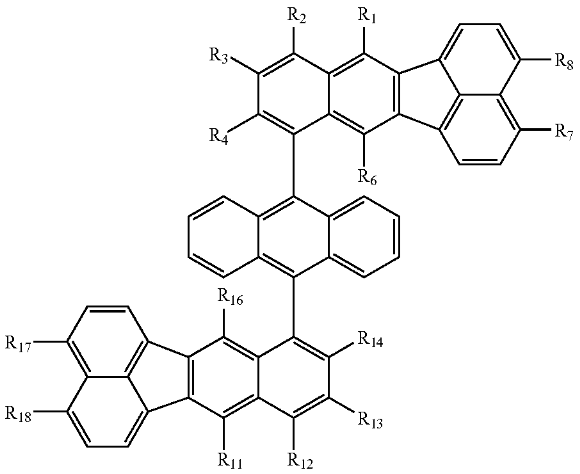
C51
(AAA')
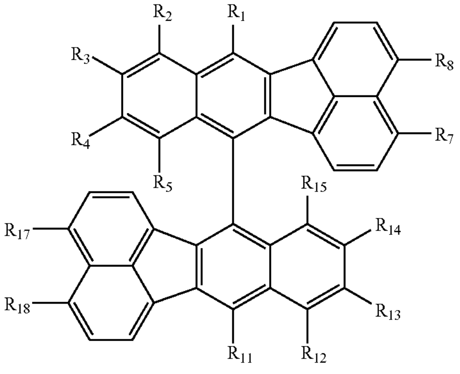
-continued
(BBB')
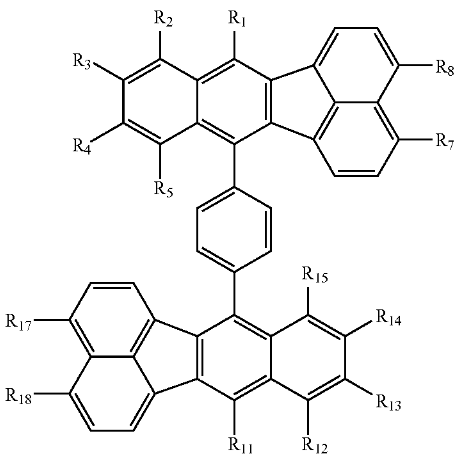
(CCC')
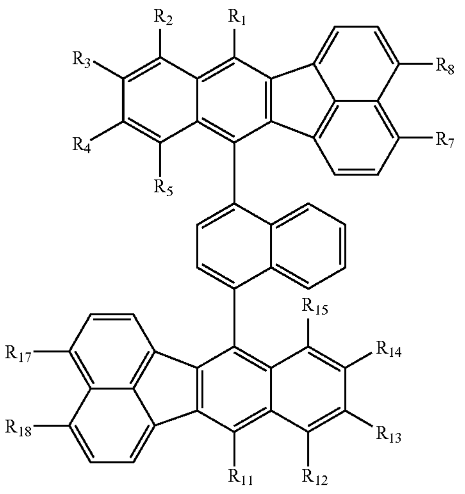
(DDD')
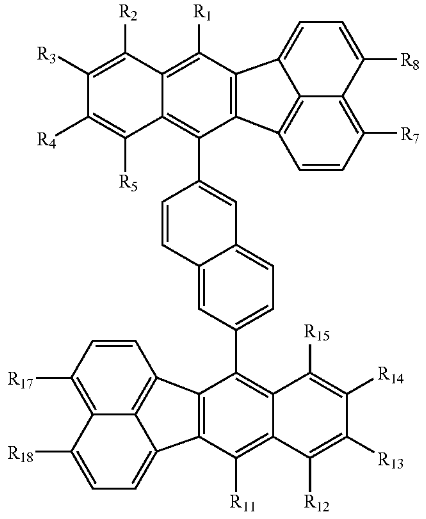

-continued
(EEE')
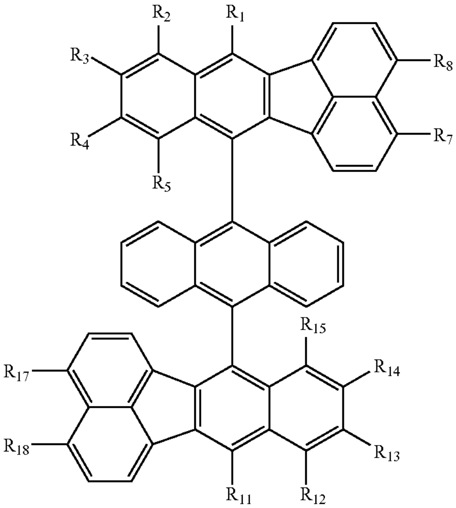
(FFF')
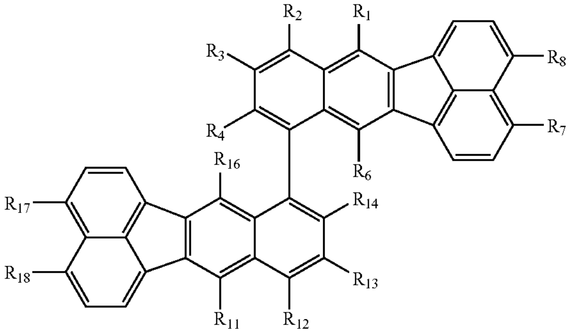
(GGG')
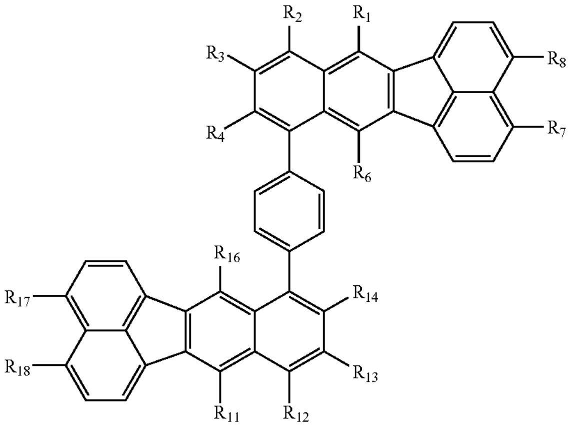
-continued
(HHH')
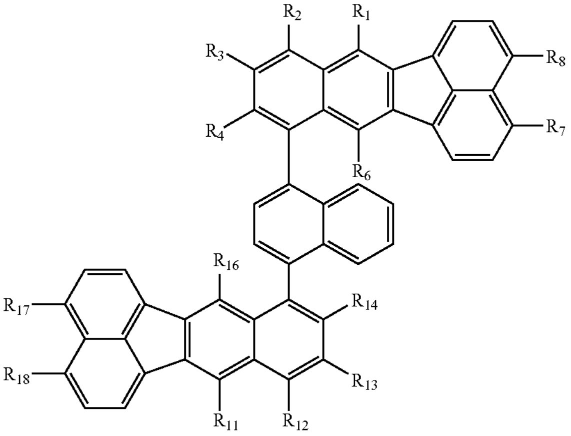
(JJJ)
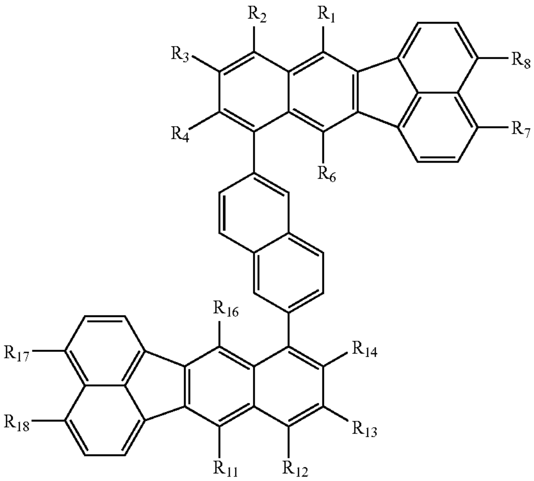
(KKK')
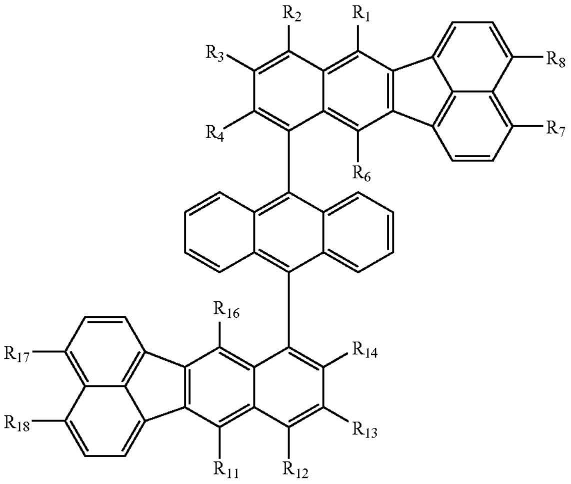

C52
(LLL)
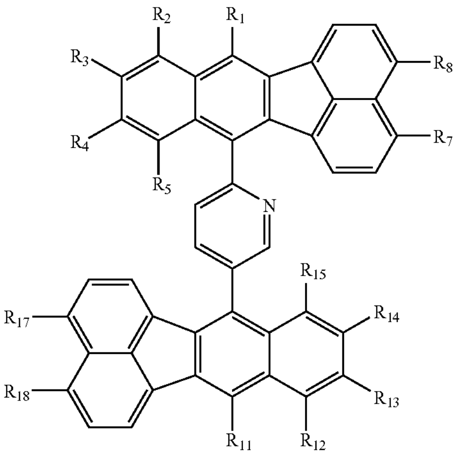
(MMM)
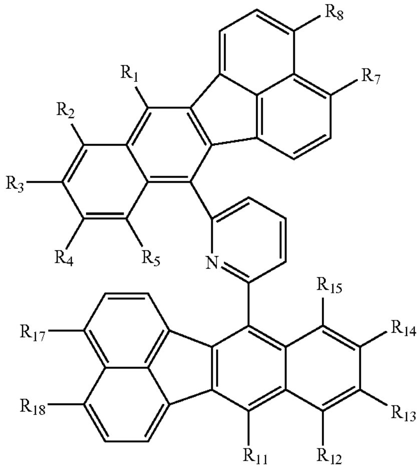
(NNN)
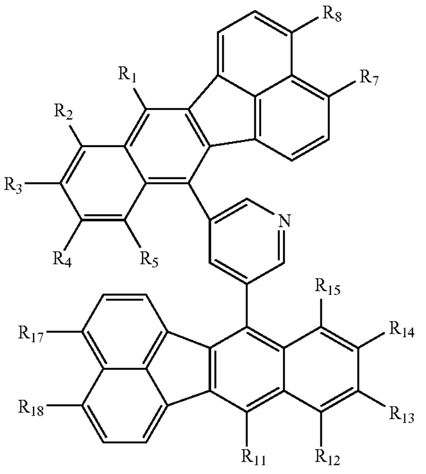
(OOO)
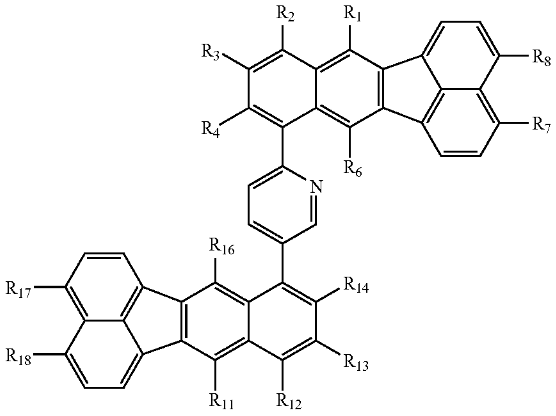
(PPP)
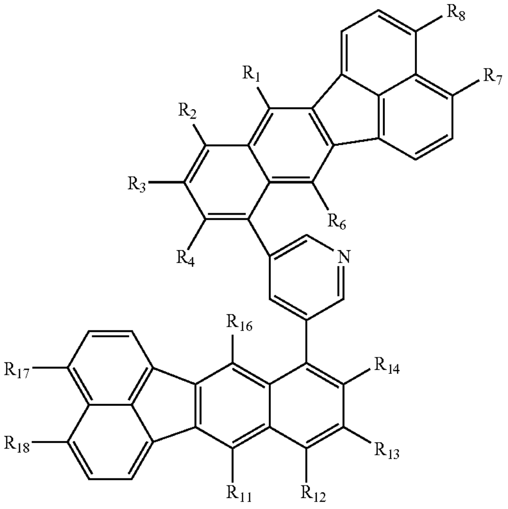
(QQQ)
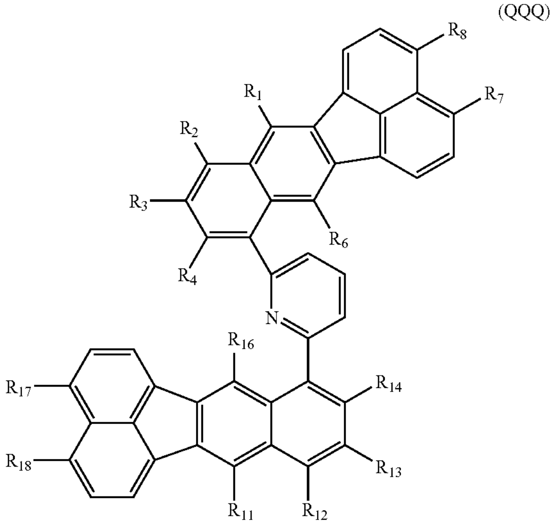

-continued
(RRR)
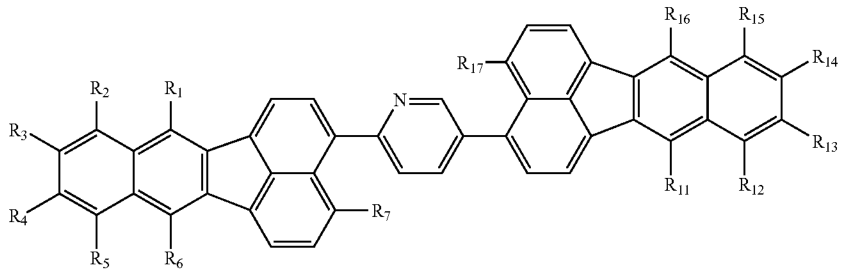
(SSS)
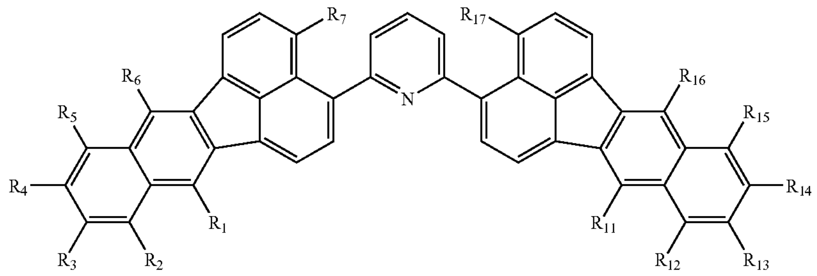
(TTT)
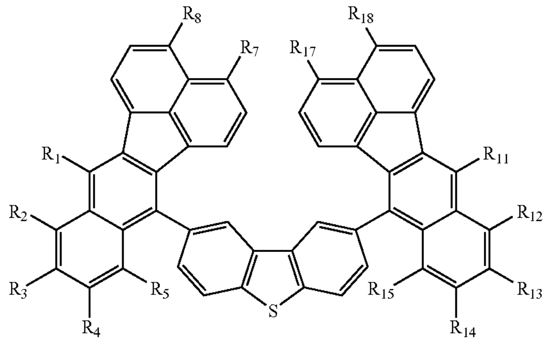
(UUU)
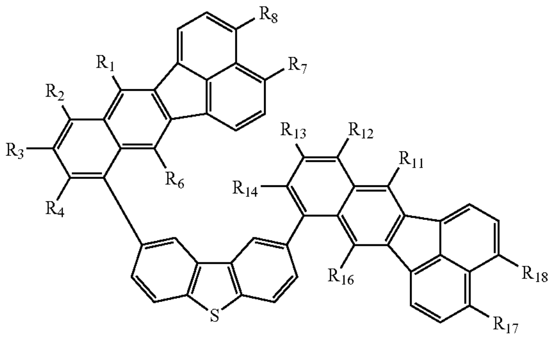
(VVV)
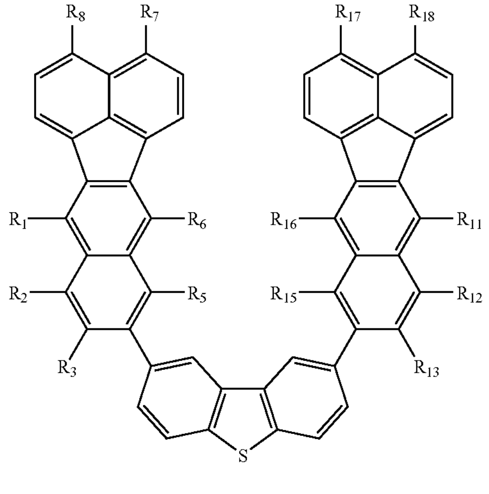

-continued
(WWW)
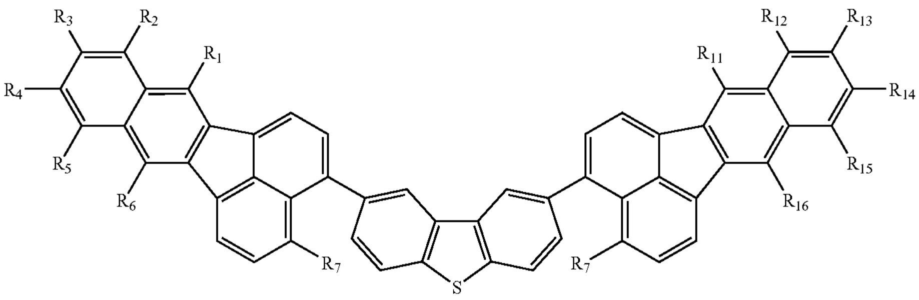
C53
(LLL')
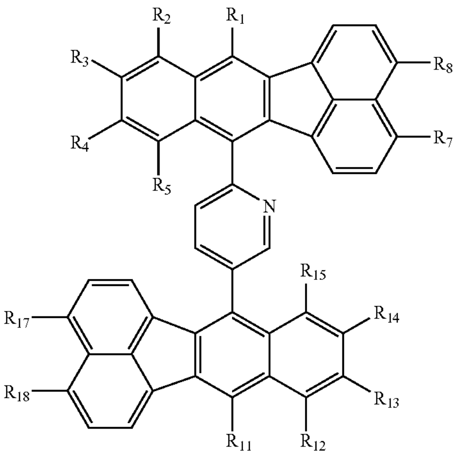
(MMM')
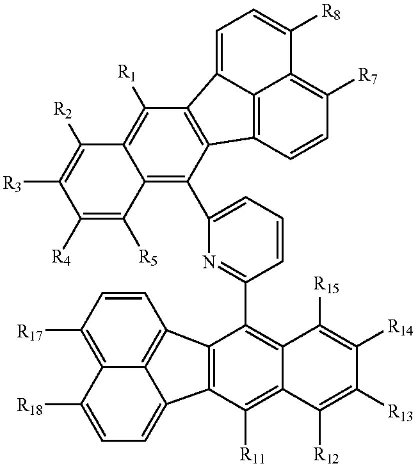
(NNN')
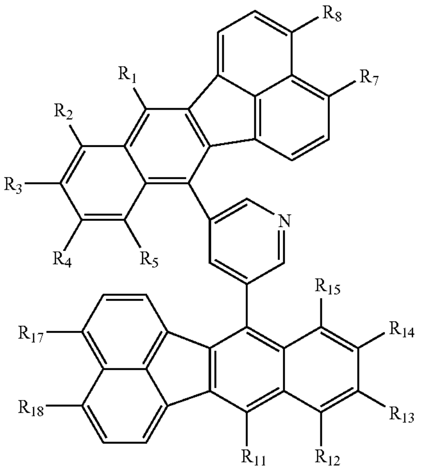
(OOO')
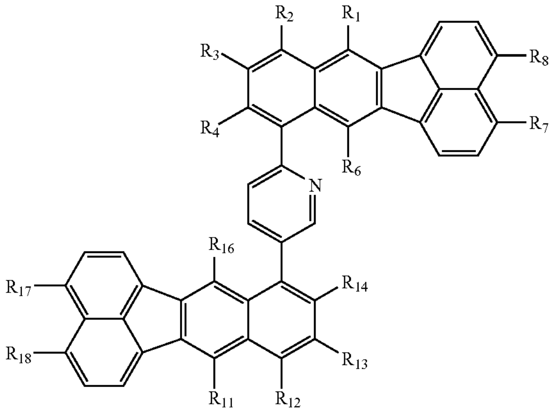

-continued
(PPP')
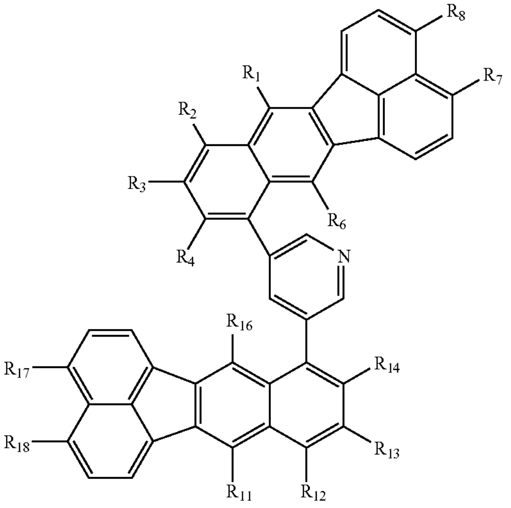
(QQQ')
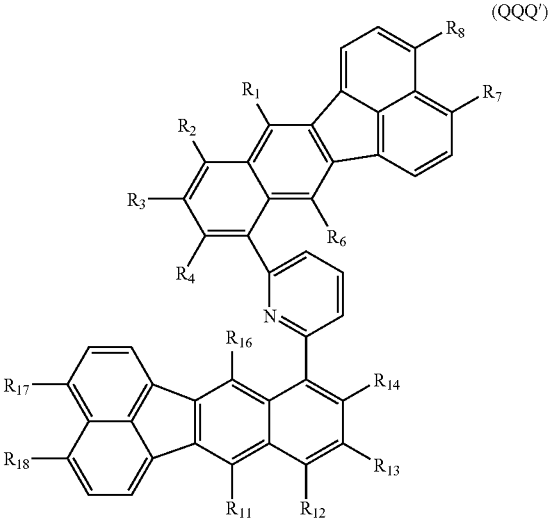
(RRR')
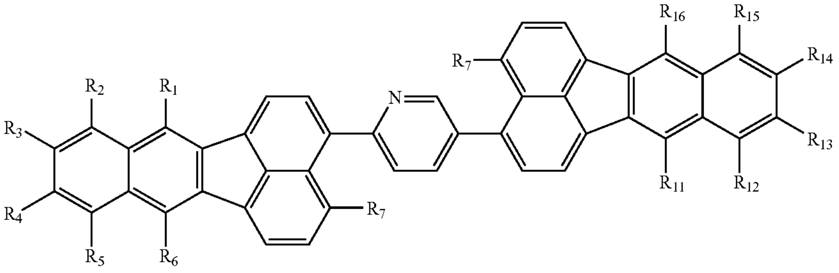
(SSS')
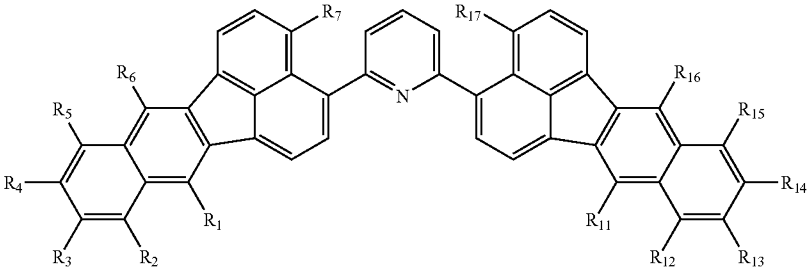
(TTT)
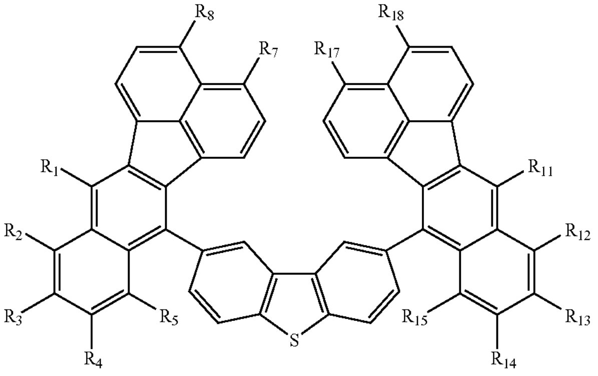
(UUU)
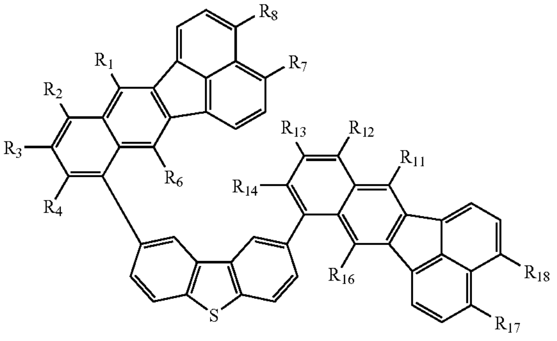

-continued
(VVV)
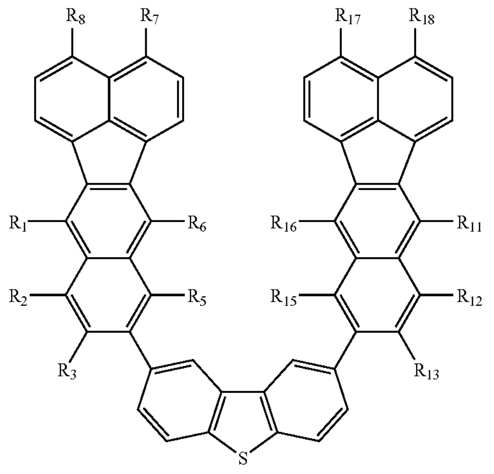
(WWW)
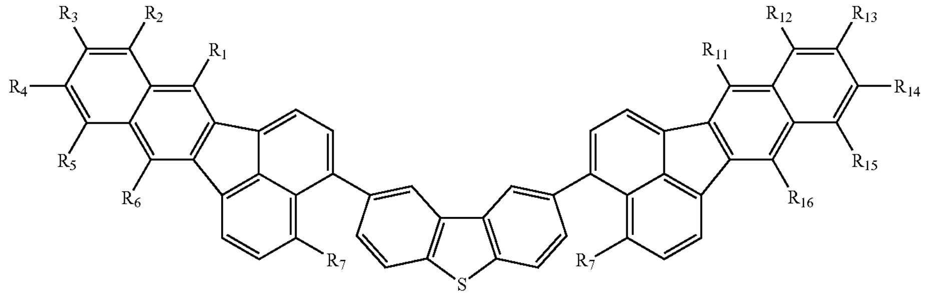
Of these compounds, especially preferred are compounds of the following formulae (A), (B), (E), (H), (X) and (Z) as well as (AAA'), (BBB'), (CCC'), (DDD'), (EEE'), (RRR') and (SSS').
C54
(A)
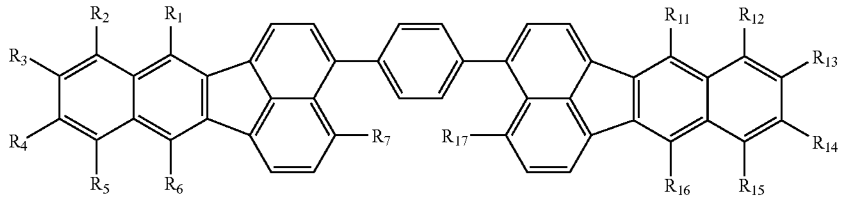
C55
(B)
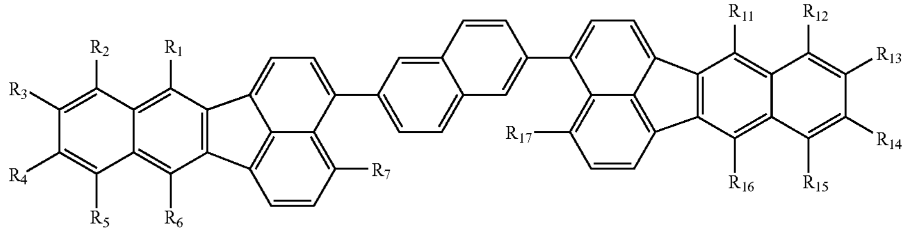

-continued
C56
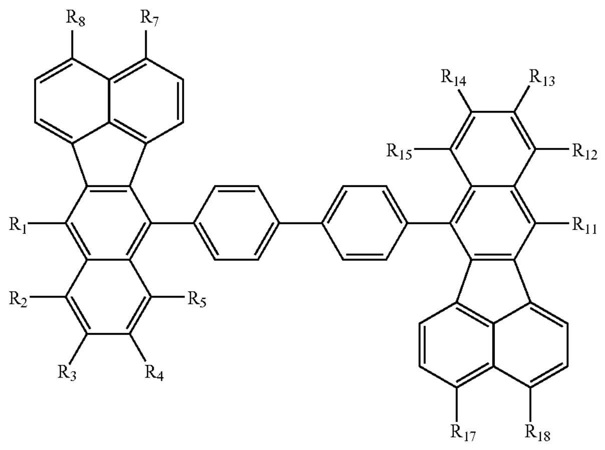
(E)
C57
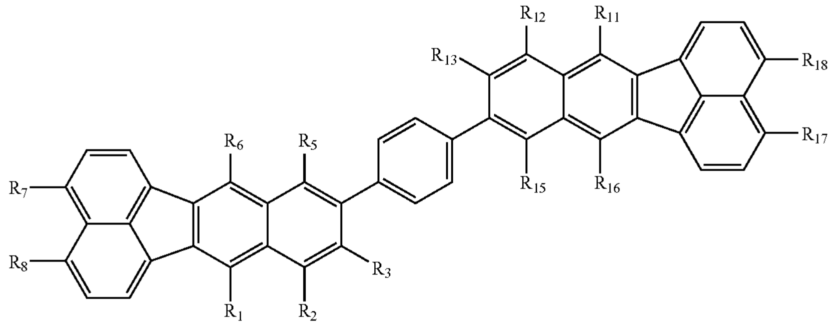
(H)
C58
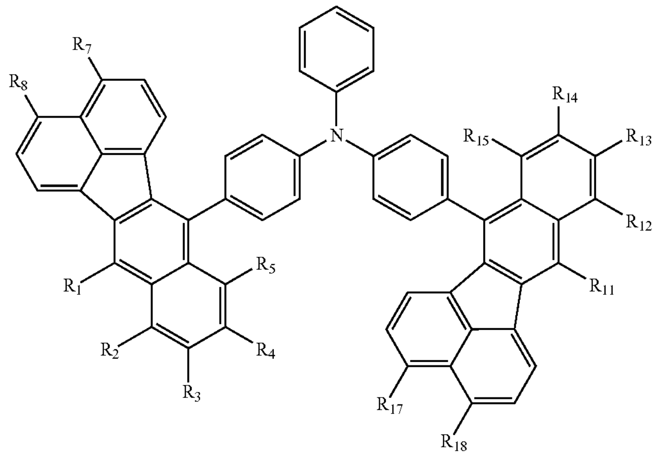
(X)

-continued
C59
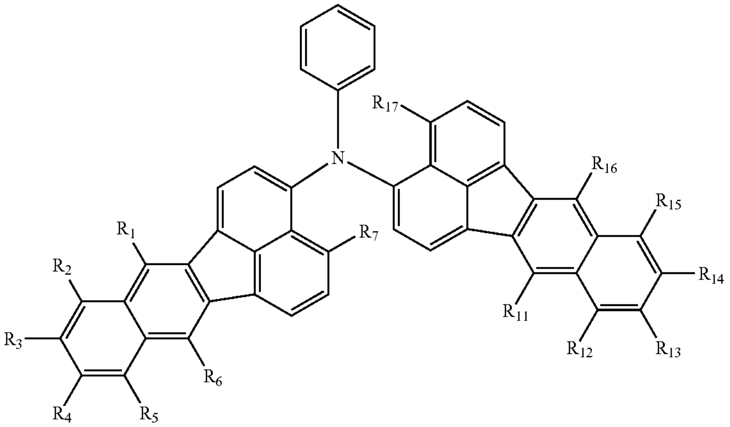
(Z)
-continued
C60
(AAA')
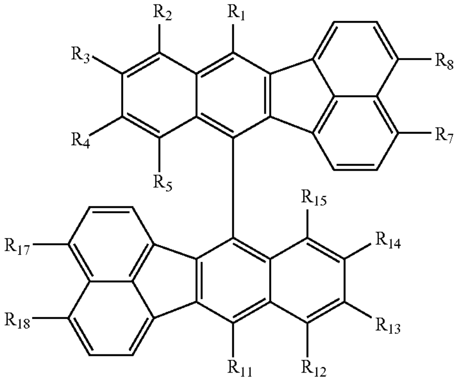
C61
(BBB')
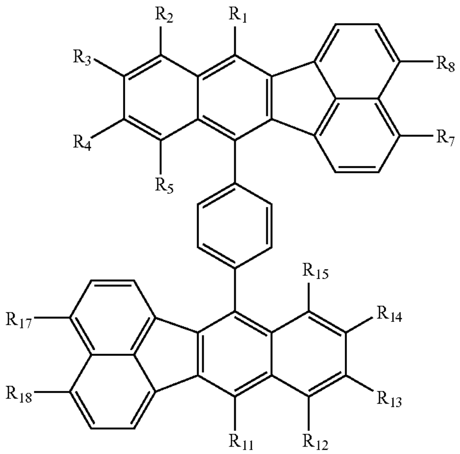
C62
(CCC')
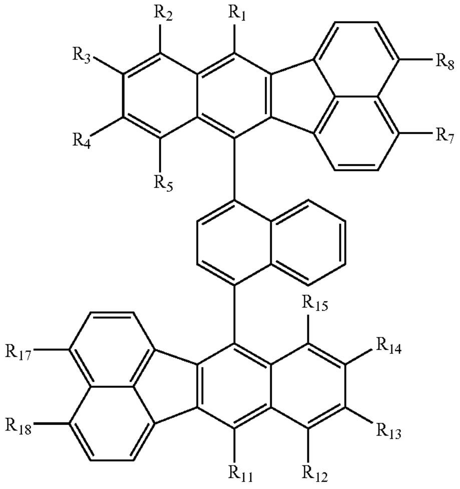
C63
(DDD')
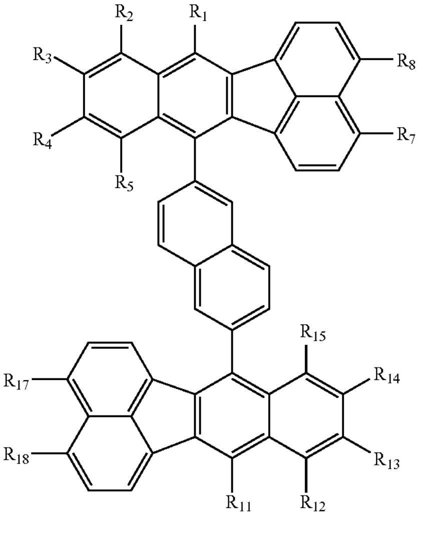

C64
(EEE')
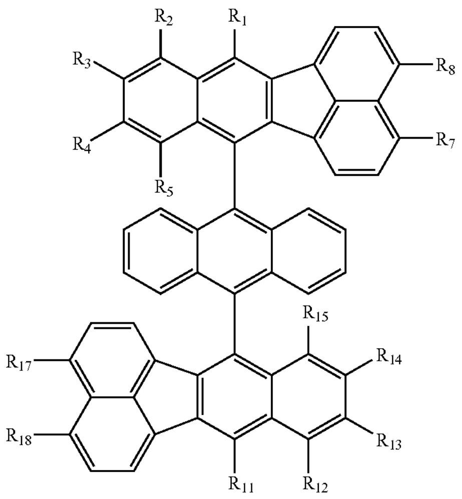
C65
(RRR')
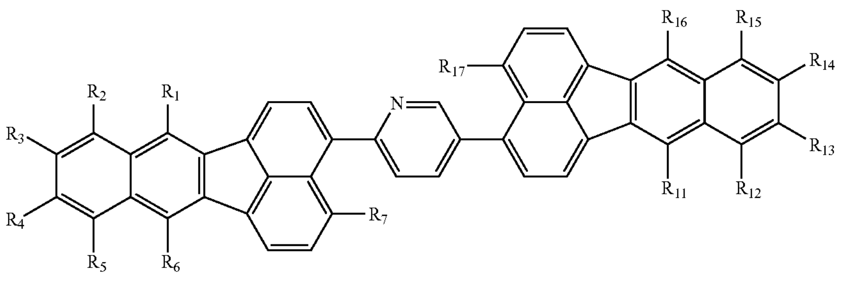
C66
(SSS')
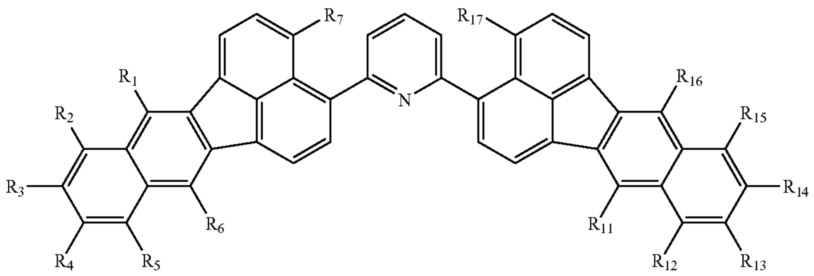
More illustrative examples of the inventive compounds are given below.

Type1 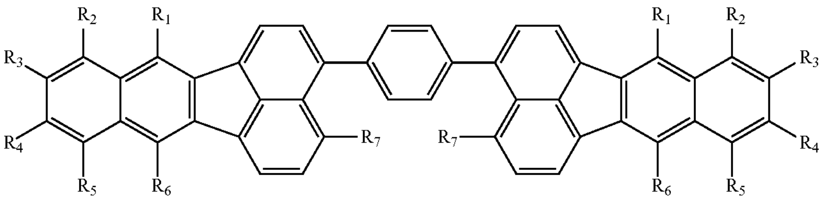 TypeA
| | $R_1$ | $R_2$ | $R_3$ | $R_4$ | $R_5$ | $R_6$ | $R_7$ |
|---|---|---|---|---|---|---|---|
| A-1 | H | H | H | H | H | H | H |
| A-2 | Ph | H | H | H | H | Ph | H |
| A-3 | Ph | Ph | H | H | Ph | Ph | H |
| A-4 | Ph | H | Ph | Ph | H | Ph | H |
| A-5 | Ph | H | Ph | H | H | Ph | H |
| A-6 | Ph | H | H | H | H | Ph | Ph |
| A-7 | Ph | Me | H | H | Me | Ph | H |
| A-8 | Ph | H | Me | Me | H | Ph | H |
| A-9 | Ph | H | H | H | H | Ph | Me |
| A-10 | 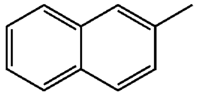 | H | H | H | H | 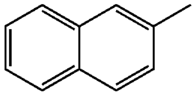 | H |
| A-11 | 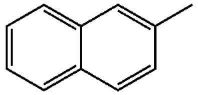 | Ph | H | H | Ph | 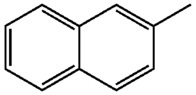 | H |
| A-12 | 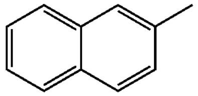 | H | Ph | Ph | H | 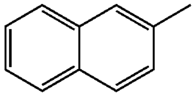 | H |
| A-13 | 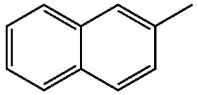 | H | Ph | H | H | 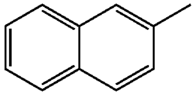 | H |
| A-14 | 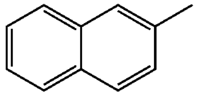 | H | H | H | H | 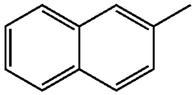 | Ph |

-continued
| | | | | | | | |
|---|---|---|---|---|---|---|---|
| A-15 | 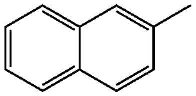 | Me | H | H | Me | 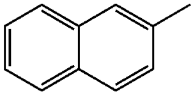 | H |
| A-16 | 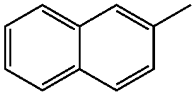 | H | Me | Me | H | 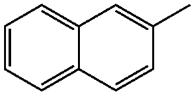 | H |
| A-17 | 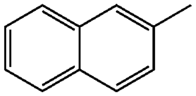 | H | H | H | H | 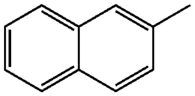 | Me |
| A-18 | 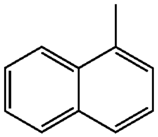 | H | H | H | H | 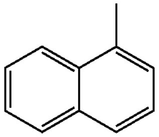 | H |
| A-19 | 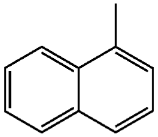 | Ph | H | H | Ph | 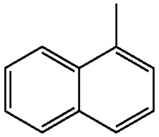 | H |
| A-20 | 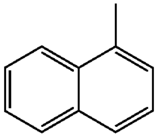 | H | Ph | Ph | H | 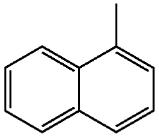 | H |
| A-21 | 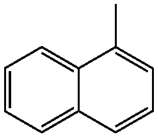 | H | Ph | H | H | 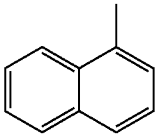 | H |

-continued
| | | | | | | | |
|---|---|---|---|---|---|---|---|
| A-22 | 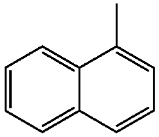 | H | H | H | H | 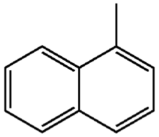 | Ph |
| A-23 | 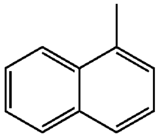 | Me | H | H | Me | 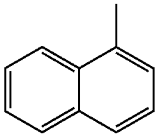 | H |
| A-24 | 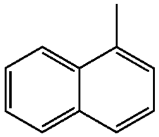 | H | Me | Me | H | 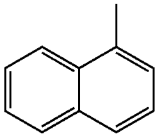 | H |
| A-25 | 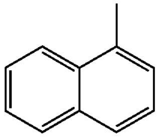 | H | H | H | H | 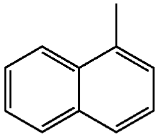 | Me |
| A-26 | 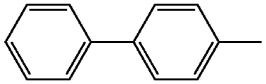 | H | H | H | H | 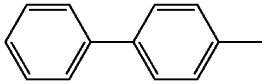 | H |
| A-27 | 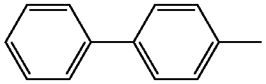 | Ph | H | H | Ph | 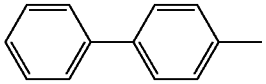 | H |
| A-28 | 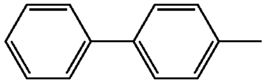 | H | Ph | Ph | H | 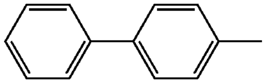 | H |
| A-29 | 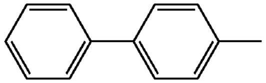 | H | Ph | H | H | 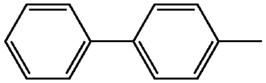 | H |
| A-30 | 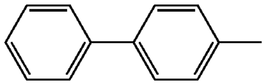 | H | H | H | H | 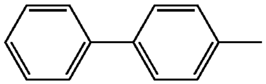 | Ph |

-continued
| | | | | | | | |
|---|---|---|---|---|---|---|---|
| A-31 | 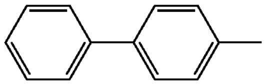 | Me | H | H | Me | 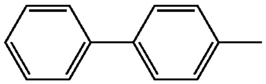 | H |
| A-32 | 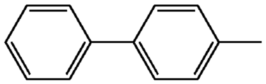 | H | Me | Me | H | 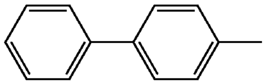 | H |
| A-33 | 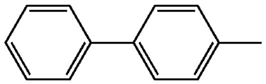 | H | H | H | H | 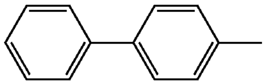 | Me |
| A-34 | 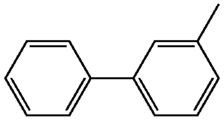 | H | H | H | H | 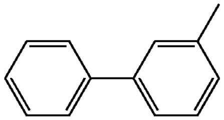 | H |
| A-35 | 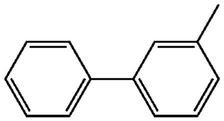 | Ph | H | H | Ph | 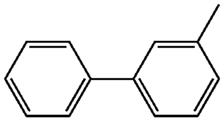 | H |
| A-36 | 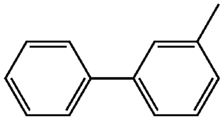 | H | Ph | Ph | H | 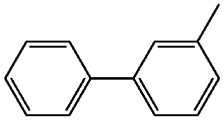 | H |
| A-37 | 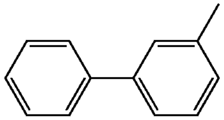 | H | Ph | H | H | 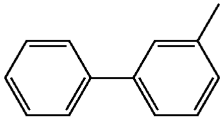 | H |
| A-38 | 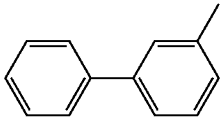 | H | H | H | H | 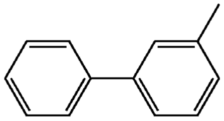 | Ph |

-continued
| | | | | | | | |
|---|---|---|---|---|---|---|---|
| A-39 | 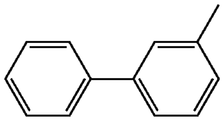 | Me | H | H | Me | 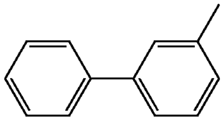 | H |
| A-40 | 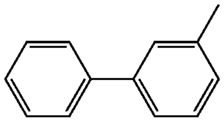 | H | Me | Me | H | 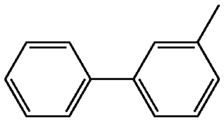 | H |
| A-41 | 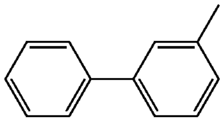 | H | H | H | H | 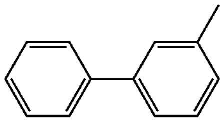 | Me |
| A-42 | 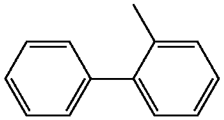 | H | H | H | H | 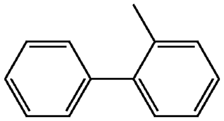 | H |
| A-43 | 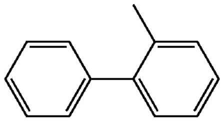 | Ph | H | H | Ph | 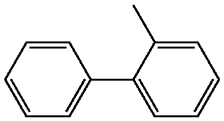 | H |
| A-44 | 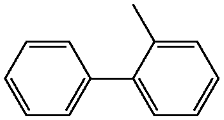 | H | Ph | Ph | H | 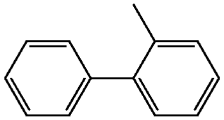 | H |
| A-45 | 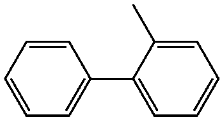 | H | Ph | H | H | 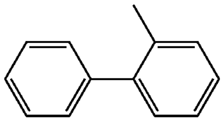 | H |
| A-46 | 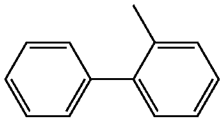 | H | H | H | H | 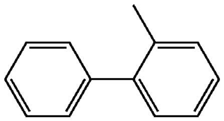 | Ph |

-continued
| | | | | | | | |
|---|---|---|---|---|---|---|---|
| A-47 | 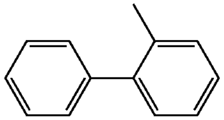 | Me | H | H | Me | 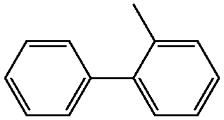 | H |
| A-48 | 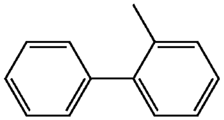 | H | Me | Me | H | 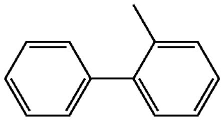 | H |
| A-49 | 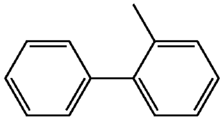 | H | H | H | H | 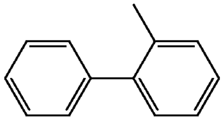 | Me |
| A-50 | Ph | H | H | H | H | 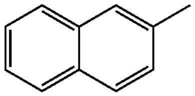 | H |
| A-51 | Ph | H | H | H | H | 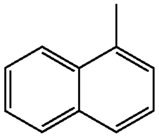 | H |
| A-52 | Ph | H | H | H | H | 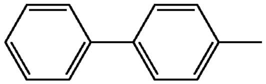 | H |
| A-53 | Ph | H | H | H | H | 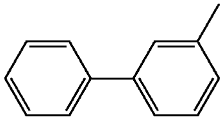 | H |
| A-54 | Ph | H | H | H | H | 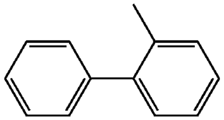 | H |

-continued
| | | | | | | | |
|---|---|---|---|---|---|---|---|
| A-55 | 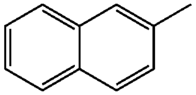 | H | H | H | H | 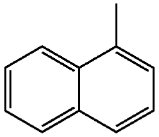 | H |
| A-56 | 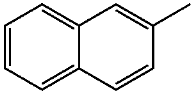 | H | H | H | H | 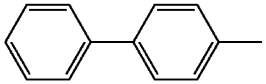 | H |
| A-57 | 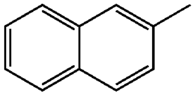 | H | H | H | H | 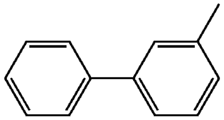 | H |
| A-58 | 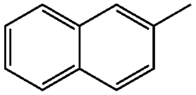 | H | H | H | H | 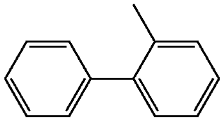 | H |
| A-59 | 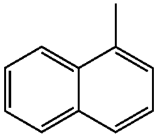 | H | H | H | H | 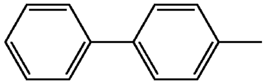 | H |
| A-60 | 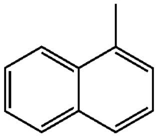 | H | H | H | H | 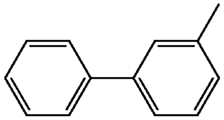 | H |
| A-61 | 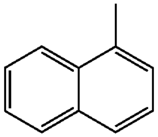 | H | H | H | H | 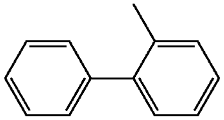 | H |

-continued
| | | | | | | | |
|---|---|---|---|---|---|---|---|
| A-62 | 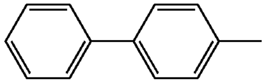 | H | H | H | H | 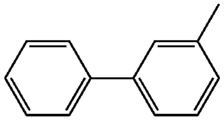 | H |
| A-63 | 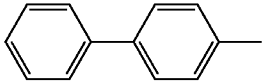 | H | H | H | H | 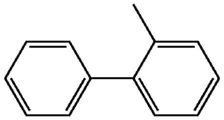 | H |
| A-64 | 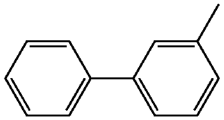 | H | H | H | H | 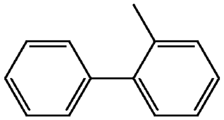 | H |
| A-65 | H | Ph | H | H | Ph | H | H |
| A-66 | H | 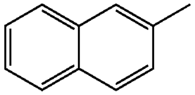 | H | H | 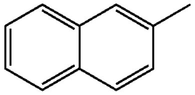 | H | H |
| A-67 | H | 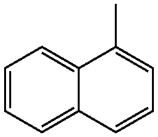 | H | H | 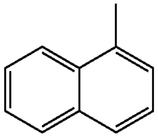 | H | H |
| A-68 | H | 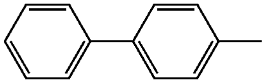 | H | H | 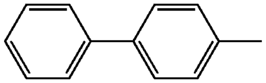 | H | H |
| A-69 | H | 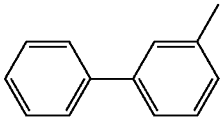 | H | H | 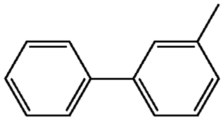 | H | H |
| A-70 | H | 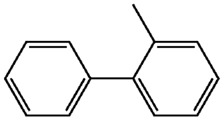 | H | H | 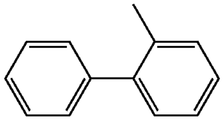 | H | H |

-continued
| | | | | | | | |
|---|---|---|---|---|---|---|---|
| A-71 | H | H | 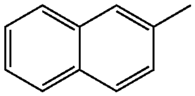 | 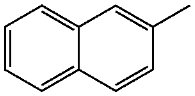 | H | H | H |
| A-72 | H | H | 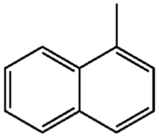 | 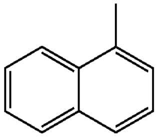 | H | H | H |
| A-73 | H | H | 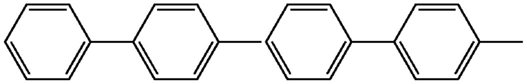 | | H | H | H |
| A-74 | H | H | 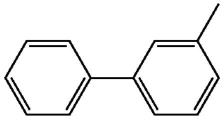 | 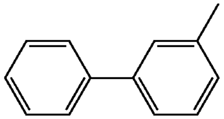 | H | H | H |
| A-75 | H | H | 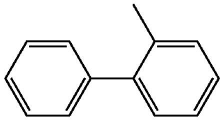 | 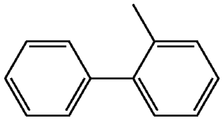 | H | H | H |
| A-76 | 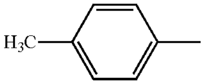 | H | H | H | H | 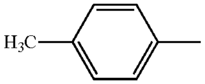 | H |
| A-77 | 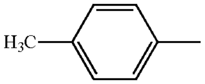 | Ph | H | H | Ph | 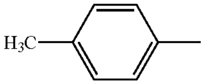 | H |
| A-78 | 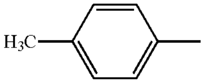 | H | Ph | Ph | H | 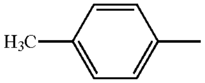 | H |
| A-79 | 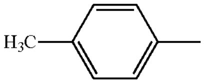 | H | Ph | H | H | 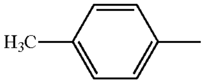 | H |

-continued
| | | | | | | | |
|---|---|---|---|---|---|---|---|
| A-80 | 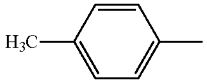 | H | H | H | H | 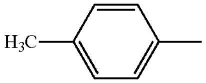 | Ph |
| A-81 | 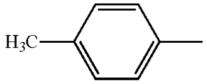 | Me | H | H | Me | 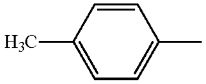 | H |
| A-82 | 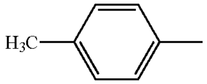 | H | Me | Me | H | 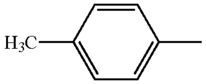 | H |
| A-83 | 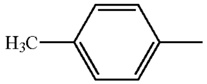 | H | H | H | H | 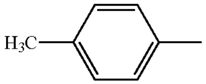 | Me |
| A-84 | 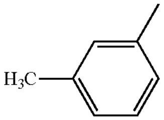 | H | H | H | H | 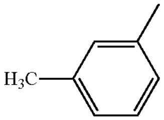 | H |
| A-85 | 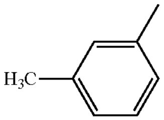 | Ph | H | H | Ph | 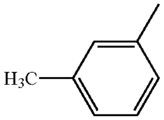 | H |
| A-86 | 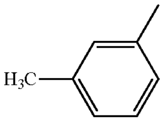 | H | Ph | Ph | H | 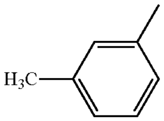 | H |
| A-87 | 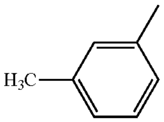 | H | Ph | H | H | 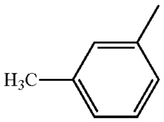 | H |
| A-88 | 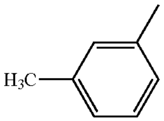 | H | H | H | H | 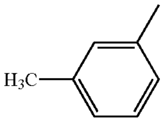 | Ph |

-continued
| | | | | | | | |
|---|---|---|---|---|---|---|---|
| A-89 | 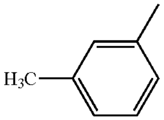 | Me | H | H | Me | 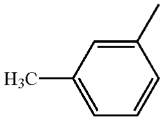 | H |
| A-90 | 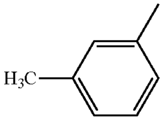 | H | Me | Me | H | 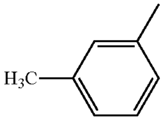 | H |
| A-91 | 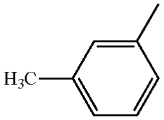 | H | H | H | H | 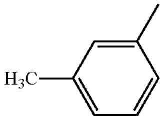 | Me |
| A-92 | 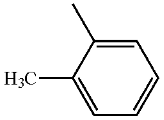 | H | H | H | H | 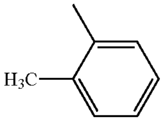 | H |
| A-93 | 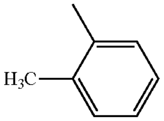 | Ph | H | H | Ph | 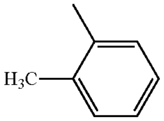 | H |
| A-94 | 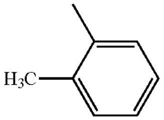 | H | Ph | Ph | H | 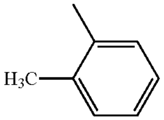 | H |
| A-96 | 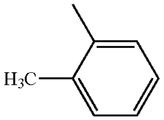 | H | Ph | H | H | 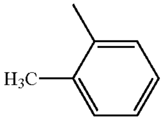 | H |

-continued
| | | | | | | | |
|---|---|---|---|---|---|---|---|
| A-96 | 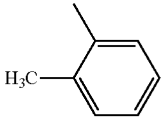 | H | H | H | H | 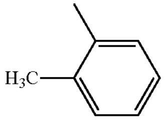 | Ph |
| A-97 | 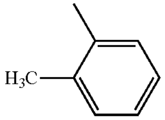 | Me | H | H | Me | 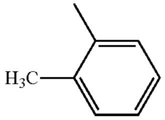 | H |
| A-98 | 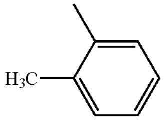 | H | Me | Me | H | 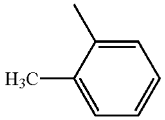 | H |
| A-99 | 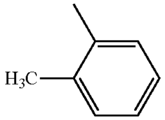 | H | H | H | H | 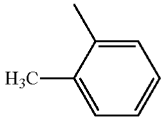 | Me |
| 100 | 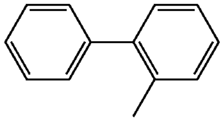 | H | H | H | H | 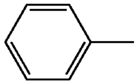 | H |
| 101 | 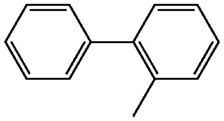 | Ph | H | H | Ph | 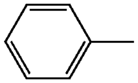 | H |
| 102 | 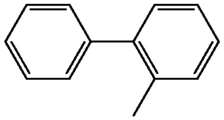 | H | Ph | Ph | H | 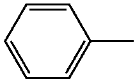 | H |
| 103 | 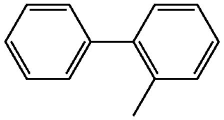 | H | Ph | H | H | 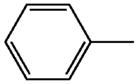 | H |

-continued
| | | | | | | | |
|---|---|---|---|---|---|---|---|
| 104 | 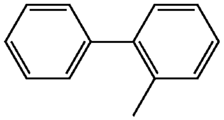 | H | H | H | H | 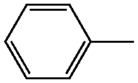 | Ph |
| 105 | 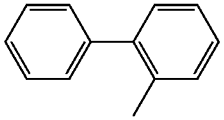 | Me | H | H | Me | 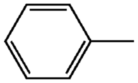 | H |
| 106 | 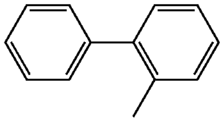 | H | Me | Me | H | 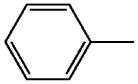 | H |
| 107 | 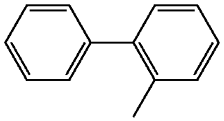 | H | H | H | H | 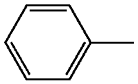 | Me |
| 108 | 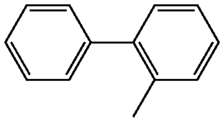 | H | H | H | H | 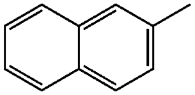 | H |
| 109 | 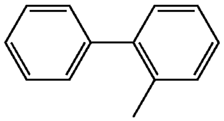 | Ph | H | H | Ph | 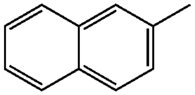 | H |
| 110 | 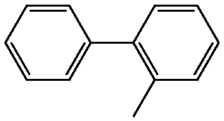 | H | Ph | Ph | H | 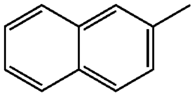 | H |

-continued
| | | | | | | | |
|---|---|---|---|---|---|---|---|
| 111 | 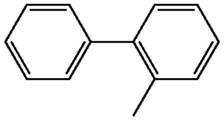 | H | Ph | H | H | 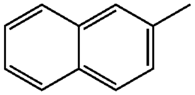 | H |
| 112 | 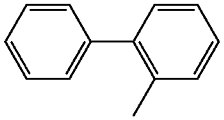 | H | H | H | H | 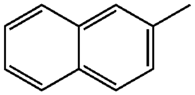 | Ph |
| 113 | 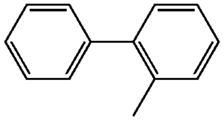 | Me | H | H | Me | 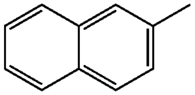 | H |
| 114 | 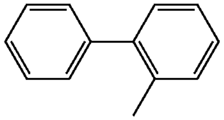 | H | Me | Me | H | 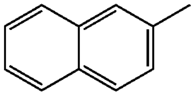 | H |
| 115 | 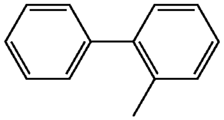 | H | H | H | H | 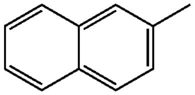 | Me |
| 116 | 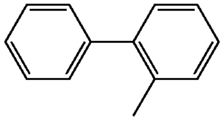 | H | H | H | H | 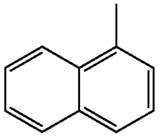 | H |
| 117 | 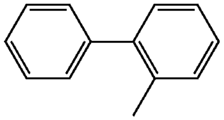 | Ph | H | H | Ph | 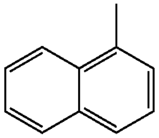 | H |

-continued
| | | | | | | | |
|---|---|---|---|---|---|---|---|
| 118 | 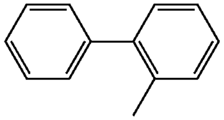 | H | Ph | Ph | H | 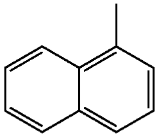 | H |
| 119 | 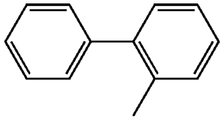 | H | Ph | H | H | 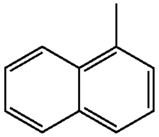 | H |
| 120 | 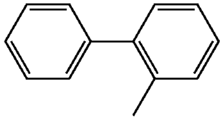 | H | H | H | H | 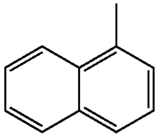 | Ph |
| 121 | 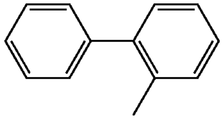 | Me | H | H | Me | 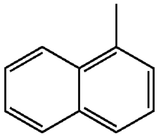 | H |
| 122 | 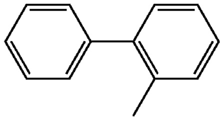 | H | Me | Me | H | 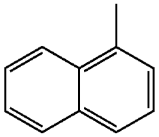 | H |
| 123 | 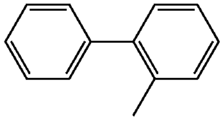 | H | H | H | H | 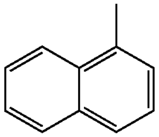 | Me |
| 124 | 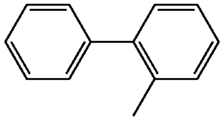 | H | H | H | H | 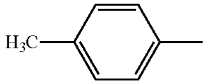 | H |

-continued
| | | | | | | | |
|---|---|---|---|---|---|---|---|
| 125 | 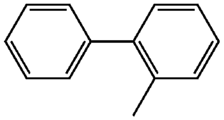 | Ph | H | H | Ph | 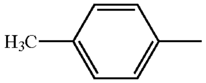 | H |
| 126 | 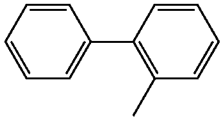 | H | Ph | Ph | H | 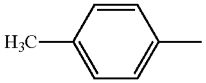 | H |
| 127 | 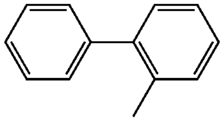 | H | Ph | H | H | 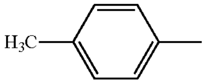 | H |
| 128 | 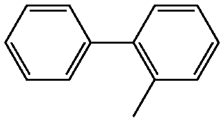 | H | H | H | H | 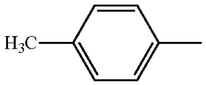 | Ph |
| 129 | 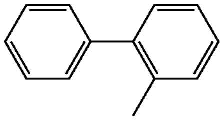 | Me | H | H | Me | 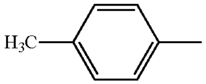 | H |
| 130 | 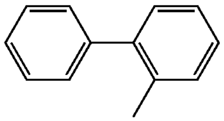 | H | Me | Me | H | 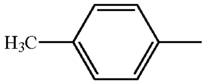 | H |

-continued
| | | | | | | | |
|---|---|---|---|---|---|---|---|
| 131 | 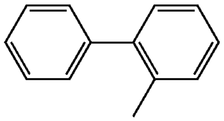 | H | H | H | H | 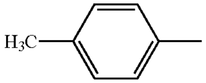 | Me |
| 132 | 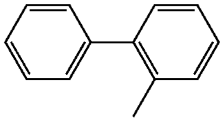 | H | H | H | H | 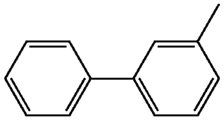 | H |
| 133 | 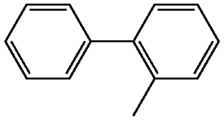 | Ph | H | H | Ph | 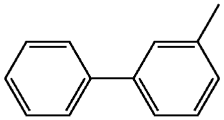 | H |
| 134 | 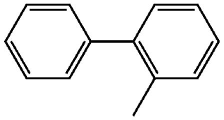 | H | Ph | Ph | H | 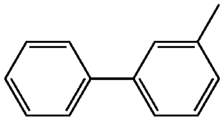 | H |
| 135 | 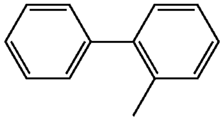 | H | Ph | H | H | 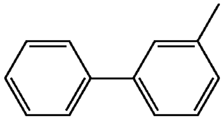 | H |
| 136 | 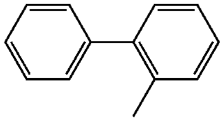 | H | H | H | H | 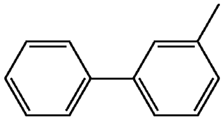 | Ph |

-continued
| | | | | | | | |
|---|---|---|---|---|---|---|---|
| 137 | 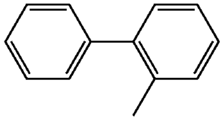 | Me | H | H | Me | 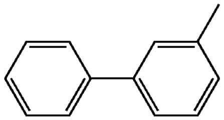 | H |
| 138 | 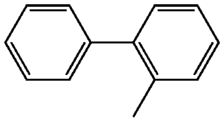 | H | Me | Me | H | 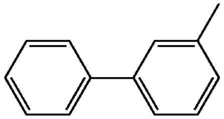 | H |
| 139 | 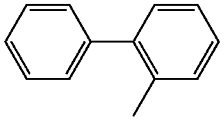 | H | H | H | H | 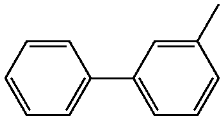 | Me |
| 140 | 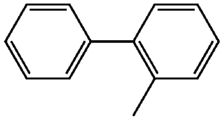 | H | H | H | H | 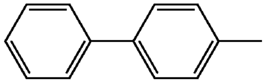 | H |
| 141 | 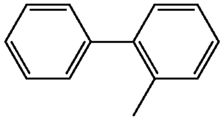 | Ph | H | H | Ph | 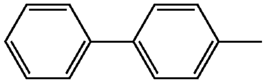 | H |
| 142 | 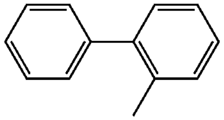 | H | Ph | Ph | H | 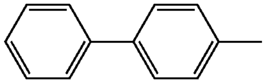 | H |

-continued
| | | | | | | |
|---|---|---|---|---|---|---|
| 143 | 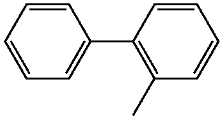 | H | Ph | H | H | 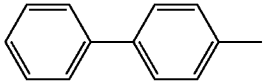 H |
| 144 | 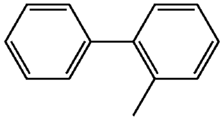 | H | H | H | H | 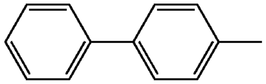 Ph |
| 145 | 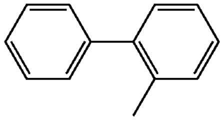 | Me | H | H | Me | 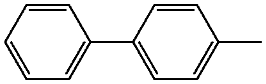 H |
| 146 | 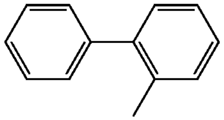 | H | Me | Me | H | 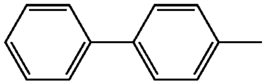 H |
| 147 | 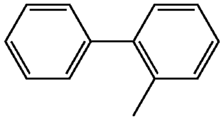 | H | H | H | H | 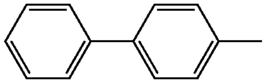 Me |

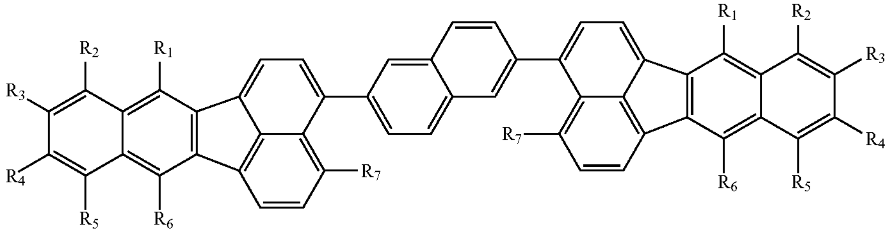
TypeB
| | $R_1$ | $R_2$ | $R_3$ | $R_4$ | $R_5$ | $R_6$ | $R_7$ |
|---|---|---|---|---|---|---|---|
| B-1 | H | H | H | H | H | H | H |
| B-2 | Ph | H | H | H | H | Ph | H |
| B-3 | Ph | Ph | H | H | Ph | Ph | H |
| B-4 | Ph | H | Ph | Ph | H | Ph | H |
| B-5 | Ph | H | Ph | H | H | Ph | H |
| B-6 | Ph | H | H | H | H | Ph | Ph |
| B-7 | Ph | Me | H | H | Me | Ph | H |
| B-8 | Ph | H | Me | Me | H | Ph | H |
| B-9 | Ph | H | H | H | H | Ph | Me |
| B-10 | 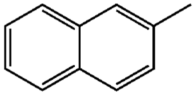 | H | H | H | H | 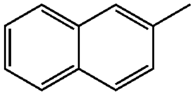 | H |
| B-11 | 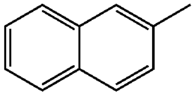 | Ph | H | H | Ph | 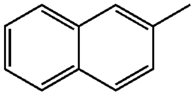 | H |
| B-12 | 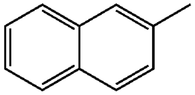 | H | Ph | Ph | H | 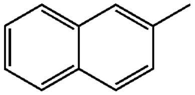 | H |
| B-13 | 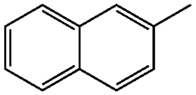 | H | Ph | H | H | 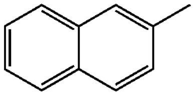 | H |
| B-14 | 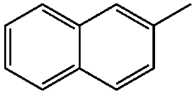 | H | H | H | H | 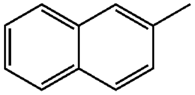 | Ph |

-continued
| | | | | | | | |
|---|---|---|---|---|---|---|---|
| B-15 | 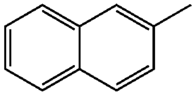 | Me | H | H | Me | 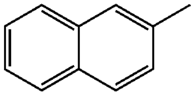 | H |
| B-16 | 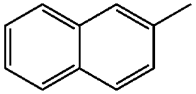 | H | Me | Me | H | 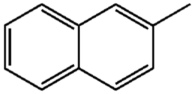 | H |
| B-17 | 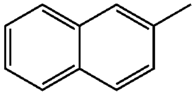 | H | H | H | H | 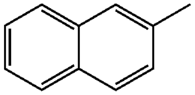 | Me |
| B-18 | 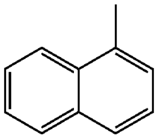 | H | H | H | H | 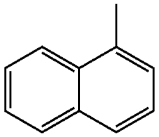 | H |
| B-19 | 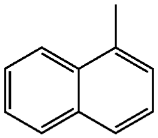 | Ph | H | H | Ph | 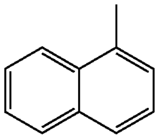 | H |
| B-20 | 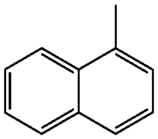 | H | Ph | Ph | H | 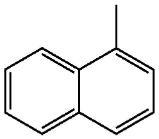 | H |
| B-21 | 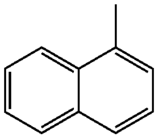 | H | Ph | H | H | 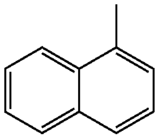 | H |

-continued
| | | | | | | | |
|---|---|---|---|---|---|---|---|
| B-22 | 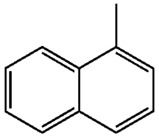 | H | H | H | H | 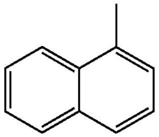 | Ph |
| B-23 | 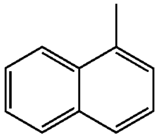 | Me | H | H | Me | 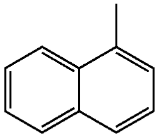 | H |
| B-24 | 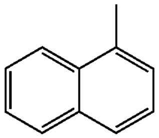 | H | Me | Me | H | 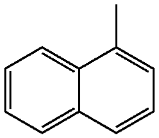 | H |
| B-25 | 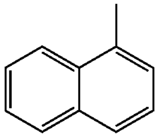 | H | H | H | H | 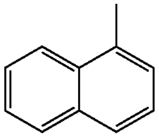 | Me |
| B-26 | 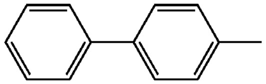 | H | H | H | H | 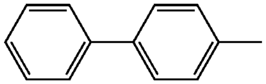 | H |
| B-27 | 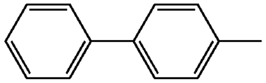 | Ph | H | H | Ph | 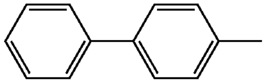 | H |
| B-28 | 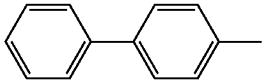 | H | Ph | Ph | H | 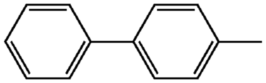 | H |
| B-29 | 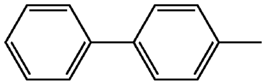 | H | Ph | H | H | 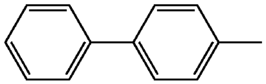 | H |
| B-30 | 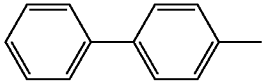 | H | H | H | H | 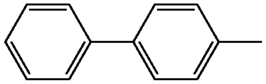 | Ph |

-continued
| | | | | | | | |
|---|---|---|---|---|---|---|---|
| B-31 | 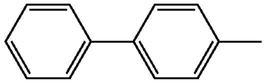 | Me | H | H | Me | 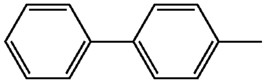 | H |
| B-32 | 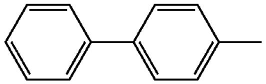 | H | Me | Me | H | 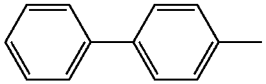 | H |
| B-33 | 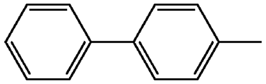 | H | H | H | H | 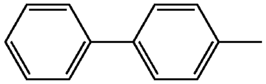 | Me |
| B-34 | 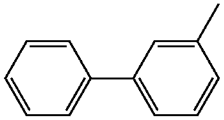 | H | H | H | H | 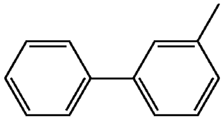 | H |
| B-35 | 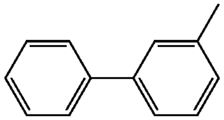 | Ph | H | H | Ph | 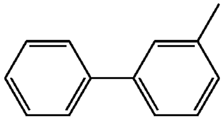 | H |
| B-36 | 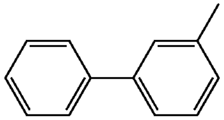 | H | Ph | Ph | H | 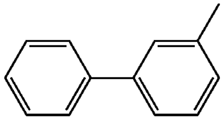 | H |
| B-37 | 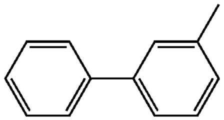 | H | Ph | H | H | 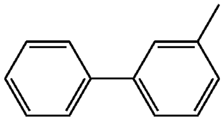 | H |
| B-38 | 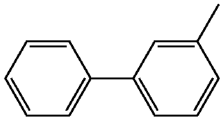 | H | H | H | H | 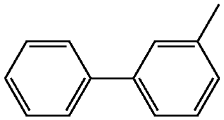 | Ph |

-continued
| | | | | | | | |
|---|---|---|---|---|---|---|---|
| B-39 | 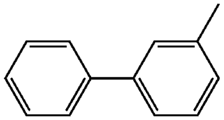 | Me | H | H | Me | 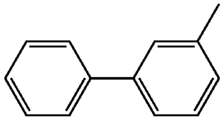 | H |
| B-40 | 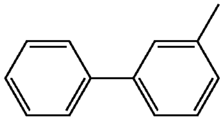 | H | Me | Me | H | 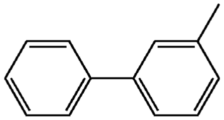 | H |
| B-41 | 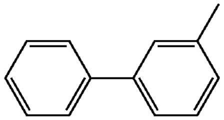 | H | H | H | H | 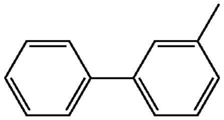 | Me |
| B-42 | 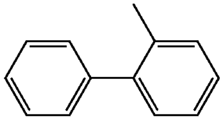 | H | H | H | H | 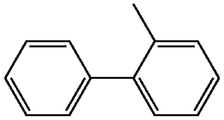 | H |
| B-43 | 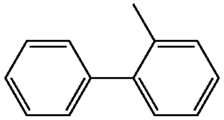 | Ph | H | H | Ph | 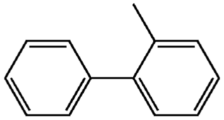 | H |
| B-44 | 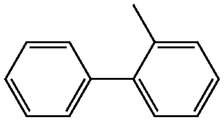 | H | Ph | Ph | H | 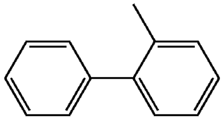 | H |
| B-45 | 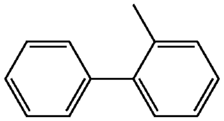 | H | Ph | H | H | 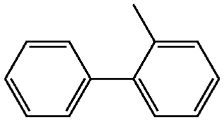 | H |
| B-46 | 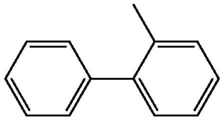 | H | H | H | H | 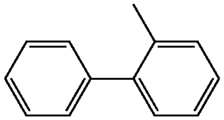 | Ph |

-continued
| | | | | | | | |
|---|---|---|---|---|---|---|---|
| B-47 | 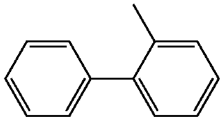 | Me | H | H | Me | 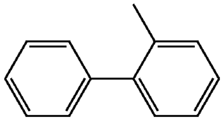 | H |
| B-48 | 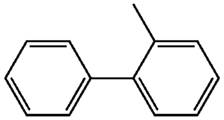 | H | Me | Me | H | 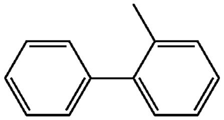 | H |
| B-49 | 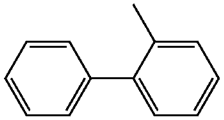 | H | H | H | H | 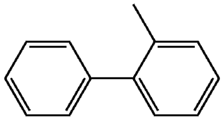 | Me |
| B-50 | Ph | H | H | H | H | 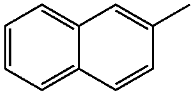 | H |
| B-51 | Ph | H | H | H | H | 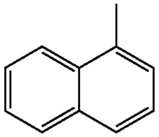 | H |
| B-52 | Ph | H | H | H | H | 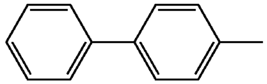 | H |
| B-53 | Ph | H | H | H | H | 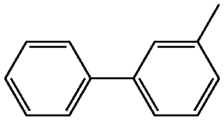 | H |
| B-54 | Ph | H | H | H | H | 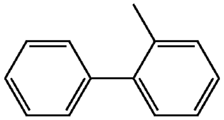 | H |

-continued
| | | | | | | | |
|---|---|---|---|---|---|---|---|
| B-55 | 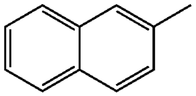 | H | H | H | H | 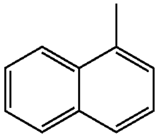 | H |
| B-56 | 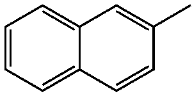 | H | H | H | H | 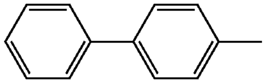 | H |
| B-57 | 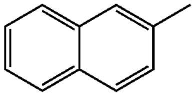 | H | H | H | H | 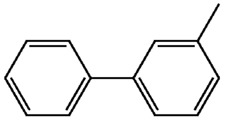 | H |
| B-58 | 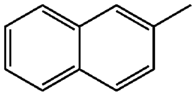 | H | H | H | H | 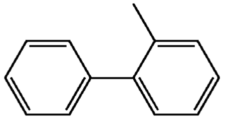 | H |
| B-59 | 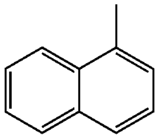 | H | H | H | H | 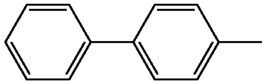 | H |
| B-60 | 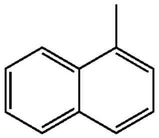 | H | H | H | H | 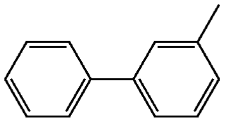 | H |
| B-61 | 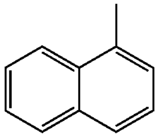 | H | H | H | H | 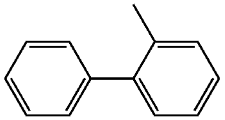 | H |

-continued
| | | | | | | | |
|---|---|---|---|---|---|---|---|
| B-62 | 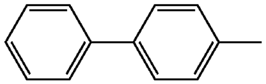 | H | H | H | H | 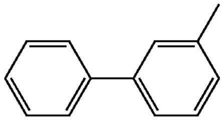 | H |
| B-63 | 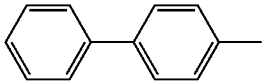 | H | H | H | H | 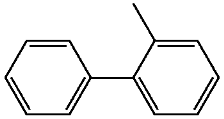 | H |
| B-64 | 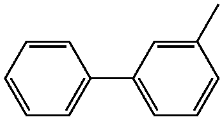 | H | H | H | H | 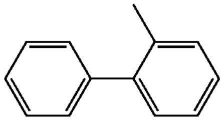 | H |
| B-65 | H | Ph | H | H | Ph | H | H |
| B-66 | H | 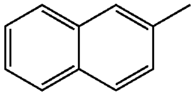 | H | H | 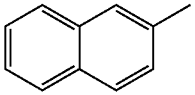 | H | H |
| B-67 | H | 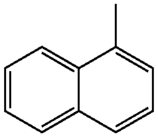 | H | H | 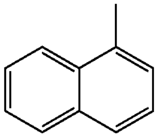 | H | H |
| B-68 | H | 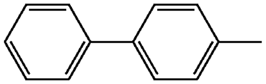 | H | H | 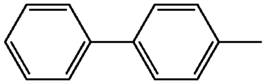 | H | H |
| B-69 | H | 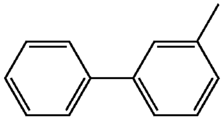 | H | H | 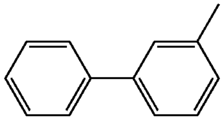 | H | H |
| B-70 | H | 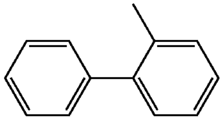 | H | H | 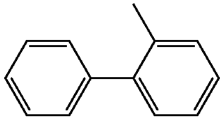 | H | H |

-continued
| | | | | | | | |
|---|---|---|---|---|---|---|---|
| B-71 | H | H | 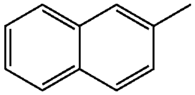 | 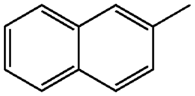 | H | H | H |
| B-72 | H | H | 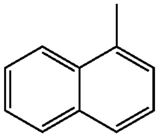 | 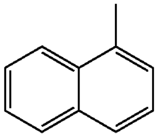 | H | H | H |
| B-73 | H | H | 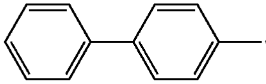 | 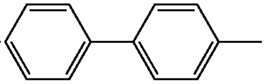 | H | H | H |
| B-74 | H | H | 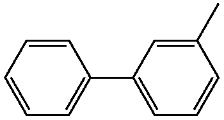 | 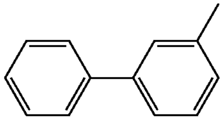 | H | H | H |
| B-75 | H | H | 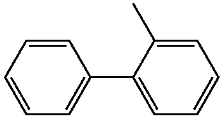 | 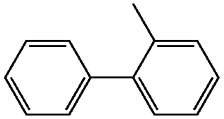 | H | H | H |
| B-76 | 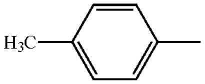 | H | H | H | H | 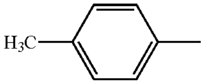 | H |
| B-77 | 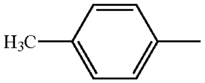 | Ph | H | H | Ph | 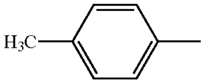 | H |
| B-78 | 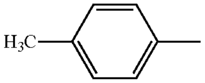 | H | Ph | Ph | H | 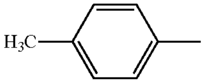 | H |
| B-79 | 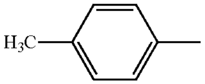 | H | Ph | H | H | 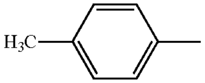 | H |

-continued
| | | | | | | | |
|---|---|---|---|---|---|---|---|
| B-80 | 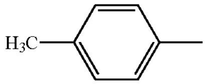 | H | H | H | H | 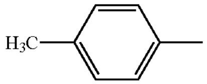 | Ph |
| B-81 | 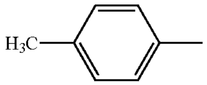 | Me | H | H | Me | 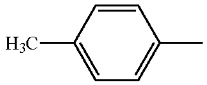 | H |
| B-82 | 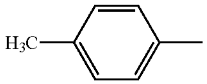 | H | Me | Me | H | 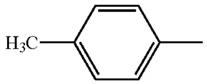 | H |
| B-83 | 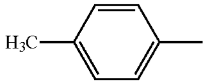 | H | H | H | H | 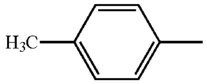 | Me |
| B-84 | 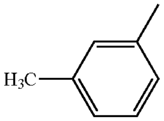 | H | H | H | H | 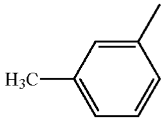 | H |
| B-85 | 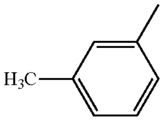 | Ph | H | H | Ph | 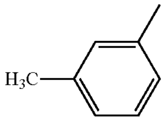 | H |
| B-86 | 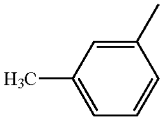 | H | Ph | Ph | H | 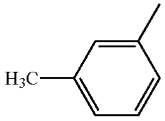 | H |
| B-87 | 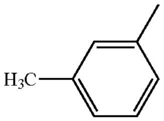 | H | Ph | H | H | 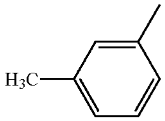 | H |
| B-88 | 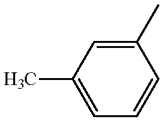 | H | H | H | H | 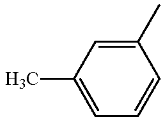 | Ph |

-continued
| | | | | | | | |
|---|---|---|---|---|---|---|---|
| B-89 | 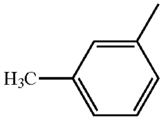 | Me | H | H | Me | 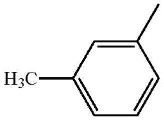 | H |
| B-90 | 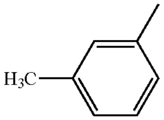 | H | Me | Me | H | 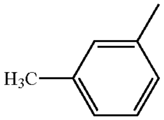 | H |
| B-91 | 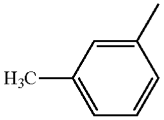 | H | H | H | H | 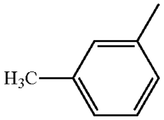 | Me |
| B-92 | 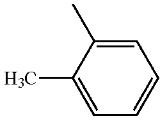 | H | H | H | H | 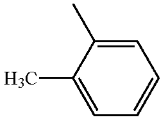 | H |
| B-93 | 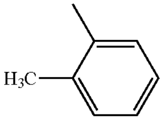 | Ph | H | H | Ph | 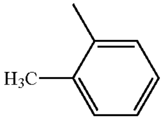 | H |
| B-94 | 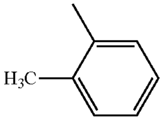 | H | Ph | Ph | H | 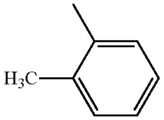 | H |
| B-96 | 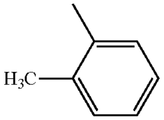 | H | Ph | H | H | 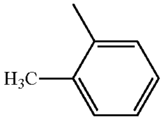 | H |
| B-96 | 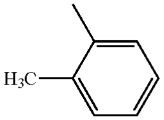 | H | H | H | H | 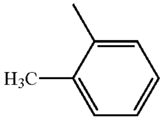 | Ph |

-continued
| | | | | | | | |
|---|---|---|---|---|---|---|---|
| B-97 | 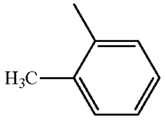 | Me | H | H | Me | 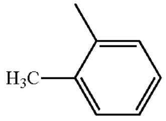 | H |
| B-98 | 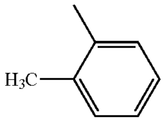 | H | Me | Me | H | 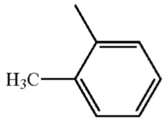 | H |
| B-99 | 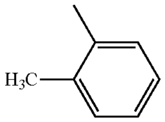 | H | H | H | H | 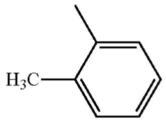 | Me |
| 100 | 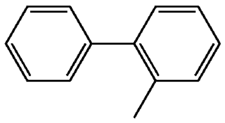 | H | H | H | H | 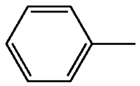 | H |
| 101 | 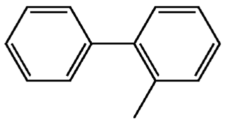 | Ph | H | H | Ph | 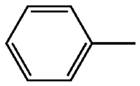 | H |
| 102 | 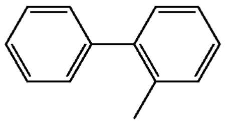 | H | Ph | Ph | H | 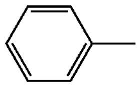 | H |
| 103 | 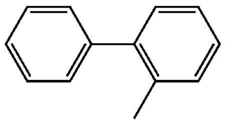 | H | Ph | H | H | 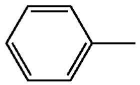 | H |
| 104 | 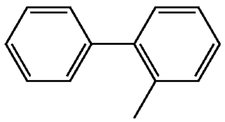 | H | H | H | H | 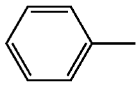 | Ph |

-continued
| | | | | | | | |
|---|---|---|---|---|---|---|---|
| 105 | 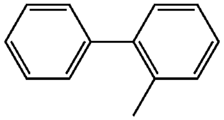 | Me | H | H | Me | 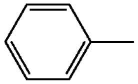 | H |
| 106 | 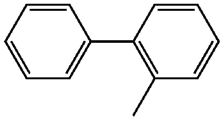 | H | Me | Me | H | 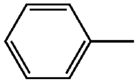 | H |
| 107 | 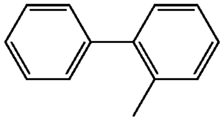 | H | H | H | H | 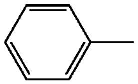 | Me |
| 108 | 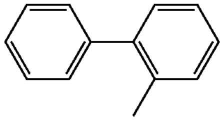 | H | H | H | H | 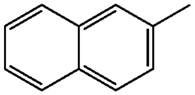 | H |
| 109 | 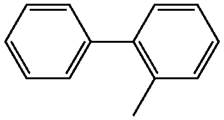 | Ph | H | H | Ph | 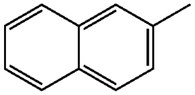 | H |
| 110 | 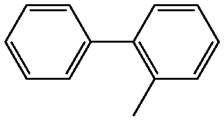 | H | Ph | Ph | H | 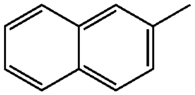 | H |
| 111 | 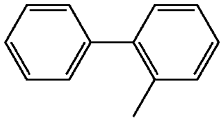 | H | Ph | H | H | 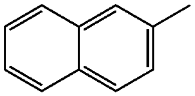 | H |
| 112 | 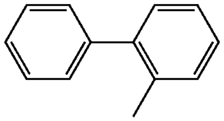 | H | H | H | H | 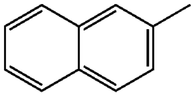 | Ph |

-continued
| | | | | | | | |
|---|---|---|---|---|---|---|---|
| 113 | 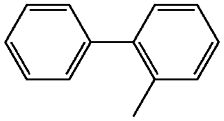 | Me | H | H | Me | 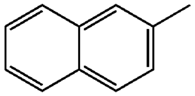 | H |
| 114 | 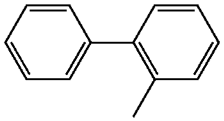 | H | Me | Me | H | 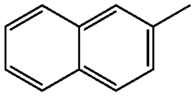 | H |
| 115 | 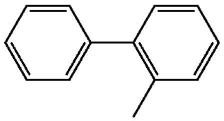 | H | H | H | H | 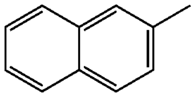 | Me |
| 116 | 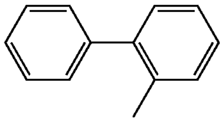 | H | H | H | H | 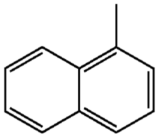 | H |
| 117 | 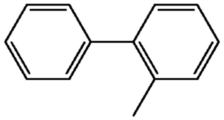 | Ph | H | H | Ph | 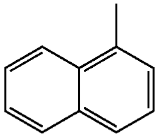 | H |
| 118 | 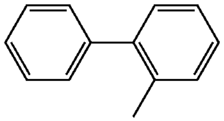 | H | Ph | Ph | H | 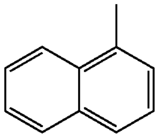 | H |
| 119 | 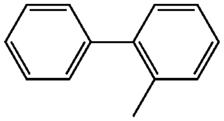 | H | Ph | H | H | 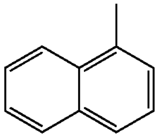 | H |

-continued
| | | | | | | | |
|---|---|---|---|---|---|---|---|
| 120 | 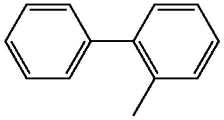 | H | H | H | H | 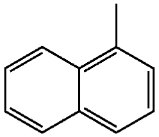 | Ph |
| 121 | 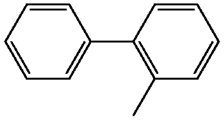 | Me | H | H | Me | 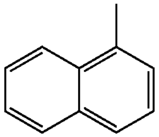 | H |
| 122 | 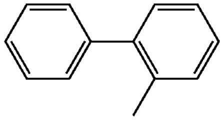 | H | Me | Me | H | 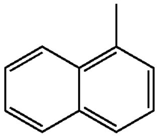 | H |
| 123 | 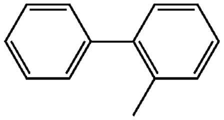 | H | H | H | H | 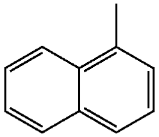 | Me |
| 124 | 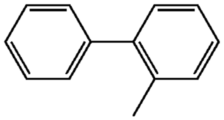 | H | H | H | H | 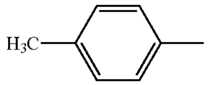 | H |
| 125 | 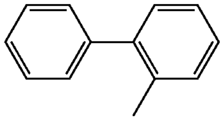 | Ph | H | H | Ph | 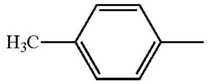 | H |
| 126 | 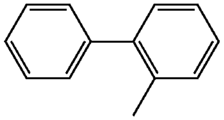 | H | Ph | Ph | H | 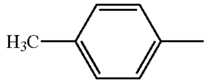 | H |

-continued
| | | | | | | | |
|---|---|---|---|---|---|---|---|
| 127 | 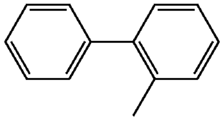 | H | Ph | H | H | 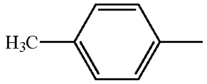 | H |
| 128 | 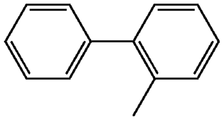 | H | H | H | H | 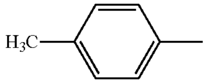 | Ph |
| 129 | 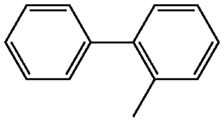 | Me | H | H | Me | 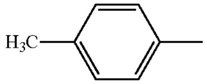 | H |
| 130 | 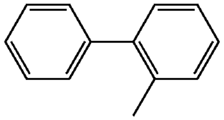 | H | Me | Me | H | 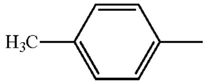 | H |
| 131 | 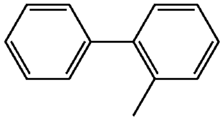 | H | H | H | H | 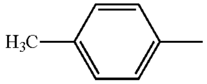 | Me |
| 132 | 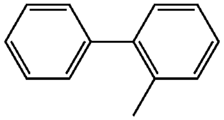 | H | H | H | H | 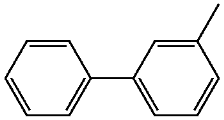 | H |
| 133 | 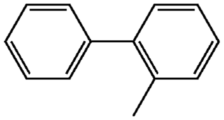 | Ph | H | H | Ph | 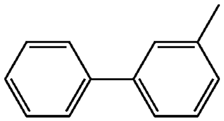 | H |
| 134 | 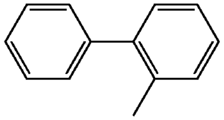 | H | Ph | Ph | H | 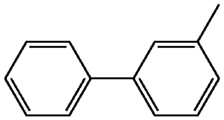 | H |

-continued
| | | | | | | | |
|---|---|---|---|---|---|---|---|
| 135 | 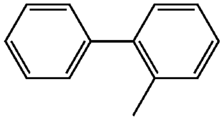 | H | Ph | H | H | 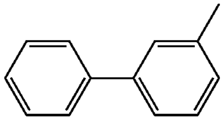 | H |
| 136 | 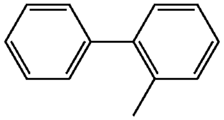 | H | H | H | H | 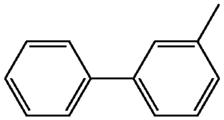 | Ph |
| 137 | 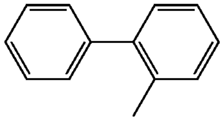 | Me | H | H | Me | 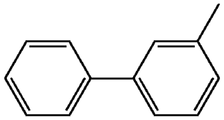 | H |
| 138 | 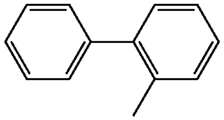 | H | Me | Me | H | 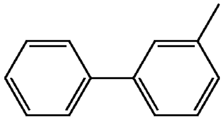 | H |
| 139 | 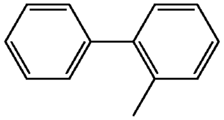 | H | H | H | H | 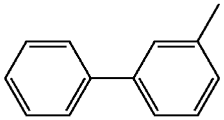 | Me |
| 140 | 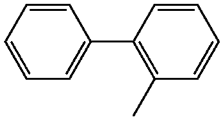 | H | H | H | H | 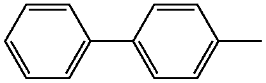 | H |
| 141 | 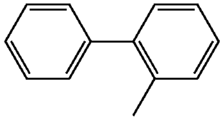 | Ph | H | H | Ph | 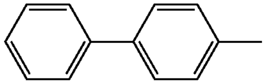 | H |

-continued
| | | | | | | |
|---|---|---|---|---|---|---|
| 142 | 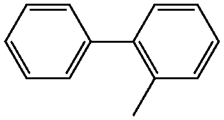 | H | Ph | Ph | H | 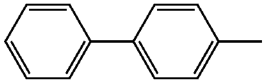 H |
| 143 | 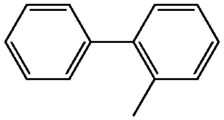 | H | Ph | H | H | 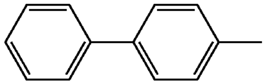 H |
| 144 | 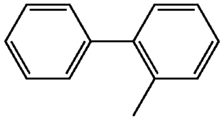 | H | H | H | H | 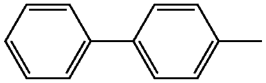 Ph |
| 145 | 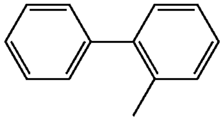 | Me | H | H | Me | 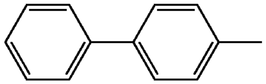 H |
| 146 | 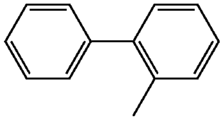 | H | Me | Me | H | 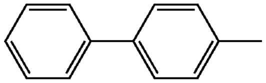 H |
| 147 | 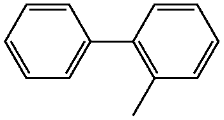 | H | H | H | H | 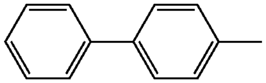 Me |

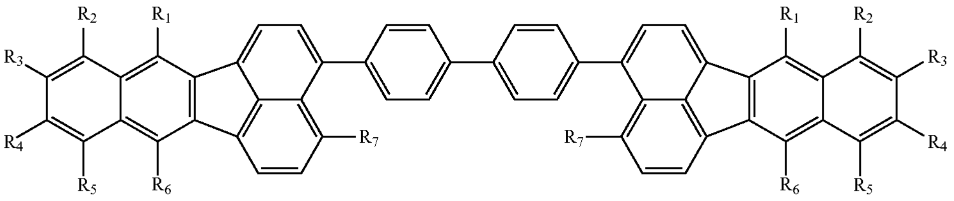
TypeC
| | $R_1$ | $R_2$ | $R_3$ | $R_4$ | $R_5$ | $R_6$ | $R_7$ |
|---|---|---|---|---|---|---|---|
| C-1 | H | H | H | H | H | H | H |
| C-2 | Ph | H | H | H | H | Ph | H |
| C-3 | Ph | Ph | H | H | Ph | Ph | H |
| C-4 | Ph | H | Ph | Ph | H | Ph | H |
| C-5 | Ph | H | Ph | H | H | Ph | H |
| C-6 | Ph | H | H | H | H | Ph | Ph |
| C-7 | Ph | Me | H | H | Me | Ph | H |
| C-8 | Ph | H | Me | Me | H | Ph | H |
| C-9 | Ph | H | H | H | H | Ph | Me |
| C-10 | 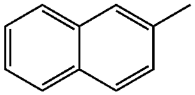 | H | H | H | H | 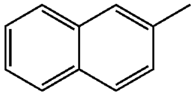 | H |
| C-11 | 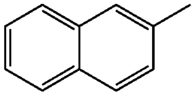 | Ph | H | H | Ph | 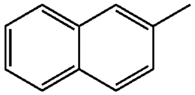 | H |
| C-12 | 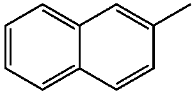 | H | Ph | Ph | H | 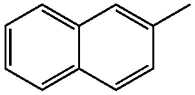 | H |
| C-13 | 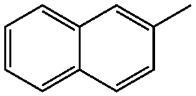 | H | Ph | H | H | 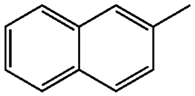 | H |
| C-14 | 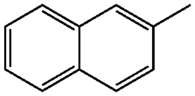 | H | H | H | H | 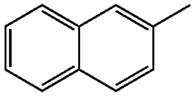 | Ph |

-continued
| | | | | | | | |
|---|---|---|---|---|---|---|---|
| C-15 | 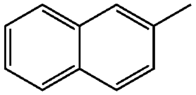 | Me | H | H | Me | 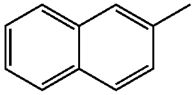 | H |
| C-16 | 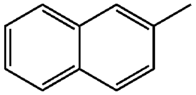 | H | Me | Me | H | 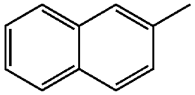 | H |
| C-17 | 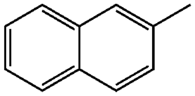 | H | H | H | H | 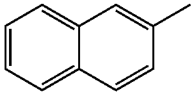 | Me |
| C-18 | 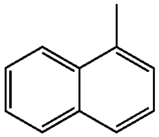 | H | H | H | H | 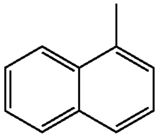 | H |
| C-19 | 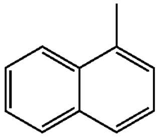 | Ph | H | H | Ph | 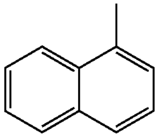 | H |
| C-20 | 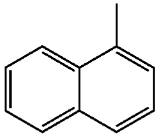 | H | Ph | Ph | H | 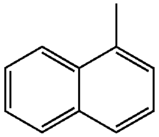 | H |
| C-21 | 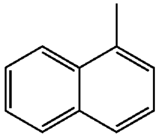 | H | Ph | H | H | 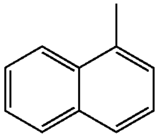 | H |

-continued
| | | | | | | | |
|---|---|---|---|---|---|---|---|
| C-22 | 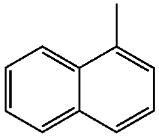 | H | H | H | H | 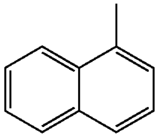 | Ph |
| C-23 | 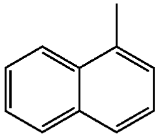 | Me | H | H | Me | 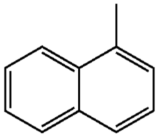 | H |
| C-24 | 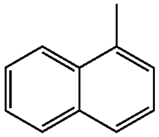 | H | Me | Me | H | 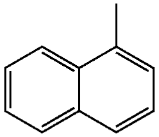 | H |
| C-25 | 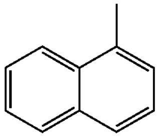 | H | H | H | H | 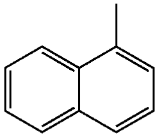 | Me |
| C-26 | 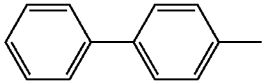 | H | H | H | H | 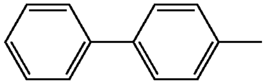 | H |
| C-27 | 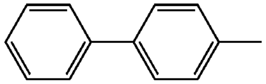 | Ph | H | H | Ph | 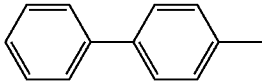 | H |
| C-28 | 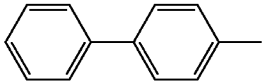 | H | Ph | Ph | H | 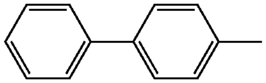 | H |
| C-29 | 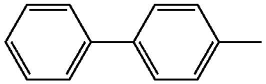 | H | Ph | H | H | 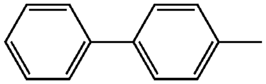 | H |

-continued
| | | | | | | | |
|---|---|---|---|---|---|---|---|
| C-30 | 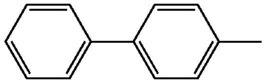 | H | H | H | H | 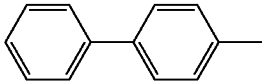 | Ph |
| C-31 | 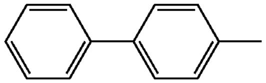 | Me | H | H | Me | 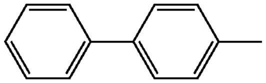 | H |
| C-32 | 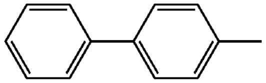 | H | Me | Me | H | 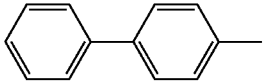 | H |
| C-33 | 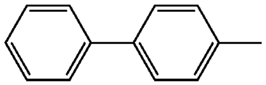 | H | H | H | H | 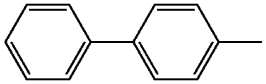 | Me |
| C-34 | 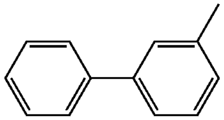 | H | H | H | H | 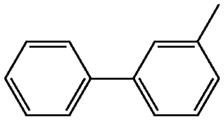 | H |
| C-35 | 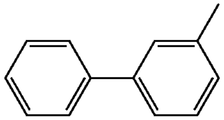 | Ph | H | H | Ph | 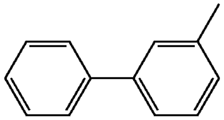 | H |
| C-36 | 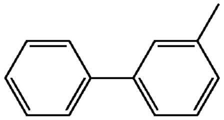 | H | Ph | Ph | H | 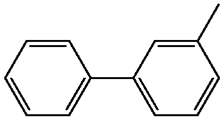 | H |
| C-37 | 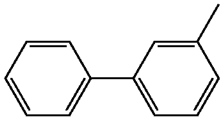 | H | Ph | H | H | 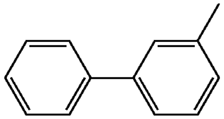 | H |
| C-38 | 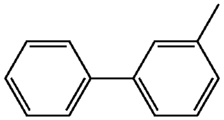 | H | H | H | H | 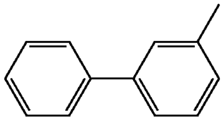 | Ph |

-continued
| | | | | | | | |
|---|---|---|---|---|---|---|---|
| C-39 | 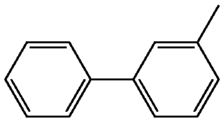 | Me | H | H | Me | 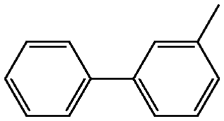 | H |
| C-40 | 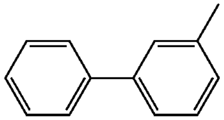 | H | Me | Me | H | 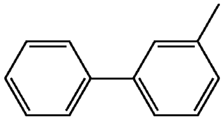 | H |
| C-41 | 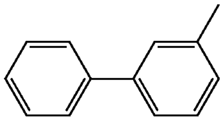 | H | H | H | H | 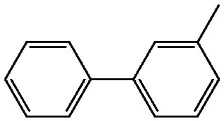 | Me |
| C-42 | 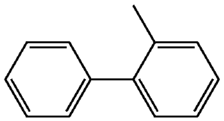 | H | H | H | H | 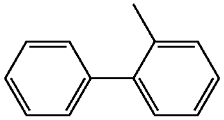 | H |
| C-43 | 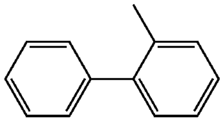 | Ph | H | H | Ph | 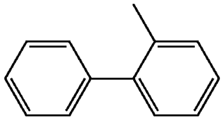 | H |
| C-44 | 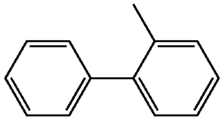 | H | Ph | Ph | H | 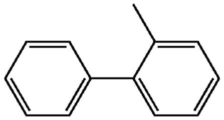 | H |
| C-45 | 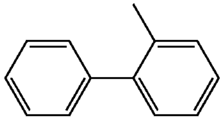 | H | Ph | H | H | 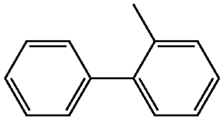 | H |

-continued
| | | | | | | | |
|---|---|---|---|---|---|---|---|
| C-46 | 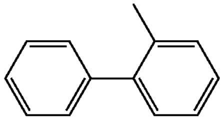 | H | H | H | H | 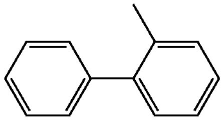 | Ph |
| C-47 | 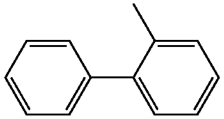 | Me | H | H | Me | 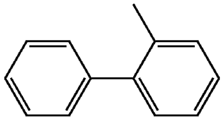 | H |
| C-48 | 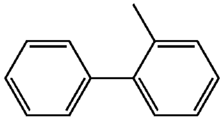 | H | Me | Me | H | 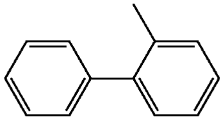 | H |
| C-49 | 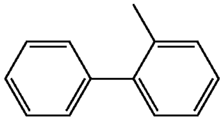 | H | H | H | H | 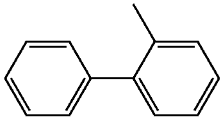 | Me |
| C-50 | Ph | H | H | H | H | 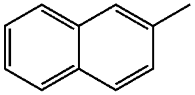 | H |
| C-51 | Ph | H | H | H | H | 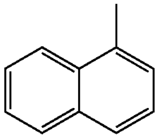 | H |
| C-52 | Ph | H | H | H | H | 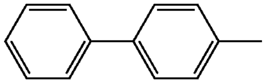 | H |
| C-53 | Ph | H | H | H | H | 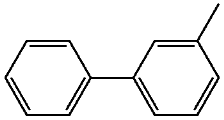 | H |

-continued
| | | | | | | | |
|---|---|---|---|---|---|---|---|
| C-54 | Ph | H | H | H | H | 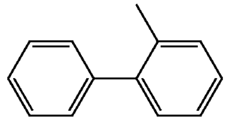 | H |
| C-55 | 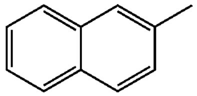 | H | H | H | H | 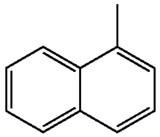 | H |
| C-56 | 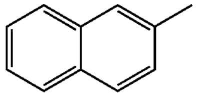 | H | H | H | H | 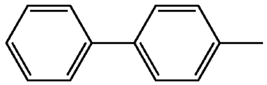 | H |
| C-57 | 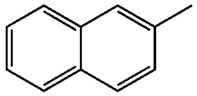 | H | H | H | H | 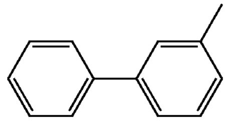 | H |
| C-58 | 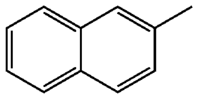 | H | H | H | H | 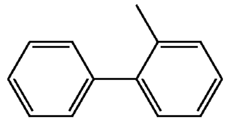 | H |
| C-59 | 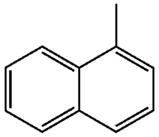 | H | H | H | H | 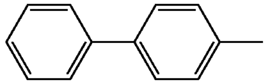 | H |
| C-60 | 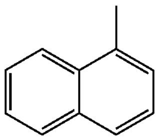 | H | H | H | H | 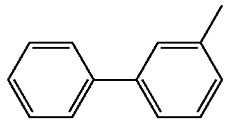 | H |

-continued
| | | | | | | | |
|---|---|---|---|---|---|---|---|
| C-61 | 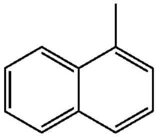 | H | H | H | H | 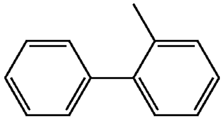 | H |
| C-62 | 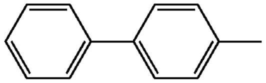 | H | H | H | H | 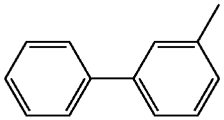 | H |
| C-63 | 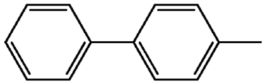 | H | H | H | H | 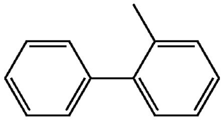 | H |
| C-64 | 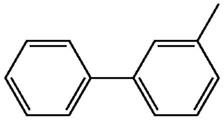 | H | H | H | H | 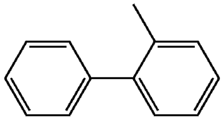 | H |
| C-65 | H | Ph | H | H | Ph | H | H |
| C-66 | H | 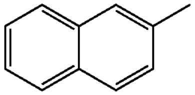 | H | H | 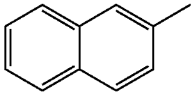 | H | H |
| C-67 | H | 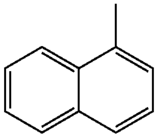 | H | H | 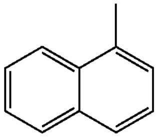 | H | H |
| C-68 | H | 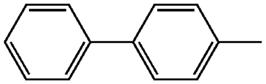 | H | H | 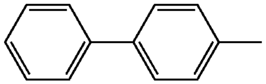 | H | H |
| C-69 | H | 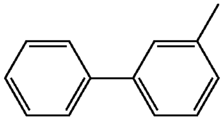 | H | H | 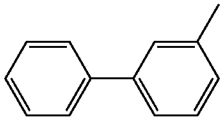 | H | H |

-continued
| | | | | | | | |
|---|---|---|---|---|---|---|---|
| C-70 | H | 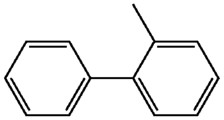 | H | H | 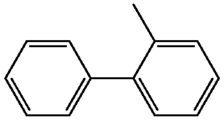 | H | H |
| C-71 | H | H | 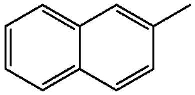 | 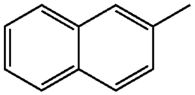 | H | H | H |
| C-72 | H | H | 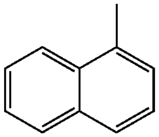 | 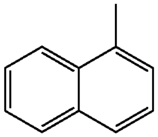 | H | H | H |
| C-73 | H | H | 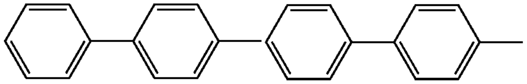 | | H | H | H |
| C-74 | H | H | 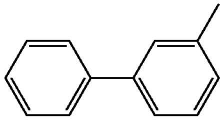 | 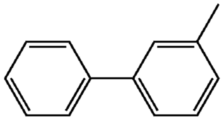 | H | H | H |
| C-75 | H | H | 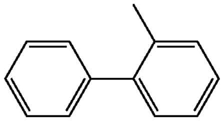 | 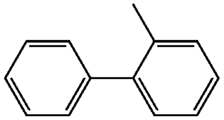 | H | H | H |
| C-76 | 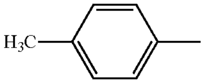 | H | H | H | H | 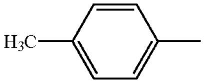 | H |
| C-77 | 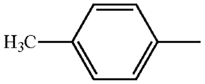 | Ph | H | H | Ph | 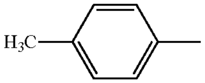 | H |

-continued
| | | | | | | | |
|---|---|---|---|---|---|---|---|
| C-78 | 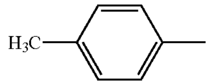 | H | Ph | Ph | H | 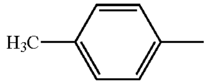 | H |
| C-79 | 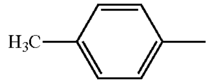 | H | Ph | H | H | 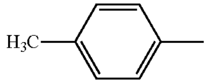 | H |
| C-80 | 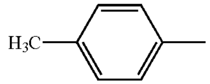 | H | H | H | H | 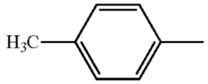 | Ph |
| C-81 | 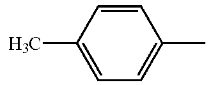 | Me | H | H | Me | 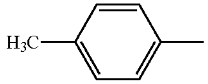 | H |
| C-82 | 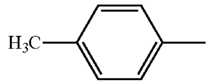 | H | Me | Me | H | 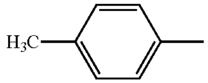 | H |
| C-83 | 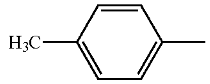 | H | H | H | H | 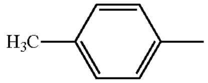 | Me |
| C-84 | 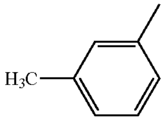 | H | H | H | H | 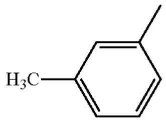 | H |
| C-85 | 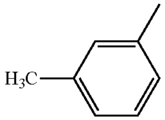 | Ph | H | H | Ph | 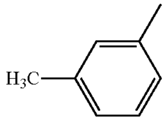 | H |
| C-86 | 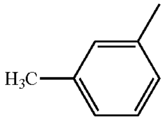 | H | Ph | Ph | H | 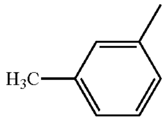 | H |

-continued
| | | | | | | | |
|---|---|---|---|---|---|---|---|
| C-87 | 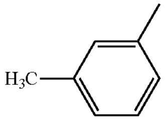 | H | Ph | H | H | 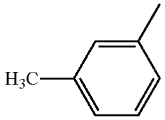 | H |
| C-88 | 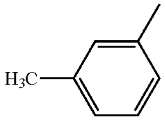 | H | H | H | H | 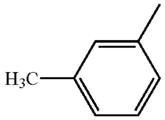 | Ph |
| C-89 | 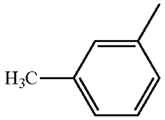 | Me | H | H | Me | 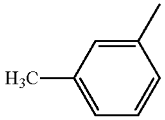 | H |
| C-90 | 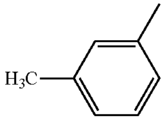 | H | Me | Me | H | 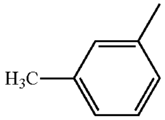 | H |
| C-91 | 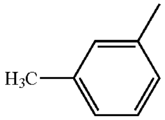 | H | H | H | H | 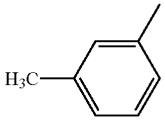 | Me |
| C-92 | 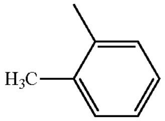 | H | H | H | H | 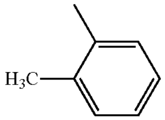 | H |
| C-93 | 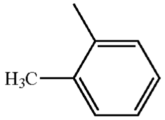 | Ph | H | H | Ph | 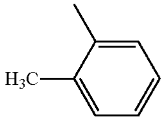 | H |
| C-94 | 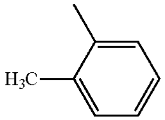 | H | Ph | Ph | H | 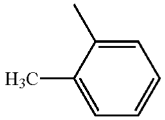 | H |

-continued
| | | | | | | | |
|---|---|---|---|---|---|---|---|
| C-96 | 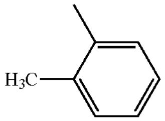 | H | Ph | H | H | 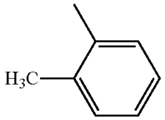 | H |
| C-96 | 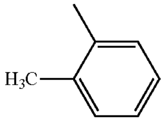 | H | H | H | H | 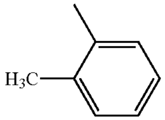 | Ph |
| C-97 | 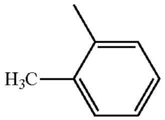 | Me | H | H | Me | 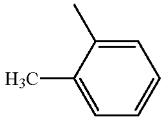 | H |
| C-98 | 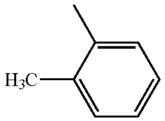 | H | Me | Me | H | 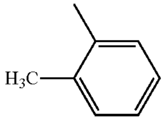 | H |
| C-99 | 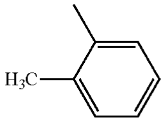 | H | H | H | H | 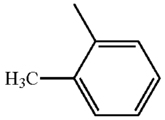 | Me |
| 100 | 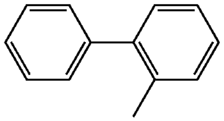 | H | H | H | H | 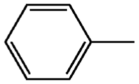 | H |
| 101 | 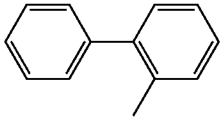 | Ph | H | H | Ph | 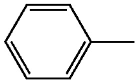 | H |

-continued
| | | | | | | | |
|---|---|---|---|---|---|---|---|
| 102 | 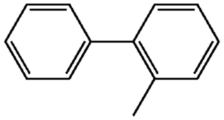 | H | Ph | Ph | H | 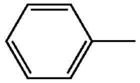 | H |
| 103 | 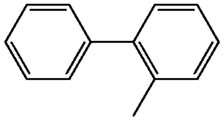 | H | Ph | H | H | 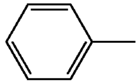 | H |
| 104 | 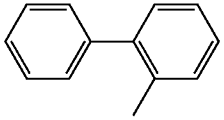 | H | H | H | H | 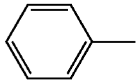 | Ph |
| 105 | 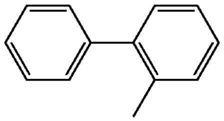 | Me | H | H | Me | 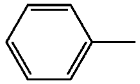 | H |
| 106 | 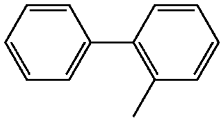 | H | Me | Me | H | 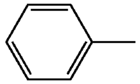 | H |
| 107 | 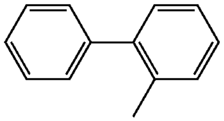 | H | H | H | H | 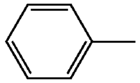 | Me |
| 108 | 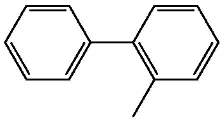 | H | H | H | H | 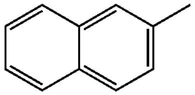 | H |
| 109 | 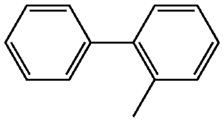 | Ph | H | H | Ph | 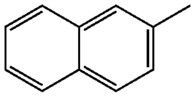 | H |

-continued
| | | | | | | | |
|---|---|---|---|---|---|---|---|
| 110 | 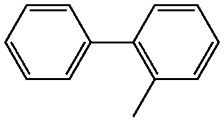 | H | Ph | Ph | H | 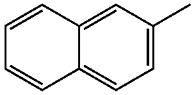 | H |
| 111 | 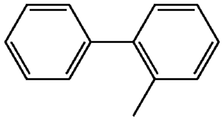 | H | Ph | H | H | 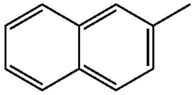 | H |
| 112 | 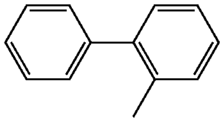 | H | H | H | H | 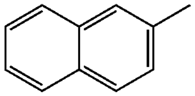 | Ph |
| 113 | 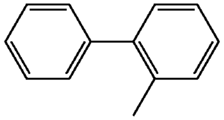 | Me | H | H | Me | 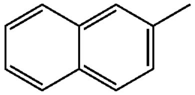 | H |
| 114 | 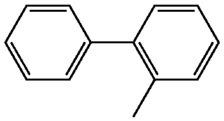 | H | Me | Me | H | 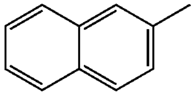 | H |
| 115 | 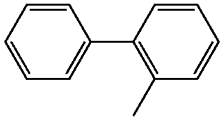 | H | H | H | H | 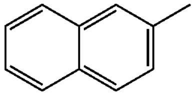 | Me |
| 116 | 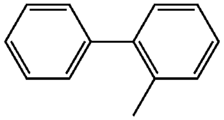 | H | H | H | H | 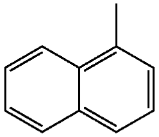 | H |

-continued
| | | | | | | | |
|---|---|---|---|---|---|---|---|
| 117 | 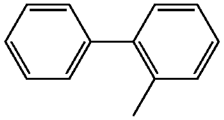 | Ph | H | H | Ph | 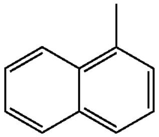 | H |
| 118 | 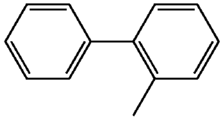 | H | Ph | Ph | H | 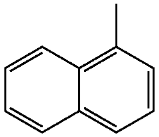 | H |
| 119 | 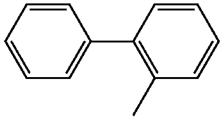 | H | Ph | H | H | 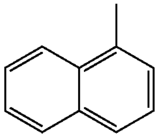 | H |
| 120 | 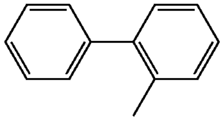 | H | H | H | H | 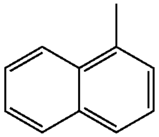 | Ph |
| 121 | 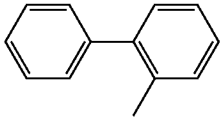 | Me | H | H | Me | 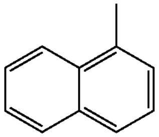 | H |
| 122 | 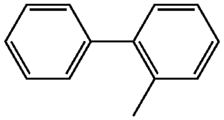 | H | Me | Me | H | 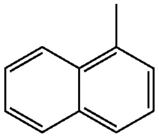 | H |
| 123 | 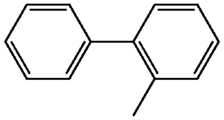 | H | H | H | H | 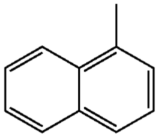 | Me |

-continued
| | | | | | | | |
|---|---|---|---|---|---|---|---|
| 124 | 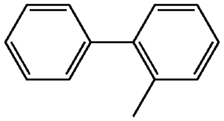 | H | H | H | H | 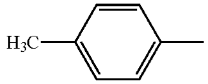 | H |
| 125 | 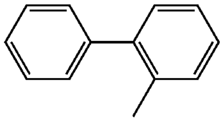 | Ph | H | H | Ph | 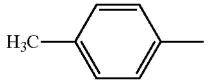 | H |
| 126 | 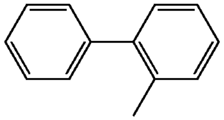 | H | Ph | Ph | H | 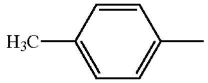 | H |
| 127 | 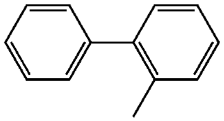 | H | Ph | H | H | 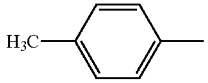 | H |
| 128 | 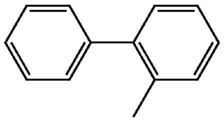 | H | H | H | H | 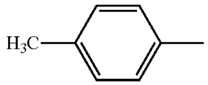 | Ph |
| 129 | 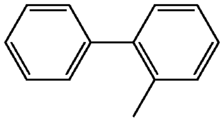 | Me | H | H | Me | 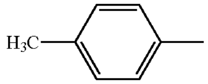 | H |
| 130 | 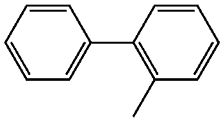 | H | Me | Me | H | 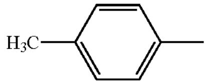 | H |
| 131 | 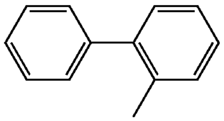 | H | H | H | H | 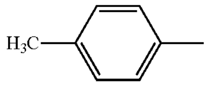 | Me |

-continued
| | | | | | | | |
|---|---|---|---|---|---|---|---|
| 132 | 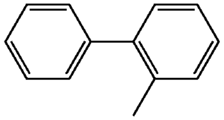 | H | H | H | H | 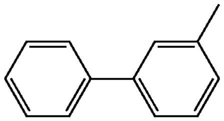 | H |
| 133 | 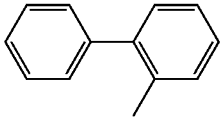 | Ph | H | H | Ph | 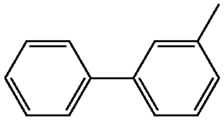 | H |
| 134 | 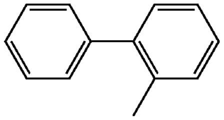 | H | Ph | Ph | H | 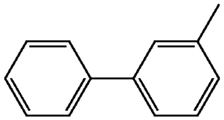 | H |
| 135 | 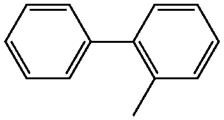 | H | Ph | H | H | 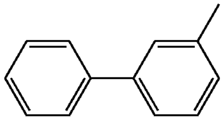 | H |
| 136 | 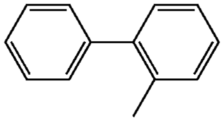 | H | H | H | H | 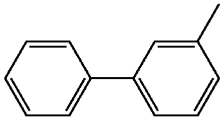 | Ph |

-continued
| | | | | | | |
|---|---|---|---|---|---|---|
| 137 | 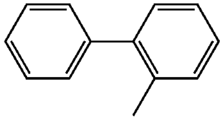 | Me | H | H | Me | 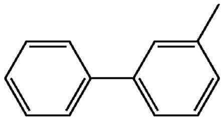 H |
| 138 | 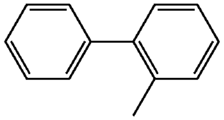 | H | Me | Me | H | 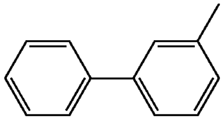 H |
| 139 | 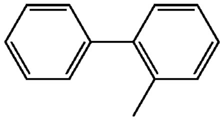 | H | H | H | H | 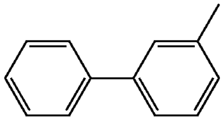 Me |
| 140 | 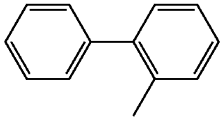 | H | H | H | H | 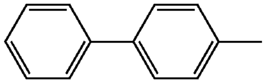 H |
| 141 | 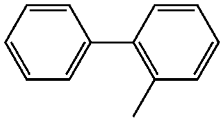 | Ph | H | H | Ph | 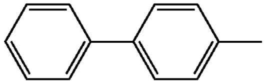 H |

-continued
| | | | | | | |
|---|---|---|---|---|---|---|
| 142 | 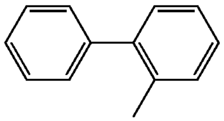 | H | Ph | Ph | H | 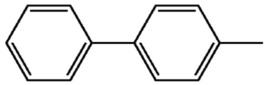 H |
| 143 | 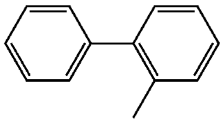 | H | Ph | H | H | 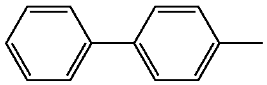 H |
| 144 | 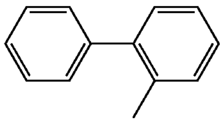 | H | H | H | H | 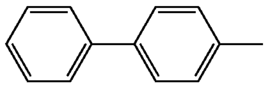 Ph |
| 145 | 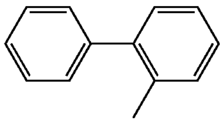 | Me | H | H | Me | 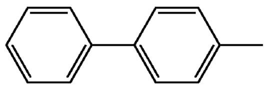 H |
| 146 | 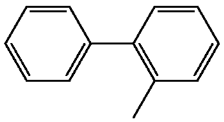 | H | Me | Me | H | 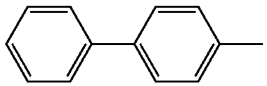 H |
| 147 | 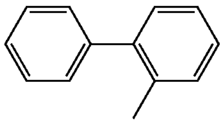 | H | H | H | H | 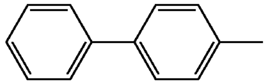 Me |

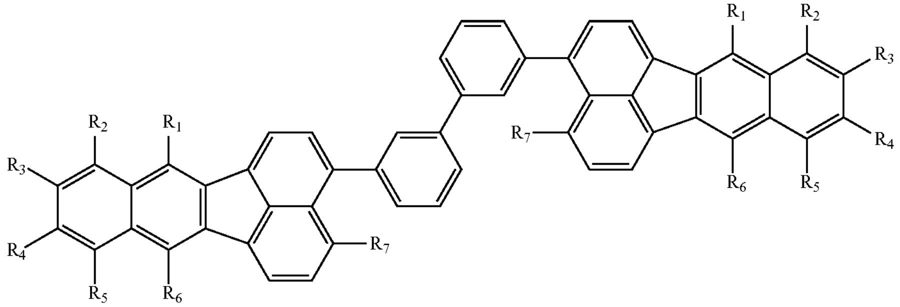
TypeD
| | $R_1$ | $R_2$ | $R_3$ | $R_4$ | $R_5$ | $R_6$ | $R_7$ |
|---|---|---|---|---|---|---|---|
| D-1 | H | H | H | H | H | H | H |
| D-2 | Ph | H | H | H | H | Ph | H |
| D-3 | Ph | Ph | H | H | Ph | Ph | H |
| D-4 | Ph | H | Ph | Ph | H | Ph | H |
| D-5 | Ph | H | Ph | H | H | Ph | H |
| D-6 | Ph | H | H | H | H | Ph | Ph |
| D-7 | Ph | Me | H | H | Me | Ph | H |
| D-8 | Ph | H | Me | Me | H | Ph | H |
| D-9 | Ph | H | H | H | H | Ph | Me |
| D-10 | 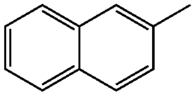 | H | H | H | H | 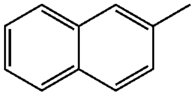 | H |
| D-11 | 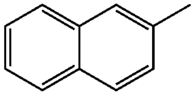 | Ph | H | H | Ph | 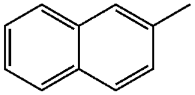 | H |
| D-12 | 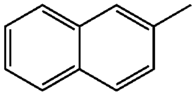 | H | Ph | Ph | H | 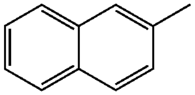 | H |
| D-13 | 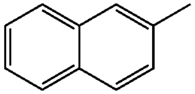 | H | Ph | H | H | 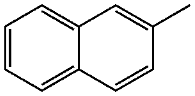 | H |

-continued
| | | | | | | | |
|---|---|---|---|---|---|---|---|
| D-14 | 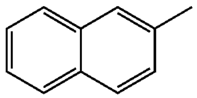 | H | H | H | H | 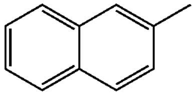 | Ph |
| D-15 | 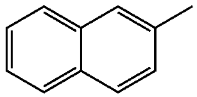 | Me | H | H | Me | 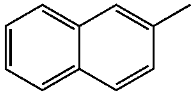 | H |
| D-16 | 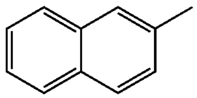 | H | Me | Me | H | 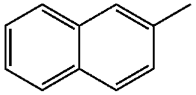 | H |
| D-17 | 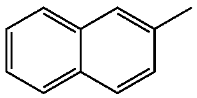 | H | H | H | H | 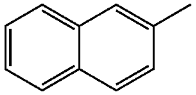 | Me |
| D-18 | 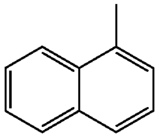 | H | H | H | H | 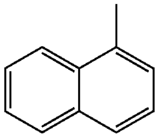 | H |
| D-19 | 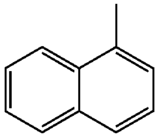 | Ph | H | H | Ph | 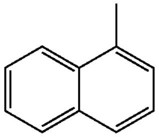 | H |
| D-20 | 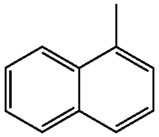 | H | Ph | Ph | H | 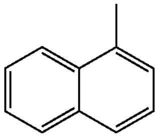 | H |
| D-21 | 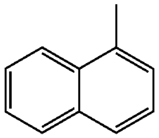 | H | Ph | H | H | 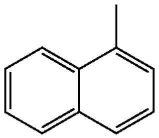 | H |

-continued
| | | | | | | | |
|---|---|---|---|---|---|---|---|
| D-22 | 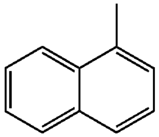 | H | H | H | H | 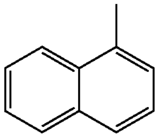 | Ph |
| D-23 | 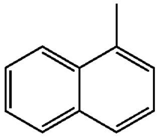 | Me | H | H | Me | 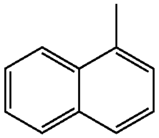 | H |
| D-24 | 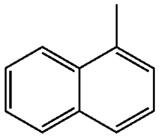 | H | Me | Me | H | 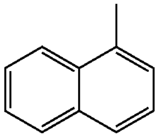 | H |
| D-25 | 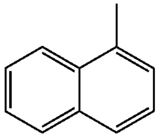 | H | H | H | H | 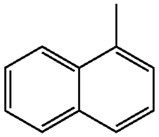 | Me |
| D-26 | 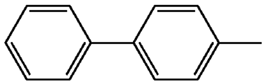 | H | H | H | H | 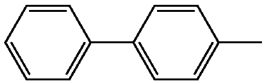 | H |
| D-27 | 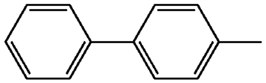 | Ph | H | H | Ph | 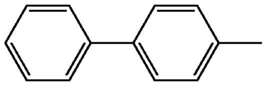 | H |
| D-28 | 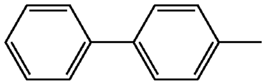 | H | Ph | Ph | H | 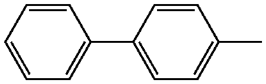 | H |
| D-29 | 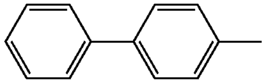 | H | Ph | H | H | 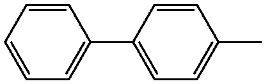 | H |

-continued
| | | | | | | | |
|---|---|---|---|---|---|---|---|
| D-30 | 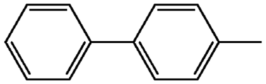 | H | H | H | H | 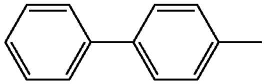 | Ph |
| D-31 | 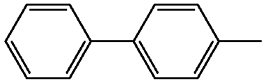 | Me | H | H | Me | 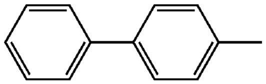 | H |
| D-32 | 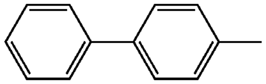 | H | Me | Me | H | 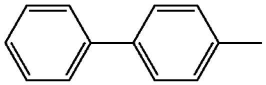 | H |
| D-33 | 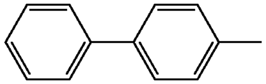 | H | H | H | H | 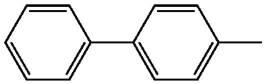 | Me |
| D-34 | 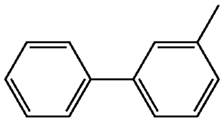 | H | H | H | H | 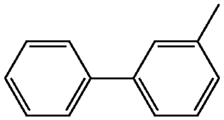 | H |
| D-35 | 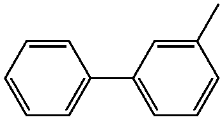 | Ph | H | H | Ph | 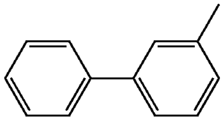 | H |
| D-36 | 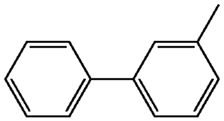 | H | Ph | Ph | H | 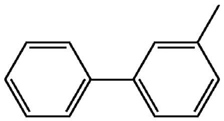 | H |
| D-37 | 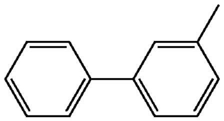 | H | Ph | H | H | 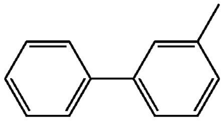 | H |
| D-38 | 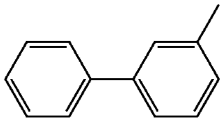 | H | H | H | H | 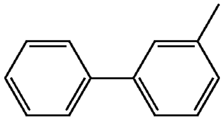 | Ph |

-continued
| | | | | | | | |
|---|---|---|---|---|---|---|---|
| D-39 | 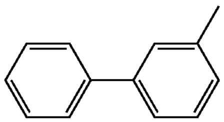 | Me | H | H | Me | 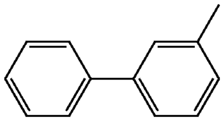 | H |
| D-40 | 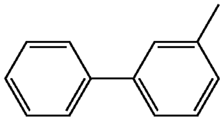 | H | Me | Me | H | 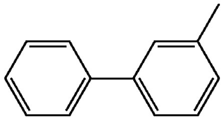 | H |
| D-41 | 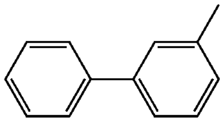 | H | H | H | H | 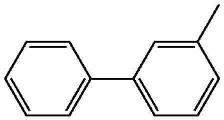 | Me |
| D-42 | 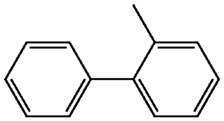 | H | H | H | H | 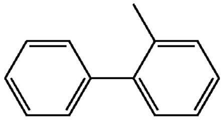 | H |
| D-43 | 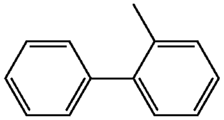 | Ph | H | H | Ph | 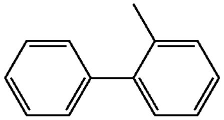 | H |
| D-44 | 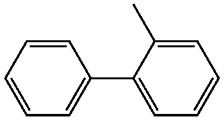 | H | Ph | Ph | H | 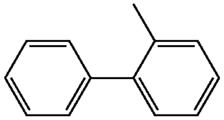 | H |
| D-45 | 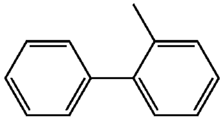 | H | Ph | H | H | 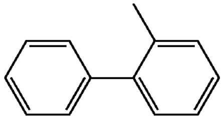 | H |

-continued
| | | | | | | | |
|---|---|---|---|---|---|---|---|
| D-46 | 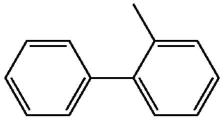 | H | H | H | H | 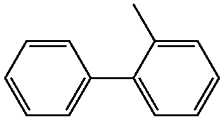 | Ph |
| D-47 | 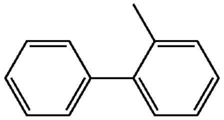 | Me | H | H | Me | 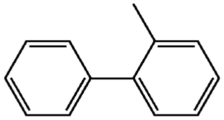 | H |
| D-48 | 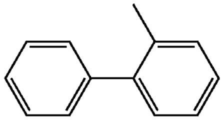 | H | Me | Me | H | 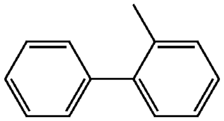 | H |
| D-49 | 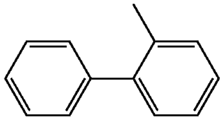 | H | H | H | H | 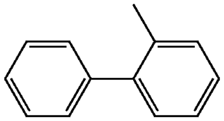 | Me |
| D-50 | Ph | H | H | H | H | 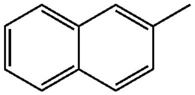 | H |
| D-51 | Ph | H | H | H | H | 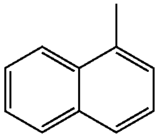 | H |
| D-52 | Ph | H | H | H | H | 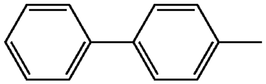 | H |
| D-53 | Ph | H | H | H | H | 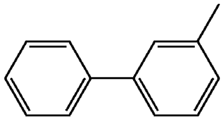 | H |

-continued
| | | | | | | | |
|---|---|---|---|---|---|---|---|
| D-54 | Ph | H | H | H | H | 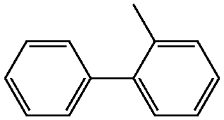 | H |
| D-55 | 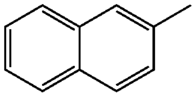 | H | H | H | H | 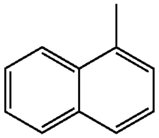 | H |
| D-56 | 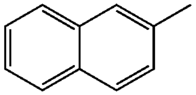 | H | H | H | H | 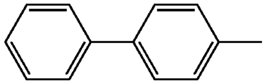 | H |
| D-57 | 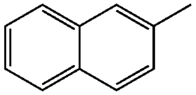 | H | H | H | H | 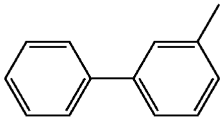 | H |
| D-58 | 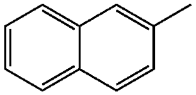 | H | H | H | H | 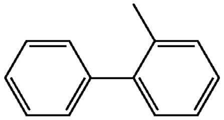 | H |
| D-59 | 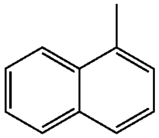 | H | H | H | H | 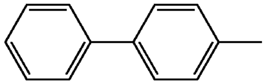 | H |
| D-60 | 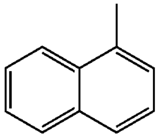 | H | H | H | H | 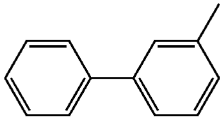 | H |

-continued
| | | | | | | | |
|---|---|---|---|---|---|---|---|
| D-61 | 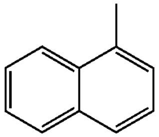 | H | H | H | H | 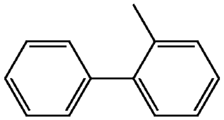 | H |
| D-62 | 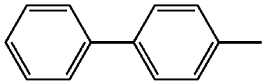 | H | H | H | H | 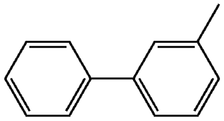 | H |
| D-63 | 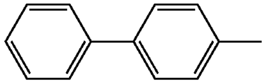 | H | H | H | H | 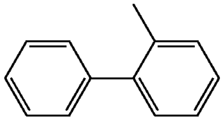 | H |
| D-64 | 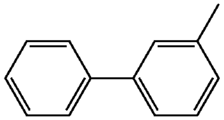 | H | H | H | H | 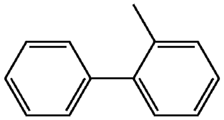 | H |
| D-65 | H | Ph | H | H | Ph | H | H |
| D-66 | H | 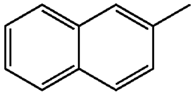 | H | H | 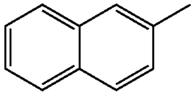 | H | H |
| D-67 | H | 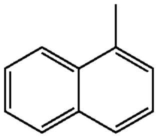 | H | H | 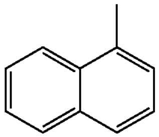 | H | H |
| D-68 | H | 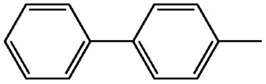 | H | H | 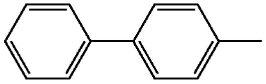 | H | H |

-continued
| | | | | | | | |
|---|---|---|---|---|---|---|---|
| D-69 | H | 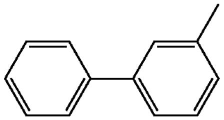 | H | H | 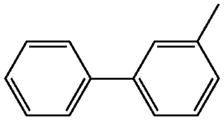 | H | H |
| D-70 | H | 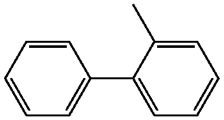 | H | H | 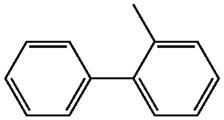 | H | H |
| D-71 | H | H | 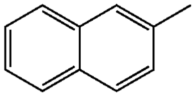 | 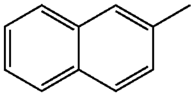 | H | H | H |
| D-72 | H | H | 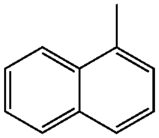 | 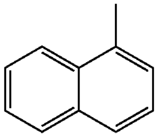 | H | H | H |
| D-73 | H | H | 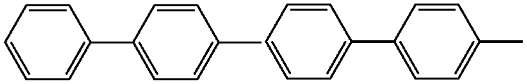 | | H | H | H |
| D-74 | H | H | 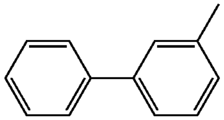 | 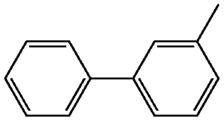 | H | H | H |
| D-75 | H | H | 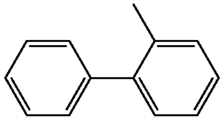 | 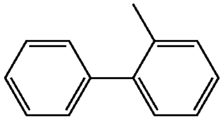 | H | H | H |
| D-76 | 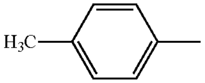 | H | H | H | H | 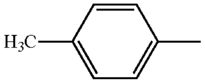 | H |

-continued
| | | | | | | | |
|---|---|---|---|---|---|---|---|
| D-77 | 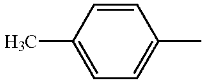 | Ph | H | H | Ph | 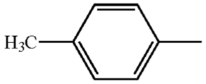 | H |
| D-78 | 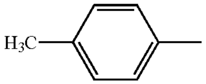 | H | Ph | Ph | H | 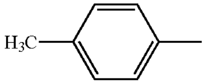 | H |
| D-79 | 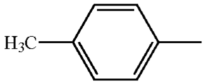 | H | Ph | H | H | 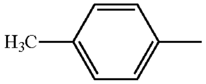 | H |
| D-80 | 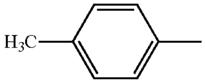 | H | H | H | H | 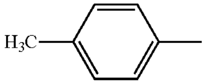 | Ph |
| D-81 | 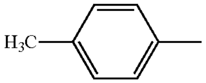 | Me | H | H | Me | 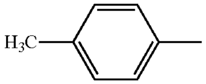 | H |
| D-82 | 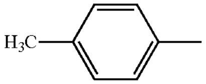 | H | Me | Me | H | 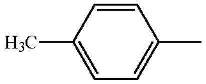 | H |
| D-83 | 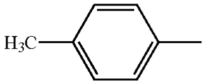 | H | H | H | H | 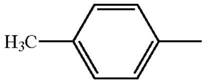 | Me |
| D-84 | 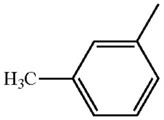 | H | H | H | H | 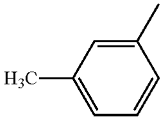 | H |
| D-85 | 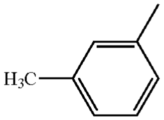 | Ph | H | H | Ph | 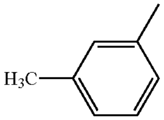 | H |

-continued
| | | | | | | | |
|---|---|---|---|---|---|---|---|
| D-86 | 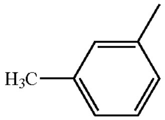 | H | Ph | Ph | H | 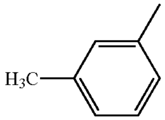 | H |
| D-87 | 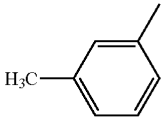 | H | Ph | H | H | 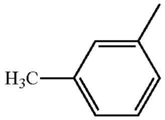 | H |
| D-88 | 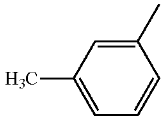 | H | H | H | H | 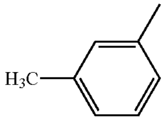 | Ph |
| D-89 | 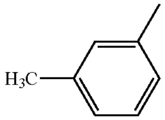 | Me | H | H | Me | 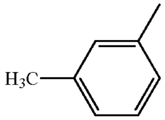 | H |
| D-90 | 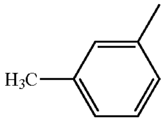 | H | Me | Me | H | 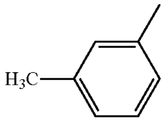 | H |
| D-91 | 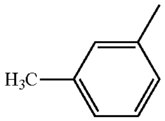 | H | H | H | H | 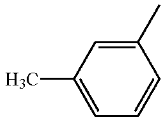 | Me |
| D-92 | 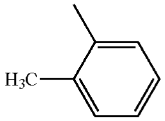 | H | H | H | H | 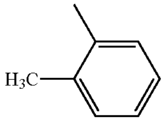 | H |
| D-93 | 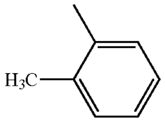 | Ph | H | H | Ph | 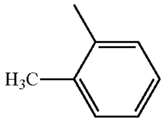 | H |

-continued
| | | | | | | | |
|---|---|---|---|---|---|---|---|
| D-94 | 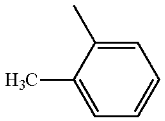 | H | Ph | Ph | H | 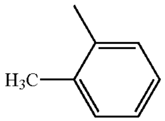 | H |
| D-96 | 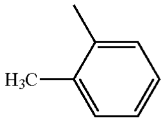 | H | Ph | H | H | 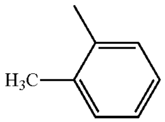 | H |
| D-96 | 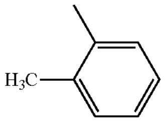 | H | H | H | H | 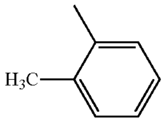 | Ph |
| D-97 | 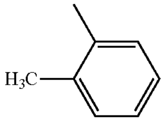 | Me | H | H | Me | 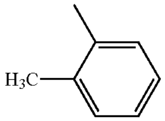 | H |
| D-98 | 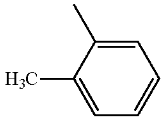 | H | Me | Me | H | 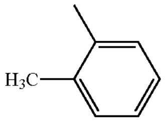 | H |
| D-99 | 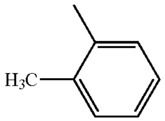 | H | H | H | H | 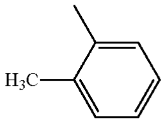 | Me |
| 100 | 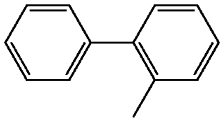 | H | H | H | H | 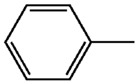 | H |

-continued
| | | | | | | | |
|---|---|---|---|---|---|---|---|
| 101 | 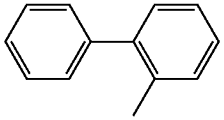 | Ph | H | H | Ph | 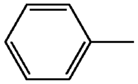 | H |
| 102 | 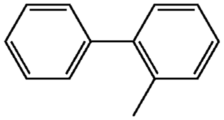 | H | Ph | Ph | H | 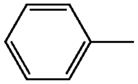 | H |
| 103 | 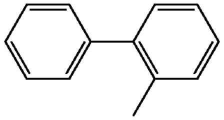 | H | Ph | H | H | 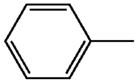 | H |
| 104 | 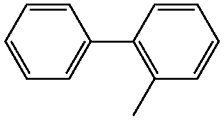 | H | H | H | H | 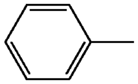 | Ph |
| 105 | 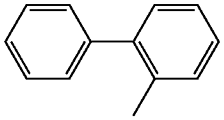 | Me | H | H | Me | 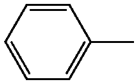 | H |
| 106 | 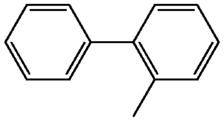 | H | Me | Me | H | 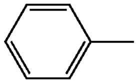 | H |
| 107 | 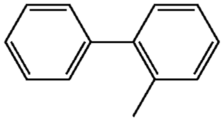 | H | H | H | H | 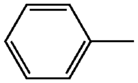 | Me |
| 108 | 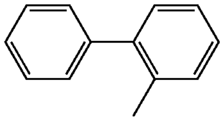 | H | H | H | H | 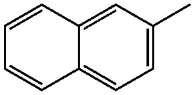 | H |

-continued
| | | | | | | | |
|---|---|---|---|---|---|---|---|
| 109 | 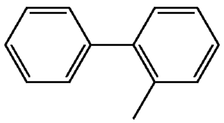 | Ph | H | H | Ph | 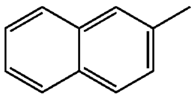 | H |
| 110 | 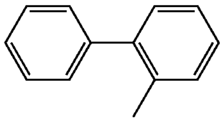 | H | Ph | Ph | H | 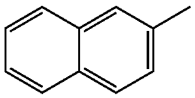 | H |
| 111 | 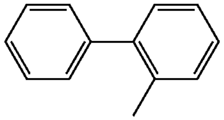 | H | Ph | H | H | 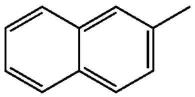 | H |
| 112 | 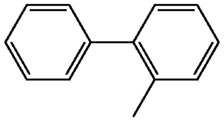 | H | H | H | H | 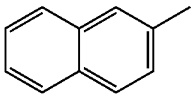 | Ph |
| 113 | 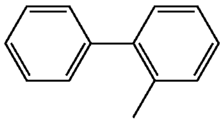 | Me | H | H | Me | 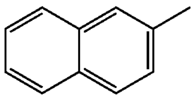 | H |
| 114 | 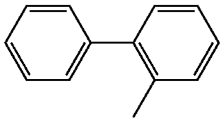 | H | Me | Me | H | 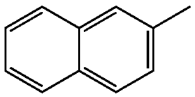 | H |
| 115 | 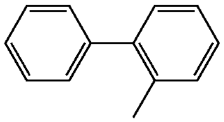 | H | H | H | H | 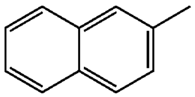 | Me |

-continued
| | | | | | | | |
|---|---|---|---|---|---|---|---|
| 116 | 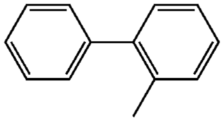 | H | H | H | H | 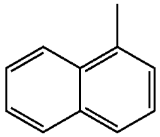 | H |
| 117 | 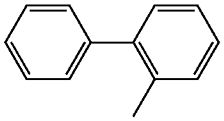 | Ph | H | H | Ph | 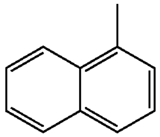 | H |
| 118 | 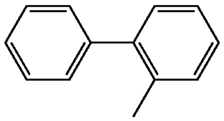 | H | Ph | Ph | H | 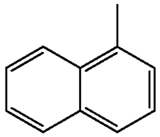 | H |
| 119 | 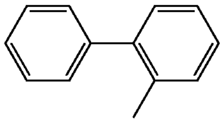 | H | Ph | H | H | 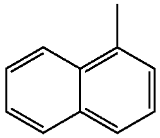 | H |
| 120 | 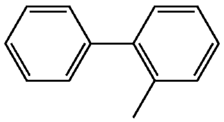 | H | H | H | H | 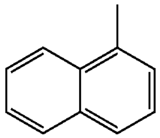 | Ph |
| 121 | 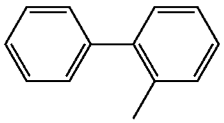 | Me | H | H | Me | 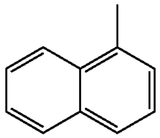 | H |
| 122 | 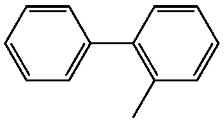 | H | Me | Me | H | 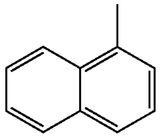 | H |

-continued
| | | | | | | | |
|---|---|---|---|---|---|---|---|
| 123 | 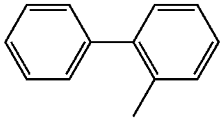 | H | H | H | H | 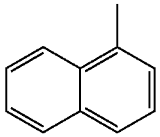 | Me |
| 124 | 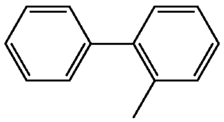 | H | H | H | H | 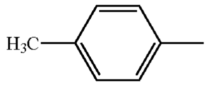 | H |
| 125 | 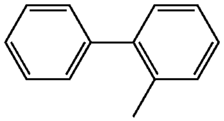 | Ph | H | H | Ph | 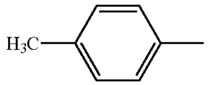 | H |
| 126 | 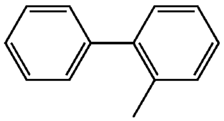 | H | Ph | Ph | H | 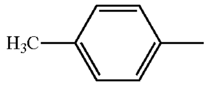 | H |
| 127 | 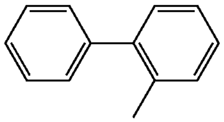 | H | Ph | H | H | 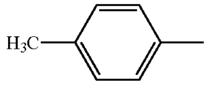 | H |
| 128 | 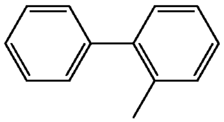 | H | H | H | H | 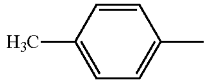 | Ph |
| 129 | 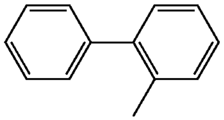 | Me | H | H | Me | 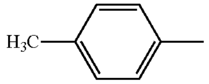 | H |

-continued
| | | | | | | | |
|---|---|---|---|---|---|---|---|
| 130 | 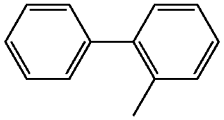 | H | Me | Me | H | 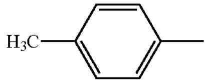 | H |
| 131 | 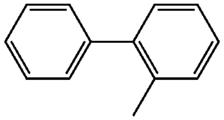 | H | H | H | H | 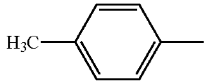 | Me |
| 132 | 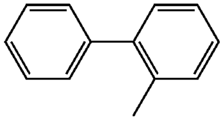 | H | H | H | H | 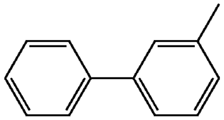 | H |
| 133 | 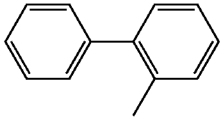 | Ph | H | H | Ph | 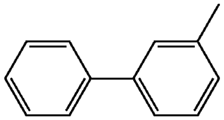 | H |
| 134 | 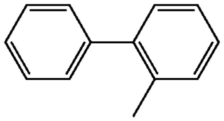 | H | Ph | Ph | H | 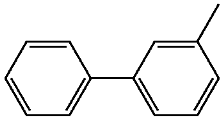 | H |
| 135 | 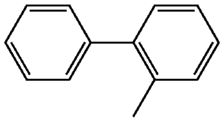 | H | Ph | H | H | 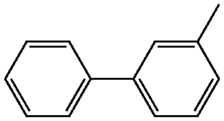 | H |
| 136 | 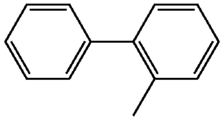 | H | H | H | H | 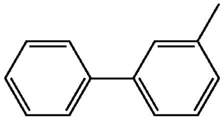 | Ph |
| 137 | 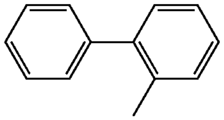 | Me | H | H | Me | 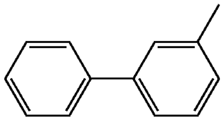 | H |

-continued
| | | | | | | | |
|---|---|---|---|---|---|---|---|
| 138 | 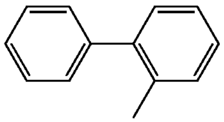 | H | Me | Me | H | 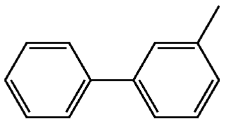 | H |
| 139 | 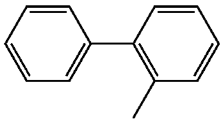 | H | H | H | H | 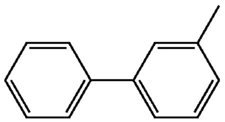 | Me |
| 140 | 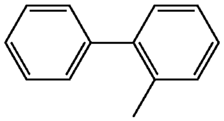 | H | H | H | H | 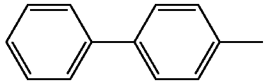 | H |
| 141 | 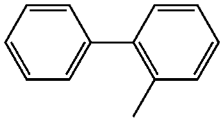 | Ph | H | H | Ph | 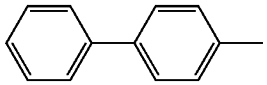 | H |
| 142 | 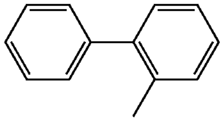 | H | Ph | Ph | H | 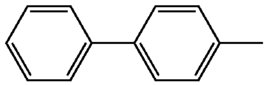 | H |

-continued
| | | | | | | | |
|---|---|---|---|---|---|---|---|
| 143 | 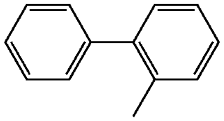 | H | Ph | H | H | 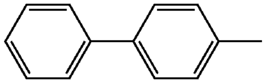 | H |
| 144 | 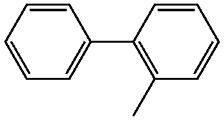 | H | H | H | H | 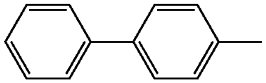 | Ph |
| 145 | 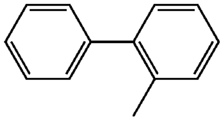 | Me | H | H | Me | 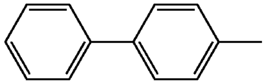 | H |
| 146 | 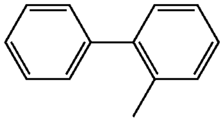 | H | Me | Me | H | 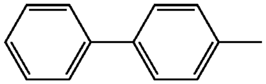 | H |
| 147 | 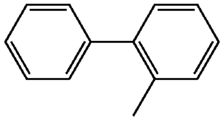 | H | H | H | H | 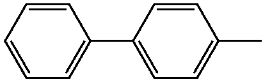 | Me |

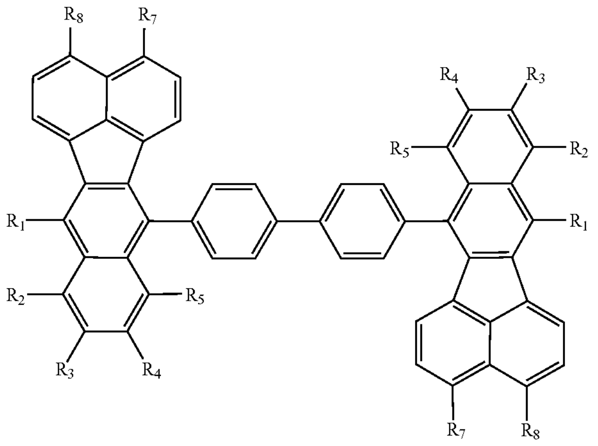

TypeE

| | $R_1$ | $R_2$ | $R_3$ | $R_4$ | $R_5$ | $R_7$ | $R_8$ |
|---|---|---|---|---|---|---|---|
| E-1 | H | H | H | H | H | H | H |
| E-2 | Ph | H | H | H | H | H | H |
| E-3 | Ph | Ph | H | H | Ph | H | H |
| E-4 | Ph | H | Ph | Ph | H | H | H |
| E-5 | Ph | H | Ph | H | H | H | H |
| E-6 | Ph | H | H | Ph | H | H | H |
| E-7 | Ph | H | H | H | H | Ph | H |
| E-8 | Ph | H | H | H | H | H | Ph |
| E-9 | Ph | H | H | H | H | Ph | Ph |
| E-10 | Ph | H | H | H | H | 1-naphthyl | H |
| E-11 | Ph | H | H | H | H | H | 1-naphthyl |
| E-12 | Ph | H | H | H | H | 1-naphthyl | 1-naphthyl |
| E-13 | Ph | H | H | H | H | 2-naphthyl | H |
| E-14 | Ph | H | H | H | H | H | 2-naphthyl |
| E-15 | Ph | H | H | H | H | 2-naphthyl | 2-naphthyl |
| E-16 | Ph | H | H | H | H | o-biphenylyl | H |
| E-17 | Ph | H | H | H | H | H | o-biphenylyl |
| E-18 | Ph | H | H | H | H | o-biphenylyl | o-biphenylyl |
| E-19 | Ph | H | H | H | H | m-biphenylyl | H |
| E-20 | Ph | H | H | H | H | H | m-biphenylyl |
| E-21 | Ph | H | H | H | H | m-biphenylyl | m-biphenylyl |
| E-22 | Ph | H | H | H | H | p-biphenylyl | H |
| E-23 | Ph | H | H | H | H | H | p-biphenylyl |
| E-24 | Ph | H | H | H | H | p-biphenylyl | p-biphenylyl |
| E-25 | 1-naphthyl | H | H | H | H | H | H |
| E-26 | 1-naphthyl | Ph | H | H | Ph | H | H |
| E-27 | 1-naphthyl | H | Ph | Ph | H | H | H |
| E-28 | 1-naphthyl | H | Ph | H | H | H | H |
| E-29 | 1-naphthyl | H | H | Ph | H | H | H |
| E-30 | 1-naphthyl | H | H | H | H | Ph | H |
| E-31 | 1-naphthyl | H | H | H | H | H | Ph |
| E-32 | 1-naphthyl | H | H | H | H | Ph | Ph |
| E-33 | 1-naphthyl | H | H | H | H | 1-naphthyl | H |
| E-34 | 1-naphthyl | H | H | H | H | H | 1-naphthyl |
| E-35 | 1-naphthyl | H | H | H | H | 1-naphthyl | 1-naphthyl |
| E-36 | 1-naphthyl | H | H | H | H | 2-naphthyl | H |
| E-37 | 1-naphthyl | H | H | H | H | H | 2-naphthyl |
| E-38 | 1-naphthyl | H | H | H | H | 2-naphthyl | 2-naphthyl |
| E-39 | 1-naphthyl | H | H | H | H | o-biphenylyl | H |
| E-40 | 1-naphthyl | H | H | H | H | H | o-biphenylyl |
| E-41 | 1-naphthyl | H | H | H | H | o-biphenylyl | o-biphenylyl |
| E-42 | 1-naphthyl | H | H | H | H | m-biphenylyl | H |
| E-43 | 1-naphthyl | H | H | H | H | H | m-biphenylyl |
| E-44 | 1-naphthyl | H | H | H | H | m-biphenylyl | m-biphenylyl |
| E-45 | 1-naphthyl | H | H | H | H | p-biphenylyl | H |
| E-46 | 1-naphthyl | H | H | H | H | H | p-biphenylyl |
| E-47 | 1-naphthyl | H | H | H | H | p-biphenylyl | p-biphenylyl |
| E-48 | 2-naphthyl | H | H | H | H | H | H |
| E-49 | 2-naphthyl | Ph | H | H | Ph | H | H |
| E-50 | 2-naphthyl | H | Ph | Ph | H | H | H |
| E-51 | 2-naphthyl | H | Ph | H | H | H | H |
| E-52 | 2-naphthyl | H | H | Ph | H | H | H |
| E-53 | 2-naphthyl | H | H | H | H | Ph | H |

-continued

| | | | | | | | |
|---|---|---|---|---|---|---|---|
| E-54 | 2-naphthyl | H | H | H | H | H | Ph |
| E-55 | 2-naphthyl | H | H | H | H | Ph | Ph |
| E-56 | 2-naphthyl | H | H | H | H | 1-naphthyl | H |
| E-57 | 2-naphthyl | H | H | H | H | H | 1-naphthyl |
| E-58 | 2-naphthyl | H | H | H | H | 1-naphthyl | 1-naphthyl |
| E-59 | 2-naphthyl | H | H | H | H | 2-naphthyl | H |
| E-60 | 2-naphthyl | H | H | H | H | H | 2-naphthyl |
| E-61 | 2-naphthyl | H | H | H | H | 2-naphthyl | 2-naphthyl |
| E-62 | 2-naphthyl | H | H | H | H | o-biphenylyl | H |
| E-63 | 2-naphthyl | H | H | H | H | H | o-biphenylyl |
| E-64 | 2-naphthyl | H | H | H | H | o-biphenylyl | o-biphenylyl |
| E-65 | 2-naphthyl | H | H | H | H | m-biphenylyl | H |
| E-66 | 2-naphthyl | H | H | H | H | H | m-biphenylyl |
| E-67 | 2-naphthyl | H | H | H | H | m-biphenylyl | m-biphenylyl |
| E-68 | 2-naphthyl | H | H | H | H | p-biphenylyl | H |
| E-69 | 2-naphthyl | H | H | H | H | H | p-biphenylyl |
| E-70 | 2-naphthyl | H | H | H | H | p-biphenylyl | p-biphenylyl |
| E-71 | o-biphenylyl | H | H | H | H | H | H |
| E-72 | o-biphenylyl | Ph | H | H | Ph | H | H |
| E-73 | o-biphenylyl | H | Ph | Ph | H | H | H |
| E-74 | o-biphenylyl | H | Ph | H | H | H | H |
| E-75 | o-biphenylyl | H | H | Ph | H | H | H |
| E-76 | o-biphenylyl | H | H | H | H | Ph | H |
| E-77 | o-biphenylyl | H | H | H | H | H | Ph |
| E-78 | o-biphenylyl | H | H | H | H | Ph | Ph |
| E-79 | o-biphenylyl | H | H | H | H | 1-naphthyl | H |
| E-80 | o-biphenylyl | H | H | H | H | H | 1-naphthyl |
| E-81 | o-biphenylyl | H | H | H | H | 1-naphthyl | 1-naphthyl |
| E-82 | o-biphenylyl | H | H | H | H | 2-naphthyl | H |
| E-83 | o-biphenylyl | H | H | H | H | H | 2-naphthyl |
| E-84 | o-biphenylyl | H | H | H | H | 2-naphthyl | 2-naphthyl |
| E-85 | o-biphenylyl | H | H | H | H | o-biphenylyl | H |
| E-86 | o-biphenylyl | H | H | H | H | H | o-biphenylyl |
| E-87 | o-biphenylyl | H | H | H | H | o-biphenylyl | o-biphenylyl |
| E-88 | o-biphenylyl | H | H | H | H | m-biphenylyl | H |
| E-89 | o-biphenylyl | H | H | H | H | H | m-biphenylyl |
| E-90 | o-biphenylyl | H | H | H | H | m-biphenylyl | m-biphenylyl |
| E-91 | o-biphenylyl | H | H | H | H | p-biphenylyl | H |
| E-92 | o-biphenylyl | H | H | H | H | H | p-biphenylyl |
| E-93 | o-biphenylyl | H | H | H | H | p-biphenylyl | p-biphenylyl |
| E-94 | m-biphenylyl | H | H | H | H | H | H |
| E-95 | m-biphenylyl | Ph | H | H | Ph | H | H |
| E-98 | m-biphenylyl | H | Ph | Ph | H | H | H |
| E-97 | m-biphenylyl | H | Ph | H | H | H | H |
| E-98 | m-biphenylyl | H | H | Ph | H | H | H |
| E-99 | m-biphenylyl | H | H | H | H | Ph | H |
| E-100 | m-biphenylyl | H | H | H | H | H | Ph |
| E-101 | m-biphenylyl | H | H | H | H | Ph | Ph |
| E-102 | m-biphenylyl | H | H | H | H | 1-naphthyl | H |
| E-103 | m-biphenylyl | H | H | H | H | H | 1-naphthyl |
| E-104 | m-biphenylyl | H | H | H | H | 1-naphthyl | 1-naphthyl |
| E-105 | m-biphenylyl | H | H | H | H | 2-naphthyl | H |
| E-106 | m-biphenylyl | H | H | H | H | H | 2-naphthyl |
| E-107 | m-biphenylyl | H | H | H | H | 2-naphthyl | 2-naphthyl |
| E-108 | m-biphenylyl | H | H | H | H | o-biphenylyl | H |
| E-109 | m-biphenylyl | H | H | H | H | H | o-biphenylyl |
| E-110 | m-biphenylyl | H | H | H | H | o-biphenylyl | o-biphenylyl |
| E-111 | m-biphenylyl | H | H | H | H | m-biphenylyl | H |
| E-112 | m-biphenylyl | H | H | H | H | H | m-biphenylyl |
| E-113 | m-biphenylyl | H | H | H | H | m-biphenylyl | m-biphenylyl |
| E-114 | m-biphenylyl | H | H | H | H | p-biphenylyl | H |
| E-115 | m-biphenylyl | H | H | H | H | H | p-biphenylyl |
| E-116 | m-biphenylyl | H | H | H | H | p-biphenylyl | p-biphenylyl |
| E-117 | p-biphenylyl | H | H | H | H | H | H |
| E-118 | p-biphenylyl | Ph | H | H | Ph | H | H |
| E-119 | p-biphenylyl | H | Ph | Ph | H | H | H |
| E-120 | p-biphenylyl | H | Ph | H | H | H | H |
| E-121 | p-biphenylyl | H | H | Ph | H | H | H |
| E-122 | p-biphenylyl | H | H | H | H | Ph | H |
| E-123 | p-biphenylyl | H | H | H | H | H | Ph |
| E-124 | p-biphenylyl | H | H | H | H | Ph | Ph |
| E-125 | p-biphenylyl | H | H | H | H | 1-naphthyl | H |
| E-128 | p-biphenylyl | H | H | H | H | H | 1-naphthyl |
| E-127 | p-biphenylyl | H | H | H | H | 1-naphthyl | 1-naphthyl |
| E-128 | p-biphenylyl | H | H | H | H | 2-naphthyl | H |
| E-129 | p-biphenylyl | H | H | H | H | H | 2-naphthyl |
| E-130 | p-biphenylyl | H | H | H | H | 2-naphthyl | 2-naphthyl |
| E-131 | p-biphenylyl | H | H | H | H | o-biphenylyl | H |
| E-132 | p-biphenylyl | H | H | H | H | H | o-biphenylyl |

-continued

| | | | | | | | |
|---|---|---|---|---|---|---|---|
| E-133 | p-biphenylyl | H | H | H | H | o-biphenylyl | o-biphenylyl |
| E-134 | p-biphenylyl | H | H | H | H | m-biphenylyl | H |
| E-135 | p-biphenylyl | H | H | H | H | H | m-biphenylyl |
| E-136 | p-biphenylyl | H | H | H | H | m-biphenylyl | m-biphenylyl |
| E-137 | p-biphenylyl | H | H | H | H | p-biphenylyl | H |
| E-138 | p-biphenylyl | H | H | H | H | H | p-biphenylyl |
| E-139 | p-biphenylyl | H | H | H | H | p-biphenylyl | p-biphenylyl |
| E-140 | o-tolyl | H | H | H | H | H | H |
| E-141 | o-tolyl | Ph | H | H | Ph | H | H |
| E-142 | o-tolyl | H | Ph | Ph | H | H | H |
| E-143 | o-tolyl | H | H | H | H | Ph | H |
| E-144 | o-tolyl | H | H | H | H | H | Ph |
| E-145 | o-tolyl | H | H | H | H | 1-naphthyl | H |
| E-146 | o-tolyl | H | H | H | H | H | 1-naphthyl |
| E-147 | o-tolyl | H | H | H | H | 2-naphthyl | H |
| E-148 | o-tolyl | H | H | H | H | H | 2-naphthyl |
| E-149 | o-tolyl | H | H | H | H | o-biphenylyl | H |
| E-150 | o-tolyl | H | H | H | H | H | o-biphenylyl |
| E-151 | o-tolyl | H | H | H | H | m-biphenylyl | H |
| E-152 | o-tolyl | H | H | H | H | H | m-biphenylyl |
| E-153 | o-tolyl | H | H | H | H | p-biphenylyl | H |
| E-154 | o-tolyl | H | H | H | H | H | p-biphenylyl |
| E-155 | o-tolyl | H | H | H | H | o-tolyl | H |
| E-156 | o-tolyl | H | H | H | H | H | o-tolyl |
| E-157 | m-tolyl | H | H | H | H | H | H |
| E-158 | m-tolyl | Ph | H | H | Ph | H | H |
| E-159 | m-tolyl | H | Ph | Ph | H | H | H |
| E-160 | m-tolyl | H | H | H | H | Ph | H |
| E-161 | m-tolyl | H | H | H | H | H | Ph |
| E-162 | m-tolyl | H | H | H | H | 1-naphthyl | H |
| E-163 | m-tolyl | H | H | H | H | H | 1-naphthyl |
| E-164 | m-tolyl | H | H | H | H | 2-naphthyl | H |
| E-165 | m-tolyl | H | H | H | H | H | 2-naphthyl |
| E-166 | m-tolyl | H | H | H | H | o-biphenylyl | H |
| E-167 | m-tolyl | H | H | H | H | H | o-biphenylyl |
| E-168 | m-tolyl | H | H | H | H | m-biphenylyl | H |
| E-169 | m-tolyl | H | H | H | H | H | m-biphenylyl |
| E-170 | m-tolyl | H | H | H | H | p-biphenylyl | H |
| E-171 | m-tolyl | H | H | H | H | H | p-biphenylyl |
| E-172 | m-tolyl | H | H | H | H | m-tolyl | H |
| E-173 | m-tolyl | H | H | H | H | H | m-tolyl |
| E-174 | p-tolyl | H | H | H | H | H | H |
| E-175 | p-tolyl | Ph | H | H | Ph | H | H |
| E-176 | p-tolyl | H | Ph | Ph | H | H | H |
| E-177 | p-tolyl | H | H | H | H | Ph | H |
| E-178 | p-tolyl | H | H | H | H | H | Ph |
| E-179 | p-tolyl | H | H | H | H | 1-naphthyl | H |
| E-180 | p-tolyl | H | H | H | H | H | 1-naphthyl |
| E-181 | p-tolyl | H | H | H | H | 2-naphthyl | H |
| E-182 | p-tolyl | H | H | H | H | H | 2-naphthyl |
| E-183 | p-tolyl | H | H | H | H | o-biphenylyl | H |
| E-184 | p-tolyl | H | H | H | H | H | o-biphenylyl |
| E-185 | p-tolyl | H | H | H | H | m-biphenylyl | H |
| E-186 | p-tolyl | H | H | H | H | H | m-biphenylyl |
| E-187 | p-tolyl | H | H | H | H | p-biphenylyl | H |
| E-188 | p-tolyl | H | H | H | H | H | p-biphenylyl |
| E-189 | p-tolyl | H | H | H | H | p-tolyl | H |
| E-190 | p-tolyl | H | H | H | H | H | p-tolyl |
| E-191 | Ph | H | —CH3 | —CH3 | H | H | H |
| E-192 | 1-naphtyl | H | —CH3 | —CH3 | H | H | H |
| E-193 | 2-naphthyl | H | —CH3 | —CH3 | H | H | H |
| E-194 | o-biphenylyl | H | —CH3 | —CH3 | H | H | H |
| E-195 | m-biphenylyl | H | —CH3 | —CH3 | H | H | H |
| E-196 | p-biphenylyl | H | —CH3 | —CH3 | H | H | H |
| E-197 | o-tolyl | H | —CH3 | —CH3 | H | H | H |
| E-198 | m-tolyl | H | —CH3 | —CH3 | H | H | H |
| E-199 | p-tolyl | H | —CH3 | —CH3 | H | H | H |
| E-200 | Ph | H | H | H | H | —CH3 | H |
| E-201 | 1-naphtyl | H | H | H | H | —CH3 | H |
| E-202 | 2-naphthyl | H | H | H | H | —CH3 | H |
| E-203 | o-biphenylyl | H | H | H | H | —CH3 | H |
| E-204 | m-biphenylyl | H | H | H | H | —CH3 | H |
| E-205 | p-biphenylyl | H | H | H | H | —CH3 | H |
| E-206 | o-tolyl | H | H | H | H | —CH3 | H |
| E-207 | m-tolyl | H | H | H | H | —CH3 | H |
| E-208 | p-tolyl | H | H | H | H | —CH3 | H |
| E-209 | Ph | H | H | H | H | H | —CH3 |
| E-210 | 1-naphtyl | H | H | H | H | H | —CH3 |
| E-211 | 2-naphthyl | H | H | H | H | H | —CH3 |

-continued

| | | | | | | | |
|---|---|---|---|---|---|---|---|
| E-212 | o-biphenylyl | H | H | H | H | H | —CH3 |
| E-213 | m-biphenylyl | H | H | H | H | H | —CH3 |
| E-214 | p-biphenylyl | H | H | H | H | H | —CH3 |
| E-215 | o-tolyl | H | H | H | H | H | —CH3 |
| E-216 | m-tolyl | H | H | H | H | H | —CH3 |
| E-217 | p-tolyl | H | H | H | H | H | —CH3 |
| E-218 | Ph | H | H | H | H | —CH3 | —CH3 |
| E-219 | 1-naphtyl | H | H | H | H | —CH3 | —CH3 |
| E-220 | 2-naphthyl | H | H | H | H | —CH3 | —CH3 |
| E-221 | o-biphenylyl | H | H | H | H | —CH3 | —CH3 |
| E-222 | m-biphenylyl | H | H | H | H | —CH3 | —CH3 |
| E-223 | p-biphenylyl | H | H | H | H | —CH3 | —CH3 |
| E-224 | o-tolyl | H | H | H | H | —CH3 | —CH3 |
| E-225 | m-tolyl | H | H | H | H | —CH3 | —CH3 |
| E-226 | p-tolyl | H | H | H | H | —CH3 | —CH3 |
| E-227 | Ph | H | H | H | H | H | DPA |
| E-228 | 1-naphtyl | H | H | H | H | H | DPA |
| E-229 | 2-naphthyl | H | H | H | H | H | DPA |
| E-230 | o-biphenylyl | H | H | H | H | H | DPA |
| E-231 | m-biphenylyl | H | H | H | H | H | DPA |
| E-232 | p-biphenylyl | H | H | H | H | H | DPA |
| E-233 | Ph | H | H | H | H | DPA | H |
| E-234 | 1-naphtyl | H | H | H | H | DPA | H |
| E-235 | 2-naphthyl | H | H | H | H | DPA | H |
| E-236 | o-biphenylyl | H | H | H | H | DPA | H |
| E-237 | m-biphenylyl | H | H | H | H | DPA | H |
| E-238 | p-biphenylyl | H | H | H | H | DPA | H |
| E-239 | Ph | H | H | H | H | H | TPA |
| E-240 | 1-naphtyl | H | H | H | H | H | TPA |
| E-241 | 2-naphthyl | H | H | H | H | H | TPA |
| E-242 | o-biphenylyl | H | H | H | H | H | TPA |
| E-243 | m-biphenylyl | H | H | H | H | H | TPA |
| E-244 | p-biphenylyl | H | H | H | H | H | TPA |
| E-245 | Ph | H | H | H | H | TPA | H |
| E-246 | 1-naphtyl | H | H | H | H | TPA | H |
| E-247 | 2-naphthyl | H | H | H | H | TPA | H |
| E-248 | o-biphenylyl | H | H | H | H | TPA | H |
| E-249 | m-biphenylyl | H | H | H | H | TPA | H |
| E-250 | p-biphenylyl | H | H | H | H | TPA | H |

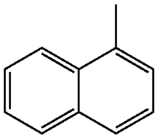

1-naphthyl

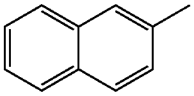

2-naphthyl

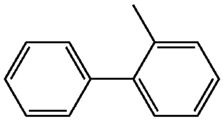

o-biphenylyl

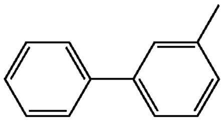

m-biphenylyl

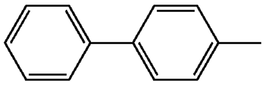

p-biphenylyl

-continued
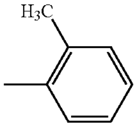
o-tolyl
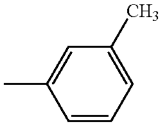
m-tolyl
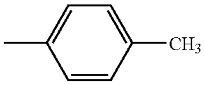
p-tolyl
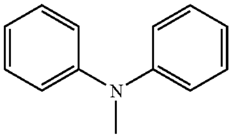
DPA
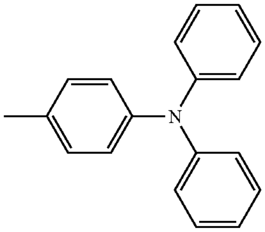
TPA
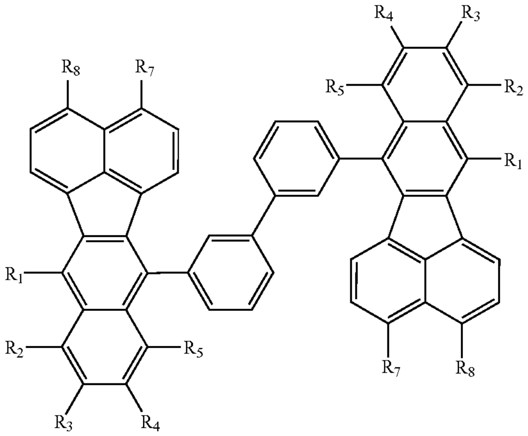
TypeF
| | $R_1$ | $R_2$ | $R_3$ | $R_4$ | $R_5$ | $R_7$ | $R_8$ |
|---|---|---|---|---|---|---|---|
| F-1 | H | H | H | H | H | H | H |
| F-2 | Ph | H | H | H | H | H | H |
| F-3 | Ph | Ph | H | H | Ph | H | H |
| F-4 | Ph | H | Ph | Ph | H | H | H |
| F-5 | Ph | H | Ph | H | H | H | H |
| F-6 | Ph | H | H | Ph | H | H | H |

-continued

| | | | | | | | |
|---|---|---|---|---|---|---|---|
| F-7 | Ph | H | H | H | H | Ph | H |
| F-8 | Ph | H | H | H | H | H | Ph |
| F-9 | Ph | H | H | H | H | Ph | Ph |
| F-10 | Ph | H | H | H | H | 1-naphthyl | H |
| F-11 | Ph | H | H | H | H | H | 1-naphthyl |
| F-12 | Ph | H | H | H | H | 1-naphthyl | 1-naphthyl |
| F-13 | Ph | H | H | H | H | 2-naphthyl | H |
| F-14 | Ph | H | H | H | H | H | 2-naphthyl |
| F-15 | Ph | H | H | H | H | 2-naphthyl | 2-naphthyl |
| F-16 | Ph | H | H | H | H | o-biphenylyl | H |
| F-17 | Ph | H | H | H | H | H | o-biphenylyl |
| F-18 | Ph | H | H | H | H | o-biphenylyl | o-biphenylyl |
| F-19 | Ph | H | H | H | H | m-biphenylyl | H |
| F-20 | Ph | H | H | H | H | H | m-biphenylyl |
| F-21 | Ph | H | H | H | H | m-biphenylyl | m-biphenylyl |
| F-22 | Ph | H | H | H | H | p-biphenylyl | H |
| F-23 | Ph | H | H | H | H | H | p-biphenylyl |
| F-24 | Ph | H | H | H | H | p-biphenylyl | p-biphenylyl |
| F-25 | 1-naphthyl | H | H | H | H | H | H |
| F-26 | 1-naphthyl | Ph | H | H | Ph | H | H |
| F-27 | 1-naphthyl | H | Ph | Ph | H | H | H |
| F-28 | 1-naphthyl | H | Ph | H | H | H | H |
| F-29 | 1-naphthyl | H | H | Ph | H | H | H |
| F-30 | 1-naphthyl | H | H | H | H | Ph | H |
| F-31 | 1-naphthyl | H | H | H | H | H | Ph |
| F-32 | 1-naphthyl | H | H | H | H | Ph | Ph |
| F-33 | 1-naphthyl | H | H | H | H | 1-naphthyl | H |
| F-34 | 1-naphthyl | H | H | H | H | H | 1-naphthyl |
| F-35 | 1-naphthyl | H | H | H | H | 1-naphthyl | 1-naphthyl |
| F-36 | 1-naphthyl | H | H | H | H | 2-naphthyl | H |
| F-37 | 1-naphthyl | H | H | H | H | H | 2-naphthyl |
| F-38 | 1-naphthyl | H | H | H | H | 2-naphthyl | 2-naphthyl |
| F-39 | 1-naphthyl | H | H | H | H | o-biphenylyl | H |
| F-40 | 1-naphthyl | H | H | H | H | H | o-biphenylyl |
| F-41 | 1-naphthyl | H | H | H | H | o-biphenylyl | o-biphenylyl |
| F-42 | 1-naphthyl | H | H | H | H | m-biphenylyl | H |
| F-43 | 1-naphthyl | H | H | H | H | H | m-biphenylyl |
| F-44 | 1-naphthyl | H | H | H | H | m-biphenylyl | m-biphenylyl |
| F-45 | 1-naphthyl | H | H | H | H | p-biphenylyl | H |
| F-46 | 1-naphthyl | H | H | H | H | H | p-biphenylyl |
| F-47 | 1-naphthyl | H | H | H | H | p-biphenylyl | p-biphenylyl |
| F-48 | 2-naphthyl | H | H | H | H | H | H |
| F-49 | 2-naphthyl | Ph | H | H | Ph | H | H |
| F-50 | 2-naphthyl | H | Ph | Ph | H | H | H |
| F-51 | 2-naphthyl | H | Ph | H | H | H | H |
| F-52 | 2-naphthyl | H | H | Ph | H | H | H |
| F-53 | 2-naphthyl | H | H | H | H | Ph | H |
| F-54 | 2-naphthyl | H | H | H | H | H | Ph |
| F-55 | 2-naphthyl | H | H | H | H | Ph | Ph |
| F-56 | 2-naphthyl | H | H | H | H | 1-naphthyl | H |
| F-57 | 2-naphthyl | H | H | H | H | H | 1-naphthyl |
| F-58 | 2-naphthyl | H | H | H | H | 1-naphthyl | 1-naphthyl |
| F-59 | 2-naphthyl | H | H | H | H | 2-naphthyl | H |
| F-60 | 2-naphthyl | H | H | H | H | H | 2-naphthyl |
| F-61 | 2-naphthyl | H | H | H | H | 2-naphthyl | 2-naphthyl |
| F-62 | 2-naphthyl | H | H | H | H | o-biphenylyl | H |
| F-63 | 2-naphthyl | H | H | H | H | H | o-biphenylyl |
| F-64 | 2-naphthyl | H | H | H | H | o-biphenylyl | o-biphenylyl |
| F-65 | 2-naphthyl | H | H | H | H | m-biphenylyl | H |
| F-66 | 2-naphthyl | H | H | H | H | H | m-biphenylyl |
| F-67 | 2-naphthyl | H | H | H | H | m-biphenylyl | m-biphenylyl |
| F-68 | 2-naphthyl | H | H | H | H | p-biphenylyl | H |
| F-69 | 2-naphthyl | H | H | H | H | H | p-biphenylyl |
| F-70 | 2-naphthyl | H | H | H | H | p-biphenylyl | p-biphenylyl |
| F-71 | o-biphenylyl | H | H | H | H | H | H |
| F-72 | o-biphenylyl | Ph | H | H | Ph | H | H |
| F-73 | o-biphenylyl | H | Ph | Ph | H | H | H |
| F-74 | o-biphenylyl | H | Ph | H | H | H | H |
| F-75 | o-biphenylyl | H | H | Ph | H | H | H |
| F-76 | o-biphenylyl | H | H | H | H | Ph | H |
| F-77 | o-biphenylyl | H | H | H | H | H | Ph |
| F-78 | o-biphenylyl | H | H | H | H | Ph | Ph |
| F-79 | o-biphenylyl | H | H | H | H | 1-naphthyl | H |
| F-80 | o-biphenylyl | H | H | H | H | H | 1-naphthyl |
| F-81 | o-biphenylyl | H | H | H | H | 1-naphthyl | 1-naphthyl |
| F-82 | o-biphenylyl | H | H | H | H | 2-naphthyl | H |
| F-83 | o-biphenylyl | H | H | H | H | H | 2-naphthyl |
| F-84 | o-biphenylyl | H | H | H | H | 2-naphthyl | 2-naphthyl |
| F-85 | o-biphenylyl | H | H | H | H | o-biphenylyl | H |

-continued

| | | | | | | | |
|---|---|---|---|---|---|---|---|
| F-86 | o-biphenylyl | H | H | H | H | H | o-biphenylyl |
| F-87 | o-biphenylyl | H | H | H | H | o-biphenylyl | o-biphenylyl |
| F-88 | o-biphenylyl | H | H | H | H | m-biphenylyl | H |
| F-89 | o-biphenylyl | H | H | H | H | H | m-biphenylyl |
| F-90 | o-biphenylyl | H | H | H | H | m-biphenylyl | m-biphenylyl |
| F-91 | o-biphenylyl | H | H | H | H | p-biphenylyl | H |
| F-92 | o-biphenylyl | H | H | H | H | H | p-biphenylyl |
| F-93 | o-biphenylyl | H | H | H | H | p-biphenylyl | p-biphenylyl |
| F-94 | m-biphenylyl | H | H | H | H | H | H |
| F-95 | m-biphenylyl | Ph | H | H | Ph | H | H |
| F-96 | m-biphenylyl | H | Ph | Ph | H | H | H |
| F-97 | m-biphenylyl | H | Ph | H | H | H | H |
| F-98 | m-biphenylyl | H | H | Ph | H | H | H |
| F-99 | m-biphenylyl | H | H | H | H | Ph | H |
| F-100 | m-biphenylyl | H | H | H | H | H | Ph |
| F-101 | m-biphenylyl | H | H | H | H | Ph | Ph |
| F-102 | m-biphenylyl | H | H | H | H | 1-naphthyl | H |
| F-103 | m-biphenylyl | H | H | H | H | H | 1-naphthyl |
| F-104 | m-biphenylyl | H | H | H | H | 1-naphthyl | 1-naphthyl |
| F-105 | m-biphenylyl | H | H | H | H | 2-naphthyl | H |
| F-106 | m-biphenylyl | H | H | H | H | H | 2-naphthyl |
| F-107 | m-biphenylyl | H | H | H | H | 2-naphthyl | 2-naphthyl |
| F-108 | m-biphenylyl | H | H | H | H | o-biphenylyl | H |
| F-109 | m-biphenylyl | H | H | H | H | H | o-biphenylyl |
| F-110 | m-biphenylyl | H | H | H | H | o-biphenylyl | o-biphenylyl |
| F-111 | m-biphenylyl | H | H | H | H | m-biphenylyl | H |
| F-112 | m-biphenylyl | H | H | H | H | H | m-biphenylyl |
| F-113 | m-biphenylyl | H | H | H | H | m-biphenylyl | m-biphenylyl |
| F-114 | m-biphenylyl | H | H | H | H | p-biphenylyl | H |
| F-115 | m-biphenylyl | H | H | H | H | H | p-biphenylyl |
| F-116 | m-biphenylyl | H | H | H | H | p-biphenylyl | p-biphenylyl |
| F-117 | p-biphenylyl | H | H | H | H | H | H |
| F-118 | p-biphenylyl | Ph | H | H | Ph | H | H |
| F-119 | p-biphenylyl | H | Ph | Ph | H | H | H |
| F-120 | p-biphenylyl | H | Ph | H | H | H | H |
| F-121 | p-biphenylyl | H | H | Ph | H | H | H |
| F-122 | p-biphenylyl | H | H | H | H | Ph | H |
| F-123 | p-biphenylyl | H | H | H | H | H | Ph |
| F-124 | p-biphenylyl | H | H | H | H | Ph | Ph |
| F-125 | p-biphenylyl | H | H | H | H | 1-naphthyl | H |
| F-126 | p-biphenylyl | H | H | H | H | H | 1-naphthyl |
| F-127 | p-biphenylyl | H | H | H | H | 1-naphthyl | 1-naphthyl |
| F-128 | p-biphenylyl | H | H | H | H | 2-naphthyl | H |
| F-129 | p-biphenylyl | H | H | H | H | H | 2-naphthyl |
| F-130 | p-biphenylyl | H | H | H | H | 2-naphthyl | 2-naphthyl |
| F-131 | p-biphenylyl | H | H | H | H | o-biphenylyl | H |
| F-132 | p-biphenylyl | H | H | H | H | H | o-biphenylyl |
| F-133 | p-biphenylyl | H | H | H | H | o-biphenylyl | o-biphenylyl |
| F-134 | p-biphenylyl | H | H | H | H | m-biphenylyl | H |
| F-135 | p-biphenylyl | H | H | H | H | H | m-biphenylyl |
| F-136 | p-biphenylyl | H | H | H | H | m-biphenylyl | m-biphenylyl |
| F-137 | p-biphenylyl | H | H | H | H | p-biphenylyl | H |
| F-138 | p-biphenylyl | H | H | H | H | H | p-biphenylyl |
| F-139 | p-biphenylyl | H | H | H | H | p-biphenylyl | p-biphenylyl |
| F-140 | o-tolyl | H | H | H | H | H | H |
| F-141 | o-tolyl | Ph | H | H | Ph | H | H |
| F-142 | o-tolyl | H | Ph | Ph | H | H | H |
| F-143 | o-tolyl | H | H | H | H | Ph | H |
| F-144 | o-tolyl | H | H | H | H | H | Ph |
| F-145 | o-tolyl | H | H | H | H | 1-naphthyl | H |
| F-146 | o-tolyl | H | H | H | H | H | 1-naphthyl |
| F-147 | o-tolyl | H | H | H | H | 2-naphthyl | H |
| F-148 | o-tolyl | H | H | H | H | H | 2-naphthyl |
| F-149 | o-tolyl | H | H | H | H | o-biphenylyl | H |
| F-150 | o-tolyl | H | H | H | H | H | o-biphenylyl |
| F-151 | o-tolyl | H | H | H | H | m-biphenylyl | H |
| F-152 | o-tolyl | H | H | H | H | H | m-biphenylyl |
| F-153 | o-tolyl | H | H | H | H | p-biphenylyl | H |
| F-154 | o-tolyl | H | H | H | H | H | p-biphenylyl |
| F-155 | o-tolyl | H | H | H | H | o-tolyl | H |
| F-156 | o-tolyl | H | H | H | H | H | o-tolyl |
| F-157 | m-tolyl | H | H | H | H | H | H |
| F-158 | m-tolyl | Ph | H | H | Ph | H | H |
| F-159 | m-tolyl | H | Ph | Ph | H | H | H |
| F-160 | m-tolyl | H | H | H | H | Ph | H |
| F-161 | m-tolyl | H | H | H | H | H | Ph |
| F-162 | m-tolyl | H | H | H | H | 1-naphthyl | H |
| F-163 | m-tolyl | H | H | H | H | H | 1-naphthyl |
| F-164 | m-tolyl | H | H | H | H | 2-naphthyl | H |

-continued

| | | | | | | | |
|---|---|---|---|---|---|---|---|
| F-165 | m-tolyl | H | H | H | H | H | 2-naphthyl |
| F-166 | m-tolyl | H | H | H | H | o-biphenylyl | H |
| F-167 | m-tolyl | H | H | H | H | H | o-biphenylyl |
| F-168 | m-tolyl | H | H | H | H | m-biphenylyl | H |
| F-169 | m-tolyl | H | H | H | H | H | m-biphenylyl |
| F-170 | m-tolyl | H | H | H | H | p-biphenylyl | H |
| F-171 | m-tolyl | H | H | H | H | H | p-biphenylyl |
| F-172 | m-tolyl | H | H | H | H | m-tolyl | H |
| F-173 | m-tolyl | H | H | H | H | H | m-tolyl |
| F-174 | p-tolyl | H | H | H | H | H | H |
| F-175 | p-tolyl | Ph | H | H | Ph | H | H |
| F-176 | p-tolyl | H | Ph | Ph | H | H | H |
| F-177 | p-tolyl | H | H | H | H | Ph | H |
| F-178 | p-tolyl | H | H | H | H | H | Ph |
| F-179 | p-tolyl | H | H | H | H | 1-naphthyl | H |
| F-180 | p-tolyl | H | H | H | H | H | 1-naphthyl |
| F-181 | p-tolyl | H | H | H | H | 2-naphthyl | H |
| F-182 | p-tolyl | H | H | H | H | H | 2-naphthyl |
| F-183 | p-tolyl | H | H | H | H | o-biphenylyl | H |
| F-184 | p-tolyl | H | H | H | H | H | o-biphenylyl |
| F-185 | p-tolyl | H | H | H | H | m-biphenylyl | H |
| F-186 | p-tolyl | H | H | H | H | H | m-biphenylyl |
| F-187 | p-tolyl | H | H | H | H | p-biphenylyl | H |
| F-188 | p-tolyl | H | H | H | H | H | p-biphenylyl |
| F-189 | p-tolyl | H | H | H | H | p-tolyl | H |
| F-190 | p-tolyl | H | H | H | H | H | p-tolyl |
| F-191 | Ph | H | —CH3 | —CH3 | H | H | H |
| F-192 | 1-naphtyl | H | —CH3 | —CH3 | H | H | H |
| F-193 | 2-naphthyl | H | —CH3 | —CH3 | H | H | H |
| F-194 | o-biphenylyl | H | —CH3 | —CH3 | H | H | H |
| F-195 | m-biphenylyl | H | —CH3 | —CH3 | H | H | H |
| F-196 | p-biphenylyl | H | —CH3 | —CH3 | H | H | H |
| F-197 | o-tolyl | H | —CH3 | —CH3 | H | H | H |
| F-198 | m-tolyl | H | —CH3 | —CH3 | H | H | H |
| F-199 | p-tolyl | H | —CH3 | —CH3 | H | H | H |
| F-200 | Ph | H | H | H | H | —CH3 | H |
| F-201 | 1-naphtyl | H | H | H | H | —CH3 | H |
| F-202 | 2-naphthyl | H | H | H | H | —CH3 | H |
| F-203 | o-biphenylyl | H | H | H | H | —CH3 | H |
| F-204 | m-biphenylyl | H | H | H | H | —CH3 | H |
| F-205 | p-biphenylyl | H | H | H | H | —CH3 | H |
| F-206 | o-tolyl | H | H | H | H | —CH3 | H |
| F-207 | m-tolyl | H | H | H | H | —CH3 | H |
| F-208 | p-tolyl | H | H | H | H | —CH3 | H |
| F-209 | Ph | H | H | H | H | H | —CH3 |
| F-210 | 1-naphtyl | H | H | H | H | H | —CH3 |
| F-211 | 2-naphthyl | H | H | H | H | H | —CH3 |
| F-212 | o-biphenylyl | H | H | H | H | H | —CH3 |
| F-213 | m-biphenylyl | H | H | H | H | H | —CH3 |
| F-214 | p-biphenylyl | H | H | H | H | H | —CH3 |
| F-215 | o-tolyl | H | H | H | H | H | —CH3 |
| F-216 | m-tolyl | H | H | H | H | H | —CH3 |
| F-217 | p-tolyl | H | H | H | H | H | —CH3 |
| F-218 | Ph | H | H | H | H | —CH3 | —CH3 |
| F-219 | 1-naphtyl | H | H | H | H | —CH3 | —CH3 |
| F-220 | 2-naphthyl | H | H | H | H | —CH3 | —CH3 |
| F-221 | o-biphenylyl | H | H | H | H | —CH3 | —CH3 |
| F-222 | m-biphenylyl | H | H | H | H | —CH3 | —CH3 |
| F-223 | p-biphenylyl | H | H | H | H | —CH3 | —CH3 |
| F-224 | o-tolyl | H | H | H | H | —CH3 | —CH3 |
| F-225 | m-tolyl | H | H | H | H | —CH3 | —CH3 |
| F-226 | p-tolyl | H | H | H | H | —CH3 | —CH3 |
| F-227 | Ph | H | H | H | H | H | DPA |
| F-228 | 1-naphtyl | H | H | H | H | H | DPA |
| F-229 | 2-naphthyl | H | H | H | H | H | DPA |
| F-230 | o-biphenylyl | H | H | H | H | H | DPA |
| F-231 | m-biphenylyl | H | H | H | H | H | DPA |
| F-232 | p-biphenylyl | H | H | H | H | H | DPA |
| F-233 | Ph | H | H | H | H | DPA | H |
| F-234 | 1-naphtyl | H | H | H | H | DPA | H |
| F-235 | 2-naphthyl | H | H | H | H | DPA | H |
| F-236 | o-biphenylyl | H | H | H | H | DPA | H |
| F-237 | m-biphenylyl | H | H | H | H | DPA | H |
| F-238 | p-biphenylyl | H | H | H | H | DPA | H |
| F-239 | Ph | H | H | H | H | H | TPA |
| F-240 | 1-naphtyl | H | H | H | H | H | TPA |
| F-241 | 2-naphthyl | H | H | H | H | H | TPA |
| F-242 | o-biphenylyl | H | H | H | H | H | TPA |
| F-243 | m-biphenylyl | H | H | H | H | H | TPA |

-continued
| | | | | | | | |
|---|---|---|---|---|---|---|---|
| F-244 | p-biphenylyl | H | H | H | H | H | TPA |
| F-245 | Ph | H | H | H | H | TPA | H |
| F-246 | 1-naphtyl | H | H | H | H | TPA | H |
| F-247 | 2-naphthyl | H | H | H | H | TPA | H |
| F-248 | o-biphenylyl | H | H | H | H | TPA | H |
| F-249 | m-biphenylyl | H | H | H | H | TPA | H |
| F-250 | p-biphenylyl | H | H | H | H | TPA | H |
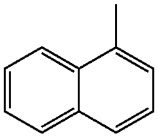
1-naphthyl
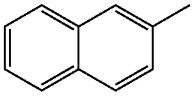
2-naphthyl
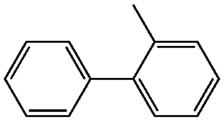
o-biphenylyl
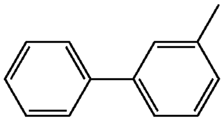
m-biphenylyl
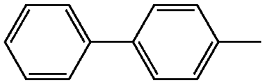
p-biphenylyl
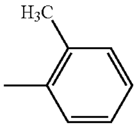
o-tolyl
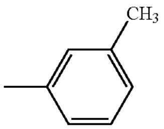
m-tolyl
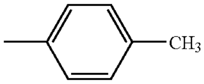
p-tolyl
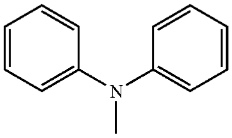
DPA -continued

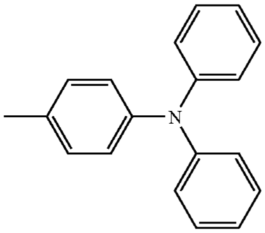

TPA

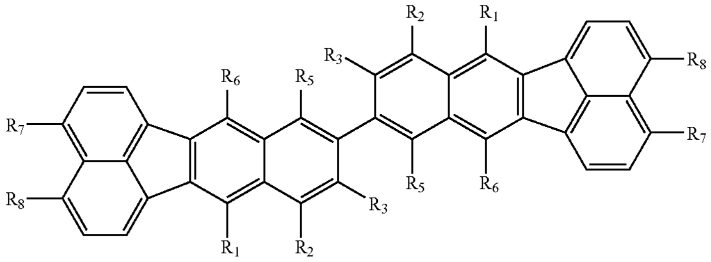

TypeG

| | $R_1$ | $R_2$ | $R_3$ | $R_5$ | $R_6$ | $R_7$ | $R_8$ |
|---|---|---|---|---|---|---|---|
| G-1 | H | H | H | H | H | H | H |
| G-2 | Ph | H | H | H | Ph | H | H |
| G-3 | Ph | Ph | H | H | Ph | H | H |
| G-4 | Ph | H | H | Ph | Ph | H | H |
| G-5 | Ph | Ph | H | Ph | Ph | H | H |
| G-6 | Ph | H | Ph | H | Ph | H | H |
| G-7 | Ph | H | H | H | Ph | Ph | H |
| G-8 | Ph | H | H | H | Ph | H | Ph |
| G-9 | Ph | H | H | H | Ph | Ph | Ph |
| G-10 | Ph | H | H | H | Ph | 1-naphthyl | H |
| G-11 | Ph | H | H | H | Ph | H | 1-naphthyl |
| G-12 | Ph | H | H | H | Ph | 1-naphthyl | 1-naphthyl |
| G-13 | Ph | H | H | H | Ph | 2-naphthyl | H |
| G-14 | Ph | H | H | H | Ph | H | 2-naphthyl |
| G-15 | Ph | H | H | H | Ph | 2-naphthyl | 2-naphthyl |
| G-16 | Ph | H | H | H | Ph | o-biphenylyl | H |
| G-17 | Ph | H | H | H | Ph | H | o-biphenylyl |
| G-18 | Ph | H | H | H | Ph | o-biphenylyl | o-biphenylyl |
| G-19 | Ph | H | H | H | Ph | m-biphenylyl | H |
| G-20 | Ph | H | H | H | Ph | H | m-biphenylyl |
| G-21 | Ph | H | H | H | Ph | m-biphenylyl | m-biphenylyl |
| G-22 | Ph | H | H | H | Ph | p-biphenylyl | H |
| G-23 | Ph | H | H | H | Ph | H | p-biphenylyl |
| G-24 | Ph | H | H | H | Ph | p-biphenylyl | p-biphenylyl |
| G-25 | 1-naphthyl | H | H | H | 1-naphthyl | H | H |
| G-26 | 1-naphthyl | Ph | H | H | 1-naphthyl | H | H |
| G-27 | 1-naphthyl | H | H | Ph | 1-naphthyl | H | H |
| G-28 | 1-naphthyl | Ph | H | Ph | 1-naphthyl | H | H |
| G-29 | 1-naphthyl | H | Ph | H | 1-naphthyl | H | H |
| G-30 | 1-naphthyl | H | H | H | 1-naphthyl | Ph | H |
| G-31 | 1-naphthyl | H | H | H | 1-naphthyl | H | Ph |
| G-32 | 1-naphthyl | H | H | H | 1-naphthyl | Ph | Ph |
| G-33 | 1-naphthyl | H | H | H | 1-naphthyl | 1-naphthyl | H |
| G-34 | 1-naphthyl | H | H | H | 1-naphthyl | H | 1-naphthyl |
| G-35 | 1-naphthyl | H | H | H | 1-naphthyl | 1-naphthyl | 1-naphthyl |
| G-36 | 1-naphthyl | H | H | H | 1-naphthyl | 2-naphthyl | H |
| G-37 | 1-naphthyl | H | H | H | 1-naphthyl | H | 2-naphthyl |
| G-38 | 1-naphthyl | H | H | H | 1-naphthyl | 2-naphthyl | 2-naphthyl |
| G-39 | 1-naphthyl | H | H | H | 1-naphthyl | o-biphenylyl | H |
| G-40 | 1-naphthyl | H | H | H | 1-naphthyl | H | o-biphenylyl |
| G-41 | 1-naphthyl | H | H | H | 1-naphthyl | o-biphenylyl | o-biphenylyl |
| G-42 | 1-naphthyl | H | H | H | 1-naphthyl | m-biphenylyl | H |
| G-43 | 1-naphthyl | H | H | H | 1-naphthyl | H | m-biphenylyl |
| G-44 | 1-naphthyl | H | H | H | 1-naphthyl | m-biphenylyl | m-biphenylyl |

-continued

| | | | | | | | |
|---|---|---|---|---|---|---|---|
| G-45 | 1-naphthyl | H | H | H | 1-naphthyl | p-biphenylyl | H |
| G-46 | 1-naphthyl | H | H | H | 1-naphthyl | H | p-biphenylyl |
| G-47 | 1-naphthyl | H | H | H | 1-naphthyl | p-biphenylyl | p-biphenylyl |
| G-48 | 2-naphthyl | H | H | H | 2-naphthyl | H | H |
| G-49 | 2-naphthyl | Ph | H | H | 2-naphthyl | H | H |
| G-50 | 2-naphthyl | H | H | Ph | 2-naphthyl | H | H |
| G-51 | 2-naphthyl | Ph | H | Ph | 2-naphthyl | H | H |
| G-52 | 2-naphthyl | H | Ph | H | 2-naphthyl | H | H |
| G-53 | 2-naphthyl | H | H | H | 2-naphthyl | Ph | H |
| G-54 | 2-naphthyl | H | H | H | 2-naphthyl | H | Ph |
| G-55 | 2-naphthyl | H | H | H | 2-naphthyl | Ph | Ph |
| G-56 | 2-naphthyl | H | H | H | 2-naphthyl | 1-naphthyl | H |
| G-57 | 2-naphthyl | H | H | H | 2-naphthyl | H | 1-naphthyl |
| G-58 | 2-naphthyl | H | H | H | 2-naphthyl | 1-naphthyl | 1-naphthyl |
| G-59 | 2-naphthyl | H | H | H | 2-naphthyl | 2-naphthyl | H |
| G-60 | 2-naphthyl | H | H | H | 2-naphthyl | H | 2-naphthyl |
| G-61 | 2-naphthyl | H | H | H | 2-naphthyl | 2-naphthyl | 2-naphthyl |
| G-62 | 2-naphthyl | H | H | H | 2-naphthyl | o-biphenylyl | H |
| G-63 | 2-naphthyl | H | H | H | 2-naphthyl | H | o-biphenylyl |
| G-64 | 2-naphthyl | H | H | H | 2-naphthyl | o-biphenylyl | o-biphenylyl |
| G-65 | 2-naphthyl | H | H | H | 2-naphthyl | m-biphenylyl | H |
| G-66 | 2-naphthyl | H | H | H | 2-naphthyl | H | m-biphenylyl |
| G-67 | 2-naphthyl | H | H | H | 2-naphthyl | m-biphenylyl | m-biphenylyl |
| G-68 | 2-naphthyl | H | H | H | 2-naphthyl | p-biphenylyl | H |
| G-69 | 2-naphthyl | H | H | H | 2-naphthyl | H | p-biphenylyl |
| G-70 | 2-naphthyl | H | H | H | 2-naphthyl | p-biphenylyl | p-biphenylyl |
| G-71 | o-biphenylyl | H | H | H | o-biphenylyl | H | H |
| G-72 | o-biphenylyl | Ph | H | H | o-biphenylyl | H | H |
| G-73 | o-biphenylyl | H | H | Ph | o-biphenylyl | H | H |
| G-74 | o-biphenylyl | Ph | H | Ph | o-biphenylyl | H | H |
| G-75 | o-biphenylyl | H | Ph | H | o-biphenylyl | H | H |
| G-76 | o-biphenylyl | H | H | H | o-biphenylyl | Ph | H |
| G-77 | o-biphenylyl | H | H | H | o-biphenylyl | H | Ph |
| G-78 | o-biphenylyl | H | H | H | o-biphenylyl | Ph | Ph |
| G-79 | o-biphenylyl | H | H | H | o-biphenylyl | 1-naphthyl | H |
| G-80 | o-biphenylyl | H | H | H | o-biphenylyl | H | 1-naphthyl |
| G-81 | o-biphenylyl | H | H | H | o-biphenylyl | 1-naphthyl | 1-naphthyl |
| G-82 | o-biphenylyl | H | H | H | o-biphenylyl | 2-naphthyl | H |
| G-83 | o-biphenylyl | H | H | H | o-biphenylyl | H | 2-naphthyl |
| G-84 | o-biphenylyl | H | H | H | o-biphenylyl | 2-naphthyl | 2-naphthyl |
| G-85 | o-biphenylyl | H | H | H | o-biphenylyl | o-biphenylyl | H |
| G-86 | o-biphenylyl | H | H | H | o-biphenylyl | H | o-biphenylyl |
| G-87 | o-biphenylyl | H | H | H | o-biphenylyl | o-biphenylyl | o-biphenylyl |
| G-88 | o-biphenylyl | H | H | H | o-biphenylyl | m-biphenylyl | H |
| G-89 | o-biphenylyl | H | H | H | o-biphenylyl | H | m-biphenylyl |
| G-90 | o-biphenylyl | H | H | H | o-biphenylyl | m-biphenylyl | m-biphenylyl |
| G-91 | o-biphenylyl | H | H | H | o-biphenylyl | p-biphenylyl | H |
| G-92 | o-biphenylyl | H | H | H | o-biphenylyl | H | p-biphenylyl |
| G-93 | o-biphenylyl | H | H | H | o-biphenylyl | p-biphenylyl | p-biphenylyl |
| G-94 | m-biphenylyl | H | H | H | m-biphenylyl | H | H |
| G-95 | m-biphenylyl | Ph | H | H | m-biphenylyl | H | H |
| G-96 | m-biphenylyl | H | H | Ph | m-biphenylyl | H | H |
| G-97 | m-biphenylyl | Ph | H | Ph | m-biphenylyl | H | H |
| G-98 | m-biphenylyl | H | Ph | H | m-biphenylyl | H | H |
| G-99 | m-biphenylyl | H | H | H | m-biphenylyl | Ph | H |
| G-100 | m-biphenylyl | H | H | H | m-biphenylyl | H | Ph |
| G-101 | m-biphenylyl | H | H | H | m-biphenylyl | Ph | Ph |
| G-102 | m-biphenylyl | H | H | H | m-biphenylyl | 1-naphthyl | H |
| G-103 | m-biphenylyl | H | H | H | m-biphenylyl | H | 1-naphthyl |
| G-104 | m-biphenylyl | H | H | H | m-biphenylyl | 1-naphthyl | 1-naphthyl |
| G-105 | m-biphenylyl | H | H | H | m-biphenylyl | 2-naphthyl | H |
| G-106 | m-biphenylyl | H | H | H | m-biphenylyl | H | 2-naphthyl |
| G-107 | m-biphenylyl | H | H | H | m-biphenylyl | 2-naphthyl | 2-naphthyl |
| G-108 | m-biphenylyl | H | H | H | m-biphenylyl | o-biphenylyl | H |
| G-109 | m-biphenylyl | H | H | H | m-biphenylyl | H | o-biphenylyl |
| G-110 | m-biphenylyl | H | H | H | m-biphenylyl | o-biphenylyl | o-biphenylyl |
| G-111 | m-biphenylyl | H | H | H | m-biphenylyl | m-biphenylyl | H |
| G-112 | m-biphenylyl | H | H | H | m-biphenylyl | H | m-biphenylyl |
| G-113 | m-biphenylyl | H | H | H | m-biphenylyl | m-biphenylyl | m-biphenylyl |
| G-114 | m-biphenylyl | H | H | H | m-biphenylyl | p-biphenylyl | H |
| G-115 | m-biphenylyl | H | H | H | m-biphenylyl | H | p-biphenylyl |
| G-116 | m-biphenylyl | H | H | H | m-biphenylyl | p-biphenylyl | p-biphenylyl |
| G-117 | p-biphenylyl | H | H | H | p-biphenylyl | H | H |
| G-118 | p-biphenylyl | Ph | H | H | p-biphenylyl | H | H |
| G-119 | p-biphenylyl | H | H | Ph | p-biphenylyl | H | H |
| G-120 | p-biphenylyl | Ph | H | Ph | p-biphenylyl | H | H |
| G-121 | p-biphenylyl | H | Ph | H | p-biphenylyl | H | H |
| G-122 | p-biphenylyl | H | H | H | p-biphenylyl | Ph | H |
| G-123 | p-biphenylyl | H | H | H | p-biphenylyl | H | Ph |

-continued

| | | | | | | | |
|---|---|---|---|---|---|---|---|
| G-124 | p-biphenylyl | H | H | H | p-biphenylyl | Ph | Ph |
| G-125 | p-biphenylyl | H | H | H | p-biphenylyl | 1-naphthyl | H |
| G-126 | p-biphenylyl | H | H | H | p-biphenylyl | H | 1-naphthyl |
| G-127 | p-biphenylyl | H | H | H | p-biphenylyl | 1-naphthyl | 1-naphthyl |
| G-128 | p-biphenylyl | H | H | H | p-biphenylyl | 2-naphthyl | H |
| G-129 | p-biphenylyl | H | H | H | p-biphenylyl | H | 2-naphthyl |
| G-130 | p-biphenylyl | H | H | H | p-biphenylyl | 2-naphthyl | 2-naphthyl |
| G-131 | p-biphenylyl | H | H | H | p-biphenylyl | o-biphenylyl | H |
| G-132 | p-biphenylyl | H | H | H | p-biphenylyl | H | o-biphenylyl |
| G-133 | p-biphenylyl | H | H | H | p-biphenylyl | o-biphenylyl | o-biphenylyl |
| G-134 | p-biphenylyl | H | H | H | p-biphenylyl | m-biphenylyl | H |
| G-135 | p-biphenylyl | H | H | H | p-biphenylyl | H | m-biphenylyl |
| G-136 | p-biphenylyl | H | H | H | p-biphenylyl | m-biphenylyl | m-biphenylyl |
| G-137 | p-biphenylyl | H | H | H | p-biphenylyl | p-biphenylyl | H |
| G-138 | p-biphenylyl | H | H | H | p-biphenylyl | H | p-biphenylyl |
| G-139 | p-biphenylyl | H | H | H | p-biphenylyl | p-biphenylyl | p-biphenylyl |
| G-140 | o-tolyl | H | H | H | o-tolyl | H | H |
| G-141 | o-tolyl | Ph | H | Ph | o-tolyl | H | H |
| G-142 | o-tolyl | H | Ph | H | o-tolyl | H | H |
| G-143 | o-tolyl | H | H | H | o-tolyl | Ph | H |
| G-144 | o-tolyl | H | H | H | o-tolyl | H | Ph |
| G-145 | o-tolyl | H | H | H | o-tolyl | 1-naphthyl | H |
| G-146 | o-tolyl | H | H | H | o-tolyl | H | 1-naphthyl |
| G-147 | o-tolyl | H | H | H | o-tolyl | 2-naphthyl | H |
| G-148 | o-tolyl | H | H | H | o-tolyl | H | 2-naphthyl |
| G-149 | o-tolyl | H | H | H | o-tolyl | o-biphenylyl | H |
| G-150 | o-tolyl | H | H | H | o-tolyl | H | o-biphenylyl |
| G-151 | o-tolyl | H | H | H | o-tolyl | m-biphenylyl | H |
| G-152 | o-tolyl | H | H | H | o-tolyl | H | m-biphenylyl |
| G-153 | o-tolyl | H | H | H | o-tolyl | p-biphenylyl | H |
| G-154 | o-tolyl | H | H | H | o-tolyl | H | p-biphenylyl |
| G-155 | o-tolyl | H | H | H | o-tolyl | o-tolyl | H |
| G-156 | o-tolyl | H | H | H | o-tolyl | H | o-tolyl |
| G-157 | m-tolyl | H | H | H | m-tolyl | H | H |
| G-158 | m-tolyl | Ph | H | Ph | m-tolyl | H | H |
| G-159 | m-tolyl | H | Ph | H | m-tolyl | H | H |
| G-160 | m-tolyl | H | H | H | m-tolyl | Ph | H |
| G-161 | m-tolyl | H | H | H | m-tolyl | H | Ph |
| G-162 | m-tolyl | H | H | H | m-tolyl | 1-naphthyl | H |
| G-163 | m-tolyl | H | H | H | m-tolyl | H | 1-naphthyl |
| G-164 | m-tolyl | H | H | H | m-tolyl | 2-naphthyl | H |
| G-165 | m-tolyl | H | H | H | m-tolyl | H | 2-naphthyl |
| G-166 | m-tolyl | H | H | H | m-tolyl | o-biphenylyl | H |
| G-167 | m-tolyl | H | H | H | m-tolyl | H | o-biphenylyl |
| G-168 | m-tolyl | H | H | H | m-tolyl | m-biphenylyl | H |
| G-169 | m-tolyl | H | H | H | m-tolyl | H | m-biphenylyl |
| G-170 | m-tolyl | H | H | H | m-tolyl | p-biphenylyl | H |
| G-171 | m-tolyl | H | H | H | m-tolyl | H | p-biphenylyl |
| G-172 | m-tolyl | H | H | H | m-tolyl | m-tolyl | H |
| G-173 | m-tolyl | H | H | H | m-tolyl | H | m-tolyl |
| G-174 | p-tolyl | H | H | H | p-tolyl | H | H |
| G-175 | p-tolyl | Ph | H | Ph | p-tolyl | H | H |
| G-176 | p-tolyl | H | Ph | H | p-tolyl | H | H |
| G-177 | p-tolyl | H | H | H | p-tolyl | Ph | H |
| G-178 | p-tolyl | H | H | H | p-tolyl | H | Ph |
| G-179 | p-tolyl | H | H | H | p-tolyl | 1-naphthyl | H |
| G-180 | p-tolyl | H | H | H | p-tolyl | H | 1-naphthyl |
| G-181 | p-tolyl | H | H | H | p-tolyl | 2-naphthyl | H |
| G-182 | p-tolyl | H | H | H | p-tolyl | H | 2-naphthyl |
| G-183 | p-tolyl | H | H | H | p-tolyl | o-biphenylyl | H |
| G-184 | p-tolyl | H | H | H | p-tolyl | H | o-biphenylyl |
| G-185 | p-tolyl | H | H | H | p-tolyl | m-biphenylyl | H |
| G-186 | p-tolyl | H | H | H | p-tolyl | H | m-biphenylyl |
| G-187 | p-tolyl | H | H | H | p-tolyl | p-biphenylyl | H |
| G-188 | p-tolyl | H | H | H | p-tolyl | H | p-biphenylyl |
| G-189 | p-tolyl | H | H | H | p-tolyl | p-tolyl | H |
| G-190 | p-tolyl | H | H | H | p-tolyl | H | p-tolyl |
| G-191 | Ph | H | —CH3 | H | Ph | H | H |
| G-192 | 1-naphtyl | H | —CH3 | H | 1-naphtyl | H | H |
| G-193 | 2-naphthyl | H | —CH3 | H | 2-naphthyl | H | H |
| G-194 | o-biphenylyl | H | —CH3 | H | o-biphenylyl | H | H |
| G-195 | m-biphenylyl | H | —CH3 | H | m-biphenylyl | H | H |
| G-196 | p-biphenylyl | H | —CH3 | H | p-biphenylyl | H | H |
| G-197 | o-tolyl | H | —CH3 | H | o-tolyl | H | H |
| G-198 | m-tolyl | H | —CH3 | H | m-tolyl | H | H |
| G-199 | p-tolyl | H | —CH3 | H | p-tolyl | H | H |
| G-200 | Ph | H | H | H | Ph | —CH3 | H |
| G-201 | 1-naphtyl | H | H | H | 1-naphtyl | —CH3 | H |
| G-202 | 2-naphthyl | H | H | H | 2-naphthyl | —CH3 | H |

-continued

| | | | | | | | |
|---|---|---|---|---|---|---|---|
| G-203 | o-biphenylyl | H | H | H | o-biphenylyl | —CH3 | H |
| G-204 | m-biphenylyl | H | H | H | m-biphenylyl | —CH3 | H |
| G-205 | p-biphenylyl | H | H | H | p-biphenylyl | —CH3 | H |
| G-206 | o-tolyl | H | H | H | o-tolyl | —CH3 | H |
| G-207 | m-tolyl | H | H | H | m-tolyl | —CH3 | H |
| G-208 | p-tolyl | H | H | H | p-tolyl | —CH3 | H |
| G-209 | Ph | H | H | H | Ph | H | —CH3 |
| G-210 | 1-naphtyl | H | H | H | 1-naphtyl | H | —CH3 |
| G-211 | 2-naphthyl | H | H | H | 2-naphthyl | H | —CH3 |
| G-212 | o-biphenylyl | H | H | H | o-biphenylyl | H | —CH3 |
| G-213 | m-biphenylyl | H | H | H | m-biphenylyl | H | —CH3 |
| G-214 | p-biphenylyl | H | H | H | p-biphenylyl | H | —CH3 |
| G-215 | o-tolyl | H | H | H | o-tolyl | H | —CH3 |
| G-216 | m-tolyl | H | H | H | m-tolyl | H | —CH3 |
| G-217 | p-tolyl | H | H | H | p-tolyl | H | —CH3 |
| G-218 | Ph | H | H | H | Ph | —CH3 | —CH3 |
| G-219 | 1-naphtyl | H | H | H | 1-naphtyl | —CH3 | —CH3 |
| G-220 | 2-naphthyl | H | H | H | 2-naphthyl | —CH3 | —CH3 |
| G-221 | o-biphenylyl | H | H | H | o-biphenylyl | —CH3 | —CH3 |
| G-222 | m-biphenylyl | H | H | H | m-biphenylyl | —CH3 | —CH3 |
| G-223 | p-biphenylyl | H | H | H | p-biphenylyl | —CH3 | —CH3 |
| G-224 | o-tolyl | H | H | H | o-tolyl | —CH3 | —CH3 |
| G-225 | m-tolyl | H | H | H | m-tolyl | —CH3 | —CH3 |
| G-226 | p-tolyl | H | H | H | p-tolyl | —CH3 | —CH3 |
| G-227 | Ph | H | H | H | Ph | H | DPA |
| G-228 | 1-naphtyl | H | H | H | 1-naphtyl | H | DPA |
| G-229 | 2-naphthyl | H | H | H | 2-naphthyl | H | DPA |
| G-230 | o-biphenylyl | H | H | H | o-biphenylyl | H | DPA |
| G-231 | m-biphenylyl | H | H | H | m-biphenylyl | H | DPA |
| G-232 | p-biphenylyl | H | H | H | p-biphenylyl | H | DPA |
| G-233 | Ph | H | H | H | Ph | DPA | H |
| G-234 | 1-naphtyl | H | H | H | 1-naphtyl | DPA | H |
| G-235 | 2-naphthyl | H | H | H | 2-naphthyl | DPA | H |
| G-236 | o-biphenylyl | H | H | H | o-biphenylyl | DPA | H |
| G-237 | m-biphenylyl | H | H | H | m-biphenylyl | DPA | H |
| G-238 | p-biphenylyl | H | H | H | p-biphenylyl | DPA | H |
| G-239 | Ph | H | H | H | Ph | H | TPA |
| G-240 | 1-naphtyl | H | H | H | 1-naphtyl | H | TPA |
| G-241 | 2-naphthyl | H | H | H | 2-naphthyl | H | TPA |
| G-242 | o-biphenylyl | H | H | H | o-biphenylyl | H | TPA |
| G-243 | m-biphenylyl | H | H | H | m-biphenylyl | H | TPA |
| G-244 | p-biphenylyl | H | H | H | p-biphenylyl | H | TPA |
| G-245 | Ph | H | H | H | Ph | TPA | H |
| G-246 | 1-naphtyl | H | H | H | 1-naphtyl | TPA | H |
| G-247 | 2-naphthyl | H | H | H | 2-naphthyl | TPA | H |
| G-248 | o-biphenylyl | H | H | H | o-biphenylyl | TPA | H |
| G-249 | m-biphenylyl | H | H | H | m-biphenylyl | TPA | H |
| G-250 | p-biphenylyl | H | H | H | p-biphenylyl | TPA | H |
| G-251 | Ph | H | H | H | 1-naphthyl | H | H |
| G-252 | Ph | H | H | H | 2-naphthyl | H | H |
| G-253 | Ph | H | H | H | o-biphenylyl | H | H |
| G-254 | Ph | H | H | H | m-biphenylyl | H | H |
| G-255 | Ph | H | H | H | p-biphenylyl | H | H |
| G-256 | Ph | H | H | H | O-tolyly | H | H |
| G-257 | Ph | H | H | H | m-tolyl | H | H |
| G-258 | Ph | H | H | H | p-tolyl | H | H |
| G-259 | 1-naphthyl | H | H | H | 2-naphthyl | H | H |
| G-260 | 1-naphthyl | H | H | H | o-biphenylyl | H | H |
| G-261 | 1-naphthyl | H | H | H | m-biphenylyl | H | H |
| G-262 | 1-naphthyl | H | H | H | p-biphenylyl | H | H |
| G-263 | 1-naphthyl | H | H | H | O-tolyly | H | H |
| G-264 | 1-naphthyl | H | H | H | m-tolyl | H | H |
| G-265 | 1-naphthyl | H | H | H | p-tolyl | H | H |
| G-266 | 2-naphthyl | H | H | H | o-biphenylyl | H | H |
| G-267 | 2-naphthyl | H | H | H | m-biphenylyl | H | H |
| G-268 | 2-naphthyl | H | H | H | p-biphenylyl | H | H |
| G-269 | 2-naphthyl | H | H | H | O-tolyly | H | H |
| G-270 | 2-naphthyl | H | H | H | m-tolyl | H | H |
| G-271 | 2-naphthyl | H | H | H | p-tolyl | H | H |
| G-272 | o-biphenylyl | H | H | H | m-biphenylyl | H | H |
| G-273 | o-biphenylyl | H | H | H | p-biphenylyl | H | H |
| G-274 | o-biphenylyl | H | H | H | O-tolyly | H | H |
| G-275 | o-biphenylyl | H | H | H | m-tolyl | H | H |
| G-276 | o-biphenylyl | H | H | H | p-tolyl | H | H |
| G-277 | m-biphenylyl | H | H | H | p-biphenylyl | H | H |
| G-278 | m-biphenylyl | H | H | H | O-tolyly | H | H |
| G-279 | m-biphenylyl | H | H | H | m-tolyl | H | H |
| G-280 | m-biphenylyl | H | H | H | p-tolyl | H | H |
| G-281 | p-biphenylyl | H | H | H | O-tolyly | H | H |

-continued
| | | | | | | | |
|---|---|---|---|---|---|---|---|
| G-282 | p-biphenylyl | H | H | H | m-tolyl | H | H |
| G-283 | p-biphenylyl | H | H | H | p-tolyl | H | H |
| G-284 | O-tolyly | H | H | H | m-tolyl | H | H |
| G-285 | O-tolyly | H | H | H | p-tolyl | H | H |
| G-286 | m-tolyly | H | H | H | p-tolyl | H | H |
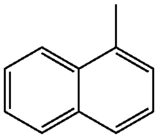
1-naphthyl
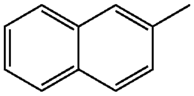
2-naphthyl
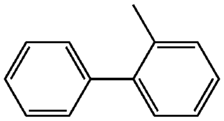
o-biphenylyl
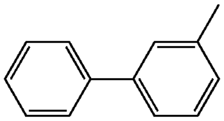
m-biphenylyl
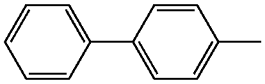
p-biphenylyl
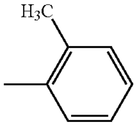
o-tolyl
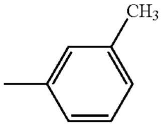
m-tolyl
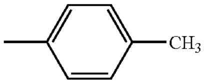
p-tolyl
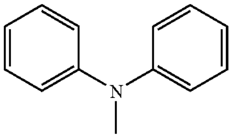
DPA
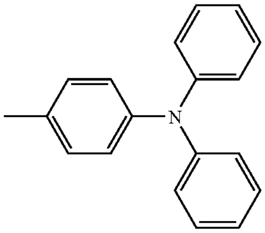
TPA

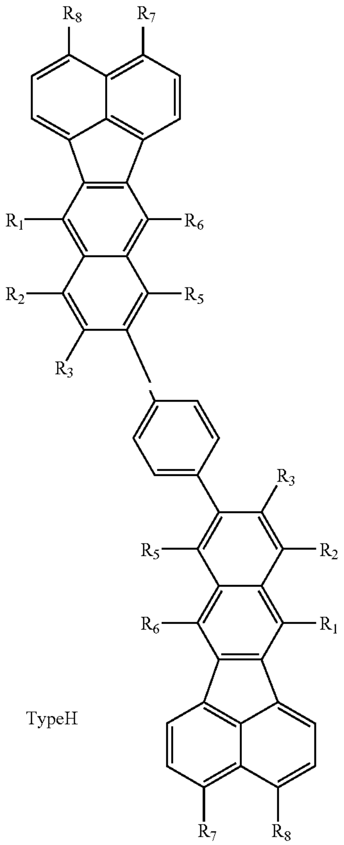

TypeH

| | $R_1$ | $R_2$ | $R_3$ | $R_5$ | $R_6$ | $R_7$ | $R_8$ |
|---|---|---|---|---|---|---|---|
| H-1 | H | H | H | H | H | H | H |
| H-2 | Ph | H | H | H | Ph | H | H |
| H-3 | Ph | Ph | H | H | Ph | H | H |
| H-4 | Ph | H | H | Ph | Ph | H | H |
| H-5 | Ph | Ph | H | Ph | Ph | H | H |
| H-6 | Ph | H | Ph | H | Ph | H | H |
| H-7 | Ph | H | H | H | Ph | Ph | H |
| H-8 | Ph | H | H | H | Ph | H | Ph |
| H-9 | Ph | H | H | H | Ph | Ph | Ph |
| H-10 | Ph | H | H | H | Ph | 1-naphthyl | H |
| H-11 | Ph | H | H | H | Ph | H | 1-naphthyl |
| H-12 | Ph | H | H | H | Ph | 1-naphthyl | 1-naphthyl |
| H-13 | Ph | H | H | H | Ph | 2-naphthyl | H |
| H-14 | Ph | H | H | H | Ph | H | 2-naphthyl |
| H-15 | Ph | H | H | H | Ph | 2-naphthyl | 2-naphthyl |
| H-16 | Ph | H | H | H | Ph | o-biphenylyl | H |
| H-17 | Ph | H | H | H | Ph | H | o-biphenylyl |
| H-18 | Ph | H | H | H | Ph | o-biphenylyl | o-biphenylyl |
| H-19 | Ph | H | H | H | Ph | m-biphenylyl | H |
| H-20 | Ph | H | H | H | Ph | H | m-biphenylyl |
| H-21 | Ph | H | H | H | Ph | m-biphenylyl | m-biphenylyl |
| H-22 | Ph | H | H | H | Ph | p-biphenylyl | H |
| H-23 | Ph | H | H | H | Ph | H | p-biphenylyl |
| H-24 | Ph | H | H | H | Ph | p-biphenylyl | p-biphenylyl |
| H-25 | 1-naphthyl | H | H | H | 1-naphthyl | H | H |
| H-26 | 1-naphthyl | Ph | H | H | 1-naphthyl | H | H |
| H-27 | 1-naphthyl | H | H | Ph | 1-naphthyl | H | H |
| H-28 | 1-naphthyl | Ph | H | Ph | 1-naphthyl | H | H |
| H-29 | 1-naphthyl | H | Ph | H | 1-naphthyl | H | H |
| H-30 | 1-naphthyl | H | H | H | 1-naphthyl | Ph | H |
| H-31 | 1-naphthyl | H | H | H | 1-naphthyl | H | Ph |
| H-32 | 1-naphthyl | H | H | H | 1-naphthyl | Ph | Ph |
| H-33 | 1-naphthyl | H | H | H | 1-naphthyl | 1-naphthyl | H |
| H-34 | 1-naphthyl | H | H | H | 1-naphthyl | H | 1-naphthyl |
| H-35 | 1-naphthyl | H | H | H | 1-naphthyl | 1-naphthyl | 1-naphthyl |
| H-36 | 1-naphthyl | H | H | H | 1-naphthyl | 2-naphthyl | H |

-continued

| | | | | | | | |
|---|---|---|---|---|---|---|---|
| H-37 | 1-naphthyl | H | H | H | 1-naphthyl | H | 2-naphthyl |
| H-38 | 1-naphthyl | H | H | H | 1-naphthyl | 2-naphthyl | 2-naphthyl |
| H-39 | 1-naphthyl | H | H | H | 1-naphthyl | o-biphenylyl | H |
| H-40 | 1-naphthyl | H | H | H | 1-naphthyl | H | o-biphenylyl |
| H-41 | 1-naphthyl | H | H | H | 1-naphthyl | o-biphenylyl | o-biphenylyl |
| H-42 | 1-naphthyl | H | H | H | 1-naphthyl | m-biphenylyl | H |
| H-43 | 1-naphthyl | H | H | H | 1-naphthyl | H | m-biphenylyl |
| H-44 | 1-naphthyl | H | H | H | 1-naphthyl | m-biphenylyl | m-biphenylyl |
| H-45 | 1-naphthyl | H | H | H | 1-naphthyl | p-biphenylyl | H |
| H-46 | 1-naphthyl | H | H | H | 1-naphthyl | H | p-biphenylyl |
| H-47 | 1-naphthyl | H | H | H | 1-naphthyl | p-biphenylyl | p-biphenylyl |
| H-48 | 2-naphthyl | H | H | H | 2-naphthyl | H | H |
| H-49 | 2-naphthyl | Ph | H | H | 2-naphthyl | H | H |
| H-50 | 2-naphthyl | H | H | Ph | 2-naphthyl | H | H |
| H-51 | 2-naphthyl | Ph | H | Ph | 2-naphthyl | H | H |
| H-52 | 2-naphthyl | H | Ph | H | 2-naphthyl | H | H |
| H-53 | 2-naphthyl | H | H | H | 2-naphthyl | Ph | H |
| H-54 | 2-naphthyl | H | H | H | 2-naphthyl | H | Ph |
| H-55 | 2-naphthyl | H | H | H | 2-naphthyl | Ph | Ph |
| H-56 | 2-naphthyl | H | H | H | 2-naphthyl | 1-naphthyl | H |
| H-57 | 2-naphthyl | H | H | H | 2-naphthyl | H | 1-naphthyl |
| H-58 | 2-naphthyl | H | H | H | 2-naphthyl | 1-naphthyl | 1-naphthyl |
| H-59 | 2-naphthyl | H | H | H | 2-naphthyl | 2-naphthyl | H |
| H-60 | 2-naphthyl | H | H | H | 2-naphthyl | H | 2-naphthyl |
| H-61 | 2-naphthyl | H | H | H | 2-naphthyl | 2-naphthyl | 2-naphthyl |
| H-62 | 2-naphthyl | H | H | H | 2-naphthyl | o-biphenylyl | H |
| H-63 | 2-naphthyl | H | H | H | 2-naphthyl | H | o-biphenylyl |
| H-64 | 2-naphthyl | H | H | H | 2-naphthyl | o-biphenylyl | o-biphenylyl |
| H-65 | 2-naphthyl | H | H | H | 2-naphthyl | m-biphenylyl | H |
| H-66 | 2-naphthyl | H | H | H | 2-naphthyl | H | m-biphenylyl |
| H-67 | 2-naphthyl | H | H | H | 2-naphthyl | m-biphenylyl | m-biphenylyl |
| H-68 | 2-naphthyl | H | H | H | 2-naphthyl | p-biphenylyl | H |
| H-69 | 2-naphthyl | H | H | H | 2-naphthyl | H | p-biphenylyl |
| H-70 | 2-naphthyl | H | H | H | 2-naphthyl | p-biphenylyl | p-biphenylyl |
| H-71 | o-biphenylyl | H | H | H | o-biphenylyl | H | H |
| H-72 | o-biphenylyl | Ph | H | H | o-biphenylyl | H | H |
| H-73 | o-biphenylyl | H | H | Ph | o-biphenylyl | H | H |
| H-74 | o-biphenylyl | Ph | H | Ph | o-biphenylyl | H | H |
| H-75 | o-biphenylyl | H | Ph | H | o-biphenylyl | H | H |
| H-76 | o-biphenylyl | H | H | H | o-biphenylyl | Ph | H |
| H-77 | o-biphenylyl | H | H | H | o-biphenylyl | H | Ph |
| H-78 | o-biphenylyl | H | H | H | o-biphenylyl | Ph | Ph |
| H-79 | o-biphenylyl | H | H | H | o-biphenylyl | 1-naphthyl | H |
| H-80 | o-biphenylyl | H | H | H | o-biphenylyl | H | 1-naphthyl |
| H-81 | o-biphenylyl | H | H | H | o-biphenylyl | 1-naphthyl | 1-naphthyl |
| H-82 | o-biphenylyl | H | H | H | o-biphenylyl | 2-naphthyl | H |
| H-83 | o-biphenylyl | H | H | H | o-biphenylyl | H | 2-naphthyl |
| H-84 | o-biphenylyl | H | H | H | o-biphenylyl | 2-naphthyl | 2-naphthyl |
| H-85 | o-biphenylyl | H | H | H | o-biphenylyl | o-biphenylyl | H |
| H-86 | o-biphenylyl | H | H | H | o-biphenylyl | H | o-biphenylyl |
| H-87 | o-biphenylyl | H | H | H | o-biphenylyl | o-biphenylyl | o-biphenylyl |
| H-88 | o-biphenylyl | H | H | H | o-biphenylyl | m-biphenylyl | H |
| H-89 | o-biphenylyl | H | H | H | o-biphenylyl | H | m-biphenylyl |
| H-90 | o-biphenylyl | H | H | H | o-biphenylyl | m-biphenylyl | m-biphenylyl |
| H-91 | o-biphenylyl | H | H | H | o-biphenylyl | p-biphenylyl | H |
| H-92 | o-biphenylyl | H | H | H | o-biphenylyl | H | p-biphenylyl |
| H-93 | o-biphenylyl | H | H | H | o-biphenylyl | p-biphenylyl | p-biphenylyl |
| H-94 | m-biphenylyl | H | H | H | m-biphenylyl | H | H |
| H-95 | m-biphenylyl | Ph | H | H | m-biphenylyl | H | H |
| H-96 | m-biphenylyl | H | H | Ph | m-biphenylyl | H | H |
| H-97 | m-biphenylyl | Ph | H | Ph | m-biphenylyl | H | H |
| H-98 | m-biphenylyl | H | Ph | H | m-biphenylyl | H | H |
| H-99 | m-biphenylyl | H | H | H | m-biphenylyl | Ph | H |
| H-100 | m-biphenylyl | H | H | H | m-biphenylyl | H | Ph |
| H-101 | m-biphenylyl | H | H | H | m-biphenylyl | Ph | Ph |
| H-102 | m-biphenylyl | H | H | H | m-biphenylyl | 1-naphthyl | H |
| H-103 | m-biphenylyl | H | H | H | m-biphenylyl | H | 1-naphthyl |
| H-104 | m-biphenylyl | H | H | H | m-biphenylyl | 1-naphthyl | 1-naphthyl |
| H-105 | m-biphenylyl | H | H | H | m-biphenylyl | 2-naphthyl | H |
| H-106 | m-biphenylyl | H | H | H | m-biphenylyl | H | 2-naphthyl |
| H-107 | m-biphenylyl | H | H | H | m-biphenylyl | 2-naphthyl | 2-naphthyl |
| H-108 | m-biphenylyl | H | H | H | m-biphenylyl | o-biphenylyl | H |
| H-109 | m-biphenylyl | H | H | H | m-biphenylyl | H | o-biphenylyl |
| H-110 | m-biphenylyl | H | H | H | m-biphenylyl | o-biphenylyl | o-biphenylyl |
| H-111 | m-biphenylyl | H | H | H | m-biphenylyl | m-biphenylyl | H |
| H-112 | m-biphenylyl | H | H | H | m-biphenylyl | H | m-biphenylyl |
| H-113 | m-biphenylyl | H | H | H | m-biphenylyl | m-biphenylyl | m-biphenylyl |
| H-114 | m-biphenylyl | H | H | H | m-biphenylyl | p-biphenylyl | H |
| H-115 | m-biphenylyl | H | H | H | m-biphenylyl | H | p-biphenylyl |

-continued

| | | | | | | | |
|---|---|---|---|---|---|---|---|
| H-116 | m-biphenylyl | H | H | H | m-biphenylyl | p-biphenylyl | p-biphenylyl |
| H-117 | p-biphenylyl | H | H | H | p-biphenylyl | H | H |
| H-118 | p-biphenylyl | Ph | H | H | p-biphenylyl | H | H |
| H-119 | p-biphenylyl | H | H | Ph | p-biphenylyl | H | H |
| H-120 | p-biphenylyl | Ph | H | Ph | p-biphenylyl | H | H |
| H-121 | p-biphenylyl | H | Ph | H | p-biphenylyl | H | H |
| H-122 | p-biphenylyl | H | H | H | p-biphenylyl | Ph | H |
| H-123 | p-biphenylyl | H | H | H | p-biphenylyl | H | Ph |
| H-124 | p-biphenylyl | H | H | H | p-biphenylyl | Ph | Ph |
| H-125 | p-biphenylyl | H | H | H | p-biphenylyl | 1-naphthyl | H |
| H-126 | p-biphenylyl | H | H | H | p-biphenylyl | H | 1-naphthyl |
| H-127 | p-biphenylyl | H | H | H | p-biphenylyl | 1-naphthyl | 1-naphthyl |
| H-128 | p-biphenylyl | H | H | H | p-biphenylyl | 2-naphthyl | H |
| H-129 | p-biphenylyl | H | H | H | p-biphenylyl | H | 2-naphthyl |
| H-130 | p-biphenylyl | H | H | H | p-biphenylyl | 2-naphthyl | 2-naphthyl |
| H-131 | p-biphenylyl | H | H | H | p-biphenylyl | o-biphenylyl | H |
| H-132 | p-biphenylyl | H | H | H | p-biphenylyl | H | o-biphenylyl |
| H-133 | p-biphenylyl | H | H | H | p-biphenylyl | o-biphenylyl | o-biphenylyl |
| H-134 | p-biphenylyl | H | H | H | p-biphenylyl | m-biphenylyl | H |
| H-135 | p-biphenylyl | H | H | H | p-biphenylyl | H | m-biphenylyl |
| H-136 | p-biphenylyl | H | H | H | p-biphenylyl | m-biphenylyl | m-biphenylyl |
| H-137 | p-biphenylyl | H | H | H | p-biphenylyl | p-biphenylyl | H |
| H-138 | p-biphenylyl | H | H | H | p-biphenylyl | H | p-biphenylyl |
| H-139 | p-biphenylyl | H | H | H | p-biphenylyl | p-biphenylyl | p-biphenylyl |
| H-140 | o-tolyl | H | H | H | o-tolyl | H | H |
| H-141 | o-tolyl | Ph | H | Ph | o-tolyl | H | H |
| H-142 | o-tolyl | H | Ph | H | o-tolyl | H | H |
| H-143 | o-tolyl | H | H | H | o-tolyl | Ph | H |
| H-144 | o-tolyl | H | H | H | o-tolyl | H | Ph |
| H-145 | o-tolyl | H | H | H | o-tolyl | 1-naphthyl | H |
| H-146 | o-tolyl | H | H | H | o-tolyl | H | 1-naphthyl |
| H-147 | o-tolyl | H | H | H | o-tolyl | 2-naphthyl | H |
| H-148 | o-tolyl | H | H | H | o-tolyl | H | 2-naphthyl |
| H-149 | o-tolyl | H | H | H | o-tolyl | o-biphenylyl | H |
| H-150 | o-tolyl | H | H | H | o-tolyl | H | o-biphenylyl |
| H-151 | o-tolyl | H | H | H | o-tolyl | m-biphenylyl | H |
| H-152 | o-tolyl | H | H | H | o-tolyl | H | m-biphenylyl |
| H-153 | o-tolyl | H | H | H | o-tolyl | p-biphenylyl | H |
| H-154 | o-tolyl | H | H | H | o-tolyl | H | p-biphenylyl |
| H-155 | o-tolyl | H | H | H | o-tolyl | o-tolyl | H |
| H-156 | o-tolyl | H | H | H | o-tolyl | H | o-tolyl |
| H-157 | m-tolyl | H | H | H | m-tolyl | H | H |
| H-158 | m-tolyl | Ph | H | Ph | m-tolyl | H | H |
| H-159 | m-tolyl | H | Ph | H | m-tolyl | H | H |
| H-160 | m-tolyl | H | H | H | m-tolyl | Ph | H |
| H-161 | m-tolyl | H | H | H | m-tolyl | H | Ph |
| H-162 | m-tolyl | H | H | H | m-tolyl | 1-naphthyl | H |
| H-163 | m-tolyl | H | H | H | m-tolyl | H | 1-naphthyl |
| H-164 | m-tolyl | H | H | H | m-tolyl | 2-naphthyl | H |
| H-165 | m-tolyl | H | H | H | m-tolyl | H | 2-naphthyl |
| H-166 | m-tolyl | H | H | H | m-tolyl | o-biphenylyl | H |
| H-167 | m-tolyl | H | H | H | m-tolyl | H | o-biphenylyl |
| H-168 | m-tolyl | H | H | H | m-tolyl | m-biphenylyl | H |
| H-169 | m-tolyl | H | H | H | m-tolyl | H | m-biphenylyl |
| H-170 | m-tolyl | H | H | H | m-tolyl | p-biphenylyl | H |
| H-171 | m-tolyl | H | H | H | m-tolyl | H | p-biphenylyl |
| H-172 | m-tolyl | H | H | H | m-tolyl | m-tolyl | H |
| H-173 | m-tolyl | H | H | H | m-tolyl | H | m-tolyl |
| H-174 | p-tolyl | H | H | H | p-tolyl | H | H |
| H-175 | p-tolyl | Ph | H | Ph | p-tolyl | H | H |
| H-176 | p-tolyl | H | Ph | H | p-tolyl | H | H |
| H-177 | p-tolyl | H | H | H | p-tolyl | Ph | H |
| H-178 | p-tolyl | H | H | H | p-tolyl | H | Ph |
| H-179 | p-tolyl | H | H | H | p-tolyl | 1-naphthyl | H |
| H-180 | p-tolyl | H | H | H | p-tolyl | H | 1-naphthyl |
| H-181 | p-tolyl | H | H | H | p-tolyl | 2-naphthyl | H |
| H-182 | p-tolyl | H | H | H | p-tolyl | H | 2-naphthyl |
| H-183 | p-tolyl | H | H | H | p-tolyl | o-biphenylyl | H |
| H-184 | p-tolyl | H | H | H | p-tolyl | H | o-biphenylyl |
| H-185 | p-tolyl | H | H | H | p-tolyl | m-biphenylyl | H |
| H-186 | p-tolyl | H | H | H | p-tolyl | H | m-biphenylyl |
| H-187 | p-tolyl | H | H | H | p-tolyl | p-biphenylyl | H |
| H-188 | p-tolyl | H | H | H | p-tolyl | H | p-biphenylyl |
| H-189 | p-tolyl | H | H | H | p-tolyl | p-tolyl | H |
| H-190 | p-tolyl | H | H | H | p-tolyl | H | p-tolyl |
| H-191 | Ph | H | —CH3 | H | Ph | H | H |
| H-192 | 1-naphtyl | H | —CH3 | H | 1-naphtyl | H | H |
| H-193 | 2-naphthyl | H | —CH3 | H | 2-naphthyl | H | H |
| H-194 | o-biphenylyl | H | —CH3 | H | o-biphenylyl | H | H |

-continued

| | | | | | | | |
|---|---|---|---|---|---|---|---|
| H-195 | m-biphenylyl | H | —CH3 | H | m-biphenylyl | H | H |
| H-196 | p-biphenylyl | H | —CH3 | H | p-biphenylyl | H | H |
| H-197 | o-tolyl | H | —CH3 | H | o-tolyl | H | H |
| H-198 | m-tolyl | H | —CH3 | H | m-tolyl | H | H |
| H-199 | p-tolyl | H | —CH3 | H | p-tolyl | H | H |
| H-200 | Ph | H | H | H | Ph | —CH3 | H |
| H-201 | 1-naphtyl | H | H | H | 1-naphtyl | —CH3 | H |
| H-202 | 2-naphthyl | H | H | H | 2-naphthyl | —CH3 | H |
| H-203 | o-biphenylyl | H | H | H | o-biphenylyl | —CH3 | H |
| H-204 | m-biphenylyl | H | H | H | m-biphenylyl | —CH3 | H |
| H-205 | p-biphenylyl | H | H | H | p-biphenylyl | —CH3 | H |
| H-206 | o-tolyl | H | H | H | o-tolyl | —CH3 | H |
| H-207 | m-tolyl | H | H | H | m-tolyl | —CH3 | H |
| H-208 | p-tolyl | H | H | H | p-tolyl | —CH3 | H |
| H-209 | Ph | H | H | H | Ph | H | —CH3 |
| H-210 | 1-naphtyl | H | H | H | 1-naphtyl | H | —CH3 |
| H-211 | 2-naphthyl | H | H | H | 2-naphthyl | H | —CH3 |
| H-212 | o-biphenylyl | H | H | H | o-biphenylyl | H | —CH3 |
| H-213 | m-biphenylyl | H | H | H | m-biphenylyl | H | —CH3 |
| H-214 | p-biphenylyl | H | H | H | p-biphenylyl | H | —CH3 |
| H-215 | o-tolyl | H | H | H | o-tolyl | H | —CH3 |
| H-216 | m-tolyl | H | H | H | m-tolyl | H | —CH3 |
| H-217 | p-tolyl | H | H | H | p-tolyl | H | —CH3 |
| H-218 | Ph | H | H | H | Ph | —CH3 | —CH3 |
| H-219 | 1-naphtyl | H | H | H | 1-naphtyl | —CH3 | —CH3 |
| H-220 | 2-naphthyl | H | H | H | 2-naphthyl | —CH3 | —CH3 |
| H-221 | o-biphenylyl | H | H | H | o-biphenylyl | —CH3 | —CH3 |
| H-222 | m-biphenylyl | H | H | H | m-biphenylyl | —CH3 | —CH3 |
| H-223 | p-biphenylyl | H | H | H | p-biphenylyl | —CH3 | —CH3 |
| H-224 | o-tolyl | H | H | H | o-tolyl | —CH3 | —CH3 |
| H-225 | m-tolyl | H | H | H | m-tolyl | —CH3 | —CH3 |
| H-226 | p-tolyl | H | H | H | p-tolyl | —CH3 | —CH3 |
| H-227 | Ph | H | H | H | Ph | H | DPA |
| H-228 | 1-naphtyl | H | H | H | 1-naphtyl | H | DPA |
| H-229 | 2-naphthyl | H | H | H | 2-naphthyl | H | DPA |
| H-230 | o-biphenylyl | H | H | H | o-biphenylyl | H | DPA |
| H-231 | m-biphenylyl | H | H | H | m-biphenylyl | H | DPA |
| H-232 | p-biphenylyl | H | H | H | p-biphenylyl | H | DPA |
| H-233 | Ph | H | H | H | Ph | DPA | H |
| H-234 | 1-naphtyl | H | H | H | 1-naphtyl | DPA | H |
| H-235 | 2-naphthyl | H | H | H | 2-naphthyl | DPA | H |
| H-236 | o-biphenylyl | H | H | H | o-biphenylyl | DPA | H |
| H-237 | m-biphenylyl | H | H | H | m-biphenylyl | DPA | H |
| H-238 | p-biphenylyl | H | H | H | p-biphenylyl | DPA | H |
| H-239 | Ph | H | H | H | Ph | H | TPA |
| H-240 | 1-naphtyl | H | H | H | 1-naphtyl | H | TPA |
| H-241 | 2-naphthyl | H | H | H | 2-naphthyl | H | TPA |
| H-242 | o-biphenylyl | H | H | H | o-biphenylyl | H | TPA |
| H-243 | m-biphenylyl | H | H | H | m-biphenylyl | H | TPA |
| H-244 | p-biphenylyl | H | H | H | p-biphenylyl | H | TPA |
| H-245 | Ph | H | H | H | Ph | TPA | H |
| H-246 | 1-naphtyl | H | H | H | 1-naphtyl | TPA | H |
| H-247 | 2-naphthyl | H | H | H | 2-naphthyl | TPA | H |
| H-248 | o-biphenylyl | H | H | H | o-biphenylyl | TPA | H |
| H-249 | m-biphenylyl | H | H | H | m-biphenylyl | TPA | H |
| H-250 | p-biphenylyl | H | H | H | p-biphenylyl | TPA | H |
| H-251 | Ph | H | H | H | 1-naphthyl | H | H |
| H-252 | Ph | H | H | H | 2-naphthyl | H | H |
| H-253 | Ph | H | H | H | o-biphenylyl | H | H |
| H-254 | Ph | H | H | H | m-biphenylyl | H | H |
| H-255 | Ph | H | H | H | p-biphenylyl | H | H |
| H-256 | Ph | H | H | H | O-tolyly | H | H |
| H-257 | Ph | H | H | H | m-tolyl | H | H |
| H-258 | Ph | H | H | H | p-tolyl | H | H |
| H-259 | 1-naphthyl | H | H | H | 2-naphthyl | H | H |
| H-260 | 1-naphthyl | H | H | H | o-biphenylyl | H | H |
| H-261 | 1-naphthyl | H | H | H | m-biphenylyl | H | H |
| H-262 | 1-naphthyl | H | H | H | p-biphenylyl | H | H |
| H-263 | 1-naphthyl | H | H | H | O-tolyly | H | H |
| H-264 | 1-naphthyl | H | H | H | m-tolyl | H | H |
| H-265 | 1-naphthyl | H | H | H | p-tolyl | H | H |
| H-266 | 2-naphthyl | H | H | H | o-biphenylyl | H | H |
| H-267 | 2-naphthyl | H | H | H | m-biphenylyl | H | H |
| H-268 | 2-naphthyl | H | H | H | p-biphenylyl | H | H |
| H-269 | 2-naphthyl | H | H | H | O-tolyly | H | H |
| H-270 | 2-naphthyl | H | H | H | m-tolyl | H | H |
| H-271 | 2-naphthyl | H | H | H | p-tolyl | H | H |
| H-272 | o-biphenylyl | H | H | H | m-biphenylyl | H | H |
| H-273 | o-biphenylyl | H | H | H | p-biphenylyl | H | H |

-continued

| | | | | | | | |
|---|---|---|---|---|---|---|---|
| H-274 | o-biphenylyl | H | H | H | O-tolyly | H | H |
| H-275 | o-biphenylyl | H | H | H | m-tolyl | H | H |
| H-276 | o-biphenylyl | H | H | H | p-tolyl | H | H |
| H-277 | m-biphenylyl | H | H | H | p-biphenylyl | H | H |
| H-278 | m-biphenylyl | H | H | H | O-tolyly | H | H |
| H-279 | m-biphenylyl | H | H | H | m-tolyl | H | H |
| H-280 | m-biphenylyl | H | H | H | p-tolyl | H | H |
| H-281 | p-biphenylyl | H | H | H | O-tolyly | H | H |
| H-282 | p-biphenylyl | H | H | H | m-tolyl | H | H |
| H-283 | p-biphenylyl | H | H | H | p-tolyl | H | H |
| H-284 | O-tolyly | H | H | H | m-tolyl | H | H |
| H-285 | O-tolyly | H | H | H | p-tolyl | H | H |
| H-286 | m-tolyly | H | H | H | p-tolyl | H | H |

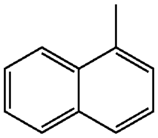

1-naphthyl

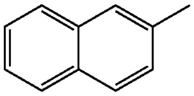

2-naphthyl

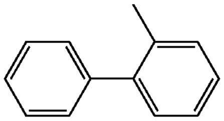

o-biphenylyl

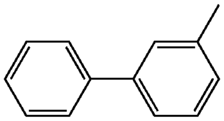

m-biphenylyl

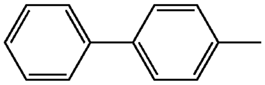

p-biphenylyl

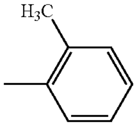

o-tolyl

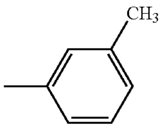

m-tolyl

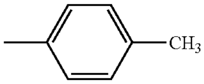

p-tolyl

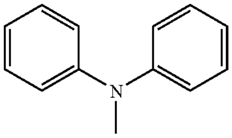

DPA

-continued
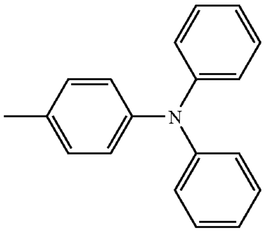
TPA
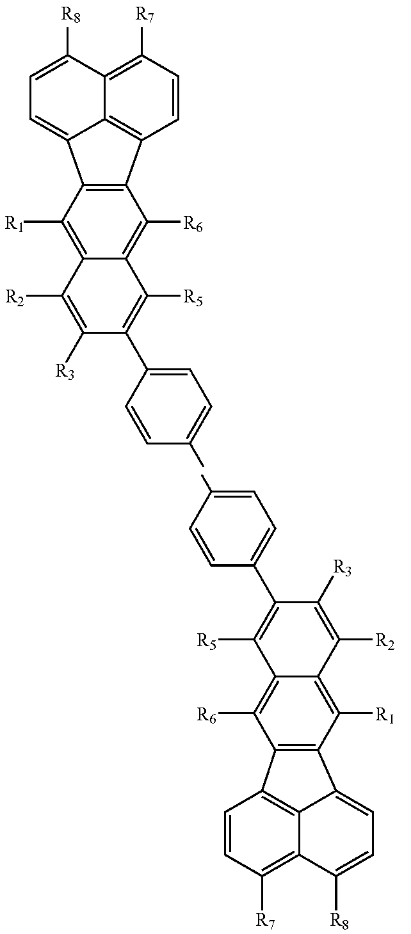
TypeI
| | $R_1$ | $R_2$ | $R_3$ | $R_5$ | $R_6$ | $R_7$ | $R_8$ |
|---|---|---|---|---|---|---|---|
| I-1 | H | H | H | H | H | H | H |
| I-2 | Ph | H | H | H | Ph | H | H |
| I-3 | Ph | Ph | H | H | Ph | H | H |
| I-4 | Ph | H | H | Ph | Ph | H | H |
| I-5 | Ph | Ph | H | Ph | Ph | H | H |
| I-6 | Ph | H | Ph | H | Ph | H | H |
| I-7 | Ph | H | H | H | Ph | Ph | H |
| I-8 | Ph | H | H | H | Ph | H | Ph |
| I-9 | Ph | H | H | H | Ph | Ph | Ph |
| I-10 | Ph | H | H | H | Ph | 1-naphthyl | H |
| I-11 | Ph | H | H | H | Ph | H | 1-naphthyl |
| I-12 | Ph | H | H | H | Ph | 1-naphthyl | 1-naphthyl |
| I-13 | Ph | H | H | H | Ph | 2-naphthyl | H |
| I-14 | Ph | H | H | H | Ph | H | 2-naphthyl |

-continued

| | | | | | | | |
|---|---|---|---|---|---|---|---|
| I-15 | Ph | H | H | H | Ph | 2-naphthyl | 2-naphthyl |
| I-16 | Ph | H | H | H | Ph | o-biphenylyl | H |
| I-17 | Ph | H | H | H | Ph | H | o-biphenylyl |
| I-18 | Ph | H | H | H | Ph | o-biphenylyl | o-biphenylyl |
| I-19 | Ph | H | H | H | Ph | m-biphenylyl | H |
| I-20 | Ph | H | H | H | Ph | H | m-biphenylyl |
| I-21 | Ph | H | H | H | Ph | m-biphenylyl | m-biphenylyl |
| I-22 | Ph | H | H | H | Ph | p-biphenylyl | H |
| I-23 | Ph | H | H | H | Ph | H | p-biphenylyl |
| I-24 | Ph | H | H | H | Ph | p-biphenylyl | p-biphenylyl |
| I-25 | 1-naphthyl | H | H | H | 1-naphthyl | H | H |
| I-26 | 1-naphthyl | Ph | H | H | 1-naphthyl | H | H |
| I-27 | 1-naphthyl | H | H | Ph | 1-naphthyl | H | H |
| I-28 | 1-naphthyl | Ph | H | Ph | 1-naphthyl | H | H |
| I-29 | 1-naphthyl | H | Ph | H | 1-naphthyl | H | H |
| I-30 | 1-naphthyl | H | H | H | 1-naphthyl | Ph | H |
| I-31 | 1-naphthyl | H | H | H | 1-naphthyl | H | Ph |
| I-32 | 1-naphthyl | H | H | H | 1-naphthyl | Ph | Ph |
| I-33 | 1-naphthyl | H | H | H | 1-naphthyl | 1-naphthyl | H |
| I-34 | 1-naphthyl | H | H | H | 1-naphthyl | H | 1-naphthyl |
| I-35 | 1-naphthyl | H | H | H | 1-naphthyl | 1-naphthyl | 1-naphthyl |
| I-36 | 1-naphthyl | H | H | H | 1-naphthyl | 2-naphthyl | H |
| I-37 | 1-naphthyl | H | H | H | 1-naphthyl | H | 2-naphthyl |
| I-38 | 1-naphthyl | H | H | H | 1-naphthyl | 2-naphthyl | 2-naphthyl |
| I-39 | 1-naphthyl | H | H | H | 1-naphthyl | o-biphenylyl | H |
| I-40 | 1-naphthyl | H | H | H | 1-naphthyl | H | o-biphenylyl |
| I-41 | 1-naphthyl | H | H | H | 1-naphthyl | o-biphenylyl | o-biphenylyl |
| I-42 | 1-naphthyl | H | H | H | 1-naphthyl | m-biphenylyl | H |
| I-43 | 1-naphthyl | H | H | H | 1-naphthyl | H | m-biphenylyl |
| I-44 | 1-naphthyl | H | H | H | 1-naphthyl | m-biphenylyl | m-biphenylyl |
| I-45 | 1-naphthyl | H | H | H | 1-naphthyl | p-biphenylyl | H |
| I-46 | 1-naphthyl | H | H | H | 1-naphthyl | H | p-biphenylyl |
| I-47 | 1-naphthyl | H | H | H | 1-naphthyl | p-biphenylyl | p-biphenylyl |
| I-48 | 2-naphthyl | H | H | H | 2-naphthyl | H | H |
| I-49 | 2-naphthyl | Ph | H | H | 2-naphthyl | H | H |
| I-50 | 2-naphthyl | H | H | Ph | 2-naphthyl | H | H |
| I-51 | 2-naphthyl | Ph | H | Ph | 2-naphthyl | H | H |
| I-52 | 2-naphthyl | H | Ph | H | 2-naphthyl | H | H |
| I-53 | 2-naphthyl | H | H | H | 2-naphthyl | Ph | H |
| I-54 | 2-naphthyl | H | H | H | 2-naphthyl | H | Ph |
| I-55 | 2-naphthyl | H | H | H | 2-naphthyl | Ph | Ph |
| I-56 | 2-naphthyl | H | H | H | 2-naphthyl | 1-naphthyl | H |
| I-57 | 2-naphthyl | H | H | H | 2-naphthyl | H | 1-naphthyl |
| I-58 | 2-naphthyl | H | H | H | 2-naphthyl | 1-naphthyl | 1-naphthyl |
| I-59 | 2-naphthyl | H | H | H | 2-naphthyl | 2-naphthyl | H |
| I-60 | 2-naphthyl | H | H | H | 2-naphthyl | H | 2-naphthyl |
| I-61 | 2-naphthyl | H | H | H | 2-naphthyl | 2-naphthyl | 2-naphthyl |
| I-62 | 2-naphthyl | H | H | H | 2-naphthyl | o-biphenylyl | H |
| I-63 | 2-naphthyl | H | H | H | 2-naphthyl | H | o-biphenylyl |
| I-64 | 2-naphthyl | H | H | H | 2-naphthyl | o-biphenylyl | o-biphenylyl |
| I-65 | 2-naphthyl | H | H | H | 2-naphthyl | m-biphenylyl | H |
| I-66 | 2-naphthyl | H | H | H | 2-naphthyl | H | m-biphenylyl |
| I-67 | 2-naphthyl | H | H | H | 2-naphthyl | m-biphenylyl | m-biphenylyl |
| I-68 | 2-naphthyl | H | H | H | 2-naphthyl | p-biphenylyl | H |
| I-69 | 2-naphthyl | H | H | H | 2-naphthyl | H | p-biphenylyl |
| I-70 | 2-naphthyl | H | H | H | 2-naphthyl | p-biphenylyl | p-biphenylyl |
| I-71 | o-biphenylyl | H | H | H | o-biphenylyl | H | H |
| I-72 | o-biphenylyl | Ph | H | H | o-biphenylyl | H | H |
| I-73 | o-biphenylyl | H | H | Ph | o-biphenylyl | H | H |
| I-74 | o-biphenylyl | Ph | H | Ph | o-biphenylyl | H | H |
| I-75 | o-biphenylyl | H | Ph | H | o-biphenylyl | H | H |
| I-76 | o-biphenylyl | H | H | H | o-biphenylyl | Ph | H |
| I-77 | o-biphenylyl | H | H | H | o-biphenylyl | H | Ph |
| I-78 | o-biphenylyl | H | H | H | o-biphenylyl | Ph | Ph |
| I-79 | o-biphenylyl | H | H | H | o-biphenylyl | 1-naphthyl | H |
| I-80 | o-biphenylyl | H | H | H | o-biphenylyl | H | 1-naphthyl |
| I-81 | o-biphenylyl | H | H | H | o-biphenylyl | 1-naphthyl | 1-naphthyl |
| I-82 | o-biphenylyl | H | H | H | o-biphenylyl | 2-naphthyl | H |
| I-83 | o-biphenylyl | H | H | H | o-biphenylyl | H | 2-naphthyl |
| I-84 | o-biphenylyl | H | H | H | o-biphenylyl | 2-naphthyl | 2-naphthyl |
| I-85 | o-biphenylyl | H | H | H | o-biphenylyl | o-biphenylyl | H |
| I-86 | o-biphenylyl | H | H | H | o-biphenylyl | H | o-biphenylyl |
| I-87 | o-biphenylyl | H | H | H | o-biphenylyl | o-biphenylyl | o-biphenylyl |
| I-88 | o-biphenylyl | H | H | H | o-biphenylyl | m-biphenylyl | H |
| I-89 | o-biphenylyl | H | H | H | o-biphenylyl | H | m-biphenylyl |
| I-90 | o-biphenylyl | H | H | H | o-biphenylyl | m-biphenylyl | m-biphenylyl |
| I-91 | o-biphenylyl | H | H | H | o-biphenylyl | p-biphenylyl | H |
| I-92 | o-biphenylyl | H | H | H | o-biphenylyl | H | p-biphenylyl |
| I-93 | o-biphenylyl | H | H | H | o-biphenylyl | p-biphenylyl | p-biphenylyl |
| I-94 | m-biphenylyl | H | H | H | m-biphenylyl | H | H |

-continued

| | | | | | | | |
|---|---|---|---|---|---|---|---|
| I-95 | m-biphenylyl | Ph | H | H | m-biphenylyl | H | H |
| I-96 | m-biphenylyl | H | H | Ph | m-biphenylyl | H | H |
| I-97 | m-biphenylyl | Ph | H | Ph | m-biphenylyl | H | H |
| I-98 | m-biphenylyl | H | Ph | H | m-biphenylyl | H | H |
| I-99 | m-biphenylyl | H | H | H | m-biphenylyl | Ph | H |
| I-100 | m-biphenylyl | H | H | H | m-biphenylyl | H | Ph |
| I-101 | m-biphenylyl | H | H | H | m-biphenylyl | Ph | Ph |
| I-102 | m-biphenylyl | H | H | H | m-biphenylyl | 1-naphthyl | H |
| I-103 | m-biphenylyl | H | H | H | m-biphenylyl | H | 1-naphthyl |
| I-104 | m-biphenylyl | H | H | H | m-biphenylyl | 1-naphthyl | 1-naphthyl |
| I-105 | m-biphenylyl | H | H | H | m-biphenylyl | 2-naphthyl | H |
| I-106 | m-biphenylyl | H | H | H | m-biphenylyl | H | 2-naphthyl |
| I-107 | m-biphenylyl | H | H | H | m-biphenylyl | 2-naphthyl | 2-naphthyl |
| I-108 | m-biphenylyl | H | H | H | m-biphenylyl | o-biphenylyl | H |
| I-109 | m-biphenylyl | H | H | H | m-biphenylyl | H | o-biphenylyl |
| I-110 | m-biphenylyl | H | H | H | m-biphenylyl | o-biphenylyl | o-biphenylyl |
| I-111 | m-biphenylyl | H | H | H | m-biphenylyl | m-biphenylyl | H |
| I-112 | m-biphenylyl | H | H | H | m-biphenylyl | H | m-biphenylyl |
| I-113 | m-biphenylyl | H | H | H | m-biphenylyl | m-biphenylyl | m-biphenylyl |
| I-114 | m-biphenylyl | H | H | H | m-biphenylyl | p-biphenylyl | H |
| I-115 | m-biphenylyl | H | H | H | m-biphenylyl | H | p-biphenylyl |
| I-116 | m-biphenylyl | H | H | H | m-biphenylyl | p-biphenylyl | p-biphenylyl |
| I-117 | p-biphenylyl | H | H | H | p-biphenylyl | H | H |
| I-118 | p-biphenylyl | Ph | H | H | p-biphenylyl | H | H |
| I-119 | p-biphenylyl | H | H | Ph | p-biphenylyl | H | H |
| I-120 | p-biphenylyl | Ph | H | Ph | p-biphenylyl | H | H |
| I-121 | p-biphenylyl | H | Ph | H | p-biphenylyl | H | H |
| I-122 | p-biphenylyl | H | H | H | p-biphenylyl | Ph | H |
| I-123 | p-biphenylyl | H | H | H | p-biphenylyl | H | Ph |
| I-124 | p-biphenylyl | H | H | H | p-biphenylyl | Ph | Ph |
| I-125 | p-biphenylyl | H | H | H | p-biphenylyl | 1-naphthyl | H |
| I-126 | p-biphenylyl | H | H | H | p-biphenylyl | H | 1-naphthyl |
| I-127 | p-biphenylyl | H | H | H | p-biphenylyl | 1-naphthyl | 1-naphthyl |
| I-128 | p-biphenylyl | H | H | H | p-biphenylyl | 2-naphthyl | H |
| I-129 | p-biphenylyl | H | H | H | p-biphenylyl | H | 2-naphthyl |
| I-130 | p-biphenylyl | H | H | H | p-biphenylyl | 2-naphthyl | 2-naphthyl |
| I-131 | p-biphenylyl | H | H | H | p-biphenylyl | o-biphenylyl | H |
| I-132 | p-biphenylyl | H | H | H | p-biphenylyl | H | o-biphenylyl |
| I-133 | p-biphenylyl | H | H | H | p-biphenylyl | o-biphenylyl | o-biphenylyl |
| I-134 | p-biphenylyl | H | H | H | p-biphenylyl | m-biphenylyl | H |
| I-135 | p-biphenylyl | H | H | H | p-biphenylyl | H | m-biphenylyl |
| I-136 | p-biphenylyl | H | H | H | p-biphenylyl | m-biphenylyl | m-biphenylyl |
| I-137 | p-biphenylyl | H | H | H | p-biphenylyl | p-biphenylyl | H |
| I-138 | p-biphenylyl | H | H | H | p-biphenylyl | H | p-biphenylyl |
| I-139 | p-biphenylyl | H | H | H | p-biphenylyl | p-biphenylyl | p-biphenylyl |
| I-140 | o-tolyl | H | H | H | o-tolyl | H | H |
| I-141 | o-tolyl | Ph | H | Ph | o-tolyl | H | H |
| I-142 | o-tolyl | H | Ph | H | o-tolyl | H | H |
| I-143 | o-tolyl | H | H | H | o-tolyl | Ph | H |
| I-144 | o-tolyl | H | H | H | o-tolyl | H | Ph |
| I-145 | o-tolyl | H | H | H | o-tolyl | 1-naphthyl | H |
| I-146 | o-tolyl | H | H | H | o-tolyl | H | 1-naphthyl |
| I-147 | o-tolyl | H | H | H | o-tolyl | 2-naphthyl | H |
| I-148 | o-tolyl | H | H | H | o-tolyl | H | 2-naphthyl |
| I-149 | o-tolyl | H | H | H | o-tolyl | o-biphenylyl | H |
| I-150 | o-tolyl | H | H | H | o-tolyl | H | o-biphenylyl |
| I-151 | o-tolyl | H | H | H | o-tolyl | m-biphenylyl | H |
| I-152 | o-tolyl | H | H | H | o-tolyl | H | m-biphenylyl |
| I-153 | o-tolyl | H | H | H | o-tolyl | p-biphenylyl | H |
| I-154 | o-tolyl | H | H | H | o-tolyl | H | p-biphenylyl |
| I-155 | o-tolyl | H | H | H | o-tolyl | o-tolyl | H |
| I-156 | o-tolyl | H | H | H | o-tolyl | H | o-tolyl |
| I-157 | m-tolyl | H | H | H | m-tolyl | H | H |
| I-158 | m-tolyl | Ph | H | Ph | m-tolyl | H | H |
| I-159 | m-tolyl | H | Ph | H | m-tolyl | H | H |
| I-160 | m-tolyl | H | H | H | m-tolyl | Ph | H |
| I-161 | m-tolyl | H | H | H | m-tolyl | H | Ph |
| I-162 | m-tolyl | H | H | H | m-tolyl | 1-naphthyl | H |
| I-163 | m-tolyl | H | H | H | m-tolyl | H | 1-naphthyl |
| I-164 | m-tolyl | H | H | H | m-tolyl | 2-naphthyl | H |
| I-165 | m-tolyl | H | H | H | m-tolyl | H | 2-naphthyl |
| I-166 | m-tolyl | H | H | H | m-tolyl | o-biphenylyl | H |
| I-167 | m-tolyl | H | H | H | m-tolyl | H | o-biphenylyl |
| I-168 | m-tolyl | H | H | H | m-tolyl | m-biphenylyl | H |
| I-169 | m-tolyl | H | H | H | m-tolyl | H | m-biphenylyl |
| I-170 | m-tolyl | H | H | H | m-tolyl | p-biphenylyl | H |
| I-171 | m-tolyl | H | H | H | m-tolyl | H | p-biphenylyl |
| I-172 | m-tolyl | H | H | H | m-tolyl | m-tolyl | H |
| I-173 | m-tolyl | H | H | H | m-tolyl | H | m-tolyl |
| I-174 | p-tolyl | H | H | H | p-tolyl | H | H |

-continued

| | | | | | | | |
|---|---|---|---|---|---|---|---|
| I-175 | p-tolyl | Ph | H | Ph | p-tolyl | H | H |
| I-176 | p-tolyl | H | Ph | H | p-tolyl | H | H |
| I-177 | p-tolyl | H | H | H | p-tolyl | Ph | H |
| I-178 | p-tolyl | H | H | H | p-tolyl | H | Ph |
| I-179 | p-tolyl | H | H | H | p-tolyl | 1-naphthyl | H |
| I-180 | p-tolyl | H | H | H | p-tolyl | H | 1-naphthyl |
| I-181 | p-tolyl | H | H | H | p-tolyl | 2-naphthyl | H |
| I-182 | p-tolyl | H | H | H | p-tolyl | H | 2-naphthyl |
| I-183 | p-tolyl | H | H | H | p-tolyl | o-biphenylyl | H |
| I-184 | p-tolyl | H | H | H | p-tolyl | H | o-biphenylyl |
| I-185 | p-tolyl | H | H | H | p-tolyl | m-biphenylyl | H |
| I-186 | p-tolyl | H | H | H | p-tolyl | H | m-biphenylyl |
| I-187 | p-tolyl | H | H | H | p-tolyl | p-biphenylyl | H |
| I-188 | p-tolyl | H | H | H | p-tolyl | H | p-biphenylyl |
| I-189 | p-tolyl | H | H | H | p-tolyl | p-tolyl | H |
| I-190 | p-tolyl | H | H | H | p-tolyl | H | p-tolyl |
| I-191 | Ph | H | —CH3 | H | Ph | H | H |
| I-192 | 1-naphtyl | H | —CH3 | H | 1-naphtyl | H | H |
| I-193 | 2-naphthyl | H | —CH3 | H | 2-naphthyl | H | H |
| I-194 | o-biphenylyl | H | —CH3 | H | o-biphenylyl | H | H |
| I-195 | m-biphenylyl | H | —CH3 | H | m-biphenylyl | H | H |
| I-196 | p-biphenylyl | H | —CH3 | H | p-biphenylyl | H | H |
| I-197 | o-tolyl | H | —CH3 | H | o-tolyl | H | H |
| I-198 | m-tolyl | H | —CH3 | H | m-tolyl | H | H |
| I-199 | p-tolyl | H | —CH3 | H | p-tolyl | H | H |
| I-200 | Ph | H | H | H | Ph | —CH3 | H |
| I-201 | 1-naphtyl | H | H | H | 1-naphtyl | —CH3 | H |
| I-202 | 2-naphthyl | H | H | H | 2-naphthyl | —CH3 | H |
| I-203 | o-biphenylyl | H | H | H | o-biphenylyl | —CH3 | H |
| I-204 | m-biphenylyl | H | H | H | m-biphenylyl | —CH3 | H |
| I-205 | p-biphenylyl | H | H | H | p-biphenylyl | —CH3 | H |
| I-206 | o-tolyl | H | H | H | o-tolyl | —CH3 | H |
| I-207 | m-tolyl | H | H | H | m-tolyl | —CH3 | H |
| I-208 | p-tolyl | H | H | H | p-tolyl | —CH3 | H |
| I-209 | Ph | H | H | H | Ph | H | —CH3 |
| I-210 | 1-naphtyl | H | H | H | 1-naphtyl | H | —CH3 |
| I-211 | 2-naphthyl | H | H | H | 2-naphthyl | H | —CH3 |
| I-212 | o-biphenylyl | H | H | H | o-biphenylyl | H | —CH3 |
| I-213 | m-biphenylyl | H | H | H | m-biphenylyl | H | —CH3 |
| I-214 | p-biphenylyl | H | H | H | p-biphenylyl | H | —CH3 |
| I-215 | o-tolyl | H | H | H | o-tolyl | H | —CH3 |
| I-216 | m-tolyl | H | H | H | m-tolyl | H | —CH3 |
| I-217 | p-tolyl | H | H | H | p-tolyl | H | —CH3 |
| I-218 | Ph | H | H | H | Ph | —CH3 | —CH3 |
| I-219 | 1-naphtyl | H | H | H | 1-naphtyl | —CH3 | —CH3 |
| I-220 | 2-naphthyl | H | H | H | 2-naphthyl | —CH3 | —CH3 |
| I-221 | o-biphenylyl | H | H | H | o-biphenylyl | —CH3 | —CH3 |
| I-222 | m-biphenylyl | H | H | H | m-biphenylyl | —CH3 | —CH3 |
| I-223 | p-biphenylyl | H | H | H | p-biphenylyl | —CH3 | —CH3 |
| I-224 | o-tolyl | H | H | H | o-tolyl | —CH3 | —CH3 |
| I-225 | m-tolyl | H | H | H | m-tolyl | —CH3 | —CH3 |
| I-226 | p-tolyl | H | H | H | p-tolyl | —CH3 | —CH3 |
| I-227 | Ph | H | H | H | Ph | H | DPA |
| I-228 | 1-naphtyl | H | H | H | 1-naphtyl | H | DPA |
| I-229 | 2-naphthyl | H | H | H | 2-naphthyl | H | DPA |
| I-230 | o-biphenylyl | H | H | H | o-biphenylyl | H | DPA |
| I-231 | m-biphenylyl | H | H | H | m-biphenylyl | H | DPA |
| I-232 | p-biphenylyl | H | H | H | p-biphenylyl | H | DPA |
| I-233 | Ph | H | H | H | Ph | DPA | H |
| I-234 | 1-naphtyl | H | H | H | 1-naphtyl | DPA | H |
| I-235 | 2-naphthyl | H | H | H | 2-naphthyl | DPA | H |
| I-236 | o-biphenylyl | H | H | H | o-biphenylyl | DPA | H |
| I-237 | m-biphenylyl | H | H | H | m-biphenylyl | DPA | H |
| I-238 | p-biphenylyl | H | H | H | p-biphenylyl | DPA | H |
| I-239 | Ph | H | H | H | Ph | H | TPA |
| I-240 | 1-naphtyl | H | H | H | 1-naphtyl | H | TPA |
| I-241 | 2-naphthyl | H | H | H | 2-naphthyl | H | TPA |
| I-242 | o-biphenylyl | H | H | H | o-biphenylyl | H | TPA |
| I-243 | m-biphenylyl | H | H | H | m-biphenylyl | H | TPA |
| I-244 | p-biphenylyl | H | H | H | p-biphenylyl | H | TPA |
| I-245 | Ph | H | H | H | Ph | TPA | H |
| I-246 | 1-naphtyl | H | H | H | 1-naphtyl | TPA | H |
| I-247 | 2-naphthyl | H | H | H | 2-naphthyl | TPA | H |
| I-248 | o-biphenylyl | H | H | H | o-biphenylyl | TPA | H |
| I-249 | m-biphenylyl | H | H | H | m-biphenylyl | TPA | H |
| I-250 | p-biphenylyl | H | H | H | p-biphenylyl | TPA | H |
| I-251 | Ph | H | H | H | 1-naphthyl | H | H |
| I-252 | Ph | H | H | H | 2-naphthyl | H | H |
| I-253 | Ph | H | H | H | o-biphenylyl | H | H |
| I-254 | Ph | H | H | H | m-biphenylyl | H | H |

-continued

| | | | | | | | |
|---|---|---|---|---|---|---|---|
| I-255 | Ph | H | H | H | p-biphenylyl | H | H |
| I-256 | Ph | H | H | H | O-tolyly | H | H |
| I-257 | Ph | H | H | H | m-tolyl | H | H |
| I-258 | Ph | H | H | H | p-tolyl | H | H |
| I-259 | 1-naphthyl | H | H | H | 2-naphthyl | H | H |
| I-260 | 1-naphthyl | H | H | H | o-biphenylyl | H | H |
| I-261 | 1-naphthyl | H | H | H | m-biphenylyl | H | H |
| I-262 | 1-naphthyl | H | H | H | p-biphenylyl | H | H |
| I-263 | 1-naphthyl | H | H | H | O-tolyly | H | H |
| I-264 | 1-naphthyl | H | H | H | m-tolyl | H | H |
| I-265 | 1-naphthyl | H | H | H | p-tolyl | H | H |
| I-266 | 2-naphthyl | H | H | H | o-biphenylyl | H | H |
| I-267 | 2-naphthyl | H | H | H | m-biphenylyl | H | H |
| I-268 | 2-naphthyl | H | H | H | p-biphenylyl | H | H |
| I-269 | 2-naphthyl | H | H | H | O-tolyly | H | H |
| I-270 | 2-naphthyl | H | H | H | m-tolyl | H | H |
| I-271 | 2-naphthyl | H | H | H | p-tolyl | H | H |
| I-272 | o-biphenylyl | H | H | H | m-biphenylyl | H | H |
| I-273 | o-biphenylyl | H | H | H | p-biphenylyl | H | H |
| I-274 | o-biphenylyl | H | H | H | O-tolyly | H | H |
| I-275 | o-biphenylyl | H | H | H | m-tolyl | H | H |
| I-276 | o-biphenylyl | H | H | H | p-tolyl | H | H |
| I-277 | m-biphenylyl | H | H | H | p-biphenylyl | H | H |
| I-278 | m-biphenylyl | H | H | H | O-tolyly | H | H |
| I-279 | m-biphenylyl | H | H | H | m-tolyl | H | H |
| I-280 | m-biphenylyl | H | H | H | p-tolyl | H | H |
| I-281 | p-biphenylyl | H | H | H | O-tolyly | H | H |
| I-282 | p-biphenylyl | H | H | H | m-tolyl | H | H |
| I-283 | p-biphenylyl | H | H | H | p-tolyl | H | H |
| I-284 | O-tolyly | H | H | H | m-tolyl | H | H |
| I-285 | O-tolyly | H | H | H | p-tolyl | H | H |
| I-286 | m-tolyly | H | H | H | p-tolyl | H | H |

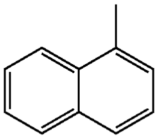

1-naphthyl

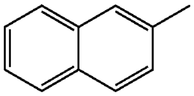

2-naphthyl

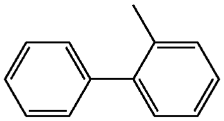

o-biphenylyl

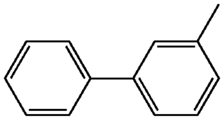

m-biphenylyl

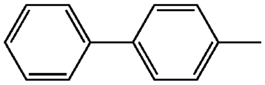

p-biphenylyl

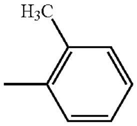

o-tolyl

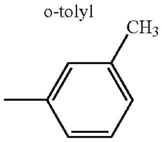

m-tolyl

-continued
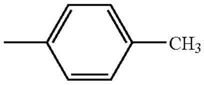
p-tolyl
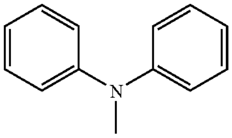
DPA
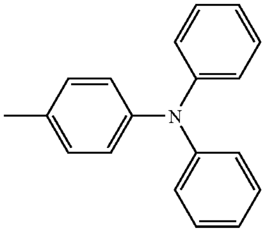
TPA
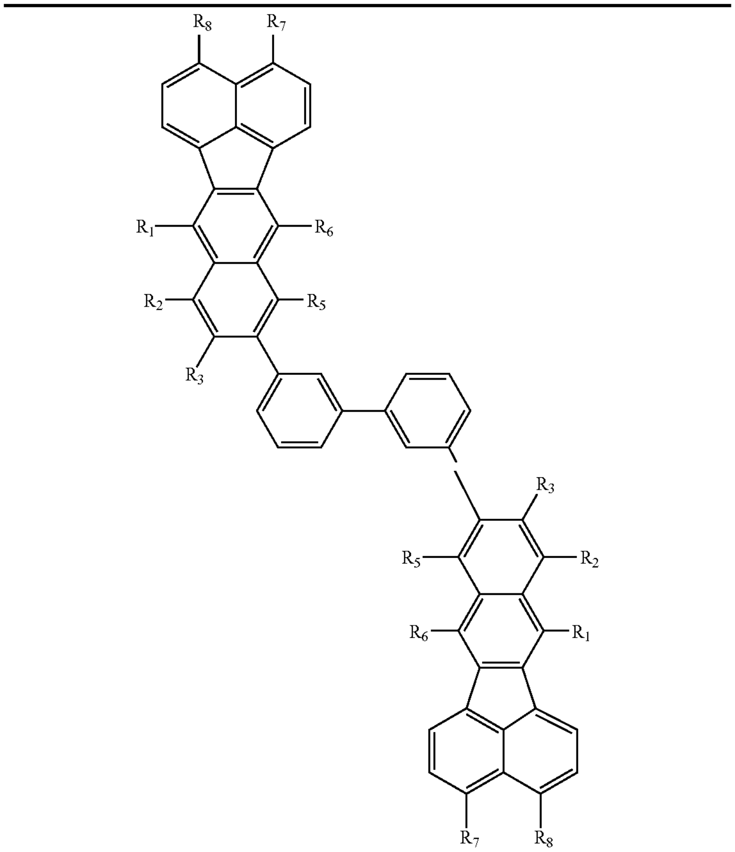
TypeJ
| | $R_1$ | $R_2$ | $R_3$ | $R_5$ | $R_6$ | $R_7$ | $R_8$ |
|---|---|---|---|---|---|---|---|
| J-1 | H | H | H | H | H | H | H |
| J-2 | Ph | H | H | H | Ph | H | H |
| J-3 | Ph | Ph | H | H | Ph | H | H |
| J-4 | Ph | H | H | Ph | Ph | H | H |
| J-5 | Ph | Ph | H | Ph | Ph | H | H |
| J-6 | Ph | H | Ph | H | Ph | H | H |

-continued

| | | | | | | | |
|---|---|---|---|---|---|---|---|
| J-7 | Ph | H | H | H | Ph | Ph | H |
| J-8 | Ph | H | H | H | Ph | H | Ph |
| J-9 | Ph | H | H | H | Ph | Ph | Ph |
| J-10 | Ph | H | H | H | Ph | 1-naphthyl | H |
| J-11 | Ph | H | H | H | Ph | H | 1-naphthyl |
| J-12 | Ph | H | H | H | Ph | 1-naphthyl | 1-naphthyl |
| J-13 | Ph | H | H | H | Ph | 2-naphthyl | H |
| J-14 | Ph | H | H | H | Ph | H | 2-naphthyl |
| J-15 | Ph | H | H | H | Ph | 2-naphthyl | 2-naphthyl |
| J-16 | Ph | H | H | H | Ph | o-biphenylyl | H |
| J-17 | Ph | H | H | H | Ph | H | o-biphenylyl |
| J-18 | Ph | H | H | H | Ph | o-biphenylyl | o-biphenylyl |
| J-19 | Ph | H | H | H | Ph | m-biphenylyl | H |
| J-20 | Ph | H | H | H | Ph | H | m-biphenylyl |
| J-21 | Ph | H | H | H | Ph | m-biphenylyl | m-biphenylyl |
| J-22 | Ph | H | H | H | Ph | p-biphenylyl | H |
| J-23 | Ph | H | H | H | Ph | H | p-biphenylyl |
| J-24 | Ph | H | H | H | Ph | p-biphenylyl | p-biphenylyl |
| J-25 | 1-naphthyl | H | H | H | 1-naphthyl | H | H |
| J-26 | 1-naphthyl | Ph | H | H | 1-naphthyl | H | H |
| J-27 | 1-naphthyl | H | H | Ph | 1-naphthyl | H | H |
| J-28 | 1-naphthyl | Ph | H | Ph | 1-naphthyl | H | H |
| J-29 | 1-naphthyl | H | Ph | H | 1-naphthyl | H | H |
| J-30 | 1-naphthyl | H | H | H | 1-naphthyl | Ph | H |
| J-31 | 1-naphthyl | H | H | H | 1-naphthyl | H | Ph |
| J-32 | 1-naphthyl | H | H | H | 1-naphthyl | Ph | Ph |
| J-33 | 1-naphthyl | H | H | H | 1-naphthyl | 1-naphthyl | H |
| J-34 | 1-naphthyl | H | H | H | 1-naphthyl | H | 1-naphthyl |
| J-35 | 1-naphthyl | H | H | H | 1-naphthyl | 1-naphthyl | 1-naphthyl |
| J-36 | 1-naphthyl | H | H | H | 1-naphthyl | 2-naphthyl | H |
| J-37 | 1-naphthyl | H | H | H | 1-naphthyl | H | 2-naphthyl |
| J-38 | 1-naphthyl | H | H | H | 1-naphthyl | 2-naphthyl | 2-naphthyl |
| J-39 | 1-naphthyl | H | H | H | 1-naphthyl | o-biphenylyl | H |
| J-40 | 1-naphthyl | H | H | H | 1-naphthyl | H | o-biphenylyl |
| J-41 | 1-naphthyl | H | H | H | 1-naphthyl | o-biphenylyl | o-biphenylyl |
| J-42 | 1-naphthyl | H | H | H | 1-naphthyl | m-biphenylyl | H |
| J-43 | 1-naphthyl | H | H | H | 1-naphthyl | H | m-biphenylyl |
| J-44 | 1-naphthyl | H | H | H | 1-naphthyl | m-biphenylyl | m-biphenylyl |
| J-45 | 1-naphthyl | H | H | H | 1-naphthyl | p-biphenylyl | H |
| J-46 | 1-naphthyl | H | H | H | 1-naphthyl | H | p-biphenylyl |
| J-47 | 1-naphthyl | H | H | H | 1-naphthyl | p-biphenylyl | p-biphenylyl |
| J-48 | 2-naphthyl | H | H | H | 2-naphthyl | H | H |
| J-49 | 2-naphthyl | Ph | H | H | 2-naphthyl | H | H |
| J-50 | 2-naphthyl | H | H | Ph | 2-naphthyl | H | H |
| J-51 | 2-naphthyl | Ph | H | Ph | 2-naphthyl | H | H |
| J-52 | 2-naphthyl | H | Ph | H | 2-naphthyl | H | H |
| J-53 | 2-naphthyl | H | H | H | 2-naphthyl | Ph | H |
| J-54 | 2-naphthyl | H | H | H | 2-naphthyl | H | Ph |
| J-55 | 2-naphthyl | H | H | H | 2-naphthyl | Ph | Ph |
| J-56 | 2-naphthyl | H | H | H | 2-naphthyl | 1-naphthyl | H |
| J-57 | 2-naphthyl | H | H | H | 2-naphthyl | H | 1-naphthyl |
| J-58 | 2-naphthyl | H | H | H | 2-naphthyl | 1-naphthyl | 1-naphthyl |
| J-59 | 2-naphthyl | H | H | H | 2-naphthyl | 2-naphthyl | H |
| J-60 | 2-naphthyl | H | H | H | 2-naphthyl | H | 2-naphthyl |
| J-61 | 2-naphthyl | H | H | H | 2-naphthyl | 2-naphthyl | 2-naphthyl |
| J-62 | 2-naphthyl | H | H | H | 2-naphthyl | o-biphenylyl | H |
| J-63 | 2-naphthyl | H | H | H | 2-naphthyl | H | o-biphenylyl |
| J-64 | 2-naphthyl | H | H | H | 2-naphthyl | o-biphenylyl | o-biphenylyl |
| J-65 | 2-naphthyl | H | H | H | 2-naphthyl | m-biphenylyl | H |
| J-66 | 2-naphthyl | H | H | H | 2-naphthyl | H | m-biphenylyl |
| J-67 | 2-naphthyl | H | H | H | 2-naphthyl | m-biphenylyl | m-biphenylyl |
| J-68 | 2-naphthyl | H | H | H | 2-naphthyl | p-biphenylyl | H |
| J-69 | 2-naphthyl | H | H | H | 2-naphthyl | H | p-biphenylyl |
| J-70 | 2-naphthyl | H | H | H | 2-naphthyl | p-biphenylyl | p-biphenylyl |
| J-71 | o-biphenylyl | H | H | H | o-biphenylyl | H | H |
| J-72 | o-biphenylyl | Ph | H | H | o-biphenylyl | H | H |
| J-73 | o-biphenylyl | H | H | Ph | o-biphenylyl | H | H |
| J-74 | o-biphenylyl | Ph | H | Ph | o-biphenylyl | H | H |
| J-75 | o-biphenylyl | H | Ph | H | o-biphenylyl | H | H |
| J-76 | o-biphenylyl | H | H | H | o-biphenylyl | Ph | H |
| J-77 | o-biphenylyl | H | H | H | o-biphenylyl | H | Ph |
| J-78 | o-biphenylyl | H | H | H | o-biphenylyl | Ph | Ph |
| J-79 | o-biphenylyl | H | H | H | o-biphenylyl | 1-naphthyl | H |
| J-80 | o-biphenylyl | H | H | H | o-biphenylyl | H | 1-naphthyl |
| J-81 | o-biphenylyl | H | H | H | o-biphenylyl | 1-naphthyl | 1-naphthyl |
| J-82 | o-biphenylyl | H | H | H | o-biphenylyl | 2-naphthyl | H |
| J-83 | o-biphenylyl | H | H | H | o-biphenylyl | H | 2-naphthyl |
| J-84 | o-biphenylyl | H | H | H | o-biphenylyl | 2-naphthyl | 2-naphthyl |
| J-85 | o-biphenylyl | H | H | H | o-biphenylyl | o-biphenylyl | H |
| J-86 | o-biphenylyl | H | H | H | o-biphenylyl | H | o-biphenylyl |

-continued

| | | | | | | | |
|---|---|---|---|---|---|---|---|
| J-87 | o-biphenylyl | H | H | H | o-biphenylyl | o-biphenylyl | o-biphenylyl |
| J-88 | o-biphenylyl | H | H | H | o-biphenylyl | m-biphenylyl | H |
| J-89 | o-biphenylyl | H | H | H | o-biphenylyl | H | m-biphenylyl |
| J-90 | o-biphenylyl | H | H | H | o-biphenylyl | m-biphenylyl | m-biphenylyl |
| J-91 | o-biphenylyl | H | H | H | o-biphenylyl | p-biphenylyl | H |
| J-92 | o-biphenylyl | H | H | H | o-biphenylyl | H | p-biphenylyl |
| J-93 | o-biphenylyl | H | H | H | o-biphenylyl | p-biphenylyl | p-biphenylyl |
| J-94 | m-biphenylyl | H | H | H | m-biphenylyl | H | H |
| J-95 | m-biphenylyl | Ph | H | H | m-biphenylyl | H | H |
| J-96 | m-biphenylyl | H | H | Ph | m-biphenylyl | H | H |
| J-97 | m-biphenylyl | Ph | H | Ph | m-biphenylyl | H | H |
| J-98 | m-biphenylyl | H | Ph | H | m-biphenylyl | H | H |
| J-99 | m-biphenylyl | H | H | H | m-biphenylyl | Ph | H |
| J-100 | m-biphenylyl | H | H | H | m-biphenylyl | H | Ph |
| J-101 | m-biphenylyl | H | H | H | m-biphenylyl | Ph | Ph |
| J-102 | m-biphenylyl | H | H | H | m-biphenylyl | 1-naphthyl | H |
| J-103 | m-biphenylyl | H | H | H | m-biphenylyl | H | 1-naphthyl |
| J-104 | m-biphenylyl | H | H | H | m-biphenylyl | 1-naphthyl | 1-naphthyl |
| J-105 | m-biphenylyl | H | H | H | m-biphenylyl | 2-naphthyl | H |
| J-106 | m-biphenylyl | H | H | H | m-biphenylyl | H | 2-naphthyl |
| J-107 | m-biphenylyl | H | H | H | m-biphenylyl | 2-naphthyl | 2-naphthyl |
| J-108 | m-biphenylyl | H | H | H | m-biphenylyl | o-biphenylyl | H |
| J-109 | m-biphenylyl | H | H | H | m-biphenylyl | H | o-biphenylyl |
| J-110 | m-biphenylyl | H | H | H | m-biphenylyl | o-biphenylyl | o-biphenylyl |
| J-111 | m-biphenylyl | H | H | H | m-biphenylyl | m-biphenylyl | H |
| J-112 | m-biphenylyl | H | H | H | m-biphenylyl | H | m-biphenylyl |
| J-113 | m-biphenylyl | H | H | H | m-biphenylyl | m-biphenylyl | m-biphenylyl |
| J-114 | m-biphenylyl | H | H | H | m-biphenylyl | p-biphenylyl | H |
| J-115 | m-biphenylyl | H | H | H | m-biphenylyl | H | p-biphenylyl |
| J-116 | m-biphenylyl | H | H | H | m-biphenylyl | p-biphenylyl | p-biphenylyl |
| J-117 | p-biphenylyl | H | H | H | p-biphenylyl | H | H |
| J-118 | p-biphenylyl | Ph | H | H | p-biphenylyl | H | H |
| J-119 | p-biphenylyl | H | H | Ph | p-biphenylyl | H | H |
| J-120 | p-biphenylyl | Ph | H | Ph | p-biphenylyl | H | H |
| J-121 | p-biphenylyl | H | Ph | H | p-biphenylyl | H | H |
| J-122 | p-biphenylyl | H | H | H | p-biphenylyl | Ph | H |
| J-123 | p-biphenylyl | H | H | H | p-biphenylyl | H | Ph |
| J-124 | p-biphenylyl | H | H | H | p-biphenylyl | Ph | Ph |
| J-125 | p-biphenylyl | H | H | H | p-biphenylyl | 1-naphthyl | H |
| J-126 | p-biphenylyl | H | H | H | p-biphenylyl | H | 1-naphthyl |
| J-127 | p-biphenylyl | H | H | H | p-biphenylyl | 1-naphthyl | 1-naphthyl |
| J-128 | p-biphenylyl | H | H | H | p-biphenylyl | 2-naphthyl | H |
| J-129 | p-biphenylyl | H | H | H | p-biphenylyl | H | 2-naphthyl |
| J-130 | p-biphenylyl | H | H | H | p-biphenylyl | 2-naphthyl | 2-naphthyl |
| J-131 | p-biphenylyl | H | H | H | p-biphenylyl | o-biphenylyl | H |
| J-132 | p-biphenylyl | H | H | H | p-biphenylyl | H | o-biphenylyl |
| J-133 | p-biphenylyl | H | H | H | p-biphenylyl | o-biphenylyl | o-biphenylyl |
| J-134 | p-biphenylyl | H | H | H | p-biphenylyl | m-biphenylyl | H |
| J-135 | p-biphenylyl | H | H | H | p-biphenylyl | H | m-biphenylyl |
| J-136 | p-biphenylyl | H | H | H | p-biphenylyl | m-biphenylyl | m-biphenylyl |
| J-137 | p-biphenylyl | H | H | H | p-biphenylyl | p-biphenylyl | H |
| J-138 | p-biphenylyl | H | H | H | p-biphenylyl | H | p-biphenylyl |
| J-139 | p-biphenylyl | H | H | H | p-biphenylyl | p-biphenylyl | p-biphenylyl |
| J-140 | o-tolyl | H | H | H | o-tolyl | H | H |
| J-141 | o-tolyl | Ph | H | Ph | o-tolyl | H | H |
| J-142 | o-tolyl | H | Ph | H | o-tolyl | H | H |
| J-143 | o-tolyl | H | H | H | o-tolyl | Ph | H |
| J-144 | o-tolyl | H | H | H | o-tolyl | H | Ph |
| J-145 | o-tolyl | H | H | H | o-tolyl | 1-naphthyl | H |
| J-146 | o-tolyl | H | H | H | o-tolyl | H | 1-naphthyl |
| J-147 | o-tolyl | H | H | H | o-tolyl | 2-naphthyl | H |
| J-148 | o-tolyl | H | H | H | o-tolyl | H | 2-naphthyl |
| J-149 | o-tolyl | H | H | H | o-tolyl | o-biphenylyl | H |
| J-150 | o-tolyl | H | H | H | o-tolyl | H | o-biphenylyl |
| J-151 | o-tolyl | H | H | H | o-tolyl | m-biphenylyl | H |
| J-152 | o-tolyl | H | H | H | o-tolyl | H | m-biphenylyl |
| J-153 | o-tolyl | H | H | H | o-tolyl | p-biphenylyl | H |
| J-154 | o-tolyl | H | H | H | o-tolyl | H | p-biphenylyl |
| J-155 | o-tolyl | H | H | H | o-tolyl | o-tolyl | H |
| J-156 | o-tolyl | H | H | H | o-tolyl | H | o-tolyl |
| J-157 | m-tolyl | H | H | H | m-tolyl | H | H |
| J-158 | m-tolyl | Ph | H | Ph | m-tolyl | H | H |
| J-159 | m-tolyl | H | Ph | H | m-tolyl | H | H |
| J-160 | m-tolyl | H | H | H | m-tolyl | Ph | H |
| J-161 | m-tolyl | H | H | H | m-tolyl | H | Ph |
| J-162 | m-tolyl | H | H | H | m-tolyl | 1-naphthyl | H |
| J-163 | m-tolyl | H | H | H | m-tolyl | H | 1-naphthyl |
| J-164 | m-tolyl | H | H | H | m-tolyl | 2-naphthyl | H |
| J-165 | m-tolyl | H | H | H | m-tolyl | H | 2-naphthyl |
| J-166 | m-tolyl | H | H | H | m-tolyl | o-biphenylyl | H |

-continued

| | | | | | | | |
|---|---|---|---|---|---|---|---|
| J-167 | m-tolyl | H | H | H | m-tolyl | H | o-biphenylyl |
| J-168 | m-tolyl | H | H | H | m-tolyl | m-biphenylyl | H |
| J-169 | m-tolyl | H | H | H | m-tolyl | H | m-biphenylyl |
| J-170 | m-tolyl | H | H | H | m-tolyl | p-biphenylyl | H |
| J-171 | m-tolyl | H | H | H | m-tolyl | H | p-biphenylyl |
| J-172 | m-tolyl | H | H | H | m-tolyl | m-tolyl | H |
| J-173 | m-tolyl | H | H | H | m-tolyl | H | m-tolyl |
| J-174 | p-tolyl | H | H | H | p-tolyl | H | H |
| J-175 | p-tolyl | Ph | H | Ph | p-tolyl | H | H |
| J-176 | p-tolyl | H | Ph | H | p-tolyl | H | H |
| J-177 | p-tolyl | H | H | H | p-tolyl | Ph | H |
| J-178 | p-tolyl | H | H | H | p-tolyl | H | Ph |
| J-179 | p-tolyl | H | H | H | p-tolyl | 1-naphthyl | H |
| J-180 | p-tolyl | H | H | H | p-tolyl | H | 1-naphthyl |
| J-181 | p-tolyl | H | H | H | p-tolyl | 2-naphthyl | H |
| J-182 | p-tolyl | H | H | H | p-tolyl | H | 2-naphthyl |
| J-183 | p-tolyl | H | H | H | p-tolyl | o-biphenylyl | H |
| J-184 | p-tolyl | H | H | H | p-tolyl | H | o-biphenylyl |
| J-185 | p-tolyl | H | H | H | p-tolyl | m-biphenylyl | H |
| J-186 | p-tolyl | H | H | H | p-tolyl | H | m-biphenylyl |
| J-187 | p-tolyl | H | H | H | p-tolyl | p-biphenylyl | H |
| J-188 | p-tolyl | H | H | H | p-tolyl | H | p-biphenylyl |
| J-189 | p-tolyl | H | H | H | p-tolyl | p-tolyl | H |
| J-190 | p-tolyl | H | H | H | p-tolyl | H | p-tolyl |
| J-191 | Ph | H | —CH3 | H | Ph | H | H |
| J-192 | 1-naphtyl | H | —CH3 | H | 1-naphtyl | H | H |
| J-193 | 2-naphthyl | H | —CH3 | H | 2-naphthyl | H | H |
| J-194 | o-biphenylyl | H | —CH3 | H | o-biphenylyl | H | H |
| J-195 | m-biphenylyl | H | —CH3 | H | m-biphenylyl | H | H |
| J-196 | p-biphenylyl | H | —CH3 | H | p-biphenylyl | H | H |
| J-197 | o-tolyl | H | —CH3 | H | o-tolyl | H | H |
| J-198 | m-tolyl | H | —CH3 | H | m-tolyl | H | H |
| J-199 | p-tolyl | H | —CH3 | H | p-tolyl | H | H |
| J-200 | Ph | H | H | H | Ph | —CH3 | H |
| J-201 | 1-naphtyl | H | H | H | 1-naphtyl | —CH3 | H |
| J-202 | 2-naphthyl | H | H | H | 2-naphthyl | —CH3 | H |
| J-203 | o-biphenylyl | H | H | H | o-biphenylyl | —CH3 | H |
| J-204 | m-biphenylyl | H | H | H | m-biphenylyl | —CH3 | H |
| J-205 | p-biphenylyl | H | H | H | p-biphenylyl | —CH3 | H |
| J-206 | o-tolyl | H | H | H | o-tolyl | —CH3 | H |
| J-207 | m-tolyl | H | H | H | m-tolyl | —CH3 | H |
| J-208 | p-tolyl | H | H | H | p-tolyl | —CH3 | H |
| J-209 | Ph | H | H | H | Ph | H | —CH3 |
| J-210 | 1-naphtyl | H | H | H | 1-naphtyl | H | —CH3 |
| J-211 | 2-naphthyl | H | H | H | 2-naphthyl | H | —CH3 |
| J-212 | o-biphenylyl | H | H | H | o-biphenylyl | H | —CH3 |
| J-213 | m-biphenylyl | H | H | H | m-biphenylyl | H | —CH3 |
| J-214 | p-biphenylyl | H | H | H | p-biphenylyl | H | —CH3 |
| J-215 | o-tolyl | H | H | H | o-tolyl | H | —CH3 |
| J-216 | m-tolyl | H | H | H | m-tolyl | H | —CH3 |
| J-217 | p-tolyl | H | H | H | p-tolyl | H | —CH3 |
| J-218 | Ph | H | H | H | Ph | —CH3 | —CH3 |
| J-219 | 1-naphtyl | H | H | H | 1-naphtyl | —CH3 | —CH3 |
| J-220 | 2-naphthyl | H | H | H | 2-naphthyl | —CH3 | —CH3 |
| J-221 | o-biphenylyl | H | H | H | o-biphenylyl | —CH3 | —CH3 |
| J-222 | m-biphenylyl | H | H | H | m-biphenylyl | —CH3 | —CH3 |
| J-223 | p-biphenylyl | H | H | H | p-biphenylyl | —CH3 | —CH3 |
| J-224 | o-tolyl | H | H | H | o-tolyl | —CH3 | —CH3 |
| J-225 | m-tolyl | H | H | H | m-tolyl | —CH3 | —CH3 |
| J-226 | p-tolyl | H | H | H | p-tolyl | —CH3 | —CH3 |
| J-227 | Ph | H | H | H | Ph | H | DPA |
| J-228 | 1-naphtyl | H | H | H | 1-naphtyl | H | DPA |
| J-229 | 2-naphthyl | H | H | H | 2-naphthyl | H | DPA |
| J-230 | o-biphenylyl | H | H | H | o-biphenylyl | H | DPA |
| J-231 | m-biphenylyl | H | H | H | m-biphenylyl | H | DPA |
| J-232 | p-biphenylyl | H | H | H | p-biphenylyl | H | DPA |
| J-233 | Ph | H | H | H | Ph | DPA | H |
| J-234 | 1-naphtyl | H | H | H | 1-naphtyl | DPA | H |
| J-235 | 2-naphthyl | H | H | H | 2-naphthyl | DPA | H |
| J-236 | o-biphenylyl | H | H | H | o-biphenylyl | DPA | H |
| J-237 | m-biphenylyl | H | H | H | m-biphenylyl | DPA | H |
| J-238 | p-biphenylyl | H | H | H | p-biphenylyl | DPA | H |
| J-239 | Ph | H | H | H | Ph | H | TPA |
| J-240 | 1-naphtyl | H | H | H | 1-naphtyl | H | TPA |
| J-241 | 2-naphthyl | H | H | H | 2-naphthyl | H | TPA |
| J-242 | o-biphenylyl | H | H | H | o-biphenylyl | H | TPA |
| J-243 | m-biphenylyl | H | H | H | m-biphenylyl | H | TPA |
| J-244 | p-biphenylyl | H | H | H | p-biphenylyl | H | TPA |
| J-245 | Ph | H | H | H | Ph | TPA | H |
| J-246 | 1-naphtyl | H | H | H | 1-naphtyl | TPA | H |

-continued

| | | | | | | | |
|---|---|---|---|---|---|---|---|
| J-247 | 2-naphthyl | H | H | H | 2-naphthyl | TPA | H |
| J-248 | o-biphenylyl | H | H | H | o-biphenylyl | TPA | H |
| J-249 | m-biphenylyl | H | H | H | m-biphenylyl | TPA | H |
| J-250 | p-biphenylyl | H | H | H | p-biphenylyl | TPA | H |
| J-251 | Ph | H | H | H | 1-naphthyl | H | H |
| J-252 | Ph | H | H | H | 2-naphthyl | H | H |
| J-253 | Ph | H | H | H | o-biphenylyl | H | H |
| J-254 | Ph | H | H | H | m-biphenylyl | H | H |
| J-255 | Ph | H | H | H | p-biphenylyl | H | H |
| J-256 | Ph | H | H | H | O-tolyly | H | H |
| J-257 | Ph | H | H | H | m-tolyl | H | H |
| J-258 | Ph | H | H | H | p-tolyl | H | H |
| J-259 | 1-naphthyl | H | H | H | 2-naphthyl | H | H |
| J-260 | 1-naphthyl | H | H | H | o-biphenylyl | H | H |
| J-261 | 1-naphthyl | H | H | H | m-biphenylyl | H | H |
| J-262 | 1-naphthyl | H | H | H | p-biphenylyl | H | H |
| J-263 | 1-naphthyl | H | H | H | o-tolyly | H | H |
| J-264 | 1-naphthyl | H | H | H | m-tolyl | H | H |
| J-265 | 1-naphthyl | H | H | H | p-tolyl | H | H |
| J-266 | 2-naphthyl | H | H | H | o-biphenylyl | H | H |
| J-267 | 2-naphthyl | H | H | H | m-biphenylyl | H | H |
| J-268 | 2-naphthyl | H | H | H | p-biphenylyl | H | H |
| J-269 | 2-naphthyl | H | H | H | O-tolyly | H | H |
| J-270 | 2-naphthyl | H | H | H | m-tolyl | H | H |
| J-271 | 2-naphthyl | H | H | H | p-tolyl | H | H |
| J-272 | o-biphenylyl | H | H | H | m-biphenylyl | H | H |
| J-273 | o-biphenylyl | H | H | H | p-biphenylyl | H | H |
| J-274 | o-biphenylyl | H | H | H | O-tolyly | H | H |
| J-275 | o-biphenylyl | H | H | H | m-tolyl | H | H |
| J-276 | o-biphenylyl | H | H | H | p-tolyl | H | H |
| J-277 | m-biphenylyl | H | H | H | p-biphenylyl | H | H |
| J-278 | m-biphenylyl | H | H | H | O-tolyly | H | H |
| J-279 | m-biphenylyl | H | H | H | m-tolyl | H | H |
| J-280 | m-biphenylyl | H | H | H | p-tolyl | H | H |
| J-281 | p-biphenylyl | H | H | H | O-tolyly | H | H |
| J-282 | p-biphenylyl | H | H | H | m-tolyl | H | H |
| J-283 | p-biphenylyl | H | H | H | p-tolyl | H | H |
| J-284 | O-tolyly | H | H | H | m-tolyl | H | H |
| J-285 | O-tolyly | H | H | H | p-tolyl | H | H |
| J-286 | m-tolyly | H | H | H | p-tolyl | H | H |

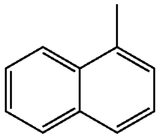

1-naphthyl

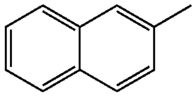

2-naphthyl

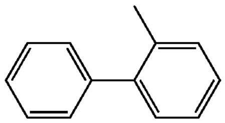

o-biphenylyl

-continued
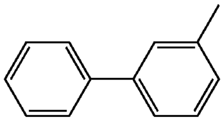
m-biphenylyl
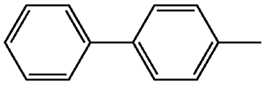
p-biphenylyl
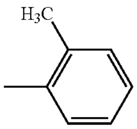
o-tolyl
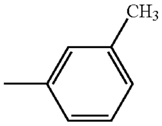
m-tolyl
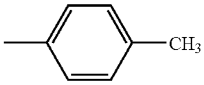
p-tolyl
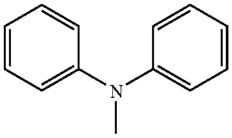
DPA
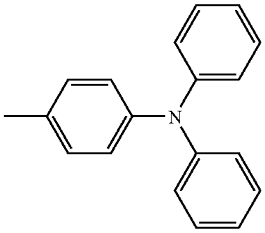
TPA

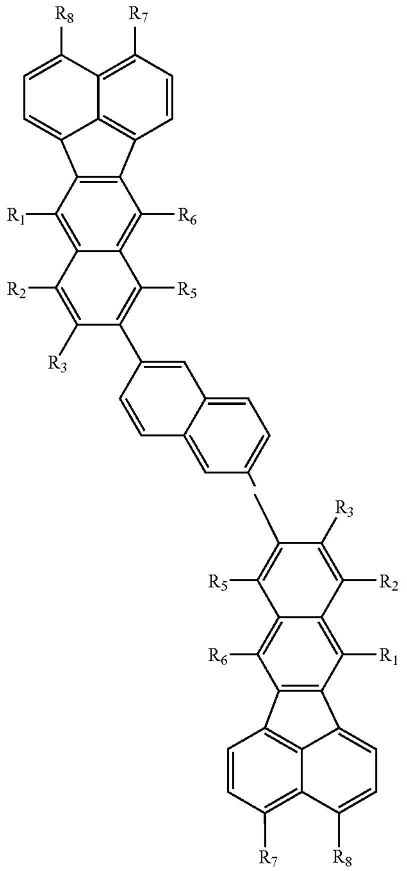

TypeK

| | $R_1$ | $R_2$ | $R_3$ | $R_5$ | $R_6$ | $R_7$ | $R_8$ |
|---|---|---|---|---|---|---|---|
| K-1 | H | H | H | H | H | H | H |
| K-2 | Ph | H | H | H | Ph | H | H |
| K-3 | Ph | Ph | H | H | Ph | H | H |
| K-4 | Ph | H | H | Ph | Ph | H | H |
| K-5 | Ph | Ph | H | Ph | Ph | H | H |
| K-6 | Ph | H | Ph | H | Ph | H | H |
| K-7 | Ph | H | H | H | Ph | Ph | H |
| K-8 | Ph | H | H | H | Ph | H | Ph |
| K-9 | Ph | H | H | H | Ph | Ph | Ph |
| K-10 | Ph | H | H | H | Ph | 1-naphthyl | H |
| K-11 | Ph | H | H | H | Ph | H | 1-naphthyl |
| K-12 | Ph | H | H | H | Ph | 1-naphthyl | 1-naphthyl |
| K-13 | Ph | H | H | H | Ph | 2-naphthyl | H |
| K-14 | Ph | H | H | H | Ph | H | 2-naphthyl |
| K-15 | Ph | H | H | H | Ph | 2-naphthyl | 2-naphthyl |
| K-16 | Ph | H | H | H | Ph | o-biphenylyl | H |
| K-17 | Ph | H | H | H | Ph | H | o-biphenylyl |
| K-18 | Ph | H | H | H | Ph | o-biphenylyl | o-biphenylyl |
| K-19 | Ph | H | H | H | Ph | m-biphenylyl | H |
| K-20 | Ph | H | H | H | Ph | H | m-biphenylyl |
| K-21 | Ph | H | H | H | Ph | m-biphenylyl | m-biphenylyl |
| K-22 | Ph | H | H | H | Ph | p-biphenylyl | H |
| K-23 | Ph | H | H | H | Ph | H | p-biphenylyl |
| K-24 | Ph | H | H | H | Ph | p-biphenylyl | p-biphenylyl |
| K-25 | 1-naphthyl | H | H | H | 1-naphthyl | H | H |
| K-26 | 1-naphthyl | Ph | H | H | 1-naphthyl | H | H |
| K-27 | 1-naphthyl | H | H | Ph | 1-naphthyl | H | H |
| K-28 | 1-naphthyl | Ph | H | Ph | 1-naphthyl | H | H |
| K-29 | 1-naphthyl | H | Ph | H | 1-naphthyl | H | H |
| K-30 | 1-naphthyl | H | H | H | 1-naphthyl | Ph | H |
| K-31 | 1-naphthyl | H | H | H | 1-naphthyl | H | Ph |
| K-32 | 1-naphthyl | H | H | H | 1-naphthyl | Ph | Ph |
| K-33 | 1-naphthyl | H | H | H | 1-naphthyl | 1-naphthyl | H |

-continued

| | | | | | | | |
|---|---|---|---|---|---|---|---|
| K-34 | 1-naphthyl | H | H | H | 1-naphthyl | H | 1-naphthyl |
| K-35 | 1-naphthyl | H | H | H | 1-naphthyl | 1-naphthyl | 1-naphthyl |
| K-36 | 1-naphthyl | H | H | H | 1-naphthyl | 2-naphthyl | H |
| K-37 | 1-naphthyl | H | H | H | 1-naphthyl | H | 2-naphthyl |
| K-38 | 1-naphthyl | H | H | H | 1-naphthyl | 2-naphthyl | 2-naphthyl |
| K-39 | 1-naphthyl | H | H | H | 1-naphthyl | o-biphenylyl | H |
| K-40 | 1-naphthyl | H | H | H | 1-naphthyl | H | o-biphenylyl |
| K-41 | 1-naphthyl | H | H | H | 1-naphthyl | o-biphenylyl | o-biphenylyl |
| K-42 | 1-naphthyl | H | H | H | 1-naphthyl | m-biphenylyl | H |
| K-43 | 1-naphthyl | H | H | H | 1-naphthyl | H | m-biphenylyl |
| K-44 | 1-naphthyl | H | H | H | 1-naphthyl | m-biphenylyl | m-biphenylyl |
| K-45 | 1-naphthyl | H | H | H | 1-naphthyl | p-biphenylyl | H |
| K-46 | 1-naphthyl | H | H | H | 1-naphthyl | H | p-biphenylyl |
| K-47 | 1-naphthyl | H | H | H | 1-naphthyl | p-biphenylyl | p-biphenylyl |
| K-48 | 2-naphthyl | H | H | H | 2-naphthyl | H | H |
| K-49 | 2-naphthyl | Ph | H | H | 2-naphthyl | H | H |
| K-50 | 2-naphthyl | H | H | Ph | 2-naphthyl | H | H |
| K-51 | 2-naphthyl | Ph | H | Ph | 2-naphthyl | H | H |
| K-52 | 2-naphthyl | H | Ph | H | 2-naphthyl | H | H |
| K-53 | 2-naphthyl | H | H | H | 2-naphthyl | Ph | H |
| K-54 | 2-naphthyl | H | H | H | 2-naphthyl | H | Ph |
| K-55 | 2-naphthyl | H | H | H | 2-naphthyl | Ph | Ph |
| K-56 | 2-naphthyl | H | H | H | 2-naphthyl | 1-naphthyl | H |
| K-57 | 2-naphthyl | H | H | H | 2-naphthyl | H | 1-naphthyl |
| K-58 | 2-naphthyl | H | H | H | 2-naphthyl | 1-naphthyl | 1-naphthyl |
| K-59 | 2-naphthyl | H | H | H | 2-naphthyl | 2-naphthyl | H |
| K-60 | 2-naphthyl | H | H | H | 2-naphthyl | H | 2-naphthyl |
| K-61 | 2-naphthyl | H | H | H | 2-naphthyl | 2-naphthyl | 2-naphthyl |
| K-62 | 2-naphthyl | H | H | H | 2-naphthyl | o-biphenylyl | H |
| K-63 | 2-naphthyl | H | H | H | 2-naphthyl | H | o-biphenylyl |
| K-64 | 2-naphthyl | H | H | H | 2-naphthyl | o-biphenylyl | o-biphenylyl |
| K-65 | 2-naphthyl | H | H | H | 2-naphthyl | m-biphenylyl | H |
| K-66 | 2-naphthyl | H | H | H | 2-naphthyl | H | m-biphenylyl |
| K-67 | 2-naphthyl | H | H | H | 2-naphthyl | m-biphenylyl | m-biphenylyl |
| K-68 | 2-naphthyl | H | H | H | 2-naphthyl | p-biphenylyl | H |
| K-69 | 2-naphthyl | H | H | H | 2-naphthyl | H | p-biphenylyl |
| K-70 | 2-naphthyl | H | H | H | 2-naphthyl | p-biphenylyl | p-biphenylyl |
| K-71 | o-biphenylyl | H | H | H | o-biphenylyl | H | H |
| K-72 | o-biphenylyl | Ph | H | H | o-biphenylyl | H | H |
| K-73 | o-biphenylyl | H | H | Ph | o-biphenylyl | H | H |
| K-74 | o-biphenylyl | Ph | H | Ph | o-biphenylyl | H | H |
| K-75 | o-biphenylyl | H | Ph | H | o-biphenylyl | H | H |
| K-76 | o-biphenylyl | H | H | H | o-biphenylyl | Ph | H |
| K-77 | o-biphenylyl | H | H | H | o-biphenylyl | H | Ph |
| K-78 | o-biphenylyl | H | H | H | o-biphenylyl | Ph | Ph |
| K-79 | o-biphenylyl | H | H | H | o-biphenylyl | 1-naphthyl | H |
| K-80 | o-biphenylyl | H | H | H | o-biphenylyl | H | 1-naphthyl |
| K-81 | o-biphenylyl | H | H | H | o-biphenylyl | 1-naphthyl | 1-naphthyl |
| K-82 | o-biphenylyl | H | H | H | o-biphenylyl | 2-naphthyl | H |
| K-83 | o-biphenylyl | H | H | H | o-biphenylyl | H | 2-naphthyl |
| K-84 | o-biphenylyl | H | H | H | o-biphenylyl | 2-naphthyl | 2-naphthyl |
| K-85 | o-biphenylyl | H | H | H | o-biphenylyl | o-biphenylyl | H |
| K-86 | o-biphenylyl | H | H | H | o-biphenylyl | H | o-biphenylyl |
| K-87 | o-biphenylyl | H | H | H | o-biphenylyl | o-biphenylyl | o-biphenylyl |
| K-88 | o-biphenylyl | H | H | H | o-biphenylyl | m-biphenylyl | H |
| K-89 | o-biphenylyl | H | H | H | o-biphenylyl | H | m-biphenylyl |
| K-90 | o-biphenylyl | H | H | H | o-biphenylyl | m-biphenylyl | m-biphenylyl |
| K-91 | o-biphenylyl | H | H | H | o-biphenylyl | p-biphenylyl | H |
| K-92 | o-biphenylyl | H | H | H | o-biphenylyl | H | p-biphenylyl |
| K-93 | o-biphenylyl | H | H | H | o-biphenylyl | p-biphenylyl | p-biphenylyl |
| K-94 | m-biphenylyl | H | H | H | m-biphenylyl | H | H |
| K-95 | m-biphenylyl | Ph | H | H | m-biphenylyl | H | H |
| K-96 | m-biphenylyl | H | H | Ph | m-biphenylyl | H | H |
| K-97 | m-biphenylyl | Ph | H | Ph | m-biphenylyl | H | H |
| K-98 | m-biphenylyl | H | Ph | H | m-biphenylyl | H | H |
| K-99 | m-biphenylyl | H | H | H | m-biphenylyl | Ph | H |
| K-100 | m-biphenylyl | H | H | H | m-biphenylyl | H | Ph |
| K-101 | m-biphenylyl | H | H | H | m-biphenylyl | Ph | Ph |
| K-102 | m-biphenylyl | H | H | H | m-biphenylyl | 1-naphthyl | H |
| K-103 | m-biphenylyl | H | H | H | m-biphenylyl | H | 1-naphthyl |
| K-104 | m-biphenylyl | H | H | H | m-biphenylyl | 1-naphthyl | 1-naphthyl |
| K-105 | m-biphenylyl | H | H | H | m-biphenylyl | 2-naphthyl | H |
| K-106 | m-biphenylyl | H | H | H | m-biphenylyl | H | 2-naphthyl |
| K-107 | m-biphenylyl | H | H | H | m-biphenylyl | 2-naphthyl | 2-naphthyl |
| K-108 | m-biphenylyl | H | H | H | m-biphenylyl | o-biphenylyl | H |
| K-109 | m-biphenylyl | H | H | H | m-biphenylyl | H | o-biphenylyl |
| K-110 | m-biphenylyl | H | H | H | m-biphenylyl | o-biphenylyl | o-biphenylyl |
| K-111 | m-biphenylyl | H | H | H | m-biphenylyl | m-biphenylyl | H |
| K-112 | m-biphenylyl | H | H | H | m-biphenylyl | H | m-biphenylyl |

-continued

| | | | | | | | |
|---|---|---|---|---|---|---|---|
| K-113 | m-biphenylyl | H | H | H | m-biphenylyl | m-biphenylyl | m-biphenylyl |
| K-114 | m-biphenylyl | H | H | H | m-biphenylyl | p-biphenylyl | H |
| K-115 | m-biphenylyl | H | H | H | m-biphenylyl | H | p-biphenylyl |
| K-116 | m-biphenylyl | H | H | H | m-biphenylyl | p-biphenylyl | p-biphenylyl |
| K-117 | p-biphenylyl | H | H | H | p-biphenylyl | H | H |
| K-118 | p-biphenylyl | Ph | H | H | p-biphenylyl | H | H |
| K-119 | p-biphenylyl | H | H | Ph | p-biphenylyl | H | H |
| K-120 | p-biphenylyl | Ph | H | Ph | p-biphenylyl | H | H |
| K-121 | p-biphenylyl | H | Ph | H | p-biphenylyl | H | H |
| K-122 | p-biphenylyl | H | H | H | p-biphenylyl | Ph | H |
| K-123 | p-biphenylyl | H | H | H | p-biphenylyl | H | Ph |
| K-124 | p-biphenylyl | H | H | H | p-biphenylyl | Ph | Ph |
| K-125 | p-biphenylyl | H | H | H | p-biphenylyl | 1-naphthyl | H |
| K-126 | p-biphenylyl | H | H | H | p-biphenylyl | H | 1-naphthyl |
| K-127 | p-biphenylyl | H | H | H | p-biphenylyl | 1-naphthyl | 1-naphthyl |
| K-128 | p-biphenylyl | H | H | H | p-biphenylyl | 2-naphthyl | H |
| K-129 | p-biphenylyl | H | H | H | p-biphenylyl | H | 2-naphthyl |
| K-130 | p-biphenylyl | H | H | H | p-biphenylyl | 2-naphthyl | 2-naphthyl |
| K-131 | p-biphenylyl | H | H | H | p-biphenylyl | o-biphenylyl | H |
| K-132 | p-biphenylyl | H | H | H | p-biphenylyl | H | o-biphenylyl |
| K-133 | p-biphenylyl | H | H | H | p-biphenylyl | o-biphenylyl | o-biphenylyl |
| K-134 | p-biphenylyl | H | H | H | p-biphenylyl | m-biphenylyl | H |
| K-135 | p-biphenylyl | H | H | H | p-biphenylyl | H | m-biphenylyl |
| K-136 | p-biphenylyl | H | H | H | p-biphenylyl | m-biphenylyl | m-biphenylyl |
| K-137 | p-biphenylyl | H | H | H | p-biphenylyl | p-biphenylyl | H |
| K-138 | p-biphenylyl | H | H | H | p-biphenylyl | H | p-biphenylyl |
| K-139 | p-biphenylyl | H | H | H | p-biphenylyl | p-biphenylyl | p-biphenylyl |
| K-140 | o-tolyl | H | H | H | o-tolyl | H | H |
| K-141 | o-tolyl | Ph | H | Ph | o-tolyl | H | H |
| K-142 | o-tolyl | H | Ph | H | o-tolyl | H | H |
| K-143 | o-tolyl | H | H | H | o-tolyl | Ph | H |
| K-144 | o-tolyl | H | H | H | o-tolyl | H | Ph |
| K-145 | o-tolyl | H | H | H | o-tolyl | 1-naphthyl | H |
| K-146 | o-tolyl | H | H | H | o-tolyl | H | 1-naphthyl |
| K-147 | o-tolyl | H | H | H | o-tolyl | 2-naphthyl | H |
| K-148 | o-tolyl | H | H | H | o-tolyl | H | 2-naphthyl |
| K-149 | o-tolyl | H | H | H | o-tolyl | o-biphenylyl | H |
| K-150 | o-tolyl | H | H | H | o-tolyl | H | o-biphenylyl |
| K-151 | o-tolyl | H | H | H | o-tolyl | m-biphenylyl | H |
| K-152 | o-tolyl | H | H | H | o-tolyl | H | m-biphenylyl |
| K-153 | o-tolyl | H | H | H | o-tolyl | p-biphenylyl | H |
| K-154 | o-tolyl | H | H | H | o-tolyl | H | p-biphenylyl |
| K-155 | o-tolyl | H | H | H | o-tolyl | o-tolyl | H |
| K-156 | o-tolyl | H | H | H | o-tolyl | H | o-tolyl |
| K-157 | m-tolyl | H | H | H | m-tolyl | H | H |
| K-158 | m-tolyl | Ph | H | Ph | m-tolyl | H | H |
| K-159 | m-tolyl | H | Ph | H | m-tolyl | H | H |
| K-160 | m-tolyl | H | H | H | m-tolyl | Ph | H |
| K-161 | m-tolyl | H | H | H | m-tolyl | H | Ph |
| K-162 | m-tolyl | H | H | H | m-tolyl | 1-naphthyl | H |
| K-163 | m-tolyl | H | H | H | m-tolyl | H | 1-naphthyl |
| K-164 | m-tolyl | H | H | H | m-tolyl | 2-naphthyl | H |
| K-165 | m-tolyl | H | H | H | m-tolyl | H | 2-naphthyl |
| K-166 | m-tolyl | H | H | H | m-tolyl | o-biphenylyl | H |
| K-167 | m-tolyl | H | H | H | m-tolyl | H | o-biphenylyl |
| K-168 | m-tolyl | H | H | H | m-tolyl | m-biphenylyl | H |
| K-169 | m-tolyl | H | H | H | m-tolyl | H | m-biphenylyl |
| K-170 | m-tolyl | H | H | H | m-tolyl | p-biphenylyl | H |
| K-171 | m-tolyl | H | H | H | m-tolyl | H | p-biphenylyl |
| K-172 | m-tolyl | H | H | H | m-tolyl | m-tolyl | H |
| K-173 | m-tolyl | H | H | H | m-tolyl | H | m-tolyl |
| K-174 | p-tolyl | H | H | H | p-tolyl | H | H |
| K-175 | p-tolyl | Ph | H | Ph | p-tolyl | H | H |
| K-176 | p-tolyl | H | Ph | H | p-tolyl | H | H |
| K-177 | p-tolyl | H | H | H | p-tolyl | Ph | H |
| K-178 | p-tolyl | H | H | H | p-tolyl | H | Ph |
| K-179 | p-tolyl | H | H | H | p-tolyl | 1-naphthyl | H |
| K-180 | p-tolyl | H | H | H | p-tolyl | H | 1-naphthyl |
| K-181 | p-tolyl | H | H | H | p-tolyl | 2-naphthyl | H |
| K-182 | p-tolyl | H | H | H | p-tolyl | H | 2-naphthyl |
| K-183 | p-tolyl | H | H | H | p-tolyl | o-biphenylyl | H |
| K-184 | p-tolyl | H | H | H | p-tolyl | H | o-biphenylyl |
| K-185 | p-tolyl | H | H | H | p-tolyl | m-biphenylyl | H |
| K-186 | p-tolyl | H | H | H | p-tolyl | H | m-biphenylyl |
| K-187 | p-tolyl | H | H | H | p-tolyl | p-biphenylyl | H |
| K-188 | p-tolyl | H | H | H | p-tolyl | H | p-biphenylyl |
| K-189 | p-tolyl | H | H | H | p-tolyl | p-tolyl | H |
| K-190 | p-tolyl | H | H | H | p-tolyl | H | p-tolyl |
| K-191 | Ph | H | —CH3 | H | Ph | H | H |

-continued

| | | | | | | | |
|---|---|---|---|---|---|---|---|
| K-192 | 1-naphtyl | H | —CH3 | H | 1-naphtyl | H | H |
| K-193 | 2-naphthyl | H | —CH3 | H | 2-naphthyl | H | H |
| K-194 | o-biphenylyl | H | —CH3 | H | o-biphenylyl | H | H |
| K-195 | m-biphenylyl | H | —CH3 | H | m-biphenylyl | H | H |
| K-196 | p-biphenylyl | H | —CH3 | H | p-biphenylyl | H | H |
| K-197 | o-tolyl | H | —CH3 | H | o-tolyl | H | H |
| K-198 | m-tolyl | H | —CH3 | H | m-tolyl | H | H |
| K-199 | p-tolyl | H | —CH3 | H | p-tolyl | H | H |
| K-200 | Ph | H | H | H | Ph | —CH3 | H |
| K-201 | 1-naphtyl | H | H | H | 1-naphtyl | —CH3 | H |
| K-202 | 2-naphthyl | H | H | H | 2-naphthyl | —CH3 | H |
| K-203 | o-biphenylyl | H | H | H | o-biphenylyl | —CH3 | H |
| K-204 | m-biphenylyl | H | H | H | m-biphenylyl | —CH3 | H |
| K-205 | p-biphenylyl | H | H | H | p-biphenylyl | —CH3 | H |
| K-206 | o-tolyl | H | H | H | o-tolyl | —CH3 | H |
| K-207 | m-tolyl | H | H | H | m-tolyl | —CH3 | H |
| K-208 | p-tolyl | H | H | H | p-tolyl | —CH3 | H |
| K-209 | Ph | H | H | H | Ph | H | —CH3 |
| K-210 | 1-naphtyl | H | H | H | 1-naphtyl | H | —CH3 |
| K-211 | 2-naphthyl | H | H | H | 2-naphthyl | H | —CH3 |
| K-212 | o-biphenylyl | H | H | H | o-biphenylyl | H | —CH3 |
| K-213 | m-biphenylyl | H | H | H | m-biphenylyl | H | —CH3 |
| K-214 | p-biphenylyl | H | H | H | p-biphenylyl | H | —CH3 |
| K-215 | o-tolyl | H | H | H | o-tolyl | H | —CH3 |
| K-216 | m-tolyl | H | H | H | m-tolyl | H | —CH3 |
| K-217 | p-tolyl | H | H | H | p-tolyl | H | —CH3 |
| K-218 | Ph | H | H | H | Ph | —CH3 | —CH3 |
| K-219 | 1-naphtyl | H | H | H | 1-naphtyl | —CH3 | —CH3 |
| K-220 | 2-naphthyl | H | H | H | 2-naphthyl | —CH3 | —CH3 |
| K-221 | o-biphenylyl | H | H | H | o-biphenylyl | —CH3 | —CH3 |
| K-222 | m-biphenylyl | H | H | H | m-biphenylyl | —CH3 | —CH3 |
| K-223 | p-biphenylyl | H | H | H | p-biphenylyl | —CH3 | —CH3 |
| K-224 | o-tolyl | H | H | H | o-tolyl | —CH3 | —CH3 |
| K-225 | m-tolyl | H | H | H | m-tolyl | —CH3 | —CH3 |
| K-226 | p-tolyl | H | H | H | p-tolyl | —CH3 | —CH3 |
| K-227 | Ph | H | H | H | Ph | H | DPA |
| K-228 | 1-naphtyl | H | H | H | 1-naphtyl | H | DPA |
| K-229 | 2-naphthyl | H | H | H | 2-naphthyl | H | DPA |
| K-230 | o-biphenylyl | H | H | H | o-biphenylyl | H | DPA |
| K-231 | m-biphenylyl | H | H | H | m-biphenylyl | H | DPA |
| K-232 | p-biphenylyl | H | H | H | p-biphenylyl | H | DPA |
| K-233 | Ph | H | H | H | Ph | DPA | H |
| K-234 | 1-naphtyl | H | H | H | 1-naphtyl | DPA | H |
| K-235 | 2-naphthyl | H | H | H | 2-naphthyl | DPA | H |
| K-236 | o-biphenylyl | H | H | H | o-biphenylyl | DPA | H |
| K-237 | m-biphenylyl | H | H | H | m-biphenylyl | DPA | H |
| K-238 | p-biphenylyl | H | H | H | p-biphenylyl | DPA | H |
| K-239 | Ph | H | H | H | Ph | H | TPA |
| K-240 | 1-naphtyl | H | H | H | 1-naphtyl | H | TPA |
| K-241 | 2-naphthyl | H | H | H | 2-naphthyl | H | TPA |
| K-242 | o-biphenylyl | H | H | H | o-biphenylyl | H | TPA |
| K-243 | m-biphenylyl | H | H | H | m-biphenylyl | H | TPA |
| K-244 | p-biphenylyl | H | H | H | p-biphenylyl | H | TPA |
| K-245 | Ph | H | H | H | Ph | TPA | H |
| K-246 | 1-naphtyl | H | H | H | 1-naphtyl | TPA | H |
| K-247 | 2-naphthyl | H | H | H | 2-naphthyl | TPA | H |
| K-248 | o-biphenylyl | H | H | H | o-biphenylyl | TPA | H |
| K-249 | m-biphenylyl | H | H | H | m-biphenylyl | TPA | H |
| K-250 | p-biphenylyl | H | H | H | p-biphenylyl | TPA | H |
| K-251 | Ph | H | H | H | 1-naphthyl | H | H |
| K-252 | Ph | H | H | H | 2-naphthyl | H | H |
| K-253 | Ph | H | H | H | o-biphenylyl | H | H |
| K-254 | Ph | H | H | H | m-biphenylyl | H | H |
| K-255 | Ph | H | H | H | p-biphenylyl | H | H |
| K-256 | Ph | H | H | H | O-tolyly | H | H |
| K-257 | Ph | H | H | H | m-tolyl | H | H |
| K-258 | Ph | H | H | H | p-tolyl | H | H |
| K-259 | 1-naphthyl | H | H | H | 2-naphthyl | H | H |
| K-260 | 1-naphthyl | H | H | H | o-biphenylyl | H | H |
| K-261 | 1-naphthyl | H | H | H | m-biphenylyl | H | H |
| K-262 | 1-naphthyl | H | H | H | p-biphenylyl | H | H |
| K-263 | 1-naphthyl | H | H | H | O-tolyly | H | H |
| K-264 | 1-naphthyl | H | H | H | m-tolyl | H | H |
| K-265 | 1-naphthyl | H | H | H | p-tolyl | H | H |
| K-266 | 2-naphthyl | H | H | H | o-biphenylyl | H | H |
| K-267 | 2-naphthyl | H | H | H | m-biphenylyl | H | H |
| K-268 | 2-naphthyl | H | H | H | p-biphenylyl | H | H |
| K-269 | 2-naphthyl | H | H | H | O-tolyly | H | H |
| K-270 | 2-naphthyl | H | H | H | m-tolyl | H | H |

-continued

| | | | | | | | |
|---|---|---|---|---|---|---|---|
| K-271 | 2-naphthyl | H | H | H | p-tolyl | H | H |
| K-272 | o-biphenylyl | H | H | H | m-biphenylyl | H | H |
| K-273 | o-biphenylyl | H | H | H | p-biphenylyl | H | H |
| K-274 | o-biphenylyl | H | H | H | O-tolyly | H | H |
| K-275 | o-biphenylyl | H | H | H | m-tolyl | H | H |
| K-276 | o-biphenylyl | H | H | H | p-tolyl | H | H |
| K-277 | m-biphenylyl | H | H | H | p-biphenylyl | H | H |
| K-278 | m-biphenylyl | H | H | H | O-tolyly | H | H |
| K-279 | m-biphenylyl | H | H | H | m-tolyl | H | H |
| K-280 | m-biphenylyl | H | H | H | p-tolyl | H | H |
| K-281 | p-biphenylyl | H | H | H | O-tolyly | H | H |
| K-282 | p-biphenylyl | H | H | H | m-tolyl | H | H |
| K-283 | p-biphenylyl | H | H | H | p-tolyl | H | H |
| K-284 | O-tolyly | H | H | H | m-tolyl | H | H |
| K-285 | O-tolyly | H | H | H | p-tolyl | H | H |
| K-286 | m-tolyly | H | H | H | p-tolyl | H | H |

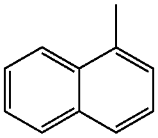

1-naphthyl

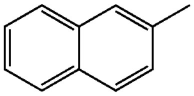

2-naphthyl

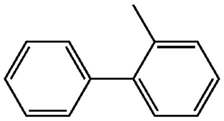

o-biphenylyl

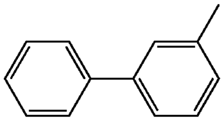

m-biphenylyl

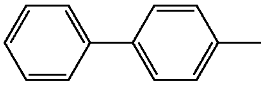

p-biphenylyl

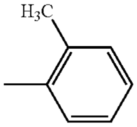

o-tolyl

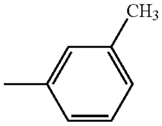

m-tolyl

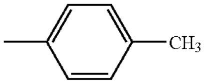

p-tolyl

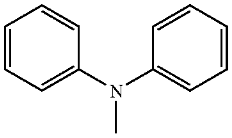

DPA

-continued

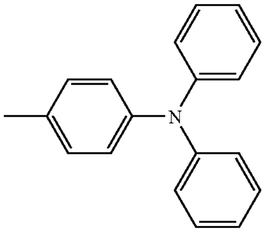

TPA

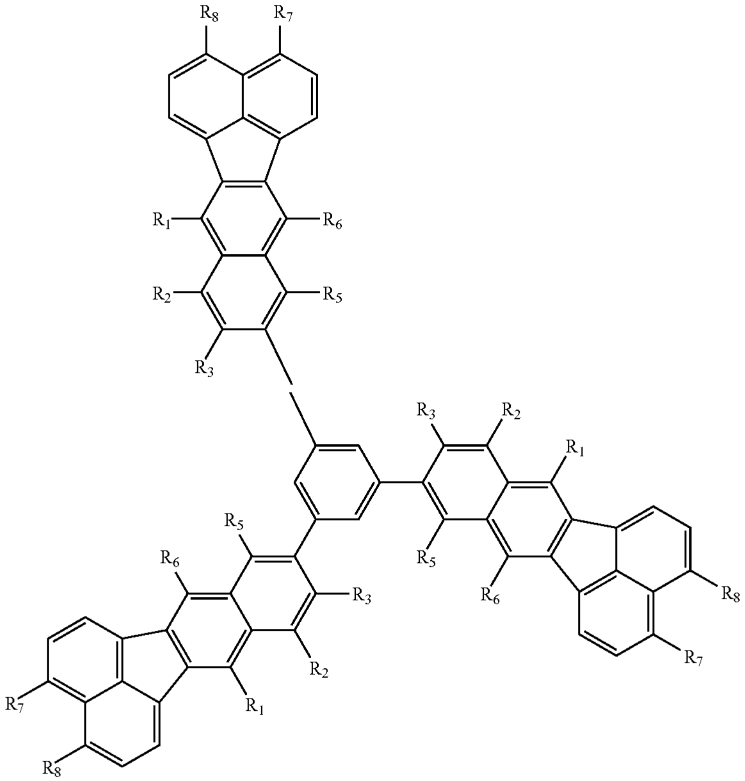

TypeL

| | $R_1$ | $R_2$ | $R_3$ | $R_5$ | $R_6$ | $R_7$ | $R_8$ |
|---|---|---|---|---|---|---|---|
| L-1 | H | H | H | H | H | H | H |
| L-2 | Ph | H | H | H | Ph | H | H |
| L-3 | Ph | Ph | H | H | Ph | H | H |
| L-4 | Ph | H | H | Ph | Ph | H | H |
| L-5 | Ph | Ph | H | Ph | Ph | H | H |
| L-6 | Ph | H | Ph | H | Ph | H | H |
| L-7 | Ph | H | H | H | Ph | Ph | H |
| L-8 | Ph | H | H | H | Ph | H | Ph |
| L-9 | Ph | H | H | H | Ph | Ph | Ph |
| L-10 | Ph | H | H | H | Ph | 1-naphthyl | H |
| L-11 | Ph | H | H | H | Ph | H | 1-naphthyl |
| L-12 | Ph | H | H | H | Ph | 1-naphthyl | 1-naphthyl |
| L-13 | Ph | H | H | H | Ph | 2-naphthyl | H |
| L-14 | Ph | H | H | H | Ph | H | 2-naphthyl |
| L-15 | Ph | H | H | H | Ph | 2-naphthyl | 2-naphthyl |
| L-16 | Ph | H | H | H | Ph | o-biphenylyl | H |
| L-17 | Ph | H | H | H | Ph | H | o-biphenylyl |
| L-18 | Ph | H | H | H | Ph | o-biphenylyl | o-biphenylyl |

-continued

| | | | | | | | |
|---|---|---|---|---|---|---|---|
| L-19 | Ph | H | H | H | Ph | m-biphenylyl | H |
| L-20 | Ph | H | H | H | Ph | H | m-biphenylyl |
| L-21 | Ph | H | H | H | Ph | m-biphenylyl | m-biphenylyl |
| L-22 | Ph | H | H | H | Ph | p-biphenylyl | H |
| L-23 | Ph | H | H | H | Ph | H | p-biphenylyl |
| L-24 | Ph | H | H | H | Ph | p-biphenylyl | p-biphenylyl |
| L-25 | 1-naphthyl | H | H | H | 1-naphthyl | H | H |
| L-26 | 1-naphthyl | Ph | H | H | 1-naphthyl | H | H |
| L-27 | 1-naphthyl | H | H | Ph | 1-naphthyl | H | H |
| L-28 | 1-naphthyl | Ph | H | Ph | 1-naphthyl | H | H |
| L-29 | 1-naphthyl | H | Ph | H | 1-naphthyl | H | H |
| L-30 | 1-naphthyl | H | H | H | 1-naphthyl | Ph | H |
| L-31 | 1-naphthyl | H | H | H | 1-naphthyl | H | Ph |
| L-32 | 1-naphthyl | H | H | H | 1-naphthyl | Ph | Ph |
| L-33 | 1-naphthyl | H | H | H | 1-naphthyl | 1-naphthyl | H |
| L-34 | 1-naphthyl | H | H | H | 1-naphthyl | H | 1-naphthyl |
| L-35 | 1-naphthyl | H | H | H | 1-naphthyl | 1-naphthyl | 1-naphthyl |
| L-36 | 1-naphthyl | H | H | H | 1-naphthyl | 2-naphthyl | H |
| L-37 | 1-naphthyl | H | H | H | 1-naphthyl | H | 2-naphthyl |
| L-38 | 1-naphthyl | H | H | H | 1-naphthyl | 2-naphthyl | 2-naphthyl |
| L-39 | 1-naphthyl | H | H | H | 1-naphthyl | o-biphenylyl | H |
| L-40 | 1-naphthyl | H | H | H | 1-naphthyl | H | o-biphenylyl |
| L-41 | 1-naphthyl | H | H | H | 1-naphthyl | o-biphenylyl | o-biphenylyl |
| L-42 | 1-naphthyl | H | H | H | 1-naphthyl | m-biphenylyl | H |
| L-43 | 1-naphthyl | H | H | H | 1-naphthyl | H | m-biphenylyl |
| L-44 | 1-naphthyl | H | H | H | 1-naphthyl | m-biphenylyl | m-biphenylyl |
| L-45 | 1-naphthyl | H | H | H | 1-naphthyl | p-biphenylyl | H |
| L-46 | 1-naphthyl | H | H | H | 1-naphthyl | H | p-biphenylyl |
| L-47 | 1-naphthyl | H | H | H | 1-naphthyl | p-biphenylyl | p-biphenylyl |
| L-48 | 2-naphthyl | H | H | H | 2-naphthyl | H | H |
| L-49 | 2-naphthyl | Ph | H | H | 2-naphthyl | H | H |
| L-50 | 2-naphthyl | H | H | Ph | 2-naphthyl | H | H |
| L-51 | 2-naphthyl | Ph | H | Ph | 2-naphthyl | H | H |
| L-52 | 2-naphthyl | H | Ph | H | 2-naphthyl | H | H |
| L-53 | 2-naphthyl | H | H | H | 2-naphthyl | Ph | H |
| L-54 | 2-naphthyl | H | H | H | 2-naphthyl | H | Ph |
| L-55 | 2-naphthyl | H | H | H | 2-naphthyl | Ph | Ph |
| L-56 | 2-naphthyl | H | H | H | 2-naphthyl | 1-naphthyl | H |
| L-57 | 2-naphthyl | H | H | H | 2-naphthyl | H | 1-naphthyl |
| L-58 | 2-naphthyl | H | H | H | 2-naphthyl | 1-naphthyl | 1-naphthyl |
| L-59 | 2-naphthyl | H | H | H | 2-naphthyl | 2-naphthyl | H |
| L-60 | 2-naphthyl | H | H | H | 2-naphthyl | H | 2-naphthyl |
| L-61 | 2-naphthyl | H | H | H | 2-naphthyl | 2-naphthyl | 2-naphthyl |
| L-62 | 2-naphthyl | H | H | H | 2-naphthyl | o-biphenylyl | H |
| L-63 | 2-naphthyl | H | H | H | 2-naphthyl | H | o-biphenylyl |
| L-64 | 2-naphthyl | H | H | H | 2-naphthyl | o-biphenylyl | o-biphenylyl |
| L-65 | 2-naphthyl | H | H | H | 2-naphthyl | m-biphenylyl | H |
| L-66 | 2-naphthyl | H | H | H | 2-naphthyl | H | m-biphenylyl |
| L-67 | 2-naphthyl | H | H | H | 2-naphthyl | m-biphenylyl | m-biphenylyl |
| L-68 | 2-naphthyl | H | H | H | 2-naphthyl | p-biphenylyl | H |
| L-69 | 2-naphthyl | H | H | H | 2-naphthyl | H | p-biphenylyl |
| L-70 | 2-naphthyl | H | H | H | 2-naphthyl | p-biphenylyl | p-biphenylyl |
| L-71 | o-biphenylyl | H | H | H | o-biphenylyl | H | H |
| L-72 | o-biphenylyl | Ph | H | H | o-biphenylyl | H | H |
| L-73 | o-biphenylyl | H | H | Ph | o-biphenylyl | H | H |
| L-74 | o-biphenylyl | Ph | H | Ph | o-biphenylyl | H | H |
| L-75 | o-biphenylyl | H | Ph | H | o-biphenylyl | H | H |
| L-76 | o-biphenylyl | H | H | H | o-biphenylyl | Ph | H |
| L-77 | o-biphenylyl | H | H | H | o-biphenylyl | H | Ph |
| L-78 | o-biphenylyl | H | H | H | o-biphenylyl | Ph | Ph |
| L-79 | o-biphenylyl | H | H | H | o-biphenylyl | 1-naphthyl | H |
| L-80 | o-biphenylyl | H | H | H | o-biphenylyl | H | 1-naphthyl |
| L-81 | o-biphenylyl | H | H | H | o-biphenylyl | 1-naphthyl | 1-naphthyl |
| L-82 | o-biphenylyl | H | H | H | o-biphenylyl | 2-naphthyl | H |
| L-83 | o-biphenylyl | H | H | H | o-biphenylyl | H | 2-naphthyl |
| L-84 | o-biphenylyl | H | H | H | o-biphenylyl | 2-naphthyl | 2-naphthyl |
| L-85 | o-biphenylyl | H | H | H | o-biphenylyl | o-biphenylyl | H |
| L-86 | o-biphenylyl | H | H | H | o-biphenylyl | H | o-biphenylyl |
| L-87 | o-biphenylyl | H | H | H | o-biphenylyl | o-biphenylyl | o-biphenylyl |
| L-88 | o-biphenylyl | H | H | H | o-biphenylyl | m-biphenylyl | H |
| L-89 | o-biphenylyl | H | H | H | o-biphenylyl | H | m-biphenylyl |
| L-90 | o-biphenylyl | H | H | H | o-biphenylyl | m-biphenylyl | m-biphenylyl |
| L-91 | o-biphenylyl | H | H | H | o-biphenylyl | p-biphenylyl | H |
| L-92 | o-biphenylyl | H | H | H | o-biphenylyl | H | p-biphenylyl |
| L-93 | o-biphenylyl | H | H | H | o-biphenylyl | p-biphenylyl | p-biphenylyl |
| L-94 | m-biphenylyl | H | H | H | m-biphenylyl | H | H |
| L-95 | m-biphenylyl | Ph | H | H | m-biphenylyl | H | H |
| L-96 | m-biphenylyl | H | H | Ph | m-biphenylyl | H | H |
| L-97 | m-biphenylyl | Ph | H | Ph | m-biphenylyl | H | H |

-continued

| | | | | | | | |
|---|---|---|---|---|---|---|---|
| L-98 | m-biphenylyl | H | Ph | H | m-biphenylyl | H | H |
| L-99 | m-biphenylyl | H | H | H | m-biphenylyl | Ph | H |
| L-100 | m-biphenylyl | H | H | H | m-biphenylyl | H | Ph |
| L-101 | m-biphenylyl | H | H | H | m-biphenylyl | Ph | Ph |
| L-102 | m-biphenylyl | H | H | H | m-biphenylyl | 1-naphthyl | H |
| L-103 | m-biphenylyl | H | H | H | m-biphenylyl | H | 1-naphthyl |
| L-104 | m-biphenylyl | H | H | H | m-biphenylyl | 1-naphthyl | 1-naphthyl |
| L-105 | m-biphenylyl | H | H | H | m-biphenylyl | 2-naphthyl | H |
| L-106 | m-biphenylyl | H | H | H | m-biphenylyl | H | 2-naphthyl |
| L-107 | m-biphenylyl | H | H | H | m-biphenylyl | 2-naphthyl | 2-naphthyl |
| L-108 | m-biphenylyl | H | H | H | m-biphenylyl | o-biphenylyl | H |
| L-109 | m-biphenylyl | H | H | H | m-biphenylyl | H | o-biphenylyl |
| L-110 | m-biphenylyl | H | H | H | m-biphenylyl | o-biphenylyl | o-biphenylyl |
| L-111 | m-biphenylyl | H | H | H | m-biphenylyl | m-biphenylyl | H |
| L-112 | m-biphenylyl | H | H | H | m-biphenylyl | H | m-biphenylyl |
| L-113 | m-biphenylyl | H | H | H | m-biphenylyl | m-biphenylyl | m-biphenylyl |
| L-114 | m-biphenylyl | H | H | H | m-biphenylyl | p-biphenylyl | H |
| L-115 | m-biphenylyl | H | H | H | m-biphenylyl | H | p-biphenylyl |
| L-116 | m-biphenylyl | H | H | H | m-biphenylyl | p-biphenylyl | p-biphenylyl |
| L-117 | p-biphenylyl | H | H | H | p-biphenylyl | H | H |
| L-118 | p-biphenylyl | Ph | H | H | p-biphenylyl | H | H |
| L-119 | p-biphenylyl | H | H | Ph | p-biphenylyl | H | H |
| L-120 | p-biphenylyl | Ph | H | Ph | p-biphenylyl | H | H |
| L-121 | p-biphenylyl | H | Ph | H | p-biphenylyl | H | H |
| L-122 | p-biphenylyl | H | H | H | p-biphenylyl | Ph | H |
| L-123 | p-biphenylyl | H | H | H | p-biphenylyl | H | Ph |
| L-124 | p-biphenylyl | H | H | H | p-biphenylyl | Ph | Ph |
| L-125 | p-biphenylyl | H | H | H | p-biphenylyl | 1-naphthyl | H |
| L-126 | p-biphenylyl | H | H | H | p-biphenylyl | H | 1-naphthyl |
| L-127 | p-biphenylyl | H | H | H | p-biphenylyl | 1-naphthyl | 1-naphthyl |
| L-128 | p-biphenylyl | H | H | H | p-biphenylyl | 2-naphthyl | H |
| L-129 | p-biphenylyl | H | H | H | p-biphenylyl | H | 2-naphthyl |
| L-130 | p-biphenylyl | H | H | H | p-biphenylyl | 2-naphthyl | 2-naphthyl |
| L-131 | p-biphenylyl | H | H | H | p-biphenylyl | o-biphenylyl | H |
| L-132 | p-biphenylyl | H | H | H | p-biphenylyl | H | o-biphenylyl |
| L-133 | p-biphenylyl | H | H | H | p-biphenylyl | o-biphenylyl | o-biphenylyl |
| L-134 | p-biphenylyl | H | H | H | p-biphenylyl | m-biphenylyl | H |
| L-135 | p-biphenylyl | H | H | H | p-biphenylyl | H | m-biphenylyl |
| L-136 | p-biphenylyl | H | H | H | p-biphenylyl | m-biphenylyl | m-biphenylyl |
| L-137 | p-biphenylyl | H | H | H | p-biphenylyl | p-biphenylyl | H |
| L-138 | p-biphenylyl | H | H | H | p-biphenylyl | H | p-biphenylyl |
| L-139 | p-biphenylyl | H | H | H | p-biphenylyl | p-biphenylyl | p-biphenylyl |
| L-140 | o-tolyl | H | H | H | o-tolyl | H | H |
| L-141 | o-tolyl | Ph | H | Ph | o-tolyl | H | H |
| L-142 | o-tolyl | H | Ph | H | o-tolyl | H | H |
| L-143 | o-tolyl | H | H | H | o-tolyl | Ph | H |
| L-144 | o-tolyl | H | H | H | o-tolyl | H | Ph |
| L-145 | o-tolyl | H | H | H | o-tolyl | 1-naphthyl | H |
| L-146 | o-tolyl | H | H | H | o-tolyl | H | 1-naphthyl |
| L-147 | o-tolyl | H | H | H | o-tolyl | 2-naphthyl | H |
| L-148 | o-tolyl | H | H | H | o-tolyl | H | 2-naphthyl |
| L-149 | o-tolyl | H | H | H | o-tolyl | o-biphenylyl | H |
| L-150 | o-tolyl | H | H | H | o-tolyl | H | o-biphenylyl |
| L-151 | o-tolyl | H | H | H | o-tolyl | m-biphenylyl | H |
| L-152 | o-tolyl | H | H | H | o-tolyl | H | m-biphenylyl |
| L-153 | o-tolyl | H | H | H | o-tolyl | p-biphenylyl | H |
| L-154 | o-tolyl | H | H | H | o-tolyl | H | p-biphenylyl |
| L-155 | o-tolyl | H | H | H | o-tolyl | o-tolyl | H |
| L-156 | o-tolyl | H | H | H | o-tolyl | H | o-tolyl |
| L-157 | m-tolyl | H | H | H | m-tolyl | H | H |
| L-158 | m-tolyl | Ph | H | Ph | m-tolyl | H | H |
| L-159 | m-tolyl | H | Ph | H | m-tolyl | H | H |
| L-160 | m-tolyl | H | H | H | m-tolyl | Ph | H |
| L-161 | m-tolyl | H | H | H | m-tolyl | H | Ph |
| L-162 | m-tolyl | H | H | H | m-tolyl | 1-naphthyl | H |
| L-163 | m-tolyl | H | H | H | m-tolyl | H | 1-naphthyl |
| L-164 | m-tolyl | H | H | H | m-tolyl | 2-naphthyl | H |
| L-165 | m-tolyl | H | H | H | m-tolyl | H | 2-naphthyl |
| L-166 | m-tolyl | H | H | H | m-tolyl | o-biphenylyl | H |
| L-167 | m-tolyl | H | H | H | m-tolyl | H | o-biphenylyl |
| L-168 | m-tolyl | H | H | H | m-tolyl | m-biphenylyl | H |
| L-169 | m-tolyl | H | H | H | m-tolyl | H | m-biphenylyl |
| L-170 | m-tolyl | H | H | H | m-tolyl | p-biphenylyl | H |
| L-171 | m-tolyl | H | H | H | m-tolyl | H | p-biphenylyl |
| L-172 | m-tolyl | H | H | H | m-tolyl | m-tolyl | H |
| L-173 | m-tolyl | H | H | H | m-tolyl | H | m-tolyl |
| L-174 | p-tolyl | H | H | H | p-tolyl | H | H |
| L-175 | p-tolyl | Ph | H | Ph | p-tolyl | H | H |
| L-176 | p-tolyl | H | Ph | H | p-tolyl | H | H |

-continued

| | | | | | | | |
|---|---|---|---|---|---|---|---|
| L-177 | p-tolyl | H | H | H | p-tolyl | Ph | H |
| L-178 | p-tolyl | H | H | H | p-tolyl | H | Ph |
| L-179 | p-tolyl | H | H | H | p-tolyl | 1-naphthyl | H |
| L-180 | p-tolyl | H | H | H | p-tolyl | H | 1-naphthyl |
| L-181 | p-tolyl | H | H | H | p-tolyl | 2-naphthyl | H |
| L-182 | p-tolyl | H | H | H | p-tolyl | H | 2-naphthyl |
| L-183 | p-tolyl | H | H | H | p-tolyl | o-biphenylyl | H |
| L-184 | p-tolyl | H | H | H | p-tolyl | H | o-biphenylyl |
| L-185 | p-tolyl | H | H | H | p-tolyl | m-biphenylyl | H |
| L-186 | p-tolyl | H | H | H | p-tolyl | H | m-biphenylyl |
| L-187 | p-tolyl | H | H | H | p-tolyl | p-biphenylyl | H |
| L-188 | p-tolyl | H | H | H | p-tolyl | H | p-biphenylyl |
| L-189 | p-tolyl | H | H | H | p-tolyl | p-tolyl | H |
| L-190 | p-tolyl | H | H | H | p-tolyl | H | p-tolyl |
| L-191 | Ph | H | —CH3 | H | Ph | H | H |
| L-192 | 1-naphtyl | H | —CH3 | H | 1-naphtyl | H | H |
| L-193 | 2-naphthyl | H | —CH3 | H | 2-naphthyl | H | H |
| L-194 | o-biphenylyl | H | —CH3 | H | o-biphenylyl | H | H |
| L-195 | m-biphenylyl | H | —CH3 | H | m-biphenylyl | H | H |
| L-196 | p-biphenylyl | H | —CH3 | H | p-biphenylyl | H | H |
| L-197 | o-tolyl | H | —CH3 | H | o-tolyl | H | H |
| L-198 | m-tolyl | H | —CH3 | H | m-tolyl | H | H |
| L-199 | p-tolyl | H | —CH3 | H | p-tolyl | H | H |
| L-200 | Ph | H | H | H | Ph | —CH3 | H |
| L-201 | 1-naphtyl | H | H | H | 1-naphtyl | —CH3 | H |
| L-202 | 2-naphthyl | H | H | H | 2-naphthyl | —CH3 | H |
| L-203 | o-biphenylyl | H | H | H | o-biphenylyl | —CH3 | H |
| L-204 | m-biphenylyl | H | H | H | m-biphenylyl | —CH3 | H |
| L-205 | p-biphenylyl | H | H | H | p-biphenylyl | —CH3 | H |
| L-206 | o-tolyl | H | H | H | o-tolyl | —CH3 | H |
| L-207 | m-tolyl | H | H | H | m-tolyl | —CH3 | H |
| L-208 | p-tolyl | H | H | H | p-tolyl | —CH3 | H |
| L-209 | Ph | H | H | H | Ph | H | —CH3 |
| L-210 | 1-naphtyl | H | H | H | 1-naphtyl | H | —CH3 |
| L-211 | 2-naphthyl | H | H | H | 2-naphthyl | H | —CH3 |
| L-212 | o-biphenylyl | H | H | H | o-biphenylyl | H | —CH3 |
| L-213 | m-biphenylyl | H | H | H | m-biphenylyl | H | —CH3 |
| L-214 | p-biphenylyl | H | H | H | p-biphenylyl | H | —CH3 |
| L-215 | o-tolyl | H | H | H | o-tolyl | H | —CH3 |
| L-216 | m-tolyl | H | H | H | m-tolyl | H | —CH3 |
| L-217 | p-tolyl | H | H | H | p-tolyl | H | —CH3 |
| L-218 | Ph | H | H | H | Ph | —CH3 | —CH3 |
| L-219 | 1-naphtyl | H | H | H | 1-naphtyl | —CH3 | —CH3 |
| L-220 | 2-naphthyl | H | H | H | 2-naphthyl | —CH3 | —CH3 |
| L-221 | o-biphenylyl | H | H | H | o-biphenylyl | —CH3 | —CH3 |
| L-222 | m-biphenylyl | H | H | H | m-biphenylyl | —CH3 | —CH3 |
| L-223 | p-biphenylyl | H | H | H | p-biphenylyl | —CH3 | —CH3 |
| L-224 | o-tolyl | H | H | H | o-tolyl | —CH3 | —CH3 |
| L-225 | m-tolyl | H | H | H | m-tolyl | —CH3 | —CH3 |
| L-226 | p-tolyl | H | H | H | p-tolyl | —CH3 | —CH3 |
| L-227 | Ph | H | H | H | Ph | H | DPA |
| L-228 | 1-naphtyl | H | H | H | 1-naphtyl | H | DPA |
| L-229 | 2-naphthyl | H | H | H | 2-naphthyl | H | DPA |
| L-230 | o-biphenylyl | H | H | H | o-biphenylyl | H | DPA |
| L-231 | m-biphenylyl | H | H | H | m-biphenylyl | H | DPA |
| L-232 | p-biphenylyl | H | H | H | p-biphenylyl | H | DPA |
| L-233 | Ph | H | H | H | Ph | DPA | H |
| L-234 | 1-naphtyl | H | H | H | 1-naphtyl | DPA | H |
| L-235 | 2-naphthyl | H | H | H | 2-naphthyl | DPA | H |
| L-236 | o-biphenylyl | H | H | H | o-biphenylyl | DPA | H |
| L-237 | m-biphenylyl | H | H | H | m-biphenylyl | DPA | H |
| L-238 | p-biphenylyl | H | H | H | p-biphenylyl | DPA | H |
| L-239 | Ph | H | H | H | Ph | H | TPA |
| L-240 | 1-naphtyl | H | H | H | 1-naphtyl | H | TPA |
| L-241 | 2-naphthyl | H | H | H | 2-naphthyl | H | TPA |
| L-242 | o-biphenylyl | H | H | H | o-biphenylyl | H | TPA |
| L-243 | m-biphenylyl | H | H | H | m-biphenylyl | H | TPA |
| L-244 | p-biphenylyl | H | H | H | p-biphenylyl | H | TPA |
| L-245 | Ph | H | H | H | Ph | TPA | H |
| L-246 | 1-naphtyl | H | H | H | 1-naphtyl | TPA | H |
| L-247 | 2-naphthyl | H | H | H | 2-naphthyl | TPA | H |
| L-248 | o-biphenylyl | H | H | H | o-biphenylyl | TPA | H |
| L-249 | m-biphenylyl | H | H | H | m-biphenylyl | TPA | H |
| L-250 | p-biphenylyl | H | H | H | p-biphenylyl | TPA | H |
| L-251 | Ph | H | H | H | 1-naphthyl | H | H |
| L-252 | Ph | H | H | H | 2-naphthyl | H | H |
| L-253 | Ph | H | H | H | o-biphenylyl | H | H |
| L-254 | Ph | H | H | H | m-biphenylyl | H | H |
| L-255 | Ph | H | H | H | p-biphenylyl | H | H |

-continued

| | | | | | | | |
|---|---|---|---|---|---|---|---|
| L-256 | Ph | H | H | H | O-tolyly | H | H |
| L-257 | Ph | H | H | H | m-tolyl | H | H |
| L-258 | Ph | H | H | H | p-tolyl | H | H |
| L-259 | 1-naphthyl | H | H | H | 2-naphthyl | H | H |
| L-260 | 1-naphthyl | H | H | H | o-biphenylyl | H | H |
| L-261 | 1-naphthyl | H | H | H | m-biphenylyl | H | H |
| L-262 | 1-naphthyl | H | H | H | p-biphenylyl | H | H |
| L-263 | 1-naphthyl | H | H | H | O-tolyly | H | H |
| L-264 | 1-naphthyl | H | H | H | m-tolyl | H | H |
| L-265 | 1-naphthyl | H | H | H | p-tolyl | H | H |
| L-266 | 2-naphthyl | H | H | H | o-biphenylyl | H | H |
| L-267 | 2-naphthyl | H | H | H | m-biphenylyl | H | H |
| L-268 | 2-naphthyl | H | H | H | p-biphenylyl | H | H |
| L-269 | 2-naphthyl | H | H | H | O-tolyly | H | H |
| L-270 | 2-naphthyl | H | H | H | m-tolyl | H | H |
| L-271 | 2-naphthyl | H | H | H | p-tolyl | H | H |
| L-272 | o-biphenylyl | H | H | H | m-biphenylyl | H | H |
| L-273 | o-biphenylyl | H | H | H | p-biphenylyl | H | H |
| L-274 | o-biphenylyl | H | H | H | O-tolyly | H | H |
| L-275 | o-biphenylyl | H | H | H | m-tolyl | H | H |
| L-276 | o-biphenylyl | H | H | H | p-tolyl | H | H |
| L-277 | m-biphenylyl | H | H | H | p-biphenylyl | H | H |
| L-278 | m-biphenylyl | H | H | H | O-tolyly | H | H |
| L-279 | m-biphenylyl | H | H | H | m-tolyl | H | H |
| L-280 | m-biphenylyl | H | H | H | p-tolyl | H | H |
| L-281 | p-biphenylyl | H | H | H | O-tolyly | H | H |
| L-282 | p-biphenylyl | H | H | H | m-tolyl | H | H |
| L-283 | p-biphenylyl | H | H | H | p-tolyl | H | H |
| L-284 | O-tolyly | H | H | H | m-tolyl | H | H |
| L-285 | O-tolyly | H | H | H | p-tolyl | H | H |
| L-286 | m-tolyly | H | H | H | p-tolyl | H | H |

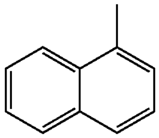

1-naphthyl

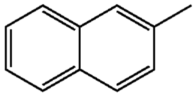

2-naphthyl

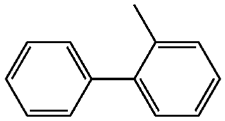

o-biphenylyl

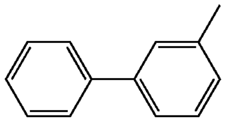

m-biphenylyl

-continued
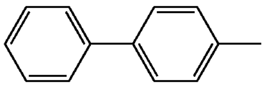
p-biphenylyl
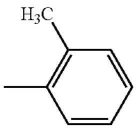
o-tolyl
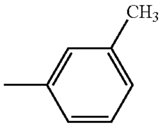
m-tolyl
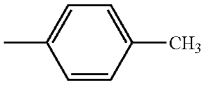
p-tolyl
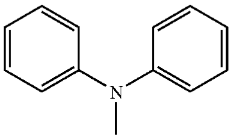
DPA
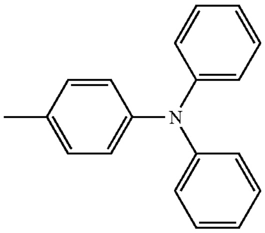
TPA

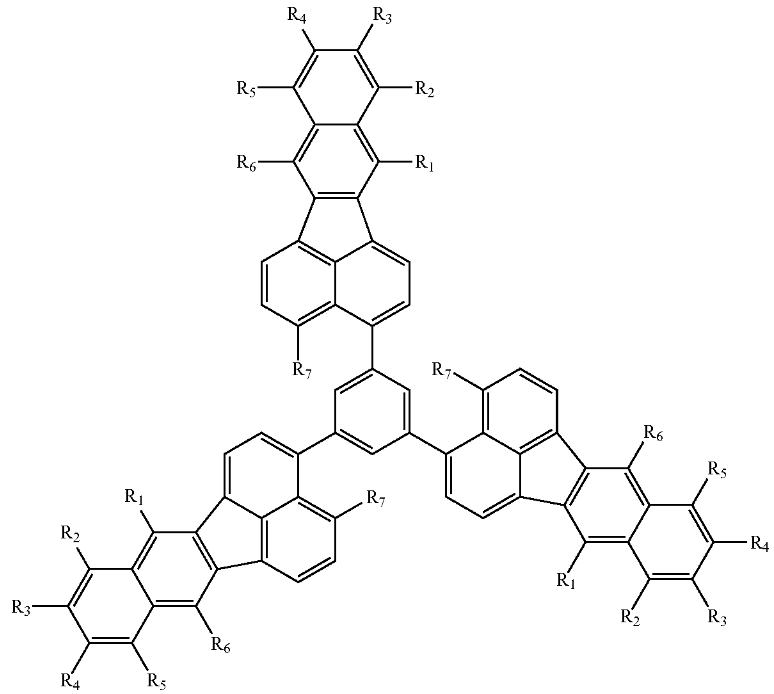
TypeM
| | $R_1$ | $R_2$ | $R_3$ | $R_4$ | $R_5$ | $R_6$ | $R_7$ |
|---|---|---|---|---|---|---|---|
| M-1 | H | H | H | H | H | H | H |
| M-2 | Ph | H | H | H | H | Ph | H |
| M-3 | Ph | Ph | H | H | Ph | Ph | H |
| M-4 | Ph | H | Ph | Ph | H | Ph | H |
| M-5 | Ph | H | Ph | H | H | Ph | H |
| M-6 | Ph | H | H | H | H | Ph | Ph |
| M-7 | Ph | Me | H | H | Me | Ph | H |
| M-8 | Ph | H | Me | Me | H | Ph | H |
| M-9 | Ph | H | H | H | H | Ph | Me |

-continued
| | | | | | | | |
|---|---|---|---|---|---|---|---|
| M-10 | 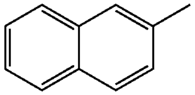 | H | H | H | H | 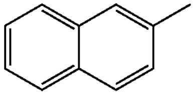 | H |
| M-11 | 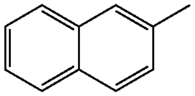 | Ph | H | H | Ph | 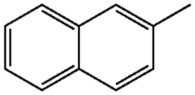 | H |
| M-12 | 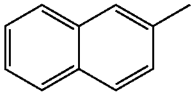 | H | Ph | Ph | H | 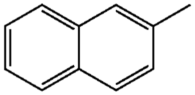 | H |
| M-13 | 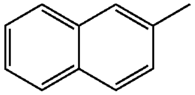 | H | Ph | H | H | 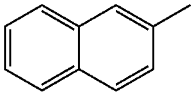 | H |
| M-14 | 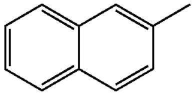 | H | H | H | H | 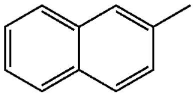 | Ph |
| M-15 | 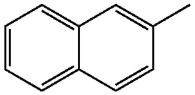 | Me | H | H | Me | 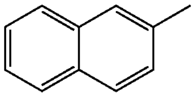 | H |
| M-16 | 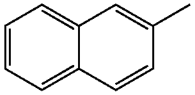 | H | Me | Me | H | 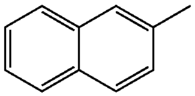 | H |
| M-17 | 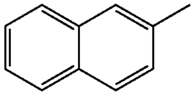 | H | H | H | H | 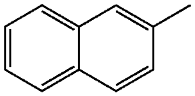 | Me |
| M-18 | 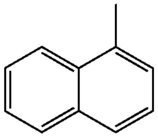 | H | H | H | H | 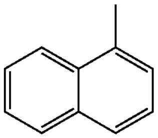 | H |

-continued
| | | | | | | | |
|---|---|---|---|---|---|---|---|
| M-19 | 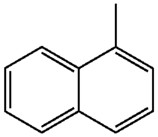 | Ph | H | H | Ph | 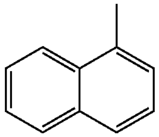 | H |
| M-20 | 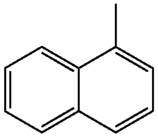 | H | Ph | Ph | H | 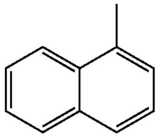 | H |
| M-21 | 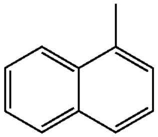 | H | Ph | H | H | 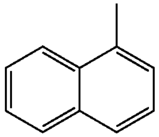 | H |
| M-22 | 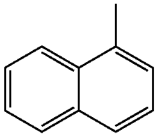 | H | H | H | H | 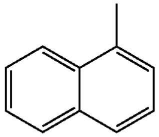 | Ph |
| M-23 | 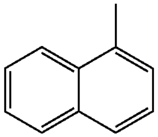 | Me | H | H | Me | 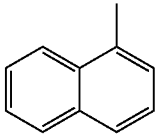 | H |
| M-24 | 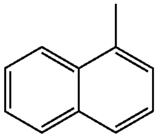 | H | Me | Me | H | 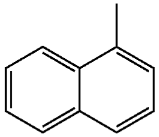 | H |
| M-25 | 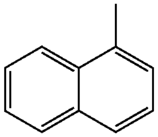 | H | H | H | H | 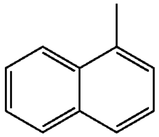 | Me |

-continued
| | | | | | | | |
|---|---|---|---|---|---|---|---|
| M-26 | 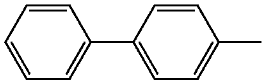 | H | H | H | H | 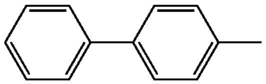 | H |
| M-27 | 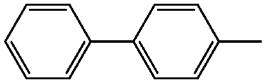 | Ph | H | H | Ph | 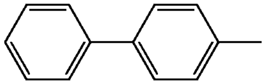 | H |
| M-28 | 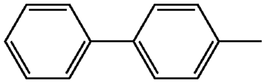 | H | Ph | Ph | H | 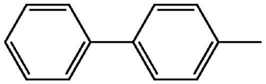 | H |
| M-29 | 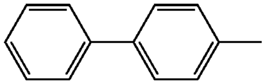 | H | Ph | H | H | 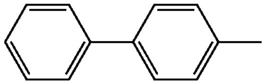 | H |
| M-30 | 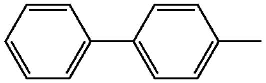 | H | H | H | H | 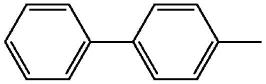 | Ph |
| M-31 | 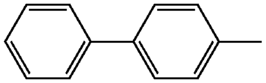 | Me | H | H | Me | 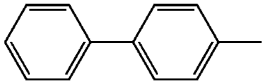 | H |
| M-32 | 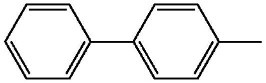 | H | Me | Me | H | 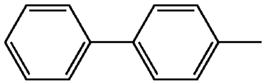 | H |
| M-33 | 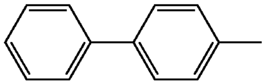 | H | H | H | H | 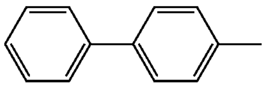 | Me |
| M-34 | 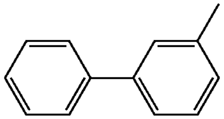 | H | H | H | H | 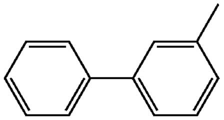 | H |

-continued
| | | | | | | | |
|---|---|---|---|---|---|---|---|
| M-35 | 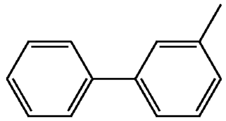 | Ph | H | H | Ph | 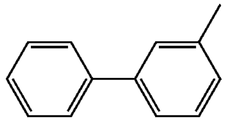 | H |
| M-36 | 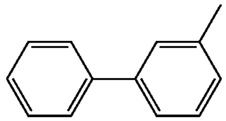 | H | Ph | Ph | H | 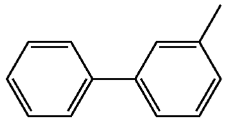 | H |
| M-37 | 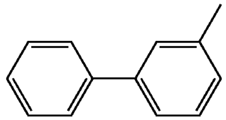 | H | Ph | H | H | 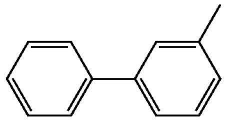 | H |
| M-38 | 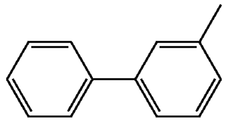 | H | H | H | H | 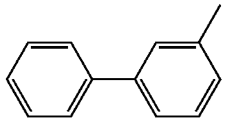 | Ph |
| M-39 | 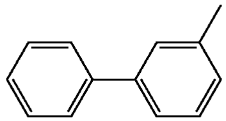 | Me | H | H | Me | 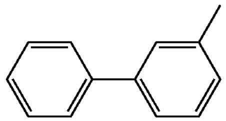 | H |
| M-40 | 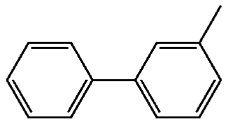 | H | Me | Me | H | 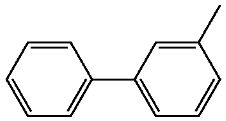 | H |
| M-41 | 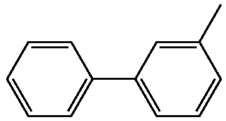 | H | H | H | H | 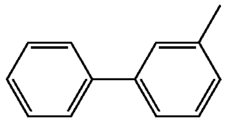 | Me |
| M-42 | 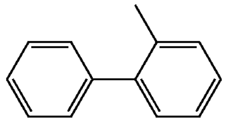 | H | H | H | H | 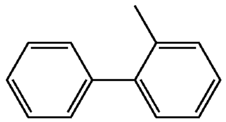 | H |

-continued
| | | | | | | | |
|---|---|---|---|---|---|---|---|
| M-43 | 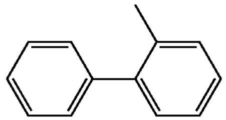 | Ph | H | H | Ph | 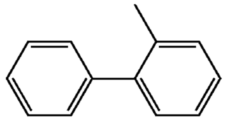 | H |
| M-44 | 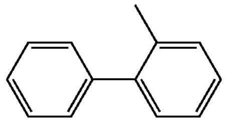 | H | Ph | Ph | H | 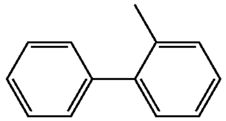 | H |
| M-45 | 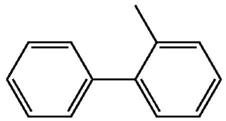 | H | Ph | H | H | 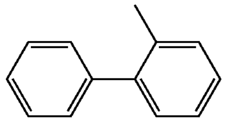 | H |
| M-46 | 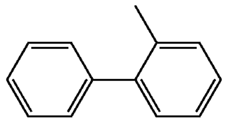 | H | H | H | H | 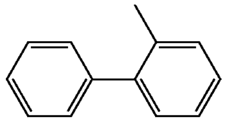 | Ph |
| M-47 | 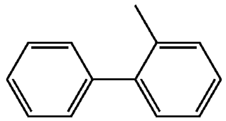 | Me | H | H | Me | 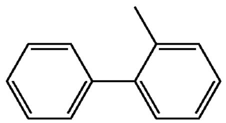 | H |
| M-48 | 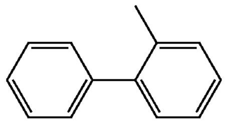 | H | Me | Me | H | 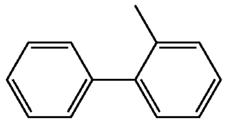 | H |
| M-49 | 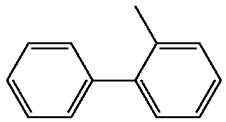 | H | H | H | H | 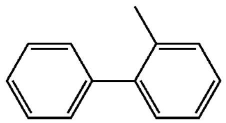 | Me |
| M-50 | Ph | H | H | H | H | 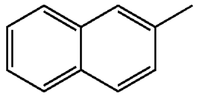 | H |

-continued
| | | | | | | | |
|---|---|---|---|---|---|---|---|
| M-51 | Ph | H | H | H | H | 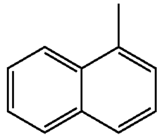 | H |
| M-52 | Ph | H | H | H | H | 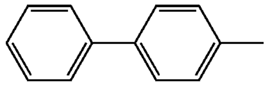 | H |
| M-53 | Ph | H | H | H | H | 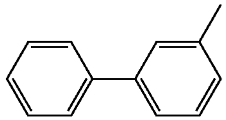 | H |
| M-54 | Ph | H | H | H | H | 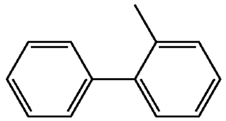 | H |
| M-55 | 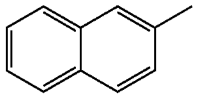 | H | H | H | H | 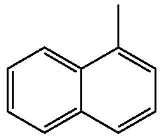 | H |
| M-56 | 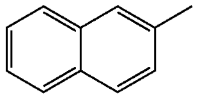 | H | H | H | H | 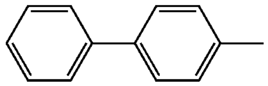 | H |
| M-57 | 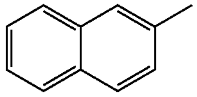 | H | H | H | H | 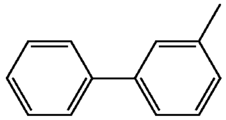 | H |
| M-58 | 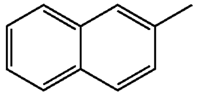 | H | H | H | H | 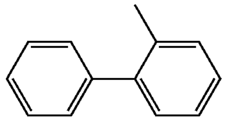 | H |

-continued
| | | | | | | | |
|---|---|---|---|---|---|---|---|
| M-59 | 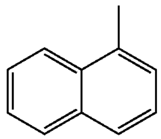 | H | H | H | H | 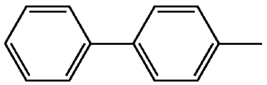 | H |
| M-60 | 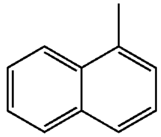 | H | H | H | H | 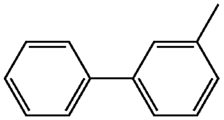 | H |
| M-61 | 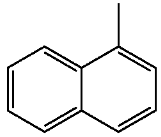 | H | H | H | H | 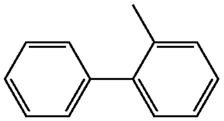 | H |
| M-62 | 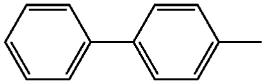 | H | H | H | H | 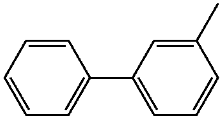 | H |
| M-63 | 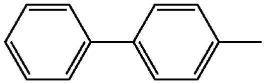 | H | H | H | H | 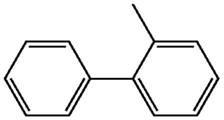 | H |
| M-64 | 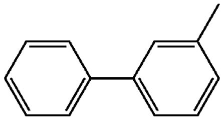 | H | H | H | H | 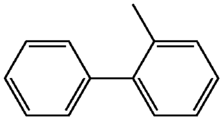 | H |
| M-65 | H | Ph | H | H | Ph | H | H |
| M-66 | H | 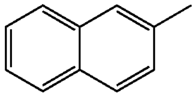 | H | H | 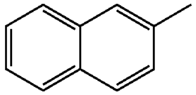 | H | H |

-continued
| | | | | | | | |
|---|---|---|---|---|---|---|---|
| M-67 | H | 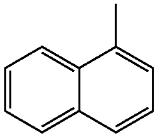 | H | H | 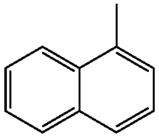 | H | H |
| M-68 | H | 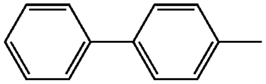 | H | H | 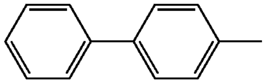 | H | H |
| M-69 | H | 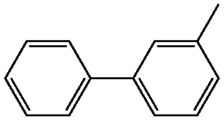 | H | H | 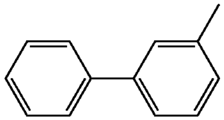 | H | H |
| M-70 | H | 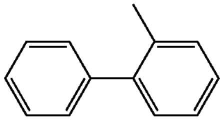 | H | H | 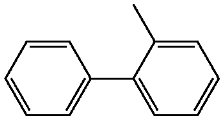 | H | H |
| M-71 | H | H | 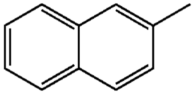 | 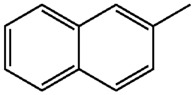 | H | H | H |
| M-72 | H | H | 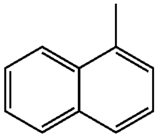 | 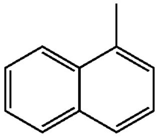 | H | H | H |
| M-73 | H | H | 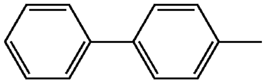 | 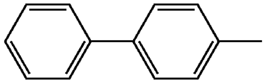 | H | H | H |
| M-74 | H | H | 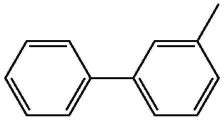 | 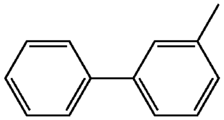 | H | H | H |

-continued
| | | | | | | | |
|---|---|---|---|---|---|---|---|
| M-75 | H | H | 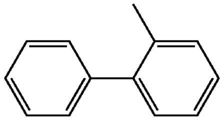 | 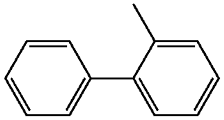 | H | H | H |
| M-76 | 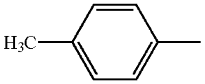 | H | H | H | H | 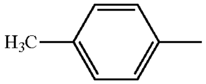 | H |
| M-77 | 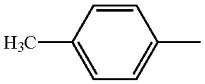 | Ph | H | H | Ph | 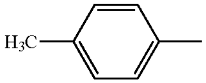 | H |
| M-78 | 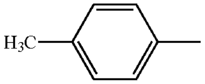 | H | Ph | Ph | H | 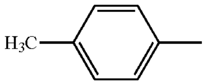 | H |
| M-79 | 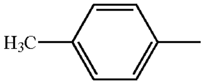 | H | Ph | H | H | 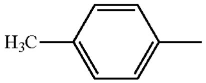 | H |
| M-80 | 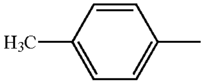 | H | H | H | H | 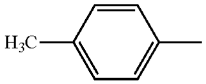 | Ph |
| M-81 | 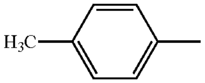 | Me | H | H | Me | 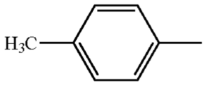 | H |
| M-82 | 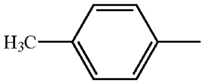 | H | Me | Me | H | 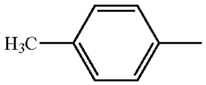 | H |
| M-83 | 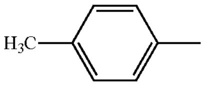 | H | H | H | H | 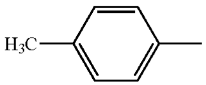 | Me |
| M-84 | 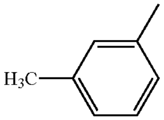 | H | H | H | H | 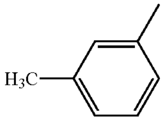 | H |

-continued
| | | | | | | |
|---|---|---|---|---|---|---|
| M-85 | 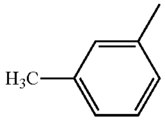 | Ph | H | H | Ph | 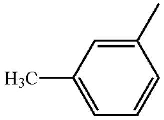 | H |
| M-86 | 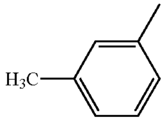 | H | Ph | Ph | H | 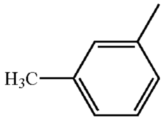 | H |
| M-87 | 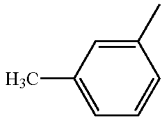 | H | Ph | H | H | 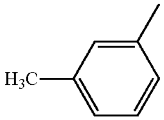 | H |
| M-88 | 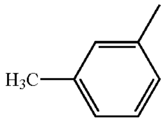 | H | H | H | H | 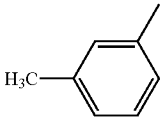 | Ph |
| M-89 | 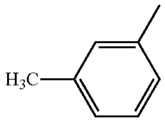 | Me | H | H | Me | 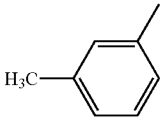 | H |
| M-90 | 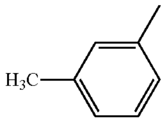 | H | Me | Me | H | 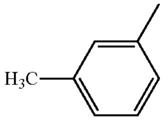 | H |
| M-91 | 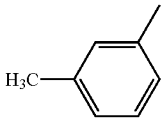 | H | H | H | H | 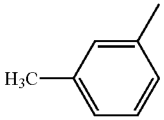 | Me |
| M-92 | 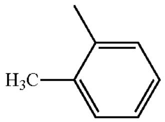 | H | H | H | H | 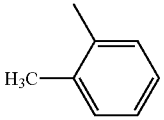 | H |

-continued
| | | | | | | | |
|---|---|---|---|---|---|---|---|
| M-93 | 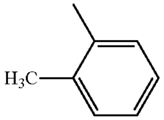 | Ph | H | H | Ph | 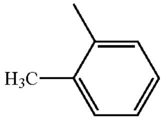 | H |
| M-94 | 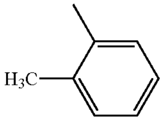 | H | Ph | Ph | H | 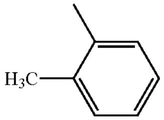 | H |
| M-96 | 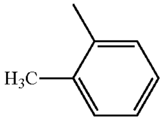 | H | Ph | H | H | 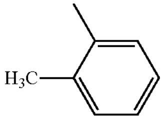 | H |
| M-96 | 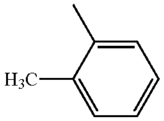 | H | H | H | H | 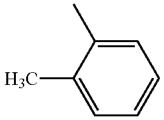 | Ph |
| M-97 | 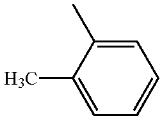 | Me | H | H | Me | 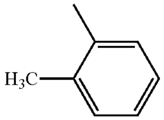 | H |
| M-98 | 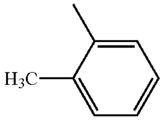 | H | Me | Me | H | 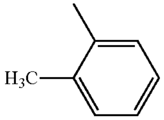 | H |
| M-99 | 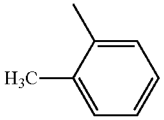 | H | H | H | H | 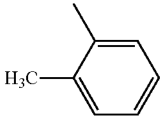 | Me |

-continued
| | | | | | | | |
|---|---|---|---|---|---|---|---|
| 100 | 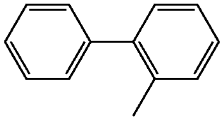 | H | H | H | H | 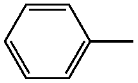 | H |
| 101 | 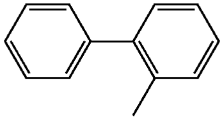 | Ph | H | H | Ph | 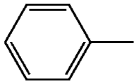 | H |
| 102 | 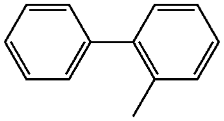 | H | Ph | Ph | H | 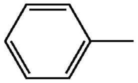 | H |
| 103 | 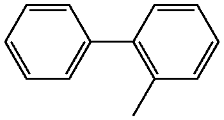 | H | Ph | H | H | 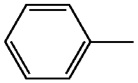 | H |
| 104 | 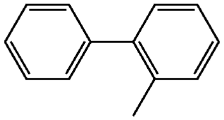 | H | H | H | H | 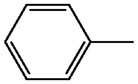 | Ph |
| 105 | 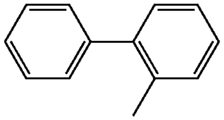 | Me | H | H | Me | 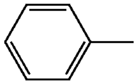 | H |
| 106 | 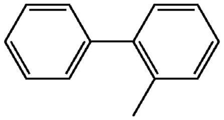 | H | Me | Me | H | 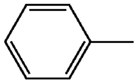 | H |
| 107 | 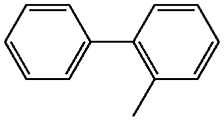 | H | H | H | H | 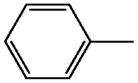 | Me |

-continued
| | | | | | | | |
|---|---|---|---|---|---|---|---|
| 108 | 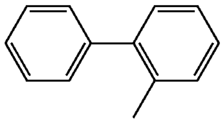 | H | H | H | H | 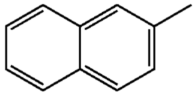 | H |
| 109 | 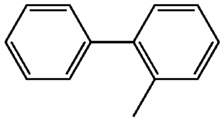 | Ph | H | H | Ph | 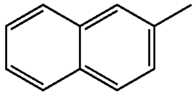 | H |
| 110 | 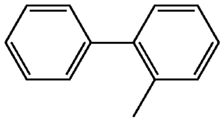 | H | Ph | Ph | H | 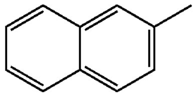 | H |
| 111 | 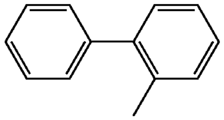 | H | Ph | H | H | 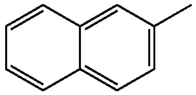 | H |
| 112 | 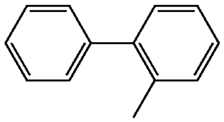 | H | H | H | H | 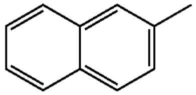 | Ph |
| 113 | 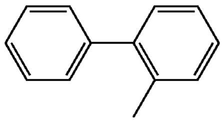 | Me | H | H | Me | 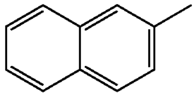 | H |
| 114 | 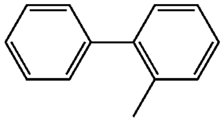 | H | Me | Me | H | 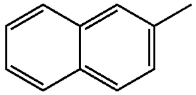 | H |

-continued
| | | | | | | | |
|---|---|---|---|---|---|---|---|
| 115 | 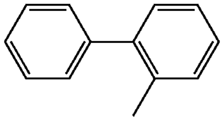 | H | H | H | H | 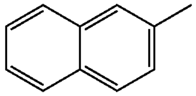 | Me |
| 116 | 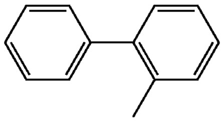 | H | H | H | H | 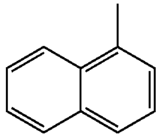 | H |
| 117 | 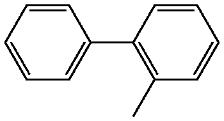 | Ph | H | H | Ph | 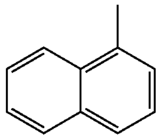 | H |
| 118 | 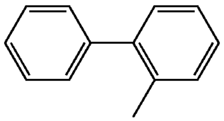 | H | Ph | Ph | H | 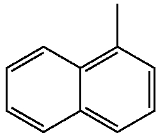 | H |
| 119 | 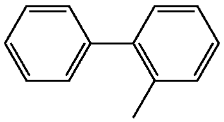 | H | Ph | H | H | 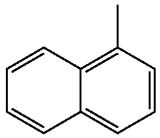 | H |
| 120 | 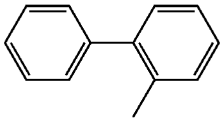 | H | H | H | H | 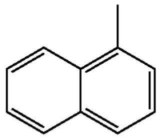 | Ph |
| 121 | 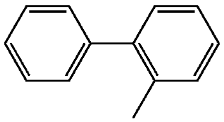 | Me | H | H | Me | 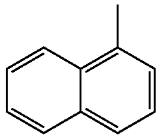 | H |

-continued
| | | | | | | | |
|---|---|---|---|---|---|---|---|
| 122 | 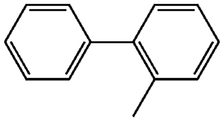 | H | Me | Me | H | 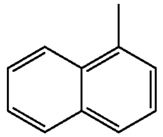 | H |
| 123 | 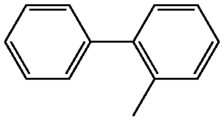 | H | H | H | H | 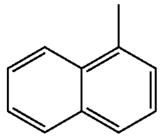 | Me |
| 124 | 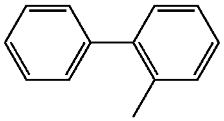 | H | H | H | H | 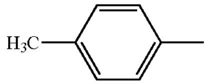 | H |
| 125 | 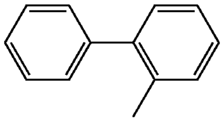 | Ph | H | H | Ph | 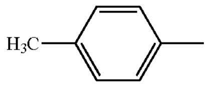 | H |
| 126 | 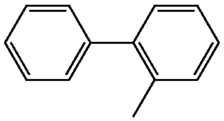 | H | Ph | Ph | H | 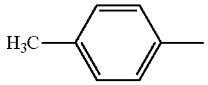 | H |
| 127 | 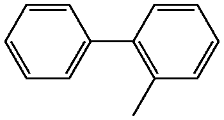 | H | Ph | H | H | 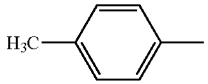 | H |
| 128 | 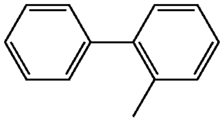 | H | H | H | H | 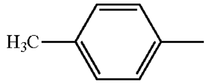 | Ph |

-continued
| | | | | | | | |
|---|---|---|---|---|---|---|---|
| 129 | 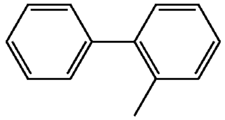 | Me | H | H | Me | 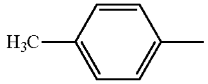 | H |
| 130 | 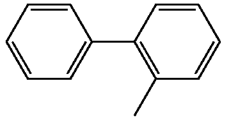 | H | Me | Me | H | 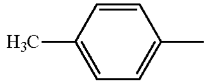 | H |
| 131 | 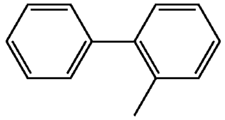 | H | H | H | H | 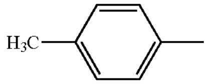 | Me |
| 132 | 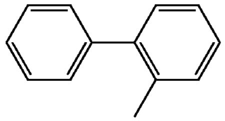 | H | H | H | H | 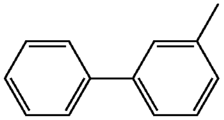 | H |
| 133 | 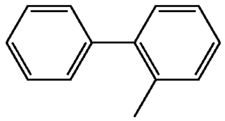 | Ph | H | H | Ph | 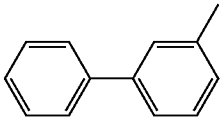 | H |
| 134 | 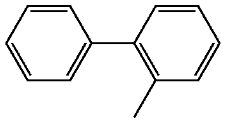 | H | Ph | Ph | H | 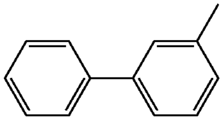 | H |
| 135 | 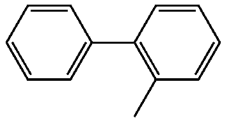 | H | Ph | H | H | 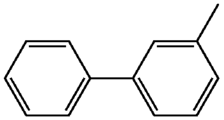 | H |
| 136 | 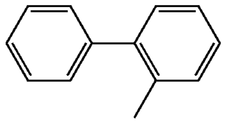 | H | H | H | H | 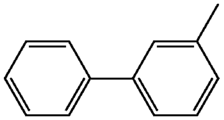 | Ph |

-continued
| | | | | | | | |
|---|---|---|---|---|---|---|---|
| 137 | 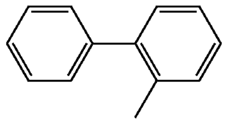 | Me | H | H | Me | 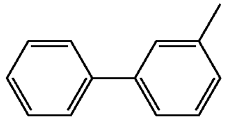 | H |
| 138 | 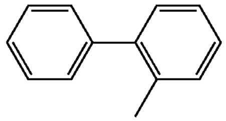 | H | Me | Me | H | 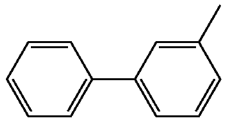 | H |
| 139 | 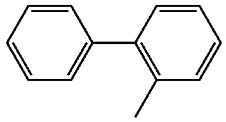 | H | H | H | H | 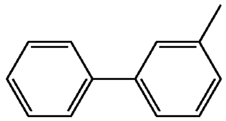 | Me |
| 140 | 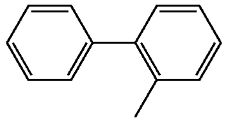 | H | H | H | H | 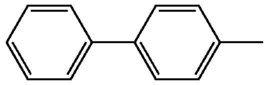 | H |
| 141 | 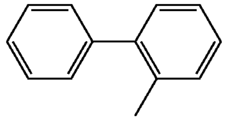 | Ph | H | H | Ph | 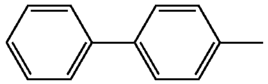 | H |

-continued
| | | | | | | | |
|---|---|---|---|---|---|---|---|
| 142 | 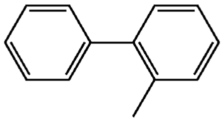 | H | Ph | Ph | H | 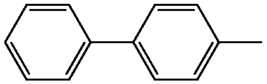 | H |
| 143 | 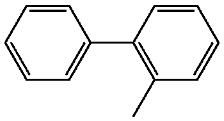 | H | Ph | H | H | 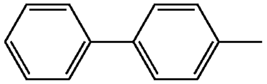 | H |
| 144 | 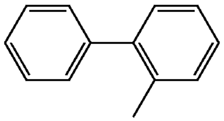 | H | H | H | H | 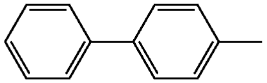 | Ph |
| 145 | 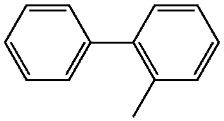 | Me | H | H | Me | 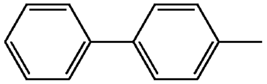 | H |
| 146 | 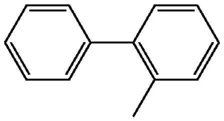 | H | Me | Me | H | 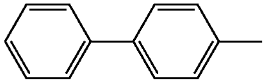 | H |
| 147 | 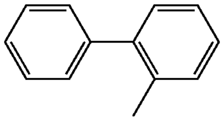 | H | H | H | H | 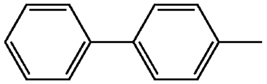 | Me |

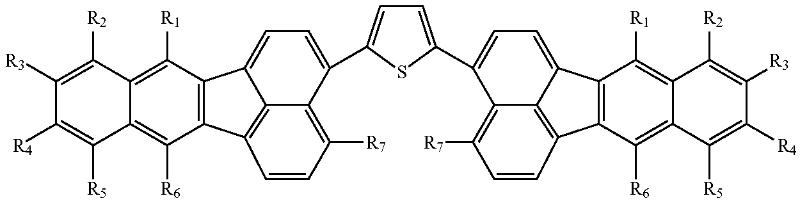
TypeN
| | $R_1$ | $R_2$ | $R_3$ | $R_4$ | $R_5$ | $R_6$ | $R_7$ |
|---|---|---|---|---|---|---|---|
| N-1 | H | H | H | H | H | H | H |
| N-2 | Ph | H | H | H | H | Ph | H |
| N-3 | Ph | Ph | H | H | Ph | Ph | H |
| N-4 | Ph | H | Ph | Ph | H | Ph | H |
| N-5 | Ph | H | Ph | H | H | Ph | H |
| N-6 | Ph | H | H | H | H | Ph | Ph |
| N-7 | Ph | Me | H | H | Me | Ph | H |
| N-8 | Ph | H | Me | Me | H | Ph | H |
| N-9 | Ph | H | H | H | H | Ph | Me |
| N-10 | 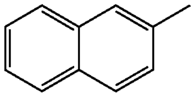 | H | H | H | H | 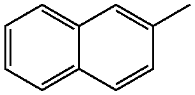 | H |
| N-11 | 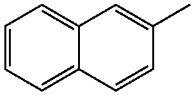 | Ph | H | H | Ph | 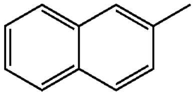 | H |
| N-12 | 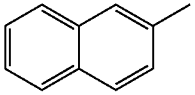 | H | Ph | Ph | H | 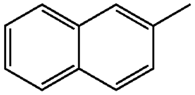 | H |
| N-13 | 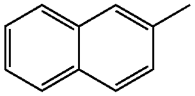 | H | Ph | H | H | 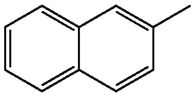 | H |
| N-14 | 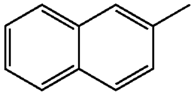 | H | H | H | H | 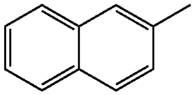 | Ph |

-continued
| | | | | | | | |
|---|---|---|---|---|---|---|---|
| N-15 | 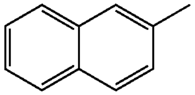 | Me | H | H | Me | 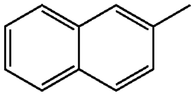 | H |
| N-16 | 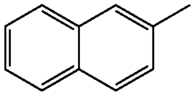 | H | Me | Me | H | 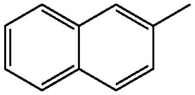 | H |
| N-17 | 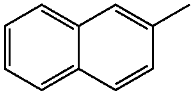 | H | H | H | H | 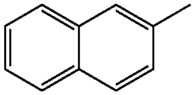 | Me |
| N-18 | 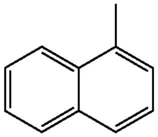 | H | H | H | H | 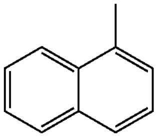 | H |
| N-19 | 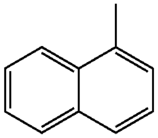 | Ph | H | H | Ph | 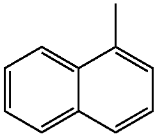 | H |
| N-20 | 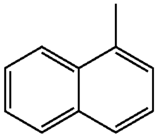 | H | Ph | Ph | H | 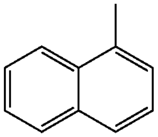 | H |
| N-21 | 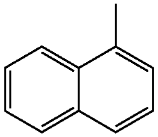 | H | Ph | H | H | 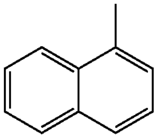 | H |

-continued
| | | | | | | | |
|---|---|---|---|---|---|---|---|
| N-22 | 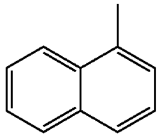 | H | H | H | H | 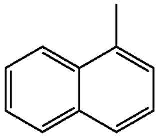 | Ph |
| N-23 | 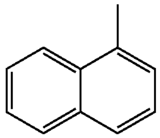 | Me | H | H | Me | 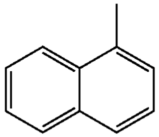 | H |
| N-24 | 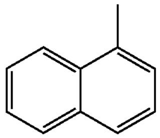 | H | Me | Me | H | 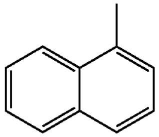 | H |
| N-25 | 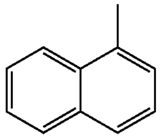 | H | H | H | H | 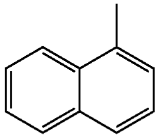 | Me |
| N-26 | 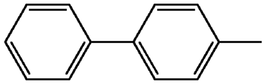 | H | H | H | H | 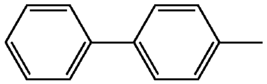 | H |
| N-27 | 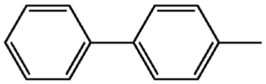 | Ph | H | H | Ph | 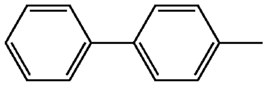 | H |
| N-28 | 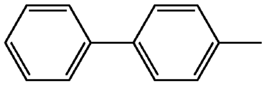 | H | Ph | Ph | H | 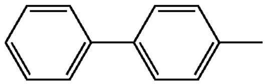 | H |
| N-29 | 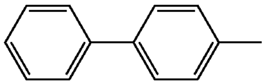 | H | Ph | H | H | 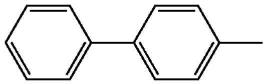 | H |

-continued
| | | | | | | | |
|---|---|---|---|---|---|---|---|
| N-30 | 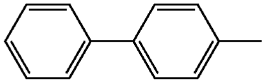 | H | H | H | H | 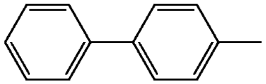 | Ph |
| N-31 | 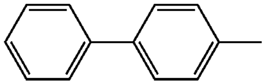 | Me | H | H | Me | 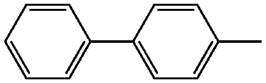 | H |
| N-32 | 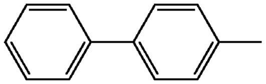 | H | Me | Me | H | 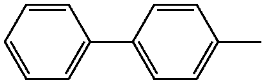 | H |
| N-33 | 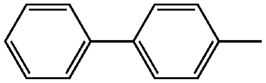 | H | H | H | H | 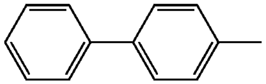 | Me |
| N-34 | 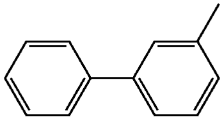 | H | H | H | H | 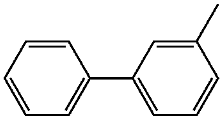 | H |
| N-35 | 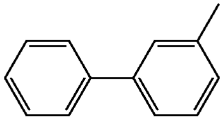 | Ph | H | H | Ph | 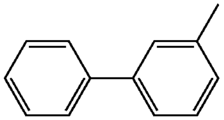 | H |
| N-36 | 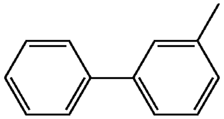 | H | Ph | Ph | H | 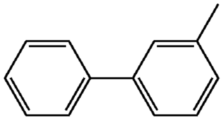 | H |
| N-37 | 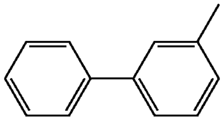 | H | Ph | H | H | 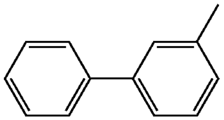 | H |
| N-38 | 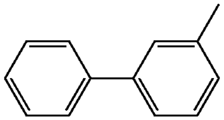 | H | H | H | H | 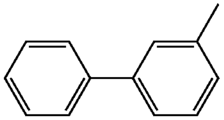 | Ph |

-continued
| | | | | | | | |
|---|---|---|---|---|---|---|---|
| N-39 | 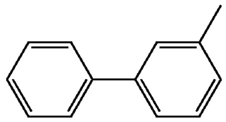 | Me | H | H | Me | 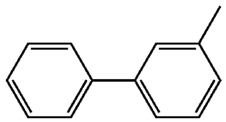 | H |
| N-40 | 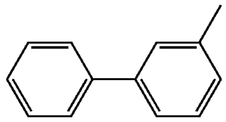 | H | Me | Me | H | 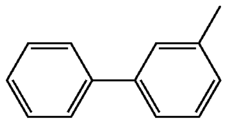 | H |
| N-41 | 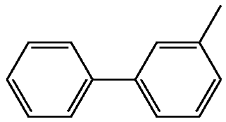 | H | H | H | H | 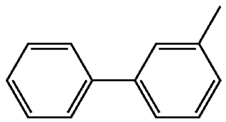 | Me |
| N-42 | 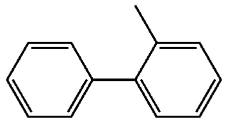 | H | H | H | H | 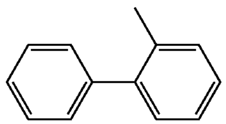 | H |
| N-43 | 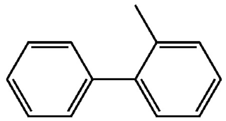 | Ph | H | H | Ph | 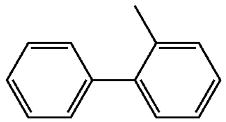 | H |
| N-44 | 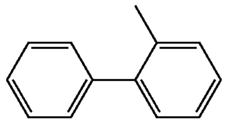 | H | Ph | Ph | H | 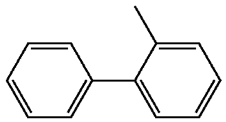 | H |
| N-45 | 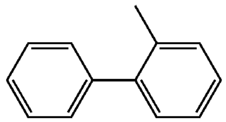 | H | Ph | H | H | 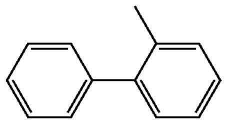 | H |

-continued
| | | | | | | | |
|---|---|---|---|---|---|---|---|
| N-46 | 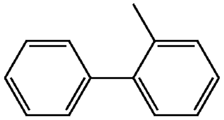 | H | H | H | H | 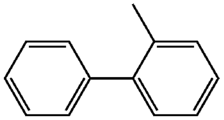 | Ph |
| N-47 | 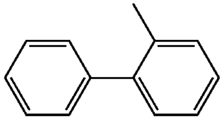 | Me | H | H | Me | 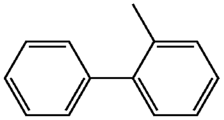 | H |
| N-48 | 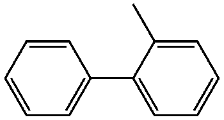 | H | Me | Me | H | 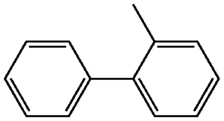 | H |
| N-49 | 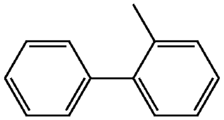 | H | H | H | H | 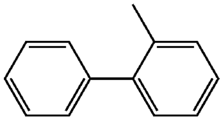 | Me |
| N-50 | Ph | H | H | H | H | 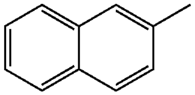 | H |
| N-51 | Ph | H | H | H | H | 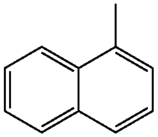 | H |
| N-52 | Ph | H | H | H | H | 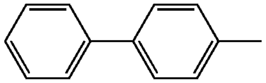 | H |
| N-53 | Ph | H | H | H | H | 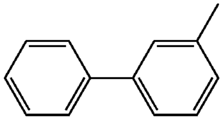 | H |

-continued
| | | | | | | | |
|---|---|---|---|---|---|---|---|
| N-54 | Ph | H | H | H | H | 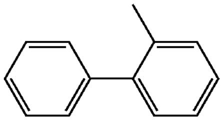 | H |
| N-55 | 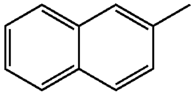 | H | H | H | H | 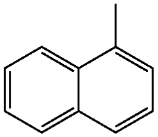 | H |
| N-56 | 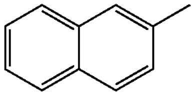 | H | H | H | H | 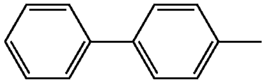 | H |
| N-57 | 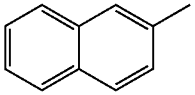 | H | H | H | H | 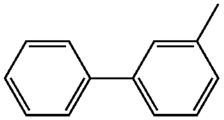 | H |
| N-58 | 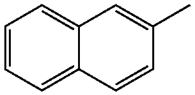 | H | H | H | H | 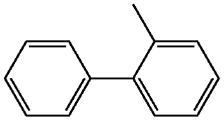 | H |
| N-59 | 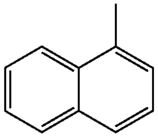 | H | H | H | H | 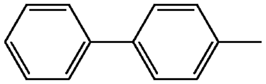 | H |
| N-60 | 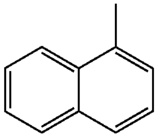 | H | H | H | H | 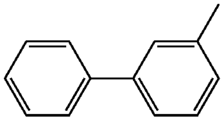 | H |

-continued
| | | | | | | | |
|---|---|---|---|---|---|---|---|
| N-61 | 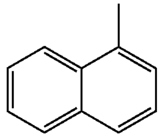 | H | H | H | H | 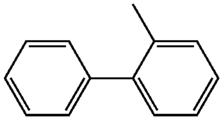 | H |
| N-62 | 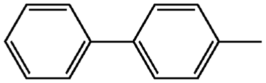 | H | H | H | H | 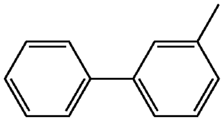 | H |
| N-63 | 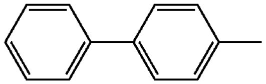 | H | H | H | H | 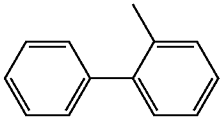 | H |
| N-64 | 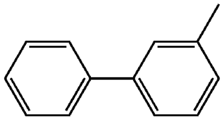 | H | H | H | H | 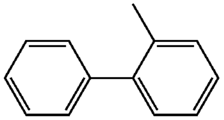 | H |
| N-65 | H | Ph | H | H | Ph | H | H |
| N-66 | H | 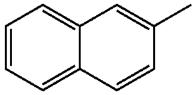 | H | H | 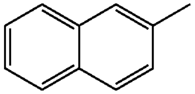 | H | H |
| N-67 | H | 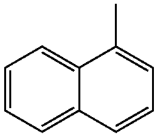 | H | H | 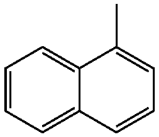 | H | H |
| N-68 | H | 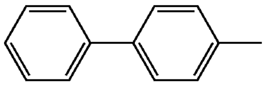 | H | H | 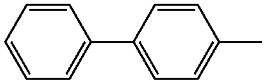 | H | H |

-continued
| | | | | | | | |
|---|---|---|---|---|---|---|---|
| N-69 | H | 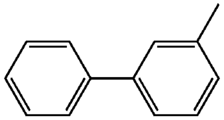 | H | H | 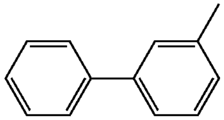 | H | H |
| N-70 | H | 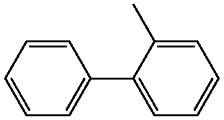 | H | H | 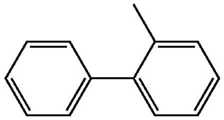 | H | H |
| N-71 | H | H | 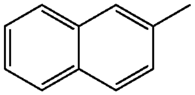 | 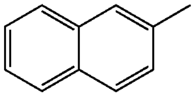 | H | H | H |
| N-72 | H | H | 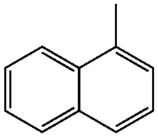 | 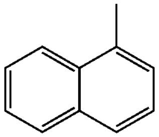 | H | H | H |
| N-73 | H | H | 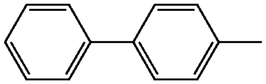 | 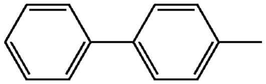 | H | H | H |
| N-74 | H | H | 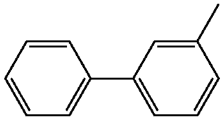 | 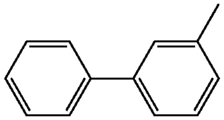 | H | H | H |
| N-75 | H | H | 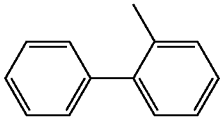 | 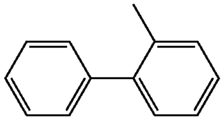 | H | H | H |
| N-76 | 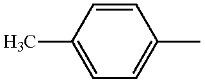 | H | H | H | H | 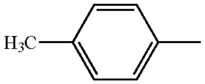 | H |

-continued
| | | | | | | | |
|---|---|---|---|---|---|---|---|
| N-77 | 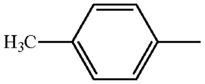 | Ph | H | H | Ph | 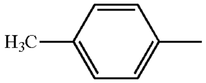 | H |
| N-78 | 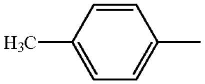 | H | Ph | Ph | H | 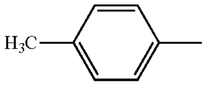 | H |
| N-79 | 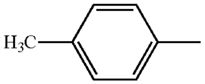 | H | Ph | H | H | 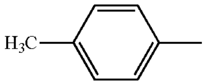 | H |
| N-80 | 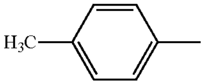 | H | H | H | H | 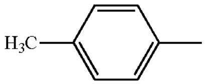 | Ph |
| N-81 | 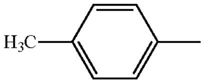 | Me | H | H | Me | 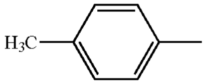 | H |
| N-82 | 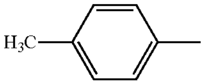 | H | Me | Me | H | 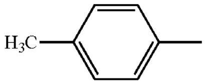 | H |
| N-83 | 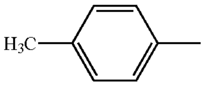 | H | H | H | H | 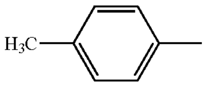 | Me |
| N-84 | 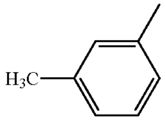 | H | H | H | H | 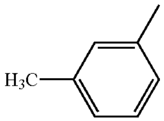 | H |
| N-85 | 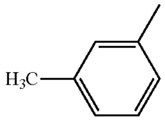 | Ph | H | H | Ph | 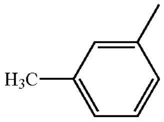 | H |

-continued
| | | | | | | | |
|---|---|---|---|---|---|---|---|
| N-86 | 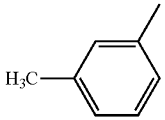 | H | Ph | Ph | H | 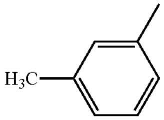 | H |
| N-87 | 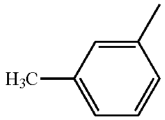 | H | Ph | H | H | 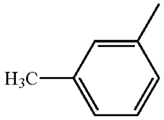 | H |
| N-88 | 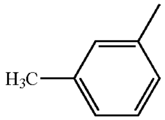 | H | H | H | H | 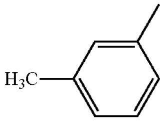 | Ph |
| N-89 | 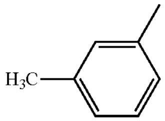 | Me | H | H | Me | 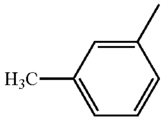 | H |
| N-90 | 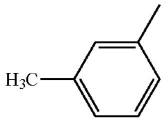 | H | Me | Me | H | 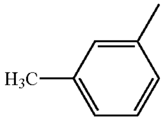 | H |
| N-91 | 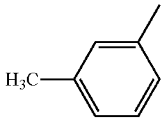 | H | H | H | H | 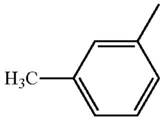 | Me |
| N-92 | 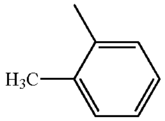 | H | H | H | H | 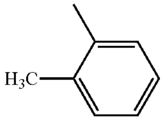 | H |
| N-93 | 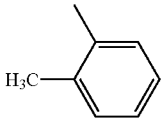 | Ph | H | H | Ph | 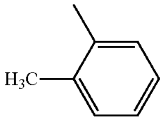 | H |

-continued
| | | | | | | | |
|---|---|---|---|---|---|---|---|
| N-94 | 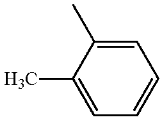 | H | Ph | Ph | H | 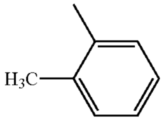 | H |
| N-96 | 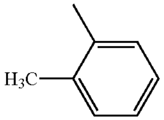 | H | Ph | H | H | 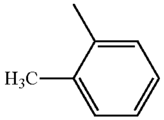 | H |
| N-96 | 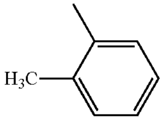 | H | H | H | H | 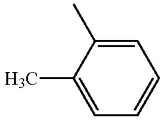 | Ph |
| N-97 | 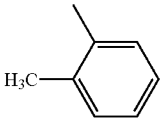 | Me | H | H | Me | 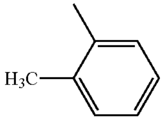 | H |
| N-98 | 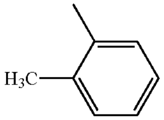 | H | Me | Me | H | 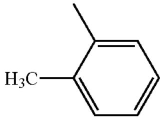 | H |
| N-99 | 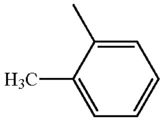 | H | H | H | H | 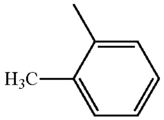 | Me |
| 100 | 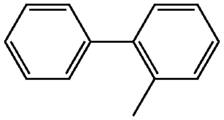 | H | H | H | H | 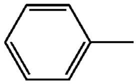 | H |

-continued
| | | | | | | | |
|---|---|---|---|---|---|---|---|
| 101 | 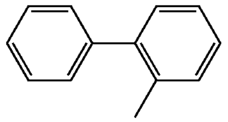 | Ph | H | H | Ph | 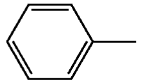 | H |
| 102 | 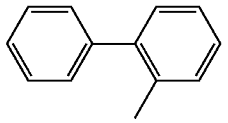 | H | Ph | Ph | H | 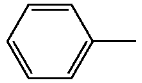 | H |
| 103 | 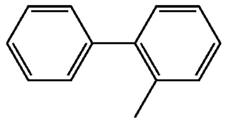 | H | Ph | H | H | 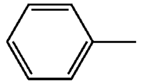 | H |
| 104 | 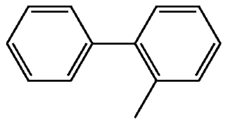 | H | H | H | H | 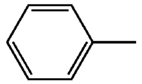 | Ph |
| 105 | 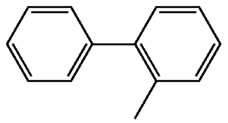 | Me | H | H | Me | 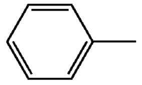 | H |
| 106 | 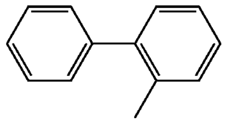 | H | Me | Me | H | 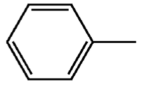 | H |
| 107 | 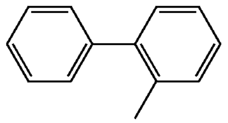 | H | H | H | H | 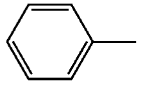 | Me |
| 108 | 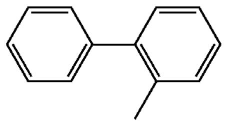 | H | H | H | H | 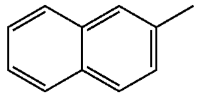 | H |

-continued
| | | | | | | | |
|---|---|---|---|---|---|---|---|
| 109 | 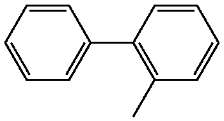 | Ph | H | H | Ph | 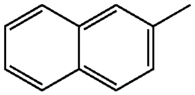 | H |
| 110 | 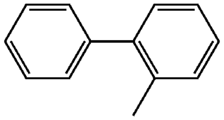 | H | Ph | Ph | H | 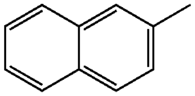 | H |
| 111 | 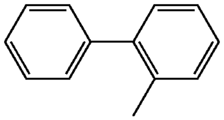 | H | Ph | H | H | 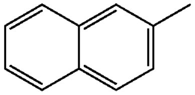 | H |
| 112 | 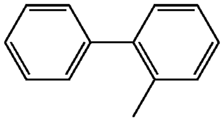 | H | H | H | H | 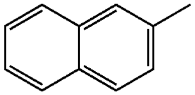 | Ph |
| 113 | 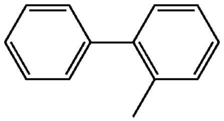 | Me | H | H | Me | 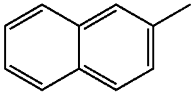 | H |
| 114 | 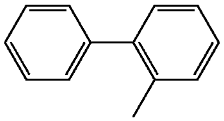 | H | Me | Me | H | 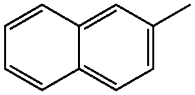 | H |
| 115 | 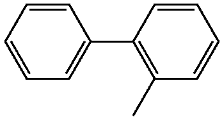 | H | H | H | H | 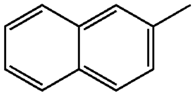 | Me |

-continued
| | | | | | | | |
|---|---|---|---|---|---|---|---|
| 116 | 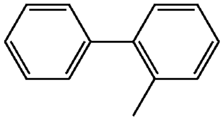 | H | H | H | H | 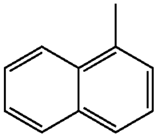 | H |
| 117 | 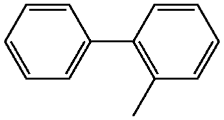 | Ph | H | H | Ph | 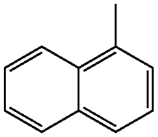 | H |
| 118 | 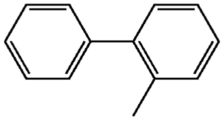 | H | Ph | Ph | H | 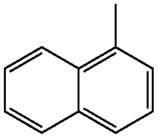 | H |
| 119 | 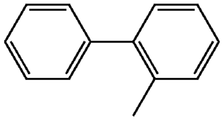 | H | Ph | H | H | 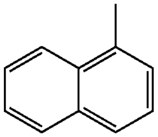 | H |
| 120 | 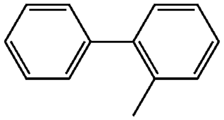 | H | H | H | H | 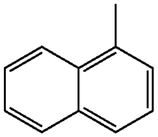 | Ph |
| 121 | 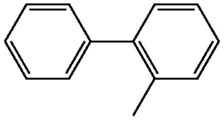 | Me | H | H | Me | 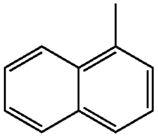 | H |
| 122 | 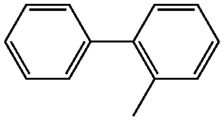 | H | Me | Me | H | 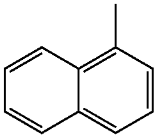 | H |

-continued
| | | | | | | | |
|---|---|---|---|---|---|---|---|
| 123 | 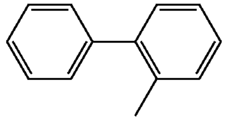 | H | H | H | H | 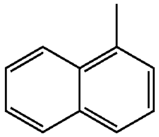 | Me |
| 124 | 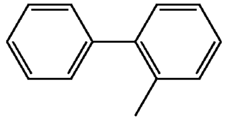 | H | H | H | H | 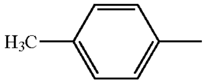 | H |
| 125 | 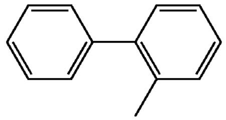 | Ph | H | H | Ph | 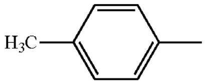 | H |
| 126 | 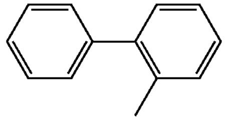 | H | Ph | Ph | H | 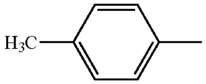 | H |
| 127 | 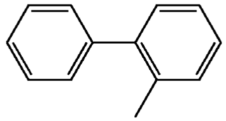 | H | Ph | H | H | 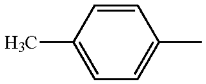 | H |
| 128 | 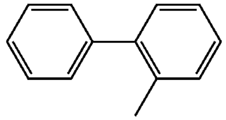 | H | H | H | H | 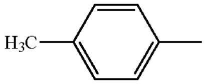 | Ph |
| 129 | 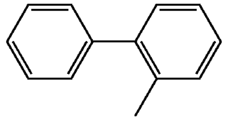 | Me | H | H | Me | 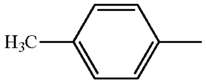 | H |

-continued
| | | | | | | | |
|---|---|---|---|---|---|---|---|
| 130 | 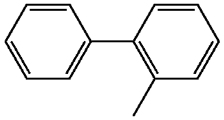 | H | Me | Me | H | 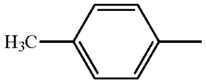 | H |
| 131 | 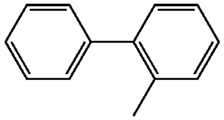 | H | H | H | H | 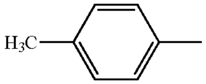 | Me |
| 132 | 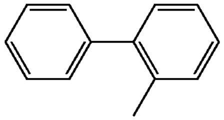 | H | H | H | H | 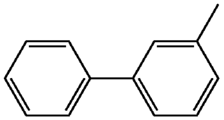 | H |
| 133 | 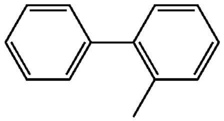 | Ph | H | H | Ph | 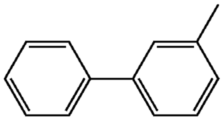 | H |
| 134 | 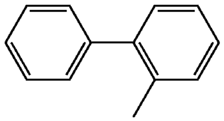 | H | Ph | Ph | H | 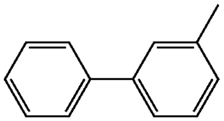 | H |
| 135 | 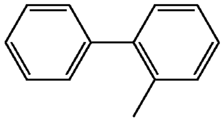 | H | Ph | H | H | 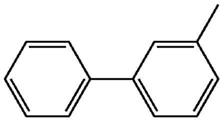 | H |
| 136 | 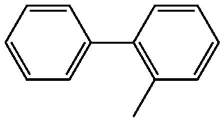 | H | H | H | H | 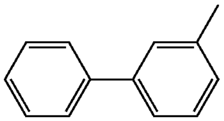 | Ph |
| 137 | 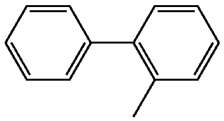 | Me | H | H | Me | 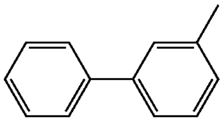 | H |

-continued
| | | | | | | |
|---|---|---|---|---|---|---|
| 138 | 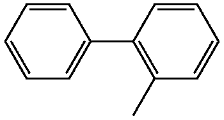 | H | Me | Me | H | 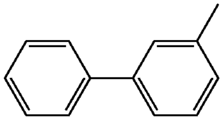 H |
| 139 | 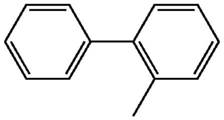 | H | H | H | H | 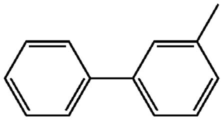 Me |
| 140 | 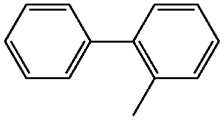 | H | H | H | H | 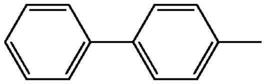 H |
| 141 | 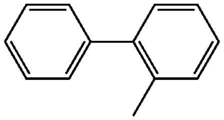 | Ph | H | H | Ph | 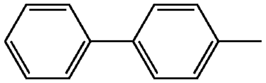 H |
| 142 | 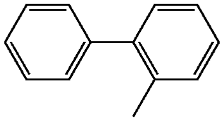 | H | Ph | Ph | H | 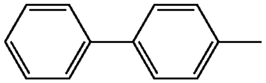 H |
| 143 | 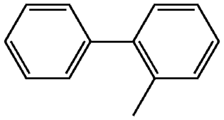 | H | Ph | H | H | 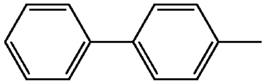 H |

-continued
| | | | | | | | |
|---|---|---|---|---|---|---|---|
| 144 | 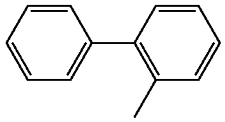 | H | H | H | H | 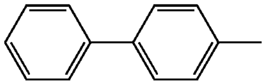 | Ph |
| 145 | 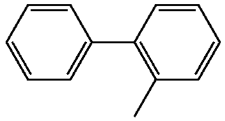 | Me | H | H | Me | 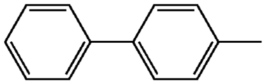 | H |
| 146 | 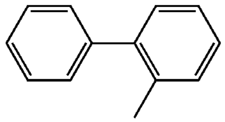 | H | Me | Me | H | 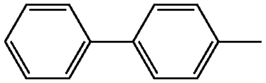 | H |
| 147 | 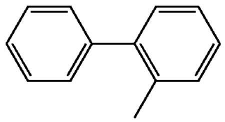 | H | H | H | H | 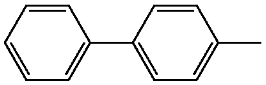 | Me |

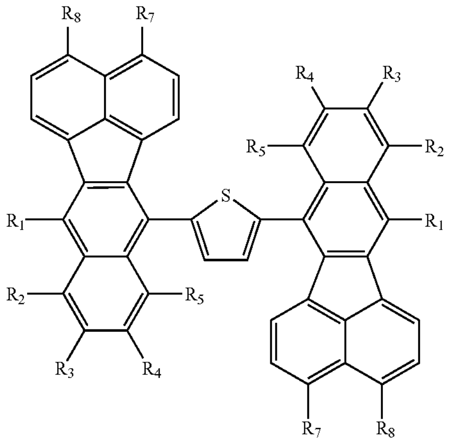

TypeO

|  | $R_1$ | $R_2$ | $R_3$ | $R_4$ | $R_5$ | $R_7$ | $R_8$ |
|---|---|---|---|---|---|---|---|
| O-1 | H | H | H | H | H | H | H |
| O-2 | Ph | H | H | H | H | H | H |
| O-3 | Ph | Ph | H | H | Ph | H | H |
| O-4 | Ph | H | Ph | Ph | H | H | H |
| O-5 | Ph | H | Ph | H | H | H | H |
| O-6 | Ph | H | H | Ph | H | H | H |
| O-7 | Ph | H | H | H | H | Ph | H |
| O-8 | Ph | H | H | H | H | H | Ph |
| O-9 | Ph | H | H | H | H | Ph | Ph |
| O-10 | Ph | H | H | H | H | 1-naphthyl | H |
| O-11 | Ph | H | H | H | H | H | 1-naphthyl |
| O-12 | Ph | H | H | H | H | 1-naphthyl | 1-naphthyl |
| O-13 | Ph | H | H | H | H | 2-naphthyl | H |
| O-14 | Ph | H | H | H | H | H | 2-naphthyl |
| O-15 | Ph | H | H | H | H | 2-naphthyl | 2-naphthyl |
| O-16 | Ph | H | H | H | H | o-biphenylyl | H |
| O-17 | Ph | H | H | H | H | H | o-biphenylyl |
| O-18 | Ph | H | H | H | H | o-biphenylyl | o-biphenylyl |
| O-19 | Ph | H | H | H | H | m-biphenylyl | H |
| O-20 | Ph | H | H | H | H | H | m-biphenylyl |
| O-21 | Ph | H | H | H | H | m-biphenylyl | m-biphenylyl |
| O-22 | Ph | H | H | H | H | p-biphenylyl | H |
| O-23 | Ph | H | H | H | H | H | p-biphenylyl |
| O-24 | Ph | H | H | H | H | p-biphenylyl | p-biphenylyl |
| O-25 | 1-naphthyl | H | H | H | H | H | H |
| O-26 | 1-naphthyl | Ph | H | H | Ph | H | H |
| O-27 | 1-naphthyl | H | Ph | Ph | H | H | H |
| O-28 | 1-naphthyl | H | Ph | H | H | H | H |
| O-29 | 1-naphthyl | H | H | Ph | H | H | H |
| O-30 | 1-naphthyl | H | H | H | H | Ph | H |
| O-31 | 1-naphthyl | H | H | H | H | H | Ph |
| O-32 | 1-naphthyl | H | H | H | H | Ph | Ph |
| O-33 | 1-naphthyl | H | H | H | H | 1-naphthyl | H |
| O-34 | 1-naphthyl | H | H | H | H | H | 1-naphthyl |
| O-35 | 1-naphthyl | H | H | H | H | 1-naphthyl | 1-naphthyl |
| O-36 | 1-naphthyl | H | H | H | H | 2-naphthyl | H |
| O-37 | 1-naphthyl | H | H | H | H | H | 2-naphthyl |
| O-38 | 1-naphthyl | H | H | H | H | 2-naphthyl | 2-naphthyl |
| O-39 | 1-naphthyl | H | H | H | H | o-biphenylyl | H |
| O-40 | 1-naphthyl | H | H | H | H | H | o-biphenylyl |
| O-41 | 1-naphthyl | H | H | H | H | o-biphenylyl | o-biphenylyl |
| O-42 | 1-naphthyl | H | H | H | H | m-biphenylyl | H |
| O-43 | 1-naphthyl | H | H | H | H | H | m-biphenylyl |
| O-44 | 1-naphthyl | H | H | H | H | m-biphenylyl | m-biphenylyl |
| O-45 | 1-naphthyl | H | H | H | H | p-biphenylyl | H |
| O-46 | 1-naphthyl | H | H | H | H | H | p-biphenylyl |
| O-47 | 1-naphthyl | H | H | H | H | p-biphenylyl | p-biphenylyl |
| O-48 | 2-naphthyl | H | H | H | H | H | H |
| O-49 | 2-naphthyl | Ph | H | H | Ph | H | H |
| O-50 | 2-naphthyl | H | Ph | Ph | H | H | H |
| O-51 | 2-naphthyl | H | Ph | H | H | H | H |
| O-52 | 2-naphthyl | H | H | Ph | H | H | H |
| O-53 | 2-naphthyl | H | H | H | H | Ph | H |

-continued

| | | | | | | | |
|---|---|---|---|---|---|---|---|
| O-54 | 2-naphthyl | H | H | H | H | H | Ph |
| O-55 | 2-naphthyl | H | H | H | H | Ph | Ph |
| O-56 | 2-naphthyl | H | H | H | H | 1-naphthyl | H |
| O-57 | 2-naphthyl | H | H | H | H | H | 1-naphthyl |
| O-58 | 2-naphthyl | H | H | H | H | 1-naphthyl | 1-naphthyl |
| O-59 | 2-naphthyl | H | H | H | H | 2-naphthyl | H |
| O-60 | 2-naphthyl | H | H | H | H | H | 2-naphthyl |
| O-61 | 2-naphthyl | H | H | H | H | 2-naphthyl | 2-naphthyl |
| O-62 | 2-naphthyl | H | H | H | H | o-biphenylyl | H |
| O-63 | 2-naphthyl | H | H | H | H | H | o-biphenylyl |
| O-64 | 2-naphthyl | H | H | H | H | o-biphenylyl | o-biphenylyl |
| O-65 | 2-naphthyl | H | H | H | H | m-biphenylyl | H |
| O-66 | 2-naphthyl | H | H | H | H | H | m-biphenylyl |
| O-67 | 2-naphthyl | H | H | H | H | m-biphenylyl | m-biphenylyl |
| O-68 | 2-naphthyl | H | H | H | H | p-biphenylyl | H |
| O-69 | 2-naphthyl | H | H | H | H | H | p-biphenylyl |
| O-70 | 2-naphthyl | H | H | H | H | p-biphenylyl | p-biphenylyl |
| O-71 | o-biphenylyl | H | H | H | H | H | H |
| O-72 | o-biphenylyl | Ph | H | H | Ph | H | H |
| O-73 | o-biphenylyl | H | Ph | Ph | H | H | H |
| O-74 | o-biphenylyl | H | Ph | H | H | H | H |
| O-75 | o-biphenylyl | H | H | Ph | H | H | H |
| O-76 | o-biphenylyl | H | H | H | H | Ph | H |
| O-77 | o-biphenylyl | H | H | H | H | H | Ph |
| O-78 | o-biphenylyl | H | H | H | H | Ph | Ph |
| O-79 | o-biphenylyl | H | H | H | H | 1-naphthyl | H |
| O-80 | o-biphenylyl | H | H | H | H | H | 1-naphthyl |
| O-81 | o-biphenylyl | H | H | H | H | 1-naphthyl | 1-naphthyl |
| O-82 | o-biphenylyl | H | H | H | H | 2-naphthyl | H |
| O-83 | o-biphenylyl | H | H | H | H | H | 2-naphthyl |
| O-84 | o-biphenylyl | H | H | H | H | 2-naphthyl | 2-naphthyl |
| O-85 | o-biphenylyl | H | H | H | H | o-biphenylyl | H |
| O-86 | o-biphenylyl | H | H | H | H | H | o-biphenylyl |
| O-87 | o-biphenylyl | H | H | H | H | o-biphenylyl | o-biphenylyl |
| O-88 | o-biphenylyl | H | H | H | H | m-biphenylyl | H |
| O-89 | o-biphenylyl | H | H | H | H | H | m-biphenylyl |
| O-90 | o-biphenylyl | H | H | H | H | m-biphenylyl | m-biphenylyl |
| O-91 | o-biphenylyl | H | H | H | H | p-biphenylyl | H |
| O-92 | o-biphenylyl | H | H | H | H | H | p-biphenylyl |
| O-93 | o-biphenylyl | H | H | H | H | p-biphenylyl | p-biphenylyl |
| O-94 | m-biphenylyl | H | H | H | H | H | H |
| O-95 | m-biphenylyl | Ph | H | H | Ph | H | H |
| O-96 | m-biphenylyl | H | Ph | Ph | H | H | H |
| O-97 | m-biphenylyl | H | Ph | H | H | H | H |
| O-98 | m-biphenylyl | H | H | Ph | H | H | H |
| O-99 | m-biphenylyl | H | H | H | H | Ph | H |
| O-100 | m-biphenylyl | H | H | H | H | H | Ph |
| O-101 | m-biphenylyl | H | H | H | H | Ph | Ph |
| O-102 | m-biphenylyl | H | H | H | H | 1-naphthyl | H |
| O-103 | m-biphenylyl | H | H | H | H | H | 1-naphthyl |
| O-104 | m-biphenylyl | H | H | H | H | 1-naphthyl | 1-naphthyl |
| O-105 | m-biphenylyl | H | H | H | H | 2-naphthyl | H |
| O-106 | m-biphenylyl | H | H | H | H | H | 2-naphthyl |
| O-107 | m-biphenylyl | H | H | H | H | 2-naphthyl | 2-naphthyl |
| O-108 | m-biphenylyl | H | H | H | H | o-biphenylyl | H |
| O-109 | m-biphenylyl | H | H | H | H | H | o-biphenylyl |
| O-110 | m-biphenylyl | H | H | H | H | o-biphenylyl | o-biphenylyl |
| O-111 | m-biphenylyl | H | H | H | H | m-biphenylyl | H |
| O-112 | m-biphenylyl | H | H | H | H | H | m-biphenylyl |
| O-113 | m-biphenylyl | H | H | H | H | m-biphenylyl | m-biphenylyl |
| O-114 | m-biphenylyl | H | H | H | H | p-biphenylyl | H |
| O-115 | m-biphenylyl | H | H | H | H | H | p-biphenylyl |
| O-116 | m-biphenylyl | H | H | H | H | p-biphenylyl | p-biphenylyl |
| O-117 | p-biphenylyl | H | H | H | H | H | H |
| O-118 | p-biphenylyl | Ph | H | H | Ph | H | H |
| O-119 | p-biphenylyl | H | Ph | Ph | H | H | H |
| O-120 | p-biphenylyl | H | Ph | H | H | H | H |
| O-121 | p-biphenylyl | H | H | Ph | H | H | H |
| O-122 | p-biphenylyl | H | H | H | H | Ph | H |
| O-123 | p-biphenylyl | H | H | H | H | H | Ph |
| O-124 | p-biphenylyl | H | H | H | H | Ph | Ph |
| O-125 | p-biphenylyl | H | H | H | H | 1-naphthyl | H |
| O-126 | p-biphenylyl | H | H | H | H | H | 1-naphthyl |
| O-127 | p-biphenylyl | H | H | H | H | 1-naphthyl | 1-naphthyl |
| O-128 | p-biphenylyl | H | H | H | H | 2-naphthyl | H |
| O-129 | p-biphenylyl | H | H | H | H | H | 2-naphthyl |
| O-130 | p-biphenylyl | H | H | H | H | 2-naphthyl | 2-naphthyl |
| O-131 | p-biphenylyl | H | H | H | H | o-biphenylyl | H |
| O-132 | p-biphenylyl | H | H | H | H | H | o-biphenylyl |

-continued

| | | | | | | | |
|---|---|---|---|---|---|---|---|
| O-133 | p-biphenylyl | H | H | H | H | o-biphenylyl | o-biphenylyl |
| O-134 | p-biphenylyl | H | H | H | H | m-biphenylyl | H |
| O-135 | p-biphenylyl | H | H | H | H | H | m-biphenylyl |
| O-136 | p-biphenylyl | H | H | H | H | m-biphenylyl | m-biphenylyl |
| O-137 | p-biphenylyl | H | H | H | H | p-biphenylyl | H |
| O-138 | p-biphenylyl | H | H | H | H | H | p-biphenylyl |
| O-139 | p-biphenylyl | H | H | H | H | p-biphenylyl | p-biphenylyl |
| O-140 | o-tolyl | H | H | H | H | H | H |
| O-141 | o-tolyl | Ph | H | H | Ph | H | H |
| O-142 | o-tolyl | H | Ph | Ph | H | H | H |
| O-143 | o-tolyl | H | H | H | H | Ph | H |
| O-144 | o-tolyl | H | H | H | H | H | Ph |
| O-145 | o-tolyl | H | H | H | H | 1-naphthyl | H |
| O-146 | o-tolyl | H | H | H | H | H | 1-naphthyl |
| O-147 | o-tolyl | H | H | H | H | 2-naphthyl | H |
| O-148 | o-tolyl | H | H | H | H | H | 2-naphthyl |
| O-149 | o-tolyl | H | H | H | H | o-biphenylyl | H |
| O-150 | o-tolyl | H | H | H | H | H | o-biphenylyl |
| O-151 | o-tolyl | H | H | H | H | m-biphenylyl | H |
| O-152 | o-tolyl | H | H | H | H | H | m-biphenylyl |
| O-153 | o-tolyl | H | H | H | H | p-biphenylyl | H |
| O-154 | o-tolyl | H | H | H | H | H | p-biphenylyl |
| O-155 | o-tolyl | H | H | H | H | o-tolyl | H |
| O-156 | o-tolyl | H | H | H | H | H | o-tolyl |
| O-157 | m-tolyl | H | H | H | H | H | H |
| O-158 | m-tolyl | Ph | H | H | Ph | H | H |
| O-159 | m-tolyl | H | Ph | Ph | H | H | H |
| O-160 | m-tolyl | H | H | H | H | Ph | H |
| O-161 | m-tolyl | H | H | H | H | H | Ph |
| O-162 | m-tolyl | H | H | H | H | 1-naphthyl | H |
| O-163 | m-tolyl | H | H | H | H | H | 1-naphthyl |
| O-164 | m-tolyl | H | H | H | H | 2-naphthyl | H |
| O-165 | m-tolyl | H | H | H | H | H | 2-naphthyl |
| O-166 | m-tolyl | H | H | H | H | o-biphenylyl | H |
| O-167 | m-tolyl | H | H | H | H | H | o-biphenylyl |
| O-168 | m-tolyl | H | H | H | H | m-biphenylyl | H |
| O-169 | m-tolyl | H | H | H | H | H | m-biphenylyl |
| O-170 | m-tolyl | H | H | H | H | p-biphenylyl | H |
| O-171 | m-tolyl | H | H | H | H | H | p-biphenylyl |
| O-172 | m-tolyl | H | H | H | H | m-tolyl | H |
| O-173 | m-tolyl | H | H | H | H | H | m-tolyl |
| O-174 | p-tolyl | H | H | H | H | H | H |
| O-175 | p-tolyl | Ph | H | H | Ph | H | H |
| O-176 | p-tolyl | H | Ph | Ph | H | H | H |
| O-177 | p-tolyl | H | H | H | H | Ph | H |
| O-178 | p-tolyl | H | H | H | H | H | Ph |
| O-179 | p-tolyl | H | H | H | H | 1-naphthyl | H |
| O-180 | p-tolyl | H | H | H | H | H | 1-naphthyl |
| O-181 | p-tolyl | H | H | H | H | 2-naphthyl | H |
| O-182 | p-tolyl | H | H | H | H | H | 2-naphthyl |
| O-183 | p-tolyl | H | H | H | H | o-biphenylyl | H |
| O-184 | p-tolyl | H | H | H | H | H | o-biphenylyl |
| O-185 | p-tolyl | H | H | H | H | m-biphenylyl | H |
| O-186 | p-tolyl | H | H | H | H | H | m-biphenylyl |
| O-187 | p-tolyl | H | H | H | H | p-biphenylyl | H |
| O-188 | p-tolyl | H | H | H | H | H | p-biphenylyl |
| O-189 | p-tolyl | H | H | H | H | p-tolyl | H |
| O-190 | p-tolyl | H | H | H | H | H | p-tolyl |
| O-191 | Ph | H | —CH3 | —CH3 | H | H | H |
| O-192 | 1-naphtyl | H | —CH3 | —CH3 | H | H | H |
| O-193 | 2-naphthyl | H | —CH3 | —CH3 | H | H | H |
| O-194 | o-biphenylyl | H | —CH3 | —CH3 | H | H | H |
| O-195 | m-biphenylyl | H | —CH3 | —CH3 | H | H | H |
| O-196 | p-biphenylyl | H | —CH3 | —CH3 | H | H | H |
| O-197 | o-tolyl | H | —CH3 | —CH3 | H | H | H |
| O-198 | m-tolyl | H | —CH3 | —CH3 | H | H | H |
| O-199 | p-tolyl | H | —CH3 | —CH3 | H | H | H |
| O-200 | Ph | H | H | H | H | —CH3 | H |
| O-201 | 1-naphtyl | H | H | H | H | —CH3 | H |
| O-202 | 2-naphthyl | H | H | H | H | —CH3 | H |
| O-203 | o-biphenylyl | H | H | H | H | —CH3 | H |
| O-204 | m-biphenylyl | H | H | H | H | —CH3 | H |
| O-205 | p-biphenylyl | H | H | H | H | —CH3 | H |
| O-206 | o-tolyl | H | H | H | H | —CH3 | H |
| O-207 | m-tolyl | H | H | H | H | —CH3 | H |
| O-208 | p-tolyl | H | H | H | H | —CH3 | H |
| O-209 | Ph | H | H | H | H | H | —CH3 |
| O-210 | 1-naphtyl | H | H | H | H | H | —CH3 |
| O-211 | 2-naphthyl | H | H | H | H | H | —CH3 |

-continued

| | | | | | | | |
|---|---|---|---|---|---|---|---|
| O-212 | o-biphenylyl | H | H | H | H | H | —CH3 |
| O-213 | m-biphenylyl | H | H | H | H | H | —CH3 |
| O-214 | p-biphenylyl | H | H | H | H | H | —CH3 |
| O-215 | o-tolyl | H | H | H | H | H | —CH3 |
| O-216 | m-tolyl | H | H | H | H | H | —CH3 |
| O-217 | p-tolyl | H | H | H | H | H | —CH3 |
| O-218 | Ph | H | H | H | H | —CH3 | —CH3 |
| O-219 | 1-naphtyl | H | H | H | H | —CH3 | —CH3 |
| O-220 | 2-naphthyl | H | H | H | H | —CH3 | —CH3 |
| O-221 | o-biphenylyl | H | H | H | H | —CH3 | —CH3 |
| O-222 | m-biphenylyl | H | H | H | H | —CH3 | —CH3 |
| O-223 | p-biphenylyl | H | H | H | H | —CH3 | —CH3 |
| O-224 | o-tolyl | H | H | H | H | —CH3 | —CH3 |
| O-225 | m-tolyl | H | H | H | H | —CH3 | —CH3 |
| O-226 | p-tolyl | H | H | H | H | —CH3 | —CH3 |
| O-227 | Ph | H | H | H | H | H | DPA |
| O-228 | 1-naphtyl | H | H | H | H | H | DPA |
| O-229 | 2-naphthyl | H | H | H | H | H | DPA |
| O-230 | o-biphenylyl | H | H | H | H | H | DPA |
| O-231 | m-biphenylyl | H | H | H | H | H | DPA |
| O-232 | p-biphenylyl | H | H | H | H | H | DPA |
| O-233 | Ph | H | H | H | H | DPA | H |
| O-234 | 1-naphtyl | H | H | H | H | DPA | H |
| O-235 | 2-naphthyl | H | H | H | H | DPA | H |
| O-236 | o-biphenylyl | H | H | H | H | DPA | H |
| O-237 | m-biphenylyl | H | H | H | H | DPA | H |
| O-238 | p-biphenylyl | H | H | H | H | DPA | H |
| O-239 | Ph | H | H | H | H | H | TPA |
| O-240 | 1-naphtyl | H | H | H | H | H | TPA |
| O-241 | 2-naphthyl | H | H | H | H | H | TPA |
| O-242 | o-biphenylyl | H | H | H | H | H | TPA |
| O-243 | m-biphenylyl | H | H | H | H | H | TPA |
| O-244 | p-biphenylyl | H | H | H | H | H | TPA |
| O-245 | Ph | H | H | H | H | TPA | H |
| O-246 | 1-naphtyl | H | H | H | H | TPA | H |
| O-247 | 2-naphthyl | H | H | H | H | TPA | H |
| O-248 | o-biphenylyl | H | H | H | H | TPA | H |
| O-249 | m-biphenylyl | H | H | H | H | TPA | H |
| O-250 | p-biphenylyl | H | H | H | H | TPA | H |

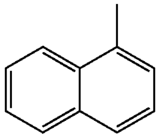

1-naphthyl

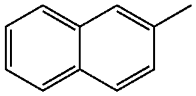

2-naphthyl

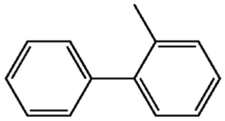

o-biphenylyl

-continued
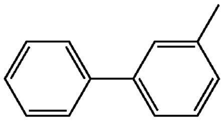
m-biphenylyl
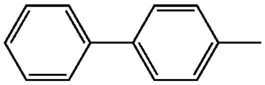
p-biphenylyl
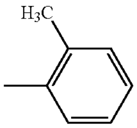
o-tolyl
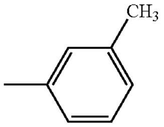
m-tolyl
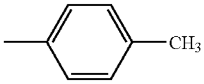
p-tolyl
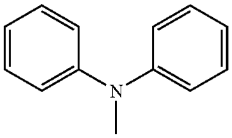
DPA
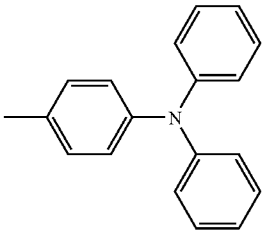
TPA

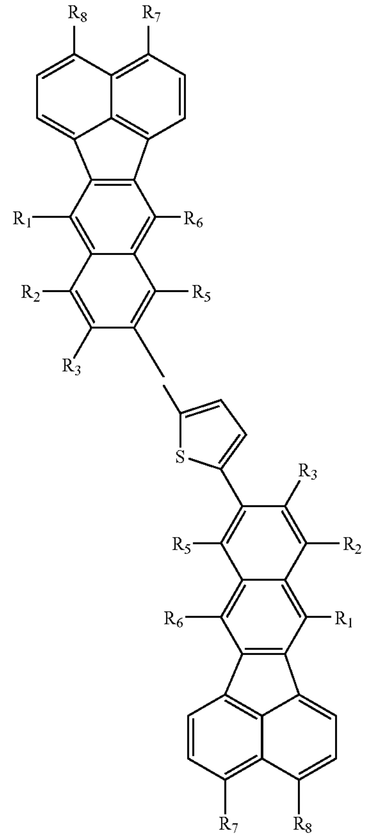

TypeP

| | $R_1$ | $R_2$ | $R_3$ | $R_5$ | $R_6$ | $R_7$ | $R_8$ |
|---|---|---|---|---|---|---|---|
| P-1 | H | H | H | H | H | H | H |
| P-2 | Ph | H | H | H | Ph | H | H |
| P-3 | Ph | Ph | H | H | Ph | H | H |
| P-4 | Ph | H | H | Ph | Ph | H | H |
| P-5 | Ph | Ph | H | Ph | Ph | H | H |
| P-6 | Ph | H | Ph | H | Ph | H | H |
| P-7 | Ph | H | H | H | Ph | Ph | H |
| P-8 | Ph | H | H | H | Ph | H | Ph |
| P-9 | Ph | H | H | H | Ph | Ph | Ph |
| P-10 | Ph | H | H | H | Ph | 1-naphthyl | H |
| P-11 | Ph | H | H | H | Ph | H | 1-naphthyl |
| P-12 | Ph | H | H | H | Ph | 1-naphthyl | 1-naphthyl |
| P-13 | Ph | H | H | H | Ph | 2-naphthyl | H |
| P-14 | Ph | H | H | H | Ph | H | 2-naphthyl |
| P-15 | Ph | H | H | H | Ph | 2-naphthyl | 2-naphthyl |
| P-16 | Ph | H | H | H | Ph | o-biphenylyl | H |
| P-17 | Ph | H | H | H | Ph | H | o-biphenylyl |
| P-18 | Ph | H | H | H | Ph | o-biphenylyl | o-biphenylyl |
| P-19 | Ph | H | H | H | Ph | m-biphenylyl | H |
| P-20 | Ph | H | H | H | Ph | H | m-biphenylyl |
| P-21 | Ph | H | H | H | Ph | m-biphenylyl | m-biphenylyl |
| P-22 | Ph | H | H | H | Ph | p-biphenylyl | H |
| P-23 | Ph | H | H | H | Ph | H | p-biphenylyl |
| P-24 | Ph | H | H | H | Ph | p-biphenylyl | p-biphenylyl |
| P-25 | 1-naphthyl | H | H | H | 1-naphthyl | H | H |
| P-26 | 1-naphthyl | Ph | H | H | 1-naphthyl | H | H |
| P-27 | 1-naphthyl | H | H | Ph | 1-naphthyl | H | H |
| P-28 | 1-naphthyl | Ph | H | Ph | 1-naphthyl | H | H |
| P-29 | 1-naphthyl | H | Ph | H | 1-naphthyl | H | H |
| P-30 | 1-naphthyl | H | H | H | 1-naphthyl | Ph | H |
| P-31 | 1-naphthyl | H | H | H | 1-naphthyl | H | Ph |
| P-32 | 1-naphthyl | H | H | H | 1-naphthyl | Ph | Ph |
| P-33 | 1-naphthyl | H | H | H | 1-naphthyl | 1-naphthyl | H |
| P-34 | 1-naphthyl | H | H | H | 1-naphthyl | H | 1-naphthyl |
| P-35 | 1-naphthyl | H | H | H | 1-naphthyl | 1-naphthyl | 1-naphthyl |

-continued

| | | | | | | | |
|---|---|---|---|---|---|---|---|
| P-36 | 1-naphthyl | H | H | H | 1-naphthyl | 2-naphthyl | H |
| P-37 | 1-naphthyl | H | H | H | 1-naphthyl | H | 2-naphthyl |
| P-38 | 1-naphthyl | H | H | H | 1-naphthyl | 2-naphthyl | 2-naphthyl |
| P-39 | 1-naphthyl | H | H | H | 1-naphthyl | o-biphenylyl | H |
| P-40 | 1-naphthyl | H | H | H | 1-naphthyl | H | o-biphenylyl |
| P-41 | 1-naphthyl | H | H | H | 1-naphthyl | o-biphenylyl | o-biphenylyl |
| P-42 | 1-naphthyl | H | H | H | 1-naphthyl | m-biphenylyl | H |
| P-43 | 1-naphthyl | H | H | H | 1-naphthyl | H | m-biphenylyl |
| P-44 | 1-naphthyl | H | H | H | 1-naphthyl | m-biphenylyl | m-biphenylyl |
| P-45 | 1-naphthyl | H | H | H | 1-naphthyl | p-biphenylyl | H |
| P-46 | 1-naphthyl | H | H | H | 1-naphthyl | H | p-biphenylyl |
| P-47 | 1-naphthyl | H | H | H | 1-naphthyl | p-biphenylyl | p-biphenylyl |
| P-48 | 2-naphthyl | H | H | H | 2-naphthyl | H | H |
| P-49 | 2-naphthyl | Ph | H | H | 2-naphthyl | H | H |
| P-50 | 2-naphthyl | H | H | Ph | 2-naphthyl | H | H |
| P-51 | 2-naphthyl | Ph | H | Ph | 2-naphthyl | H | H |
| P-52 | 2-naphthyl | H | Ph | H | 2-naphthyl | H | H |
| P-53 | 2-naphthyl | H | H | H | 2-naphthyl | Ph | H |
| P-54 | 2-naphthyl | H | H | H | 2-naphthyl | H | Ph |
| P-55 | 2-naphthyl | H | H | H | 2-naphthyl | Ph | Ph |
| P-56 | 2-naphthyl | H | H | H | 2-naphthyl | 1-naphthyl | H |
| P-57 | 2-naphthyl | H | H | H | 2-naphthyl | H | 1-naphthyl |
| P-58 | 2-naphthyl | H | H | H | 2-naphthyl | 1-naphthyl | 1-naphthyl |
| P-59 | 2-naphthyl | H | H | H | 2-naphthyl | 2-naphthyl | H |
| P-60 | 2-naphthyl | H | H | H | 2-naphthyl | H | 2-naphthyl |
| P-61 | 2-naphthyl | H | H | H | 2-naphthyl | 2-naphthyl | 2-naphthyl |
| P-62 | 2-naphthyl | H | H | H | 2-naphthyl | o-biphenylyl | H |
| P-63 | 2-naphthyl | H | H | H | 2-naphthyl | H | o-biphenylyl |
| P-64 | 2-naphthyl | H | H | H | 2-naphthyl | o-biphenylyl | o-biphenylyl |
| P-65 | 2-naphthyl | H | H | H | 2-naphthyl | m-biphenylyl | H |
| P-66 | 2-naphthyl | H | H | H | 2-naphthyl | H | m-biphenylyl |
| P-67 | 2-naphthyl | H | H | H | 2-naphthyl | m-biphenylyl | m-biphenylyl |
| P-68 | 2-naphthyl | H | H | H | 2-naphthyl | p-biphenylyl | H |
| P-69 | 2-naphthyl | H | H | H | 2-naphthyl | H | p-biphenylyl |
| P-70 | 2-naphthyl | H | H | H | 2-naphthyl | p-biphenylyl | p-biphenylyl |
| P-71 | o-biphenylyl | H | H | H | o-biphenylyl | H | H |
| P-72 | o-biphenylyl | Ph | H | H | o-biphenylyl | H | H |
| P-73 | o-biphenylyl | H | H | Ph | o-biphenylyl | H | H |
| P-74 | o-biphenylyl | Ph | H | Ph | o-biphenylyl | H | H |
| P-75 | o-biphenylyl | H | Ph | H | o-biphenylyl | H | H |
| P-76 | o-biphenylyl | H | H | H | o-biphenylyl | Ph | H |
| P-77 | o-biphenylyl | H | H | H | o-biphenylyl | H | Ph |
| P-78 | o-biphenylyl | H | H | H | o-biphenylyl | Ph | Ph |
| P-79 | o-biphenylyl | H | H | H | o-biphenylyl | 1-naphthyl | H |
| P-80 | o-biphenylyl | H | H | H | o-biphenylyl | H | 1-naphthyl |
| P-81 | o-biphenylyl | H | H | H | o-biphenylyl | 1-naphthyl | 1-naphthyl |
| P-82 | o-biphenylyl | H | H | H | o-biphenylyl | 2-naphthyl | H |
| P-83 | o-biphenylyl | H | H | H | o-biphenylyl | H | 2-naphthyl |
| P-84 | o-biphenylyl | H | H | H | o-biphenylyl | 2-naphthyl | 2-naphthyl |
| P-85 | o-biphenylyl | H | H | H | o-biphenylyl | o-biphenylyl | H |
| P-86 | o-biphenylyl | H | H | H | o-biphenylyl | H | o-biphenylyl |
| P-87 | o-biphenylyl | H | H | H | o-biphenylyl | o-biphenylyl | o-biphenylyl |
| P-88 | o-biphenylyl | H | H | H | o-biphenylyl | m-biphenylyl | H |
| P-89 | o-biphenylyl | H | H | H | o-biphenylyl | H | m-biphenylyl |
| P-90 | o-biphenylyl | H | H | H | o-biphenylyl | m-biphenylyl | m-biphenylyl |
| P-91 | o-biphenylyl | H | H | H | o-biphenylyl | p-biphenylyl | H |
| P-92 | o-biphenylyl | H | H | H | o-biphenylyl | H | p-biphenylyl |
| P-93 | o-biphenylyl | H | H | H | o-biphenylyl | p-biphenylyl | p-biphenylyl |
| P-94 | m-biphenylyl | H | H | H | m-biphenylyl | H | H |
| P-95 | m-biphenylyl | Ph | H | H | m-biphenylyl | H | H |
| P-96 | m-biphenylyl | H | H | Ph | m-biphenylyl | H | H |
| P-97 | m-biphenylyl | Ph | H | Ph | m-biphenylyl | H | H |
| P-98 | m-biphenylyl | H | Ph | H | m-biphenylyl | H | H |
| P-99 | m-biphenylyl | H | H | H | m-biphenylyl | Ph | H |
| P-100 | m-biphenylyl | H | H | H | m-biphenylyl | H | Ph |
| P-101 | m-biphenylyl | H | H | H | m-biphenylyl | Ph | Ph |
| P-102 | m-biphenylyl | H | H | H | m-biphenylyl | 1-naphthyl | H |
| P-103 | m-biphenylyl | H | H | H | m-biphenylyl | H | 1-naphthyl |
| P-104 | m-biphenylyl | H | H | H | m-biphenylyl | 1-naphthyl | 1-naphthyl |
| P-105 | m-biphenylyl | H | H | H | m-biphenylyl | 2-naphthyl | H |
| P-106 | m-biphenylyl | H | H | H | m-biphenylyl | H | 2-naphthyl |
| P-107 | m-biphenylyl | H | H | H | m-biphenylyl | 2-naphthyl | 2-naphthyl |
| P-108 | m-biphenylyl | H | H | H | m-biphenylyl | o-biphenylyl | H |
| P-109 | m-biphenylyl | H | H | H | m-biphenylyl | H | o-biphenylyl |
| P-110 | m-biphenylyl | H | H | H | m-biphenylyl | o-biphenylyl | o-biphenylyl |
| P-111 | m-biphenylyl | H | H | H | m-biphenylyl | m-biphenylyl | H |
| P-112 | m-biphenylyl | H | H | H | m-biphenylyl | H | m-biphenylyl |
| P-113 | m-biphenylyl | H | H | H | m-biphenylyl | m-biphenylyl | m-biphenylyl |

-continued

| | | | | | | | |
|---|---|---|---|---|---|---|---|
| P-114 | m-biphenylyl | H | H | H | m-biphenylyl | p-biphenylyl | H |
| P-115 | m-biphenylyl | H | H | H | m-biphenylyl | H | p-biphenylyl |
| P-116 | m-biphenylyl | H | H | H | m-biphenylyl | p-biphenylyl | p-biphenylyl |
| P-117 | p-biphenylyl | H | H | H | p-biphenylyl | H | H |
| P-118 | p-biphenylyl | Ph | H | H | p-biphenylyl | H | H |
| P-119 | p-biphenylyl | H | H | Ph | p-biphenylyl | H | H |
| P-120 | p-biphenylyl | Ph | H | Ph | p-biphenylyl | H | H |
| P-121 | p-biphenylyl | H | Ph | H | p-biphenylyl | H | H |
| P-122 | p-biphenylyl | H | H | H | p-biphenylyl | Ph | H |
| P-123 | p-biphenylyl | H | H | H | p-biphenylyl | H | Ph |
| P-124 | p-biphenylyl | H | H | H | p-biphenylyl | Ph | Ph |
| P-125 | p-biphenylyl | H | H | H | p-biphenylyl | 1-naphthyl | H |
| P-126 | p-biphenylyl | H | H | H | p-biphenylyl | H | 1-naphthyl |
| P-127 | p-biphenylyl | H | H | H | p-biphenylyl | 1-naphthyl | 1-naphthyl |
| P-128 | p-biphenylyl | H | H | H | p-biphenylyl | 2-naphthyl | H |
| P-129 | p-biphenylyl | H | H | H | p-biphenylyl | H | 2-naphthyl |
| P-130 | p-biphenylyl | H | H | H | p-biphenylyl | 2-naphthyl | 2-naphthyl |
| P-131 | p-biphenylyl | H | H | H | p-biphenylyl | o-biphenylyl | H |
| P-132 | p-biphenylyl | H | H | H | p-biphenylyl | H | o-biphenylyl |
| P-133 | p-biphenylyl | H | H | H | p-biphenylyl | o-biphenylyl | o-biphenylyl |
| P-134 | p-biphenylyl | H | H | H | p-biphenylyl | m-biphenylyl | H |
| P-135 | p-biphenylyl | H | H | H | p-biphenylyl | H | m-biphenylyl |
| P-136 | p-biphenylyl | H | H | H | p-biphenylyl | m-biphenylyl | m-biphenylyl |
| P-137 | p-biphenylyl | H | H | H | p-biphenylyl | p-biphenylyl | H |
| P-138 | p-biphenylyl | H | H | H | p-biphenylyl | H | p-biphenylyl |
| P-139 | p-biphenylyl | H | H | H | p-biphenylyl | p-biphenylyl | p-biphenylyl |
| P-140 | o-tolyl | H | H | H | o-tolyl | H | H |
| P-141 | o-tolyl | Ph | H | Ph | o-tolyl | H | H |
| P-142 | o-tolyl | H | Ph | H | o-tolyl | H | H |
| P-143 | o-tolyl | H | H | H | o-tolyl | Ph | H |
| P-144 | o-tolyl | H | H | H | o-tolyl | H | Ph |
| P-145 | o-tolyl | H | H | H | o-tolyl | 1-naphthyl | H |
| P-146 | o-tolyl | H | H | H | o-tolyl | H | 1-naphthyl |
| P-147 | o-tolyl | H | H | H | o-tolyl | 2-naphthyl | H |
| P-148 | o-tolyl | H | H | H | o-tolyl | H | 2-naphthyl |
| P-149 | o-tolyl | H | H | H | o-tolyl | o-biphenylyl | H |
| P-150 | o-tolyl | H | H | H | o-tolyl | H | o-biphenylyl |
| P-151 | o-tolyl | H | H | H | o-tolyl | m-biphenylyl | H |
| P-152 | o-tolyl | H | H | H | o-tolyl | H | m-biphenylyl |
| P-153 | o-tolyl | H | H | H | o-tolyl | p-biphenylyl | H |
| P-154 | o-tolyl | H | H | H | o-tolyl | H | p-biphenylyl |
| P-155 | o-tolyl | H | H | H | o-tolyl | o-tolyl | H |
| P-156 | o-tolyl | H | H | H | o-tolyl | H | o-tolyl |
| P-157 | m-tolyl | H | H | H | m-tolyl | H | H |
| P-158 | m-tolyl | Ph | H | Ph | m-tolyl | H | H |
| P-159 | m-tolyl | H | Ph | H | m-tolyl | H | H |
| P-160 | m-tolyl | H | H | H | m-tolyl | Ph | H |
| P-161 | m-tolyl | H | H | H | m-tolyl | H | Ph |
| P-162 | m-tolyl | H | H | H | m-tolyl | 1-naphthyl | H |
| P-163 | m-tolyl | H | H | H | m-tolyl | H | 1-naphthyl |
| P-164 | m-tolyl | H | H | H | m-tolyl | 2-naphthyl | H |
| P-165 | m-tolyl | H | H | H | m-tolyl | H | 2-naphthyl |
| P-166 | m-tolyl | H | H | H | m-tolyl | o-biphenylyl | H |
| P-167 | m-tolyl | H | H | H | m-tolyl | H | o-biphenylyl |
| P-168 | m-tolyl | H | H | H | m-tolyl | m-biphenylyl | H |
| P-169 | m-tolyl | H | H | H | m-tolyl | H | m-biphenylyl |
| P-170 | m-tolyl | H | H | H | m-tolyl | p-biphenylyl | H |
| P-171 | m-tolyl | H | H | H | m-tolyl | H | p-biphenylyl |
| P-172 | m-tolyl | H | H | H | m-tolyl | m-tolyl | H |
| P-173 | m-tolyl | H | H | H | m-tolyl | H | m-tolyl |
| P-174 | p-tolyl | H | H | H | p-tolyl | H | H |
| P-175 | p-tolyl | Ph | H | Ph | p-tolyl | H | H |
| P-176 | p-tolyl | H | Ph | H | p-tolyl | H | H |
| P-177 | p-tolyl | H | H | H | p-tolyl | Ph | H |
| P-178 | p-tolyl | H | H | H | p-tolyl | H | Ph |
| P-179 | p-tolyl | H | H | H | p-tolyl | 1-naphthyl | H |
| P-180 | p-tolyl | H | H | H | p-tolyl | H | 1-naphthyl |
| P-181 | p-tolyl | H | H | H | p-tolyl | 2-naphthyl | H |
| P-182 | p-tolyl | H | H | H | p-tolyl | H | 2-naphthyl |
| P-183 | p-tolyl | H | H | H | p-tolyl | o-biphenylyl | H |
| P-184 | p-tolyl | H | H | H | p-tolyl | H | o-biphenylyl |
| P-185 | p-tolyl | H | H | H | p-tolyl | m-biphenylyl | H |
| P-186 | p-tolyl | H | H | H | p-tolyl | H | m-biphenylyl |
| P-187 | p-tolyl | H | H | H | p-tolyl | p-biphenylyl | H |
| P-188 | p-tolyl | H | H | H | p-tolyl | H | p-biphenylyl |
| P-189 | p-tolyl | H | H | H | p-tolyl | p-tolyl | H |
| P-190 | p-tolyl | H | H | H | p-tolyl | H | p-tolyl |
| P-191 | Ph | H | —CH3 | H | Ph | H | H |

-continued

| | | | | | | | |
|---|---|---|---|---|---|---|---|
| P-192 | 1-naphtyl | H | —CH3 | H | 1-naphtyl | H | H |
| P-193 | 2-naphthyl | H | —CH3 | H | 2-naphthyl | H | H |
| P-194 | o-biphenylyl | H | —CH3 | H | o-biphenylyl | H | H |
| P-195 | m-biphenylyl | H | —CH3 | H | m-biphenylyl | H | H |
| P-196 | p-biphenylyl | H | —CH3 | H | p-biphenylyl | H | H |
| P-197 | o-tolyl | H | —CH3 | H | o-tolyl | H | H |
| P-198 | m-tolyl | H | —CH3 | H | m-tolyl | H | H |
| P-199 | p-tolyl | H | —CH3 | H | p-tolyl | H | H |
| P-200 | Ph | H | H | H | Ph | —CH3 | H |
| P-201 | 1-naphtyl | H | H | H | 1-naphtyl | —CH3 | H |
| P-202 | 2-naphthyl | H | H | H | 2-naphthyl | —CH3 | H |
| P-203 | o-biphenylyl | H | H | H | o-biphenylyl | —CH3 | H |
| P-204 | m-biphenylyl | H | H | H | m-biphenylyl | —CH3 | H |
| P-205 | p-biphenylyl | H | H | H | p-biphenylyl | —CH3 | H |
| P-206 | o-tolyl | H | H | H | o-tolyl | —CH3 | H |
| P-207 | m-tolyl | H | H | H | m-tolyl | —CH3 | H |
| P-208 | p-tolyl | H | H | H | p-tolyl | —CH3 | H |
| P-209 | Ph | H | H | H | Ph | H | —CH3 |
| P-210 | 1-naphtyl | H | H | H | 1-naphtyl | H | —CH3 |
| P-211 | 2-naphthyl | H | H | H | 2-naphthyl | H | —CH3 |
| P-212 | o-biphenylyl | H | H | H | o-biphenylyl | H | —CH3 |
| P-213 | m-biphenylyl | H | H | H | m-biphenylyl | H | —CH3 |
| P-214 | p-biphenylyl | H | H | H | p-biphenylyl | H | —CH3 |
| P-215 | o-tolyl | H | H | H | o-tolyl | H | —CH3 |
| P-216 | m-tolyl | H | H | H | m-tolyl | H | —CH3 |
| P-217 | p-tolyl | H | H | H | p-tolyl | H | —CH3 |
| P-218 | Ph | H | H | H | Ph | —CH3 | —CH3 |
| P-219 | 1-naphtyl | H | H | H | 1-naphtyl | —CH3 | —CH3 |
| P-220 | 2-naphthyl | H | H | H | 2-naphthyl | —CH3 | —CH3 |
| P-221 | o-biphenylyl | H | H | H | o-biphenylyl | —CH3 | —CH3 |
| P-222 | m-biphenylyl | H | H | H | m-biphenylyl | —CH3 | —CH3 |
| P-223 | p-biphenylyl | H | H | H | p-biphenylyl | —CH3 | —CH3 |
| P-224 | o-tolyl | H | H | H | o-tolyl | —CH3 | —CH3 |
| P-225 | m-tolyl | H | H | H | m-tolyl | —CH3 | —CH3 |
| P-226 | p-tolyl | H | H | H | p-tolyl | —CH3 | —CH3 |
| P-227 | Ph | H | H | H | Ph | H | DPA |
| P-228 | 1-naphtyl | H | H | H | 1-naphtyl | H | DPA |
| P-229 | 2-naphthyl | H | H | H | 2-naphthyl | H | DPA |
| P-230 | o-biphenylyl | H | H | H | o-biphenylyl | H | DPA |
| P-231 | m-biphenylyl | H | H | H | m-biphenylyl | H | DPA |
| P-232 | p-biphenylyl | H | H | H | p-biphenylyl | H | DPA |
| P-233 | Ph | H | H | H | Ph | DPA | H |
| P-234 | 1-naphtyl | H | H | H | 1-naphtyl | DPA | H |
| P-235 | 2-naphthyl | H | H | H | 2-naphthyl | DPA | H |
| P-236 | o-biphenylyl | H | H | H | o-biphenylyl | DPA | H |
| P-237 | m-biphenylyl | H | H | H | m-biphenylyl | DPA | H |
| P-238 | p-biphenylyl | H | H | H | p-biphenylyl | DPA | H |
| P-239 | Ph | H | H | H | Ph | H | TPA |
| P-240 | 1-naphtyl | H | H | H | 1-naphtyl | H | TPA |
| P-241 | 2-naphthyl | H | H | H | 2-naphthyl | H | TPA |
| P-242 | o-biphenylyl | H | H | H | o-biphenylyl | H | TPA |
| P-243 | m-biphenylyl | H | H | H | m-biphenylyl | H | TPA |
| P-244 | p-biphenylyl | H | H | H | p-biphenylyl | H | TPA |
| P-245 | Ph | H | H | H | Ph | TPA | H |
| P-246 | 1-naphtyl | H | H | H | 1-naphtyl | TPA | H |
| P-247 | 2-naphthyl | H | H | H | 2-naphthyl | TPA | H |
| P-248 | o-biphenylyl | H | H | H | o-biphenylyl | TPA | H |
| P-249 | m-biphenylyl | H | H | H | m-biphenylyl | TPA | H |
| P-250 | p-biphenylyl | H | H | H | p-biphenylyl | TPA | H |
| P-251 | Ph | H | H | H | 1-naphthyl | H | H |
| P-252 | Ph | H | H | H | 2-naphthyl | H | H |
| P-253 | Ph | H | H | H | o-biphenylyl | H | H |
| P-254 | Ph | H | H | H | m-biphenylyl | H | H |
| P-255 | Ph | H | H | H | p-biphenylyl | H | H |
| P-256 | Ph | H | H | H | O-tolyly | H | H |
| P-257 | Ph | H | H | H | m-tolyl | H | H |
| P-258 | Ph | H | H | H | p-tolyl | H | H |
| P-259 | 1-naphthyl | H | H | H | 2-naphthyl | H | H |
| P-260 | 1-naphthyl | H | H | H | o-biphenylyl | H | H |
| P-261 | 1-naphthyl | H | H | H | m-biphenylyl | H | H |
| P-262 | 1-naphthyl | H | H | H | p-biphenylyl | H | H |
| P-263 | 1-naphthyl | H | H | H | O-tolyly | H | H |
| P-264 | 1-naphthyl | H | H | H | m-tolyl | H | H |
| P-265 | 1-naphthyl | H | H | H | p-tolyl | H | H |
| P-266 | 2-naphthyl | H | H | H | o-biphenylyl | H | H |
| P-267 | 2-naphthyl | H | H | H | m-biphenylyl | H | H |
| P-268 | 2-naphthyl | H | H | H | p-biphenylyl | H | H |
| P-269 | 2-naphthyl | H | H | H | O-tolyly | H | H |

-continued

| | | | | | | | |
|---|---|---|---|---|---|---|---|
| P-270 | 2-naphthyl | H | H | H | m-tolyl | H | H |
| P-271 | 2-naphthyl | H | H | H | p-tolyl | H | H |
| P-272 | o-biphenylyl | H | H | H | m-biphenylyl | H | H |
| P-273 | o-biphenylyl | H | H | H | p-biphenylyl | H | H |
| P-274 | o-biphenylyl | H | H | H | O-tolyly | H | H |
| P-275 | o-biphenylyl | H | H | H | m-tolyl | H | H |
| P-276 | o-biphenylyl | H | H | H | p-tolyl | H | H |
| P-277 | m-biphenylyl | H | H | H | p-biphenylyl | H | H |
| P-278 | m-biphenylyl | H | H | H | O-tolyly | H | H |
| P-279 | m-biphenylyl | H | H | H | m-tolyl | H | H |
| P-280 | m-biphenylyl | H | H | H | p-tolyl | H | H |
| P-281 | p-biphenylyl | H | H | H | O-tolyly | H | H |
| P-282 | p-biphenylyl | H | H | H | m-tolyl | H | H |
| P-283 | p-biphenylyl | H | H | H | p-tolyl | H | H |
| P-284 | O-tolyly | H | H | H | m-tolyl | H | H |
| P-285 | O-tolyly | H | H | H | p-tolyl | H | H |
| P-286 | m-tolyly | H | H | H | p-tolyl | H | H |

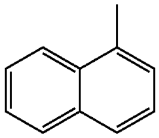

1-naphthyl

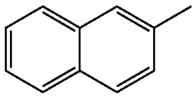

2-naphthyl

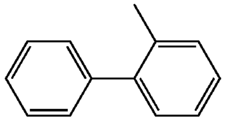

o-biphenylyl

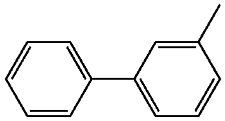

m-biphenylyl

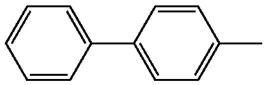

p-biphenylyl

-continued
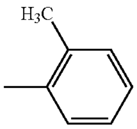
o-tolyl
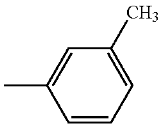
m-tolyl
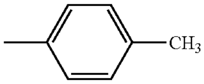
p-tolyl
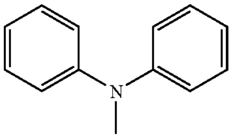
DPA
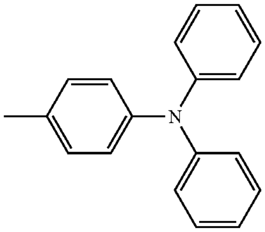
TPA

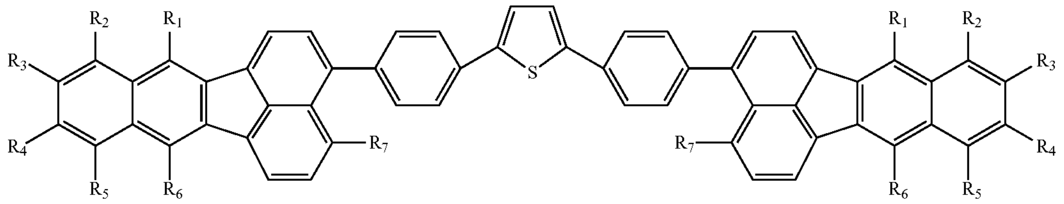
TypeQ
| | $R_1$ | $R_2$ | $R_3$ | $R_4$ | $R_5$ | $R_6$ | $R_7$ |
|---|---|---|---|---|---|---|---|
| Q-1 | H | H | H | H | H | H | H |
| Q-2 | Ph | H | H | H | H | Ph | H |
| Q-3 | Ph | Ph | H | H | Ph | Ph | H |
| Q-4 | Ph | H | Ph | Ph | H | Ph | H |
| Q-5 | Ph | H | Ph | H | H | Ph | H |
| Q-6 | Ph | H | H | H | H | Ph | Ph |
| Q-7 | Ph | Me | H | H | Me | Ph | H |
| Q-8 | Ph | H | Me | Me | H | Ph | H |
| Q-9 | Ph | H | H | H | H | Ph | Me |
| Q-10 | 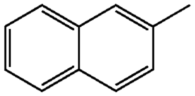 | H | H | H | H | 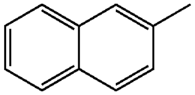 | H |
| Q-11 | 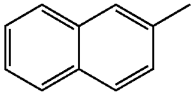 | Ph | H | H | Ph | 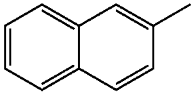 | H |
| Q-12 | 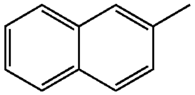 | H | Ph | Ph | H | 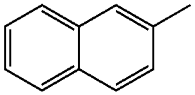 | H |
| Q-13 | 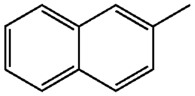 | H | Ph | H | H | 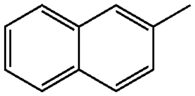 | H |
| Q-14 | 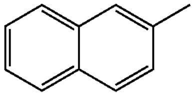 | H | H | H | H | 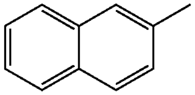 | Ph |

-continued
| | | | | | | | |
|---|---|---|---|---|---|---|---|
| Q-15 | 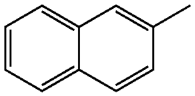 | Me | H | H | Me | 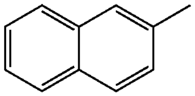 | H |
| Q-16 | 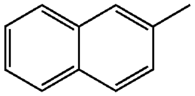 | H | Me | Me | H | 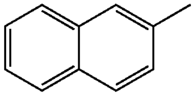 | H |
| Q-17 | 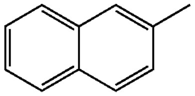 | H | H | H | H | 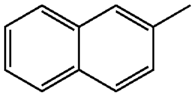 | Me |
| Q-18 | 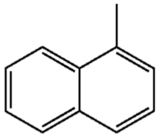 | H | H | H | H | 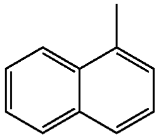 | H |
| Q-19 | 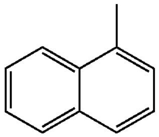 | Ph | H | H | Ph | 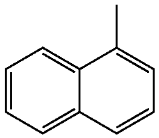 | H |
| Q-20 | 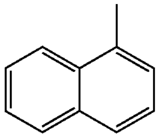 | H | Ph | Ph | H | 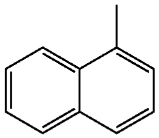 | H |
| Q-21 | 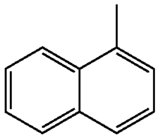 | H | Ph | H | H | 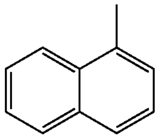 | H |

-continued
| | | | | | | | |
|---|---|---|---|---|---|---|---|
| Q-22 | 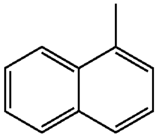 | H | H | H | H | 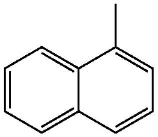 | Ph |
| Q-23 | 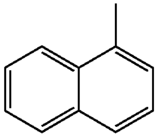 | Me | H | H | Me | 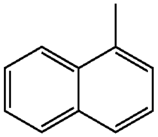 | H |
| Q-24 | 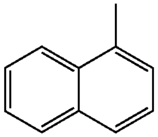 | H | Me | Me | H | 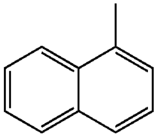 | H |
| Q-25 | 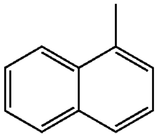 | H | H | H | H | 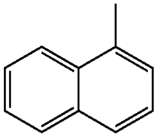 | Me |
| Q-26 | 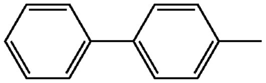 | H | H | H | H | 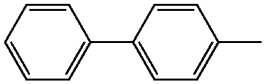 | H |
| Q-27 | 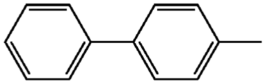 | Ph | H | H | Ph | 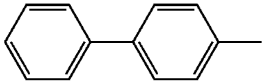 | H |
| Q-28 | 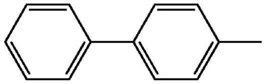 | H | Ph | Ph | H | 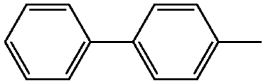 | H |
| Q-29 | 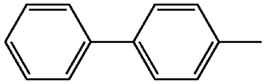 | H | Ph | H | H | 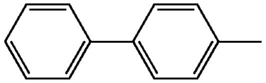 | H |

-continued
| | | | | | | | |
|---|---|---|---|---|---|---|---|
| Q-30 | 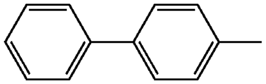 | H | H | H | H | 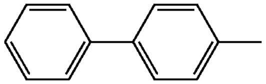 | Ph |
| Q-31 | 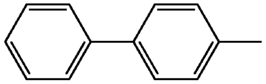 | Me | H | H | Me | 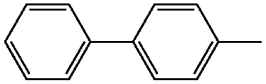 | H |
| Q-32 | 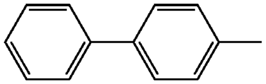 | H | Me | Me | H | 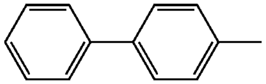 | H |
| Q-33 | 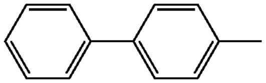 | H | H | H | H | 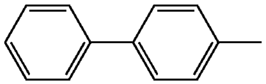 | Me |
| Q-34 | 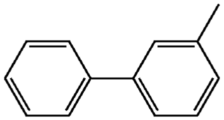 | H | H | H | H | 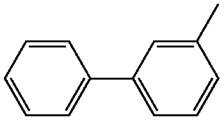 | H |
| Q-35 | 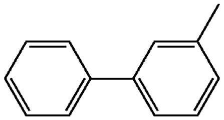 | Ph | H | H | Ph | 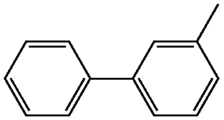 | H |
| Q-36 | 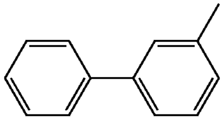 | H | Ph | Ph | H | 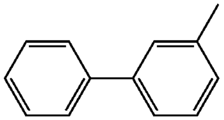 | H |
| Q-37 | 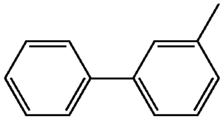 | H | Ph | H | H | 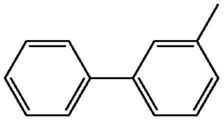 | H |
| Q-38 | 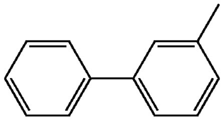 | H | H | H | H | 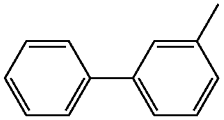 | Ph |

-continued
| | | | | | | | |
|---|---|---|---|---|---|---|---|
| Q-39 | 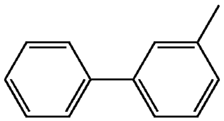 | Me | H | H | Me | 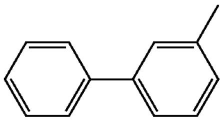 | H |
| Q-40 | 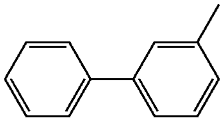 | H | Me | Me | H | 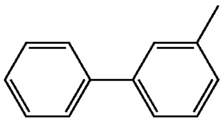 | H |
| Q-41 | 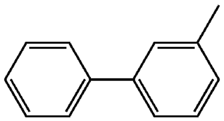 | H | H | H | H | 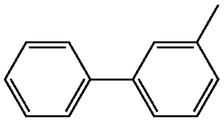 | Me |
| Q-42 | 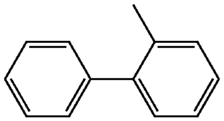 | H | H | H | H | 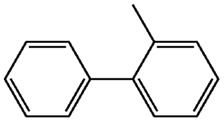 | H |
| Q-43 | 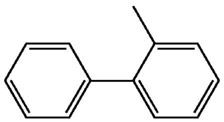 | Ph | H | H | Ph | 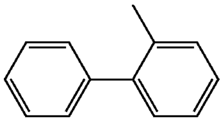 | H |
| Q-44 | 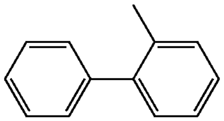 | H | Ph | Ph | H | 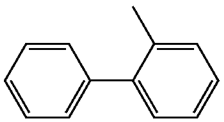 | H |
| Q-45 | 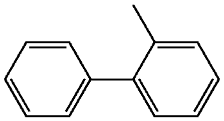 | H | Ph | H | H | 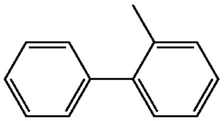 | H |

-continued
| | | | | | | | |
|---|---|---|---|---|---|---|---|
| Q-46 | 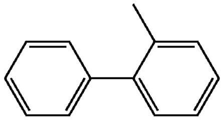 | H | H | H | H | 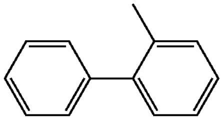 | Ph |
| Q-47 | 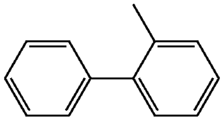 | Me | H | H | Me | 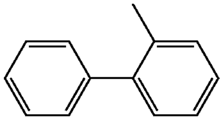 | H |
| Q-48 | 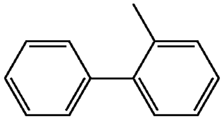 | H | Me | Me | H | 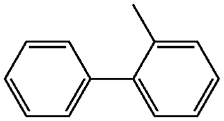 | H |
| Q-49 | 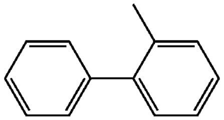 | H | H | H | H | 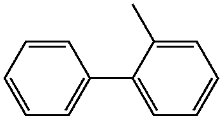 | Me |
| Q-50 | Ph | H | H | H | H | 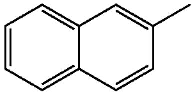 | H |
| Q-51 | Ph | H | H | H | H | 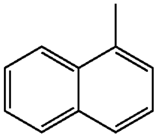 | H |
| Q-52 | Ph | H | H | H | H | 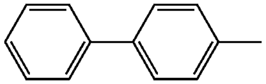 | H |
| Q-53 | Ph | H | H | H | H | 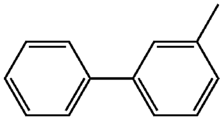 | H |

-continued
| | | | | | | | |
|---|---|---|---|---|---|---|---|
| Q-54 | Ph | H | H | H | H | 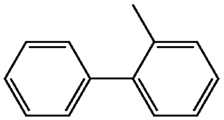 | H |
| Q-55 | 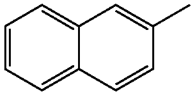 | H | H | H | H | 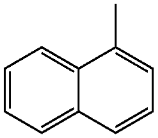 | H |
| Q-56 | 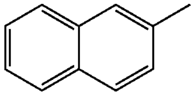 | H | H | H | H | 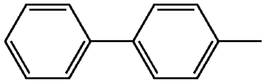 | H |
| Q-57 | 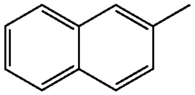 | H | H | H | H | 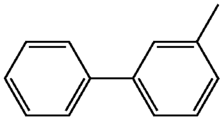 | H |
| Q-58 | 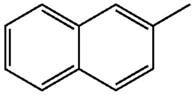 | H | H | H | H | 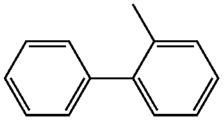 | H |
| Q-59 | 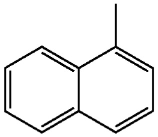 | H | H | H | H | 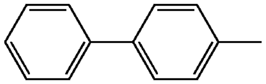 | H |
| Q-60 | 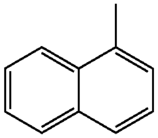 | H | H | H | H | 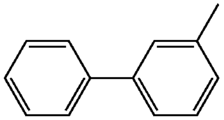 | H |

-continued
| | | | | | | | |
|---|---|---|---|---|---|---|---|
| Q-61 | 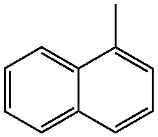 | H | H | H | H | 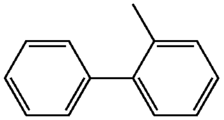 | H |
| Q-62 | 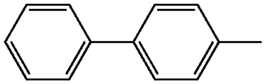 | H | H | H | H | 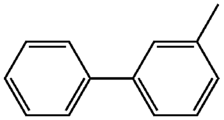 | H |
| Q-63 | 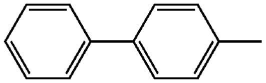 | H | H | H | H | 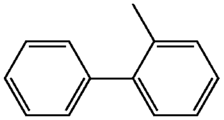 | H |
| Q-64 | 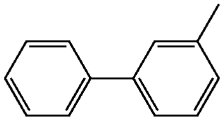 | H | H | H | H | 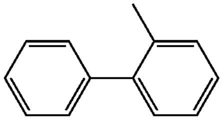 | H |
| Q-65 | H | Ph | H | H | Ph | H | H |
| Q-66 | H | 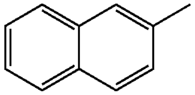 | H | H | 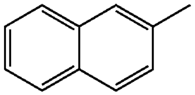 | H | H |
| Q-67 | H | 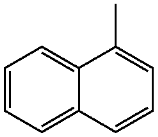 | H | H | 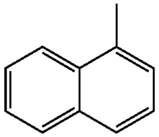 | H | H |
| Q-68 | H | 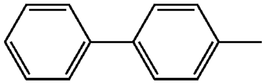 | H | H | 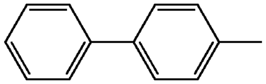 | H | H |

-continued
| | | | | | | | |
|---|---|---|---|---|---|---|---|
| Q-69 | H | 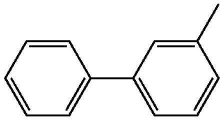 | H | H | 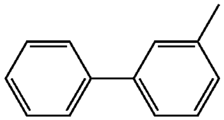 | H | H |
| Q-70 | H | 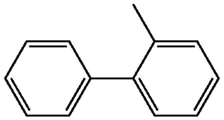 | H | H | 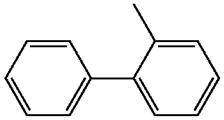 | H | H |
| Q-71 | H | H | 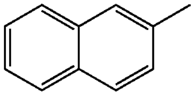 | 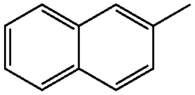 | H | H | H |
| Q-72 | H | H | 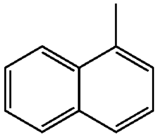 | 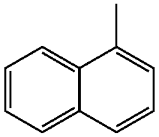 | H | H | H |
| Q-73 | H | H | 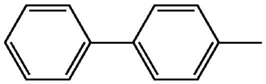 | 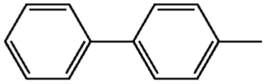 | H | H | H |
| Q-74 | H | H | 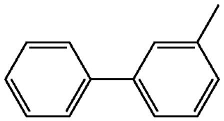 | 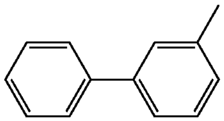 | H | H | H |
| Q-75 | H | H | 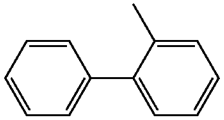 | 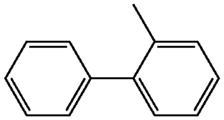 | H | H | H |
| Q-76 | 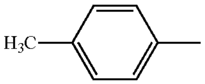 | H | H | H | H | 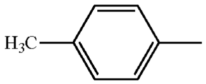 | H |

-continued
| | | | | | | | |
|---|---|---|---|---|---|---|---|
| Q-77 | 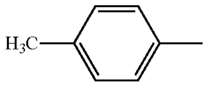 | Ph | H | H | Ph | 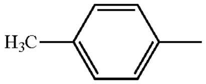 | H |
| Q-78 | 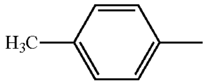 | H | Ph | Ph | H | 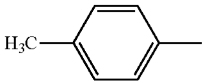 | H |
| Q-79 | 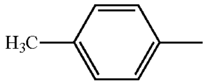 | H | Ph | H | H | 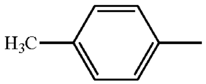 | H |
| Q-80 | 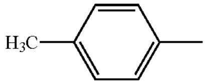 | H | H | H | H | 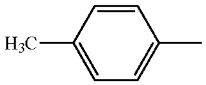 | Ph |
| Q-81 | 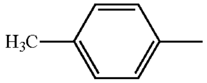 | Me | H | H | Me | 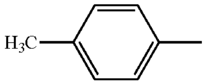 | H |
| Q-82 | 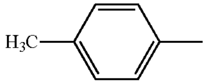 | H | Me | Me | H | 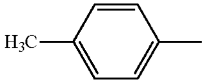 | H |
| Q-83 | 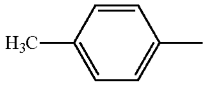 | H | H | H | H | 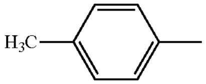 | Me |
| Q-84 | 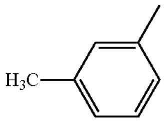 | H | H | H | H | 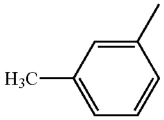 | H |
| Q-85 | 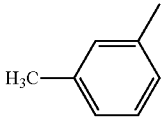 | Ph | H | H | Ph | 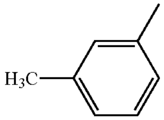 | H |

-continued
| | | | | | | | |
|---|---|---|---|---|---|---|---|
| Q-86 | 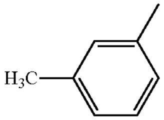 | H | Ph | Ph | H | 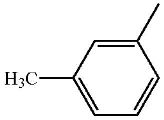 | H |
| Q-87 | 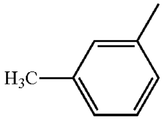 | H | Ph | H | H | 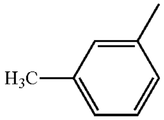 | H |
| Q-88 | 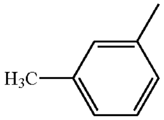 | H | H | H | H | 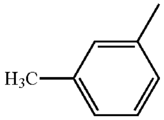 | Ph |
| Q-89 | 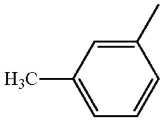 | Me | H | H | Me | 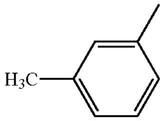 | H |
| Q-90 | 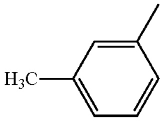 | H | Me | Me | H | 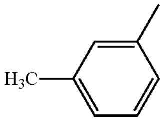 | H |
| Q-91 | 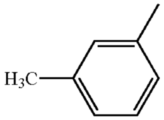 | H | H | H | H | 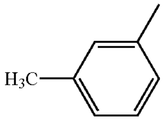 | Me |
| Q-92 | 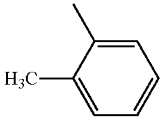 | H | H | H | H | 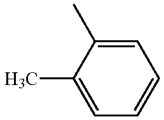 | H |
| Q-93 | 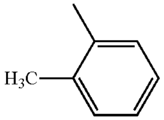 | Ph | H | H | Ph | 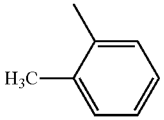 | H |

-continued
| | | | | | | | |
|---|---|---|---|---|---|---|---|
| Q-94 | 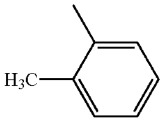 | H | Ph | Ph | H | 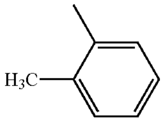 | H |
| Q-96 | 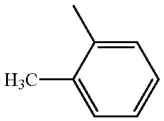 | H | Ph | H | H | 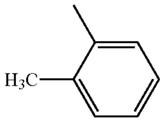 | H |
| Q-96 | 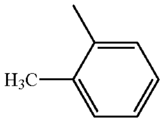 | H | H | H | H | 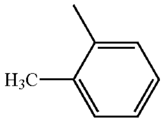 | Ph |
| Q-97 | 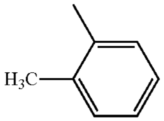 | Me | H | H | Me | 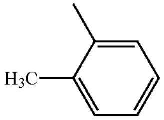 | H |
| Q-98 | 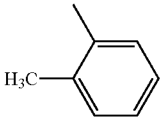 | H | Me | Me | H | 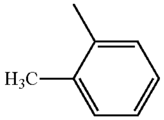 | H |
| Q-99 | 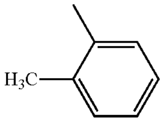 | H | H | H | H | 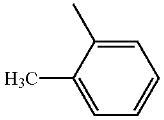 | Me |
| 100 | 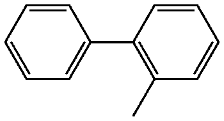 | H | H | H | H | 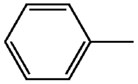 | H |

-continued
| | | | | | | | |
|---|---|---|---|---|---|---|---|
| 101 | 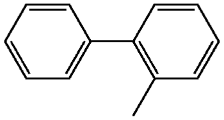 | Ph | H | H | Ph | 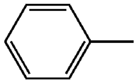 | H |
| 102 | 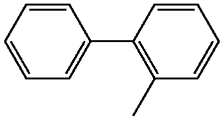 | H | Ph | Ph | H | 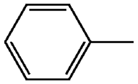 | H |
| 103 | 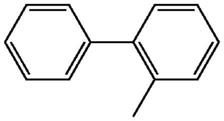 | H | Ph | H | H | 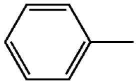 | H |
| 104 | 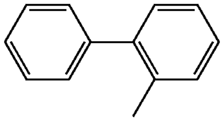 | H | H | H | H | 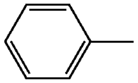 | Ph |
| 105 | 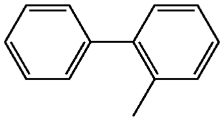 | Me | H | H | Me | 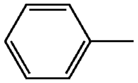 | H |
| 106 | 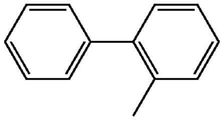 | H | Me | Me | H | 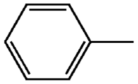 | H |
| 107 | 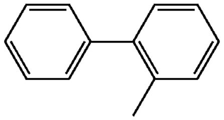 | H | H | H | H | 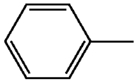 | Me |
| 108 | 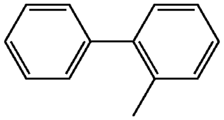 | H | H | H | H | 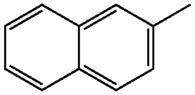 | H |

-continued
| | | | | | | | |
|---|---|---|---|---|---|---|---|
| 109 | 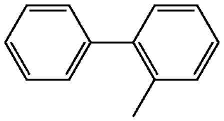 | Ph | H | H | Ph | 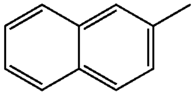 | H |
| 110 | 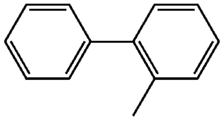 | H | Ph | Ph | H | 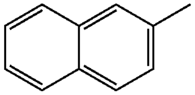 | H |
| 111 | 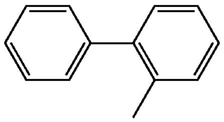 | H | Ph | H | H | 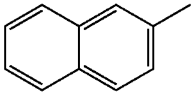 | H |
| 112 | 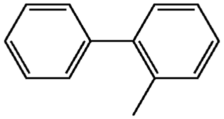 | H | H | H | H | 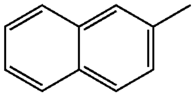 | Ph |
| 113 | 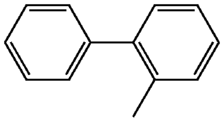 | Me | H | H | Me | 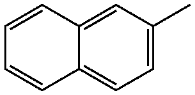 | H |
| 114 | 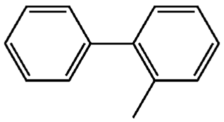 | H | Me | Me | H | 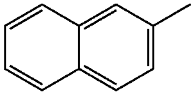 | H |
| 115 | 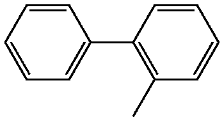 | H | H | H | H | 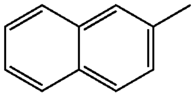 | Me |

-continued
| | | | | | | | |
|---|---|---|---|---|---|---|---|
| 116 | 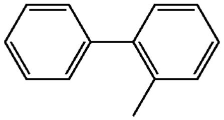 | H | H | H | H | 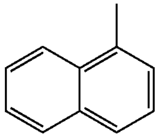 | H |
| 117 | 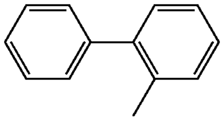 | Ph | H | H | Ph | 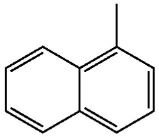 | H |
| 118 | 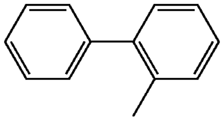 | H | Ph | Ph | H | 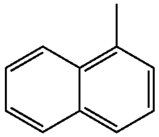 | H |
| 119 | 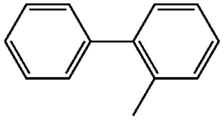 | H | Ph | H | H | 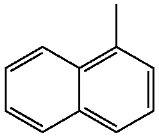 | H |
| 120 | 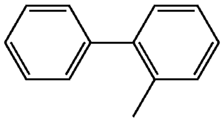 | H | H | H | H | 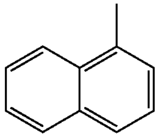 | Ph |
| 121 | 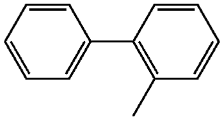 | Me | H | H | Me | 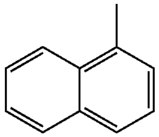 | H |
| 122 | 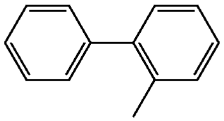 | H | Me | Me | H | 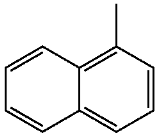 | H |

-continued
| | | | | | | | |
|---|---|---|---|---|---|---|---|
| 123 | 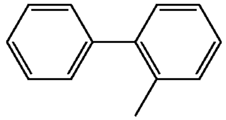 | H | H | H | H | 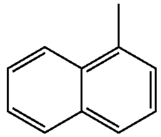 | Me |
| 124 | 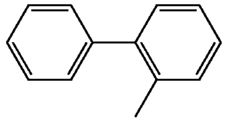 | H | H | H | H | 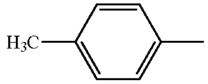 | H |
| 125 | 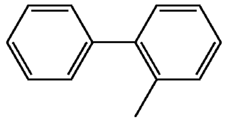 | Ph | H | H | Ph | 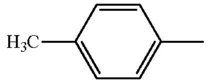 | H |
| 126 | 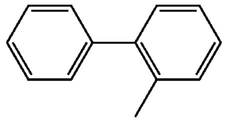 | H | Ph | Ph | H | 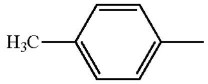 | H |
| 127 | 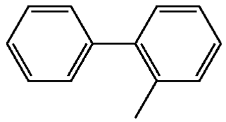 | H | Ph | H | H | 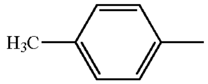 | H |
| 128 | 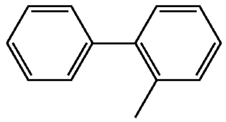 | H | H | H | H | 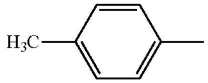 | Ph |
| 129 | 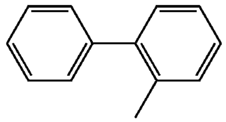 | Me | H | H | Me | 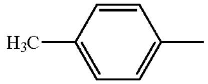 | H |

-continued
| | | | | | | | |
|---|---|---|---|---|---|---|---|
| 130 | 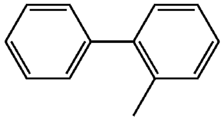 | H | Me | Me | H | 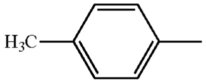 | H |
| 131 | 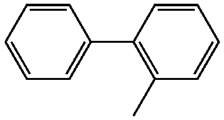 | H | H | H | H | 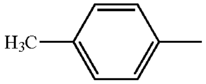 | Me |
| 132 | 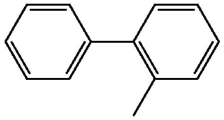 | H | H | H | H | 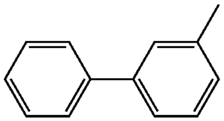 | H |
| 133 | 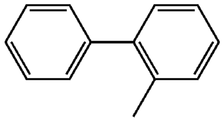 | Ph | H | H | Ph | 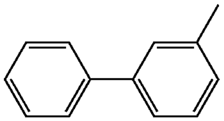 | H |
| 134 | 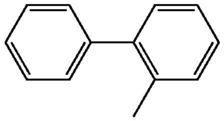 | H | Ph | Ph | H | 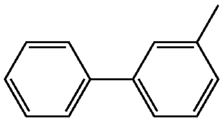 | H |
| 135 | 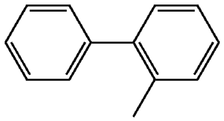 | H | Ph | H | H | 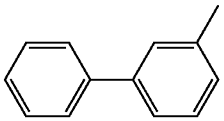 | H |
| 136 | 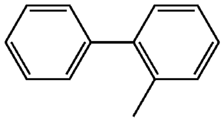 | H | H | H | H | 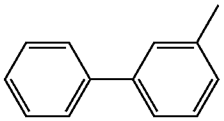 | Ph |
| 137 | 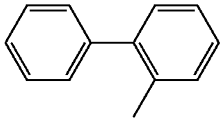 | Me | H | H | Me | 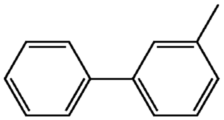 | H |

-continued
| | | | | | | | |
|---|---|---|---|---|---|---|---|
| 138 | 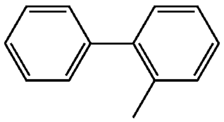 | H | Me | Me | H | 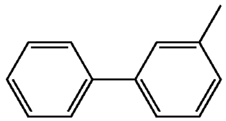 | H |
| 139 | 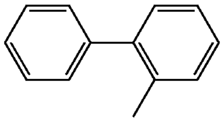 | H | H | H | H | 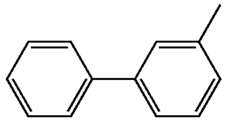 | Me |
| 140 | 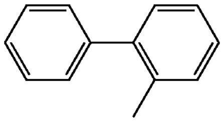 | H | H | H | H | 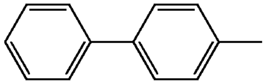 | H |
| 141 | 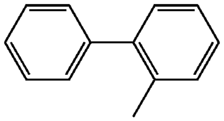 | Ph | H | H | Ph | 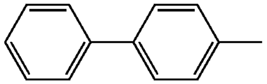 | H |
| 142 | 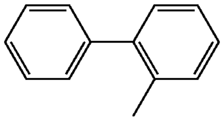 | H | Ph | Ph | H | 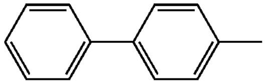 | H |

-continued
| | | | | | | | |
|---|---|---|---|---|---|---|---|
| 143 | 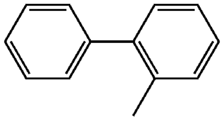 | H | Ph | H | H | 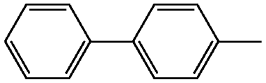 | H |
| 144 | 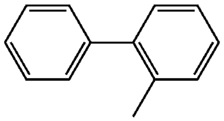 | H | H | H | H | 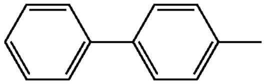 | Ph |
| 145 | 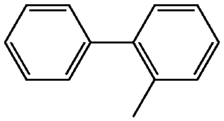 | Me | H | H | Me | 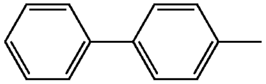 | H |
| 146 | 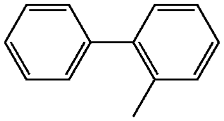 | H | Me | Me | H | 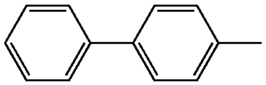 | H |
| 147 | 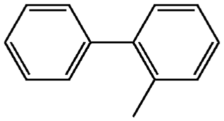 | H | H | H | H | 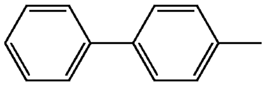 | Me |

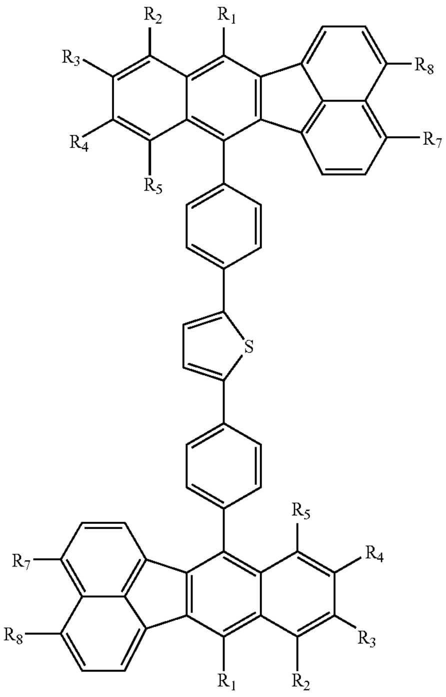

TypeR

| | $R_1$ | $R_2$ | $R_3$ | $R_4$ | $R_5$ | $R_7$ | $R_8$ |
|---|---|---|---|---|---|---|---|
| R-1 | H | H | H | H | H | H | H |
| R-2 | Ph | H | H | H | H | H | H |
| R-3 | Ph | Ph | H | H | Ph | H | H |
| R-4 | Ph | H | Ph | Ph | H | H | H |
| R-5 | Ph | H | Ph | H | H | H | H |
| R-6 | Ph | H | H | Ph | H | H | H |
| R-7 | Ph | H | H | H | H | Ph | H |
| R-8 | Ph | H | H | H | H | H | Ph |
| R-9 | Ph | H | H | H | H | Ph | Ph |
| R-10 | Ph | H | H | H | H | 1-naphthyl | H |
| R-11 | Ph | H | H | H | H | H | 1-naphthyl |
| R-12 | Ph | H | H | H | H | 1-naphthyl | 1-naphthyl |
| R-13 | Ph | H | H | H | H | 2-naphthyl | H |
| R-14 | Ph | H | H | H | H | H | 2-naphthyl |
| R-15 | Ph | H | H | H | H | 2-naphthyl | 2-naphthyl |
| R-16 | Ph | H | H | H | H | o-biphenylyl | H |
| R-17 | Ph | H | H | H | H | H | o-biphenylyl |
| R-18 | Ph | H | H | H | H | o-biphenylyl | o-biphenylyl |
| R-19 | Ph | H | H | H | H | m-biphenylyl | H |
| R-20 | Ph | H | H | H | H | H | m-biphenylyl |
| R-21 | Ph | H | H | H | H | m-biphenylyl | m-biphenylyl |
| R-22 | Ph | H | H | H | H | p-biphenylyl | H |
| R-23 | Ph | H | H | H | H | H | p-biphenylyl |
| R-24 | Ph | H | H | H | H | p-biphenylyl | p-biphenylyl |
| R-25 | 1-naphthyl | H | H | H | H | H | H |
| R-26 | 1-naphthyl | Ph | H | H | Ph | H | H |
| R-27 | 1-naphthyl | H | Ph | Ph | H | H | H |
| R-28 | 1-naphthyl | H | Ph | H | H | H | H |
| R-29 | 1-naphthyl | H | H | Ph | H | H | H |
| R-30 | 1-naphthyl | H | H | H | H | Ph | H |
| R-31 | 1-naphthyl | H | H | H | H | H | Ph |
| R-32 | 1-naphthyl | H | H | H | H | Ph | Ph |
| R-33 | 1-naphthyl | H | H | H | H | 1-naphthyl | H |
| R-34 | 1-naphthyl | H | H | H | H | H | 1-naphthyl |
| R-35 | 1-naphthyl | H | H | H | H | 1-naphthyl | 1-naphthyl |
| R-36 | 1-naphthyl | H | H | H | H | 2-naphthyl | H |
| R-37 | 1-naphthyl | H | H | H | H | H | 2-naphthyl |
| R-38 | 1-naphthyl | H | H | H | H | 2-naphthyl | 2-naphthyl |
| R-39 | 1-naphthyl | H | H | H | H | o-biphenylyl | H |
| R-40 | 1-naphthyl | H | H | H | H | H | o-biphenylyl |

-continued

| | | | | | | | |
|---|---|---|---|---|---|---|---|
| R-41 | 1-naphthyl | H | H | H | H | o-biphenylyl | o-biphenylyl |
| R-42 | 1-naphthyl | H | H | H | H | m-biphenylyl | H |
| R-43 | 1-naphthyl | H | H | H | H | H | m-biphenylyl |
| R-44 | 1-naphthyl | H | H | H | H | m-biphenylyl | m-biphenylyl |
| R-45 | 1-naphthyl | H | H | H | H | p-biphenylyl | H |
| R-46 | 1-naphthyl | H | H | H | H | H | p-biphenylyl |
| R-47 | 1-naphthyl | H | H | H | H | p-biphenylyl | p-biphenylyl |
| R-48 | 2-naphthyl | H | H | H | H | H | H |
| R-49 | 2-naphthyl | Ph | H | H | Ph | H | H |
| R-50 | 2-naphthyl | H | Ph | Ph | H | H | H |
| R-51 | 2-naphthyl | H | Ph | H | H | H | H |
| R-52 | 2-naphthyl | H | H | Ph | H | H | H |
| R-53 | 2-naphthyl | H | H | H | H | Ph | H |
| R-54 | 2-naphthyl | H | H | H | H | H | Ph |
| R-55 | 2-naphthyl | H | H | H | H | Ph | Ph |
| R-56 | 2-naphthyl | H | H | H | H | 1-naphthyl | H |
| R-57 | 2-naphthyl | H | H | H | H | H | 1-naphthyl |
| R-58 | 2-naphthyl | H | H | H | H | 1-naphthyl | 1-naphthyl |
| R-59 | 2-naphthyl | H | H | H | H | 2-naphthyl | H |
| R-60 | 2-naphthyl | H | H | H | H | H | 2-naphthyl |
| R-61 | 2-naphthyl | H | H | H | H | 2-naphthyl | 2-naphthyl |
| R-62 | 2-naphthyl | H | H | H | H | o-biphenylyl | H |
| R-63 | 2-naphthyl | H | H | H | H | H | o-biphenylyl |
| R-64 | 2-naphthyl | H | H | H | H | o-biphenylyl | o-biphenylyl |
| R-65 | 2-naphthyl | H | H | H | H | m-biphenylyl | H |
| R-66 | 2-naphthyl | H | H | H | H | H | m-biphenylyl |
| R-67 | 2-naphthyl | H | H | H | H | m-biphenylyl | m-biphenylyl |
| R-68 | 2-naphthyl | H | H | H | H | p-biphenylyl | H |
| R-69 | 2-naphthyl | H | H | H | H | H | p-biphenylyl |
| R-70 | 2-naphthyl | H | H | H | H | p-biphenylyl | p-biphenylyl |
| R-71 | o-biphenylyl | H | H | H | H | H | H |
| R-72 | o-biphenylyl | Ph | H | H | Ph | H | H |
| R-73 | o-biphenylyl | H | Ph | Ph | H | H | H |
| R-74 | o-biphenylyl | H | Ph | H | H | H | H |
| R-75 | o-biphenylyl | H | H | Ph | H | H | H |
| R-76 | o-biphenylyl | H | H | H | H | Ph | H |
| R-77 | o-biphenylyl | H | H | H | H | H | Ph |
| R-78 | o-biphenylyl | H | H | H | H | Ph | Ph |
| R-79 | o-biphenylyl | H | H | H | H | 1-naphthyl | H |
| R-80 | o-biphenylyl | H | H | H | H | H | 1-naphthyl |
| R-81 | o-biphenylyl | H | H | H | H | 1-naphthyl | 1-naphthyl |
| R-82 | o-biphenylyl | H | H | H | H | 2-naphthyl | H |
| R-83 | o-biphenylyl | H | H | H | H | H | 2-naphthyl |
| R-84 | o-biphenylyl | H | H | H | H | 2-naphthyl | 2-naphthyl |
| R-85 | o-biphenylyl | H | H | H | H | o-biphenylyl | H |
| R-86 | o-biphenylyl | H | H | H | H | H | o-biphenylyl |
| R-87 | o-biphenylyl | H | H | H | H | o-biphenylyl | o-biphenylyl |
| R-88 | o-biphenylyl | H | H | H | H | m-biphenylyl | H |
| R-89 | o-biphenylyl | H | H | H | H | H | m-biphenylyl |
| R-90 | o-biphenylyl | H | H | H | H | m-biphenylyl | m-biphenylyl |
| R-91 | o-biphenylyl | H | H | H | H | p-biphenylyl | H |
| R-92 | o-biphenylyl | H | H | H | H | H | p-biphenylyl |
| R-93 | o-biphenylyl | H | H | H | H | p-biphenylyl | p-biphenylyl |
| R-94 | m-biphenylyl | H | H | H | H | H | H |
| R-95 | m-biphenylyl | Ph | H | H | Ph | H | H |
| R-96 | m-biphenylyl | H | Ph | Ph | H | H | H |
| R-97 | m-biphenylyl | H | Ph | H | H | H | H |
| R-98 | m-biphenylyl | H | H | Ph | H | H | H |
| R-99 | m-biphenylyl | H | H | H | H | Ph | H |
| R-100 | m-biphenylyl | H | H | H | H | H | Ph |
| R-101 | m-biphenylyl | H | H | H | H | Ph | Ph |
| R-102 | m-biphenylyl | H | H | H | H | 1-naphthyl | H |
| R-103 | m-biphenylyl | H | H | H | H | H | 1-naphthyl |
| R-104 | m-biphenylyl | H | H | H | H | 1-naphthyl | 1-naphthyl |
| R-105 | m-biphenylyl | H | H | H | H | 2-naphthyl | H |
| R-106 | m-biphenylyl | H | H | H | H | H | 2-naphthyl |
| R-107 | m-biphenylyl | H | H | H | H | 2-naphthyl | 2-naphthyl |
| R-108 | m-biphenylyl | H | H | H | H | o-biphenylyl | H |
| R-109 | m-biphenylyl | H | H | H | H | H | o-biphenylyl |
| R-110 | m-biphenylyl | H | H | H | H | o-biphenylyl | o-biphenylyl |
| R-111 | m-biphenylyl | H | H | H | H | m-biphenylyl | H |
| R-112 | m-biphenylyl | H | H | H | H | H | m-biphenylyl |
| R-113 | m-biphenylyl | H | H | H | H | m-biphenylyl | m-biphenylyl |
| R-114 | m-biphenylyl | H | H | H | H | p-biphenylyl | H |
| R-115 | m-biphenylyl | H | H | H | H | H | p-biphenylyl |
| R-116 | m-biphenylyl | H | H | H | H | p-biphenylyl | p-biphenylyl |
| R-117 | p-biphenylyl | H | H | H | H | H | H |
| R-118 | p-biphenylyl | Ph | H | H | Ph | H | H |
| R-119 | p-biphenylyl | H | Ph | Ph | H | H | H |

-continued

| | | | | | | | |
|---|---|---|---|---|---|---|---|
| R-120 | p-biphenylyl | H | Ph | H | H | H | H |
| R-121 | p-biphenylyl | H | H | Ph | H | H | H |
| R-122 | p-biphenylyl | H | H | H | H | Ph | H |
| R-123 | p-biphenylyl | H | H | H | H | H | Ph |
| R-124 | p-biphenylyl | H | H | H | H | Ph | Ph |
| R-125 | p-biphenylyl | H | H | H | H | 1-naphthyl | H |
| R-126 | p-biphenylyl | H | H | H | H | H | 1-naphthyl |
| R-127 | p-biphenylyl | H | H | H | H | 1-naphthyl | 1-naphthyl |
| R-128 | p-biphenylyl | H | H | H | H | 2-naphthyl | H |
| R-129 | p-biphenylyl | H | H | H | H | H | 2-naphthyl |
| R-130 | p-biphenylyl | H | H | H | H | 2-naphthyl | 2-naphthyl |
| R-131 | p-biphenylyl | H | H | H | H | o-biphenylyl | H |
| R-132 | p-biphenylyl | H | H | H | H | H | o-biphenylyl |
| R-133 | p-biphenylyl | H | H | H | H | o-biphenylyl | o-biphenylyl |
| R-134 | p-biphenylyl | H | H | H | H | m-biphenylyl | H |
| R-135 | p-biphenylyl | H | H | H | H | H | m-biphenylyl |
| R-136 | p-biphenylyl | H | H | H | H | m-biphenylyl | m-biphenylyl |
| R-137 | p-biphenylyl | H | H | H | H | p-biphenylyl | H |
| R-138 | p-biphenylyl | H | H | H | H | H | p-biphenylyl |
| R-139 | p-biphenylyl | H | H | H | H | p-biphenylyl | p-biphenylyl |
| R-140 | o-tolyl | H | H | H | H | H | H |
| R-141 | o-tolyl | Ph | H | H | Ph | H | H |
| R-142 | o-tolyl | H | Ph | Ph | H | H | H |
| R-143 | o-tolyl | H | H | H | H | Ph | H |
| R-144 | o-tolyl | H | H | H | H | H | Ph |
| R-145 | o-tolyl | H | H | H | H | 1-naphthyl | H |
| R-146 | o-tolyl | H | H | H | H | H | 1-naphthyl |
| R-147 | o-tolyl | H | H | H | H | 2-naphthyl | H |
| R-148 | o-tolyl | H | H | H | H | H | 2-naphthyl |
| R-149 | o-tolyl | H | H | H | H | o-biphenylyl | H |
| R-150 | o-tolyl | H | H | H | H | H | o-biphenylyl |
| R-151 | o-tolyl | H | H | H | H | m-biphenylyl | H |
| R-152 | o-tolyl | H | H | H | H | H | m-biphenylyl |
| R-153 | o-tolyl | H | H | H | H | p-biphenylyl | H |
| R-154 | o-tolyl | H | H | H | H | H | p-biphenylyl |
| R-155 | o-tolyl | H | H | H | H | o-tolyl | H |
| R-156 | o-tolyl | H | H | H | H | H | o-tolyl |
| R-157 | m-tolyl | H | H | H | H | H | H |
| R-158 | m-tolyl | Ph | H | H | Ph | H | H |
| R-159 | m-tolyl | H | Ph | Ph | H | H | H |
| R-160 | m-tolyl | H | H | H | H | Ph | H |
| R-161 | m-tolyl | H | H | H | H | H | Ph |
| R-162 | m-tolyl | H | H | H | H | 1-naphthyl | H |
| R-163 | m-tolyl | H | H | H | H | H | 1-naphthyl |
| R-164 | m-tolyl | H | H | H | H | 2-naphthyl | H |
| R-165 | m-tolyl | H | H | H | H | H | 2-naphthyl |
| R-166 | m-tolyl | H | H | H | H | o-biphenylyl | H |
| R-167 | m-tolyl | H | H | H | H | H | o-biphenylyl |
| R-168 | m-tolyl | H | H | H | H | m-biphenylyl | H |
| R-169 | m-tolyl | H | H | H | H | H | m-biphenylyl |
| R-170 | m-tolyl | H | H | H | H | p-biphenylyl | H |
| R-171 | m-tolyl | H | H | H | H | H | p-biphenylyl |
| R-172 | m-tolyl | H | H | H | H | m-tolyl | H |
| R-173 | m-tolyl | H | H | H | H | H | m-tolyl |
| R-174 | p-tolyl | H | H | H | H | H | H |
| R-175 | p-tolyl | Ph | H | H | Ph | H | H |
| R-176 | p-tolyl | H | Ph | Ph | H | H | H |
| R-177 | p-tolyl | H | H | H | H | Ph | H |
| R-178 | p-tolyl | H | H | H | H | H | Ph |
| R-179 | p-tolyl | H | H | H | H | 1-naphthyl | H |
| R-180 | p-tolyl | H | H | H | H | H | 1-naphthyl |
| R-181 | p-tolyl | H | H | H | H | 2-naphthyl | H |
| R-182 | p-tolyl | H | H | H | H | H | 2-naphthyl |
| R-183 | p-tolyl | H | H | H | H | o-biphenylyl | H |
| R-184 | p-tolyl | H | H | H | H | H | o-biphenylyl |
| R-185 | p-tolyl | H | H | H | H | m-biphenylyl | H |
| R-186 | p-tolyl | H | H | H | H | H | m-biphenylyl |
| R-187 | p-tolyl | H | H | H | H | p-biphenylyl | H |
| R-188 | p-tolyl | H | H | H | H | H | p-biphenylyl |
| R-189 | p-tolyl | H | H | H | H | p-tolyl | H |
| R-190 | p-tolyl | H | H | H | H | H | p-tolyl |
| R-191 | Ph | H | —CH3 | —CH3 | H | H | H |
| R-192 | 1-naphtyl | H | —CH3 | —CH3 | H | H | H |
| R-193 | 2-naphthyl | H | —CH3 | —CH3 | H | H | H |
| R-194 | o-biphenylyl | H | —CH3 | —CH3 | H | H | H |
| R-195 | m-biphenylyl | H | —CH3 | —CH3 | H | H | H |
| R-196 | p-biphenylyl | H | —CH3 | —CH3 | H | H | H |
| R-197 | o-tolyl | H | —CH3 | —CH3 | H | H | H |
| R-198 | m-tolyl | H | —CH3 | —CH3 | H | H | H |

-continued

| | | | | | | | |
|---|---|---|---|---|---|---|---|
| R-199 | p-tolyl | H | —CH3 | —CH3 | H | H | H |
| R-200 | Ph | H | H | H | H | —CH3 | H |
| R-201 | 1-naphtyl | H | H | H | H | —CH3 | H |
| R-202 | 2-naphthyl | H | H | H | H | —CH3 | H |
| R-203 | o-biphenylyl | H | H | H | H | —CH3 | H |
| R-204 | m-biphenylyl | H | H | H | H | —CH3 | H |
| R-205 | p-biphenylyl | H | H | H | H | —CH3 | H |
| R-206 | o-tolyl | H | H | H | H | —CH3 | H |
| R-207 | m-tolyl | H | H | H | H | —CH3 | H |
| R-208 | p-tolyl | H | H | H | H | —CH3 | H |
| R-209 | Ph | H | H | H | H | H | —CH3 |
| R-210 | 1-naphtyl | H | H | H | H | H | —CH3 |
| R-211 | 2-naphthyl | H | H | H | H | H | —CH3 |
| R-212 | o-biphenylyl | H | H | H | H | H | —CH3 |
| R-213 | m-biphenylyl | H | H | H | H | H | —CH3 |
| R-214 | p-biphenylyl | H | H | H | H | H | —CH3 |
| R-215 | o-tolyl | H | H | H | H | H | —CH3 |
| R-216 | m-tolyl | H | H | H | H | H | —CH3 |
| R-217 | p-tolyl | H | H | H | H | H | —CH3 |
| R-218 | Ph | H | H | H | H | —CH3 | —CH3 |
| R-219 | 1-naphtyl | H | H | H | H | —CH3 | —CH3 |
| R-220 | 2-naphthyl | H | H | H | H | —CH3 | —CH3 |
| R-221 | o-biphenylyl | H | H | H | H | —CH3 | —CH3 |
| R-222 | m-biphenylyl | H | H | H | H | —CH3 | —CH3 |
| R-223 | p-biphenylyl | H | H | H | H | —CH3 | —CH3 |
| R-224 | o-tolyl | H | H | H | H | —CH3 | —CH3 |
| R-225 | m-tolyl | H | H | H | H | —CH3 | —CH3 |
| R-226 | p-tolyl | H | H | H | H | —CH3 | —CH3 |
| R-227 | Ph | H | H | H | H | H | DPA |
| R-228 | 1-naphtyl | H | H | H | H | H | DPA |
| R-229 | 2-naphthyl | H | H | H | H | H | DPA |
| R-230 | o-biphenylyl | H | H | H | H | H | DPA |
| R-231 | m-biphenylyl | H | H | H | H | H | DPA |
| R-232 | p-biphenylyl | H | H | H | H | H | DPA |
| R-233 | Ph | H | H | H | H | DPA | H |
| R-234 | 1-naphtyl | H | H | H | H | DPA | H |
| R-235 | 2-naphthyl | H | H | H | H | DPA | H |
| R-236 | o-biphenylyl | H | H | H | H | DPA | H |
| R-237 | m-biphenylyl | H | H | H | H | DPA | H |
| R-238 | p-biphenylyl | H | H | H | H | DPA | H |
| R-239 | Ph | H | H | H | H | H | TPA |
| R-240 | 1-naphtyl | H | H | H | H | H | TPA |
| R-241 | 2-naphthyl | H | H | H | H | H | TPA |
| R-242 | o-biphenylyl | H | H | H | H | H | TPA |
| R-243 | m-biphenylyl | H | H | H | H | H | TPA |
| R-244 | p-biphenylyl | H | H | H | H | H | TPA |
| R-245 | Ph | H | H | H | H | TPA | H |
| R-246 | 1-naphtyl | H | H | H | H | TPA | H |
| R-247 | 2-naphthyl | H | H | H | H | TPA | H |
| R-248 | o-biphenylyl | H | H | H | H | TPA | H |
| R-249 | m-biphenylyl | H | H | H | H | TPA | H |
| R-250 | p-biphenylyl | H | H | H | H | TPA | H |

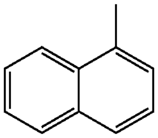

1-naphthyl

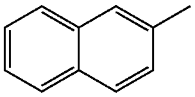

2-naphthyl

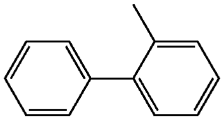

o-biphenylyl

-continued
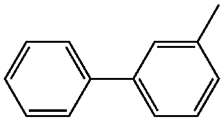
m-biphenylyl
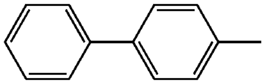
p-biphenylyl
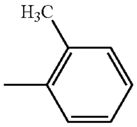
o-tolyl
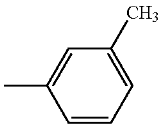
m-tolyl
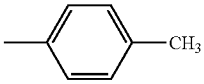
p-tolyl
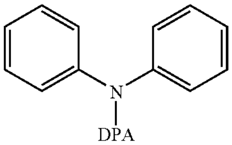
DPA
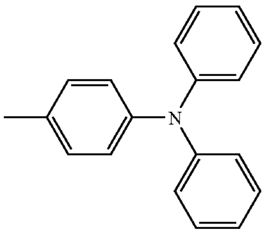
TPA

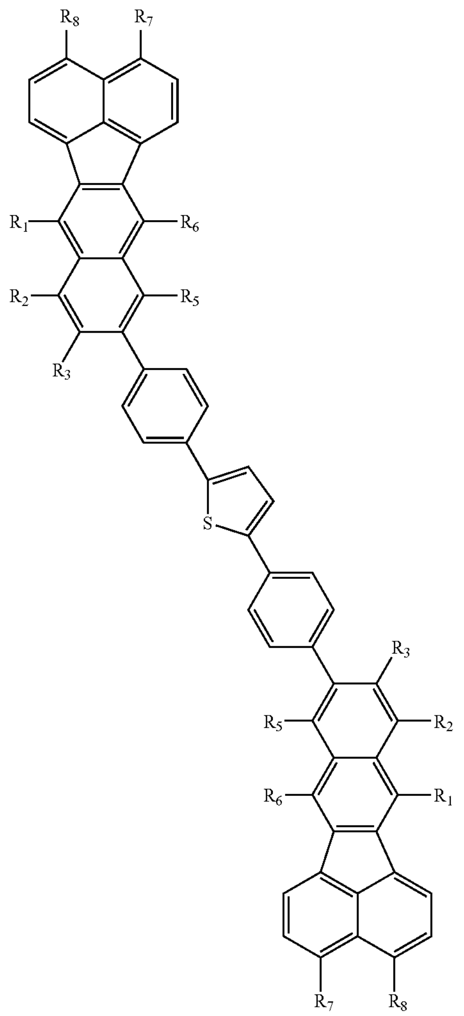

TypeS

| | $R_1$ | $R_2$ | $R_3$ | $R_5$ | $R_6$ | $R_7$ | $R_8$ |
|---|---|---|---|---|---|---|---|
| S-1 | H | H | H | H | H | H | H |
| S-2 | Ph | H | H | H | Ph | H | H |
| S-3 | Ph | Ph | H | H | Ph | H | H |
| S-4 | Ph | H | H | Ph | Ph | H | H |
| S-5 | Ph | Ph | H | Ph | Ph | H | H |
| S-6 | Ph | H | Ph | H | Ph | H | H |
| S-7 | Ph | H | H | H | Ph | Ph | H |
| S-8 | Ph | H | H | H | Ph | H | Ph |
| S-9 | Ph | H | H | H | Ph | Ph | Ph |
| S-10 | Ph | H | H | H | Ph | 1-naphthyl | H |
| S-11 | Ph | H | H | H | Ph | H | 1-naphthyl |
| S-12 | Ph | H | H | H | Ph | 1-naphthyl | 1-naphthyl |
| S-13 | Ph | H | H | H | Ph | 2-naphthyl | H |
| S-14 | Ph | H | H | H | Ph | H | 2-naphthyl |
| S-15 | Ph | H | H | H | Ph | 2-naphthyl | 2-naphthyl |
| S-16 | Ph | H | H | H | Ph | o-biphenylyl | H |
| S-17 | Ph | H | H | H | Ph | H | o-biphenylyl |
| S-18 | Ph | H | H | H | Ph | o-biphenylyl | o-biphenylyl |
| S-19 | Ph | H | H | H | Ph | m-biphenylyl | H |
| S-20 | Ph | H | H | H | Ph | H | m-biphenylyl |
| S-21 | Ph | H | H | H | Ph | m-biphenylyl | m-biphenylyl |
| S-22 | Ph | H | H | H | Ph | p-biphenylyl | H |
| S-23 | Ph | H | H | H | Ph | H | p-biphenylyl |
| S-24 | Ph | H | H | H | Ph | p-biphenylyl | p-biphenylyl |
| S-25 | 1-naphthyl | H | H | H | 1-naphthyl | H | H |
| S-26 | 1-naphthyl | Ph | H | H | 1-naphthyl | H | H |

-continued

| | | | | | | | |
|---|---|---|---|---|---|---|---|
| S-27 | 1-naphthyl | H | H | Ph | 1-naphthyl | H | H |
| S-28 | 1-naphthyl | Ph | H | Ph | 1-naphthyl | H | H |
| S-29 | 1-naphthyl | H | Ph | H | 1-naphthyl | H | H |
| S-30 | 1-naphthyl | H | H | H | 1-naphthyl | Ph | H |
| S-31 | 1-naphthyl | H | H | H | 1-naphthyl | H | Ph |
| S-32 | 1-naphthyl | H | H | H | 1-naphthyl | Ph | Ph |
| S-33 | 1-naphthyl | H | H | H | 1-naphthyl | 1-naphthyl | H |
| S-34 | 1-naphthyl | H | H | H | 1-naphthyl | H | 1-naphthyl |
| S-35 | 1-naphthyl | H | H | H | 1-naphthyl | 1-naphthyl | 1-naphthyl |
| S-36 | 1-naphthyl | H | H | H | 1-naphthyl | 2-naphthyl | H |
| S-37 | 1-naphthyl | H | H | H | 1-naphthyl | H | 2-naphthyl |
| S-38 | 1-naphthyl | H | H | H | 1-naphthyl | 2-naphthyl | 2-naphthyl |
| S-39 | 1-naphthyl | H | H | H | 1-naphthyl | o-biphenylyl | H |
| S-40 | 1-naphthyl | H | H | H | 1-naphthyl | H | o-biphenylyl |
| S-41 | 1-naphthyl | H | H | H | 1-naphthyl | o-biphenylyl | o-biphenylyl |
| S-42 | 1-naphthyl | H | H | H | 1-naphthyl | m-biphenylyl | H |
| S-43 | 1-naphthyl | H | H | H | 1-naphthyl | H | m-biphenylyl |
| S-44 | 1-naphthyl | H | H | H | 1-naphthyl | m-biphenylyl | m-biphenylyl |
| S-45 | 1-naphthyl | H | H | H | 1-naphthyl | p-biphenylyl | H |
| S-46 | 1-naphthyl | H | H | H | 1-naphthyl | H | p-biphenylyl |
| S-47 | 1-naphthyl | H | H | H | 1-naphthyl | p-biphenylyl | p-biphenylyl |
| S-48 | 2-naphthyl | H | H | H | 2-naphthyl | H | H |
| S-49 | 2-naphthyl | Ph | H | H | 2-naphthyl | H | H |
| S-50 | 2-naphthyl | H | H | Ph | 2-naphthyl | H | H |
| S-51 | 2-naphthyl | Ph | H | Ph | 2-naphthyl | H | H |
| S-52 | 2-naphthyl | H | Ph | H | 2-naphthyl | H | H |
| S-53 | 2-naphthyl | H | H | H | 2-naphthyl | Ph | H |
| S-54 | 2-naphthyl | H | H | H | 2-naphthyl | H | Ph |
| S-55 | 2-naphthyl | H | H | H | 2-naphthyl | Ph | Ph |
| S-56 | 2-naphthyl | H | H | H | 2-naphthyl | 1-naphthyl | H |
| S-57 | 2-naphthyl | H | H | H | 2-naphthyl | H | 1-naphthyl |
| S-58 | 2-naphthyl | H | H | H | 2-naphthyl | 1-naphthyl | 1-naphthyl |
| S-59 | 2-naphthyl | H | H | H | 2-naphthyl | 2-naphthyl | H |
| S-60 | 2-naphthyl | H | H | H | 2-naphthyl | H | 2-naphthyl |
| S-61 | 2-naphthyl | H | H | H | 2-naphthyl | 2-naphthyl | 2-naphthyl |
| S-62 | 2-naphthyl | H | H | H | 2-naphthyl | o-biphenylyl | H |
| S-63 | 2-naphthyl | H | H | H | 2-naphthyl | H | o-biphenylyl |
| S-64 | 2-naphthyl | H | H | H | 2-naphthyl | o-biphenylyl | o-biphenylyl |
| S-65 | 2-naphthyl | H | H | H | 2-naphthyl | m-biphenylyl | H |
| S-66 | 2-naphthyl | H | H | H | 2-naphthyl | H | m-biphenylyl |
| S-67 | 2-naphthyl | H | H | H | 2-naphthyl | m-biphenylyl | m-biphenylyl |
| S-68 | 2-naphthyl | H | H | H | 2-naphthyl | p-biphenylyl | H |
| S-69 | 2-naphthyl | H | H | H | 2-naphthyl | H | p-biphenylyl |
| S-70 | 2-naphthyl | H | H | H | 2-naphthyl | p-biphenylyl | p-biphenylyl |
| S-71 | o-biphenylyl | H | H | H | o-biphenylyl | H | H |
| S-72 | o-biphenylyl | Ph | H | H | o-biphenylyl | H | H |
| S-73 | o-biphenylyl | H | H | Ph | o-biphenylyl | H | H |
| S-74 | o-biphenylyl | Ph | H | Ph | o-biphenylyl | H | H |
| S-75 | o-biphenylyl | H | Ph | H | o-biphenylyl | H | H |
| S-76 | o-biphenylyl | H | H | H | o-biphenylyl | Ph | H |
| S-77 | o-biphenylyl | H | H | H | o-biphenylyl | H | Ph |
| S-78 | o-biphenylyl | H | H | H | o-biphenylyl | Ph | Ph |
| S-79 | o-biphenylyl | H | H | H | o-biphenylyl | 1-naphthyl | H |
| S-80 | o-biphenylyl | H | H | H | o-biphenylyl | H | 1-naphthyl |
| S-81 | o-biphenylyl | H | H | H | o-biphenylyl | 1-naphthyl | 1-naphthyl |
| S-82 | o-biphenylyl | H | H | H | o-biphenylyl | 2-naphthyl | H |
| S-83 | o-biphenylyl | H | H | H | o-biphenylyl | H | 2-naphthyl |
| S-84 | o-biphenylyl | H | H | H | o-biphenylyl | 2-naphthyl | 2-naphthyl |
| S-85 | o-biphenylyl | H | H | H | o-biphenylyl | o-biphenylyl | H |
| S-86 | o-biphenylyl | H | H | H | o-biphenylyl | H | o-biphenylyl |
| S-87 | o-biphenylyl | H | H | H | o-biphenylyl | o-biphenylyl | o-biphenylyl |
| S-88 | o-biphenylyl | H | H | H | o-biphenylyl | m-biphenylyl | H |
| S-89 | o-biphenylyl | H | H | H | o-biphenylyl | H | m-biphenylyl |
| S-90 | o-biphenylyl | H | H | H | o-biphenylyl | m-biphenylyl | m-biphenylyl |
| S-91 | o-biphenylyl | H | H | H | o-biphenylyl | p-biphenylyl | H |
| S-92 | o-biphenylyl | H | H | H | o-biphenylyl | H | p-biphenylyl |
| S-93 | o-biphenylyl | H | H | H | o-biphenylyl | p-biphenylyl | p-biphenylyl |
| S-94 | m-biphenylyl | H | H | H | m-biphenylyl | H | H |
| S-95 | m-biphenylyl | Ph | H | H | m-biphenylyl | H | H |
| S-96 | m-biphenylyl | H | H | Ph | m-biphenylyl | H | H |
| S-97 | m-biphenylyl | Ph | H | Ph | m-biphenylyl | H | H |
| S-98 | m-biphenylyl | H | Ph | H | m-biphenylyl | H | H |
| S-99 | m-biphenylyl | H | H | H | m-biphenylyl | Ph | H |
| S-100 | m-biphenylyl | H | H | H | m-biphenylyl | H | Ph |
| S-101 | m-biphenylyl | H | H | H | m-biphenylyl | Ph | Ph |
| S-102 | m-biphenylyl | H | H | H | m-biphenylyl | 1-naphthyl | H |
| S-103 | m-biphenylyl | H | H | H | m-biphenylyl | H | 1-naphthyl |
| S-104 | m-biphenylyl | H | H | H | m-biphenylyl | 1-naphthyl | 1-naphthyl |
| S-105 | m-biphenylyl | H | H | H | m-biphenylyl | 2-naphthyl | H |

-continued

| | | | | | | | |
|---|---|---|---|---|---|---|---|
| S-106 | m-biphenylyl | H | H | H | m-biphenylyl | H | 2-naphthyl |
| S-107 | m-biphenylyl | H | H | H | m-biphenylyl | 2-naphthyl | 2-naphthyl |
| S-108 | m-biphenylyl | H | H | H | m-biphenylyl | o-biphenylyl | H |
| S-109 | m-biphenylyl | H | H | H | m-biphenylyl | H | o-biphenylyl |
| S-110 | m-biphenylyl | H | H | H | m-biphenylyl | o-biphenylyl | o-biphenylyl |
| S-111 | m-biphenylyl | H | H | H | m-biphenylyl | m-biphenylyl | H |
| S-112 | m-biphenylyl | H | H | H | m-biphenylyl | H | m-biphenylyl |
| S-113 | m-biphenylyl | H | H | H | m-biphenylyl | m-biphenylyl | m-biphenylyl |
| S-114 | m-biphenylyl | H | H | H | m-biphenylyl | p-biphenylyl | H |
| S-115 | m-biphenylyl | H | H | H | m-biphenylyl | H | p-biphenylyl |
| S-116 | m-biphenylyl | H | H | H | m-biphenylyl | p-biphenylyl | p-biphenylyl |
| S-117 | p-biphenylyl | H | H | H | p-biphenylyl | H | H |
| S-118 | p-biphenylyl | Ph | H | H | p-biphenylyl | H | H |
| S-119 | p-biphenylyl | H | H | Ph | p-biphenylyl | H | H |
| S-120 | p-biphenylyl | Ph | H | Ph | p-biphenylyl | H | H |
| S-121 | p-biphenylyl | H | Ph | H | p-biphenylyl | H | H |
| S-122 | p-biphenylyl | H | H | H | p-biphenylyl | Ph | H |
| S-123 | p-biphenylyl | H | H | H | p-biphenylyl | H | Ph |
| S-124 | p-biphenylyl | H | H | H | p-biphenylyl | Ph | Ph |
| S-125 | p-biphenylyl | H | H | H | p-biphenylyl | 1-naphthyl | H |
| S-126 | p-biphenylyl | H | H | H | p-biphenylyl | H | 1-naphthyl |
| S-127 | p-biphenylyl | H | H | H | p-biphenylyl | 1-naphthyl | 1-naphthyl |
| S-128 | p-biphenylyl | H | H | H | p-biphenylyl | 2-naphthyl | H |
| S-129 | p-biphenylyl | H | H | H | p-biphenylyl | H | 2-naphthyl |
| S-130 | p-biphenylyl | H | H | H | p-biphenylyl | 2-naphthyl | 2-naphthyl |
| S-131 | p-biphenylyl | H | H | H | p-biphenylyl | o-biphenylyl | H |
| S-132 | p-biphenylyl | H | H | H | p-biphenylyl | H | o-biphenylyl |
| S-133 | p-biphenylyl | H | H | H | p-biphenylyl | o-biphenylyl | o-biphenylyl |
| S-134 | p-biphenylyl | H | H | H | p-biphenylyl | m-biphenylyl | H |
| S-135 | p-biphenylyl | H | H | H | p-biphenylyl | H | m-biphenylyl |
| S-136 | p-biphenylyl | H | H | H | p-biphenylyl | m-biphenylyl | m-biphenylyl |
| S-137 | p-biphenylyl | H | H | H | p-biphenylyl | p-biphenylyl | H |
| S-138 | p-biphenylyl | H | H | H | p-biphenylyl | H | p-biphenylyl |
| S-139 | p-biphenylyl | H | H | H | p-biphenylyl | p-biphenylyl | p-biphenylyl |
| S-140 | o-tolyl | H | H | H | o-tolyl | H | H |
| S-141 | o-tolyl | Ph | H | Ph | o-tolyl | H | H |
| S-142 | o-tolyl | H | Ph | H | o-tolyl | H | H |
| S-143 | o-tolyl | H | H | H | o-tolyl | Ph | H |
| S-144 | o-tolyl | H | H | H | o-tolyl | H | Ph |
| S-145 | o-tolyl | H | H | H | o-tolyl | 1-naphthyl | H |
| S-146 | o-tolyl | H | H | H | o-tolyl | H | 1-naphthyl |
| S-147 | o-tolyl | H | H | H | o-tolyl | 2-naphthyl | H |
| S-148 | o-tolyl | H | H | H | o-tolyl | H | 2-naphthyl |
| S-149 | o-tolyl | H | H | H | o-tolyl | o-biphenylyl | H |
| S-150 | o-tolyl | H | H | H | o-tolyl | H | o-biphenylyl |
| S-151 | o-tolyl | H | H | H | o-tolyl | m-biphenylyl | H |
| S-152 | o-tolyl | H | H | H | o-tolyl | H | m-biphenylyl |
| S-153 | o-tolyl | H | H | H | o-tolyl | p-biphenylyl | H |
| S-154 | o-tolyl | H | H | H | o-tolyl | H | p-biphenylyl |
| S-155 | o-tolyl | H | H | H | o-tolyl | o-tolyl | H |
| S-156 | o-tolyl | H | H | H | o-tolyl | H | o-tolyl |
| S-157 | m-tolyl | H | H | H | m-tolyl | H | H |
| S-158 | m-tolyl | Ph | H | Ph | m-tolyl | H | H |
| S-159 | m-tolyl | H | Ph | H | m-tolyl | H | H |
| S-160 | m-tolyl | H | H | H | m-tolyl | Ph | H |
| S-161 | m-tolyl | H | H | H | m-tolyl | H | Ph |
| S-162 | m-tolyl | H | H | H | m-tolyl | 1-naphthyl | H |
| S-163 | m-tolyl | H | H | H | m-tolyl | H | 1-naphthyl |
| S-164 | m-tolyl | H | H | H | m-tolyl | 2-naphthyl | H |
| S-165 | m-tolyl | H | H | H | m-tolyl | H | 2-naphthyl |
| S-166 | m-tolyl | H | H | H | m-tolyl | o-biphenylyl | H |
| S-167 | m-tolyl | H | H | H | m-tolyl | H | o-biphenylyl |
| S-168 | m-tolyl | H | H | H | m-tolyl | m-biphenylyl | H |
| S-169 | m-tolyl | H | H | H | m-tolyl | H | m-biphenylyl |
| S-170 | m-tolyl | H | H | H | m-tolyl | p-biphenylyl | H |
| S-171 | m-tolyl | H | H | H | m-tolyl | H | p-biphenylyl |
| S-172 | m-tolyl | H | H | H | m-tolyl | m-tolyl | H |
| S-173 | m-tolyl | H | H | H | m-tolyl | H | m-tolyl |
| S-174 | p-tolyl | H | H | H | p-tolyl | H | H |
| S-175 | p-tolyl | Ph | H | Ph | p-tolyl | H | H |
| S-176 | p-tolyl | H | Ph | H | p-tolyl | H | H |
| S-177 | p-tolyl | H | H | H | p-tolyl | Ph | H |
| S-178 | p-tolyl | H | H | H | p-tolyl | H | Ph |
| S-179 | p-tolyl | H | H | H | p-tolyl | 1-naphthyl | H |
| S-180 | p-tolyl | H | H | H | p-tolyl | H | 1-naphthyl |
| S-181 | p-tolyl | H | H | H | p-tolyl | 2-naphthyl | H |
| S-182 | p-tolyl | H | H | H | p-tolyl | H | 2-naphthyl |
| S-183 | p-tolyl | H | H | H | p-tolyl | o-biphenylyl | H |
| S-184 | p-tolyl | H | H | H | p-tolyl | H | o-biphenylyl |

-continued

| | | | | | | | |
|---|---|---|---|---|---|---|---|
| S-185 | p-tolyl | H | H | H | p-tolyl | m-biphenylyl | H |
| S-186 | p-tolyl | H | H | H | p-tolyl | H | m-biphenylyl |
| S-187 | p-tolyl | H | H | H | p-tolyl | p-biphenylyl | H |
| S-188 | p-tolyl | H | H | H | p-tolyl | H | p-biphenylyl |
| S-189 | p-tolyl | H | H | H | p-tolyl | p-tolyl | H |
| S-190 | p-tolyl | H | H | H | p-tolyl | H | p-tolyl |
| S-191 | Ph | H | —CH3 | H | Ph | H | H |
| S-192 | 1-naphtyl | H | —CH3 | H | 1-naphtyl | H | H |
| S-193 | 2-naphthyl | H | —CH3 | H | 2-naphthyl | H | H |
| S-194 | o-biphenylyl | H | —CH3 | H | o-biphenylyl | H | H |
| S-195 | m-biphenylyl | H | —CH3 | H | m-biphenylyl | H | H |
| S-196 | p-biphenylyl | H | —CH3 | H | p-biphenylyl | H | H |
| S-197 | o-tolyl | H | —CH3 | H | o-tolyl | H | H |
| S-198 | m-tolyl | H | —CH3 | H | m-tolyl | H | H |
| S-199 | p-tolyl | H | —CH3 | H | p-tolyl | H | H |
| S-200 | Ph | H | H | H | Ph | —CH3 | H |
| S-201 | 1-naphtyl | H | H | H | 1-naphtyl | —CH3 | H |
| S-202 | 2-naphthyl | H | H | H | 2-naphthyl | —CH3 | H |
| S-203 | o-biphenylyl | H | H | H | o-biphenylyl | —CH3 | H |
| S-204 | m-biphenylyl | H | H | H | m-biphenylyl | —CH3 | H |
| S-205 | p-biphenylyl | H | H | H | p-biphenylyl | —CH3 | H |
| S-206 | o-tolyl | H | H | H | o-tolyl | —CH3 | H |
| S-207 | m-tolyl | H | H | H | m-tolyl | —CH3 | H |
| S-208 | p-tolyl | H | H | H | p-tolyl | —CH3 | H |
| S-209 | Ph | H | H | H | Ph | H | —CH3 |
| S-210 | 1-naphtyl | H | H | H | 1-naphtyl | H | —CH3 |
| S-211 | 2-naphthyl | H | H | H | 2-naphthyl | H | —CH3 |
| S-212 | o-biphenylyl | H | H | H | o-biphenylyl | H | —CH3 |
| S-213 | m-biphenylyl | H | H | H | m-biphenylyl | H | —CH3 |
| S-214 | p-biphenylyl | H | H | H | p-biphenylyl | H | —CH3 |
| S-215 | o-tolyl | H | H | H | o-tolyl | H | —CH3 |
| S-216 | m-tolyl | H | H | H | m-tolyl | H | —CH3 |
| S-217 | p-tolyl | H | H | H | p-tolyl | H | —CH3 |
| S-218 | Ph | H | H | H | Ph | —CH3 | —CH3 |
| S-219 | 1-naphtyl | H | H | H | 1-naphtyl | —CH3 | —CH3 |
| S-220 | 2-naphthyl | H | H | H | 2-naphthyl | —CH3 | —CH3 |
| S-221 | o-biphenylyl | H | H | H | o-biphenylyl | —CH3 | —CH3 |
| S-222 | m-biphenylyl | H | H | H | m-biphenylyl | —CH3 | —CH3 |
| S-223 | p-biphenylyl | H | H | H | p-biphenylyl | —CH3 | —CH3 |
| S-224 | o-tolyl | H | H | H | o-tolyl | —CH3 | —CH3 |
| S-225 | m-tolyl | H | H | H | m-tolyl | —CH3 | —CH3 |
| S-226 | p-tolyl | H | H | H | p-tolyl | —CH3 | —CH3 |
| S-227 | Ph | H | H | H | Ph | H | DPA |
| S-228 | 1-naphtyl | H | H | H | 1-naphtyl | H | DPA |
| S-229 | 2-naphthyl | H | H | H | 2-naphthyl | H | DPA |
| S-230 | o-biphenylyl | H | H | H | o-biphenylyl | H | DPA |
| S-231 | m-biphenylyl | H | H | H | m-biphenylyl | H | DPA |
| S-232 | p-biphenylyl | H | H | H | p-biphenylyl | H | DPA |
| S-233 | Ph | H | H | H | Ph | DPA | H |
| S-234 | 1-naphtyl | H | H | H | 1-naphtyl | DPA | H |
| S-235 | 2-naphthyl | H | H | H | 2-naphthyl | DPA | H |
| S-236 | o-biphenylyl | H | H | H | o-biphenylyl | DPA | H |
| S-237 | m-biphenylyl | H | H | H | m-biphenylyl | DPA | H |
| S-238 | p-biphenylyl | H | H | H | p-biphenylyl | DPA | H |
| S-239 | Ph | H | H | H | Ph | H | TPA |
| S-240 | 1-naphtyl | H | H | H | 1-naphtyl | H | TPA |
| S-241 | 2-naphthyl | H | H | H | 2-naphthyl | H | TPA |
| S-242 | o-biphenylyl | H | H | H | o-biphenylyl | H | TPA |
| S-243 | m-biphenylyl | H | H | H | m-biphenylyl | H | TPA |
| S-244 | p-biphenylyl | H | H | H | p-biphenylyl | H | TPA |
| S-245 | Ph | H | H | H | Ph | TPA | H |
| S-246 | 1-naphtyl | H | H | H | 1-naphtyl | TPA | H |
| S-247 | 2-naphthyl | H | H | H | 2-naphthyl | TPA | H |
| S-248 | o-biphenylyl | H | H | H | o-biphenylyl | TPA | H |
| S-249 | m-biphenylyl | H | H | H | m-biphenylyl | TPA | H |
| S-250 | p-biphenylyl | H | H | H | p-biphenylyl | TPA | H |
| S-251 | Ph | H | H | H | 1-naphthyl | H | H |
| S-252 | Ph | H | H | H | 2-naphthyl | H | H |
| S-253 | Ph | H | H | H | o-biphenylyl | H | H |
| S-254 | Ph | H | H | H | m-biphenylyl | H | H |
| S-255 | Ph | H | H | H | p-biphenylyl | H | H |
| S-256 | Ph | H | H | H | O-tolyly | H | H |
| S-257 | Ph | H | H | H | m-tolyl | H | H |
| S-258 | Ph | H | H | H | p-tolyl | H | H |
| S-259 | 1-naphthyl | H | H | H | 2-naphthyl | H | H |
| S-260 | 1-naphthyl | H | H | H | o-biphenylyl | H | H |
| S-261 | 1-naphthyl | H | H | H | m-biphenylyl | H | H |
| S-262 | 1-naphthyl | H | H | H | p-biphenylyl | H | H |
| S-263 | 1-naphthyl | H | H | H | O-tolyly | H | H |

-continued

| | | | | | | | |
|---|---|---|---|---|---|---|---|
| S-264 | 1-naphthyl | H | H | H | m-tolyl | H | H |
| S-265 | 1-naphthyl | H | H | H | p-tolyl | H | H |
| S-266 | 2-naphthyl | H | H | H | o-biphenylyl | H | H |
| S-267 | 2-naphthyl | H | H | H | m-biphenylyl | H | H |
| S-268 | 2-naphthyl | H | H | H | p-biphenylyl | H | H |
| S-269 | 2-naphthyl | H | H | H | O-tolyly | H | H |
| S-270 | 2-naphthyl | H | H | H | m-tolyl | H | H |
| S-271 | 2-naphthyl | H | H | H | p-tolyl | H | H |
| S-272 | o-biphenylyl | H | H | H | m-biphenylyl | H | H |
| S-273 | o-biphenylyl | H | H | H | p-biphenylyl | H | H |
| S-274 | o-biphenylyl | H | H | H | O-tolyly | H | H |
| S-275 | o-biphenylyl | H | H | H | m-tolyl | H | H |
| S-276 | o-biphenylyl | H | H | H | p-tolyl | H | H |
| S-277 | m-biphenylyl | H | H | H | p-biphenylyl | H | H |
| S-278 | m-biphenylyl | H | H | H | O-tolyly | H | H |
| S-279 | m-biphenylyl | H | H | H | m-tolyl | H | H |
| S-280 | m-biphenylyl | H | H | H | p-tolyl | H | H |
| S-281 | p-biphenylyl | H | H | H | O-tolyly | H | H |
| S-282 | p-biphenylyl | H | H | H | m-tolyl | H | H |
| S-283 | p-biphenylyl | H | H | H | p-tolyl | H | H |
| S-284 | O-tolyly | H | H | H | m-tolyl | H | H |
| S-285 | O-tolyly | H | H | H | p-tolyl | H | H |
| S-286 | m-tolyly | H | H | H | p-tolyl | H | H |

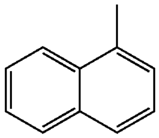

1-naphthyl

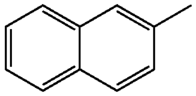

2-naphthyl

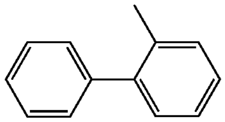

o-biphenylyl

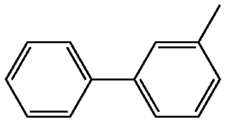

m-biphenylyl

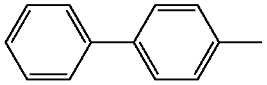

p-biphenylyl

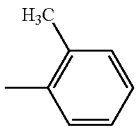

o-tolyl

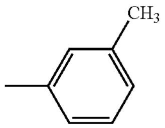

m-tolyl

-continued
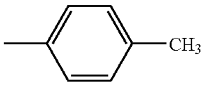
p-tolyl
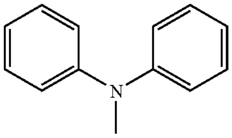
DPA
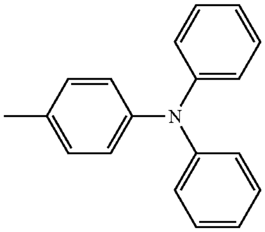
TPA
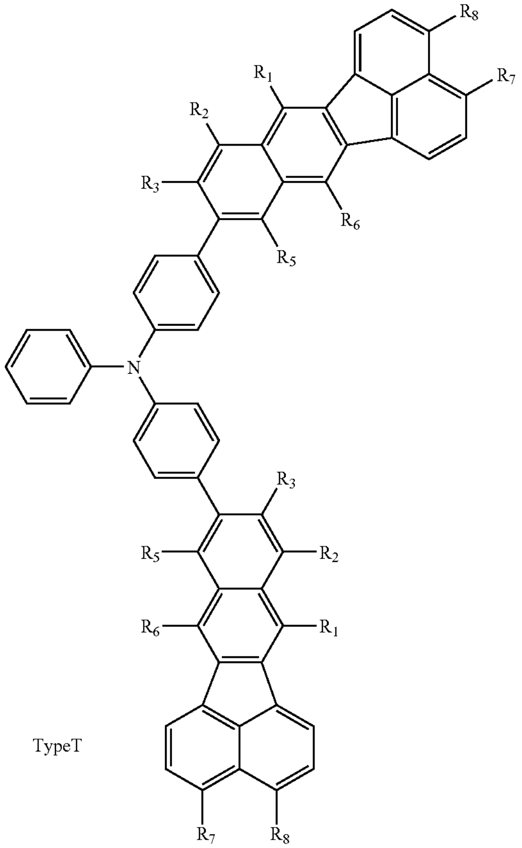
TypeT
| | $R_1$ | $R_2$ | $R_3$ | $R_5$ | $R_6$ | $R_7$ | $R_8$ |
|---|---|---|---|---|---|---|---|
| T-1 | H | H | H | H | H | H | H |
| T-2 | Ph | H | H | H | Ph | H | H |
| T-3 | Ph | Ph | H | H | Ph | H | H |
| T-4 | Ph | H | H | Ph | Ph | H | H |
| T-5 | Ph | Ph | H | Ph | Ph | H | H |

-continued

| | | | | | | | |
|---|---|---|---|---|---|---|---|
| T-6 | Ph | H | Ph | H | Ph | H | H |
| T-7 | Ph | H | H | H | Ph | Ph | H |
| T-8 | Ph | H | H | H | Ph | H | Ph |
| T-9 | Ph | H | H | H | Ph | Ph | Ph |
| T-10 | Ph | H | H | H | Ph | 1-naphthyl | H |
| 1-11 | Ph | H | H | H | Ph | H | 1-naphthyl |
| T-12 | Ph | H | H | H | Ph | 1-naphthyl | 1-naphthyl |
| T-13 | Ph | H | H | H | Ph | 2-naphthyl | H |
| T-14 | Ph | H | H | H | Ph | H | 2-naphthyl |
| T-15 | Ph | H | H | H | Ph | 2-naphthyl | 2-naphthyl |
| T-16 | Ph | H | H | H | Ph | o-biphenylyl | H |
| T-17 | Ph | H | H | H | Ph | H | o-biphenylyl |
| T-18 | Ph | H | H | H | Ph | o-biphenylyl | o-biphenylyl |
| T-19 | Ph | H | H | H | Ph | m-biphenylyl | H |
| T-20 | Ph | H | H | H | Ph | H | m-biphenylyl |
| T-21 | Ph | H | H | H | Ph | m-biphenylyl | m-biphenylyl |
| T-22 | Ph | H | H | H | Ph | p-biphenylyl | H |
| T-23 | Ph | H | H | H | Ph | H | p-biphenylyl |
| T-24 | Ph | H | H | H | Ph | p-biphenylyl | p-biphenylyl |
| T-25 | 1-naphthyl | H | H | H | 1-naphthyl | H | H |
| T-26 | 1-naphthyl | Ph | H | H | 1-naphthyl | H | H |
| T-27 | 1-naphthyl | H | H | Ph | 1-naphthyl | H | H |
| T-28 | 1-naphthyl | Ph | H | Ph | 1-naphthyl | H | H |
| T-29 | 1-naphthyl | H | Ph | H | 1-naphthyl | H | H |
| T-30 | 1-naphthyl | H | H | H | 1-naphthyl | Ph | H |
| T-31 | 1-naphthyl | H | H | H | 1-naphthyl | H | Ph |
| T-32 | 1-naphthyl | H | H | H | 1-naphthyl | Ph | Ph |
| T-33 | 1-naphthyl | H | H | H | 1-naphthyl | 1-naphthyl | H |
| T-34 | 1-naphthyl | H | H | H | 1-naphthyl | H | 1-naphthyl |
| T-35 | 1-naphthyl | H | H | H | 1-naphthyl | 1-naphthyl | 1-naphthyl |
| T-36 | 1-naphthyl | H | H | H | 1-naphthyl | 2-naphthyl | H |
| T-37 | 1-naphthyl | H | H | H | 1-naphthyl | H | 2-naphthyl |
| T-38 | 1-naphthyl | H | H | H | 1-naphthyl | 2-naphthyl | 2-naphthyl |
| T-39 | 1-naphthyl | H | H | H | 1-naphthyl | o-biphenylyl | H |
| T-40 | 1-naphthyl | H | H | H | 1-naphthyl | H | o-biphenylyl |
| T-41 | 1-naphthyl | H | H | H | 1-naphthyl | o-biphenylyl | o-biphenylyl |
| T-42 | 1-naphthyl | H | H | H | 1-naphthyl | m-biphenylyl | H |
| T-43 | 1-naphthyl | H | H | H | 1-naphthyl | H | m-biphenylyl |
| T-44 | 1-naphthyl | H | H | H | 1-naphthyl | m-biphenylyl | m-biphenylyl |
| T-45 | 1-naphthyl | H | H | H | 1-naphthyl | p-biphenylyl | H |
| T-46 | 1-naphthyl | H | H | H | 1-naphthyl | H | p-biphenylyl |
| T-47 | 1-naphthyl | H | H | H | 1-naphthyl | p-biphenylyl | p-biphenylyl |
| T-48 | 2-naphthyl | H | H | H | 2-naphthyl | H | H |
| T-49 | 2-naphthyl | Ph | H | H | 2-naphthyl | H | H |
| T-50 | 2-naphthyl | H | H | Ph | 2-naphthyl | H | H |
| T-51 | 2-naphthyl | Ph | H | Ph | 2-naphthyl | H | H |
| T-52 | 2-naphthyl | H | Ph | H | 2-naphthyl | H | H |
| T-53 | 2-naphthyl | H | H | H | 2-naphthyl | Ph | H |
| T-54 | 2-naphthyl | H | H | H | 2-naphthyl | H | Ph |
| T-55 | 2-naphthyl | H | H | H | 2-naphthyl | Ph | Ph |
| T-56 | 2-naphthyl | H | H | H | 2-naphthyl | 1-naphthyl | H |
| T-57 | 2-naphthyl | H | H | H | 2-naphthyl | H | 1-naphthyl |
| T-58 | 2-naphthyl | H | H | H | 2-naphthyl | 1-naphthyl | 1-naphthyl |
| T-59 | 2-naphthyl | H | H | H | 2-naphthyl | 2-naphthyl | H |
| T-60 | 2-naphthyl | H | H | H | 2-naphthyl | H | 2-naphthyl |
| T-61 | 2-naphthyl | H | H | H | 2-naphthyl | 2-naphthyl | 2-naphthyl |
| T-62 | 2-naphthyl | H | H | H | 2-naphthyl | o-biphenylyl | H |
| T-63 | 2-naphthyl | H | H | H | 2-naphthyl | H | o-biphenylyl |
| T-64 | 2-naphthyl | H | H | H | 2-naphthyl | o-biphenylyl | o-biphenylyl |
| T-65 | 2-naphthyl | H | H | H | 2-naphthyl | m-biphenylyl | H |
| T-66 | 2-naphthyl | H | H | H | 2-naphthyl | H | m-biphenylyl |
| T-67 | 2-naphthyl | H | H | H | 2-naphthyl | m-biphenylyl | m-biphenylyl |
| T-68 | 2-naphthyl | H | H | H | 2-naphthyl | p-biphenylyl | H |
| T-69 | 2-naphthyl | H | H | H | 2-naphthyl | H | p-biphenylyl |
| T-70 | 2-naphthyl | H | H | H | 2-naphthyl | p-biphenylyl | p-biphenylyl |
| T-71 | o-biphenylyl | H | H | H | o-biphenylyl | H | H |
| T-72 | o-biphenylyl | Ph | H | H | o-biphenylyl | H | H |
| T-73 | o-biphenylyl | H | H | Ph | o-biphenylyl | H | H |
| T-74 | o-biphenylyl | Ph | H | Ph | o-biphenylyl | H | H |
| T-75 | o-biphenylyl | H | Ph | H | o-biphenylyl | H | H |
| T-76 | o-biphenylyl | H | H | H | o-biphenylyl | Ph | H |
| T-77 | o-biphenylyl | H | H | H | o-biphenylyl | H | Ph |
| T-78 | o-biphenylyl | H | H | H | o-biphenylyl | Ph | Ph |
| T-79 | o-biphenylyl | H | H | H | o-biphenylyl | 1-naphthyl | H |
| T-80 | o-biphenylyl | H | H | H | o-biphenylyl | H | 1-naphthyl |
| T-81 | o-biphenylyl | H | H | H | o-biphenylyl | 1-naphthyl | 1-naphthyl |
| T-82 | o-biphenylyl | H | H | H | o-biphenylyl | 2-naphthyl | H |
| T-83 | o-biphenylyl | H | H | H | o-biphenylyl | H | 2-naphthyl |
| T-84 | o-biphenylyl | H | H | H | o-biphenylyl | 2-naphthyl | 2-naphthyl |

-continued

| | | | | | | | |
|---|---|---|---|---|---|---|---|
| T-85 | o-biphenylyl | H | H | H | o-biphenylyl | o-biphenylyl | H |
| T-86 | o-biphenylyl | H | H | H | o-biphenylyl | H | o-biphenylyl |
| T-87 | o-biphenylyl | H | H | H | o-biphenylyl | o-biphenylyl | o-biphenylyl |
| T-88 | o-biphenylyl | H | H | H | o-biphenylyl | m-biphenylyl | H |
| T-89 | o-biphenylyl | H | H | H | o-biphenylyl | H | m-biphenylyl |
| T-90 | o-biphenylyl | H | H | H | o-biphenylyl | m-biphenylyl | m-biphenylyl |
| T-91 | o-biphenylyl | H | H | H | o-biphenylyl | p-biphenylyl | H |
| T-92 | o-biphenylyl | H | H | H | o-biphenylyl | H | p-biphenylyl |
| T-93 | o-biphenylyl | H | H | H | o-biphenylyl | p-biphenylyl | p-biphenylyl |
| T-94 | m-biphenylyl | H | H | H | m-biphenylyl | H | H |
| T-95 | m-biphenylyl | Ph | H | H | m-biphenylyl | H | H |
| T-96 | m-biphenylyl | H | H | Ph | m-biphenylyl | H | H |
| T-97 | m-biphenylyl | Ph | H | Ph | m-biphenylyl | H | H |
| T-98 | m-biphenylyl | H | Ph | H | m-biphenylyl | H | H |
| T-99 | m-biphenylyl | H | H | H | m-biphenylyl | Ph | H |
| T-100 | m-biphenylyl | H | H | H | m-biphenylyl | H | Ph |
| T-101 | m-biphenylyl | H | H | H | m-biphenylyl | Ph | Ph |
| T-102 | m-biphenylyl | H | H | H | m-biphenylyl | 1-naphthyl | H |
| T-103 | m-biphenylyl | H | H | H | m-biphenylyl | H | 1-naphthyl |
| T-104 | m-biphenylyl | H | H | H | m-biphenylyl | 1 -naphthyl | 1-naphthyl |
| T-105 | m-biphenylyl | H | H | H | m-biphenylyl | 2-naphthyl | H |
| T-106 | m-biphenylyl | H | H | H | m-biphenylyl | H | 2-naphthyl |
| T-107 | m-biphenylyl | H | H | H | m-biphenylyl | 2-naphthyl | 2-naphthyl |
| T-108 | m-biphenylyl | H | H | H | m-biphenylyl | o-biphenylyl | H |
| T-109 | m-biphenylyl | H | H | H | m-biphenylyl | H | o-biphenylyl |
| T-110 | m-biphenylyl | H | H | H | m-biphenylyl | o-biphenylyl | o-biphenylyl |
| T-111 | m-biphenylyl | H | H | H | m-biphenylyl | m-biphenylyl | H |
| T-112 | m-biphenylyl | H | H | H | m-biphenylyl | H | m-biphenylyl |
| T-113 | m-biphenylyl | H | H | H | m-biphenylyl | m-biphenylyl | m-biphenylyl |
| T-114 | m-biphenylyl | H | H | H | m-biphenylyl | p-biphenylyl | H |
| T-115 | m-biphenylyl | H | H | H | m-biphenylyl | H | p-biphenylyl |
| T-116 | m-biphenylyl | H | H | H | m-biphenylyl | p-biphenylyl | p-biphenylyl |
| T-117 | p-biphenylyl | H | H | H | p-biphenylyl | H | H |
| T-118 | p-biphenylyl | Ph | H | H | p-biphenylyl | H | H |
| T-119 | p-biphenylyl | H | H | Ph | p-biphenylyl | H | H |
| T-120 | p-biphenylyl | Ph | H | Ph | p-biphenylyl | H | H |
| T-121 | p-biphenylyl | H | Ph | H | p-biphenylyl | H | H |
| T-122 | p-biphenylyl | H | H | H | p-biphenylyl | Ph | H |
| T-123 | p-biphenylyl | H | H | H | p-biphenylyl | H | Ph |
| T-124 | p-biphenylyl | H | H | H | p-biphenylyl | Ph | Ph |
| T-125 | p-biphenylyl | H | H | H | p-biphenylyl | 1-naphthyl | H |
| T-126 | p-biphenylyl | H | H | H | p-biphenylyl | H | 1-naphthyl |
| T-127 | p-biphenylyl | H | H | H | p-biphenylyl | 1-naphthyl | 1-naphthyl |
| T-128 | p-biphenylyl | H | H | H | p-biphenylyl | 2-naphthyl | H |
| T-129 | p-biphenylyl | H | H | H | p-biphenylyl | H | 2-naphthyl |
| T-130 | p-biphenylyl | H | H | H | p-biphenylyl | 2-naphthyl | 2-naphthyl |
| T-131 | p-biphenylyl | H | H | H | p-biphenylyl | o-biphenylyl | H |
| T-132 | p-biphenylyl | H | H | H | p-biphenylyl | H | o-biphenylyl |
| T-133 | p-biphenylyl | H | H | H | p-biphenylyl | o-biphenylyl | o-biphenylyl |
| T-134 | p-biphenylyl | H | H | H | p-biphenylyl | m-biphenylyl | H |
| T-135 | p-biphenylyl | H | H | H | p-biphenylyl | H | m-biphenylyl |
| T-136 | p-biphenylyl | H | H | H | p-biphenylyl | m-biphenylyl | m-biphenylyl |
| T-137 | p-biphenylyl | H | H | H | p-biphenylyl | p-biphenylyl | H |
| T-138 | p-biphenylyl | H | H | H | p-biphenylyl | H | p-biphenylyl |
| T-139 | p-biphenylyl | H | H | H | p-biphenylyl | p-biphenylyl | p-biphenylyl |
| T-140 | o-tolyl | H | H | H | o-tolyl | H | H |
| T-141 | o-tolyl | Ph | H | Ph | o-tolyl | H | H |
| T-142 | o-tolyl | H | Ph | H | o-tolyl | H | H |
| T-143 | o-tolyl | H | H | H | o-tolyl | Ph | H |
| T-144 | o-tolyl | H | H | H | o-tolyl | H | Ph |
| T-145 | o-tolyl | H | H | H | o-tolyl | 1-naphthyl | H |
| T-146 | o-tolyl | H | H | H | o-tolyl | H | 1-naphthyl |
| T-147 | o-tolyl | H | H | H | o-tolyl | 2-naphthyl | H |
| T-148 | o-tolyl | H | H | H | o-tolyl | H | 2-naphthyl |
| T-149 | o-tolyl | H | H | H | o-tolyl | o-biphenylyl | H |
| T-150 | o-tolyl | H | H | H | o-tolyl | H | o-biphenylyl |
| T-151 | o-tolyl | H | H | H | o-tolyl | m-biphenylyl | H |
| T-152 | o-tolyl | H | H | H | o-tolyl | H | m-biphenylyl |
| T-153 | o-tolyl | H | H | H | o-tolyl | p-biphenylyl | H |
| T-154 | o-tolyl | H | H | H | o-tolyl | H | p-biphenylyl |
| T-155 | o-tolyl | H | H | H | o-tolyl | o-tolyl | H |
| T-156 | o-tolyl | H | H | H | o-tolyl | H | o-tolyl |
| T-157 | m-tolyl | H | H | H | m-tolyl | H | H |
| T-158 | m-tolyl | Ph | H | Ph | m-tolyl | H | H |
| T-159 | m-tolyl | H | Ph | H | m-tolyl | H | H |
| T-160 | m-tolyl | H | H | H | m-tolyl | Ph | H |
| T-161 | m-tolyl | H | H | H | m-tolyl | H | Ph |
| T-162 | m-tolyl | H | H | H | m-tolyl | 1-naphthyl | H |
| T-163 | m-tolyl | H | H | H | m-tolyl | H | 1-naphthyl |

-continued

| | | | | | | | |
|---|---|---|---|---|---|---|---|
| T-164 | m-tolyl | H | H | H | m-tolyl | 2-naphthyl | H |
| T-165 | m-tolyl | H | H | H | m-tolyl | H | 2-naphthyl |
| T-166 | m-tolyl | H | H | H | m-tolyl | o-biphenylyl | H |
| T-167 | m-tolyl | H | H | H | m-tolyl | H | o-biphenylyl |
| T-168 | m-tolyl | H | H | H | m-tolyl | m-biphenylyl | H |
| T-169 | m-tolyl | H | H | H | m-tolyl | H | m-biphenylyl |
| T-170 | m-tolyl | H | H | H | m-tolyl | p-biphenylyl | H |
| T-171 | m-tolyl | H | H | H | m-tolyl | H | p-biphenylyl |
| T-172 | m-tolyl | H | H | H | m-tolyl | m-tolyl | H |
| T-173 | m-tolyl | H | H | H | m-tolyl | H | m-tolyl |
| T-174 | p-tolyl | H | H | H | p-tolyl | H | H |
| T-175 | p-tolyl | Ph | H | Ph | p-tolyl | H | H |
| T-176 | p-tolyl | H | Ph | H | p-tolyl | H | H |
| T-177 | p-tolyl | H | H | H | p-tolyl | Ph | H |
| T-178 | p-tolyl | H | H | H | p-tolyl | H | Ph |
| T-179 | p-tolyl | H | H | H | p-tolyl | 1-naphthyl | H |
| T-180 | p-tolyl | H | H | H | p-tolyl | H | 1-naphthyl |
| T-181 | p-tolyl | H | H | H | p-tolyl | 2-naphthyl | H |
| T-182 | p-tolyl | H | H | H | p-tolyl | H | 2-naphthyl |
| T-183 | p-tolyl | H | H | H | p-tolyl | o-biphenylyl | H |
| T-184 | p-tolyl | H | H | H | p-tolyl | H | o-biphenylyl |
| T-185 | p-tolyl | H | H | H | p-tolyl | m-biphenylyl | H |
| T-186 | p-tolyl | H | H | H | p-tolyl | H | m-biphenylyl |
| T-187 | p-tolyl | H | H | H | p-tolyl | p-biphenylyl | H |
| T-188 | p-tolyl | H | H | H | p-tolyl | H | p-biphenylyl |
| T-189 | p-tolyl | H | H | H | p-tolyl | p-tolyl | H |
| T-190 | p-tolyl | H | H | H | p-tolyl | H | p-tolyl |
| T-191 | Ph | H | —CH3 | H | Ph | H | H |
| T-192 | 1-naphtyl | H | —CH3 | H | 1-naphtyl | H | H |
| T-193 | 2-naphthyl | H | —CH3 | H | 2-naphthyl | H | H |
| T-194 | o-biphenylyl | H | —CH3 | H | o-biphenylyl | H | H |
| T-195 | m-biphenylyl | H | —CH3 | H | m-biphenylyl | H | H |
| T-196 | p-biphenylyl | H | —CH3 | H | p-biphenylyl | H | H |
| T-197 | o-tolyl | H | —CH3 | H | o-tolyl | H | H |
| T-198 | m-tolyl | H | —CH3 | H | m-tolyl | H | H |
| T-199 | p-tolyl | H | —CH3 | H | p-tolyl | H | H |
| T-200 | Ph | H | H | H | Ph | —CH3 | H |
| T-201 | 1-naphtyl | H | H | H | 1-naphtyl | —CH3 | H |
| T-202 | 2-naphthyl | H | H | H | 2-naphthyl | —CH3 | H |
| T-203 | o-biphenylyl | H | H | H | o-biphenylyl | —CH3 | H |
| T-204 | m-biphenylyl | H | H | H | m-biphenylyl | —CH3 | H |
| T-205 | p-biphenylyl | H | H | H | p-biphenylyl | —CH3 | H |
| T-206 | o-tolyl | H | H | H | o-tolyl | —CH3 | H |
| T-207 | m-tolyl | H | H | H | m-tolyl | —CH3 | H |
| T-208 | p-tolyl | H | H | H | p-tolyl | —CH3 | H |
| T-209 | Ph | H | H | H | Ph | H | —CH3 |
| T-210 | 1-naphtyl | H | H | H | 1-naphtyl | H | —CH3 |
| T-211 | 2-naphthyl | H | H | H | 2-naphthyl | H | —CH3 |
| T-212 | o-biphenylyl | H | H | H | o-biphenylyl | H | —CH3 |
| T-213 | m-biphenylyl | H | H | H | m-biphenylyl | H | —CH3 |
| T-214 | p-biphenylyl | H | H | H | p-biphenylyl | H | —CH3 |
| T-215 | o-tolyl | H | H | H | o-tolyl | H | —CH3 |
| T-216 | m-tolyl | H | H | H | m-tolyl | H | —CH3 |
| T-217 | p-tolyl | H | H | H | p-tolyl | H | —CH3 |
| T-218 | Ph | H | H | H | Ph | —CH3 | —CH3 |
| T-219 | 1-naphtyl | H | H | H | 1-naphtyl | —CH3 | —CH3 |
| T-220 | 2-naphthyl | H | H | H | 2-naphthyl | —CH3 | —CH3 |
| T-221 | o-biphenylyl | H | H | H | o-biphenylyl | —CH3 | —CH3 |
| T-222 | m-biphenylyl | H | H | H | m-biphenylyl | —CH3 | —CH3 |
| T-223 | p-biphenylyl | H | H | H | p-biphenylyl | —CH3 | —CH3 |
| T-224 | o-tolyl | H | H | H | o-tolyl | —CH3 | —CH3 |
| T-225 | m-tolyl | H | H | H | m-tolyl | —CH3 | —CH3 |
| T-226 | p-tolyl | H | H | H | p-tolyl | —CH3 | —CH3 |
| T-227 | Ph | H | H | H | Ph | H | DPA |
| T-228 | 1-naphtyl | H | H | H | 1-naphtyl | H | DPA |
| T-229 | 2-naphthyl | H | H | H | 2-naphthyl | H | DPA |
| T-230 | o-biphenylyl | H | H | H | o-biphenylyl | H | DPA |
| T-231 | m-biphenylyl | H | H | H | m-biphenylyl | H | DPA |
| T-232 | p-biphenylyl | H | H | H | p-biphenylyl | H | DPA |
| T-233 | Ph | H | H | H | Ph | DPA | H |
| T-234 | 1-naphtyl | H | H | H | 1-naphtyl | DPA | H |
| T-235 | 2-naphthyl | H | H | H | 2-naphthyl | DPA | H |
| T-236 | o-biphenylyl | H | H | H | o-biphenylyl | DPA | H |
| T-237 | m-biphenylyl | H | H | H | m-biphenylyl | DPA | H |
| T-238 | p-biphenylyl | H | H | H | p-biphenylyl | DPA | H |
| T-239 | Ph | H | H | H | Ph | H | TPA |
| T-240 | 1-naphtyl | H | H | H | 1-naphtyl | H | TPA |
| T-241 | 2-naphthyl | H | H | H | 2-naphthyl | H | TPA |
| T-242 | o-biphenylyl | H | H | H | o-biphenylyl | H | TPA |

-continued

| | | | | | | | |
|---|---|---|---|---|---|---|---|
| T-243 | m-biphenylyl | H | H | H | m-biphenylyl | H | TPA |
| T-244 | p-biphenylyl | H | H | H | p-biphenylyl | H | TPA |
| T-245 | Ph | H | H | H | Ph | TPA | H |
| T-246 | 1-naphtyl | H | H | H | 1-naphtyl | TPA | H |
| T-247 | 2-naphthyl | H | H | H | 2-naphthyl | TPA | H |
| T-248 | o-biphenylyl | H | H | H | o-biphenylyl | TPA | H |
| T-249 | m-biphenylyl | H | H | H | m-biphenylyl | TPA | H |
| T-250 | p-biphenylyl | H | H | H | p-biphenylyl | TPA | H |
| T-251 | Ph | H | H | H | 1-naphthyl | H | H |
| T-252 | Ph | H | H | H | 2-naphthyl | H | H |
| T-253 | Ph | H | H | H | o-biphenylyl | H | H |
| T-254 | Ph | H | H | H | m-biphenylyl | H | H |
| T-255 | Ph | H | H | H | p-biphenylyl | H | H |
| T-256 | Ph | H | H | H | O-tolyly | H | H |
| T-257 | Ph | H | H | H | m-tolyl | H | H |
| T-258 | Ph | H | H | H | p-tolyl | H | H |
| T-259 | 1-naphthyl | H | H | H | 2-naphthyl | H | H |
| T-260 | 1-naphthyl | H | H | H | o-biphenylyl | H | H |
| T-261 | 1-naphthyl | H | H | H | m-biphenylyl | H | H |
| T-262 | 1-naphthyl | H | H | H | p-biphenylyl | H | H |
| T-263 | 1-naphthyl | H | H | H | O-tolyly | H | H |
| T-264 | 1-naphthyl | H | H | H | m-tolyl | H | H |
| T-265 | 1-naphthyl | H | H | H | p-tolyl | H | H |
| T-266 | 2-naphthyl | H | H | H | o-biphenylyl | H | H |
| T-267 | 2-naphthyl | H | H | H | m-biphenylyl | H | H |
| T-268 | 2-naphthyl | H | H | H | p-biphenylyl | H | H |
| T-269 | 2-naphthyl | H | H | H | O-tolyly | H | H |
| T-270 | 2-naphthyl | H | H | H | m-tolyl | H | H |
| T-271 | 2-naphthyl | H | H | H | p-tolyl | H | H |
| T-272 | o-biphenylyl | H | H | H | m-biphenylyl | H | H |
| T-273 | o-biphenylyl | H | H | H | p-biphenylyl | H | H |
| T-274 | o-biphenylyl | H | H | H | O-tolyly | H | H |
| T-275 | o-biphenylyl | H | H | H | m-tolyl | H | H |
| T-276 | o-biphenylyl | H | H | H | p-tolyl | H | H |
| T-277 | m-biphenylyl | H | H | H | p-biphenylyl | H | H |
| T-278 | m-biphenylyl | H | H | H | O-tolyly | H | H |
| T-279 | m-biphenylyl | H | H | H | m-tolyl | H | H |
| T-280 | m-biphenylyl | H | H | H | p-tolyl | H | H |
| T-281 | p-biphenylyl | H | H | H | O-tolyly | H | H |
| T-282 | p-biphenylyl | H | H | H | m-tolyl | H | H |
| T-283 | p-biphenylyl | H | H | H | p-tolyl | H | H |
| T-284 | O-tolyly | H | H | H | m-tolyl | H | H |
| T-285 | O-tolyly | H | H | H | p-tolyl | H | H |
| T-286 | m-tolyly | H | H | H | p-tolyl | H | H |

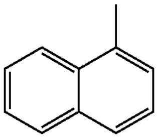

1-naphthyl

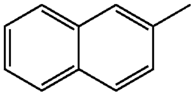

2-naphthyl

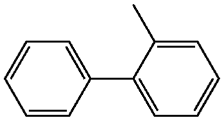

o-biphenylyl

-continued
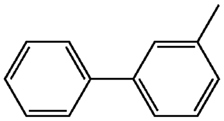
m-biphenylyl
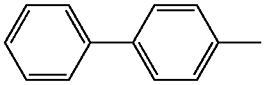
p-biphenylyl
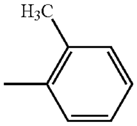
o-tolyl
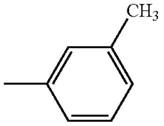
m-tolyl
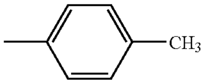
p-tolyl
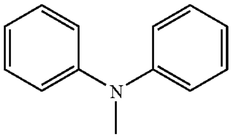
DPA
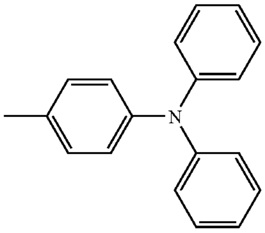
TPA

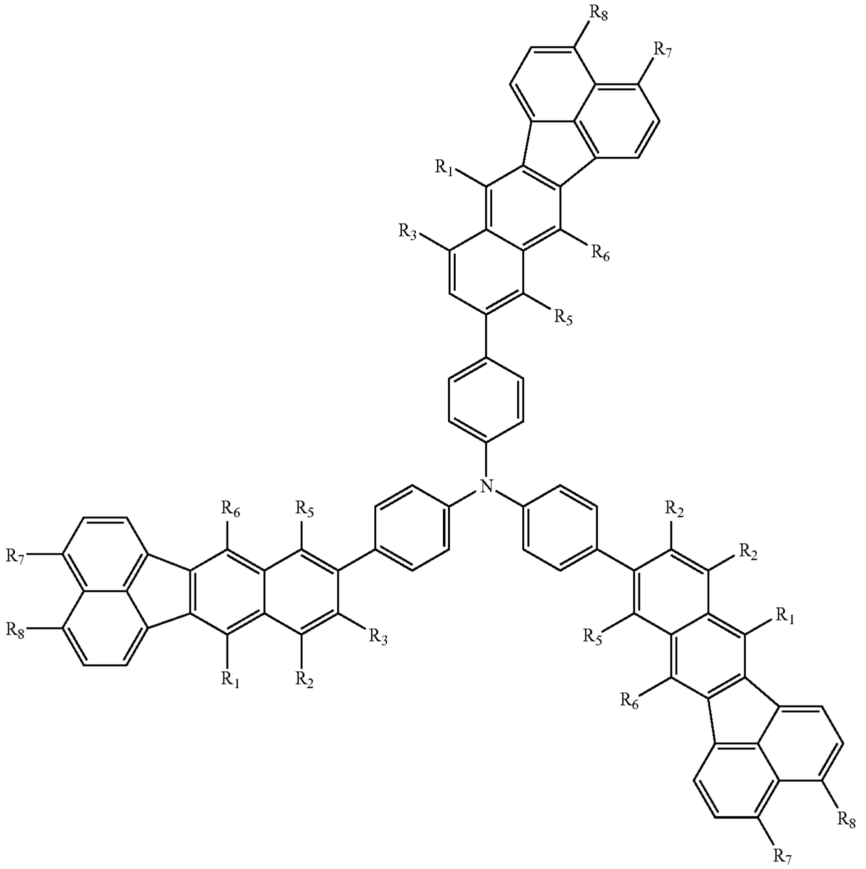

| | $R_1$ | $R_2$ | $R_3$ | $R_5$ | $R_6$ | $R_7$ | $R_8$ |
|---|---|---|---|---|---|---|---|
| U-1 | H | H | H | H | H | H | H |
| U-2 | Ph | H | H | H | Ph | H | H |
| U-3 | Ph | Ph | H | H | Ph | H | H |
| U-4 | Ph | H | H | Ph | Ph | H | H |
| U-5 | Ph | Ph | H | Ph | Ph | H | H |
| U-6 | Ph | H | Ph | H | Ph | H | H |
| U-7 | Ph | H | H | H | Ph | Ph | H |
| U-8 | Ph | H | H | H | Ph | H | Ph |
| U-9 | Ph | H | H | H | Ph | Ph | Ph |
| U-10 | Ph | H | H | H | Ph | 1-naphthyl | H |
| U-11 | Ph | H | H | H | Ph | H | 1-naphthyl |
| U-12 | Ph | H | H | H | Ph | 1-naphthyl | 1-naphthyl |
| U-13 | Ph | H | H | H | Ph | 2-naphthyl | H |
| U-14 | Ph | H | H | H | Ph | H | 2-naphthyl |
| U-15 | Ph | H | H | H | Ph | 2-naphthyl | 2-naphthyl |
| U-16 | Ph | H | H | H | Ph | o-biphenylyl | H |
| U-17 | Ph | H | H | H | Ph | H | o-biphenylyl |
| U-18 | Ph | H | H | H | Ph | o-biphenylyl | o-biphenylyl |
| U-19 | Ph | H | H | H | Ph | m-biphenylyl | H |
| U-20 | Ph | H | H | H | Ph | H | m-biphenylyl |
| U-21 | Ph | H | H | H | Ph | m-biphenylyl | m-biphenylyl |
| U-22 | Ph | H | H | H | Ph | p-biphenylyl | H |
| U-23 | Ph | H | H | H | Ph | H | p-biphenylyl |
| U-24 | Ph | H | H | H | Ph | p-biphenylyl | p-biphenylyl |
| U-25 | 1-naphthyl | H | H | H | 1-naphthyl | H | H |
| U-26 | 1-naphthyl | Ph | H | H | 1-naphthyl | H | H |
| U-27 | 1-naphthyl | H | H | Ph | 1-naphthyl | H | H |
| U-28 | 1-naphthyl | Ph | H | Ph | 1-naphthyl | H | H |
| U-29 | 1-naphthyl | H | Ph | H | 1-naphthyl | H | H |
| U-30 | 1-naphthyl | H | H | H | 1-naphthyl | Ph | H |
| U-31 | 1-naphthyl | H | H | H | 1-naphthyl | H | Ph |
| U-32 | 1-naphthyl | H | H | H | 1-naphthyl | Ph | Ph |
| U-33 | 1-naphthyl | H | H | H | 1-naphthyl | 1-naphthyl | H |
| U-34 | 1-naphthyl | H | H | H | 1-naphthyl | H | 1-naphthyl |
| U-35 | 1-naphthyl | H | H | H | 1-naphthyl | 1-naphthyl | 1-naphthyl |

-continued

| | | | | | | | |
|---|---|---|---|---|---|---|---|
| U-36 | 1-naphthyl | H | H | H | 1-naphthyl | 2-naphthyl | H |
| U-37 | 1-naphthyl | H | H | H | 1-naphthyl | H | 2-naphthyl |
| U-38 | 1-naphthyl | H | H | H | 1-naphthyl | 2-naphthyl | 2-naphthyl |
| U-39 | 1-naphthyl | H | H | H | 1-naphthyl | o-biphenylyl | H |
| U-40 | 1-naphthyl | H | H | H | 1-naphthyl | H | o-biphenylyl |
| U-41 | 1-naphthyl | H | H | H | 1-naphthyl | o-biphenylyl | o-biphenylyl |
| U-42 | 1-naphthyl | H | H | H | 1-naphthyl | m-biphenylyl | H |
| U-43 | 1-naphthyl | H | H | H | 1-naphthyl | H | m-biphenylyl |
| U-44 | 1-naphthyl | H | H | H | 1-naphthyl | m-biphenylyl | m-biphenylyl |
| U-45 | 1-naphthyl | H | H | H | 1-naphthyl | p-biphenylyl | H |
| U-46 | 1-naphthyl | H | H | H | 1-naphthyl | H | p-biphenylyl |
| U-47 | 1-naphthyl | H | H | H | 1-naphthyl | p-biphenylyl | p-biphenylyl |
| U-48 | 2-naphthyl | H | H | H | 2-naphthyl | H | H |
| U-49 | 2-naphthyl | Ph | H | H | 2-naphthyl | H | H |
| U-50 | 2-naphthyl | H | H | Ph | 2-naphthyl | H | H |
| U-51 | 2-naphthyl | Ph | H | Ph | 2-naphthyl | H | H |
| U-52 | 2-naphthyl | H | Ph | H | 2-naphthyl | H | H |
| U-53 | 2-naphthyl | H | H | H | 2-naphthyl | Ph | H |
| U-54 | 2-naphthyl | H | H | H | 2-naphthyl | H | Ph |
| U-55 | 2-naphthyl | H | H | H | 2-naphthyl | Ph | Ph |
| U-56 | 2-naphthyl | H | H | H | 2-naphthyl | 1-naphthyl | H |
| U-57 | 2-naphthyl | H | H | H | 2-naphthyl | H | 1-naphthyl |
| U-58 | 2-naphthyl | H | H | H | 2-naphthyl | 1-naphthyl | 1-naphthyl |
| U-59 | 2-naphthyl | H | H | H | 2-naphthyl | 2-naphthyl | H |
| U-60 | 2-naphthyl | H | H | H | 2-naphthyl | H | 2-naphthyl |
| U-61 | 2-naphthyl | H | H | H | 2-naphthyl | 2-naphthyl | 2-naphthyl |
| U-62 | 2-naphthyl | H | H | H | 2-naphthyl | o-biphenylyl | H |
| U-63 | 2-naphthyl | H | H | H | 2-naphthyl | H | o-biphenylyl |
| U-64 | 2-naphthyl | H | H | H | 2-naphthyl | o-biphenylyl | o-biphenylyl |
| U-65 | 2-naphthyl | H | H | H | 2-naphthyl | m-biphenylyl | H |
| U-66 | 2-naphthyl | H | H | H | 2-naphthyl | H | m-biphenylyl |
| U-67 | 2-naphthyl | H | H | H | 2-naphthyl | m-biphenylyl | m-biphenylyl |
| U-68 | 2-naphthyl | H | H | H | 2-naphthyl | p-biphenylyl | H |
| U-69 | 2-naphthyl | H | H | H | 2-naphthyl | H | p-biphenylyl |
| U-70 | 2-naphthyl | H | H | H | 2-naphthyl | p-biphenylyl | p-biphenylyl |
| U-71 | o-biphenylyl | H | H | H | o-biphenylyl | H | H |
| U-72 | o-biphenylyl | Ph | H | H | o-biphenylyl | H | H |
| U-73 | o-biphenylyl | H | H | Ph | o-biphenylyl | H | H |
| U-74 | o-biphenylyl | Ph | H | Ph | o-biphenylyl | H | H |
| U-75 | o-biphenylyl | H | Ph | H | o-biphenylyl | H | H |
| U-76 | o-biphenylyl | H | H | H | o-biphenylyl | Ph | H |
| U-77 | o-biphenylyl | H | H | H | o-biphenylyl | H | Ph |
| U-78 | o-biphenylyl | H | H | H | o-biphenylyl | Ph | Ph |
| U-79 | o-biphenylyl | H | H | H | o-biphenylyl | 1-naphthyl | H |
| U-80 | o-biphenylyl | H | H | H | o-biphenylyl | H | 1-naphthyl |
| U-81 | o-biphenylyl | H | H | H | o-biphenylyl | 1-naphthyl | 1-naphthyl |
| U-82 | o-biphenylyl | H | H | H | o-biphenylyl | 2-naphthyl | H |
| U-83 | o-biphenylyl | H | H | H | o-biphenylyl | H | 2-naphthyl |
| U-84 | o-biphenylyl | H | H | H | o-biphenylyl | 2-naphthyl | 2-naphthyl |
| U-85 | o-biphenylyl | H | H | H | o-biphenylyl | o-biphenylyl | H |
| U-86 | o-biphenylyl | H | H | H | o-biphenylyl | H | o-biphenylyl |
| U-87 | o-biphenylyl | H | H | H | o-biphenylyl | o-biphenylyl | o-biphenylyl |
| U-88 | o-biphenylyl | H | H | H | o-biphenylyl | m-biphenylyl | H |
| U-89 | o-biphenylyl | H | H | H | o-biphenylyl | H | m-biphenylyl |
| U-90 | o-biphenylyl | H | H | H | o-biphenylyl | m-biphenylyl | m-biphenylyl |
| U-91 | o-biphenylyl | H | H | H | o-biphenylyl | p-biphenylyl | H |
| U-92 | o-biphenylyl | H | H | H | o-biphenylyl | H | p-biphenylyl |
| U-93 | o-biphenylyl | H | H | H | o-biphenylyl | p-biphenylyl | p-biphenylyl |
| U-94 | m-biphenylyl | H | H | H | m-biphenylyl | H | H |
| U-95 | m-biphenylyl | Ph | H | H | m-biphenylyl | H | H |
| U-96 | m-biphenylyl | H | H | Ph | m-biphenylyl | H | H |
| U-97 | m-biphenylyl | Ph | H | Ph | m-biphenylyl | H | H |
| U-98 | m-biphenylyl | H | Ph | H | m-biphenylyl | H | H |
| U-99 | m-biphenylyl | H | H | H | m-biphenylyl | Ph | H |
| U-100 | m-biphenylyl | H | H | H | m-biphenylyl | H | Ph |
| U-101 | m-biphenylyl | H | H | H | m-biphenylyl | Ph | Ph |
| U-102 | m-biphenylyl | H | H | H | m-biphenylyl | 1-naphthyl | H |
| U-103 | m-biphenylyl | H | H | H | m-biphenylyl | H | 1-naphthyl |
| U-104 | m-biphenylyl | H | H | H | m-biphenylyl | 1-naphthyl | 1-naphthyl |
| U-105 | m-biphenylyl | H | H | H | m-biphenylyl | 2-naphthyl | H |
| U-106 | m-biphenylyl | H | H | H | m-biphenylyl | H | 2-naphthyl |
| U-107 | m-biphenylyl | H | H | H | m-biphenylyl | 2-naphthyl | 2-naphthyl |
| U-108 | m-biphenylyl | H | H | H | m-biphenylyl | o-biphenylyl | H |
| U-109 | m-biphenylyl | H | H | H | m-biphenylyl | H | o-biphenylyl |
| U-110 | m-biphenylyl | H | H | H | m-biphenylyl | o-biphenylyl | o-biphenylyl |
| U-111 | m-biphenylyl | H | H | H | m-biphenylyl | m-biphenylyl | H |
| U-112 | m-biphenylyl | H | H | H | m-biphenylyl | H | m-biphenylyl |
| U-113 | m-biphenylyl | H | H | H | m-biphenylyl | m-biphenylyl | m-biphenylyl |
| U-114 | m-biphenylyl | H | H | H | m-biphenylyl | p-biphenylyl | H |

-continued

| | | | | | | | |
|---|---|---|---|---|---|---|---|
| U-115 | m-biphenylyl | H | H | H | m-biphenylyl | H | p-biphenylyl |
| U-116 | m-biphenylyl | H | H | H | m-biphenylyl | p-biphenylyl | p-biphenylyl |
| U-117 | p-biphenylyl | H | H | H | p-biphenylyl | H | H |
| U-118 | p-biphenylyl | Ph | H | H | p-biphenylyl | H | H |
| U-119 | p-biphenylyl | H | H | Ph | p-biphenylyl | H | H |
| U-120 | p-biphenylyl | Ph | H | Ph | p-biphenylyl | H | H |
| U-121 | p-biphenylyl | H | Ph | H | p-biphenylyl | H | H |
| U-122 | p-biphenylyl | H | H | H | p-biphenylyl | Ph | H |
| U-123 | p-biphenylyl | H | H | H | p-biphenylyl | H | Ph |
| U-124 | p-biphenylyl | H | H | H | p-biphenylyl | Ph | Ph |
| U-125 | p-biphenylyl | H | H | H | p-biphenylyl | 1-naphthyl | H |
| U-126 | p-biphenylyl | H | H | H | p-biphenylyl | H | 1-naphthyl |
| U-127 | p-biphenylyl | H | H | H | p-biphenylyl | 1-naphthyl | 1-naphthyl |
| U-128 | p-biphenylyl | H | H | H | p-biphenylyl | 2-naphthyl | H |
| U-129 | p-biphenylyl | H | H | H | p-biphenylyl | H | 2-naphthyl |
| U-130 | p-biphenylyl | H | H | H | p-biphenylyl | 2-naphthyl | 2-naphthyl |
| U-131 | p-biphenylyl | H | H | H | p-biphenylyl | o-biphenylyl | H |
| U-132 | p-biphenylyl | H | H | H | p-biphenylyl | H | o-biphenylyl |
| U-133 | p-biphenylyl | H | H | H | p-biphenylyl | o-biphenylyl | o-biphenylyl |
| U-134 | p-biphenylyl | H | H | H | p-biphenylyl | m-biphenylyl | H |
| U-135 | p-biphenylyl | H | H | H | p-biphenylyl | H | m-biphenylyl |
| U-136 | p-biphenylyl | H | H | H | p-biphenylyl | m-biphenylyl | m-biphenylyl |
| U-137 | p-biphenylyl | H | H | H | p-biphenylyl | p-biphenylyl | H |
| U-138 | p-biphenylyl | H | H | H | p-biphenylyl | H | p-biphenylyl |
| U-139 | p-biphenylyl | H | H | H | p-biphenylyl | p-biphenylyl | p-biphenylyl |
| U-140 | o-tolyl | H | H | H | o-tolyl | H | H |
| U-141 | o-tolyl | Ph | H | Ph | o-tolyl | H | H |
| U-142 | o-tolyl | H | Ph | H | o-tolyl | H | H |
| U-143 | o-tolyl | H | H | H | o-tolyl | Ph | H |
| U-144 | o-tolyl | H | H | H | o-tolyl | H | Ph |
| U-145 | o-tolyl | H | H | H | o-tolyl | H | 1-naphthyl |
| U-146 | o-tolyl | H | H | H | o-tolyl | 1-naphthyl | H |
| U-147 | o-tolyl | H | H | H | o-tolyl | 2-naphthyl | H |
| U-148 | o-tolyl | H | H | H | o-tolyl | H | 2-naphthyl |
| U-149 | o-tolyl | H | H | H | o-tolyl | o-biphenylyl | H |
| U-150 | o-tolyl | H | H | H | o-tolyl | H | o-biphenylyl |
| U-151 | o-tolyl | H | H | H | o-tolyl | m-biphenylyl | H |
| U-152 | o-tolyl | H | H | H | o-tolyl | H | m-biphenylyl |
| U-153 | o-tolyl | H | H | H | o-tolyl | p-biphenylyl | H |
| U-154 | o-tolyl | H | H | H | o-tolyl | H | p-biphenylyl |
| U-155 | o-tolyl | H | H | H | o-tolyl | o-tolyl | H |
| U-156 | o-tolyl | H | H | H | o-tolyl | H | o-tolyl |
| U-157 | m-tolyl | H | H | H | m-tolyl | H | H |
| U-158 | m-tolyl | Ph | H | Ph | m-tolyl | H | H |
| U-159 | m-tolyl | H | Ph | H | m-tolyl | H | H |
| U-160 | m-tolyl | H | H | H | m-tolyl | Ph | H |
| U-161 | m-tolyl | H | H | H | m-tolyl | H | Ph |
| U-162 | m-tolyl | H | H | H | m-tolyl | 1-naphthyl | H |
| U-163 | m-tolyl | H | H | H | m-tolyl | H | 1-naphthyl |
| U-164 | m-tolyl | H | H | H | m-tolyl | 2-naphthyl | H |
| U-165 | m-tolyl | H | H | H | m-tolyl | H | 2-naphthyl |
| U-166 | m-tolyl | H | H | H | m-tolyl | o-biphenylyl | H |
| U-167 | m-tolyl | H | H | H | m-tolyl | H | o-biphenylyl |
| U-168 | m-tolyl | H | H | H | m-tolyl | m-biphenylyl | H |
| U-169 | m-tolyl | H | H | H | m-tolyl | H | m-biphenylyl |
| U-170 | m-tolyl | H | H | H | m-tolyl | p-biphenylyl | H |
| U-171 | m-tolyl | H | H | H | m-tolyl | H | p-biphenylyl |
| U-172 | m-tolyl | H | H | H | m-tolyl | m-tolyl | H |
| U-173 | m-tolyl | H | H | H | m-tolyl | H | m-tolyl |
| U-174 | p-tolyl | H | H | H | p-tolyl | H | H |
| U-175 | p-tolyl | Ph | H | Ph | p-tolyl | H | H |
| U-176 | p-tolyl | H | Ph | H | p-tolyl | H | H |
| U-177 | p-tolyl | H | H | H | p-tolyl | Ph | H |
| U-178 | p-tolyl | H | H | H | p-tolyl | H | Ph |
| U-179 | p-tolyl | H | H | H | p-tolyl | 1-naphthyl | H |
| U-180 | p-tolyl | H | H | H | p-tolyl | H | 1-naphthyl |
| U-181 | p-tolyl | H | H | H | p-tolyl | 2-naphthyl | H |
| U-182 | p-tolyl | H | H | H | p-tolyl | H | 2-naphthyl |
| U-183 | p-tolyl | H | H | H | p-tolyl | o-biphenylyl | H |
| U-184 | p-tolyl | H | H | H | p-tolyl | H | o-biphenylyl |
| U-185 | p-tolyl | H | H | H | p-tolyl | m-biphenylyl | H |
| U-186 | p-tolyl | H | H | H | p-tolyl | H | m-biphenylyl |
| U-187 | p-tolyl | H | H | H | p-tolyl | p-biphenylyl | H |
| U-188 | p-tolyl | H | H | H | p-tolyl | H | p-biphenylyl |
| U-189 | p-tolyl | H | H | H | p-tolyl | p-tolyl | H |
| U-190 | p-tolyl | H | H | H | p-tolyl | H | p-tolyl |
| U-191 | Ph | H | —CH3 | H | Ph | H | H |
| U-192 | 1-naphtyl | H | —CH3 | H | 1-naphtyl | H | H |
| U-193 | 2-naphthyl | H | —CH3 | H | 2-naphthyl | H | H |

-continued

| | | | | | | | |
|---|---|---|---|---|---|---|---|
| U-194 | o-biphenylyl | H | —CH3 | H | o-biphenylyl | H | H |
| U-195 | m-biphenylyl | H | —CH3 | H | m-biphenylyl | H | H |
| U-196 | p-biphenylyl | H | —CH3 | H | p-biphenylyl | H | H |
| U-197 | o-tolyl | H | —CH3 | H | o-tolyl | H | H |
| U-198 | m-tolyl | H | —CH3 | H | m-tolyl | H | H |
| U-199 | p-tolyl | H | —CH3 | H | p-tolyl | H | H |
| U-200 | Ph | H | H | H | Ph | —CH3 | H |
| U-201 | 1-naphtyl | H | H | H | 1-naphtyl | —CH3 | H |
| U-202 | 2-naphthyl | H | H | H | 2-naphthyl | —CH3 | H |
| U-203 | o-biphenylyl | H | H | H | o-biphenylyl | —CH3 | H |
| U-204 | m-biphenylyl | H | H | H | m-biphenylyl | —CH3 | H |
| U-205 | p-biphenylyl | H | H | H | p-biphenylyl | —CH3 | H |
| U-206 | o-tolyl | H | H | H | o-tolyl | —CH3 | H |
| U-207 | m-tolyl | H | H | H | m-tolyl | —CH3 | H |
| U-208 | p-tolyl | H | H | H | p-tolyl | —CH3 | H |
| U-209 | Ph | H | H | H | Ph | H | —CH3 |
| U-210 | 1-naphtyl | H | H | H | 1-naphtyl | H | —CH3 |
| U-211 | 2-naphthyl | H | H | H | 2-naphthyl | H | —CH3 |
| U-212 | o-biphenylyl | H | H | H | o-biphenylyl | H | —CH3 |
| U-213 | m-biphenylyl | H | H | H | m-biphenylyl | H | —CH3 |
| U-214 | p-biphenylyl | H | H | H | p-biphenylyl | H | —CH3 |
| U-215 | o-tolyl | H | H | H | o-tolyl | H | —CH3 |
| U-216 | m-tolyl | H | H | H | m-tolyl | H | —CH3 |
| U-217 | p-tolyl | H | H | H | p-tolyl | H | —CH3 |
| U-218 | Ph | H | H | H | Ph | —CH3 | —CH3 |
| U-219 | 1-naphtyl | H | H | H | 1-naphtyl | —CH3 | —CH3 |
| U-220 | 2-naphthyl | H | H | H | 2-naphthyl | —CH3 | —CH3 |
| U-221 | o-biphenylyl | H | H | H | o-biphenylyl | —CH3 | —CH3 |
| U-222 | m-biphenylyl | H | H | H | m-biphenylyl | —CH3 | —CH3 |
| U-223 | p-biphenylyl | H | H | H | p-biphenylyl | —CH3 | —CH3 |
| U-224 | o-tolyl | H | H | H | o-tolyl | —CH3 | —CH3 |
| U-225 | m-tolyl | H | H | H | m-tolyl | —CH3 | —CH3 |
| U-226 | p-tolyl | H | H | H | p-tolyl | —CH3 | —CH3 |
| U-227 | Ph | H | H | H | Ph | H | DPA |
| U-228 | 1-naphtyl | H | H | H | 1-naphtyl | H | DPA |
| U-229 | 2-naphthyl | H | H | H | 2-naphthyl | H | DPA |
| U-230 | o-biphenylyl | H | H | H | o-biphenylyl | H | DPA |
| U-231 | m-biphenylyl | H | H | H | m-biphenylyl | H | DPA |
| U-232 | p-biphenylyl | H | H | H | p-biphenylyl | H | DPA |
| U-233 | Ph | H | H | H | Ph | DPA | H |
| U-234 | 1-naphtyl | H | H | H | 1-naphtyl | DPA | H |
| U-235 | 2-naphthyl | H | H | H | 2-naphthyl | DPA | H |
| U-236 | o-biphenylyl | H | H | H | o-biphenylyl | DPA | H |
| U-237 | m-biphenylyl | H | H | H | m-biphenylyl | DPA | H |
| U-238 | p-biphenylyl | H | H | H | p-biphenylyl | DPA | H |
| U-239 | Ph | H | H | H | Ph | H | TPA |
| U-240 | 1-naphtyl | H | H | H | 1-naphtyl | H | TPA |
| U-241 | 2-naphthyl | H | H | H | 2-naphthyl | H | TPA |
| U-242 | o-biphenylyl | H | H | H | o-biphenylyl | H | TPA |
| U-243 | m-biphenylyl | H | H | H | m-biphenylyl | H | TPA |
| U-244 | p-biphenylyl | H | H | H | p-biphenylyl | H | TPA |
| U-245 | Ph | H | H | H | Ph | TPA | H |
| U-246 | 1-naphtyl | H | H | H | 1-naphtyl | TPA | H |
| U-247 | 2-naphthyl | H | H | H | 2-naphthyl | TPA | H |
| U-248 | o-biphenylyl | H | H | H | o-biphenylyl | TPA | H |
| U-249 | m-biphenylyl | H | H | H | m-biphenylyl | TPA | H |
| U-250 | p-biphenylyl | H | H | H | p-biphenylyl | TPA | H |
| U-251 | Ph | H | H | H | 1-naphthyl | H | H |
| U-252 | Ph | H | H | H | 2-naphthyl | H | H |
| U-253 | Ph | H | H | H | o-biphenylyl | H | H |
| U-254 | Ph | H | H | H | m-biphenylyl | H | H |
| U-255 | Ph | H | H | H | p-biphenylyl | H | H |
| U-256 | Ph | H | H | H | O-tolyly | H | H |
| U-257 | Ph | H | H | H | m-tolyl | H | H |
| U-258 | Ph | H | H | H | p-tolyl | H | H |
| U-259 | 1-naphthyl | H | H | H | 2-naphthyl | H | H |
| U-260 | 1-naphthyl | H | H | H | o-biphenylyl | H | H |
| U-261 | 1-naphthyl | H | H | H | m-biphenylyl | H | H |
| U-262 | 1-naphthyl | H | H | H | p-biphenylyl | H | H |
| U-263 | 1-naphthyl | H | H | H | O-tolyly | H | H |
| U-264 | 1-naphthyl | H | H | H | m-tolyl | H | H |
| U-265 | 1-naphthyl | H | H | H | p-tolyl | H | H |
| U-266 | 2-naphthyl | H | H | H | o-biphenylyl | H | H |
| U-267 | 2-naphthyl | H | H | H | m-biphenylyl | H | H |
| U-268 | 2-naphthyl | H | H | H | p-biphenylyl | H | H |
| U-269 | 2-naphthyl | H | H | H | O-tolyly | H | H |
| U-270 | 2-naphthyl | H | H | H | m-tolyl | H | H |
| U-271 | 2-naphthyl | H | H | H | p-tolyl | H | H |
| U-272 | o-biphenylyl | H | H | H | m-biphenylyl | H | H |

-continued

| | | | | | | | |
|---|---|---|---|---|---|---|---|
| U-273 | o-biphenylyl | H | H | H | p-biphenylyl | H | H |
| U-274 | o-biphenylyl | H | H | H | O-tolyly | H | H |
| U-275 | o-biphenylyl | H | H | H | m-tolyl | H | H |
| U-276 | o-biphenylyl | H | H | H | p-tolyl | H | H |
| U-277 | m-biphenylyl | H | H | H | p-biphenylyl | H | H |
| U-278 | m-biphenylyl | H | H | H | O-tolyly | H | H |
| U-279 | m-biphenylyl | H | H | H | m-tolyl | H | H |
| U-280 | m-biphenylyl | H | H | H | p-tolyl | H | H |
| U-281 | p-biphenylyl | H | H | H | O-tolyly | H | H |
| U-282 | p-biphenylyl | H | H | H | m-tolyl | H | H |
| U-283 | p-biphenylyl | H | H | H | p-tolyl | H | H |
| U-284 | O-tolyly | H | H | H | m-tolyl | H | H |
| U-285 | O-tolyly | H | H | H | p-tolyl | H | H |
| U-286 | m-tolyly | H | H | H | p-tolyl | H | H |

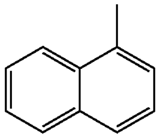

1-naphthyl

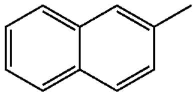

2-naphthyl

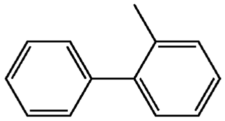

o-biphenylyl

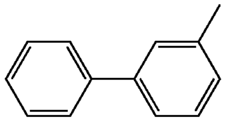

m-biphenylyl

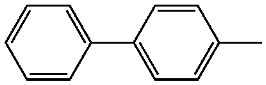

p-biphenylyl

-continued
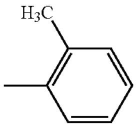
o-tolyl
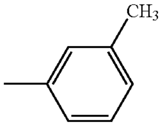
m-tolyl
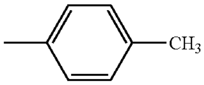
p-tolyl
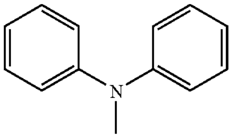
DPA
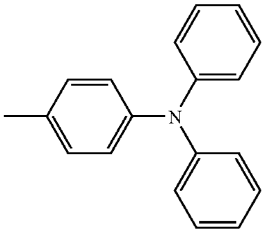
TPA

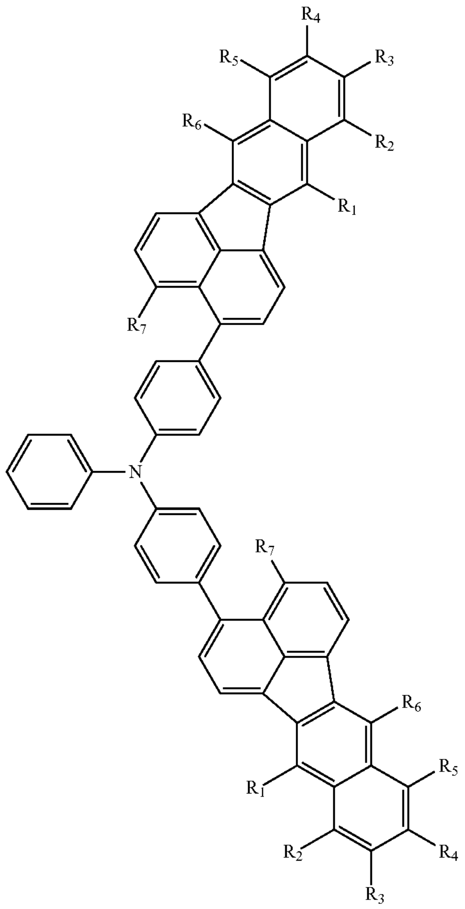
TypeV
| | $R_1$ | $R_2$ | $R_3$ | $R_4$ | $R_5$ | $R_6$ | $R_7$ |
|---|---|---|---|---|---|---|---|
| V-1 | H | H | H | H | H | H | H |
| V-2 | Ph | H | H | H | H | Ph | H |

-continued
| | | | | | | | |
|---|---|---|---|---|---|---|---|
| V-3 | Ph | Ph | H | H | Ph | Ph | H |
| V-4 | Ph | H | Ph | Ph | H | Ph | H |
| V-5 | Ph | H | Ph | H | H | Ph | H |
| V-6 | Ph | H | H | H | H | Ph | Ph |
| V-7 | Ph | Me | H | H | Me | Ph | H |
| V-8 | Ph | H | Me | Me | H | Ph | H |
| V-9 | Ph | H | H | H | H | Ph | Me |
| V-10 | 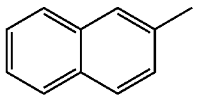 | H | H | H | H | 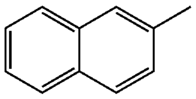 | H |
| V-11 | 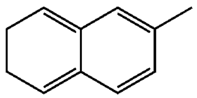 | Ph | H | H | Ph | 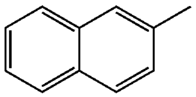 | H |
| V-12 | 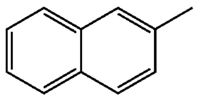 | H | Ph | Ph | H | 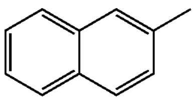 | H |
| V-13 | 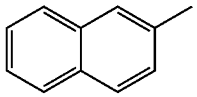 | H | Ph | H | H | 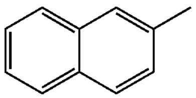 | H |
| V-14 | 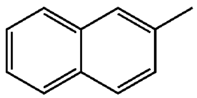 | H | H | H | H | 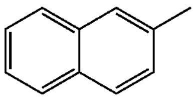 | Ph |
| V-15 | 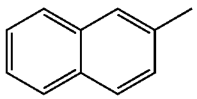 | Me | H | H | Me | 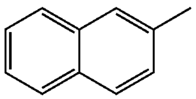 | H |
| V-16 | 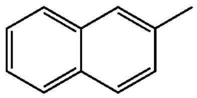 | H | Me | Me | H | 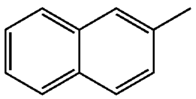 | H |
| V-17 | 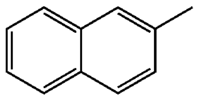 | H | H | H | H | 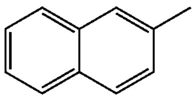 | Me |

-continued
| | | | | | | | |
|---|---|---|---|---|---|---|---|
| V-18 | 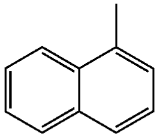 | H | H | H | H | 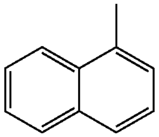 | H |
| V-19 | 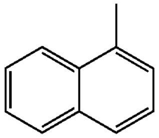 | Ph | H | H | Ph | 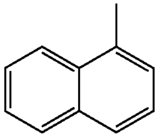 | H |
| V-20 | 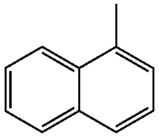 | H | Ph | Ph | H | 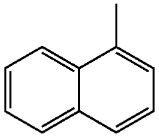 | H |
| V-21 | 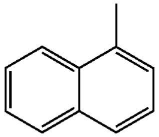 | H | Ph | H | H | 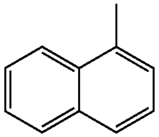 | H |
| V-22 | 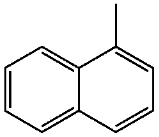 | H | H | H | H | 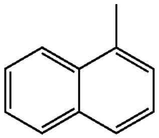 | Ph |
| V-23 | 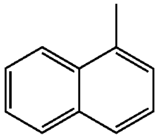 | Me | H | H | Me | 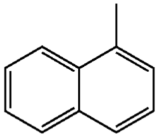 | H |
| V-24 | 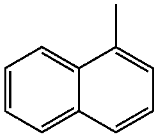 | H | Me | Me | H | 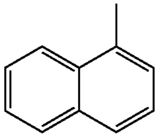 | H |

-continued
| | | | | | | | |
|---|---|---|---|---|---|---|---|
| V-25 | 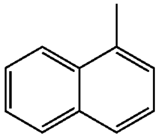 | H | H | H | H | 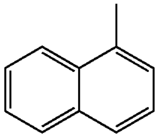 | Me |
| V-26 | 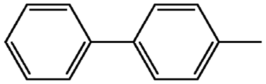 | H | H | H | H | 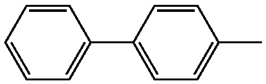 | H |
| V-27 | 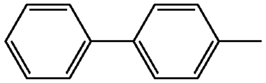 | Ph | H | H | Ph | 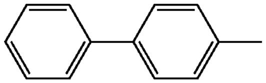 | H |
| V-28 | 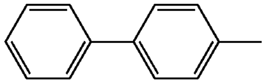 | H | Ph | Ph | H | 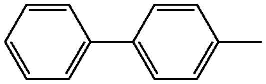 | H |
| V-29 | 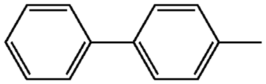 | H | Ph | H | H | 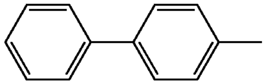 | H |
| V-30 | 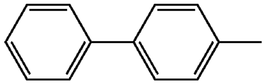 | H | H | H | H | 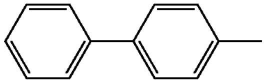 | Ph |
| V-31 | 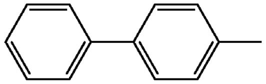 | Me | H | H | Me | 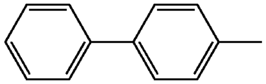 | H |
| V-32 | 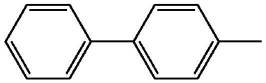 | H | Me | Me | H | 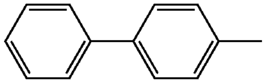 | H |
| V-33 | 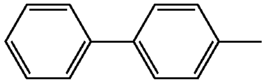 | H | H | H | H | 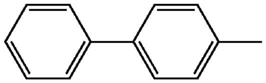 | Me |
| V-34 | 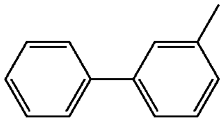 | H | H | H | H | 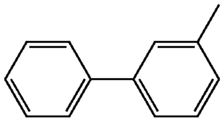 | H |

-continued
| | | | | | | | |
|---|---|---|---|---|---|---|---|
| V-35 | 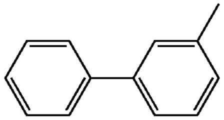 | Ph | H | H | Ph | 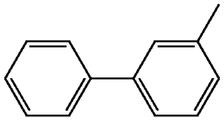 | H |
| V-36 | 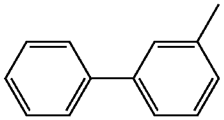 | H | Ph | Ph | H | 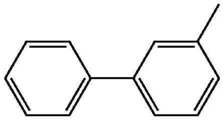 | H |
| V-37 | 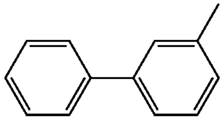 | H | Ph | H | H | 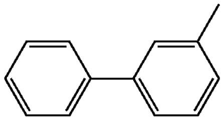 | H |
| V-38 | 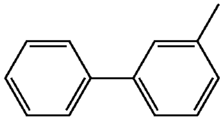 | H | H | H | H | 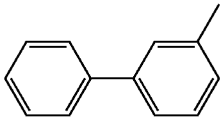 | Ph |
| V-39 | 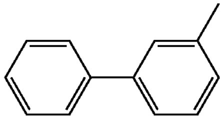 | Me | H | H | Me | 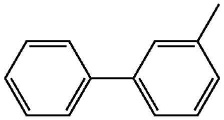 | H |
| V-40 | 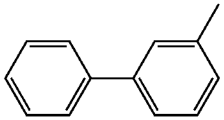 | H | Me | Me | H | 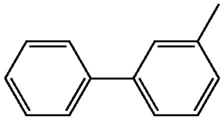 | H |
| V-41 | 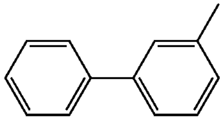 | H | H | H | H | 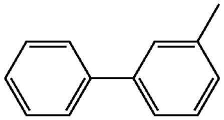 | Me |

-continued
| | | | | | | | |
|---|---|---|---|---|---|---|---|
| V-42 | 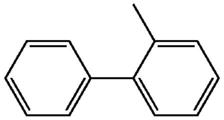 | H | H | H | H | 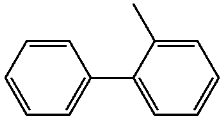 | H |
| V-43 | 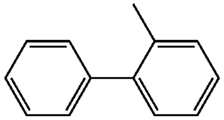 | Ph | H | H | Ph | 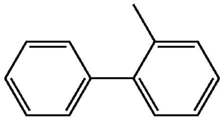 | H |
| V-44 | 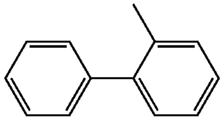 | H | Ph | Ph | H | 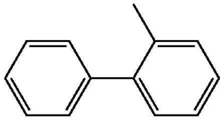 | H |
| V-45 | 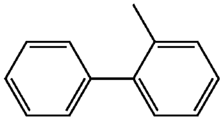 | H | Ph | H | H | 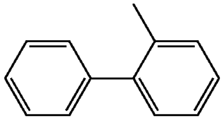 | H |
| V-46 | 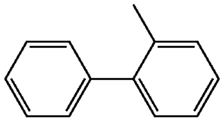 | H | H | H | H | 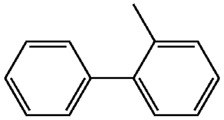 | Ph |
| V-47 | 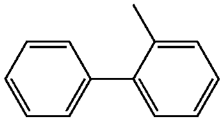 | Me | H | H | Me | 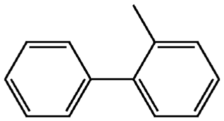 | H |
| V-48 | 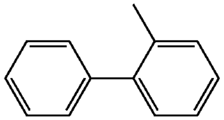 | H | Me | Me | H | 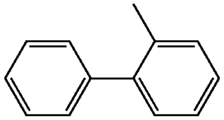 | H |
| V-49 | 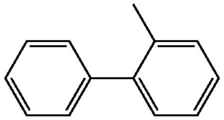 | H | H | H | H | 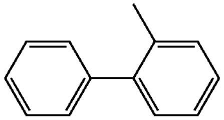 | Me |

-continued
| | | | | | | | |
|---|---|---|---|---|---|---|---|
| V-50 | Ph | H | H | H | H | 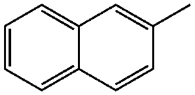 | H |
| V-51 | Ph | H | H | H | H | 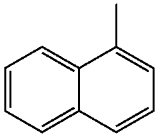 | H |
| V-52 | Ph | H | H | H | H | 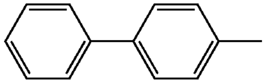 | H |
| V-53 | Ph | H | H | H | H | 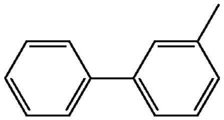 | H |
| V-54 | Ph | H | H | H | H | 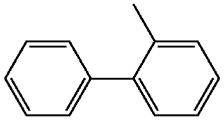 | H |
| V-55 | 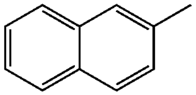 | H | H | H | H | 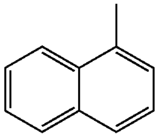 | H |
| V-56 | 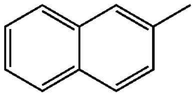 | H | H | H | H | 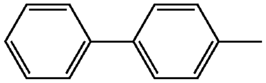 | H |
| V-57 | 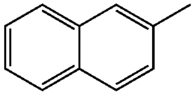 | H | H | H | H | 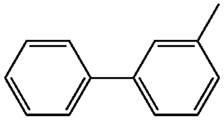 | H |

-continued
| | | | | | | | |
|---|---|---|---|---|---|---|---|
| V-58 | 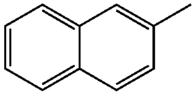 | H | H | H | H | 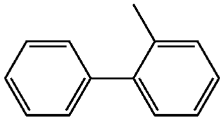 | H |
| V-59 | 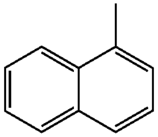 | H | H | H | H | 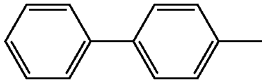 | H |
| V-60 | 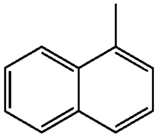 | H | H | H | H | 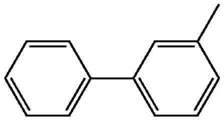 | H |
| V-61 | 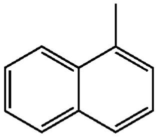 | H | H | H | H | 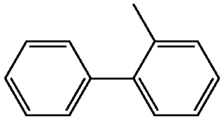 | H |
| V-62 | 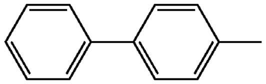 | H | H | H | H | 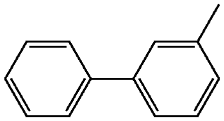 | H |
| V-63 | 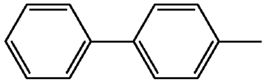 | H | H | H | H | 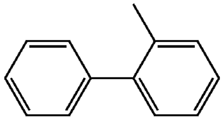 | H |
| V-64 | 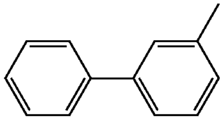 | H | H | H | H | 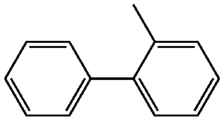 | H |
| V-65 | H | Ph | H | H | Ph | H | H |

-continued
| | | | | | | | |
|---|---|---|---|---|---|---|---|
| V-66 | H | 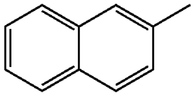 | H | H | 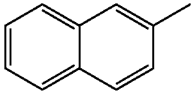 | H | H |
| V-67 | H | 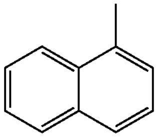 | H | H | 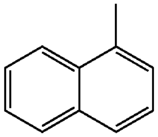 | H | H |
| V-68 | H | 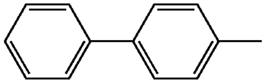 | H | H | 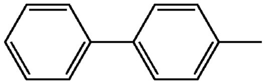 | H | H |
| V-69 | H | 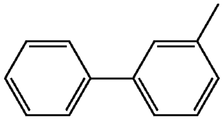 | H | H | 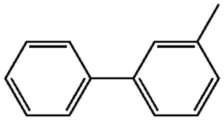 | H | H |
| V-70 | H | 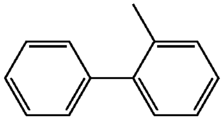 | H | H | 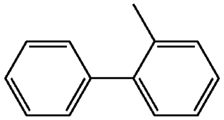 | H | H |
| V-71 | H | H | 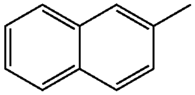 | 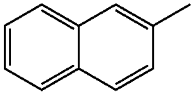 | H | H | H |
| V-72 | H | H | 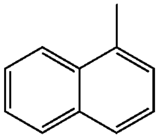 | 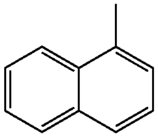 | H | H | H |
| V-73 | H | H | 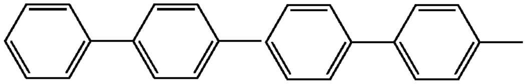 | | H | H | H |

-continued
| | | | | | | | |
|---|---|---|---|---|---|---|---|
| V-74 | H | H | 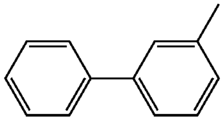 | 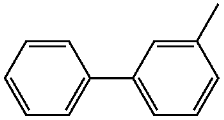 | H | H | H |
| V-75 | H | H | 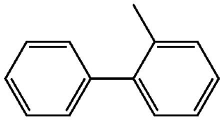 | 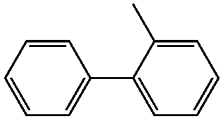 | H | H | H |
| V-76 | 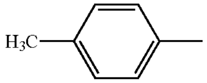 | H | H | H | H | 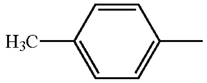 | H |
| V-77 | 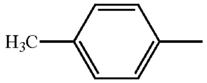 | Ph | H | H | Ph | 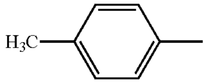 | H |
| V-78 | 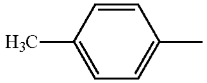 | H | Ph | Ph | H | 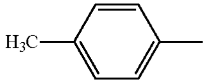 | H |
| V-79 | 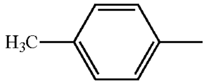 | H | Ph | H | H | 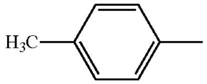 | H |
| V-80 | 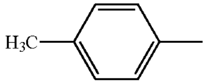 | H | H | H | H | 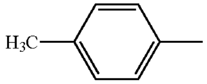 | Ph |
| V-81 | 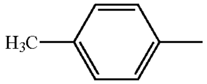 | Me | H | H | Me | 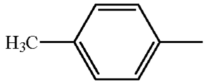 | H |
| V-82 | 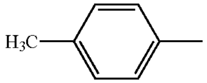 | H | Me | Me | H | 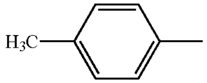 | H |
| V-83 | 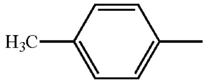 | H | H | H | H | 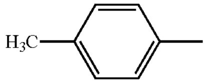 | Me |

-continued
| | | | | | | | |
|---|---|---|---|---|---|---|---|
| V-84 | 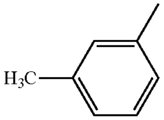 | H | H | H | H | 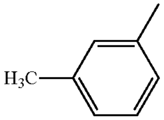 | H |
| V-85 | 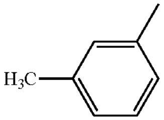 | Ph | H | H | Ph | 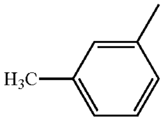 | H |
| V-86 | 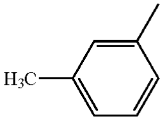 | H | Ph | Ph | H | 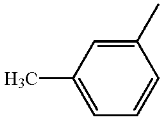 | H |
| V-87 | 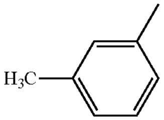 | H | Ph | H | H | 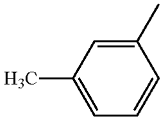 | H |
| V-88 | 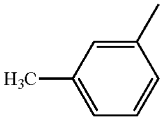 | H | H | H | H | 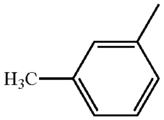 | Ph |
| V-89 | 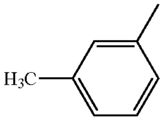 | Me | H | H | Me | 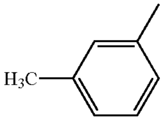 | H |
| V-90 | 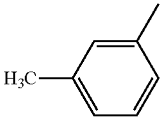 | H | Me | Me | H | 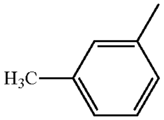 | H |
| V-91 | 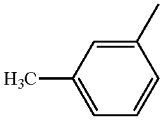 | H | H | H | H | 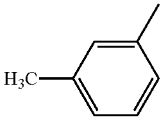 | Me |

-continued
| | | | | | | | |
|---|---|---|---|---|---|---|---|
| V-92 | 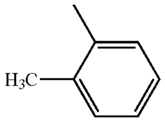 | H | H | H | H | 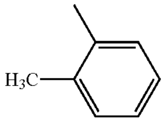 | H |
| V-93 | 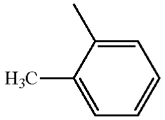 | Ph | H | H | Ph | 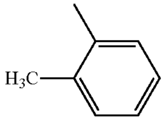 | H |
| V-94 | 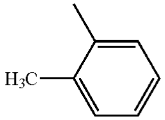 | H | Ph | Ph | H | 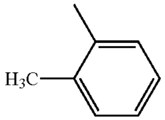 | H |
| V-95 | 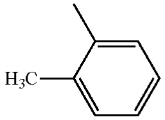 | H | Ph | H | H | 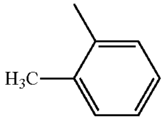 | H |
| V-96 | 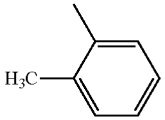 | H | H | H | H | 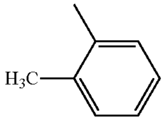 | Ph |
| V-97 | 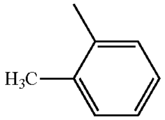 | Me | H | H | Me | 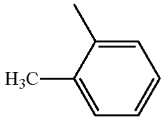 | H |
| V-98 | 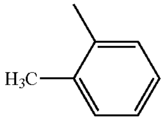 | H | Me | Me | H | 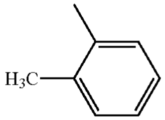 | H |

-continued
| | | | | | | | |
|---|---|---|---|---|---|---|---|
| V-99 | 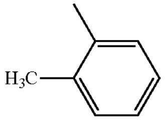 | H | H | H | H | 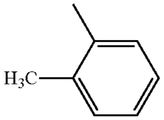 | Me |
| 100 | 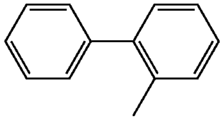 | H | H | H | H | 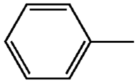 | H |
| 101 | 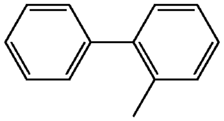 | Ph | H | H | Ph | 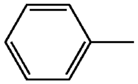 | H |
| 102 | 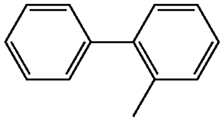 | H | Ph | Ph | H | 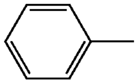 | H |
| 103 | 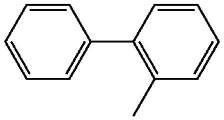 | H | Ph | H | H | 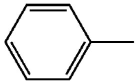 | H |
| 104 | 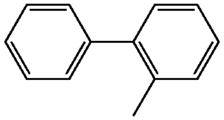 | H | H | H | H | 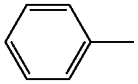 | Ph |
| 105 | 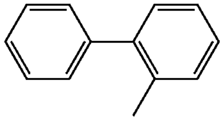 | Me | H | H | Me | 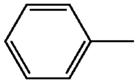 | H |
| 106 | 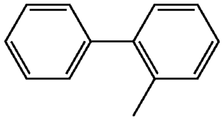 | H | Me | Me | H | 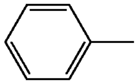 | H |

-continued
| | | | | | | | |
|---|---|---|---|---|---|---|---|
| 107 | 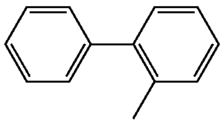 | H | H | H | H | 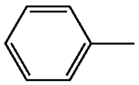 | Me |
| 108 | 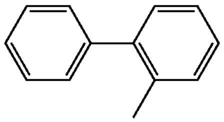 | H | H | H | H | 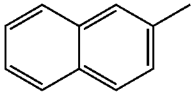 | H |
| 109 | 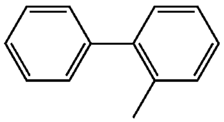 | Ph | H | H | Ph | 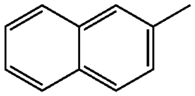 | H |
| 110 | 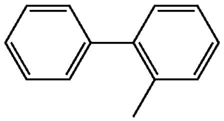 | H | Ph | Ph | H | 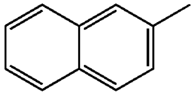 | H |
| 111 | 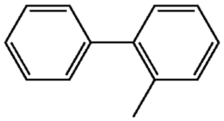 | H | Ph | H | H | 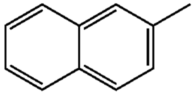 | H |
| 112 | 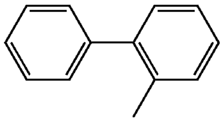 | H | H | H | H | 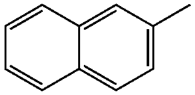 | Ph |
| 113 | 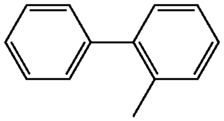 | Me | H | H | Me | 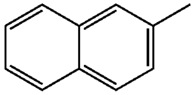 | H |

-continued
| | | | | | | | |
|---|---|---|---|---|---|---|---|
| 114 | 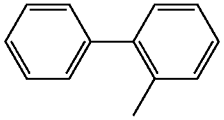 | H | Me | Me | H | 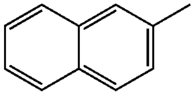 | H |
| 115 | 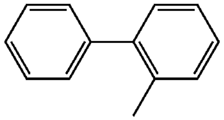 | H | H | H | H | 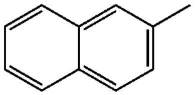 | Me |
| 116 | 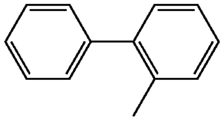 | H | H | H | H | 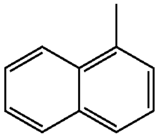 | H |
| 117 | 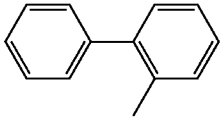 | Ph | H | H | Ph | 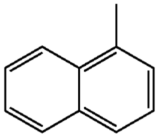 | H |
| 118 | 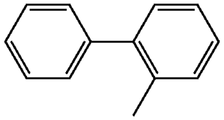 | H | Ph | Ph | H | 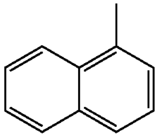 | H |
| 119 | 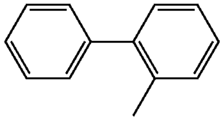 | H | Ph | H | H | 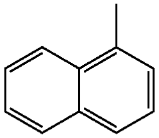 | H |
| 120 | 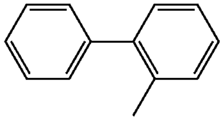 | H | H | H | H | 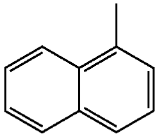 | Ph |

-continued
| | | | | | | | |
|---|---|---|---|---|---|---|---|
| 121 | 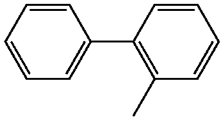 | Me | H | H | Me | 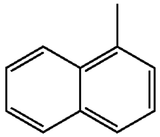 | H |
| 122 | 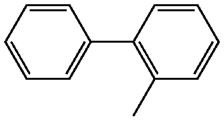 | H | Me | Me | H | 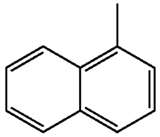 | H |
| 123 | 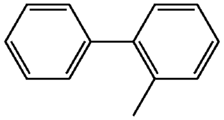 | H | H | H | H | 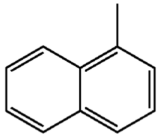 | Me |
| 124 | 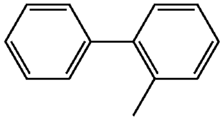 | H | H | H | H | 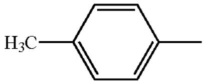 | H |
| 125 | 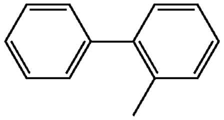 | Ph | H | H | Ph | 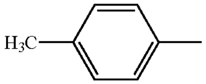 | H |
| 126 | 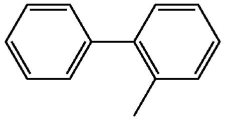 | H | Ph | Ph | H | 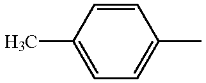 | H |
| 127 | 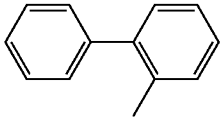 | H | Ph | H | H | 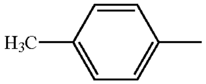 | H |

-continued
| | | | | | | | |
|---|---|---|---|---|---|---|---|
| 128 | 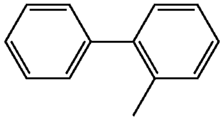 | H | H | H | H | 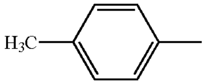 | Ph |
| 129 | 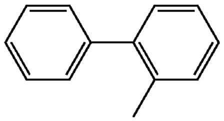 | Me | H | H | Me | 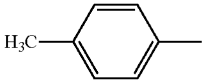 | H |
| 130 | 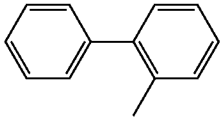 | H | Me | Me | H | 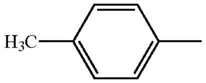 | H |
| 131 | 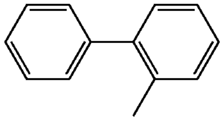 | H | H | H | H | 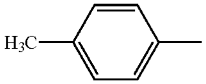 | Me |
| 132 | 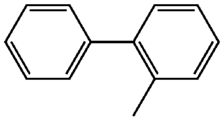 | H | H | H | H | 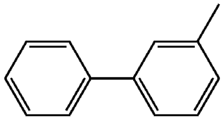 | H |
| 133 | 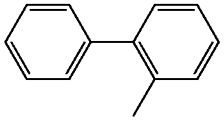 | Ph | H | H | Ph | 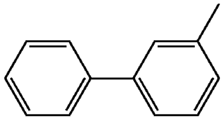 | H |
| 134 | 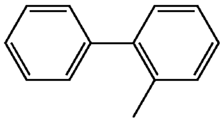 | H | Ph | Ph | H | 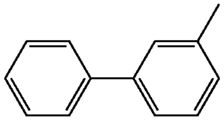 | H |
| 135 | 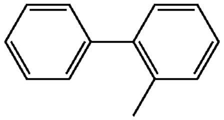 | H | Ph | H | H | 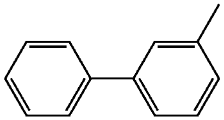 | H |

-continued
| | | | | | | | |
|---|---|---|---|---|---|---|---|
| 136 | 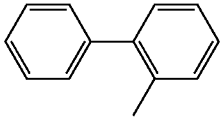 | H | H | H | H | 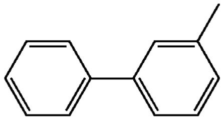 | Ph |
| 137 | 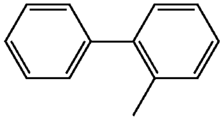 | Me | H | H | Me | 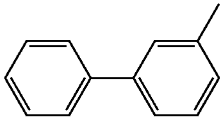 | H |
| 138 | 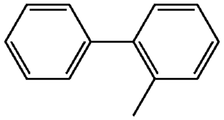 | H | Me | Me | H | 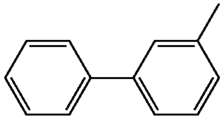 | H |
| 139 | 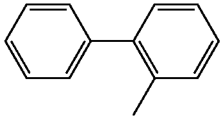 | H | H | H | H | 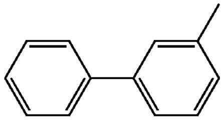 | Me |
| 140 | 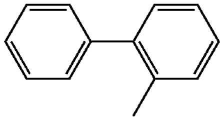 | H | H | H | H | 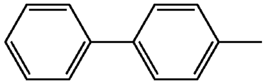 | H |
| 141 | 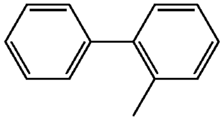 | Ph | H | H | Ph | 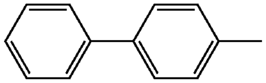 | H |

-continued
| | | | | | | |
|---|---|---|---|---|---|---|
| 142 | 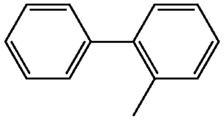 | H | Ph | Ph | H | 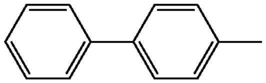 H |
| 143 | 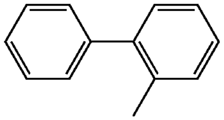 | H | Ph | H | H | 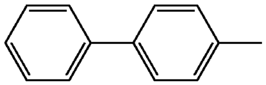 H |
| 144 | 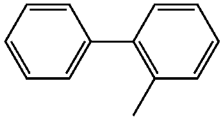 | H | H | H | H | 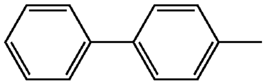 Ph |
| 145 | 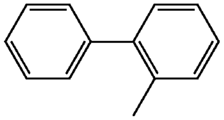 | Me | H | H | Me | 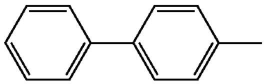 H |
| 146 | 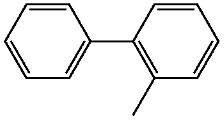 | H | Me | Me | H | 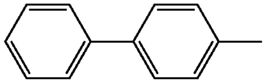 H |
| 147 | 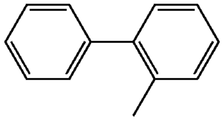 | H | H | H | H | 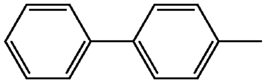 Me |

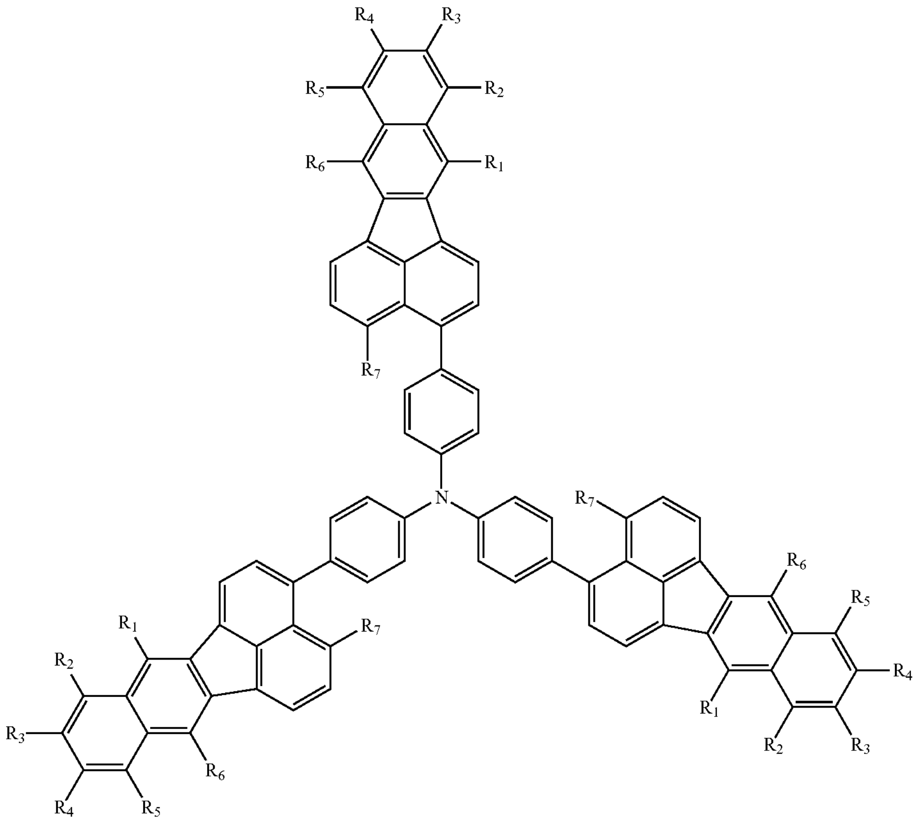
TypeW
| | $R_1$ | $R_2$ | $R_3$ | $R_4$ | $R_5$ | $R_6$ | $R_7$ |
|---|---|---|---|---|---|---|---|
| W-1 | H | H | H | H | H | H | H |
| W-2 | Ph | H | H | H | H | Ph | H |
| W-3 | Ph | Ph | H | H | Ph | Ph | H |
| W-4 | Ph | H | Ph | Ph | H | Ph | H |
| W-5 | Ph | H | Ph | H | H | Ph | H |
| W-6 | Ph | H | H | H | H | Ph | Ph |
| W-7 | Ph | Me | H | H | Me | Ph | H |
| W-8 | Ph | H | Me | Me | H | Ph | H |

-continued
| | | | | | | | |
|---|---|---|---|---|---|---|---|
| W-9 | Ph | H | H | H | H | Ph | Me |
| W-10 | 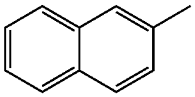 | H | H | H | H | 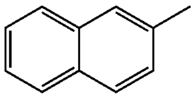 | H |
| W-11 | 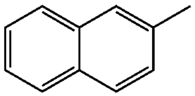 | Ph | H | H | Ph | 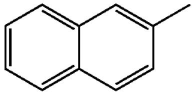 | H |
| W-12 | 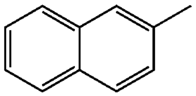 | H | Ph | Ph | H | 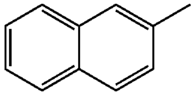 | H |
| W-13 | 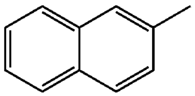 | H | Ph | H | H | 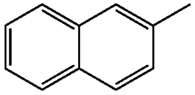 | H |
| W-14 | 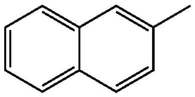 | H | H | H | H | 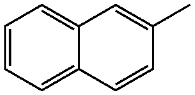 | Ph |
| W-15 | 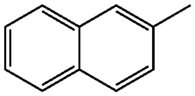 | Me | H | H | Me | 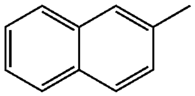 | H |
| W-16 | 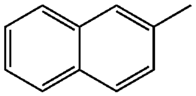 | H | Me | Me | H | 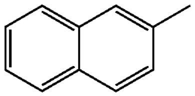 | H |
| W-17 | 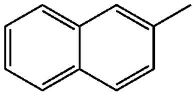 | H | H | H | H | 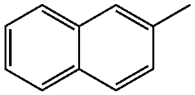 | Me |
| W-18 | 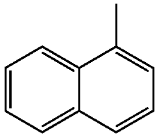 | H | H | H | H | 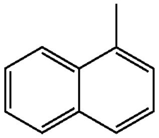 | H |

-continued
| | | | | | | | |
|---|---|---|---|---|---|---|---|
| W-19 | 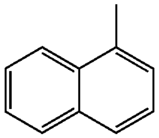 | Ph | H | H | Ph | 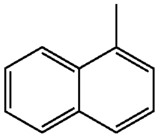 | H |
| W-20 | 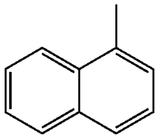 | H | Ph | Ph | H | 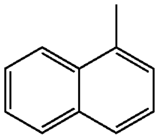 | H |
| W-21 | 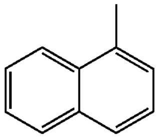 | H | Ph | H | H | 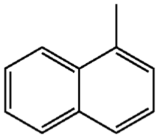 | H |
| W-22 | 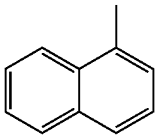 | H | H | H | H | 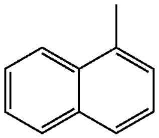 | Ph |
| W-23 | 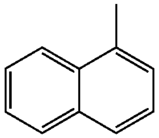 | Me | H | H | Me | 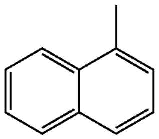 | H |
| W-24 | 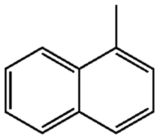 | H | Me | Me | H | 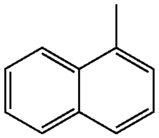 | H |
| W-25 | 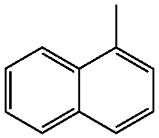 | H | H | H | H | 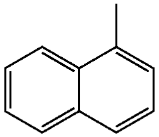 | Me |

-continued
| | | | | | | | |
|---|---|---|---|---|---|---|---|
| W-26 | 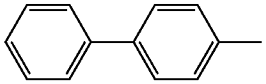 | H | H | H | H | 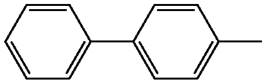 | H |
| W-27 | 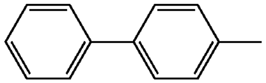 | Ph | H | H | Ph | 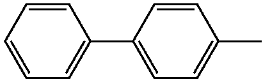 | H |
| W-28 | 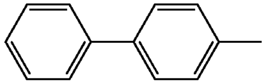 | H | Ph | Ph | H | 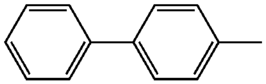 | H |
| W-29 | 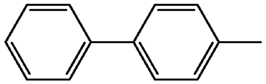 | H | Ph | H | H | 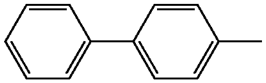 | H |
| W-30 | 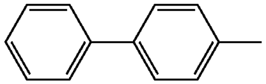 | H | H | H | H | 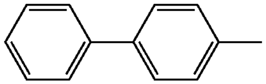 | Ph |
| W-31 | 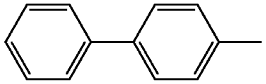 | Me | H | H | Me | 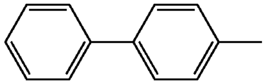 | H |
| W-32 | 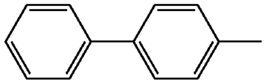 | H | Me | Me | H | 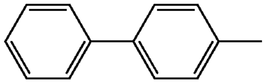 | H |
| W-33 | 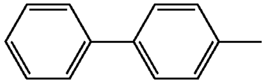 | H | H | H | H | 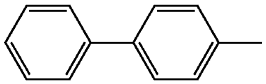 | Me |
| W-34 | 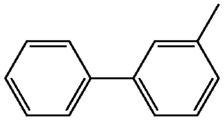 | H | H | H | H | 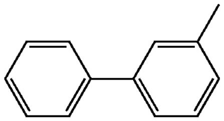 | H |

-continued
| | | | | | | | |
|---|---|---|---|---|---|---|---|
| W-35 | 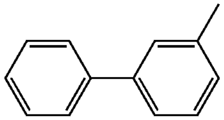 | Ph | H | H | Ph | 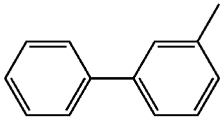 | H |
| W-36 | 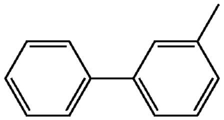 | H | Ph | Ph | H | 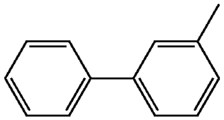 | H |
| W-37 | 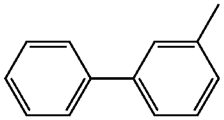 | H | Ph | H | H | 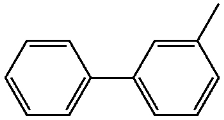 | H |
| W-38 | 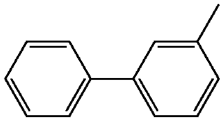 | H | H | H | H | 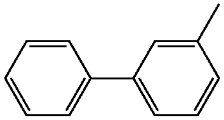 | Ph |
| W-39 | 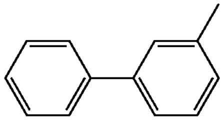 | Me | H | H | Me | 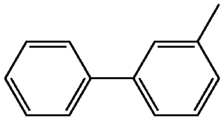 | H |
| W-40 | 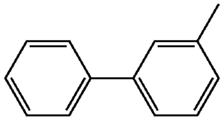 | H | Me | Me | H | 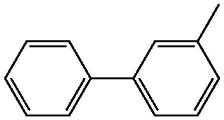 | H |
| W-41 | 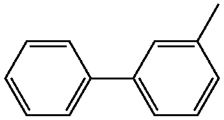 | H | H | H | H | 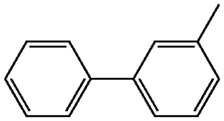 | Me |
| W-42 | 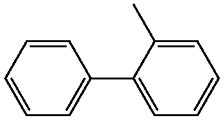 | H | H | H | H | 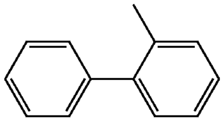 | H |

-continued
| | | | | | | | |
|---|---|---|---|---|---|---|---|
| W-43 | 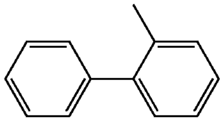 | Ph | H | H | Ph | 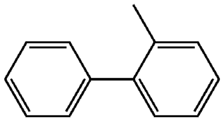 | H |
| W-44 | 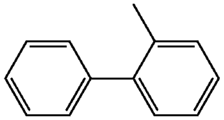 | H | Ph | Ph | H | 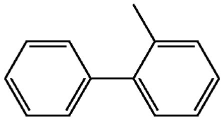 | H |
| W-45 | 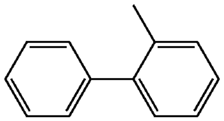 | H | Ph | H | H | 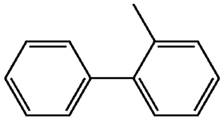 | H |
| W-46 | 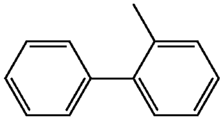 | H | H | H | H | 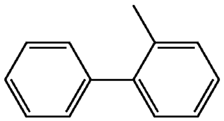 | Ph |
| W-47 | 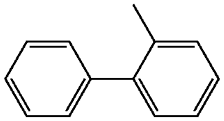 | Me | H | H | Me | 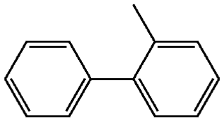 | H |
| W-48 | 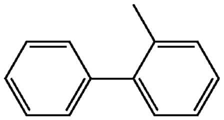 | H | Me | Me | H | 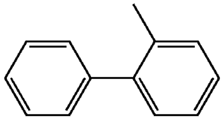 | H |
| W-49 | 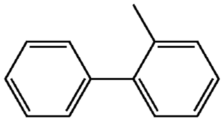 | H | H | H | H | 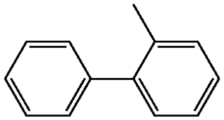 | Me |
| W-50 | Ph | H | H | H | H | 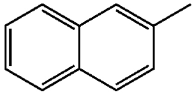 | H |

-continued
| | | | | | | | |
|---|---|---|---|---|---|---|---|
| W-51 | Ph | H | H | H | H | 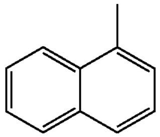 | H |
| W-52 | Ph | H | H | H | H | 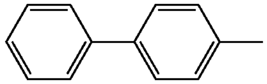 | H |
| W-53 | Ph | H | H | H | H | 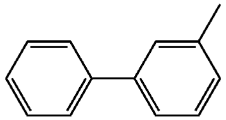 | H |
| W-54 | Ph | H | H | H | H | 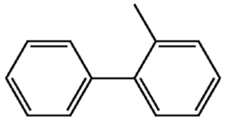 | H |
| W-55 | 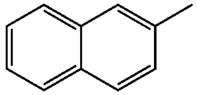 | H | H | H | H | 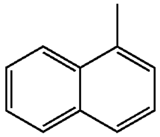 | H |
| W-56 | 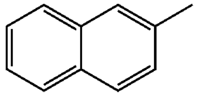 | H | H | H | H | 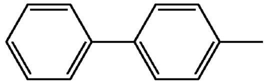 | H |
| W-57 | 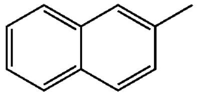 | H | H | H | H | 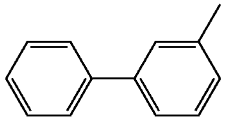 | H |
| W-58 | 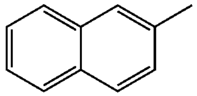 | H | H | H | H | 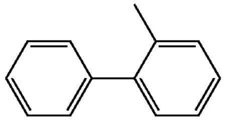 | H |

-continued
| | | | | | | | |
|---|---|---|---|---|---|---|---|
| W-59 | 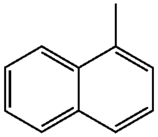 | H | H | H | H | 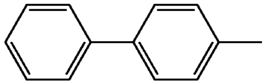 | H |
| W-60 | 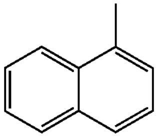 | H | H | H | H | 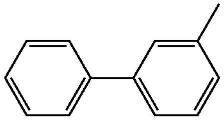 | H |
| W-61 | 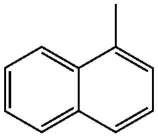 | H | H | H | H | 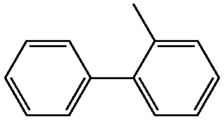 | H |
| W-62 | 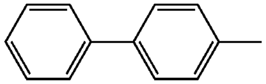 | H | H | H | H | 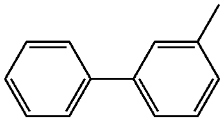 | H |
| W-63 | 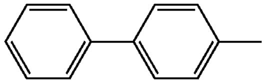 | H | H | H | H | 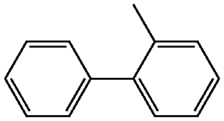 | H |
| W-64 | 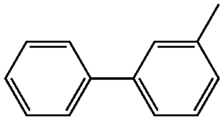 | H | H | H | H | 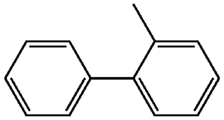 | H |
| W-65 | H | Ph | H | H | Ph | H | H |
| W-66 | H | 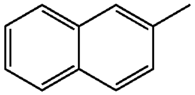 | H | H | 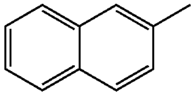 | H | H |

-continued
| | | | | | | | |
|---|---|---|---|---|---|---|---|
| W-67 | H | 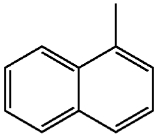 | H | H | 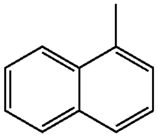 | H | H |
| W-68 | H | 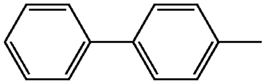 | H | H | 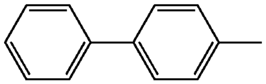 | H | H |
| W-69 | H | 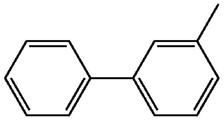 | H | H | 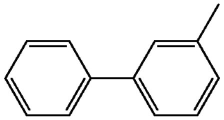 | H | H |
| W-70 | H | 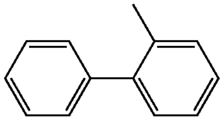 | H | H | 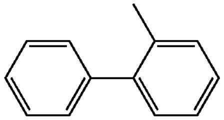 | H | H |
| W-71 | H | H | 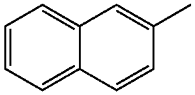 | 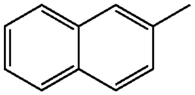 | H | H | H |
| W-72 | H | H | 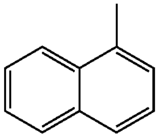 | 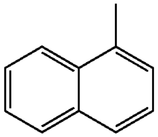 | H | H | H |
| W-73 | H | H | 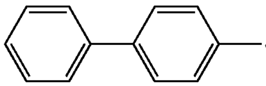 | 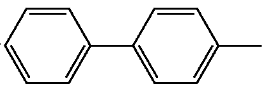 | H | H | H |
| W-74 | H | H | 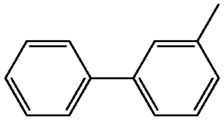 | 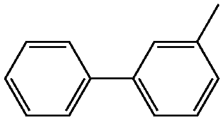 | H | H | H |

-continued
| | | | | | | | |
|---|---|---|---|---|---|---|---|
| W-75 | H | H | 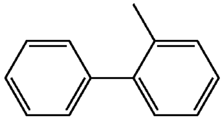 | 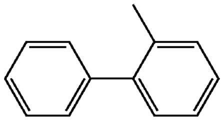 | H | H | H |
| W-76 | 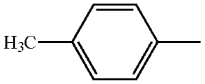 | H | H | H | H | 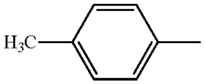 | H |
| W-77 | 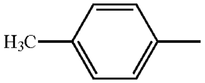 | Ph | H | H | Ph | 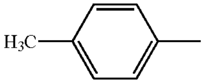 | H |
| W-78 | 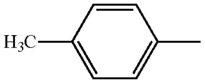 | H | Ph | Ph | H | 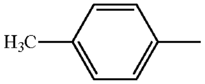 | H |
| W-79 | 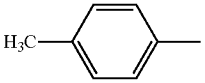 | H | Ph | H | H | 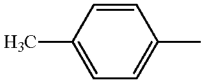 | H |
| W-80 | 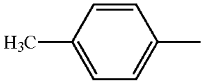 | H | H | H | H | 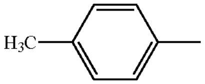 | Ph |
| W-81 | 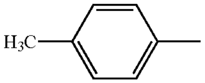 | Me | H | H | Me | 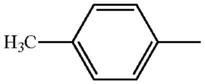 | H |
| W-82 | 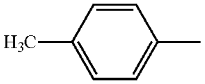 | H | Me | Me | H | 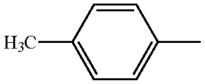 | H |
| W-83 | 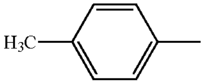 | H | H | H | H | 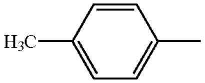 | Me |
| W-84 | 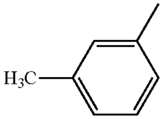 | H | H | H | H | 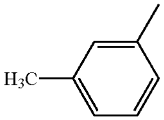 | H |

-continued
| | | | | | | | |
|---|---|---|---|---|---|---|---|
| W-85 | 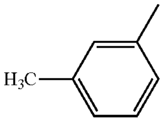 | Ph | H | H | Ph | 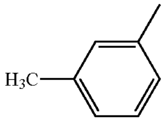 | H |
| W-86 | 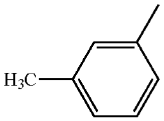 | H | Ph | Ph | H | 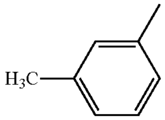 | H |
| W-87 | 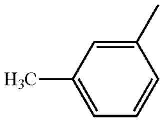 | H | Ph | H | H | 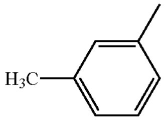 | H |
| W-88 | 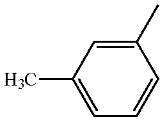 | H | H | H | H | 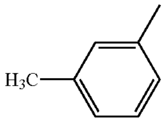 | Ph |
| W-89 | 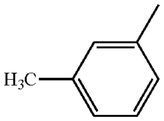 | Me | H | H | Me | 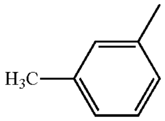 | H |
| W-90 | 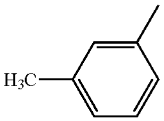 | H | Me | Me | H | 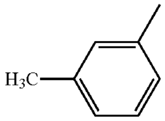 | H |
| W-91 | 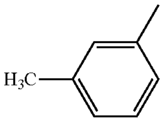 | H | H | H | H | 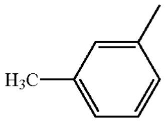 | Me |

-continued
| | | | | | | | |
|---|---|---|---|---|---|---|---|
| W-92 | 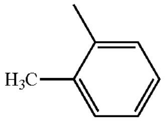 | H | H | H | H | 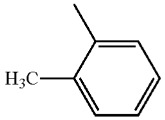 | H |
| W-93 | 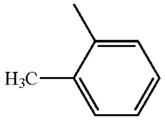 | Ph | H | H | Ph | 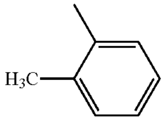 | H |
| W-94 | 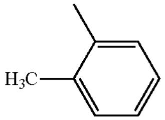 | H | Ph | Ph | H | 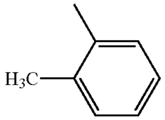 | H |
| W-96 | 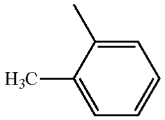 | H | Ph | H | H | 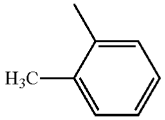 | H |
| W-96 | 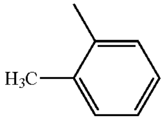 | H | H | H | H | 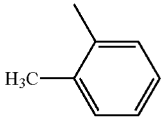 | Ph |
| W-97 | 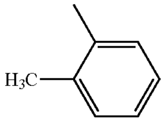 | Me | H | H | Me | 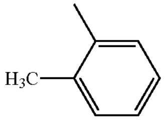 | H |
| W-98 | 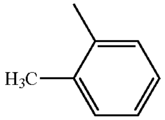 | H | Me | Me | H | 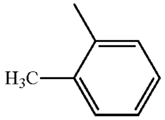 | H |
| W-99 | 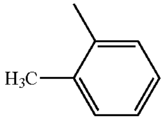 | H | H | H | H | 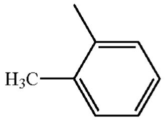 | Me |

-continued
| | | | | | | | |
|---|---|---|---|---|---|---|---|
| 100 | 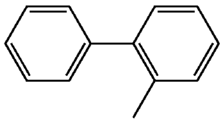 | H | H | H | H | 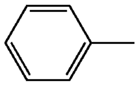 | H |
| 101 | 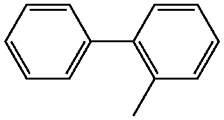 | Ph | H | H | Ph | 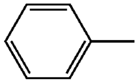 | H |
| 102 | 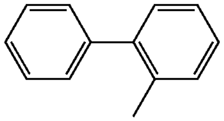 | H | Ph | Ph | H | 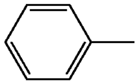 | H |
| 103 | 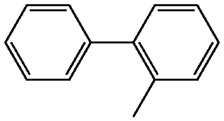 | H | Ph | H | H | 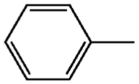 | H |
| 104 | 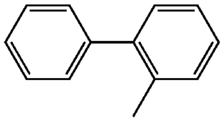 | H | H | H | H | 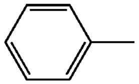 | Ph |
| 105 | 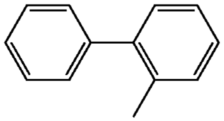 | Me | H | H | Me | 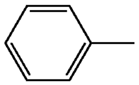 | H |
| 106 | 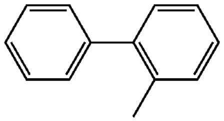 | H | Me | Me | H | 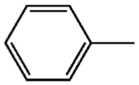 | H |

-continued
| | | | | | | | |
|---|---|---|---|---|---|---|---|
| 107 | 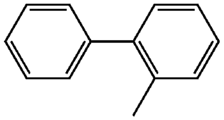 | H | H | H | H | 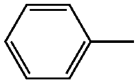 | Me |
| 108 | 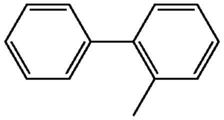 | H | H | H | H | 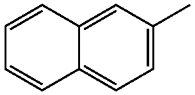 | H |
| 109 | 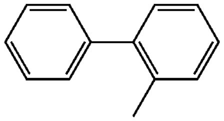 | Ph | H | H | Ph | 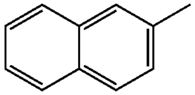 | H |
| 110 | 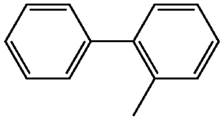 | H | Ph | Ph | H | 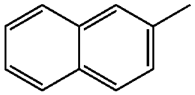 | H |
| 111 | 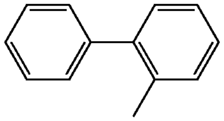 | H | Ph | H | H | 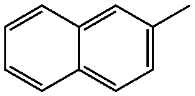 | H |
| 112 | 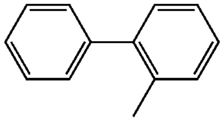 | H | H | H | H | 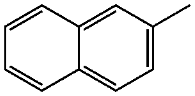 | Ph |
| 113 | 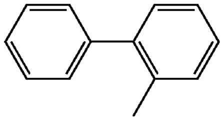 | Me | H | H | Me | 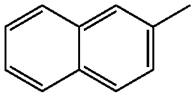 | H |
| 114 | 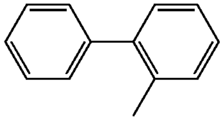 | H | Me | Me | H | 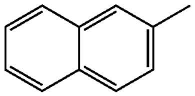 | H |

-continued
| | | | | | | | |
|---|---|---|---|---|---|---|---|
| 115 | 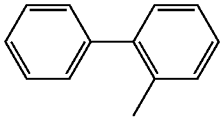 | H | H | H | H | 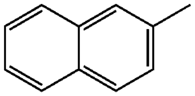 | Me |
| 116 | 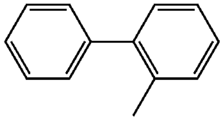 | H | H | H | H | 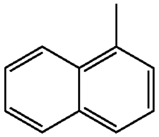 | H |
| 117 | 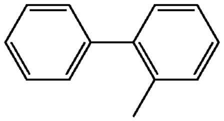 | Ph | H | H | Ph | 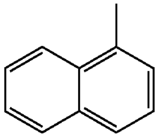 | H |
| 118 | 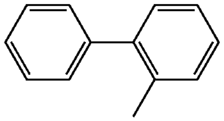 | H | Ph | Ph | H | 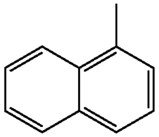 | H |
| 119 | 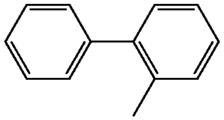 | H | Ph | H | H | 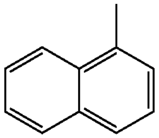 | H |
| 120 | 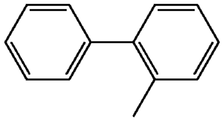 | H | H | H | H | 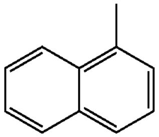 | Ph |
| 121 | 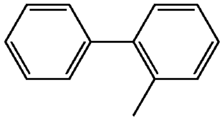 | Me | H | H | Me | 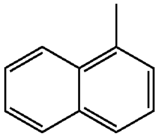 | H |

-continued
| | | | | | | | |
|---|---|---|---|---|---|---|---|
| 122 | 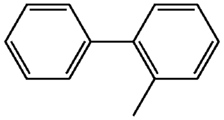 | H | Me | Me | H | 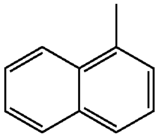 | H |
| 123 | 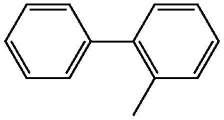 | H | H | H | H | 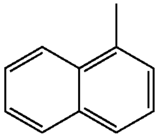 | Me |
| 124 | 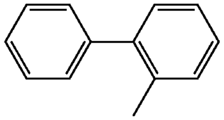 | H | H | H | H | 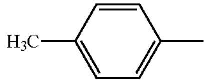 | H |
| 125 | 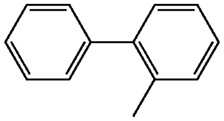 | Ph | H | H | Ph | 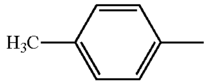 | H |
| 126 | 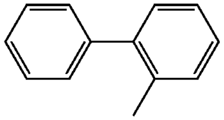 | H | Ph | Ph | H | 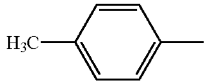 | H |
| 127 | 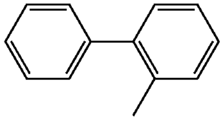 | H | Ph | H | H | 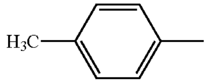 | H |
| 128 | 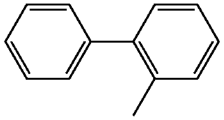 | H | H | H | H | 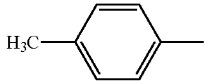 | Ph |

-continued
| | | | | | | | |
|---|---|---|---|---|---|---|---|
| 129 | 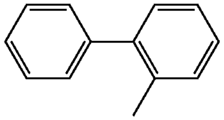 | Me | H | H | Me | 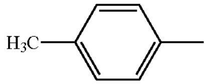 | H |
| 130 | 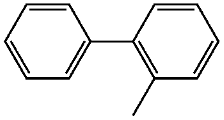 | H | Me | Me | H | 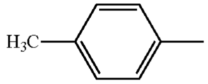 | H |
| 131 | 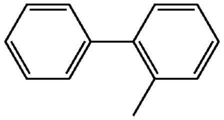 | H | H | H | H | 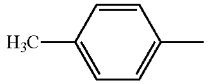 | Me |
| 132 | 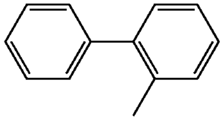 | H | H | H | H | 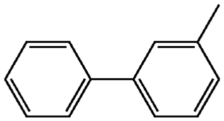 | H |
| 133 | 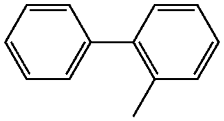 | Ph | H | H | Ph | 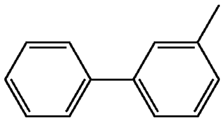 | H |
| 134 | 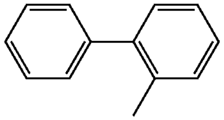 | H | Ph | Ph | H | 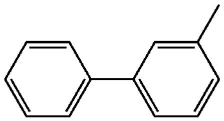 | H |
| 135 | 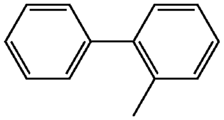 | H | Ph | H | H | 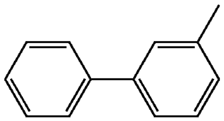 | H |
| 136 | 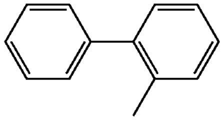 | H | H | H | H | 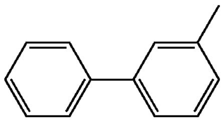 | Ph |

-continued
| | | | | | | | |
|---|---|---|---|---|---|---|---|
| 137 | 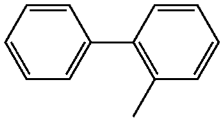 | Me | H | H | Me | 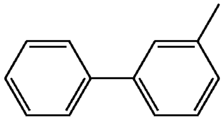 | H |
| 138 | 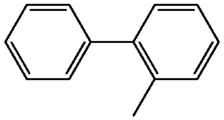 | H | Me | Me | H | 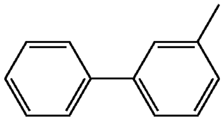 | H |
| 139 | 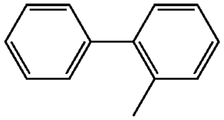 | H | H | H | H | 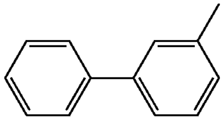 | Me |
| 140 | 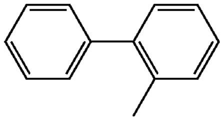 | H | H | H | H | 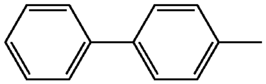 | H |
| 141 | 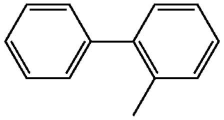 | Ph | H | H | Ph | 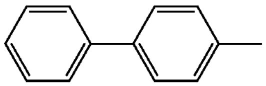 | H |
| 142 | 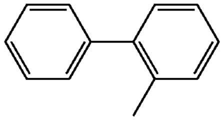 | H | Ph | Ph | H | 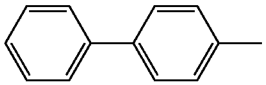 | H |

-continued
| | | | | | | | |
|---|---|---|---|---|---|---|---|
| 143 | 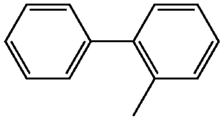 | H | Ph | H | H | 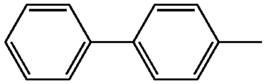 | H |
| 144 | 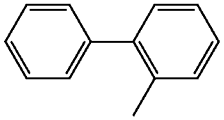 | H | H | H | H | 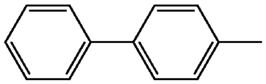 | Ph |
| 145 | 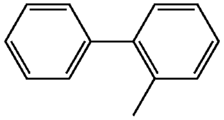 | Me | H | H | Me | 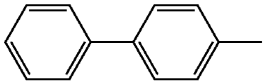 | H |
| 146 | 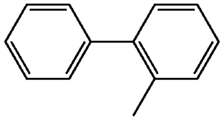 | H | Me | Me | H | 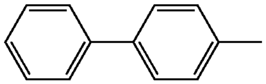 | H |
| 147 | 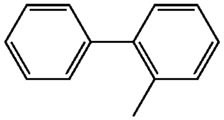 | H | H | H | H | 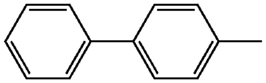 | Me |

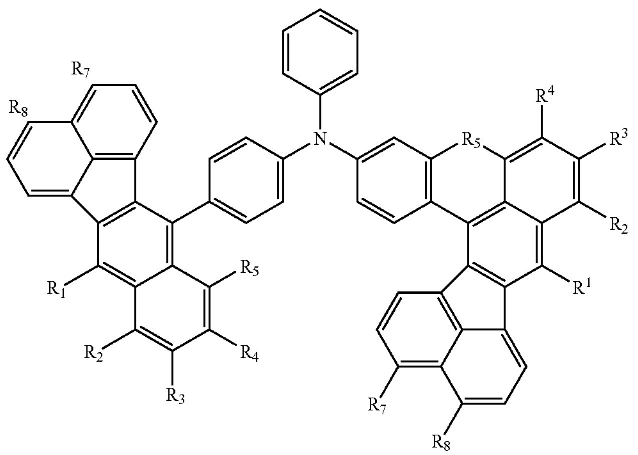

Type X

| | $R_1$ | $R_2$ | $R_3$ | $R_4$ | $R_5$ | $R_7$ | $R_8$ |
|---|---|---|---|---|---|---|---|
| X-1 | H | H | H | H | H | H | H |
| X-2 | Ph | H | H | H | H | H | H |
| X-3 | Ph | Ph | H | H | Ph | H | H |
| X-4 | Ph | H | Ph | Ph | H | H | H |
| X-5 | Ph | H | Ph | H | H | H | H |
| X-6 | Ph | H | H | Ph | H | H | H |
| X-7 | Ph | H | H | H | H | Ph | H |
| X-8 | Ph | H | H | H | H | H | Ph |
| X-9 | Ph | H | H | H | H | Ph | Ph |
| X-10 | Ph | H | H | H | H | 1-naphthyl | H |
| X-11 | Ph | H | H | H | H | H | 1-naphthyl |
| X-12 | Ph | H | H | H | H | 1-naphthyl | 1-naphthyl |
| X-13 | Ph | H | H | H | H | 2-naphthyl | H |
| X-14 | Ph | H | H | H | H | H | 2-naphthyl |
| X-15 | Ph | H | H | H | H | 2-naphthyl | 2-naphthyl |
| X-16 | Ph | H | H | H | H | o-biphenylyl | H |
| X-17 | Ph | H | H | H | H | H | o-biphenylyl |
| X-18 | Ph | H | H | H | H | o-biphenylyl | o-biphenylyl |
| X-19 | Ph | H | H | H | H | m-biphenylyl | H |
| X-20 | Ph | H | H | H | H | H | m-biphenylyl |
| X-21 | Ph | H | H | H | H | m-biphenylyl | m-biphenylyl |
| X-22 | Ph | H | H | H | H | p-biphenylyl | H |
| X-23 | Ph | H | H | H | H | H | p-biphenylyl |
| X-24 | Ph | H | H | H | H | p-biphenylyl | p-biphenylyl |
| X-25 | 1-naphthyl | H | H | H | H | H | H |
| X-26 | 1-naphthyl | Ph | H | H | Ph | H | H |
| X-27 | 1-naphthyl | H | Ph | Ph | H | H | H |
| X-28 | 1-naphthyl | H | Ph | H | H | H | H |
| X-29 | 1-naphthyl | H | H | Ph | H | H | H |
| X-30 | 1-naphthyl | H | H | H | H | Ph | H |
| X-31 | 1-naphthyl | H | H | H | H | H | Ph |
| X-32 | 1-naphthyl | H | H | H | H | Ph | Ph |
| X-33 | 1-naphthyl | H | H | H | H | 1-naphthyl | H |
| X-34 | 1-naphthyl | H | H | H | H | H | 1-naphthyl |
| X-35 | 1-naphthyl | H | H | H | H | 1-naphthyl | 1-naphthyl |
| X-36 | 1-naphthyl | H | H | H | H | 2-naphthyl | H |
| X-37 | 1-naphthyl | H | H | H | H | H | 2-naphthyl |
| X-38 | 1-naphthyl | H | H | H | H | 2-naphthyl | 2-naphthyl |
| X-39 | 1-naphthyl | H | H | H | H | o-biphenylyl | H |
| X-40 | 1-naphthyl | H | H | H | H | H | o-biphenylyl |
| X-41 | 1-naphthyl | H | H | H | H | o-biphenylyl | o-biphenylyl |
| X-42 | 1-naphthyl | H | H | H | H | m-biphenylyl | H |
| X-43 | 1-naphthyl | H | H | H | H | H | m-biphenylyl |
| X-44 | 1-naphthyl | H | H | H | H | m-biphenylyl | m-biphenylyl |
| X-45 | 1-naphthyl | H | H | H | H | p-biphenylyl | H |
| X-46 | 1-naphthyl | H | H | H | H | H | p-biphenylyl |
| X-47 | 1-naphthyl | H | H | H | H | p-biphenylyl | p-biphenylyl |
| X-48 | 2-naphthyl | H | H | H | H | H | H |
| X-49 | 2-naphthyl | Ph | H | H | Ph | H | H |
| X-50 | 2-naphthyl | H | Ph | Ph | H | H | H |
| X-51 | 2-naphthyl | H | Ph | H | H | H | H |
| X-52 | 2-naphthyl | H | H | Ph | H | H | H |

-continued

| | | | | | | | |
|---|---|---|---|---|---|---|---|
| X-53 | 2-naphthyl | H | H | H | H | Ph | H |
| X-54 | 2-naphthyl | H | H | H | H | H | Ph |
| X-55 | 2-naphthyl | H | H | H | H | Ph | Ph |
| X-56 | 2-naphthyl | H | H | H | H | 1-naphthyl | H |
| X-57 | 2-naphthyl | H | H | H | H | H | 1-naphthyl |
| X-58 | 2-naphthyl | H | H | H | H | 1-naphthyl | 1-naphthyl |
| X-59 | 2-naphthyl | H | H | H | H | 2-naphthyl | H |
| X-60 | 2-naphthyl | H | H | H | H | H | 2-naphthyl |
| X-61 | 2-naphthyl | H | H | H | H | 2-naphthyl | 2-naphthyl |
| X-62 | 2-naphthyl | H | H | H | H | o-biphenylyl | H |
| X-63 | 2-naphthyl | H | H | H | H | H | o-biphenylyl |
| X-64 | 2-naphthyl | H | H | H | H | o-biphenylyl | o-biphenylyl |
| X-65 | 2-naphthyl | H | H | H | H | m-biphenylyl | H |
| X-66 | 2-naphthyl | H | H | H | H | H | m-biphenylyl |
| X-67 | 2-naphthyl | H | H | H | H | m-biphenylyl | m-biphenylyl |
| X-68 | 2-naphthyl | H | H | H | H | p-biphenylyl | H |
| X-69 | 2-naphthyl | H | H | H | H | H | p-biphenylyl |
| X-70 | 2-naphthyl | H | H | H | H | p-biphenylyl | p-biphenylyl |
| X-71 | o-biphenylyl | H | H | H | H | H | H |
| X-72 | o-biphenylyl | Ph | H | H | Ph | H | H |
| X-73 | o-biphenylyl | H | Ph | Ph | H | H | H |
| X-74 | o-biphenylyl | H | Ph | H | H | H | H |
| X-75 | o-biphenylyl | H | H | Ph | H | H | H |
| X-76 | o-biphenylyl | H | H | H | H | Ph | H |
| X-77 | o-biphenylyl | H | H | H | H | H | Ph |
| X-78 | o-biphenylyl | H | H | H | H | Ph | Ph |
| X-79 | o-biphenylyl | H | H | H | H | 1-naphthyl | H |
| X-80 | o-biphenylyl | H | H | H | H | H | 1-naphthyl |
| X-81 | o-biphenylyl | H | H | H | H | 1-naphthyl | 1-naphthyl |
| X-82 | o-biphenylyl | H | H | H | H | 2-naphthyl | H |
| X-83 | o-biphenylyl | H | H | H | H | H | 2-naphthyl |
| X-84 | o-biphenylyl | H | H | H | H | 2-naphthyl | 2-naphthyl |
| X-85 | o-biphenylyl | H | H | H | H | o-biphenylyl | H |
| X-86 | o-biphenylyl | H | H | H | H | H | o-biphenylyl |
| X-87 | o-biphenylyl | H | H | H | H | o-biphenylyl | o-biphenylyl |
| X-88 | o-biphenylyl | H | H | H | H | m-biphenylyl | H |
| X-89 | o-biphenylyl | H | H | H | H | H | m-biphenylyl |
| X-90 | o-biphenylyl | H | H | H | H | m-biphenylyl | m-biphenylyl |
| X-91 | o-biphenylyl | H | H | H | H | p-biphenylyl | H |
| X-92 | o-biphenylyl | H | H | H | H | H | p-biphenylyl |
| X-93 | o-biphenylyl | H | H | H | H | p-biphenylyl | p-biphenylyl |
| X-94 | m-biphenylyl | H | H | H | H | H | H |
| X-95 | m-biphenylyl | Ph | H | H | Ph | H | H |
| X-96 | m-biphenylyl | H | Ph | Ph | H | H | H |
| X-97 | m-biphenylyl | H | Ph | H | H | H | H |
| X-98 | m-biphenylyl | H | H | Ph | H | H | H |
| X-99 | m-biphenylyl | H | H | H | H | Ph | H |
| X-100 | m-biphenylyl | H | H | H | H | H | Ph |
| X-101 | m-biphenylyl | H | H | H | H | Ph | Ph |
| X-102 | m-biphenylyl | H | H | H | H | 1-naphthyl | H |
| X-103 | m-biphenylyl | H | H | H | H | H | 1-naphthyl |
| X-104 | m-biphenylyl | H | H | H | H | 1-naphthyl | 1-naphthyl |
| X-105 | m-biphenylyl | H | H | H | H | 2-naphthyl | H |
| X-106 | m-biphenylyl | H | H | H | H | H | 2-naphthyl |
| X-107 | m-biphenylyl | H | H | H | H | 2-naphthyl | 2-naphthyl |
| X-108 | m-biphenylyl | H | H | H | H | o-biphenylyl | H |
| X-109 | m-biphenylyl | H | H | H | H | H | o-biphenylyl |
| X-110 | m-biphenylyl | H | H | H | H | o-biphenylyl | o-biphenylyl |
| X-111 | m-biphenylyl | H | H | H | H | m-biphenylyl | H |
| X-112 | m-biphenylyl | H | H | H | H | H | m-biphenylyl |
| X-113 | m-biphenylyl | H | H | H | H | m-biphenylyl | m-biphenylyl |
| X-114 | m-biphenylyl | H | H | H | H | p-biphenylyl | H |
| X-115 | m-biphenylyl | H | H | H | H | H | p-biphenylyl |
| X-116 | m-biphenylyl | H | H | H | H | p-biphenylyl | p-biphenylyl |
| X-117 | p-biphenylyl | H | H | H | H | H | H |
| X-118 | p-biphenylyl | Ph | H | H | Ph | H | H |
| X-119 | p-biphenylyl | H | Ph | Ph | H | H | H |
| X-120 | p-biphenylyl | H | Ph | H | H | H | H |
| X-121 | p-biphenylyl | H | H | Ph | H | H | H |
| X-122 | p-biphenylyl | H | H | H | H | Ph | H |
| X-123 | p-biphenylyl | H | H | H | H | H | Ph |
| X-124 | p-biphenylyl | H | H | H | H | Ph | Ph |
| X-125 | p-biphenylyl | H | H | H | H | 1-naphthyl | H |
| X-126 | p-biphenylyl | H | H | H | H | H | 1-naphthyl |
| X-127 | p-biphenylyl | H | H | H | H | 1-naphthyl | 1-naphthyl |
| X-128 | p-biphenylyl | H | H | H | H | 2-naphthyl | H |
| X-129 | p-biphenylyl | H | H | H | H | H | 2-naphthyl |
| X-130 | p-biphenylyl | H | H | H | H | 2-naphthyl | 2-naphthyl |
| X-131 | p-biphenylyl | H | H | H | H | o-biphenylyl | H |

-continued

| | | | | | | | |
|---|---|---|---|---|---|---|---|
| X-132 | p-biphenylyl | H | H | H | H | H | o-biphenylyl |
| X-133 | p-biphenylyl | H | H | H | H | o-biphenylyl | o-biphenylyl |
| X-134 | p-biphenylyl | H | H | H | H | m-biphenylyl | H |
| X-135 | p-biphenylyl | H | H | H | H | H | m-biphenylyl |
| X-136 | p-biphenylyl | H | H | H | H | m-biphenylyl | m-biphenylyl |
| X-137 | p-biphenylyl | H | H | H | H | p-biphenylyl | H |
| X-138 | p-biphenylyl | H | H | H | H | H | p-biphenylyl |
| X-139 | p-biphenylyl | H | H | H | H | p-biphenylyl | p-biphenylyl |
| X-140 | o-tolyl | H | H | H | H | H | H |
| X-141 | o-tolyl | Ph | H | H | Ph | H | H |
| X-142 | o-tolyl | H | Ph | Ph | H | H | H |
| X-143 | o-tolyl | H | H | H | H | Ph | H |
| X-144 | o-tolyl | H | H | H | H | H | Ph |
| X-145 | o-tolyl | H | H | H | H | 1-naphthyl | H |
| X-146 | o-tolyl | H | H | H | H | H | 1-naphthyl |
| X-147 | o-tolyl | H | H | H | H | 2-naphthyl | H |
| X-148 | o-tolyl | H | H | H | H | H | 2-naphthyl |
| X-149 | o-tolyl | H | H | H | H | o-biphenylyl | H |
| X-150 | o-tolyl | H | H | H | H | H | o-biphenylyl |
| X-151 | o-tolyl | H | H | H | H | m-biphenylyl | H |
| X-152 | o-tolyl | H | H | H | H | H | m-biphenylyl |
| X-153 | o-tolyl | H | H | H | H | p-biphenylyl | H |
| X-154 | o-tolyl | H | H | H | H | H | p-biphenylyl |
| X-155 | o-tolyl | H | H | H | H | o-tolyl | H |
| X-156 | o-tolyl | H | H | H | H | H | o-tolyl |
| X-157 | m-tolyl | H | H | H | H | H | H |
| X-158 | m-tolyl | Ph | H | H | Ph | H | H |
| X-159 | m-tolyl | H | Ph | Ph | H | H | H |
| X-160 | m-tolyl | H | H | H | H | Ph | H |
| X-161 | m-tolyl | H | H | H | H | H | Ph |
| X-162 | m-tolyl | H | H | H | H | 1-naphthyl | H |
| X-163 | m-tolyl | H | H | H | H | H | 1-naphthyl |
| X-164 | m-tolyl | H | H | H | H | 2-naphthyl | H |
| X-165 | m-tolyl | H | H | H | H | H | 2-naphthyl |
| X-166 | m-tolyl | H | H | H | H | o-biphenylyl | H |
| X-167 | m-tolyl | H | H | H | H | H | o-biphenylyl |
| X-168 | m-tolyl | H | H | H | H | m-biphenylyl | H |
| X-169 | m-tolyl | H | H | H | H | H | m-biphenylyl |
| X-170 | m-tolyl | H | H | H | H | p-biphenylyl | H |
| X-171 | m-tolyl | H | H | H | H | H | p-biphenylyl |
| X-172 | m-tolyl | H | H | H | H | m-tolyl | H |
| X-173 | m-tolyl | H | H | H | H | H | m-tolyl |
| X-174 | p-tolyl | H | H | H | H | H | H |
| X-175 | p-tolyl | Ph | H | H | Ph | H | H |
| X-176 | p-tolyl | H | Ph | Ph | H | H | H |
| X-177 | p-tolyl | H | H | H | H | Ph | H |
| X-178 | p-tolyl | H | H | H | H | H | Ph |
| X-179 | p-tolyl | H | H | H | H | 1-naphthyl | H |
| X-180 | p-tolyl | H | H | H | H | H | 1-naphthyl |
| X-181 | p-tolyl | H | H | H | H | 2-naphthyl | H |
| X-182 | p-tolyl | H | H | H | H | H | 2-naphthyl |
| X-183 | p-tolyl | H | H | H | H | o-biphenylyl | H |
| X-184 | p-tolyl | H | H | H | H | H | o-biphenylyl |
| X-185 | p-tolyl | H | H | H | H | m-biphenylyl | H |
| X-186 | p-tolyl | H | H | H | H | H | m-biphenylyl |
| X-187 | p-tolyl | H | H | H | H | p-biphenylyl | H |
| X-188 | p-tolyl | H | H | H | H | H | p-biphenylyl |
| X-189 | p-tolyl | H | H | H | H | p-tolyl | H |
| X-190 | p-tolyl | H | H | H | H | H | p-tolyl |
| X-191 | Ph | H | —CH3 | —CH3 | H | H | H |
| X-192 | 1-naphtyl | H | —CH3 | —CH3 | H | H | H |
| X-193 | 2-naphthyl | H | —CH3 | —CH3 | H | H | H |
| X-194 | o-biphenylyl | H | —CH3 | —CH3 | H | H | H |
| X-195 | m-biphenylyl | H | —CH3 | —CH3 | H | H | H |
| X-196 | p-biphenylyl | H | —CH3 | —CH3 | H | H | H |
| X-197 | o-tolyl | H | —CH3 | —CH3 | H | H | H |
| X-198 | m-tolyl | H | —CH3 | —CH3 | H | H | H |
| X-199 | p-tolyl | H | —CH3 | —CH3 | H | H | H |
| X-200 | Ph | H | H | H | H | —CH3 | H |
| X-201 | 1-naphtyl | H | H | H | H | —CH3 | H |
| X-202 | 2-naphthyl | H | H | H | H | —CH3 | H |
| X-203 | o-biphenylyl | H | H | H | H | —CH3 | H |
| X-204 | m-biphenylyl | H | H | H | H | —CH3 | H |
| X-205 | p-biphenylyl | H | H | H | H | —CH3 | H |
| X-206 | o-tolyl | H | H | H | H | —CH3 | H |
| X-207 | m-tolyl | H | H | H | H | —CH3 | H |
| X-208 | p-tolyl | H | H | H | H | —CH3 | H |
| X-209 | Ph | H | H | H | H | H | —CH3 |
| X-210 | 1-naphtyl | H | H | H | H | H | —CH3 |

-continued

| | | | | | | | |
|---|---|---|---|---|---|---|---|
| X-211 | 2-naphthyl | H | H | H | H | H | —CH3 |
| X-212 | o-biphenylyl | H | H | H | H | H | —CH3 |
| X-213 | m-biphenylyl | H | H | H | H | H | —CH3 |
| X-214 | p-biphenylyl | H | H | H | H | H | —CH3 |
| X-215 | o-tolyl | H | H | H | H | H | —CH3 |
| X-216 | m-tolyl | H | H | H | H | H | —CH3 |
| X-217 | p-tolyl | H | H | H | H | H | —CH3 |
| X-218 | Ph | H | H | H | H | —CH3 | —CH3 |
| X-219 | 1-naphtyl | H | H | H | H | —CH3 | —CH3 |
| X-220 | 2-naphthyl | H | H | H | H | —CH3 | —CH3 |
| X-221 | o-biphenylyl | H | H | H | H | —CH3 | —CH3 |
| X-222 | m-biphenylyl | H | H | H | H | —CH3 | —CH3 |
| X-223 | p-biphenylyl | H | H | H | H | —CH3 | —CH3 |
| X-224 | o-tolyl | H | H | H | H | —CH3 | —CH3 |
| X-225 | m-tolyl | H | H | H | H | —CH3 | —CH3 |
| X-226 | p-tolyl | H | H | H | H | —CH3 | —CH3 |
| X-227 | Ph | H | H | H | H | H | DPA |
| X-228 | 1-naphtyl | H | H | H | H | H | DPA |
| X-229 | 2-naphthyl | H | H | H | H | H | DPA |
| X-230 | o-biphenylyl | H | H | H | H | H | DPA |
| X-231 | m-biphenylyl | H | H | H | H | H | DPA |
| X-232 | p-biphenylyl | H | H | H | H | H | DPA |
| X-233 | Ph | H | H | H | H | DPA | H |
| X-234 | 1-naphtyl | H | H | H | H | DPA | H |
| X-235 | 2-naphthyl | H | H | H | H | DPA | H |
| X-236 | o-biphenylyl | H | H | H | H | DPA | H |
| X-237 | m-biphenylyl | H | H | H | H | DPA | H |
| X-238 | p-biphenylyl | H | H | H | H | DPA | H |
| X-239 | Ph | H | H | H | H | H | TPA |
| X-240 | 1-naphtyl | H | H | H | H | H | TPA |
| X-241 | 2-naphthyl | H | H | H | H | H | TPA |
| X-242 | o-biphenylyl | H | H | H | H | H | TPA |
| X-243 | m-biphenylyl | H | H | H | H | H | TPA |
| X-244 | p-biphenylyl | H | H | H | H | H | TPA |
| X-245 | Ph | H | H | H | H | TPA | H |
| X-246 | 1-naphtyl | H | H | H | H | TPA | H |
| X-247 | 2-naphthyl | H | H | H | H | TPA | H |
| X-248 | o-biphenylyl | H | H | H | H | TPA | H |
| X-249 | m-biphenylyl | H | H | H | H | TPA | H |
| X-250 | p-biphenylyl | H | H | H | H | TPA | H |

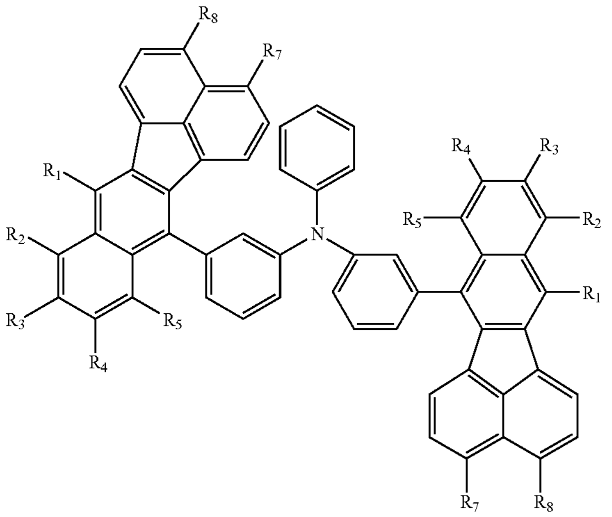

Type X'

| | $R_1$ | $R_2$ | $R_3$ | $R_4$ | $R_5$ | $R_7$ | $R_8$ |
|---|---|---|---|---|---|---|---|
| X'-1 | H | H | H | H | H | H | H |
| X'-2 | Ph | H | H | H | H | H | H |
| X'-3 | Ph | Ph | H | H | Ph | H | H |
| X'-4 | Ph | H | Ph | Ph | H | H | H |
| X'-5 | Ph | H | Ph | H | H | H | H |
| X'-6 | Ph | H | H | Ph | H | H | H |
| X'-7 | Ph | H | H | H | H | Ph | H |
| X'-8 | Ph | H | H | H | H | H | Ph |
| X'-9 | Ph | H | H | H | H | Ph | Ph |

-continued

| | | | | | | | |
|---|---|---|---|---|---|---|---|
| X'-10 | Ph | H | H | H | H | 1-naphthyl | H |
| X'-11 | Ph | H | H | H | H | H | 1-naphthyl |
| X'-12 | Ph | H | H | H | H | 1-naphthyl | 1-naphthyl |
| X-'13 | Ph | H | H | H | H | 2-naphthyl | H |
| X'-14 | Ph | H | H | H | H | H | 2-naphthyl |
| X'-15 | Ph | H | H | H | H | 2-naphthyl | 2-naphthyl |
| X'-16 | Ph | H | H | H | H | o-biphenylyl | H |
| X'-17 | Ph | H | H | H | H | H | o-biphenylyl |
| X'-18 | Ph | H | H | H | H | o-biphenylyl | o-biphenylyl |
| X'-19 | Ph | H | H | H | H | m-biphenylyl | H |
| X'-20 | Ph | H | H | H | H | H | m-biphenylyl |
| X'-21 | Ph | H | H | H | H | m-biphenylyl | m-biphenylyl |
| X'-22 | Ph | H | H | H | H | p-biphenylyl | H |
| X'-23 | Ph | H | H | H | H | H | p-biphenylyl |
| X'-24 | Ph | H | H | H | H | p-biphenylyl | p-biphenylyl |
| X'-25 | 1-naphthyl | H | H | H | H | H | H |
| X'-26 | 1-naphthyl | Ph | H | H | Ph | H | H |
| X'-27 | 1-naphthyl | H | Ph | Ph | H | H | H |
| X'-28 | 1-naphthyl | H | Ph | H | H | H | H |
| X'-29 | 1-naphthyl | H | H | Ph | H | H | H |
| X'-30 | 1-naphthyl | H | H | H | H | Ph | H |
| X'-31 | 1-naphthyl | H | H | H | H | H | Ph |
| X'-32 | 1-naphthyl | H | H | H | H | Ph | Ph |
| X'-33 | 1-naphthyl | H | H | H | H | 1-naphthyl | H |
| X'-34 | 1-naphthyl | H | H | H | H | H | 1-naphthyl |
| X'-35 | 1-naphthyl | H | H | H | H | 1-naphthyl | 1-naphthyl |
| X'-36 | 1-naphthyl | H | H | H | H | 2-naphthyl | H |
| X'-37 | 1-naphthyl | H | H | H | H | H | 2-naphthyl |
| X'-38 | 1-naphthyl | H | H | H | H | 2-naphthyl | 2-naphthyl |
| X'-39 | 1-naphthyl | H | H | H | H | o-biphenylyl | H |
| X'-40 | 1-naphthyl | H | H | H | H | H | o-biphenylyl |
| X'-41 | 1-naphthyl | H | H | H | H | o-biphenylyl | o-biphenylyl |
| X'-42 | 1-naphthyl | H | H | H | H | m-biphenylyl | H |
| X'-43 | 1-naphthyl | H | H | H | H | H | m-biphenylyl |
| X'-41 | 1-naphthyl | H | H | H | H | m-biphenylyl | m-biphenylyl |
| X'-45 | 1-naphthyl | H | H | H | H | p-biphenylyl | H |
| X'-46 | 1-naphthyl | H | H | H | H | H | p-biphenylyl |
| X'-47 | 1-naphthyl | H | H | H | H | p-biphenylyl | p-biphenylyl |
| X'-48 | 2-naphthyl | Ph | H | H | Ph | H | H |
| X'-48 | 2-naphthyl | H | H | H | H | H | H |
| X'-50 | 2-naphthyl | H | Ph | Ph | H | H | H |
| X'-51 | 2-naphthyl | H | Ph | H | H | H | H |
| X'-52 | 2-naphthyl | H | H | Ph | H | H | H |
| X'-53 | 2-naphthyl | H | H | H | H | Ph | H |
| X'-54 | 2-naphthyl | H | H | H | H | H | Ph |
| X'-55 | 2-naphthyl | H | H | H | H | Ph | Ph |
| X'-56 | 2-naphthyl | H | H | H | H | 1-naphthyl | H |
| X'-57 | 2-naphthyl | H | H | H | H | H | 1-naphthyl |
| X'-58 | 2-naphthyl | H | H | H | H | 1-naphthyl | 1-naphthyl |
| X'-59 | 2-naphthyl | H | H | H | H | 2-naphthyl | H |
| X'-60 | 2-naphthyl | H | H | H | H | H | 2-naphthyl |
| X'-61 | 2-naphthyl | H | H | H | H | 2-naphthyl | 2-naphthyl |
| X'-62 | 2-naphthyl | H | H | H | H | o-biphenylyl | H |
| X'-63 | 2-naphthyl | H | H | H | H | H | o-biphenylyl |
| X'-64 | 2-naphthyl | H | H | H | H | o-biphenylyl | o-biphenylyl |
| X'-65 | 2-naphthyl | H | H | H | H | m-biphenylyl | H |
| X'-66 | 2-naphthyl | H | H | H | H | H | m-biphenylyl |
| X'-67 | 2-naphthyl | H | H | H | H | m-biphenylyl | m-biphenylyl |
| X'-68 | 2-naphthyl | H | H | H | H | p-biphenylyl | H |
| X'-69 | 2-naphthyl | H | H | H | H | H | p-biphenylyl |
| X'-70 | 2-naphthyl | H | H | H | H | p-biphenylyl | p-biphenylyl |
| X'-71 | o-biphenylyl | H | H | H | H | H | H |
| X'-72 | o-biphenylyl | Ph | H | H | Ph | H | H |
| X'-73 | o-biphenylyl | H | Ph | Ph | H | H | H |
| X'-74 | o-biphenylyl | H | Ph | H | H | H | H |
| X'-75 | o-biphenylyl | H | H | Ph | H | H | H |
| X'-76 | o-biphenylyl | H | H | H | H | Ph | H |
| X'-77 | o-biphenylyl | H | H | H | H | H | Ph |
| X'-78 | o-biphenylyl | H | H | H | H | Ph | Ph |
| X'-79 | o-biphenylyl | H | H | H | H | 1-naphthyl | H |
| X'-80 | o-biphenylyl | H | H | H | H | H | 1-naphthyl |
| X'-82 | o-biphenylyl | H | H | H | H | 1-naphthyl | 1-naphthyl |
| X'-82 | o-biphenylyl | H | H | H | H | 2-naphthyl | H |
| X'-83 | o-biphenylyl | H | H | H | H | H | 2-naphthyl |
| X'-84 | o-biphenylyl | H | H | H | H | 2-naphthyl | 2-naphthyl |
| X'-85 | o-biphenylyl | H | H | H | H | o-biphenylyl | H |
| X'-86 | o-biphenylyl | H | H | H | H | H | o-biphenylyl |
| X'-87 | o-biphenylyl | H | H | H | H | o-biphenylyl | o-biphenylyl |
| X'-88 | o-biphenylyl | H | H | H | H | m-biphenylyl | H |

-continued

| | | | | | | | |
|---|---|---|---|---|---|---|---|
| X'-89 | o-biphenylyl | H | H | H | H | H | m-biphenylyl |
| X'-90 | o-biphenylyl | H | H | H | H | m-biphenylyl | m-biphenylyl |
| X'-91 | o-biphenylyl | H | H | H | H | p-biphenylyl | H |
| X'-92 | o-biphenylyl | H | H | H | H | H | p-biphenylyl |
| X'-93 | o-biphenylyl | H | H | H | H | p-biphenylyl | p-biphenylyl |
| X'-94 | m-biphenylyl | H | H | H | H | H | H |
| X'-95 | m-biphenylyl | Ph | H | H | Ph | H | H |
| X'-96 | m-biphenylyl | H | Ph | Ph | H | H | H |
| X'-97 | m-biphenylyl | H | Ph | H | H | H | H |
| X'-98 | m-biphenylyl | H | H | Ph | H | H | H |
| X'-99 | m-biphenylyl | H | H | H | H | Ph | H |
| X'-100 | m-biphenylyl | H | H | H | H | H | Ph |
| X'-101 | m-biphenylyl | H | H | H | H | Ph | Ph |
| X'-102 | m-biphenylyl | H | H | H | H | 1-naphthyl | H |
| X'-103 | m-biphenylyl | H | H | H | H | H | 1-naphthyl |
| X'-104 | m-biphenylyl | H | H | H | H | 1-naphthyl | 1-naphthyl |
| X'-105 | m-biphenylyl | H | H | H | H | 2-naphthyl | H |
| X'-106 | m-biphenylyl | H | H | H | H | H | 2-naphthyl |
| X'-107 | m-biphenylyl | H | H | H | H | 2-naphthyl | 2-naphthyl |
| X'-108 | m-biphenylyl | H | H | H | H | o-biphenylyl | H |
| X'-109 | m-biphenylyl | H | H | H | H | H | o-biphenylyl |
| X'-110 | m-biphenylyl | H | H | H | H | o-biphenylyl | o-biphenylyl |
| X'-111 | m-biphenylyl | H | H | H | H | m-biphenylyl | H |
| X'-112 | m-biphenylyl | H | H | H | H | H | m-biphenylyl |
| X'-113 | m-biphenylyl | H | H | H | H | m-biphenylyl | m-biphenylyl |
| X'-114 | m-biphenylyl | H | H | H | H | p-biphenylyl | H |
| X'-115 | m-biphenylyl | H | H | H | H | H | p-biphenylyl |
| X'-116 | m-biphenylyl | H | H | H | H | p-biphenylyl | p-biphenylyl |
| X'-117 | p-biphenylyl | H | H | H | H | H | H |
| X'-118 | p-biphenylyl | Ph | H | H | Ph | H | H |
| X'-119 | p-biphenylyl | H | Ph | Ph | H | H | H |
| X'-120 | p-biphenylyl | H | Ph | H | H | H | H |
| X'-121 | p-biphenylyl | H | H | Ph | H | H | H |
| X'-122 | p-biphenylyl | H | H | H | H | Ph | H |
| X'-123 | p-biphenylyl | H | H | H | H | H | Ph |
| X'-124 | p-biphenylyl | H | H | H | H | Ph | Ph |
| X'-125 | p-biphenylyl | H | H | H | H | 1-naphthyl | H |
| X'-126 | p-biphenylyl | H | H | H | H | H | 1-naphthyl |
| X'-127 | p-biphenylyl | H | H | H | H | 1-naphthyl | 1-naphthyl |
| X'-128 | p-biphenylyl | H | H | H | H | 2-naphthyl | H |
| X'-129 | p-biphenylyl | H | H | H | H | H | 2-naphthyl |
| X'-130 | p-biphenylyl | H | H | H | H | 2-naphthyl | 2-naphthyl |
| X'-131 | p-biphenylyl | H | H | H | H | o-biphenylyl | H |
| X'-132 | p-biphenylyl | H | H | H | H | H | o-biphenylyl |
| X'-133 | p-biphenylyl | H | H | H | H | o-biphenylyl | o-biphenylyl |
| X'-134 | p-biphenylyl | H | H | H | H | m-biphenylyl | H |
| X'-135 | p-biphenylyl | H | H | H | H | H | m-biphenylyl |
| X'-136 | p-biphenylyl | H | H | H | H | m-biphenylyl | m-biphenylyl |
| X'-137 | p-biphenylyl | H | H | H | H | p-biphenylyl | H |
| X'-138 | p-biphenylyl | H | H | H | H | H | p-biphenylyl |
| X'-139 | p-biphenylyl | H | H | H | H | p-biphenylyl | p-biphenylyl |
| X'-140 | o-tolyl | H | H | H | H | H | H |
| X'-141 | o-tolyl | Ph | H | H | Ph | H | H |
| X'-142 | o-tolyl | H | Ph | Ph | H | H | H |
| X'-143 | o-tolyl | H | H | H | H | Ph | H |
| X'-144 | o-tolyl | H | H | H | H | H | Ph |
| X'-145 | o-tolyl | H | H | H | H | 1-naphthyl | H |
| X'-146 | o-tolyl | H | H | H | H | H | 1-naphthyl |
| X'-147 | o-tolyl | H | H | H | H | 2-naphthyl | H |
| X'-148 | o-tolyl | H | H | H | H | H | 2-naphthyl |
| X'-149 | o-tolyl | H | H | H | H | o-biphenylyl | H |
| X'-150 | o-tolyl | H | H | H | H | H | o-biphenylyl |
| X'-151 | o-tolyl | H | H | H | H | m-biphenylyl | H |
| X'-152 | o-tolyl | H | H | H | H | H | m-biphenylyl |
| X'-153 | o-tolyl | H | H | H | H | p-biphenylyl | H |
| X'-154 | o-tolyl | H | H | H | H | H | p-biphenylyl |
| X'-155 | o-tolyl | H | H | H | H | o-tolyl | H |
| X'-156 | o-tolyl | H | H | H | H | H | o-tolyl |
| X'-157 | m-tolyl | H | H | H | H | H | H |
| X'-158 | m-tolyl | Ph | H | H | Ph | H | H |
| X'-159 | m-tolyl | H | Ph | Ph | H | H | H |
| X'-160 | m-tolyl | H | H | H | H | Ph | H |
| X'-161 | m-tolyl | H | H | H | H | H | Ph |
| X'-162 | m-tolyl | H | H | H | H | 1-naphthyl | H |
| X'-163 | m-tolyl | H | H | H | H | H | 1-naphthyl |
| X'-164 | m-tolyl | H | H | H | H | 2-naphthyl | H |
| X'-165 | m-tolyl | H | H | H | H | H | 2-naphthyl |
| X'-166 | m-tolyl | H | H | H | H | o-biphenylyl | H |
| X'-167 | m-tolyl | H | H | H | H | H | o-biphenylyl |

-continued

| | | | | | | | |
|---|---|---|---|---|---|---|---|
| X'-168 | m-tolyl | H | H | H | H | m-biphenylyl | H |
| X'-169 | m-tolyl | H | H | H | H | H | m-biphenylyl |
| X'-170 | m-tolyl | H | H | H | H | p-biphenylyl | H |
| X'-171 | m-tolyl | H | H | H | H | H | p-biphenylyl |
| X'-172 | m-tolyl | H | H | H | H | m-tolyl | H |
| X'-173 | m-tolyl | H | H | H | H | H | m-tolyl |
| X'-174 | p-tolyl | H | H | H | H | H | H |
| X'-175 | p-tolyl | Ph | H | H | Ph | H | H |
| X'-176 | p-tolyl | H | Ph | Ph | H | H | H |
| X'-177 | p-tolyl | H | H | H | H | Ph | H |
| X'-178 | p-tolyl | H | H | H | H | H | Ph |
| X'-179 | p-tolyl | H | H | H | H | 1-naphthyl | H |
| X'-180 | p-tolyl | H | H | H | H | H | 1-naphthyl |
| X'-181 | p-tolyl | H | H | H | H | 2-naphthyl | H |
| X'-182 | p-tolyl | H | H | H | H | H | 2-naphthyl |
| X'-183 | p-tolyl | H | H | H | H | o-biphenylyl | H |
| X'-184 | p-tolyl | H | H | H | H | H | o-biphenylyl |
| X'-185 | p-tolyl | H | H | H | H | m-biphenylyl | H |
| X'-186 | p-tolyl | H | H | H | H | H | m-biphenylyl |
| X'-187 | p-tolyl | H | H | H | H | p-biphenylyl | H |
| X'-188 | p-tolyl | H | H | H | H | H | p-biphenylyl |
| X'-189 | p-tolyl | H | H | H | H | p-tolyl | H |
| X'-190 | p-tolyl | H | H | H | H | H | p-tolyl |
| X'-191 | Ph | H | —CH3 | —CH3 | H | H | H |
| X'-192 | 1-naphtyl | H | —CH3 | —CH3 | H | H | H |
| X'-193 | 2-naphthyl | H | —CH3 | —CH3 | H | H | H |
| X'-194 | o-biphenylyl | H | —CH3 | —CH3 | H | H | H |
| X'-195 | m-biphenylyl | H | —CH3 | —CH3 | H | H | H |
| X'-196 | p-biphenylyl | H | —CH3 | —CH3 | H | H | H |
| X'-197 | o-tolyl | H | —CH3 | —CH3 | H | H | H |
| X'-198 | m-tolyl | H | —CH3 | —CH3 | H | H | H |
| X'-199 | p-tolyl | H | —CH3 | —CH3 | H | H | H |
| X'-200 | Ph | H | H | H | H | —CH3 | H |
| X'-201 | 1-naphtyl | H | H | H | H | —CH3 | H |
| X'-202 | 2-naphthyl | H | H | H | H | —CH3 | H |
| X'-203 | o-biphenylyl | H | H | H | H | —CH3 | H |
| X'-204 | m-biphenylyl | H | H | H | H | —CH3 | H |
| X'-205 | p-biphenylyl | H | H | H | H | —CH3 | H |
| X'-206 | o-tolyl | H | H | H | H | —CH3 | H |
| X'-207 | m-tolyl | H | H | H | H | —CH3 | H |
| X'-208 | p-tolyl | H | H | H | H | —CH3 | H |
| X'-209 | Ph | H | H | H | H | H | —CH3 |
| X'-210 | 1-naphtyl | H | H | H | H | H | —CH3 |
| X'-211 | 2-naphthyl | H | H | H | H | H | —CH3 |
| X'-212 | o-biphenylyl | H | H | H | H | H | —CH3 |
| X'-213 | m-biphenylyl | H | H | H | H | H | —CH3 |
| X'-214 | p-biphenylyl | H | H | H | H | H | —CH3 |
| X'-215 | o-tolyl | H | H | H | H | H | —CH3 |
| X'-216 | m-tolyl | H | H | H | H | H | —CH3 |
| X'-217 | p-tolyl | H | H | H | H | H | —CH3 |
| X'-218 | Ph | H | H | H | H | —CH3 | —CH3 |
| X'-219 | 1-naphtyl | H | H | H | H | —CH3 | —CH3 |
| X'-220 | 2-naphthyl | H | H | H | H | —CH3 | —CH3 |
| X'-221 | o-biphenylyl | H | H | H | H | —CH3 | —CH3 |
| X'-222 | m-biphenylyl | H | H | H | H | —CH3 | —CH3 |
| X'-223 | p-biphenylyl | H | H | H | H | —CH3 | —CH3 |
| X'-224 | o-tolyl | H | H | H | H | —CH3 | —CH3 |
| X'-225 | m-tolyl | H | H | H | H | —CH3 | —CH3 |
| X'-226 | p-tolyl | H | H | H | H | —CH3 | —CH3 |
| X'-227 | Ph | H | H | H | H | H | DPA |
| X'-228 | 1-naphtyl | H | H | H | H | H | DPA |
| X'-229 | 2-naphthyl | H | H | H | H | H | DPA |
| X'-230 | o-biphenylyl | H | H | H | H | H | DPA |
| X'-231 | m-biphenylyl | H | H | H | H | H | DPA |
| X'-232 | p-biphenylyl | H | H | H | H | H | DPA |
| X'-233 | Ph | H | H | H | H | DPA | H |
| X'-234 | 1-naphtyl | H | H | H | H | DPA | H |
| X'-235 | 2-naphthyl | H | H | H | H | DPA | H |
| X'-236 | o-biphenylyl | H | H | H | H | DPA | H |
| X'-237 | m-biphenylyl | H | H | H | H | DPA | H |
| X'-238 | p-biphenylyl | H | H | H | H | DPA | H |
| X'-239 | Ph | H | H | H | H | H | TPA |
| X'-240 | 1-naphtyl | H | H | H | H | H | TPA |
| X'-241 | 2-naphthyl | H | H | H | H | H | TPA |
| X'-242 | o-biphenylyl | H | H | H | H | H | TPA |
| X'-243 | m-biphenylyl | H | H | H | H | H | TPA |
| X'-244 | p-biphenylyl | H | H | H | H | H | TPA |
| X'-245 | Ph | H | H | H | H | TPA | H |
| X'-246 | 1-naphtyl | H | H | H | H | TPA | H |

-continued
| | | | | | | | |
|---|---|---|---|---|---|---|---|
| X'-247 | 2-naphthyl | H | H | H | H | TPA | H |
| X'-248 | o-biphenylyl | H | H | H | H | TPA | H |
| X'-249 | m-biphenylyl | H | H | H | H | TPA | H |
| X'-250 | p-biphenylyl | H | H | H | H | TPA | H |
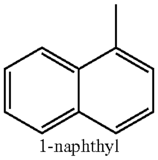
1-naphthyl
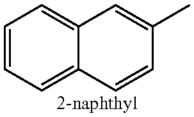
2-naphthyl
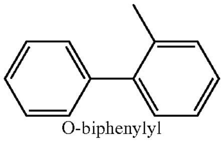
O-biphenylyl
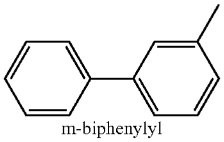
m-biphenylyl
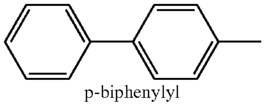
p-biphenylyl
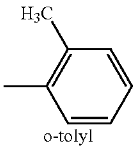
o-tolyl
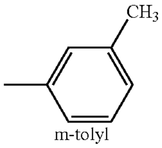
m-tolyl
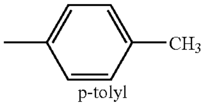
p-tolyl
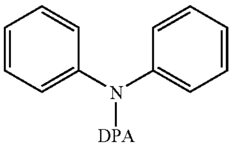
DPA
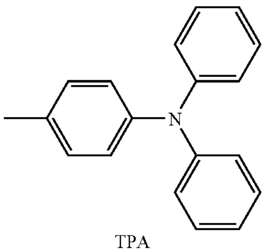
TPA

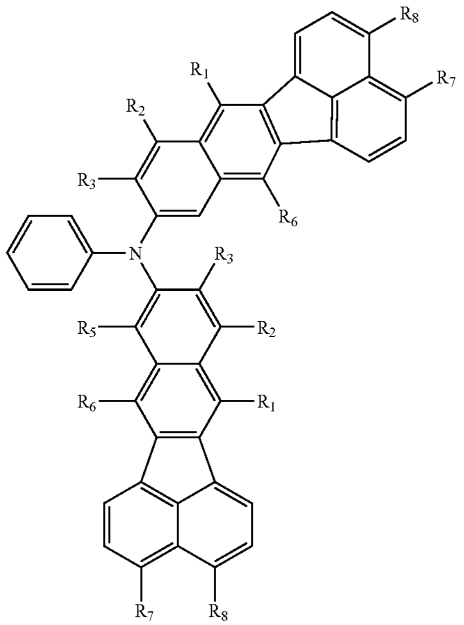

Type Y

| | $R_1$ | $R_2$ | $R_3$ | $R_5$ | $R_6$ | $R_7$ | $R_8$ |
|---|---|---|---|---|---|---|---|
| Y-1 | H | H | H | H | H | H | H |
| Y-2 | Ph | H | H | H | Ph | H | H |
| Y-3 | Ph | Ph | H | H | Ph | H | H |
| Y-4 | Ph | H | H | Ph | Ph | H | H |
| Y-5 | Ph | Ph | H | Ph | Ph | H | H |
| Y-6 | Ph | H | Ph | H | Ph | H | H |
| Y-7 | Ph | H | H | H | Ph | Ph | H |
| Y-8 | Ph | H | H | H | Ph | H | Ph |
| Y-9 | Ph | H | H | H | Ph | Ph | Ph |
| Y-10 | Ph | H | H | H | Ph | 1-naphthyl | H |
| Y-11 | Ph | H | H | H | Ph | H | 1-naphthyl |
| Y-12 | Ph | H | H | H | Ph | 1-naphthyl | 1-naphthyl |
| Y-13 | Ph | H | H | H | Ph | 2-naphthyl | H |
| Y-14 | Ph | H | H | H | Ph | H | 2-naphthyl |
| Y-15 | Ph | H | H | H | Ph | 2-naphthyl | 2-naphthyl |
| Y-16 | Ph | H | H | H | Ph | o-biphenylyl | H |
| Y-17 | Ph | H | H | H | Ph | H | o-biphenylyl |
| Y-18 | Ph | H | H | H | Ph | o-biphenylyl | o-biphenylyl |
| Y-19 | Ph | H | H | H | Ph | m-biphenylyl | H |
| Y-20 | Ph | H | H | H | Ph | H | m-biphenylyl |
| Y-21 | Ph | H | H | H | Ph | m-biphenylyl | m-biphenylyl |
| Y-22 | Ph | H | H | H | Ph | p-biphenylyl | H |
| Y-23 | Ph | H | H | H | Ph | H | p-biphenylyl |
| Y-24 | Ph | H | H | H | Ph | p-biphenylyl | p-biphenylyl |
| Y-25 | 1-naphthyl | H | H | H | 1-naphthyl | H | H |
| Y-26 | 1-naphthyl | Ph | H | H | 1-naphthyl | H | H |
| Y-27 | 1-naphthyl | H | H | Ph | 1-naphthyl | H | H |
| Y-28 | 1-naphthyl | Ph | H | Ph | 1-naphthyl | H | H |
| Y-29 | 1-naphthyl | H | Ph | H | 1-naphthyl | H | H |
| Y-30 | 1-naphthyl | H | H | H | 1-naphthyl | Ph | H |
| Y-31 | 1-naphthyl | H | H | H | 1-naphthyl | H | Ph |
| Y-32 | 1-naphthyl | H | H | H | 1-naphthyl | Ph | Ph |
| Y-33 | 1-naphthyl | H | H | H | 1-naphthyl | 1-naphthyl | H |
| Y-34 | 1-naphthyl | H | H | H | 1-naphthyl | H | 1-naphthyl |
| Y-35 | 1-naphthyl | H | H | H | 1-naphthyl | 1-naphthyl | 1-naphthyl |
| Y-36 | 1-naphthyl | H | H | H | 1-naphthyl | 2-naphthyl | H |
| Y-37 | 1-naphthyl | H | H | H | 1-naphthyl | H | 2-naphthyl |
| Y-38 | 1-naphthyl | H | H | H | 1-naphthyl | 2-naphthyl | 2-naphthyl |
| Y-39 | 1-naphthyl | H | H | H | 1-naphthyl | o-biphenylyl | H |
| Y-40 | 1-naphthyl | H | H | H | 1-naphthyl | H | o-biphenylyl |
| Y-41 | 1-naphthyl | H | H | H | 1-naphthyl | o-biphenylyl | o-biphenylyl |
| Y-42 | 1-naphthyl | H | H | H | 1-naphthyl | m-biphenylyl | H |
| Y-43 | 1-naphthyl | H | H | H | 1-naphthyl | H | m-biphenylyl |
| Y-44 | 1-naphthyl | H | H | H | 1-naphthyl | m-biphenylyl | m-biphenylyl |
| Y-45 | 1-naphthyl | H | H | H | 1-naphthyl | p-biphenylyl | H |
| Y-48 | 1-naphthyl | H | H | H | 1-naphthyl | H | p-biphenylyl |

-continued

| | | | | | | | |
|---|---|---|---|---|---|---|---|
| Y-47 | 1-naphthyl | H | H | H | 1-naphthyl | p-biphenylyl | p-biphenylyl |
| Y-48 | 2-naphthyl | H | H | H | 2-naphthyl | H | H |
| Y-49 | 2-naphthyl | Ph | H | H | 2-naphthyl | H | H |
| Y-50 | 2-naphthyl | H | H | Ph | 2-naphthyl | H | H |
| Y-51 | 2-naphthyl | Ph | H | Ph | 2-naphthyl | H | H |
| Y-52 | 2-naphthyl | H | Ph | H | 2-naphthyl | H | H |
| Y-53 | 2-naphthyl | H | H | H | 2-naphthyl | Ph | H |
| Y-54 | 2-naphthyl | H | H | H | 2-naphthyl | H | Ph |
| Y-55 | 2-naphthyl | H | H | H | 2-naphthyl | Ph | Ph |
| Y-56 | 2-naphthyl | H | H | H | 2-naphthyl | 1-naphthyl | H |
| Y-57 | 2-naphthyl | H | H | H | 2-naphthyl | H | 1-naphthyl |
| Y-58 | 2-naphthyl | H | H | H | 2-naphthyl | 1-naphthyl | 1-naphthyl |
| Y-59 | 2-naphthyl | H | H | H | 2-naphthyl | 2-naphthyl | H |
| Y-60 | 2-naphthyl | H | H | H | 2-naphthyl | H | 2-naphthyl |
| Y-61 | 2-naphthyl | H | H | H | 2-naphthyl | 2-naphthyl | 2-naphthyl |
| Y-62 | 2-naphthyl | H | H | H | 2-naphthyl | o-biphenylyl | H |
| Y-63 | 2-naphthyl | H | H | H | 2-naphthyl | H | o-biphenylyl |
| Y-64 | 2-naphthyl | H | H | H | 2-naphthyl | o-biphenylyl | o-biphenylyl |
| Y-65 | 2-naphthyl | H | H | H | 2-naphthyl | m-biphenylyl | H |
| Y-66 | 2-naphthyl | H | H | H | 2-naphthyl | H | m-biphenylyl |
| Y-67 | 2-naphthyl | H | H | H | 2-naphthyl | m-biphenylyl | m-biphenylyl |
| Y-68 | 2-naphthyl | H | H | H | 2-naphthyl | p-biphenylyl | H |
| Y-69 | 2-naphthyl | H | H | H | 2-naphthyl | H | p-biphenylyl |
| Y-70 | 2-naphthyl | H | H | H | 2-naphthyl | p-biphenylyl | p-biphenylyl |
| Y-71 | o-biphenylyl | H | H | H | o-biphenylyl | H | H |
| Y-72 | o-biphenylyl | Ph | H | H | o-biphenylyl | H | H |
| Y-73 | o-biphenylyl | H | H | Ph | o-biphenylyl | H | H |
| Y-74 | o-biphenylyl | Ph | H | Ph | o-biphenylyl | H | H |
| Y-75 | o-biphenylyl | H | Ph | H | o-biphenylyl | H | H |
| Y-76 | o-biphenylyl | H | H | H | o-biphenylyl | Ph | H |
| Y-77 | o-biphenylyl | H | H | H | o-biphenylyl | H | Ph |
| Y-78 | o-biphenylyl | H | H | H | o-biphenylyl | Ph | Ph |
| Y-79 | o-biphenylyl | H | H | H | o-biphenylyl | 1-naphthyl | H |
| Y-80 | o-biphenylyl | H | H | H | o-biphenylyl | H | 1-naphthyl |
| Y-81 | o-biphenylyl | H | H | H | o-biphenylyl | 1-naphthyl | 1-naphthyl |
| Y-82 | o-biphenylyl | H | H | H | o-biphenylyl | 2-naphthyl | H |
| Y-83 | o-biphenylyl | H | H | H | o-biphenylyl | H | 2-naphthyl |
| Y-84 | o-biphenylyl | H | H | H | o-biphenylyl | 2-naphthyl | 2-naphthyl |
| Y-85 | o-biphenylyl | H | H | H | o-biphenylyl | o-biphenylyl | H |
| Y-86 | o-biphenylyl | H | H | H | o-biphenylyl | H | o-biphenylyl |
| Y-87 | o-biphenylyl | H | H | H | o-biphenylyl | o-biphenylyl | o-biphenylyl |
| Y-88 | o-biphenylyl | H | H | H | o-biphenylyl | m-biphenylyl | H |
| Y-89 | o-biphenylyl | H | H | H | o-biphenylyl | H | m-biphenylyl |
| Y-90 | o-biphenylyl | H | H | H | o-biphenylyl | m-biphenylyl | m-biphenylyl |
| Y-91 | o-biphenylyl | H | H | H | o-biphenylyl | p-biphenylyl | H |
| Y-92 | o-biphenylyl | H | H | H | o-biphenylyl | H | p-biphenylyl |
| Y-93 | o-biphenylyl | H | H | H | o-biphenylyl | p-biphenylyl | p-biphenylyl |
| Y-94 | m-biphenylyl | H | H | H | m-biphenylyl | H | H |
| Y-95 | m-biphenylyl | Ph | H | H | m-biphenylyl | H | H |
| Y-96 | m-biphenylyl | H | H | Ph | m-biphenylyl | H | H |
| Y-97 | m-biphenylyl | Ph | H | Ph | m-biphenylyl | H | H |
| Y-98 | m-biphenylyl | H | Ph | H | m-biphenylyl | H | H |
| Y-99 | m-biphenylyl | H | H | H | m-biphenylyl | Ph | H |
| Y-100 | m-biphenylyl | H | H | H | m-biphenylyl | H | Ph |
| Y-101 | m-biphenylyl | H | H | H | m-biphenylyl | Ph | Ph |
| Y-102 | m-biphenylyl | H | H | H | m-biphenylyl | 1-naphthyl | H |
| Y-103 | m-biphenylyl | H | H | H | m-biphenylyl | H | 1-naphthyl |
| Y-104 | m-biphenylyl | H | H | H | m-biphenylyl | 1-naphthyl | 1-naphthyl |
| Y-105 | m-biphenylyl | H | H | H | m-biphenylyl | 2-naphthyl | H |
| Y-106 | m-biphenylyl | H | H | H | m-biphenylyl | H | 2-naphthyl |
| Y-107 | m-biphenylyl | H | H | H | m-biphenylyl | 2-naphthyl | 2-naphthyl |
| Y-108 | m-biphenylyl | H | H | H | m-biphenylyl | o-biphenylyl | H |
| Y-109 | m-biphenylyl | H | H | H | m-biphenylyl | H | o-biphenylyl |
| Y-110 | m-biphenylyl | H | H | H | m-biphenylyl | o-biphenylyl | o-biphenylyl |
| Y-111 | m-biphenylyl | H | H | H | m-biphenylyl | m-biphenylyl | H |
| Y-112 | m-biphenylyl | H | H | H | m-biphenylyl | H | m-biphenylyl |
| Y-113 | m-biphenylyl | H | H | H | m-biphenylyl | m-biphenylyl | m-biphenylyl |
| Y-114 | m-biphenylyl | H | H | H | m-biphenylyl | p-biphenylyl | H |
| Y-115 | m-biphenylyl | H | H | H | m-biphenylyl | H | p-biphenylyl |
| Y-116 | m-biphenylyl | H | H | H | m-biphenylyl | p-biphenylyl | p-biphenylyl |
| Y-117 | p-biphenylyl | H | H | H | p-biphenylyl | H | H |
| Y-118 | p-biphenylyl | Ph | H | H | p-biphenylyl | H | H |
| Y-119 | p-biphenylyl | H | H | Ph | p-biphenylyl | H | H |
| Y-120 | p-biphenylyl | Ph | H | Ph | p-biphenylyl | H | H |
| Y-121 | p-biphenylyl | H | Ph | H | p-biphenylyl | H | H |
| Y-122 | p-biphenylyl | H | H | H | p-biphenylyl | Ph | H |
| Y-123 | p-biphenylyl | H | H | H | p-biphenylyl | H | Ph |
| Y-124 | p-biphenylyl | H | H | H | p-biphenylyl | Ph | Ph |
| Y-125 | p-biphenylyl | H | H | H | p-biphenylyl | 1-naphthyl | H |
| Y-126 | p-biphenylyl | H | H | H | p-biphenylyl | H | 1-naphthyl |

-continued

| | | | | | | | |
|---|---|---|---|---|---|---|---|
| Y-127 | p-biphenylyl | H | H | H | p-biphenylyl | 1-naphthyl | 1-naphthyl |
| Y-128 | p-biphenylyl | H | H | H | p-biphenylyl | 2-naphthyl | H |
| Y-129 | p-biphenylyl | H | H | H | p-biphenylyl | H | 2-naphthyl |
| Y-130 | p-biphenylyl | H | H | H | p-biphenylyl | 2-naphthyl | 2-naphthyl |
| Y-131 | p-biphenylyl | H | H | H | p-biphenylyl | o-biphenylyl | H |
| Y-132 | p-biphenylyl | H | H | H | p-biphenylyl | H | o-biphenylyl |
| Y-133 | p-biphenylyl | H | H | H | p-biphenylyl | o-biphenylyl | o-biphenylyl |
| Y-134 | p-biphenylyl | H | H | H | p-biphenylyl | m-biphenylyl | H |
| Y-135 | p-biphenylyl | H | H | H | p-biphenylyl | H | m-biphenylyl |
| Y-136 | p-biphenylyl | H | H | H | p-biphenylyl | m-biphenylyl | m-biphenylyl |
| Y-137 | p-biphenylyl | H | H | H | p-biphenylyl | p-biphenylyl | H |
| Y-138 | p-biphenylyl | H | H | H | p-biphenylyl | H | p-biphenylyl |
| Y-139 | p-biphenylyl | H | H | H | p-biphenylyl | p-biphenylyl | p-biphenylyl |
| Y-140 | o-tolyl | H | H | H | o-tolyl | H | H |
| Y-141 | o-tolyl | Ph | H | Ph | o-tolyl | H | H |
| Y-142 | o-tolyl | H | Ph | H | o-tolyl | H | H |
| Y-143 | o-tolyl | H | H | H | o-tolyl | Ph | H |
| Y-144 | o-tolyl | H | H | H | o-tolyl | H | Ph |
| Y-145 | o-tolyl | H | H | H | o-tolyl | 1-naphthyl | H |
| Y-146 | o-tolyl | H | H | H | o-tolyl | H | 1-naphthyl |
| Y-147 | o-tolyl | H | H | H | o-tolyl | 2-naphthyl | H |
| Y-148 | o-tolyl | H | H | H | o-tolyl | H | 2-naphthyl |
| Y-149 | o-tolyl | H | H | H | o-tolyl | o-biphenylyl | H |
| Y-150 | o-tolyl | H | H | H | o-tolyl | H | o-biphenylyl |
| Y-151 | o-tolyl | H | H | H | o-tolyl | m-biphenylyl | H |
| Y-152 | o-tolyl | H | H | H | o-tolyl | H | m-biphenylyl |
| Y-153 | o-tolyl | H | H | H | o-tolyl | p-biphenylyl | H |
| Y-154 | o-tolyl | H | H | H | o-tolyl | H | p-biphenylyl |
| Y-155 | o-tolyl | H | H | H | o-tolyl | o-tolyl | H |
| Y-156 | o-tolyl | H | H | H | o-tolyl | H | o-tolyl |
| Y-157 | m-tolyl | H | H | H | m-tolyl | H | H |
| Y-158 | m-tolyl | Ph | H | Ph | m-tolyl | H | H |
| Y-159 | m-tolyl | H | Ph | H | m-tolyl | H | H |
| Y-160 | m-tolyl | H | H | H | m-tolyl | Ph | H |
| Y-161 | m-tolyl | H | H | H | m-tolyl | H | Ph |
| Y-162 | m-tolyl | H | H | H | m-tolyl | 1-naphthyl | H |
| Y-163 | m-tolyl | H | H | H | m-tolyl | H | 1-naphthyl |
| Y-164 | m-tolyl | H | H | H | m-tolyl | 2-naphthyl | H |
| Y-165 | m-tolyl | H | H | H | m-tolyl | H | 2-naphthyl |
| Y-166 | m-tolyl | H | H | H | m-tolyl | o-biphenylyl | H |
| Y-167 | m-tolyl | H | H | H | m-tolyl | H | o-biphenylyl |
| Y-168 | m-tolyl | H | H | H | m-tolyl | m-biphenylyl | H |
| Y-169 | m-tolyl | H | H | H | m-tolyl | H | m-biphenylyl |
| Y-170 | m-tolyl | H | H | H | m-tolyl | p-biphenylyl | H |
| Y-171 | m-tolyl | H | H | H | m-tolyl | H | p-biphenylyl |
| Y-172 | m-tolyl | H | H | H | m-tolyl | m-tolyl | H |
| Y-173 | m-tolyl | H | H | H | m-tolyl | H | m-tolyl |
| Y-174 | p-tolyl | H | H | H | p-tolyl | H | H |
| Y-175 | p-tolyl | Ph | H | Ph | p-tolyl | H | H |
| Y-176 | p-tolyl | H | Ph | H | p-tolyl | H | H |
| Y-177 | p-tolyl | H | H | H | p-tolyl | Ph | H |
| Y-178 | p-tolyl | H | H | H | p-tolyl | H | Ph |
| Y-179 | p-tolyl | H | H | H | p-tolyl | 1-naphthyl | H |
| Y-180 | p-tolyl | H | H | H | p-tolyl | H | 1-naphthyl |
| Y-181 | p-tolyl | H | H | H | p-tolyl | 2-naphthyl | H |
| Y-182 | p-tolyl | H | H | H | p-tolyl | H | 2-naphthyl |
| Y-183 | p-tolyl | H | H | H | p-tolyl | o-biphenylyl | H |
| Y-184 | p-tolyl | H | H | H | p-tolyl | H | o-biphenylyl |
| Y-185 | p-tolyl | H | H | H | p-tolyl | m-biphenylyl | H |
| Y-186 | p-tolyl | H | H | H | p-tolyl | H | m-biphenylyl |
| Y-187 | p-tolyl | H | H | H | p-tolyl | p-biphenylyl | H |
| Y-188 | p-tolyl | H | H | H | p-tolyl | H | p-biphenylyl |
| Y-189 | p-tolyl | H | H | H | p-tolyl | p-tolyl | H |
| Y-190 | p-tolyl | H | H | H | p-tolyl | H | p-tolyl |
| Y-191 | Ph | H | —CH3 | H | Ph | H | H |
| Y-192 | 1-naphtyl | H | —CH3 | H | 1-naphtyl | H | H |
| Y-193 | 2-naphthyl | H | —CH3 | H | 2-naphthyl | H | H |
| Y-194 | o-biphenylyl | H | —CH3 | H | o-biphenylyl | H | H |
| Y-195 | m-biphenylyl | H | —CH3 | H | m-biphenylyl | H | H |
| Y-196 | p-biphenylyl | H | —CH3 | H | p-biphenylyl | H | H |
| Y-197 | o-tolyl | H | —CH3 | H | o-tolyl | H | H |
| Y-198 | m-tolyl | H | —CH3 | H | m-tolyl | H | H |
| Y-199 | p-tolyl | H | —CH3 | H | p-tolyl | H | H |
| Y-200 | Ph | H | H | H | Ph | —CH3 | H |
| Y-201 | 1-naphtyl | H | H | H | 1-naphtyl | —CH3 | H |
| Y-202 | 2-naphthyl | H | H | H | 2-naphthyl | —CH3 | H |
| Y-203 | o-biphenylyl | H | H | H | o-biphenylyl | —CH3 | H |
| Y-204 | m-biphenylyl | H | H | H | m-biphenylyl | —CH3 | H |
| Y-205 | p-biphenylyl | H | H | H | p-biphenylyl | —CH3 | H |
| Y-206 | o-tolyl | H | H | H | o-tolyl | —CH3 | H |

-continued

| | | | | | | | |
|---|---|---|---|---|---|---|---|
| Y-207 | m-tolyl | H | H | H | m-tolyl | —CH3 | H |
| Y-208 | p-tolyl | H | H | H | p-tolyl | —CH3 | H |
| Y-209 | Ph | H | H | H | Ph | H | —CH3 |
| Y-210 | 1-naphtyl | H | H | H | 1-naphtyl | H | —CH3 |
| Y-211 | 2-naphthyl | H | H | H | H | 2-naphthyl | —CH3 |
| Y-212 | o-biphenylyl | H | H | H | o-biphenylyl | H | —CH3 |
| Y-213 | m-biphenylyl | H | H | H | m-biphenylyl | H | —CH3 |
| Y-214 | p-biphenylyl | H | H | H | p-biphenylyl | H | —CH3 |
| Y-215 | o-tolyl | H | H | H | o-tolyl | H | —CH3 |
| Y-216 | m-tolyl | H | H | H | m-tolyl | H | —CH3 |
| Y-217 | p-tolyl | H | H | H | p-tolyl | H | —CH3 |
| Y-218 | Ph | H | H | H | Ph | —CH3 | —CH3 |
| Y-219 | 1-naphtyl | H | H | H | 1-naphtyl | —CH3 | —CH3 |
| Y-220 | 2-naphthyl | H | H | H | 2-naphthyl | —CH3 | —CH3 |
| Y-221 | o-biphenylyl | H | H | H | o-biphenylyl | —CH3 | —CH3 |
| Y-222 | m-biphenylyl | H | H | H | m-biphenylyl | —CH3 | —CH3 |
| Y-223 | p-biphenylyl | H | H | H | p-biphenylyl | —CH3 | —CH3 |
| Y-224 | o-tolyl | H | H | H | o-tolyl | —CH3 | —CH3 |
| Y-225 | m-tolyl | H | H | H | m-tolyl | —CH3 | —CH3 |
| Y-226 | p-tolyl | H | H | H | p-tolyl | —CH3 | —CH3 |
| Y-227 | Ph | H | H | H | Ph | H | DPA |
| Y-228 | 1-naphtyl | H | H | H | 1-naphtyl | H | DPA |
| Y-229 | 2-naphthyl | H | H | H | 2-naphthyl | H | DPA |
| Y-230 | o-biphenylyl | H | H | H | o-biphenylyl | H | DPA |
| Y-231 | m-biphenylyl | H | H | H | m-biphenylyl | H | DPA |
| Y-232 | p-biphenylyl | H | H | H | p-biphenylyl | H | DPA |
| Y-233 | Ph | H | H | H | Ph | DPA | H |
| Y-234 | 1-naphtyl | H | H | H | 1-naphtyl | DPA | H |
| Y-235 | 2-naphthyl | H | H | H | 2-naphthyl | DPA | H |
| Y-236 | o-biphenylyl | H | H | H | o-biphenylyl | DPA | H |
| Y-237 | m-biphenylyl | H | H | H | m-biphenylyl | DPA | H |
| Y-238 | p-biphenylyl | H | H | H | p-biphenylyl | DPA | H |
| Y-239 | Ph | H | H | H | Ph | H | TPA |
| Y-240 | 1-naphtyl | H | H | H | 1-naphtyl | H | TPA |
| Y-241 | 2-naphthyl | H | H | H | 2-naphthyl | H | TPA |
| Y-242 | o-biphenylyl | H | H | H | o-biphenylyl | H | TPA |
| Y-243 | m-biphenylyl | H | H | H | m-biphenylyl | H | TPA |
| Y-244 | p-biphenylyl | H | H | H | p-biphenylyl | H | TPA |
| Y-245 | Ph | H | H | H | Ph | TPA | H |
| Y-246 | 1-naphtyl | H | H | H | 1-naphtyl | TPA | H |
| Y-247 | 2-naphthyl | H | H | H | 2-naphthyl | TPA | H |
| Y-248 | o-biphenylyl | H | H | H | o-biphenylyl | TPA | H |
| Y-249 | m-biphenylyl | H | H | H | m-biphenylyl | TPA | H |
| Y-250 | p-biphenylyl | H | H | H | p-biphenylyl | TPA | H |
| Y-251 | Ph | H | H | H | 1-naphthyl | H | H |
| Y-252 | Ph | H | H | H | 2-naphthyl | H | H |
| Y-253 | Ph | H | H | H | o-biphenylyl | H | H |
| Y-254 | Ph | H | H | H | m-biphenylyl | H | H |
| Y-255 | Ph | H | H | H | p-biphenylyl | H | H |
| Y-256 | Ph | H | H | H | O-tolyly | H | H |
| Y-257 | Ph | H | H | H | m-tolyl | H | H |
| Y-258 | Ph | H | H | H | p-tolyl | H | H |
| Y-259 | 1-naphthyl | H | H | H | 2-naphthyl | H | H |
| Y-260 | 1-naphthyl | H | H | H | o-biphenylyl | H | H |
| Y-261 | 1-naphthyl | H | H | H | m-biphenylyl | H | H |
| Y-262 | 1-naphthyl | H | H | H | p-biphenylyl | H | H |
| Y-263 | 1-naphthyl | H | H | H | O-tolyly | H | H |
| Y-264 | 1-naphthyl | H | H | H | m-tolyl | H | H |
| Y-265 | 1-naphthyl | H | H | H | p-tolyl | H | H |
| Y-266 | 2-naphthyl | H | H | H | o-biphenylyl | H | H |
| Y-267 | 2-naphthyl | H | H | H | m-biphenylyl | H | H |
| Y-268 | 2-naphthyl | H | H | H | p-biphenylyl | H | H |
| Y-269 | 2-naphthyl | H | H | H | O-tolyly | H | H |
| Y-270 | 2-naphthyl | H | H | H | m-tolyl | H | H |
| Y-271 | 2-naphthyl | H | H | H | p-tolyl | H | H |
| Y-272 | o-biphenylyl | H | H | H | m-biphenylyl | H | H |
| Y-273 | o-biphenylyl | H | H | H | p-biphenylyl | H | H |
| Y-274 | o-biphenylyl | H | H | H | O-tolyly | H | H |
| Y-275 | o-biphenylyl | H | H | H | m-tolyl | H | H |
| Y-276 | o-biphenylyl | H | H | H | p-tolyl | H | H |
| Y-277 | m-biphenylyl | H | H | H | p-biphenylyl | H | H |
| Y-278 | m-biphenylyl | H | H | H | O-tolyly | H | H |
| Y-279 | m-biphenylyl | H | H | H | m-tolyl | H | H |
| Y-280 | m-biphenylyl | H | H | H | p-tolyl | H | H |
| Y-281 | p-biphenylyl | H | H | H | O-tolyly | H | H |
| Y-282 | p-biphenylyl | H | H | H | m-tolyl | H | H |
| Y-283 | p-biphenylyl | H | H | H | p-tolyl | H | H |
| Y-284 | O-tolyly | H | H | H | m-tolyl | H | H |
| Y-285 | O-tolyly | H | H | H | p-tolyl | H | H |
| Y-286 | m-tolyly | H | H | H | p-tolyl | H | H |

-continued
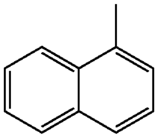
1-naphthyl
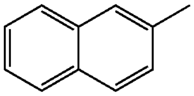
2-naphthyl
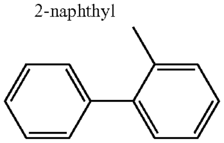
o-biphenylyl
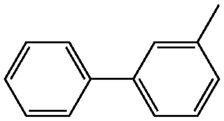
m-biphenylyl
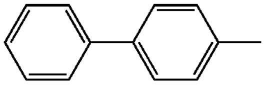
p-biphenylyl
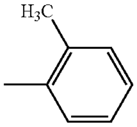
o-tolyl
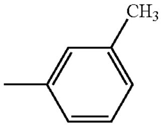
m-tolyl
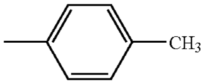
p-tolyl
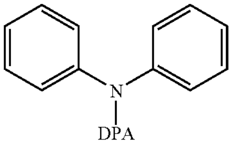
DPA
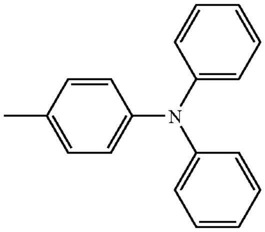
TPA

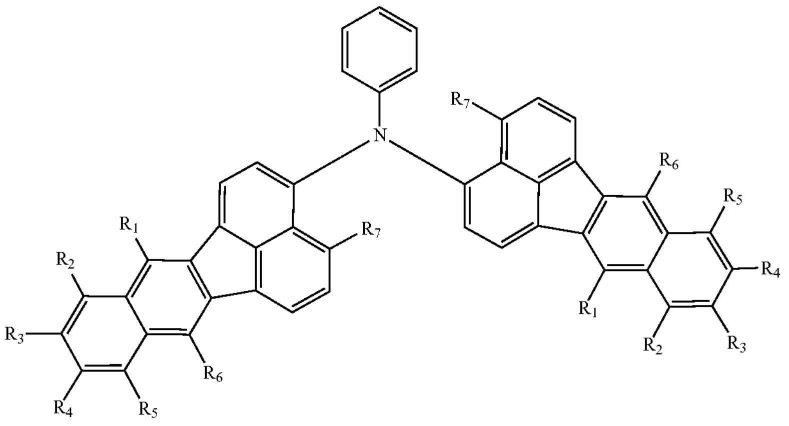
Type Z
| | $R_1$ | $R_2$ | $R_3$ | $R_4$ | $R_5$ | $R_6$ | $R_7$ |
|---|---|---|---|---|---|---|---|
| Z-1 | H | H | H | H | H | H | H |
| Z-2 | Ph | H | H | H | H | Ph | H |
| Z-3 | Ph | Ph | H | H | Ph | Ph | H |
| Z-4 | Ph | H | Ph | Ph | H | Ph | H |
| Z-5 | Ph | H | Ph | H | H | Ph | H |
| Z-6 | Ph | H | H | H | H | Ph | Ph |
| Z-7 | Ph | Me | H | H | Me | Ph | H |
| Z-8 | Ph | H | Me | Me | H | Ph | H |
| Z-5 | Ph | H | H | H | H | Ph | Me |
| Z-10 | 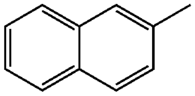 | H | H | H | H | 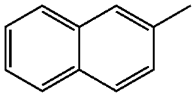 | H |
| Z-11 | 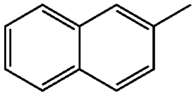 | Ph | H | H | Ph | 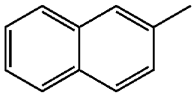 | H |
| Z-12 | 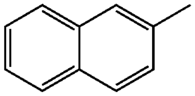 | H | Ph | Ph | H | 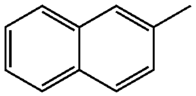 | H |

-continued
| | | | | | | | |
|---|---|---|---|---|---|---|---|
| Z-13 | 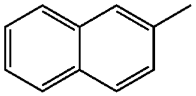 | H | Ph | H | H | 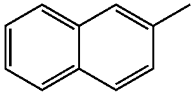 | H |
| Z-14 | 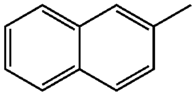 | H | H | H | H | 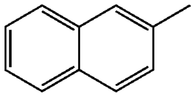 | Ph |
| Z-15 | 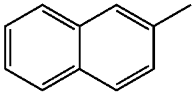 | Me | H | H | Me | 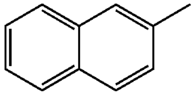 | H |
| Z-16 | 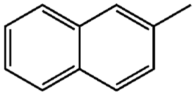 | H | Me | Me | H | 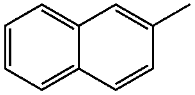 | H |
| Z-17 | 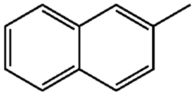 | H | H | H | H | 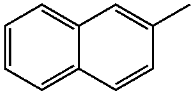 | Me |
| Z-18 | 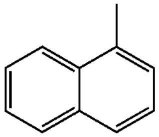 | H | H | H | H | 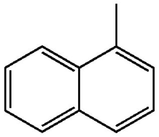 | H |
| Z-19 | 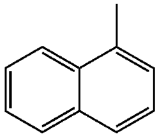 | Ph | H | H | Ph | 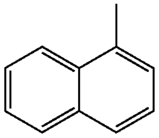 | H |
| Z-20 | 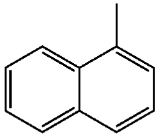 | H | Ph | Ph | H | 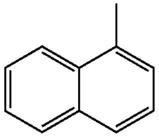 | H |

-continued
| | | | | | | | |
|---|---|---|---|---|---|---|---|
| Z-21 | 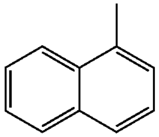 | H | Ph | H | H | 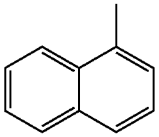 | H |
| Z-22 | 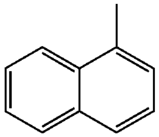 | H | H | H | H | 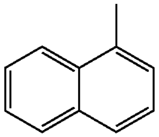 | Ph |
| Z-23 | 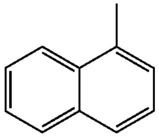 | Me | H | H | Me | 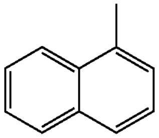 | H |
| Z-24 | 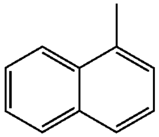 | H | Me | Me | H | 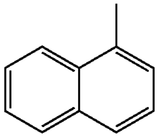 | H |
| Z-25 | 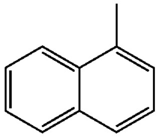 | H | H | H | H | 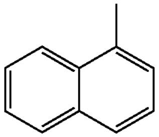 | Me |
| Z-26 | 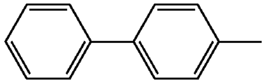 | H | H | H | H | 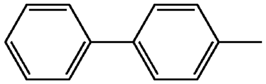 | H |
| Z-27 | 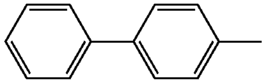 | Ph | H | H | Ph | 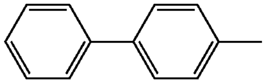 | H |
| Z-28 | 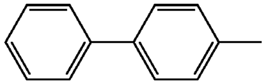 | H | Ph | Ph | H | 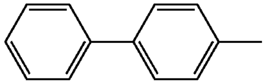 | H |

-continued
| | | | | | | | |
|---|---|---|---|---|---|---|---|
| Z-29 | 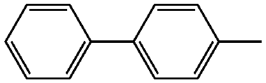 | H | Ph | H | H | 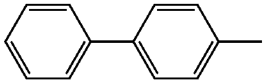 | H |
| Z-30 | 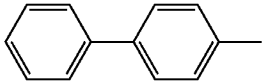 | H | H | H | H | 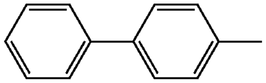 | Ph |
| Z-31 | 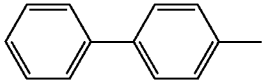 | Me | H | H | Me | 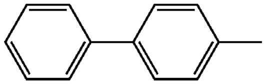 | H |
| Z-32 | 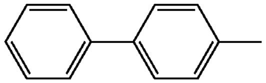 | H | Me | Me | H | 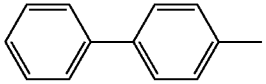 | H |
| Z-33 | 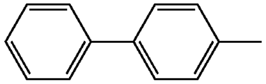 | H | H | H | H | 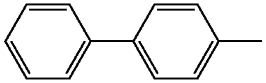 | Me |
| Z-34 | 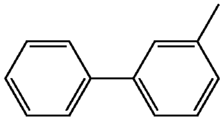 | H | H | H | H | 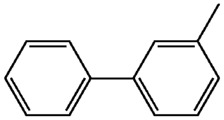 | H |
| Z-35 | 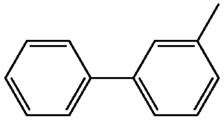 | Ph | H | H | Ph | 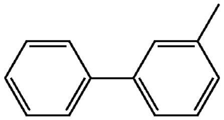 | H |
| Z-36 | 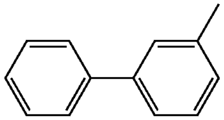 | H | Ph | Ph | H | 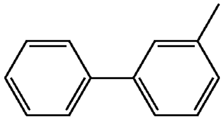 | H |
| Z-37 | 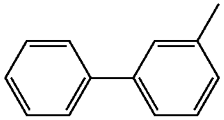 | H | Ph | H | H | 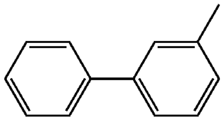 | H |

-continued
| | | | | | | | |
|---|---|---|---|---|---|---|---|
| Z-38 | 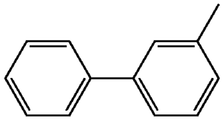 | H | H | H | H | 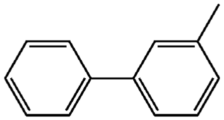 | Ph |
| Z-39 | 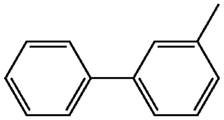 | Me | H | H | Me | 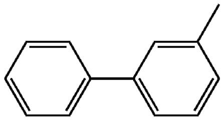 | H |
| Z-40 | 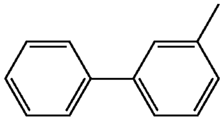 | H | Me | Me | H | 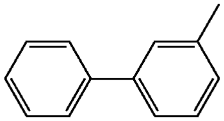 | H |
| Z-41 | 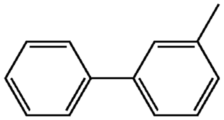 | H | H | H | H | 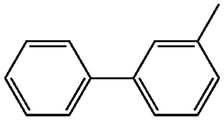 | Me |
| Z-42 | 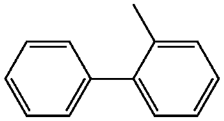 | H | H | H | H | 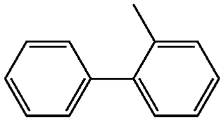 | H |
| Z-43 | 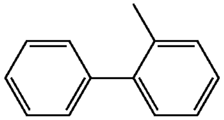 | Ph | H | H | Ph | 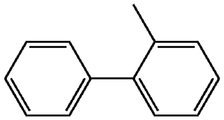 | H |
| Z-44 | 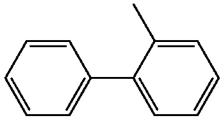 | H | Ph | Ph | H | 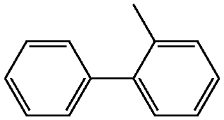 | H |
| Z-45 | 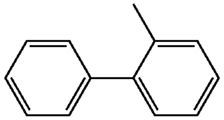 | H | Ph | H | H | 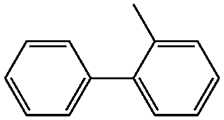 | H |

-continued
| | | | | | | | |
|---|---|---|---|---|---|---|---|
| Z-46 | 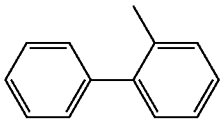 | H | H | H | H | 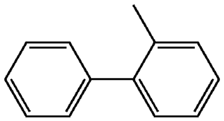 | Ph |
| Z-47 | 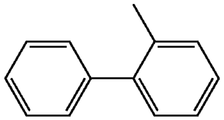 | Me | H | H | Me | 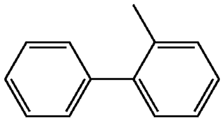 | H |
| Z-48 | 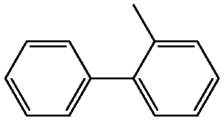 | H | Me | Me | H | 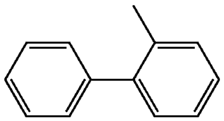 | H |
| Z-49 | 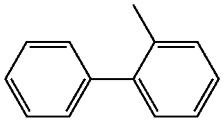 | H | H | H | H | 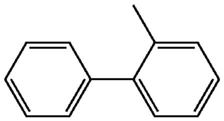 | Me |
| Z-50 | Ph | H | H | H | H | 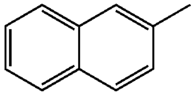 | H |
| Z-51 | Ph | H | H | H | H | 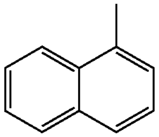 | H |
| Z-52 | Ph | H | H | H | H | 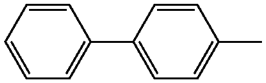 | H |
| Z-53 | Ph | H | H | H | H | 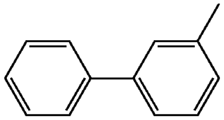 | H |

-continued
| | | | | | | | |
|---|---|---|---|---|---|---|---|
| Z-54 | Ph | H | H | H | H | 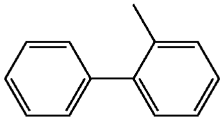 | H |
| Z-55 | 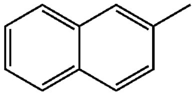 | H | H | H | H | 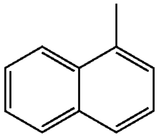 | H |
| Z-56 | 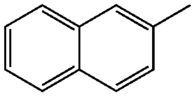 | H | H | H | H | 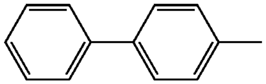 | H |
| Z-57 | 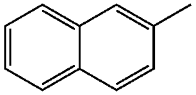 | H | H | H | H | 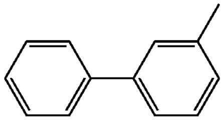 | H |
| Z-58 | 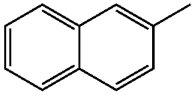 | H | H | H | H | 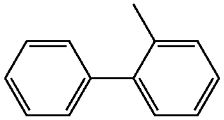 | H |
| Z-59 | 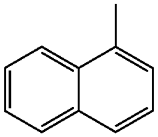 | H | H | H | H | 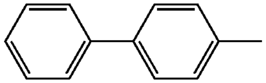 | H |
| Z-60 | 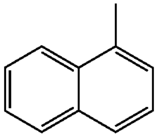 | H | H | H | H | 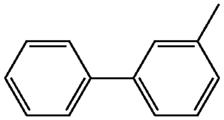 | H |

-continued
| | | | | | | | |
|---|---|---|---|---|---|---|---|
| Z-61 | 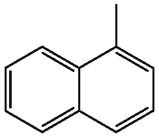 | H | H | H | H | 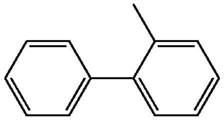 | H |
| Z-62 | 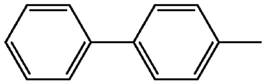 | H | H | H | H | 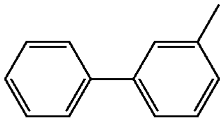 | H |
| Z-63 | 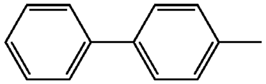 | H | H | H | H | 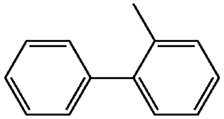 | H |
| Z-64 | 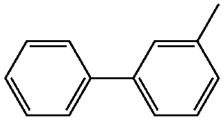 | H | H | H | H | 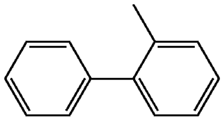 | H |
| Z-65 | H | Ph | H | H | Ph | H | H |
| Z-66 | H | 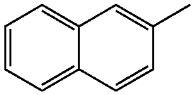 | H | H | 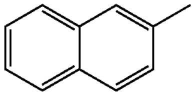 | H | H |
| Z-67 | H | 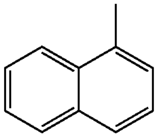 | H | H | 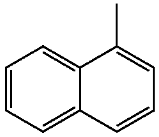 | H | H |
| Z-68 | H | 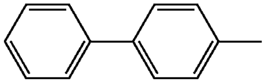 | H | H | 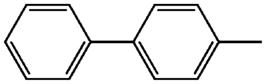 | H | H |

-continued
| | | | | | | | |
|---|---|---|---|---|---|---|---|
| Z-69 | H | 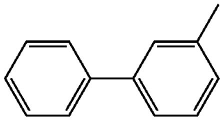 | H | H | 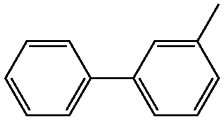 | H | H |
| Z-70 | H | 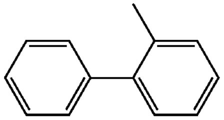 | H | H | 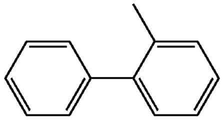 | H | H |
| Z-71 | H | H | 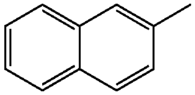 | 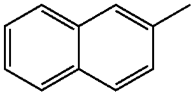 | H | H | H |
| Z-72 | H | H | 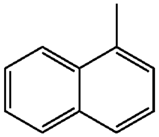 | 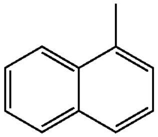 | H | H | H |
| Z-73 | H | H | 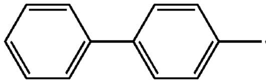 | 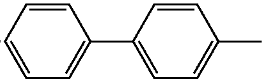 | H | H | H |
| Z-74 | H | H | 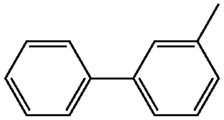 | 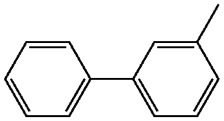 | H | H | H |
| Z-75 | H | H | 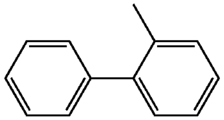 | 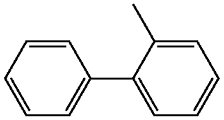 | H | H | H |
| Z-76 | 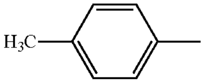 | H | H | H | H | 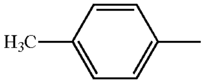 | H |

-continued
| | | | | | | | |
|---|---|---|---|---|---|---|---|
| Z-77 | 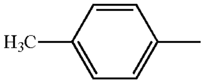 | Ph | H | H | Ph | 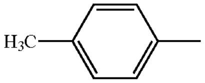 | H |
| Z-78 | 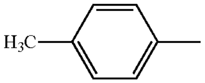 | H | Ph | Ph | H | 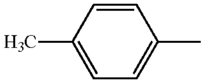 | H |
| Z-79 | 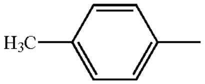 | H | Ph | H | H | 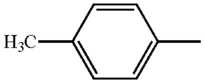 | H |
| Z-80 | 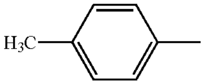 | H | H | H | H | 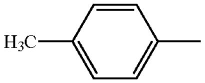 | Ph |
| Z-81 | 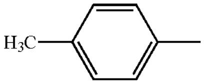 | Me | H | H | Me | 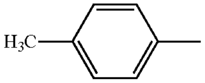 | H |
| Z-82 | 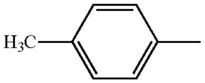 | H | Me | Me | H | 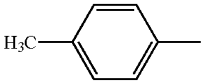 | H |
| Z-83 | 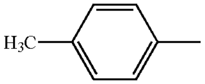 | H | H | H | H | 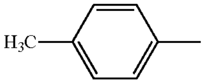 | Me |
| Z-84 | 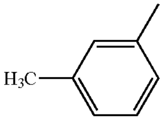 | H | H | H | H | 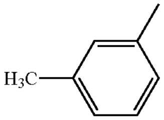 | H |
| Z-85 | 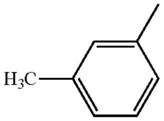 | Ph | H | H | Ph | 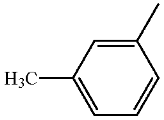 | H |

-continued
| | | | | | | | |
|---|---|---|---|---|---|---|---|
| Z-86 | 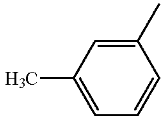 | H | Ph | Ph | H | 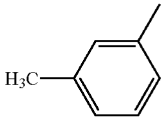 | H |
| Z-87 | 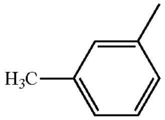 | H | Ph | H | H | 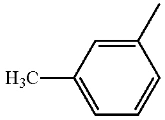 | H |
| Z-88 | 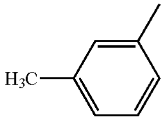 | H | H | H | H | 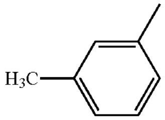 | Ph |
| Z-89 | 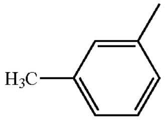 | Me | H | H | Me | 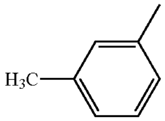 | H |
| Z-90 | 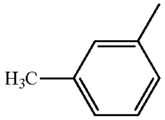 | H | Me | Me | H | 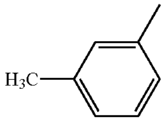 | H |
| Z-91 | 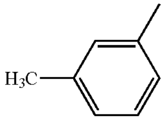 | H | H | H | H | 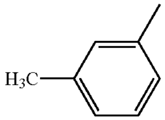 | Me |
| Z-92 | 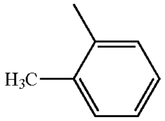 | H | H | H | H | 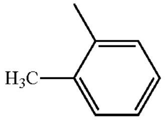 | H |
| Z-93 | 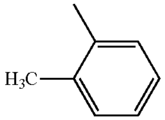 | Ph | H | H | Ph | 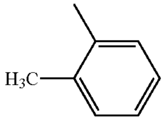 | H |

-continued
| | | | | | | | |
|---|---|---|---|---|---|---|---|
| Z-94 | 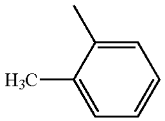 | H | Ph | Ph | H | 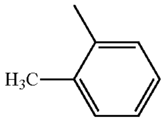 | H |
| Z-95 | 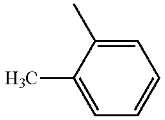 | H | Ph | H | H | 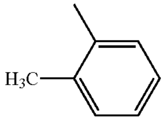 | H |
| Z-96 | 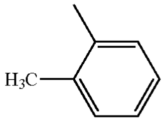 | H | H | H | H | 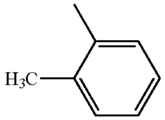 | Ph |
| Z-97 | 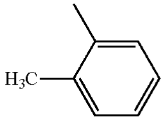 | Me | H | H | Me | 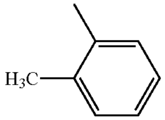 | H |
| Z-98 | 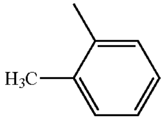 | H | Me | Me | H | 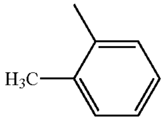 | H |
| Z-99 | 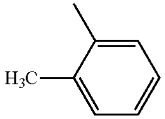 | H | H | H | H | 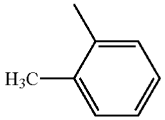 | Me |
| 100 | 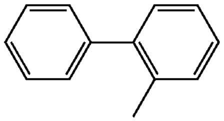 | H | H | H | H | 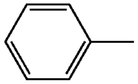 | H |

-continued
| | | | | | | | |
|---|---|---|---|---|---|---|---|
| 101 | 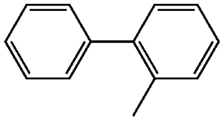 | Ph | H | H | Ph | 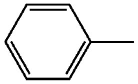 | H |
| 102 | 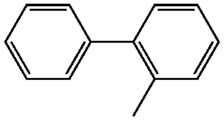 | H | Ph | Ph | H | 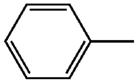 | H |
| 103 | 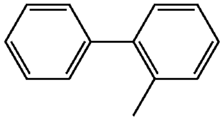 | H | Ph | H | H | 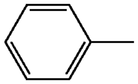 | H |
| 104 | 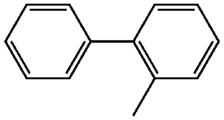 | H | H | H | H | 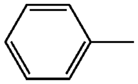 | Ph |
| 105 | 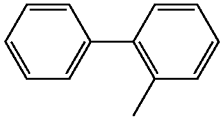 | Me | H | H | Me | 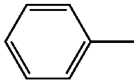 | H |
| 106 | 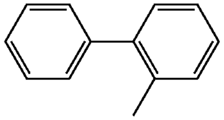 | H | Me | Me | H | 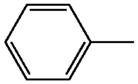 | H |
| 107 | 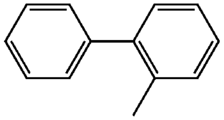 | H | H | H | H | 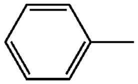 | Me |
| 108 | 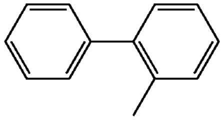 | H | H | H | H | 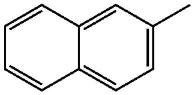 | H |

-continued
| | | | | | | | |
|---|---|---|---|---|---|---|---|
| 109 | 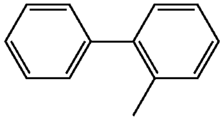 | Ph | H | H | Ph | 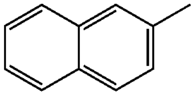 | H |
| 110 | 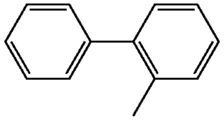 | H | Ph | Ph | H | 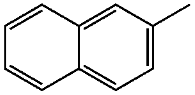 | H |
| 111 | 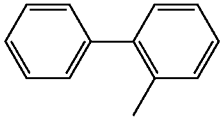 | H | Ph | H | H | 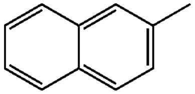 | H |
| 112 | 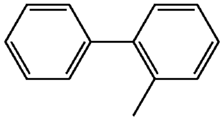 | H | H | H | H | 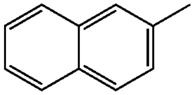 | Ph |
| 113 | 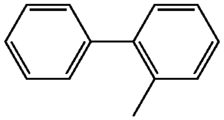 | Me | H | H | Me | 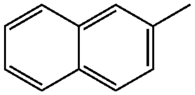 | H |
| 114 | 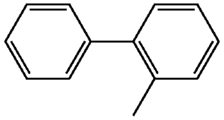 | H | Me | Me | H | 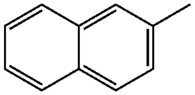 | H |
| 115 | 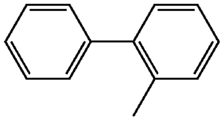 | H | H | H | H | 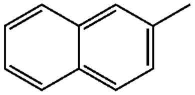 | Me |

-continued
| | | | | | | | |
|---|---|---|---|---|---|---|---|
| 116 | 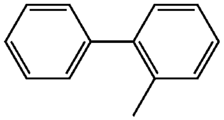 | H | H | H | H | 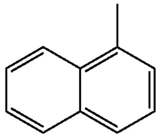 | H |
| 117 | 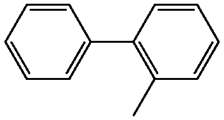 | Ph | H | H | Ph | 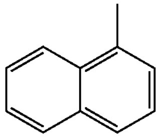 | H |
| 118 | 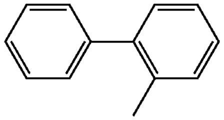 | H | Ph | Ph | H | 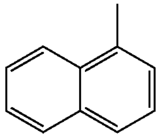 | H |
| 119 | 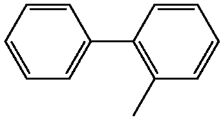 | H | Ph | H | H | 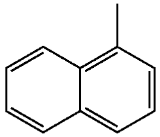 | H |
| 120 | 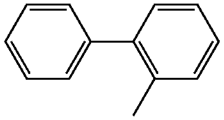 | H | H | H | H | 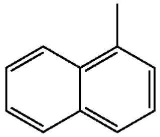 | Ph |
| 121 | 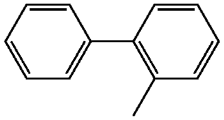 | Me | H | H | Me | 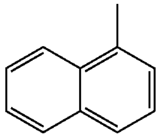 | H |
| 122 | 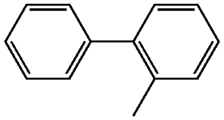 | H | Me | Me | H | 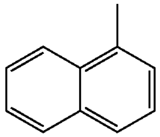 | H |

-continued
| | | | | | | | |
|---|---|---|---|---|---|---|---|
| 123 | 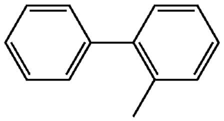 | H | H | H | H | 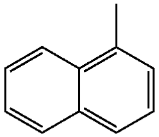 | Me |
| 124 | 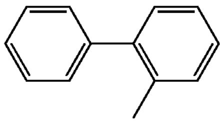 | H | H | H | H | 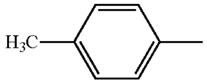 | H |
| 125 | 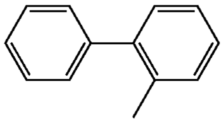 | Ph | H | H | Ph | 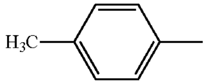 | H |
| 126 | 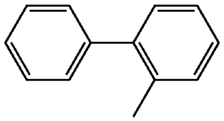 | H | Ph | Ph | H | 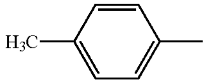 | H |
| 127 | 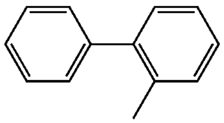 | H | Ph | H | H | 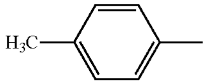 | H |
| 128 | 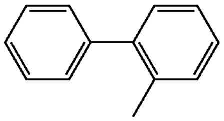 | H | H | H | H | 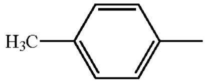 | Ph |
| 129 | 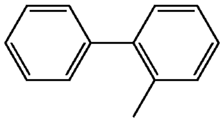 | Me | H | H | Me | 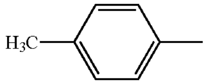 | H |

-continued
| | | | | | | | |
|---|---|---|---|---|---|---|---|
| 130 | 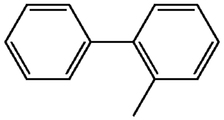 | H | Me | Me | H | 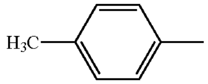 | H |
| 131 | 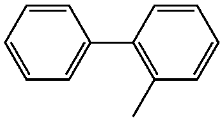 | H | H | H | H | 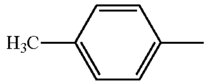 | Me |
| 132 | 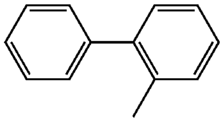 | H | H | H | H | 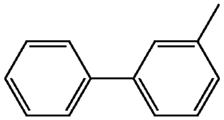 | H |
| 133 | 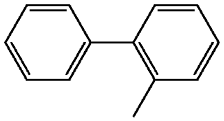 | Ph | H | H | Ph | 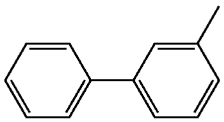 | H |
| 134 | 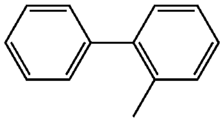 | H | Ph | Ph | H | 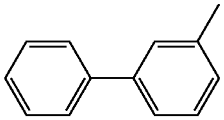 | H |
| 135 | 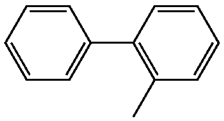 | H | Ph | H | H | 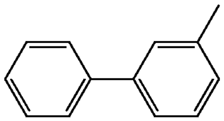 | H |
| 136 | 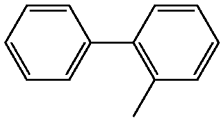 | H | H | H | H | 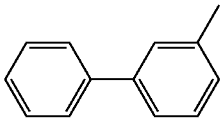 | Ph |
| 137 | 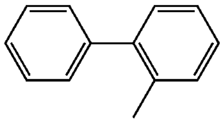 | Me | H | H | Me | | H |

-continued
| | | | | | | | |
|---|---|---|---|---|---|---|---|
| 138 | 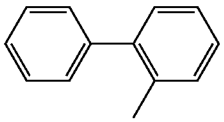 | H | Me | Me | H | 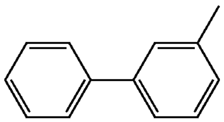 | H |
| 139 | 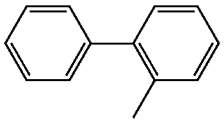 | H | H | H | H | 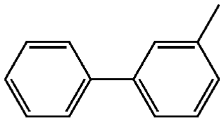 | Me |
| 140 | 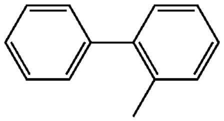 | H | H | H | H | 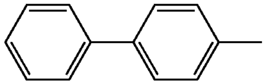 | H |
| 141 | 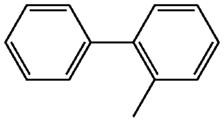 | Ph | H | H | Ph | 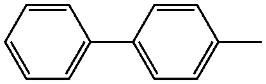 | H |
| 142 | 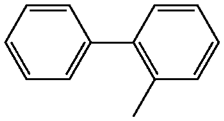 | H | Ph | Ph | H | 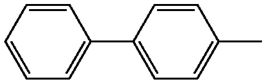 | H |

-continued
| | | | | | | | |
|---|---|---|---|---|---|---|---|
| 143 | 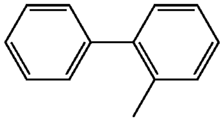 | H | Ph | H | H | 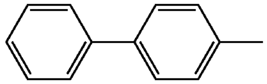 | H |
| 144 | 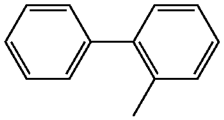 | H | H | H | H | 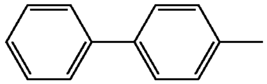 | Ph |
| 145 | 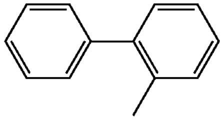 | Me | H | H | Me | 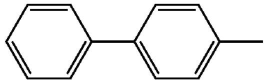 | H |
| 146 | 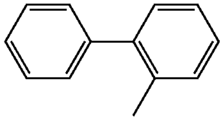 | H | Me | Me | H | 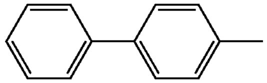 | H |
| 147 | 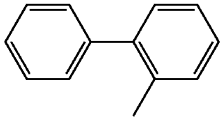 | H | H | H | H | 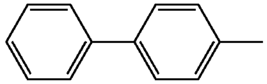 | Me |

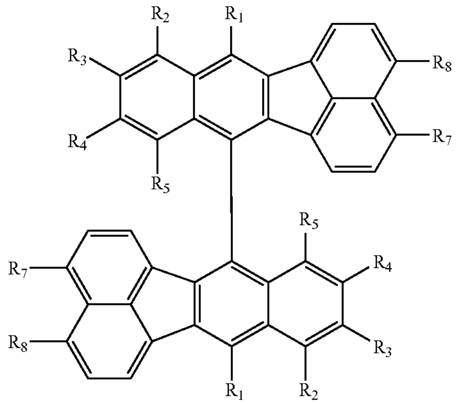

TypeAAA

| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |

-continued

| | | | | | | | |
|---|---|---|---|---|---|---|---|
| 56 | 2-naphthyl | H | H | H | H | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |

-continued

| | | | | | | | |
|---|---|---|---|---|---|---|---|
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |

-continued

| | | | | | | | |
|---|---|---|---|---|---|---|---|
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |

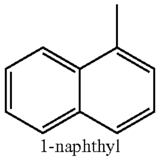
1-naphthyl

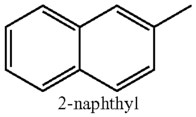
2-naphthyl

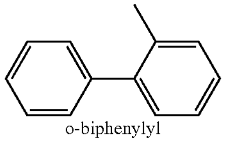
o-biphenylyl

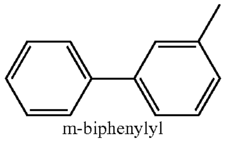
m-biphenylyl

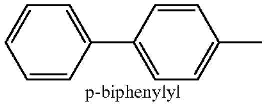
p-biphenylyl

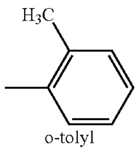
o-tolyl

-continued
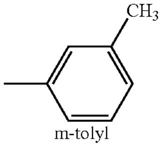
m-tolyl
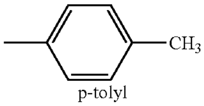
p-tolyl
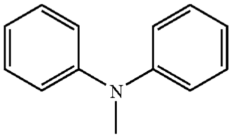
DPA
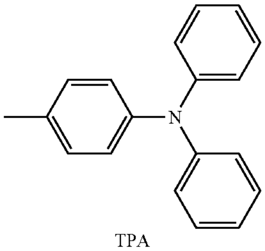
TPA
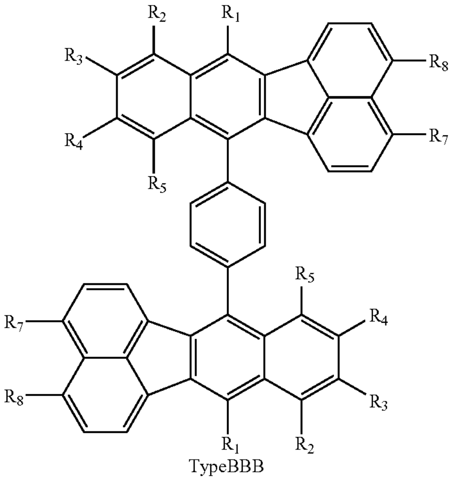
TypeBBB
| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |

-continued

| | | | | | | | |
|---|---|---|---|---|---|---|---|
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | H | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |

-continued

| | | | | | | | |
|---|---|---|---|---|---|---|---|
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |

-continued

| | | | | | | | |
|---|---|---|---|---|---|---|---|
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |

-continued
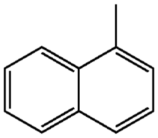
1-naphthyl
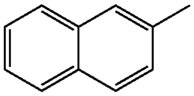
2-naphthyl
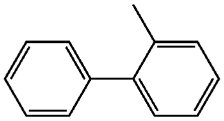
o-biphenylyl
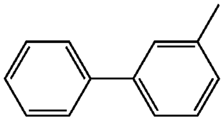
m-biphenylyl
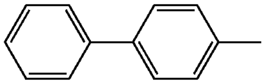
p-biphenylyl
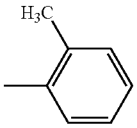
o-tolyl
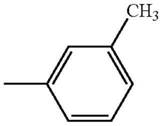
m-tolyl
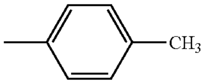
p-tolyl
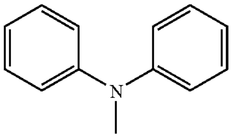
DPA
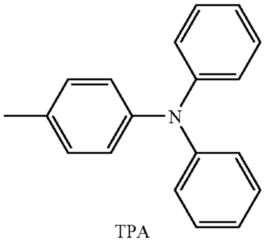
TPA

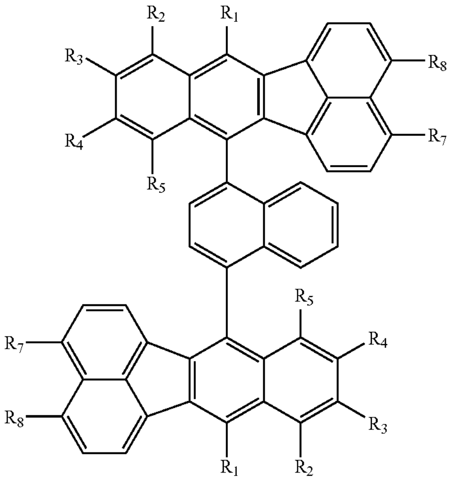

Type CCC

| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |

-continued

| | | | | | | | |
|---|---|---|---|---|---|---|---|
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | H | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |

-continued

| | | | | | | | |
|---|---|---|---|---|---|---|---|
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |

-continued

| | | | | | | | |
|---|---|---|---|---|---|---|---|
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |

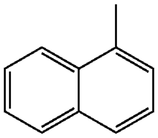

1-naphthyl

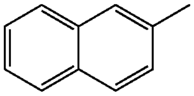

2-naphthyl

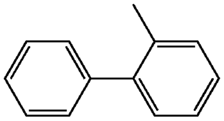

o-biphenylyl

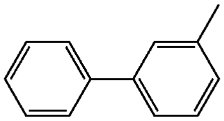

m-biphenylyl

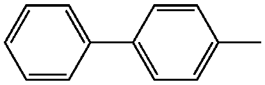

p-biphenylyl

-continued
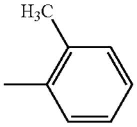
o-tolyl
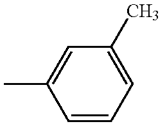
m-tolyl
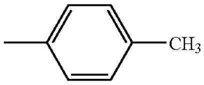
p-tolyl
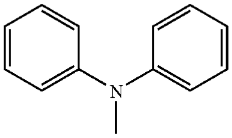
DPA
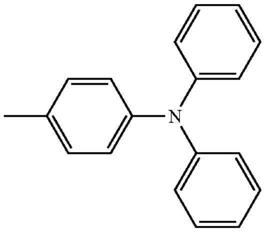
TPA
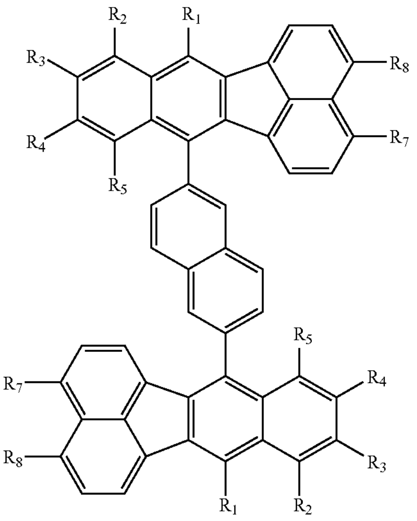
TypeDDD
| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |

-continued

| | | | | | | | |
|---|---|---|---|---|---|---|---|
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | H | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |

-continued

| | | | | | | | |
|---|---|---|---|---|---|---|---|
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |

-continued

| | | | | | | | |
|---|---|---|---|---|---|---|---|
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |

-continued
| | | | | | | | |
|---|---|---|---|---|---|---|---|
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |
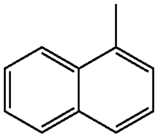
1-naphthyl
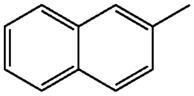
2-naphthyl
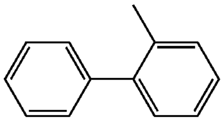
o-biphenylyl
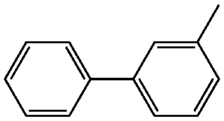
m-biphenylyl
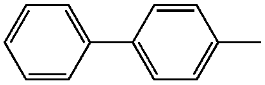
p-biphenylyl
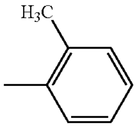
o-tolyl
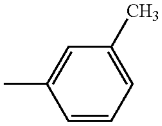
m-tolyl
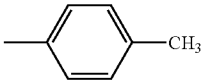
p-tolyl
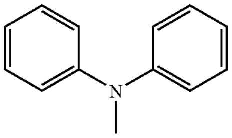
DPA -continued

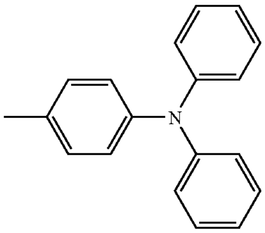

TPA

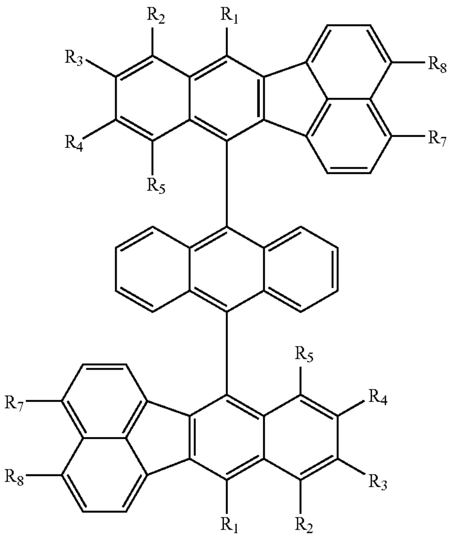

TypeEEE

| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |

-continued

| | | | | | | | |
|---|---|---|---|---|---|---|---|
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | H | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |

-continued

| | | | | | | | |
|---|---|---|---|---|---|---|---|
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |

-continued

| | | | | | | | |
|---|---|---|---|---|---|---|---|
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |

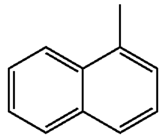

1-naphthyl

-continued
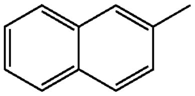
2-naphthyl
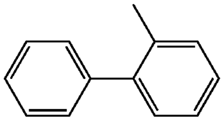
o-biphenylyl
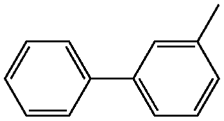
m-biphenylyl
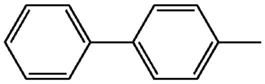
p-biphenylyl
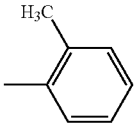
o-tolyl
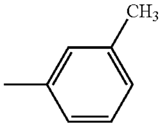
m-tolyl
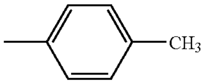
p-tolyl
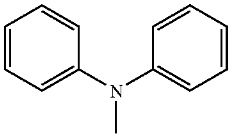
DPA
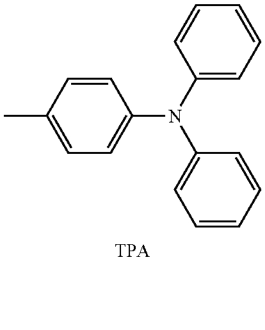
TPA

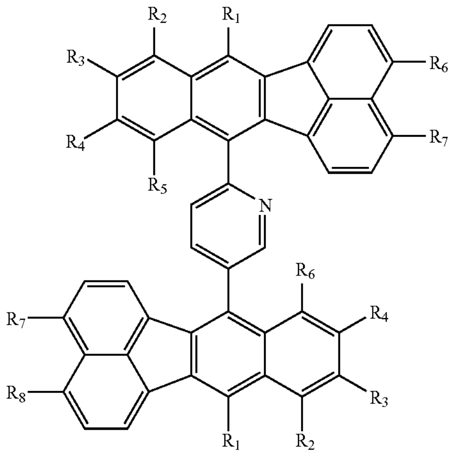

TypeLLL

| | $R_1$ | $R_2$ | $R_3$ | $R_4$ | $R_5$ | $R_6$ | $R_7$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |

-continued

| | | | | | | | |
|---|---|---|---|---|---|---|---|
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | H | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | p-biphenylyl | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |

-continued

| | | | | | | | |
|---|---|---|---|---|---|---|---|
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |

-continued

| | | | | | | | |
|---|---|---|---|---|---|---|---|
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |

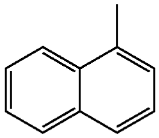

1-naphthyl

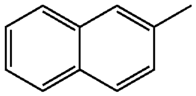

2-naphthyl

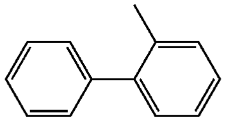

o-biphenylyl

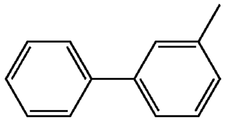

m-biphenylyl

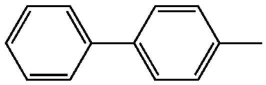

p-biphenylyl

-continued
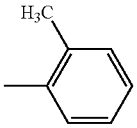
o-tolyl
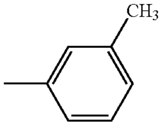
m-tolyl
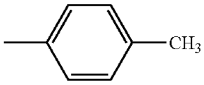
p-tolyl
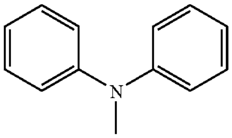
DPA
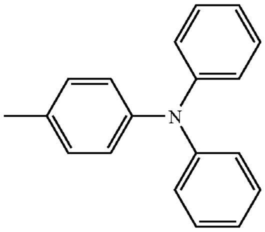
TPA
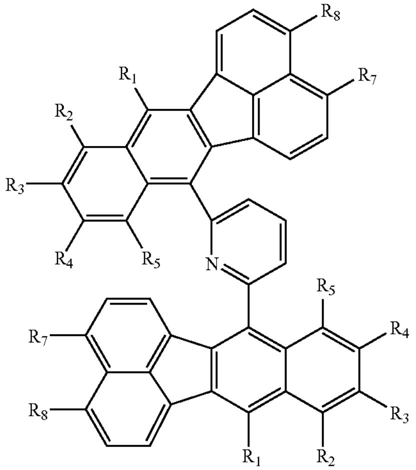
TypeMMM
| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |

-continued

| | | | | | | | |
|---|---|---|---|---|---|---|---|
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | H | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |

-continued

| | | | | | | | |
|---|---|---|---|---|---|---|---|
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |

-continued

| | | | | | | | |
|---|---|---|---|---|---|---|---|
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |

-continued
| | | | | | | | |
|---|---|---|---|---|---|---|---|
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |
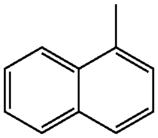
1-naphthyl
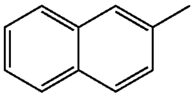
2-naphthyl
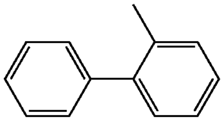
o-biphenylyl
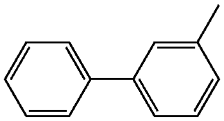
m-biphenylyl
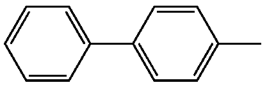
p-biphenylyl
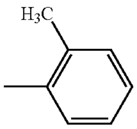
o-tolyl
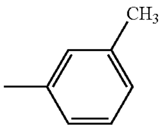
m-tolyl
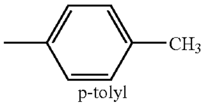
p-tolyl
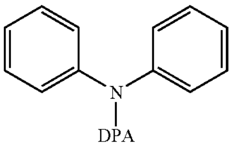
DPA -continued

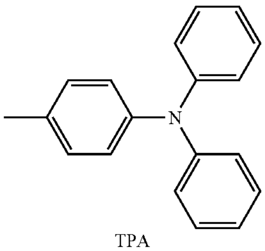

TPA

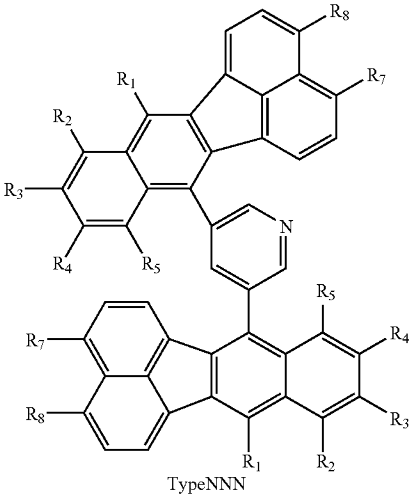

TypeNNN

| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |

-continued

| | | | | | | | |
|---|---|---|---|---|---|---|---|
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | h | 1-naphthyl | H |
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1- naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |

-continued

| | | | | | | | |
|---|---|---|---|---|---|---|---|
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |

-continued

| | | | | | | | |
|---|---|---|---|---|---|---|---|
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |

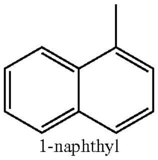

1-naphthyl

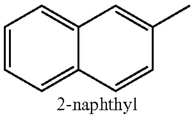

2-naphthyl

-continued
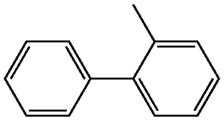
o-biphenylyl
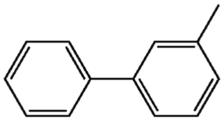
m-biphenylyl
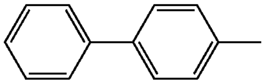
p-biphenylyl
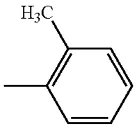
o-tolyl
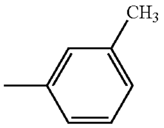
m-tolyl
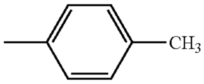
p-tolyl
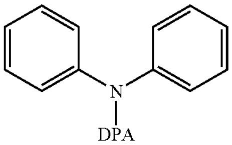
DPA
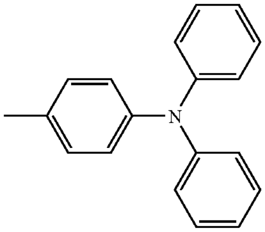
TPA

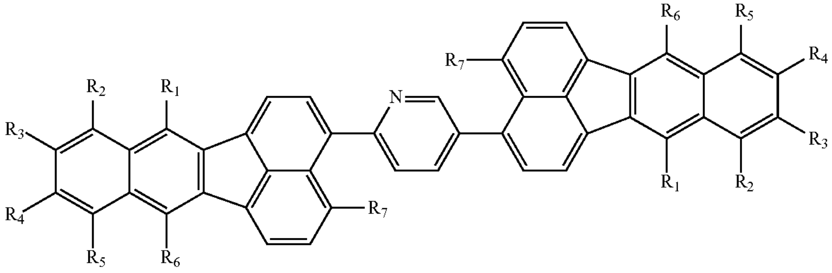
TypeRRR
| | $R_1$ | $R_2$ | $R_3$ | $R_4$ | $R_5$ | $R_6$ | $R_7$ |
|---|---|---|---|---|---|---|---|
| 1 | H | H | H | H | H | H | H |
| 2 | Ph | H | H | H | H | Ph | H |
| 3 | Ph | Ph | H | H | Ph | Ph | H |
| 4 | Ph | H | Ph | Ph | H | Ph | H |
| 5 | Ph | H | Ph | H | H | Ph | H |
| 6 | Ph | H | H | H | H | Ph | Ph |
| 7 | Ph | Me | H | H | Me | Ph | H |
| 8 | Ph | H | Me | Me | H | Ph | H |
| 9 | Ph | H | H | H | H | Ph | Me |
| 10 | 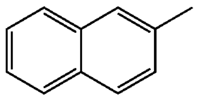 | H | H | H | H | 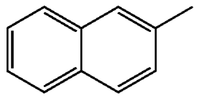 | H |
| 11 | 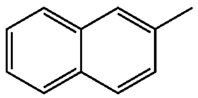 | Ph | H | H | Ph | 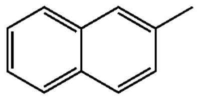 | H |
| 12 | 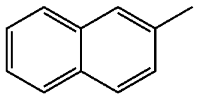 | H | Ph | Ph | H | 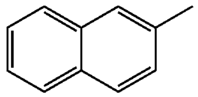 | H |
| 13 | 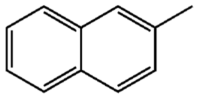 | H | Ph | H | H | 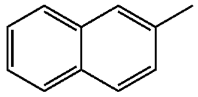 | H |

-continued
| | | | | | | | |
|---|---|---|---|---|---|---|---|
| 14 | 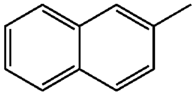 | H | H | H | H | 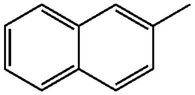 | Ph |
| 15 | 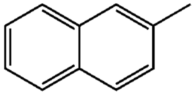 | Me | H | H | Me | 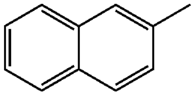 | H |
| 16 | 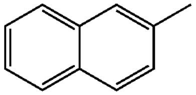 | H | Me | Me | H | 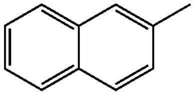 | H |
| 17 | 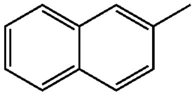 | H | H | H | H | 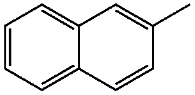 | Me |
| 18 | 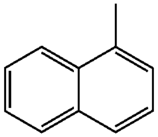 | H | H | H | H | 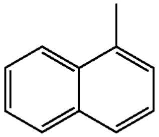 | H |
| 19 | 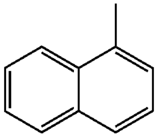 | Ph | H | H | Ph | 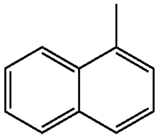 | H |
| 20 | 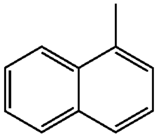 | H | Ph | Ph | H | 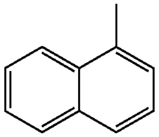 | H |
| 21 | 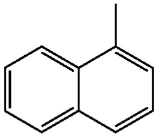 | H | Ph | H | H | 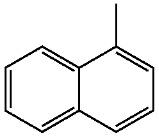 | H |

-continued
| | | | | | | |
|---|---|---|---|---|---|---|
| 22 | 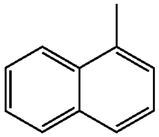 | H | H | H | H | 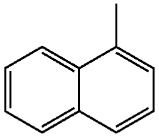 Ph |
| 23 | 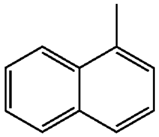 | Me | H | H | Me | 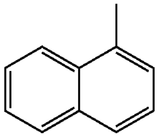 H |
| 24 | 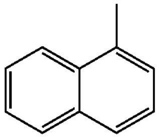 | H | Me | Me | H | 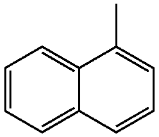 H |
| 25 | 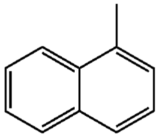 | H | H | H | H | 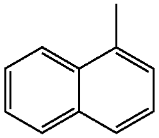 Me |
| 26 | 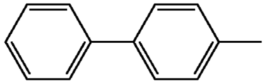 | H | H | H | H | 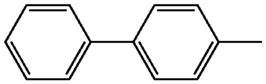 H |
| 27 | 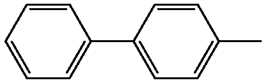 | Ph | H | H | Ph | 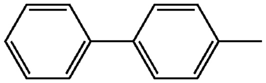 H |
| 28 | 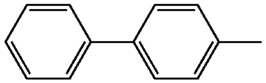 | H | Ph | Ph | H | 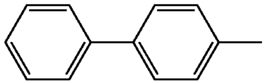 H |
| 29 | 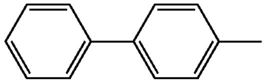 | H | Ph | H | H | 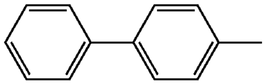 H |

-continued
| | | | | | | | |
|---|---|---|---|---|---|---|---|
| 30 | 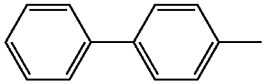 | H | H | H | H | 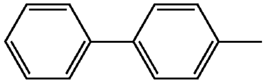 | Ph |
| 31 | 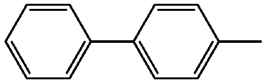 | Me | H | H | Me | 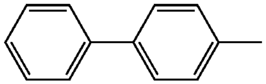 | H |
| 32 | 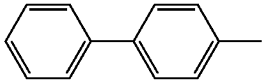 | H | Me | Me | H | 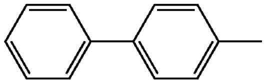 | H |
| 33 | 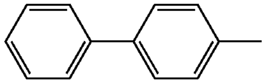 | H | H | H | H | 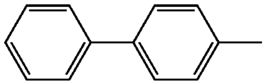 | Me |
| 34 | 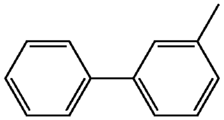 | H | H | H | H | 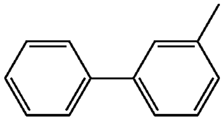 | H |
| 35 | 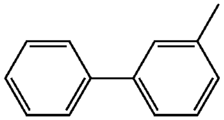 | Ph | H | H | Ph | 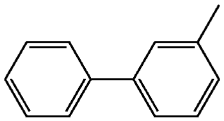 | H |
| 36 | 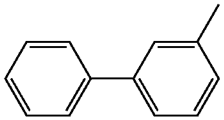 | H | Ph | Ph | H | 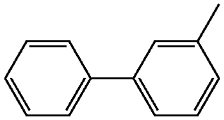 | H |
| 37 | 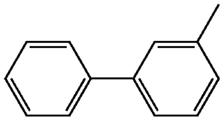 | H | Ph | H | H | 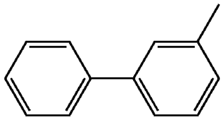 | H |
| 38 | 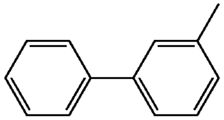 | H | H | H | H | 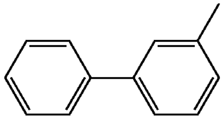 | Ph |

-continued
| | | | | | | | |
|---|---|---|---|---|---|---|---|
| 39 | 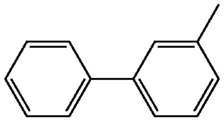 | Me | H | H | Me | 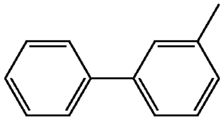 | H |
| 40 | 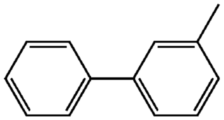 | H | Me | Me | H | 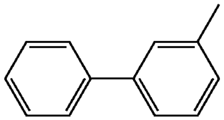 | H |
| 41 | 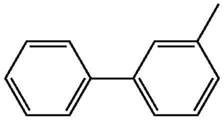 | H | H | H | H | 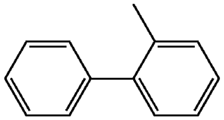 | Me |
| 42 | 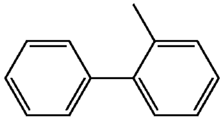 | H | H | H | H | 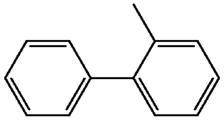 | H |
| 43 | 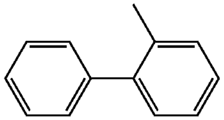 | Ph | H | H | Ph | 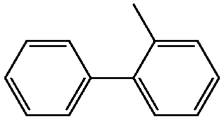 | H |
| 44 | 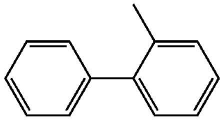 | H | Ph | Ph | H | 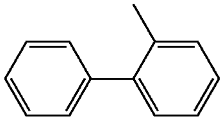 | H |
| 45 | 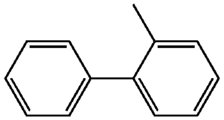 | H | Ph | H | H | 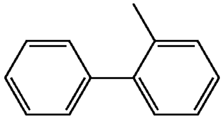 | H |

-continued
| | | | | | | | |
|---|---|---|---|---|---|---|---|
| 46 | 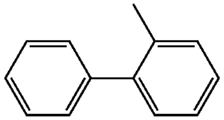 | H | H | H | H | 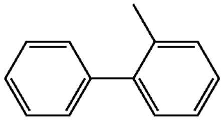 | Ph |
| 47 | 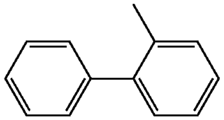 | Me | H | H | Me | 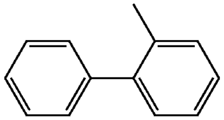 | H |
| 48 | 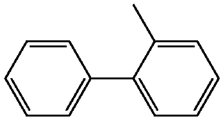 | H | Me | Me | H | 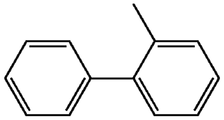 | H |
| 49 | 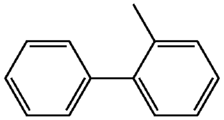 | H | H | H | H | 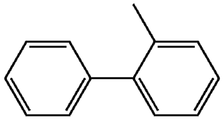 | Me |
| 50 | Ph | H | H | H | H | 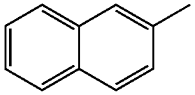 | H |
| 51 | Ph | H | H | H | H | 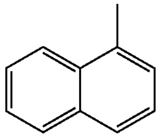 | H |
| 52 | Ph | H | H | H | H | 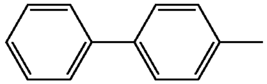 | H |
| 53 | Ph | H | H | H | H | 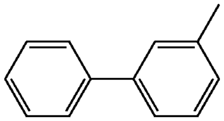 | H |

-continued
| | | | | | | | |
|---|---|---|---|---|---|---|---|
| 54 | Ph | H | H | H | H | 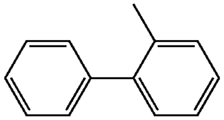 | H |
| 55 | 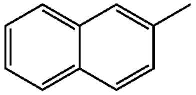 | H | H | H | H | 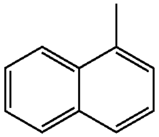 | H |
| 56 | 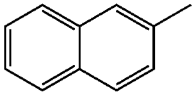 | H | H | H | H | 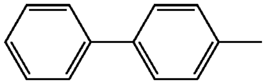 | H |
| 57 | 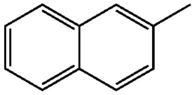 | H | H | H | H | 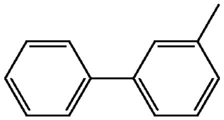 | H |
| 58 | 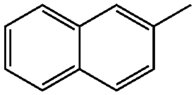 | H | H | H | H | 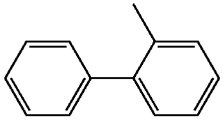 | H |
| 59 | 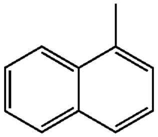 | H | H | H | H | 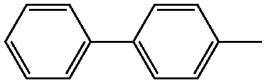 | H |
| 60 | 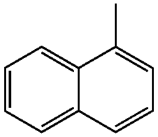 | H | H | H | H | 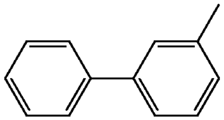 | H |

-continued
| | | | | | | | |
|---|---|---|---|---|---|---|---|
| 61 | 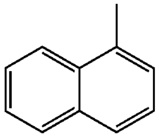 | H | H | H | H | 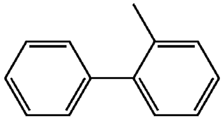 | H |
| 62 | 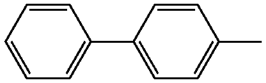 | H | H | H | H | 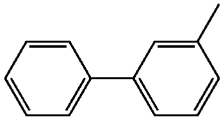 | H |
| 63 | 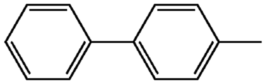 | H | H | H | H | 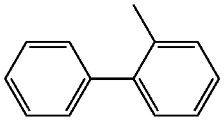 | H |
| 64 | 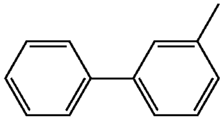 | H | H | H | H | 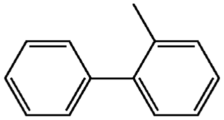 | H |
| 65 | H | Ph | H | H | Ph | H | H |
| 66 | H | 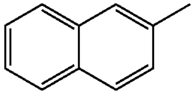 | H | H | 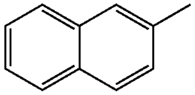 | H | H |
| 67 | H | 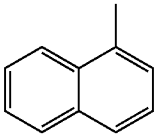 | H | H | 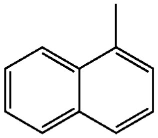 | H | H |
| 68 | H | 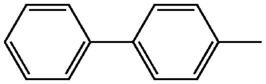 | H | H | 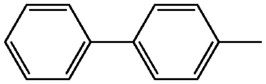 | H | H |

-continued
| | | | | | | | |
|---|---|---|---|---|---|---|---|
| 69 | H | 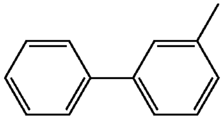 | H | H | 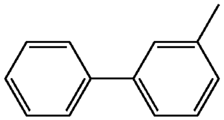 | H | H |
| 70 | H | 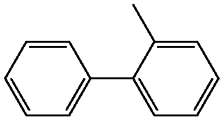 | H | H | 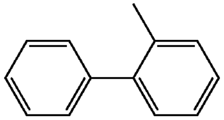 | H | H |
| 71 | H | H | 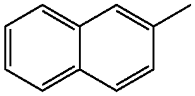 | 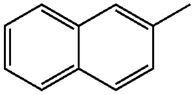 | H | H | H |
| 72 | H | H | 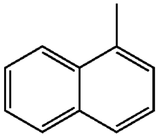 | 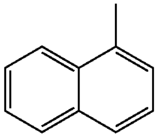 | H | H | H |
| 73 | H | H | 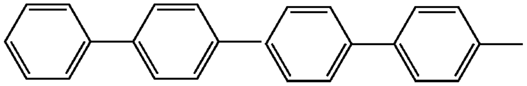 | | H | H | H |
| 74 | H | H | 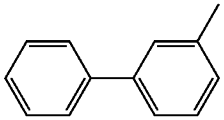 | 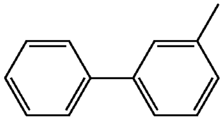 | H | H | H |
| 75 | H | H | 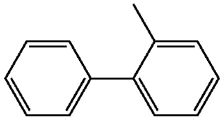 | 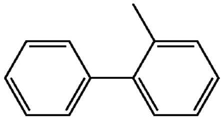 | H | H | H |
| 76 | 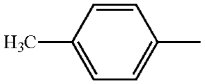 | H | H | H | H | 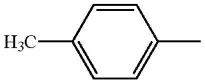 | H |

-continued
| | | | | | | | |
|---|---|---|---|---|---|---|---|
| 77 | 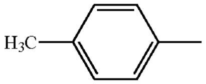 | Ph | H | H | Ph | 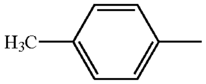 | H |
| 78 | 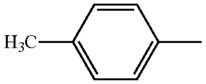 | H | Ph | Ph | H | 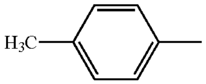 | H |
| 79 | 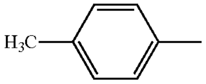 | H | Ph | H | H | 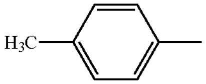 | H |
| 80 | 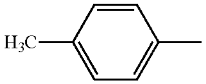 | H | H | H | H | 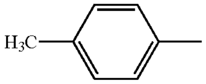 | Ph |
| 81 | 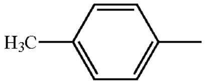 | Me | H | H | Me | 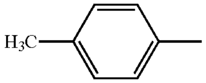 | H |
| 82 | 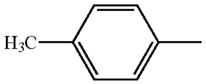 | H | Me | Me | H | 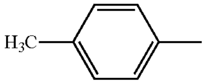 | H |
| 83 | 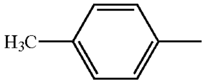 | H | H | H | H | 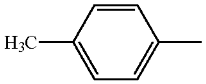 | Me |
| 84 | 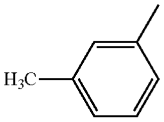 | H | H | H | H | 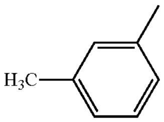 | H |
| 85 | 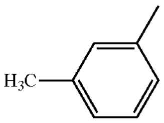 | Ph | H | H | Ph | 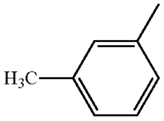 | H |

-continued
| | | | | | | | |
|---|---|---|---|---|---|---|---|
| 86 | 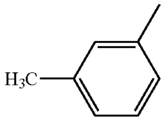 | H | Ph | Ph | H | 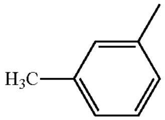 | H |
| 87 | 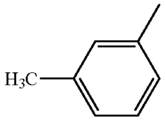 | H | Ph | H | H | 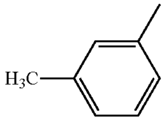 | H |
| 88 | 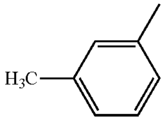 | H | H | H | H | 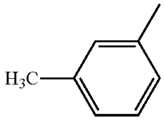 | Ph |
| 89 | 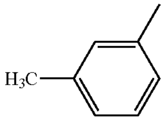 | Me | H | H | Me | 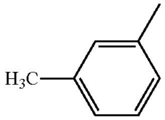 | H |
| 90 | 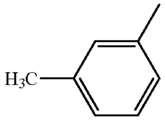 | H | Me | Me | H | 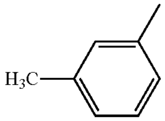 | H |
| 91 | 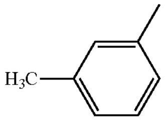 | H | H | H | H | 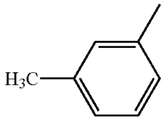 | Me |
| 92 | 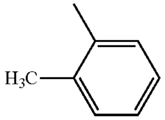 | H | H | H | H | 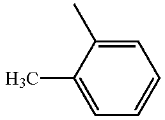 | H |
| 93 | 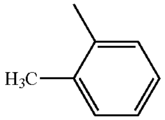 | Ph | H | H | Ph | 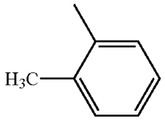 | H |

-continued
| | | | | | | | |
|---|---|---|---|---|---|---|---|
| 94 | 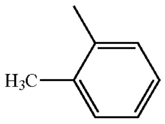 | H | Ph | Ph | H | 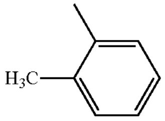 | H |
| 95 | 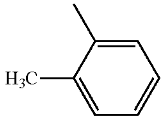 | H | Ph | H | H | 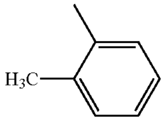 | H |
| 96 | 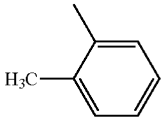 | H | H | H | H | 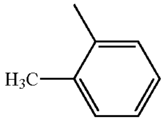 | Ph |
| 97 | 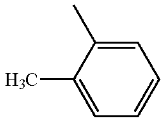 | Me | H | H | Me | 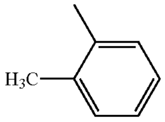 | H |
| 98 | 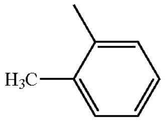 | H | Me | Me | H | 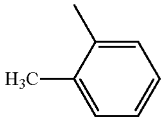 | H |
| 99 | 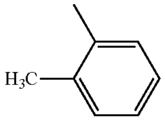 | H | H | H | H | 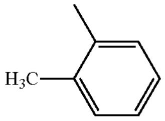 | Me |
| 100 | 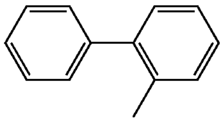 | H | H | H | H | 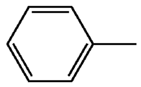 | H |

-continued
| | | | | | | | |
|---|---|---|---|---|---|---|---|
| 101 | 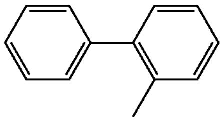 | Ph | H | H | Ph | 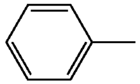 | H |
| 102 | 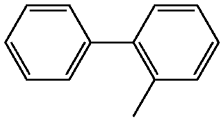 | H | Ph | Ph | H | 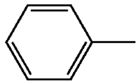 | H |
| 103 | 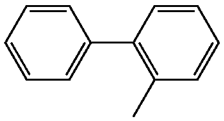 | H | Ph | H | H | 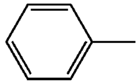 | H |
| 104 | 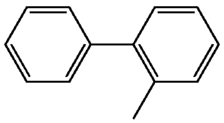 | H | H | H | H | 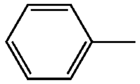 | Ph |
| 105 | 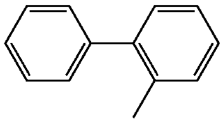 | Me | H | H | Me | 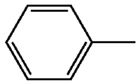 | H |
| 106 | 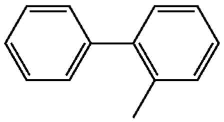 | H | Me | Me | H | 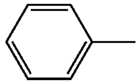 | H |
| 107 | 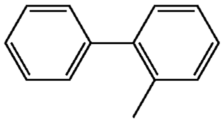 | H | H | H | H | 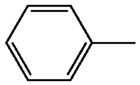 | Me |
| 108 | 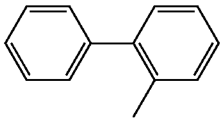 | H | H | H | H | 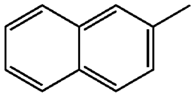 | H |

-continued
| | | | | | | | |
|---|---|---|---|---|---|---|---|
| 109 | 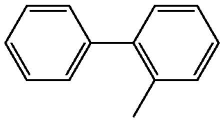 | Ph | H | H | Ph | 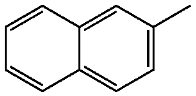 | H |
| 110 | 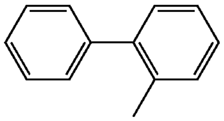 | H | Ph | Ph | H | 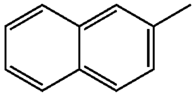 | H |
| 111 | 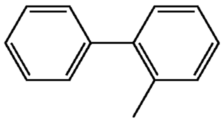 | H | Ph | H | H | 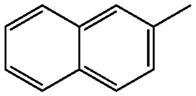 | H |
| 112 | 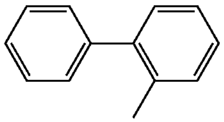 | H | H | H | H | 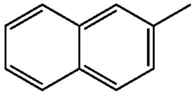 | Ph |
| 113 | 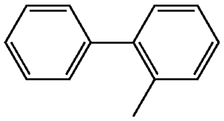 | Me | H | H | Me | 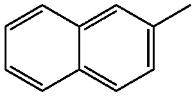 | H |
| 114 | 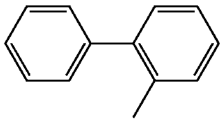 | H | Me | Me | H | 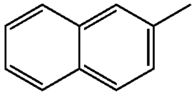 | H |
| 115 | 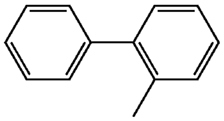 | H | H | H | H | 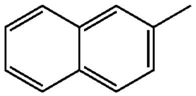 | Me |

-continued
| | | | | | | | |
|---|---|---|---|---|---|---|---|
| 116 | 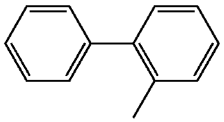 | H | H | H | H | 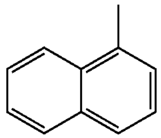 | H |
| 117 | 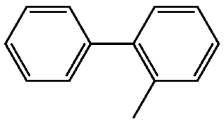 | Ph | H | H | Ph | 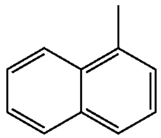 | H |
| 118 | 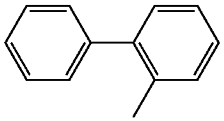 | H | Ph | Ph | H | 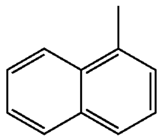 | H |
| 119 | 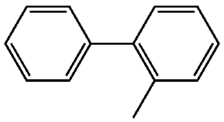 | H | Ph | H | H | 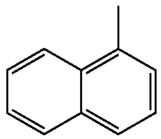 | H |
| 120 | 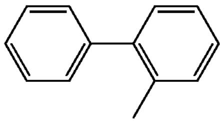 | H | H | H | H | 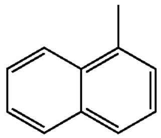 | Ph |
| 121 | 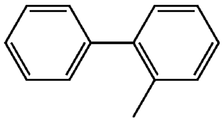 | Me | H | H | Me | 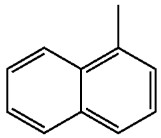 | H |
| 122 | 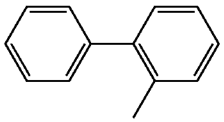 | H | Me | Me | H | 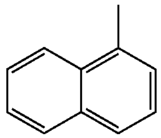 | H |

-continued
| | | | | | | | |
|---|---|---|---|---|---|---|---|
| 123 | 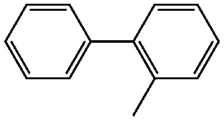 | H | H | H | H | 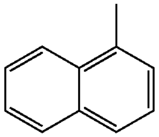 | Me |
| 124 | 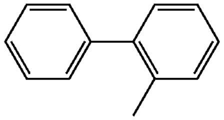 | H | H | H | H | 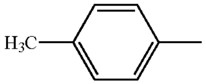 | H |
| 125 | 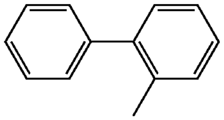 | Ph | H | H | Ph | 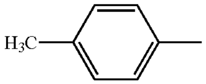 | H |
| 126 | 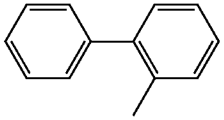 | H | Ph | Ph | H | 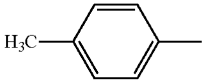 | H |
| 127 | 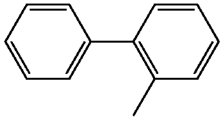 | H | Ph | H | H | 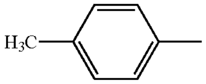 | H |
| 128 | 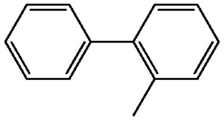 | H | H | H | H | 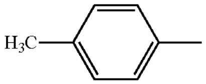 | Ph |
| 129 | 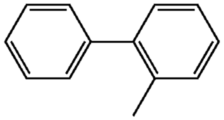 | Me | H | H | Me | 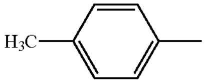 | H |

-continued
| | | | | | | | |
|---|---|---|---|---|---|---|---|
| 130 | 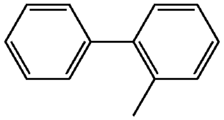 | H | Me | Me | H | 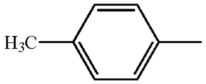 | H |
| 131 | 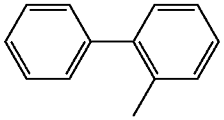 | H | H | H | H | 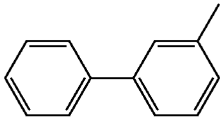 | Me |
| 132 | 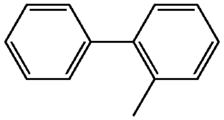 | H | H | H | H | 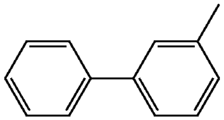 | H |
| 133 | 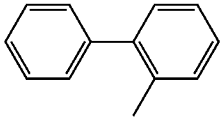 | Ph | H | H | Ph | 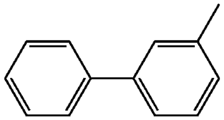 | H |
| 134 | 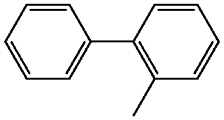 | H | Ph | Ph | H | 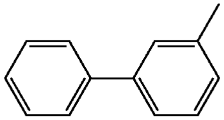 | H |
| 135 | 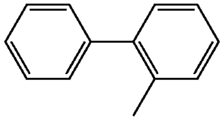 | H | Ph | H | H | 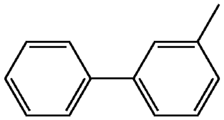 | H |
| 136 | 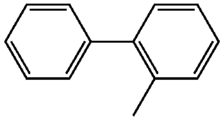 | H | H | H | H | 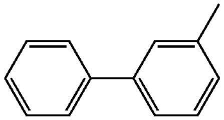 | Ph |
| 137 | 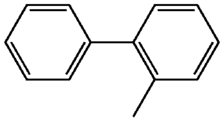 | Me | H | H | Me | 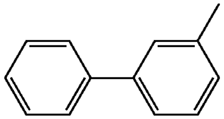 | H |

-continued
| | | | | | | | |
|---|---|---|---|---|---|---|---|
| 138 | 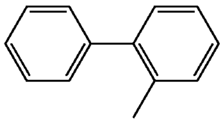 | H | Me | Me | H | 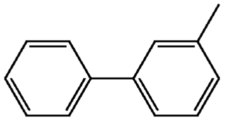 | H |
| 139 | 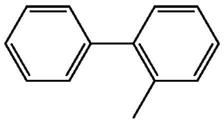 | H | H | H | H | 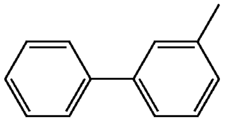 | Me |
| 140 | 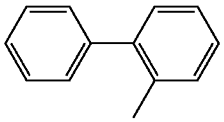 | H | H | H | H | 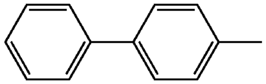 | H |
| 141 | 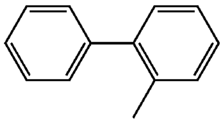 | Ph | H | H | Ph | 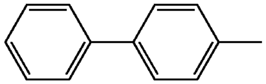 | H |
| 142 | 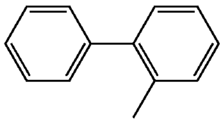 | H | Ph | Ph | H | 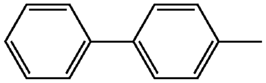 | H |

-continued
| | | | | | | | |
|---|---|---|---|---|---|---|---|
| 143 | 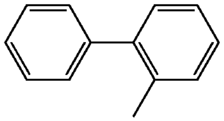 | H | Ph | H | H | 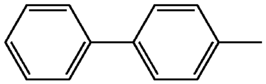 | H |
| 144 | 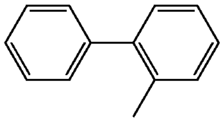 | H | H | H | H | 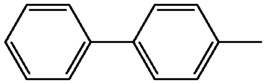 | Ph |
| 145 | 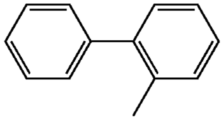 | Me | H | H | Me | 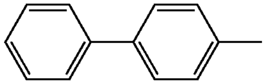 | H |
| 146 | 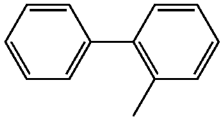 | H | Me | Me | H | 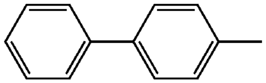 | H |
| 147 | 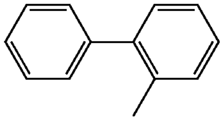 | H | H | H | H | 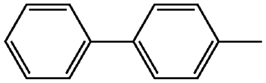 | Me |

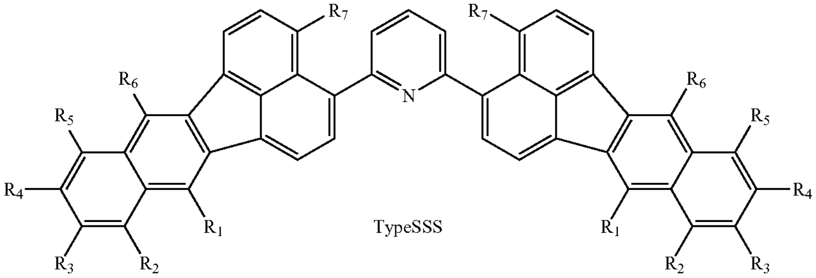
TypeSSS
| | $R_1$ | $R_2$ | $R_3$ | $R_4$ | $R_5$ | $R_6$ | $R_7$ |
|---|---|---|---|---|---|---|---|
| 1 | H | H | H | H | H | H | H |
| 2 | Ph | H | H | H | H | Ph | H |
| 3 | Ph | Ph | H | H | Ph | Ph | H |
| 4 | Ph | H | Ph | Ph | H | Ph | H |
| 5 | Ph | H | Ph | H | H | Ph | H |
| 6 | Ph | H | H | H | H | Ph | Ph |
| 7 | Ph | Me | H | H | Me | Ph | H |
| 8 | Ph | H | Me | Me | H | Ph | H |
| 9 | Ph | H | H | H | H | Ph | Me |
| 10 | 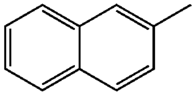 | H | H | H | H | 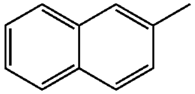 | H |
| 11 | 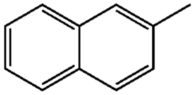 | Ph | H | H | Ph | 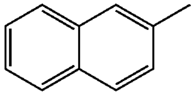 | H |
| 12 | 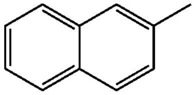 | H | Ph | Ph | H | 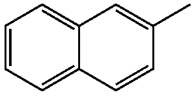 | H |
| 13 | 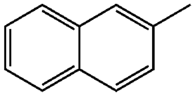 | H | Ph | H | H | 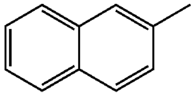 | H |

-continued
| | | | | | | | |
|---|---|---|---|---|---|---|---|
| 14 | 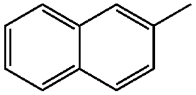 | H | H | H | H | 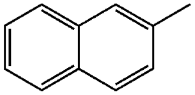 | Ph |
| 15 | 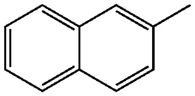 | Me | H | H | Me | 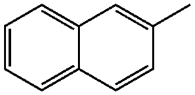 | H |
| 16 | 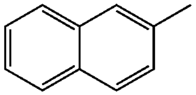 | H | Me | Me | H | 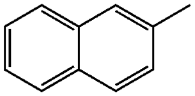 | H |
| 17 | 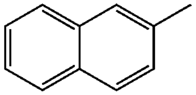 | H | H | H | H | 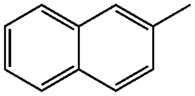 | Me |
| 18 | 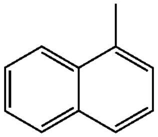 | H | H | H | H | 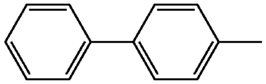 | H |
| 19 | 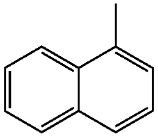 | Ph | H | H | Ph | 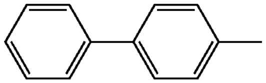 | H |
| 20 | 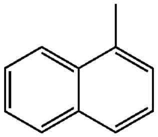 | H | Ph | Ph | H | 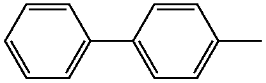 | H |
| 21 | 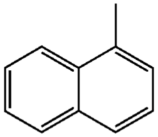 | H | Ph | H | H | 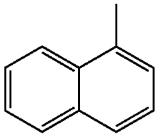 | H |

-continued
| | | | | | | | |
|---|---|---|---|---|---|---|---|
| 22 | 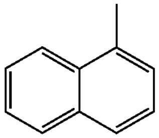 | H | H | H | H | 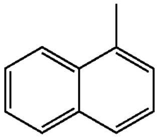 | Ph |
| 23 | 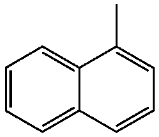 | Me | H | H | Me | 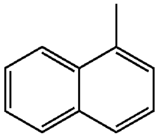 | H |
| 24 | 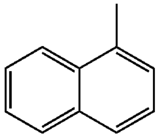 | H | Me | Me | H | 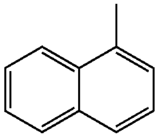 | H |
| 25 | 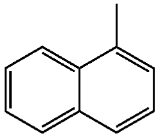 | H | H | H | H | 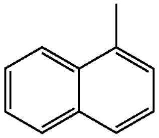 | Me |
| 26 | 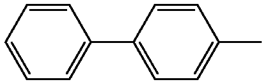 | H | H | H | H | 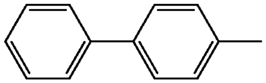 | H |
| 27 | 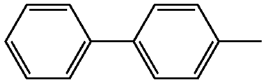 | Ph | H | H | Ph | 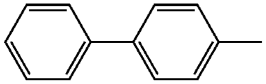 | H |
| 28 | 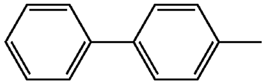 | H | Ph | Ph | H | 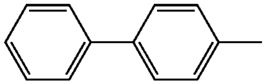 | H |
| 29 | 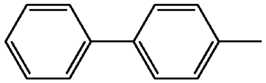 | H | Ph | H | H | 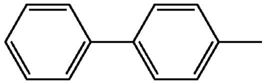 | H |

-continued
| | | | | | | | |
|---|---|---|---|---|---|---|---|
| 30 | 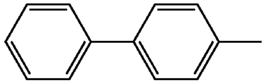 | H | H | H | H | 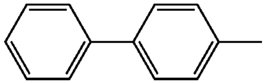 | Ph |
| 31 | 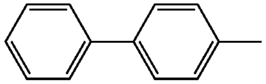 | Me | H | H | Me | 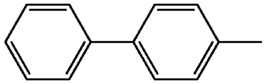 | H |
| 32 | 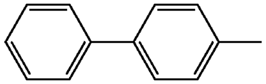 | H | Me | Me | H | 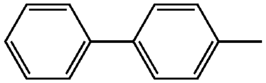 | H |
| 33 | 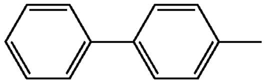 | H | H | H | H | 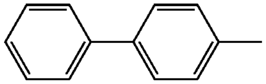 | Me |
| 34 | 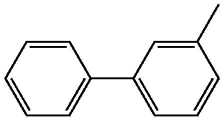 | H | H | H | H | 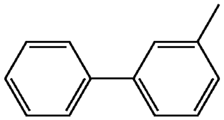 | H |
| 35 | 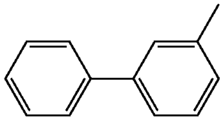 | Ph | H | H | Ph | 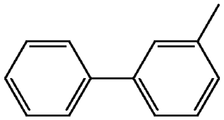 | H |
| 36 | 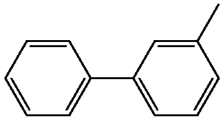 | H | Ph | Ph | H | 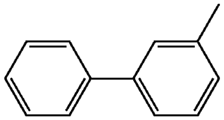 | H |
| 37 | 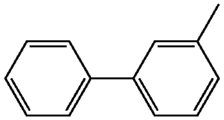 | H | Ph | H | H | 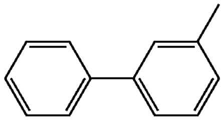 | H |
| 38 | 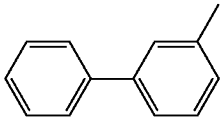 | H | H | H | H | 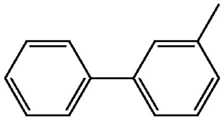 | Ph |

-continued
| | | | | | | | |
|---|---|---|---|---|---|---|---|
| 39 | 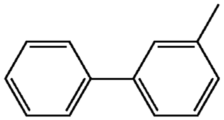 | Me | H | H | Me | 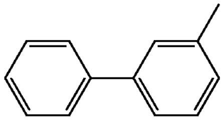 | H |
| 40 | 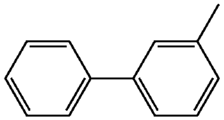 | H | Me | Me | H | 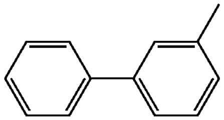 | H |
| 41 | 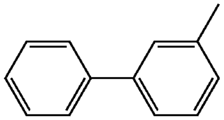 | H | H | H | H | 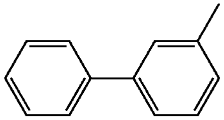 | Me |
| 42 | 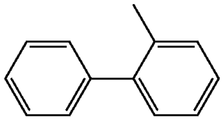 | H | H | H | H | 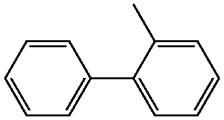 | H |
| 43 | 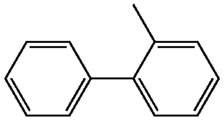 | Ph | H | H | Ph | 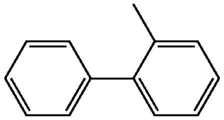 | H |
| 44 | 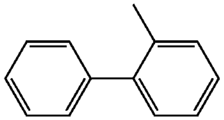 | H | Ph | Ph | H | 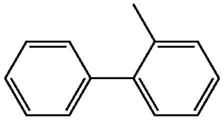 | H |
| 45 | 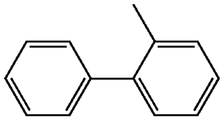 | H | Ph | H | H | 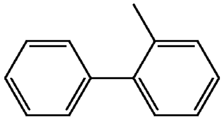 | H |

-continued
| | | | | | | | |
|---|---|---|---|---|---|---|---|
| 46 | 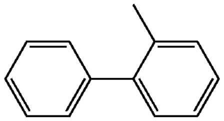 | H | H | H | H | 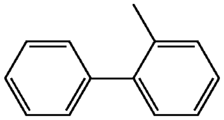 | Ph |
| 47 | 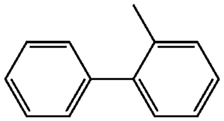 | Me | H | H | Me | 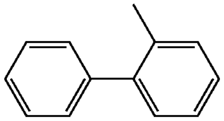 | H |
| 48 | 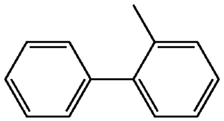 | H | Me | Me | H | 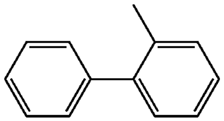 | H |
| 49 | 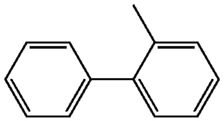 | H | H | H | H | 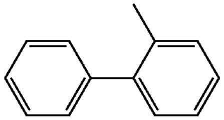 | Me |
| 50 | Ph | H | H | H | H | 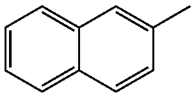 | H |
| 51 | Ph | H | H | H | H | 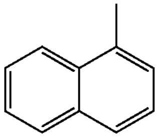 | H |
| 52 | Ph | H | H | H | H | 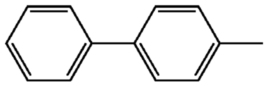 | H |
| 53 | Ph | H | H | H | H | 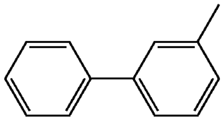 | H |

-continued
| | | | | | | | |
|---|---|---|---|---|---|---|---|
| 54 | Ph | H | H | H | H | 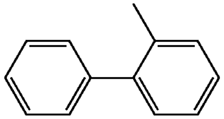 | H |
| 55 | 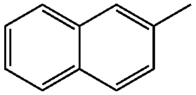 | H | H | H | H | 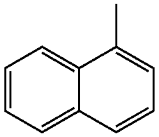 | H |
| 56 | 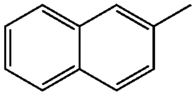 | H | H | H | H | 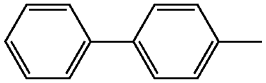 | H |
| 57 | 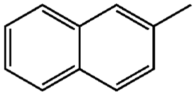 | H | H | H | H | 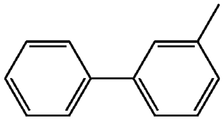 | H |
| 58 | 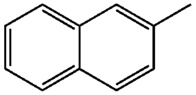 | H | H | H | H | 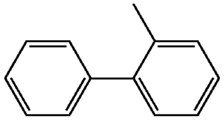 | H |
| 59 | 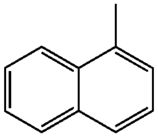 | H | H | H | H | 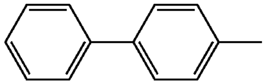 | H |
| 60 | 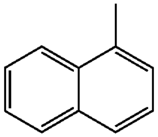 | H | H | H | H | 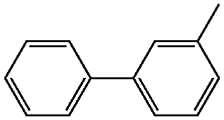 | H |

-continued
| | | | | | | | |
|---|---|---|---|---|---|---|---|
| 61 | 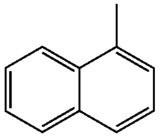 | H | H | H | H | 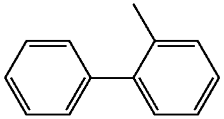 | H |
| 62 | 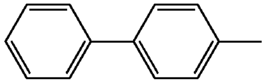 | H | H | H | H | 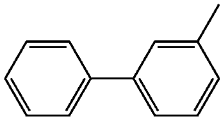 | H |
| 63 | 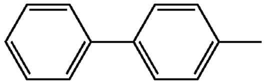 | H | H | H | H | 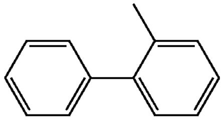 | H |
| 64 | 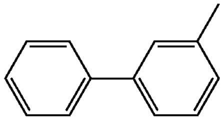 | H | H | H | H | 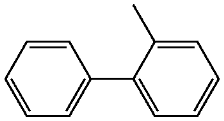 | H |
| 65 | H | Ph | H | H | Ph | H | H |
| 66 | H | 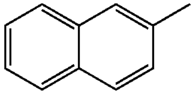 | H | H | 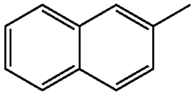 | H | H |
| 67 | H | 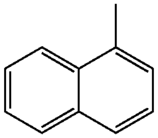 | H | H | 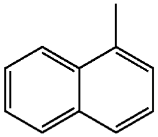 | H | H |
| 68 | H | 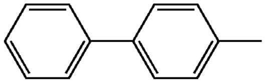 | H | H | 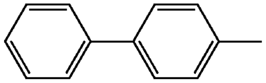 | H | H |

-continued
| | | | | | | | |
|---|---|---|---|---|---|---|---|
| 69 | H | 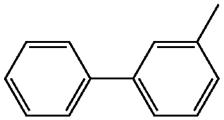 | H | H | 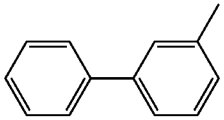 | H | H |
| 70 | H | 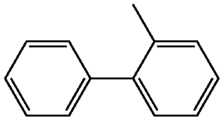 | H | H | 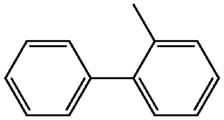 | H | H |
| 71 | H | H | 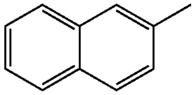 | 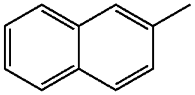 | H | H | H |
| 72 | H | H | 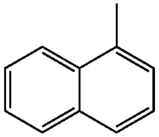 | 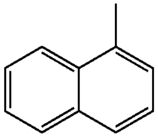 | H | H | H |
| 73 | H | H | 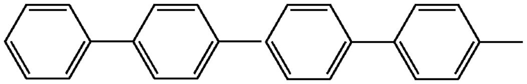 | | H | H | H |
| 74 | H | H | 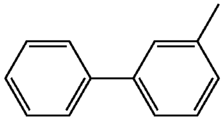 | 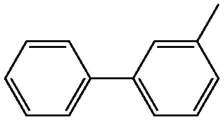 | H | H | H |
| 75 | H | H | 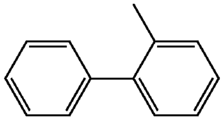 | 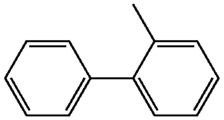 | H | H | H |
| 76 | 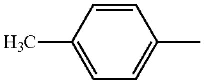 | H | H | H | H | 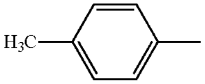 | H |

-continued
| | | | | | | | |
|---|---|---|---|---|---|---|---|
| 77 | 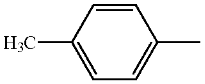 | Ph | H | H | Ph | 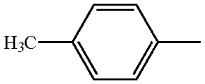 | H |
| 78 | 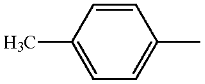 | H | Ph | Ph | H | 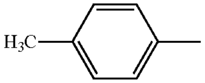 | H |
| 79 | 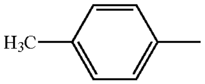 | H | Ph | H | H | 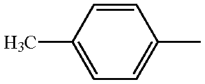 | H |
| 80 | 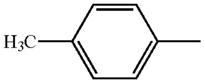 | H | H | H | H | 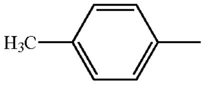 | Ph |
| 81 | 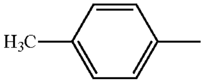 | Me | H | H | Me | 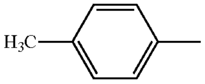 | H |
| 82 | 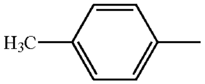 | H | Me | Me | H | 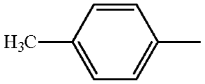 | H |
| 83 | 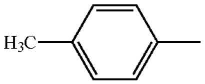 | H | H | H | H | 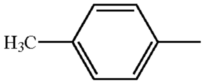 | Me |
| 84 | 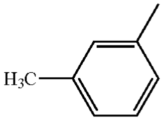 | H | H | H | H | 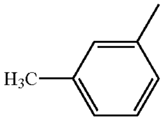 | H |
| 85 | 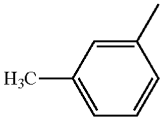 | Ph | H | H | Ph | 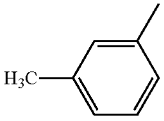 | H |

-continued
| | | | | | | | |
|---|---|---|---|---|---|---|---|
| 86 | 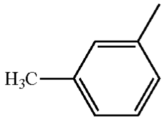 | H | Ph | Ph | H | 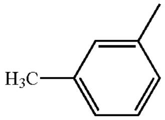 | H |
| 87 | 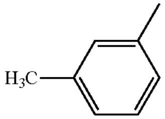 | H | Ph | H | H | 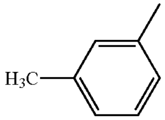 | H |
| 88 | 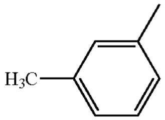 | H | H | H | H | 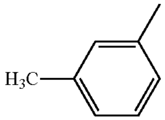 | Ph |
| 89 | 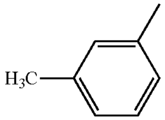 | Me | H | H | Me | 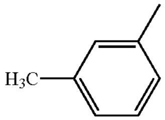 | H |
| 90 | 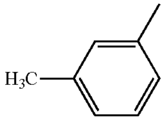 | H | Me | Me | H | 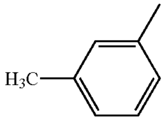 | H |
| 91 | 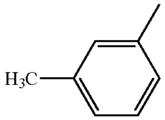 | H | H | H | H | 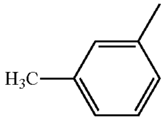 | Me |
| 92 | 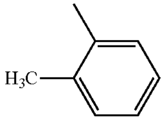 | H | H | H | H | 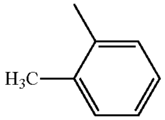 | H |
| 93 | 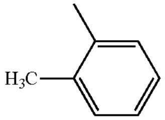 | Ph | H | H | Ph | 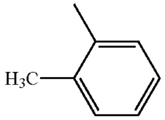 | H |

-continued
| | | | | | | | |
|---|---|---|---|---|---|---|---|
| 94 | 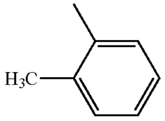 | H | Ph | Ph | H | 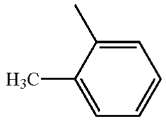 | H |
| 96 | 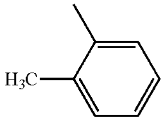 | H | Ph | H | H | 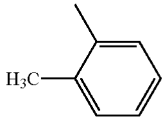 | H |
| 96 | 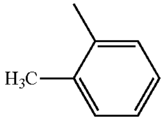 | H | H | H | H | 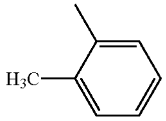 | Ph |
| 97 | 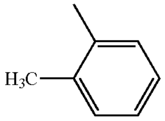 | Me | H | H | Me | 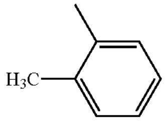 | H |
| 98 | 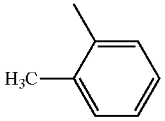 | H | Me | Me | H | 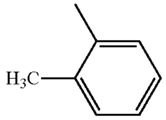 | H |
| 99 | 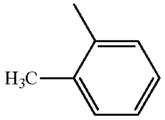 | H | H | H | H | 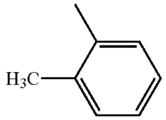 | Me |
| 100 | 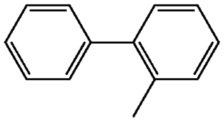 | H | H | H | H | 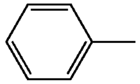 | H |

-continued
| | | | | | | | |
|---|---|---|---|---|---|---|---|
| 101 | 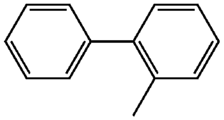 | Ph | H | H | Ph | 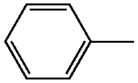 | H |
| 102 | 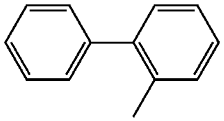 | H | Ph | Ph | H | 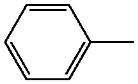 | H |
| 103 | 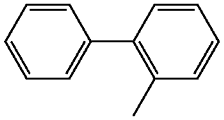 | H | Ph | H | H | 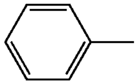 | H |
| 104 | 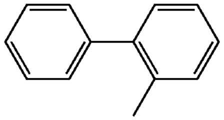 | H | H | H | H | 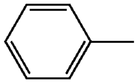 | Ph |
| 106 | 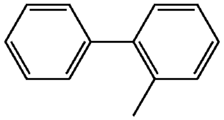 | Me | H | H | Me | 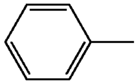 | H |
| 106 | 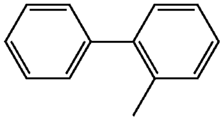 | H | Me | Me | H | 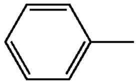 | H |
| 107 | 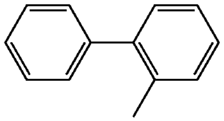 | H | H | H | H | 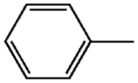 | Me |
| 108 | 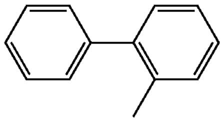 | H | H | H | H | 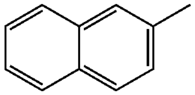 | H |

-continued
| | | | | | | | |
|---|---|---|---|---|---|---|---|
| 109 | 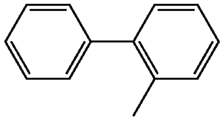 | Ph | H | H | Ph | 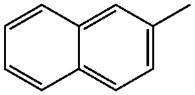 | H |
| 110 | 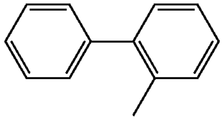 | H | Ph | Ph | H | 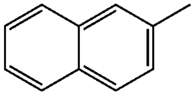 | H |
| 111 | 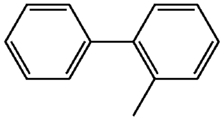 | H | Ph | H | H | 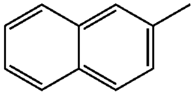 | H |
| 112 | 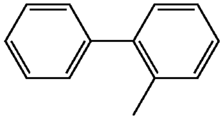 | H | H | H | H | 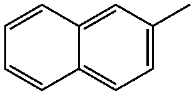 | Ph |
| 113 | 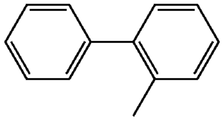 | Me | H | H | Me | 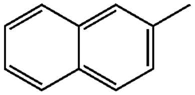 | H |
| 114 | 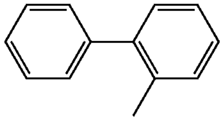 | H | Me | Me | H | 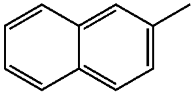 | H |
| 116 | 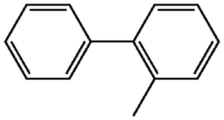 | H | H | H | H | 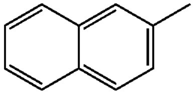 | Me |

-continued
| | | | | | | | |
|---|---|---|---|---|---|---|---|
| 116 | 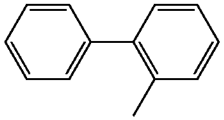 | H | H | H | H | 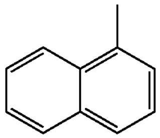 | H |
| 117 | 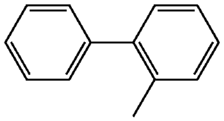 | Ph | H | H | Ph | 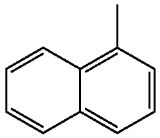 | H |
| 118 | 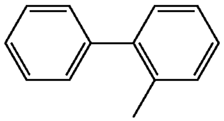 | H | Ph | Ph | H | 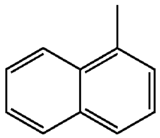 | H |
| 119 | 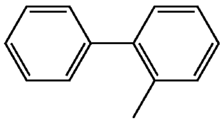 | H | Ph | H | H | 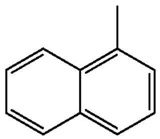 | H |
| 120 | 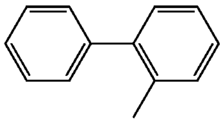 | H | H | H | H | 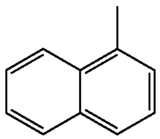 | Ph |
| 121 | 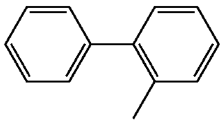 | Me | H | H | Me | 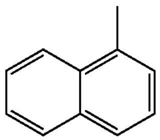 | H |
| 122 | 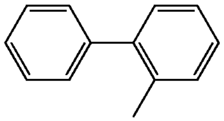 | H | Me | Me | H | 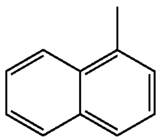 | H |

-continued
| | | | | | | | |
|---|---|---|---|---|---|---|---|
| 123 | 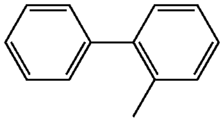 | H | H | H | H | 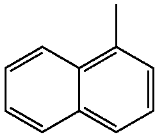 | Me |
| 124 | 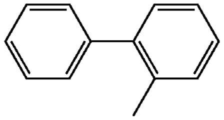 | H | H | H | H | 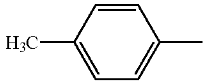 | H |
| 125 | 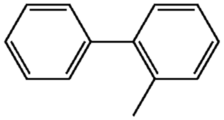 | Ph | H | H | Ph | 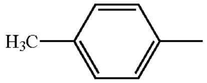 | H |
| 126 | 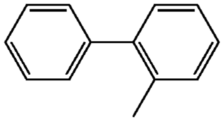 | H | Ph | Ph | H | 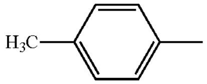 | H |
| 127 | 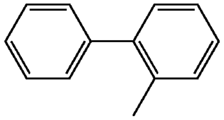 | H | Ph | H | H | 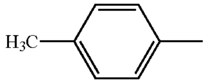 | H |
| 128 | 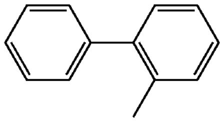 | H | H | H | H | 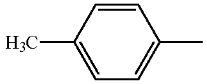 | Ph |
| 129 | 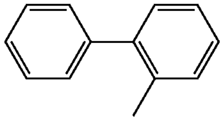 | Me | H | H | Me | 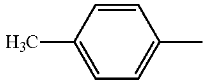 | H |

-continued
| | | | | | | | |
|---|---|---|---|---|---|---|---|
| 130 | 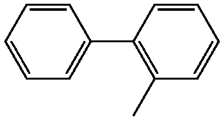 | H | Me | Me | H | 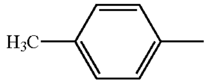 | H |
| 131 | 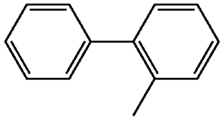 | H | H | H | H | 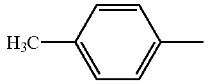 | Me |
| 132 | 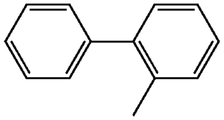 | H | H | H | H | 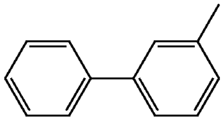 | H |
| 133 | 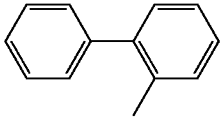 | Ph | H | H | Ph | 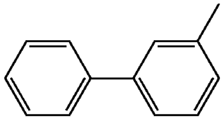 | H |
| 134 | 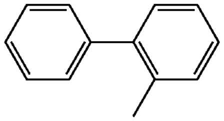 | H | Ph | Ph | H | 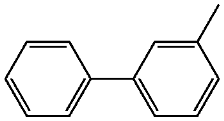 | H |
| 135 | 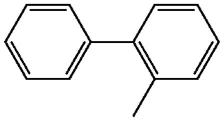 | H | Ph | H | H | 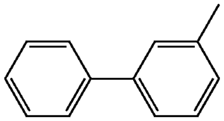 | H |
| 136 | 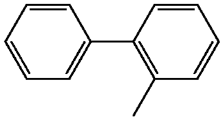 | H | H | H | H | 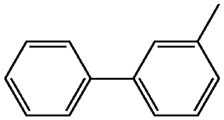 | Ph |
| 137 | 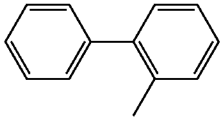 | Me | H | H | Me | 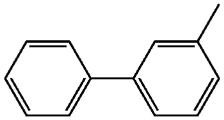 | H |

-continued
| | | | | | | | |
|---|---|---|---|---|---|---|---|
| 138 | 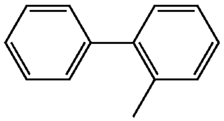 | H | Me | Me | H | 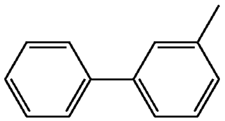 | H |
| 139 | 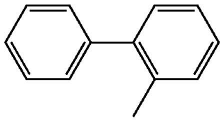 | H | H | H | H | 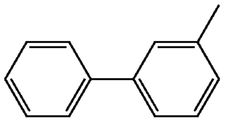 | Me |
| 140 | 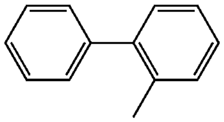 | H | H | H | H | 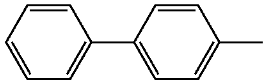 | H |
| 141 | 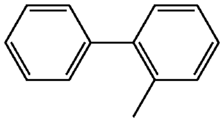 | Ph | H | H | Ph | 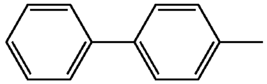 | H |
| 142 | 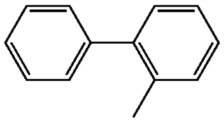 | H | Ph | Ph | H | 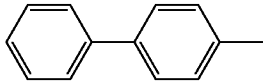 | H |

-continued
| | | | | | | | |
|---|---|---|---|---|---|---|---|
| 143 | 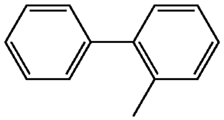 | H | Ph | H | H | 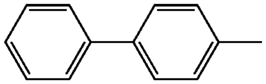 | H |
| 144 | 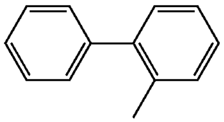 | H | H | H | H | 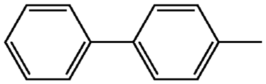 | Ph |
| 145 | 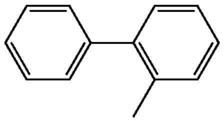 | Me | H | H | Me | 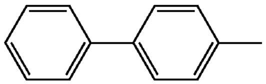 | H |
| 146 | 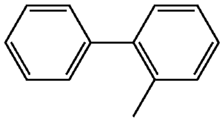 | H | Me | Me | H | 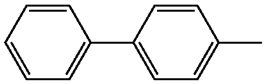 | H |
| 147 | 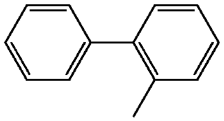 | H | H | H | H | 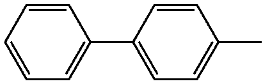 | Me |

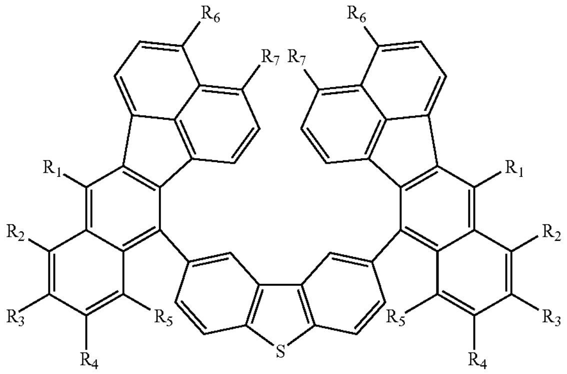

TypeTTT

| | $R_1$ | $R_2$ | $R_3$ | $R_4$ | $R_5$ | $R_7$ | $R_8$ |
|---|---|---|---|---|---|---|---|
| 1 | H | H | H | H | H | H | H |
| 2 | Ph | H | H | H | H | H | H |
| 3 | Ph | Ph | H | H | Ph | H | H |
| 4 | Ph | H | Ph | Ph | H | H | H |
| 5 | Ph | H | Ph | H | H | H | H |
| 6 | Ph | H | H | Ph | H | H | H |
| 7 | Ph | H | H | H | H | Ph | H |
| 8 | Ph | H | H | H | H | H | Ph |
| 9 | Ph | H | H | H | H | Ph | Ph |
| 10 | Ph | H | H | H | H | 1-naphthyl | H |
| 11 | Ph | H | H | H | H | H | 1-naphthyl |
| 12 | Ph | H | H | H | H | 1-naphthyl | 1-naphthyl |
| 13 | Ph | H | H | H | H | 2-naphthyl | H |
| 14 | Ph | H | H | H | H | H | 2-naphthyl |
| 15 | Ph | H | H | H | H | 2-naphthyl | 2-naphthyl |
| 16 | Ph | H | H | H | H | o-biphenylyl | H |
| 17 | Ph | H | H | H | H | H | o-biphenylyl |
| 18 | Ph | H | H | H | H | o-biphenylyl | o-biphenylyl |
| 19 | Ph | H | H | H | H | m-biphenylyl | H |
| 20 | Ph | H | H | H | H | H | m-biphenylyl |
| 21 | Ph | H | H | H | H | m-biphenylyl | m-biphenylyl |
| 22 | Ph | H | H | H | H | p-biphenylyl | H |
| 23 | Ph | H | H | H | H | H | p-biphenylyl |
| 24 | Ph | H | H | H | H | p-biphenylyl | p-biphenylyl |
| 25 | 1-naphthyl | H | H | H | H | H | H |
| 26 | 1-naphthyl | Ph | H | H | Ph | H | H |
| 27 | 1-naphthyl | H | Ph | Ph | H | H | H |
| 28 | 1-naphthyl | H | Ph | H | H | H | H |
| 29 | 1-naphthyl | H | H | Ph | H | H | H |
| 30 | 1-naphthyl | H | H | H | H | Ph | H |
| 31 | 1-naphthyl | H | H | H | H | H | Ph |
| 32 | 1-naphthyl | H | H | H | H | Ph | Ph |
| 33 | 1-naphthyl | H | H | H | H | 1-naphthyl | H |
| 34 | 1-naphthyl | H | H | H | H | H | 1-naphthyl |
| 35 | 1-naphthyl | H | H | H | H | 1-naphthyl | 1-naphthyl |
| 36 | 1-naphthyl | H | H | H | H | 2-naphthyl | H |
| 37 | 1-naphthyl | H | H | H | H | H | 2-naphthyl |
| 38 | 1-naphthyl | H | H | H | H | 2-naphthyl | 2-naphthyl |
| 39 | 1-naphthyl | H | H | H | H | o-biphenylyl | H |
| 40 | 1-naphthyl | H | H | H | H | H | o-biphenylyl |
| 41 | 1-naphthyl | H | H | H | H | o-biphenylyl | o-biphenylyl |
| 42 | 1-naphthyl | H | H | H | H | m-biphenylyl | H |
| 43 | 1-naphthyl | H | H | H | H | H | m-biphenylyl |
| 44 | 1-naphthyl | H | H | H | H | m-biphenylyl | m-biphenylyl |
| 45 | 1-naphthyl | H | H | H | H | p-biphenylyl | H |
| 46 | 1-naphthyl | H | H | H | H | H | p-biphenylyl |
| 47 | 1-naphthyl | H | H | H | H | p-biphenylyl | p-biphenylyl |
| 48 | 2-naphthyl | H | H | H | H | H | H |
| 49 | 2-naphthyl | Ph | H | H | Ph | H | H |
| 50 | 2-naphthyl | H | Ph | Ph | H | H | H |
| 51 | 2-naphthyl | H | Ph | H | H | H | H |
| 52 | 2-naphthyl | H | H | Ph | H | H | H |
| 53 | 2-naphthyl | H | H | H | H | Ph | H |
| 54 | 2-naphthyl | H | H | H | H | H | Ph |
| 55 | 2-naphthyl | H | H | H | H | Ph | Ph |
| 56 | 2-naphthyl | H | H | H | H | 1-naphthyl | H |

-continued

| | | | | | | | |
|---|---|---|---|---|---|---|---|
| 57 | 2-naphthyl | H | H | H | H | H | 1-naphthyl |
| 58 | 2-naphthyl | H | H | H | H | 1-naphthyl | 1-naphthyl |
| 59 | 2-naphthyl | H | H | H | H | 2-naphthyl | H |
| 60 | 2-naphthyl | H | H | H | H | H | 2-naphthyl |
| 61 | 2-naphthyl | H | H | H | H | 2-naphthyl | 2-naphthyl |
| 62 | 2-naphthyl | H | H | H | H | o-biphenylyl | H |
| 63 | 2-naphthyl | H | H | H | H | H | o-biphenylyl |
| 64 | 2-naphthyl | H | H | H | H | o-biphenylyl | o-biphenylyl |
| 65 | 2-naphthyl | H | H | H | H | m-biphenylyl | H |
| 66 | 2-naphthyl | H | H | H | H | H | m-biphenylyl |
| 67 | 2-naphthyl | H | H | H | H | m-biphenylyl | m-biphenylyl |
| 68 | 2-naphthyl | H | H | H | H | p-biphenylyl | H |
| 69 | 2-naphthyl | H | H | H | H | H | p-biphenylyl |
| 70 | 2-naphthyl | H | H | H | H | p-biphenylyl | p-biphenylyl |
| 71 | o-biphenylyl | H | H | H | H | H | H |
| 72 | o-biphenylyl | Ph | H | H | Ph | H | H |
| 73 | o-biphenylyl | H | Ph | Ph | H | H | H |
| 74 | o-biphenylyl | H | Ph | H | H | H | H |
| 75 | o-biphenylyl | H | H | Ph | H | H | H |
| 76 | o-biphenylyl | H | H | H | H | Ph | H |
| 77 | o-biphenylyl | H | H | H | H | H | Ph |
| 78 | o-biphenylyl | H | H | H | H | Ph | Ph |
| 79 | o-biphenylyl | H | H | H | H | 1-naphthyl | H |
| 80 | o-biphenylyl | H | H | H | H | H | 1-naphthyl |
| 81 | o-biphenylyl | H | H | H | H | 1-naphthyl | 1-naphthyl |
| 82 | o-biphenylyl | H | H | H | H | 2-naphthyl | H |
| 83 | o-biphenylyl | H | H | H | H | H | 2-naphthyl |
| 84 | o-biphenylyl | H | H | H | H | 2-naphthyl | 2-naphthyl |
| 85 | o-biphenylyl | H | H | H | H | o-biphenylyl | H |
| 86 | o-biphenylyl | H | H | H | H | H | o-biphenylyl |
| 87 | o-biphenylyl | H | H | H | H | o-biphenylyl | o-biphenylyl |
| 88 | o-biphenylyl | H | H | H | H | m-biphenylyl | H |
| 89 | o-biphenylyl | H | H | H | H | H | m-biphenylyl |
| 90 | o-biphenylyl | H | H | H | H | m-biphenylyl | m-biphenylyl |
| 91 | o-biphenylyl | H | H | H | H | p-biphenylyl | H |
| 92 | o-biphenylyl | H | H | H | H | H | p-biphenylyl |
| 93 | o-biphenylyl | H | H | H | H | p-biphenylyl | p-biphenylyl |
| 94 | m-biphenylyl | H | H | H | H | H | H |
| 95 | m-biphenylyl | Ph | H | H | Ph | H | H |
| 96 | m-biphenylyl | H | Ph | Ph | H | H | H |
| 97 | m-biphenylyl | H | Ph | H | H | H | H |
| 98 | m-biphenylyl | H | H | Ph | H | H | H |
| 99 | m-biphenylyl | H | H | H | H | Ph | H |
| 100 | m-biphenylyl | H | H | H | H | H | Ph |
| 101 | m-biphenylyl | H | H | H | H | Ph | Ph |
| 102 | m-biphenylyl | H | H | H | H | 1-naphthyl | H |
| 103 | m-biphenylyl | H | H | H | H | H | 1-naphthyl |
| 104 | m-biphenylyl | H | H | H | H | 1-naphthyl | 1-naphthyl |
| 105 | m-biphenylyl | H | H | H | H | 2-naphthyl | H |
| 106 | m-biphenylyl | H | H | H | H | H | 2-naphthyl |
| 107 | m-biphenylyl | H | H | H | H | 2-naphthyl | 2-naphthyl |
| 108 | m-biphenylyl | H | H | H | H | o-biphenylyl | H |
| 109 | m-biphenylyl | H | H | H | H | H | o-biphenylyl |
| 110 | m-biphenylyl | H | H | H | H | o-biphenylyl | o-biphenylyl |
| 111 | m-biphenylyl | H | H | H | H | m-biphenylyl | H |
| 112 | m-biphenylyl | H | H | H | H | H | m-biphenylyl |
| 113 | m-biphenylyl | H | H | H | H | m-biphenylyl | m-biphenylyl |
| 114 | m-biphenylyl | H | H | H | H | p-biphenylyl | H |
| 115 | m-biphenylyl | H | H | H | H | H | p-biphenylyl |
| 116 | m-biphenylyl | H | H | H | H | p-biphenylyl | p-biphenylyl |
| 117 | p-biphenylyl | H | H | H | H | H | H |
| 118 | p-biphenylyl | Ph | H | H | Ph | H | H |
| 119 | p-biphenylyl | H | Ph | Ph | H | H | H |
| 120 | p-biphenylyl | H | Ph | H | H | H | H |
| 121 | p-biphenylyl | H | H | Ph | H | H | H |
| 122 | p-biphenylyl | H | H | H | H | Ph | H |
| 123 | p-biphenylyl | H | H | H | H | H | Ph |
| 124 | p-biphenylyl | H | H | H | H | Ph | Ph |
| 125 | p-biphenylyl | H | H | H | H | 1-naphthyl | H |
| 126 | p-biphenylyl | H | H | H | H | H | 1-naphthyl |
| 127 | p-biphenylyl | H | H | H | H | 1-naphthyl | 1-naphthyl |
| 128 | p-biphenylyl | H | H | H | H | 2-naphthyl | H |
| 129 | p-biphenylyl | H | H | H | H | H | 2-naphthyl |
| 130 | p-biphenylyl | H | H | H | H | 2-naphthyl | 2-naphthyl |
| 131 | p-biphenylyl | H | H | H | H | o-biphenylyl | H |
| 132 | p-biphenylyl | H | H | H | H | H | o-biphenylyl |
| 133 | p-biphenylyl | H | H | H | H | o-biphenylyl | o-biphenylyl |
| 134 | p-biphenylyl | H | H | H | H | m-biphenylyl | H |

-continued

| | | | | | | | |
|---|---|---|---|---|---|---|---|
| 135 | p-biphenylyl | H | H | H | H | H | m-biphenylyl |
| 136 | p-biphenylyl | H | H | H | H | m-biphenylyl | m-biphenylyl |
| 137 | p-biphenylyl | H | H | H | H | p-biphenylyl | H |
| 138 | p-biphenylyl | H | H | H | H | H | p-biphenylyl |
| 139 | p-biphenylyl | H | H | H | H | p-biphenylyl | p-biphenylyl |
| 140 | o-tolyl | H | H | H | H | H | H |
| 141 | o-tolyl | Ph | H | H | Ph | H | H |
| 142 | o-tolyl | H | Ph | Ph | H | H | H |
| 143 | o-tolyl | H | H | H | H | Ph | H |
| 144 | o-tolyl | H | H | H | H | H | Ph |
| 145 | o-tolyl | H | H | H | H | 1-naphthyl | H |
| 146 | o-tolyl | H | H | H | H | H | 1-naphthyl |
| 147 | o-tolyl | H | H | H | H | 2-naphthyl | H |
| 148 | o-tolyl | H | H | H | H | H | 2-naphthyl |
| 149 | o-tolyl | H | H | H | H | o-biphenylyl | H |
| 150 | o-tolyl | H | H | H | H | H | o-biphenylyl |
| 151 | o-tolyl | H | H | H | H | m-biphenylyl | H |
| 152 | o-tolyl | H | H | H | H | H | m-biphenylyl |
| 153 | o-tolyl | H | H | H | H | p-biphenylyl | H |
| 154 | o-tolyl | H | H | H | H | H | p-biphenylyl |
| 155 | o-tolyl | H | H | H | H | o-tolyl | H |
| 156 | o-tolyl | H | H | H | H | H | o-tolyl |
| 157 | m-tolyl | H | H | H | H | H | H |
| 158 | m-tolyl | Ph | H | H | Ph | H | H |
| 159 | m-tolyl | H | Ph | Ph | H | H | H |
| 160 | m-tolyl | H | H | H | H | Ph | H |
| 161 | m-tolyl | H | H | H | H | H | Ph |
| 162 | m-tolyl | H | H | H | H | 1-naphthyl | H |
| 163 | m-tolyl | H | H | H | H | H | 1-naphthyl |
| 164 | m-tolyl | H | H | H | H | 2-naphthyl | H |
| 165 | m-tolyl | H | H | H | H | H | 2-naphthyl |
| 166 | m-tolyl | H | H | H | H | o-biphenylyl | H |
| 167 | m-tolyl | H | H | H | H | H | o-biphenylyl |
| 168 | m-tolyl | H | H | H | H | m-biphenylyl | H |
| 169 | m-tolyl | H | H | H | H | H | m-biphenylyl |
| 170 | m-tolyl | H | H | H | H | p-biphenylyl | H |
| 171 | m-tolyl | H | H | H | H | H | p-biphenylyl |
| 172 | m-tolyl | H | H | H | H | m-tolyl | H |
| 173 | m-tolyl | H | H | H | H | H | m-tolyl |
| 174 | p-tolyl | H | H | H | H | H | H |
| 175 | p-tolyl | Ph | H | H | Ph | H | H |
| 176 | p-tolyl | H | Ph | Ph | H | H | H |
| 177 | p-tolyl | H | H | H | H | Ph | H |
| 178 | p-tolyl | H | H | H | H | H | Ph |
| 179 | p-tolyl | H | H | H | H | 1-naphthyl | H |
| 180 | p-tolyl | H | H | H | H | H | 1-naphthyl |
| 181 | p-tolyl | H | H | H | H | 2-naphthyl | H |
| 182 | p-tolyl | H | H | H | H | H | 2-naphthyl |
| 183 | p-tolyl | H | H | H | H | o-biphenylyl | H |
| 184 | p-tolyl | H | H | H | H | H | o-biphenylyl |
| 185 | p-tolyl | H | H | H | H | m-biphenylyl | H |
| 186 | p-tolyl | H | H | H | H | H | m-biphenylyl |
| 187 | p-tolyl | H | H | H | H | p-biphenylyl | H |
| 188 | p-tolyl | H | H | H | H | H | p-biphenylyl |
| 189 | p-tolyl | H | H | H | H | p-tolyl | H |
| 190 | p-tolyl | H | H | H | H | H | p-tolyl |
| 191 | Ph | H | —CH3 | —CH3 | H | H | H |
| 192 | 1-naphtyl | H | —CH3 | —CH3 | H | H | H |
| 193 | 2-naphthyl | H | —CH3 | —CH3 | H | H | H |
| 194 | o-biphenylyl | H | —CH3 | —CH3 | H | H | H |
| 195 | m-biphenylyl | H | —CH3 | —CH3 | H | H | H |
| 196 | p-biphenylyl | H | —CH3 | —CH3 | H | H | H |
| 197 | o-tolyl | H | —CH3 | —CH3 | H | H | H |
| 198 | m-tolyl | H | —CH3 | —CH3 | H | H | H |
| 199 | p-tolyl | H | —CH3 | —CH3 | H | H | H |
| 200 | Ph | H | H | H | H | —CH3 | H |
| 201 | 1-naphtyl | H | H | H | H | —CH3 | H |
| 202 | 2-naphthyl | H | H | H | H | —CH3 | H |
| 203 | o-biphenylyl | H | H | H | H | —CH3 | H |
| 204 | m-biphenylyl | H | H | H | H | —CH3 | H |
| 205 | p-biphenylyl | H | H | H | H | —CH3 | H |
| 206 | o-tolyl | H | H | H | H | —CH3 | H |
| 207 | m-tolyl | H | H | H | H | —CH3 | H |
| 208 | p-tolyl | H | H | H | H | —CH3 | H |
| 209 | Ph | H | H | H | H | H | —CH3 |
| 210 | 1-naphtyl | H | H | H | H | H | —CH3 |
| 211 | 2-naphthyl | H | H | H | H | H | —CH3 |
| 212 | o-biphenylyl | H | H | H | H | H | —CH3 |

-continued

| | | | | | | | |
|---|---|---|---|---|---|---|---|
| 213 | m-biphenylyl | H | H | H | H | H | —CH3 |
| 214 | p-biphenylyl | H | H | H | H | H | —CH3 |
| 215 | o-tolyl | H | H | H | H | H | —CH3 |
| 216 | m-tolyl | H | H | H | H | H | —CH3 |
| 217 | p-tolyl | H | H | H | H | H | —CH3 |
| 218 | Ph | H | H | H | H | —CH3 | —CH3 |
| 219 | 1-naphtyl | H | H | H | H | —CH3 | —CH3 |
| 220 | 2-naphthyl | H | H | H | H | —CH3 | —CH3 |
| 221 | o-biphenylyl | H | H | H | H | —CH3 | —CH3 |
| 222 | m-biphenylyl | H | H | H | H | —CH3 | —CH3 |
| 223 | p-biphenylyl | H | H | H | H | —CH3 | —CH3 |
| 224 | o-tolyl | H | H | H | H | —CH3 | —CH3 |
| 225 | m-tolyl | H | H | H | H | —CH3 | —CH3 |
| 226 | p-tolyl | H | H | H | H | —CH3 | —CH3 |
| 227 | Ph | H | H | H | H | H | DPA |
| 228 | 1-naphtyl | H | H | H | H | H | DPA |
| 229 | 2-naphthyl | H | H | H | H | H | DPA |
| 230 | o-biphenylyl | H | H | H | H | H | DPA |
| 231 | m-biphenylyl | H | H | H | H | H | DPA |
| 232 | p-biphenylyl | H | H | H | H | H | DPA |
| 233 | Ph | H | H | H | H | DPA | H |
| 234 | 1-naphtyl | H | H | H | H | DPA | H |
| 235 | 2-naphthyl | H | H | H | H | DPA | H |
| 236 | o-biphenylyl | H | H | H | H | DPA | H |
| 237 | m-biphenylyl | H | H | H | H | DPA | H |
| 238 | p-biphenylyl | H | H | H | H | DPA | H |
| 239 | Ph | H | H | H | H | H | TPA |
| 240 | 1-naphtyl | H | H | H | H | H | TPA |
| 241 | 2-naphthyl | H | H | H | H | H | TPA |
| 242 | o-biphenylyl | H | H | H | H | H | TPA |
| 243 | m-biphenylyl | H | H | H | H | H | TPA |
| 244 | p-biphenylyl | H | H | H | H | H | TPA |
| 245 | Ph | H | H | H | H | TPA | H |
| 246 | 1-naphtyl | H | H | H | H | TPA | H |
| 247 | 2-naphthyl | H | H | H | H | TPA | H |
| 248 | o-biphenylyl | H | H | H | H | TPA | H |
| 249 | m-biphenylyl | H | H | H | H | TPA | H |
| 250 | p-biphenylyl | H | H | H | H | TPA | H |

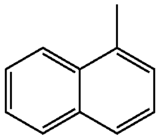

1-naphthyl

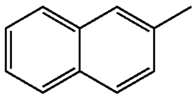

2-naphthyl

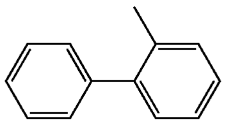

o-biphenylyl

-continued
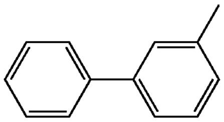
m-biphenylyl
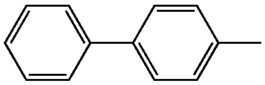
p-biphenylyl
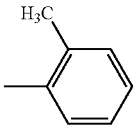
o-tolyl
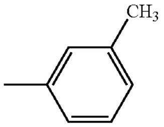
m-tolyl
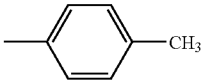
p-tolyl
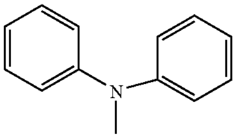
DPA
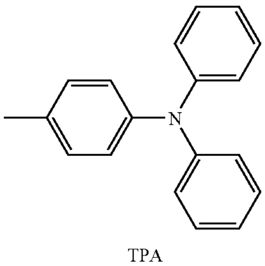
TPA

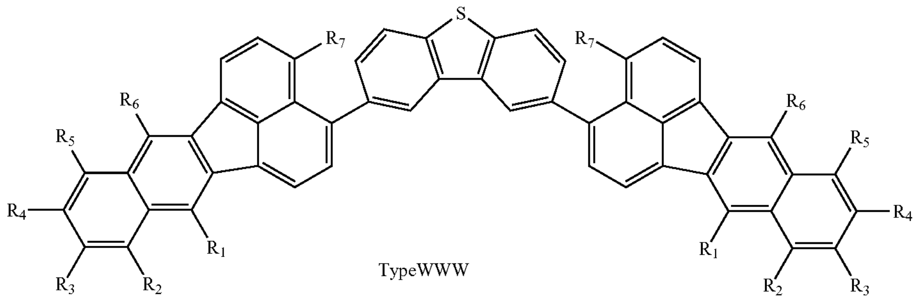
TypeWWW
| | $R_1$ | $R_2$ | $R_3$ | $R_4$ | $R_5$ | $R_6$ | $R_7$ |
|---|---|---|---|---|---|---|---|
| 1 | H | H | H | H | H | H | H |
| 2 | Ph | H | H | H | H | Ph | H |
| 3 | Ph | Ph | H | H | Ph | Ph | H |
| 4 | Ph | H | Ph | Ph | H | Ph | H |
| 5 | Ph | H | Ph | H | H | Ph | H |
| 6 | Ph | H | H | H | H | Ph | Ph |
| 7 | Ph | Me | H | H | Me | Ph | H |
| 8 | Ph | H | Me | Me | H | Ph | H |
| 9 | Ph | H | H | H | H | Ph | Me |
| 10 | 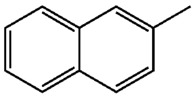 | H | H | H | H | 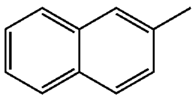 | H |
| 11 | 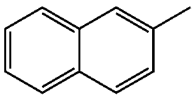 | Ph | H | H | Ph | 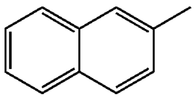 | H |
| 12 | 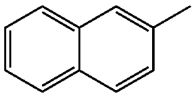 | H | Ph | Ph | H | 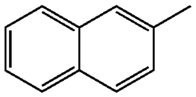 | H |
| 13 | 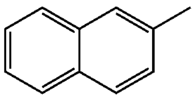 | H | Ph | H | H | 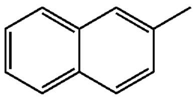 | H |

-continued
| | | | | | | | |
|---|---|---|---|---|---|---|---|
| 14 | 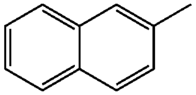 | H | H | H | H | 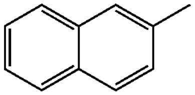 | Ph |
| 15 | 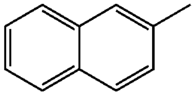 | Me | H | H | Me | 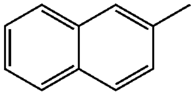 | H |
| 16 | 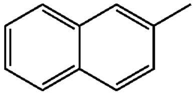 | H | Me | Me | H | 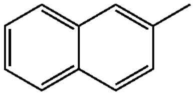 | H |
| 17 | 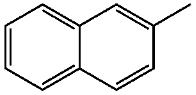 | H | H | H | H | 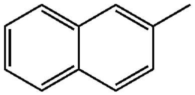 | Me |
| 18 | 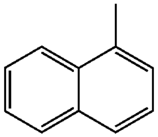 | H | H | H | H | 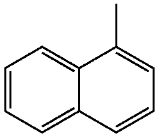 | H |
| 19 | 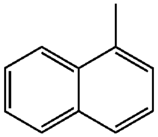 | Ph | H | H | Ph | 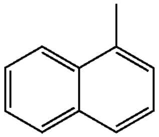 | H |
| 20 | 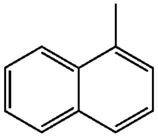 | H | Ph | Ph | H | 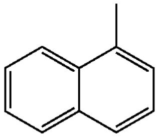 | H |
| 21 | 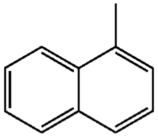 | H | Ph | H | H | 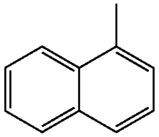 | H |

-continued
| | | | | | | | |
|---|---|---|---|---|---|---|---|
| 22 | 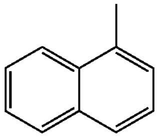 | H | H | H | H | 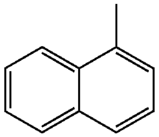 | Ph |
| 23 | 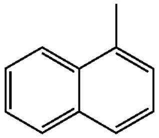 | Me | H | H | Me | 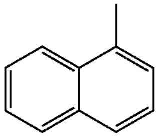 | H |
| 24 | 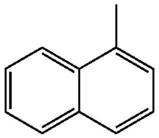 | H | Me | Me | H | 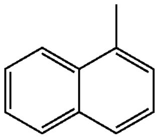 | H |
| 25 | 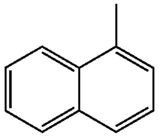 | H | H | H | H | 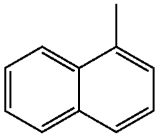 | Me |
| 26 | 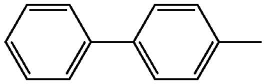 | H | H | H | H | 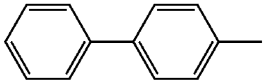 | H |
| 27 | 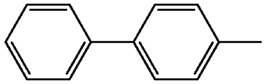 | Ph | H | H | Ph | 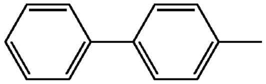 | H |
| 28 | 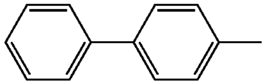 | H | Ph | Ph | H | 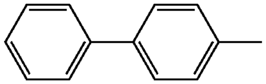 | H |
| 29 | 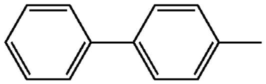 | H | Ph | H | H | 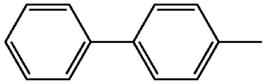 | H |

-continued
| | | | | | | | |
|---|---|---|---|---|---|---|---|
| 30 | 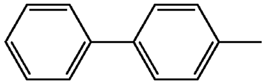 | H | H | H | H | 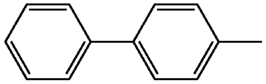 | Ph |
| 31 | 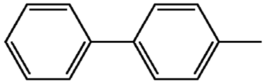 | Me | H | H | Me | 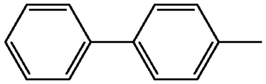 | H |
| 32 | 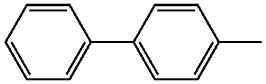 | H | Me | Me | H | 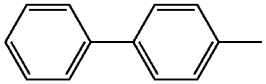 | H |
| 33 | 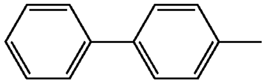 | H | H | H | H | 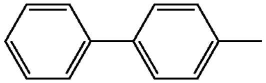 | Me |
| 34 | 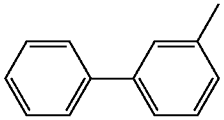 | H | H | H | H | 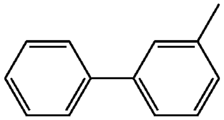 | H |
| 35 | 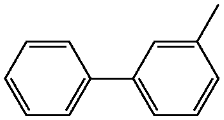 | Ph | H | H | Ph | 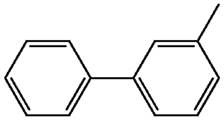 | H |
| 36 | 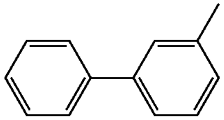 | H | Ph | Ph | H | 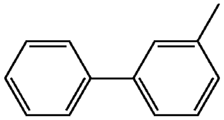 | H |
| 37 | 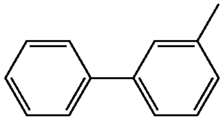 | H | Ph | H | H | 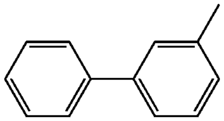 | H |
| 38 | 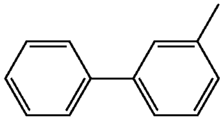 | H | H | H | H | 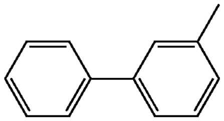 | Ph |

-continued
| | | | | | | | |
|---|---|---|---|---|---|---|---|
| 39 | 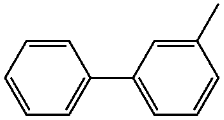 | Me | H | H | Me | 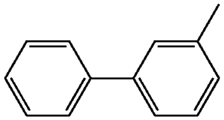 | H |
| 40 | 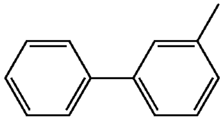 | H | Me | Me | H | 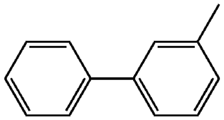 | H |
| 41 | 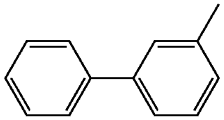 | H | H | H | H | 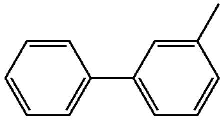 | Me |
| 42 | 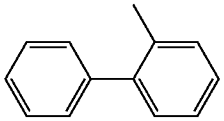 | H | H | H | H | 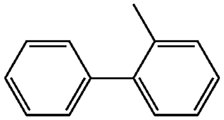 | H |
| 43 | 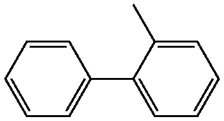 | Ph | H | H | Ph | 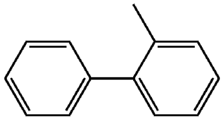 | H |
| 44 | 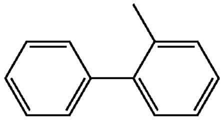 | H | Ph | Ph | H | 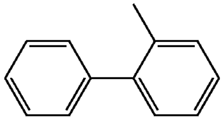 | H |
| 45 | 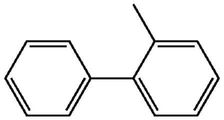 | H | Ph | H | H | 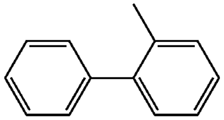 | H |

-continued
| | | | | | | | |
|---|---|---|---|---|---|---|---|
| 46 | 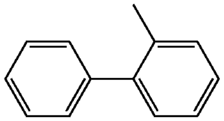 | H | H | H | H | 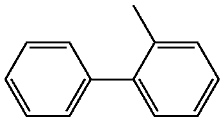 | Ph |
| 47 | 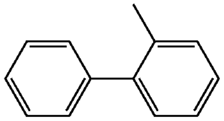 | Me | H | H | Me | 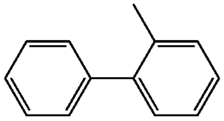 | H |
| 48 | 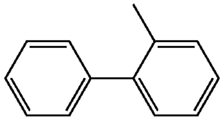 | H | Me | Me | H | 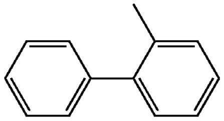 | H |
| 49 | 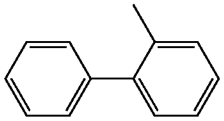 | H | H | H | H | 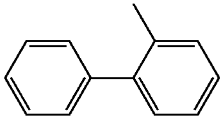 | Me |
| 50 | Ph | H | H | H | H | 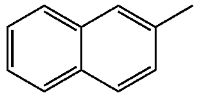 | H |
| 51 | Ph | H | H | H | H | 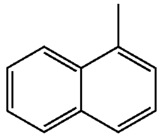 | H |
| 52 | Ph | H | H | H | H | 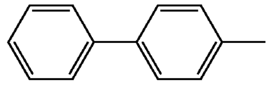 | H |
| 53 | Ph | H | H | H | H | 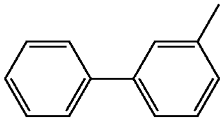 | H |

-continued
| | | | | | | | |
|---|---|---|---|---|---|---|---|
| 54 | Ph | H | H | H | H | 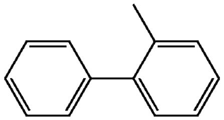 | H |
| 55 | 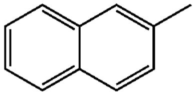 | H | H | H | H | 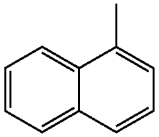 | H |
| 56 | 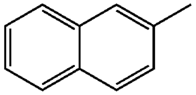 | H | H | H | H | 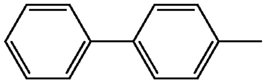 | H |
| 57 | 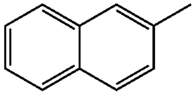 | H | H | H | H | 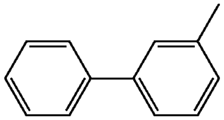 | H |
| 58 | 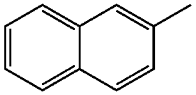 | H | H | H | H | 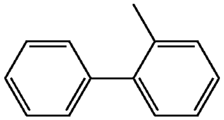 | H |
| 59 | 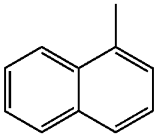 | H | H | H | H | 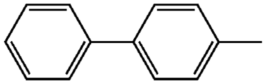 | H |
| 60 | 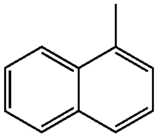 | H | H | H | H | 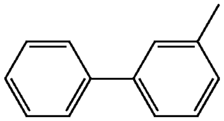 | H |

-continued
| | | | | | | | |
|---|---|---|---|---|---|---|---|
| 61 | 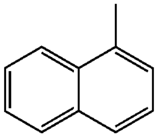 | H | H | H | H | 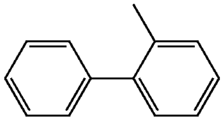 | H |
| 62 | 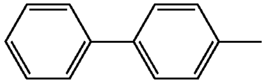 | H | H | H | H | 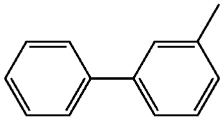 | H |
| 63 | 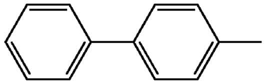 | H | H | H | H | 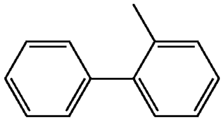 | H |
| 64 | 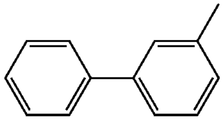 | H | H | H | H | 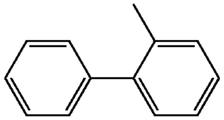 | H |
| 65 | H | Ph | H | H | Ph | H | H |
| 66 | H | 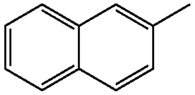 | H | H | 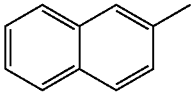 | H | H |
| 67 | H | 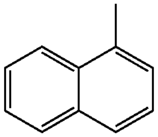 | H | H | 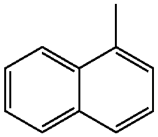 | H | H |
| 68 | H | 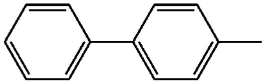 | H | H | 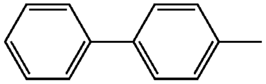 | H | H |

-continued
| | | | | | | | |
|---|---|---|---|---|---|---|---|
| 69 | H | 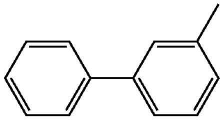 | H | H | 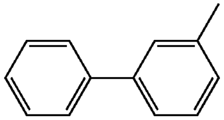 | H | H |
| 70 | H | 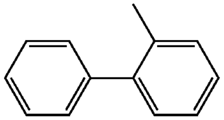 | H | H | 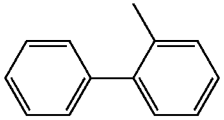 | H | H |
| 71 | H | H | 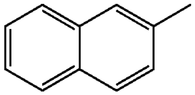 | 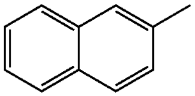 | H | H | H |
| 72 | H | H | 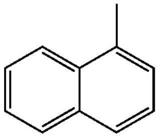 | 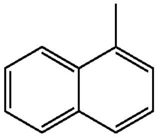 | H | H | H |
| 73 | H | H | 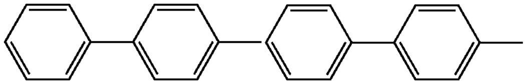 | | H | H | H |
| 74 | H | H | 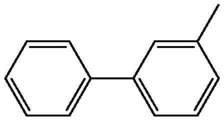 | 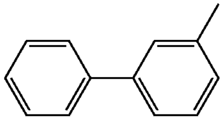 | H | H | H |
| 75 | H | H | 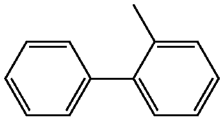 | 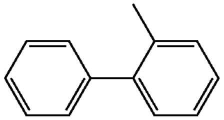 | H | H | H |
| 76 | 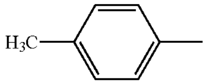 | H | H | H | H | 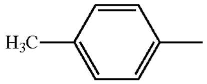 | H |

-continued
| | | | | | | | |
|---|---|---|---|---|---|---|---|
| 77 | 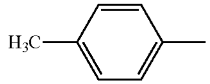 | Ph | H | H | Ph | 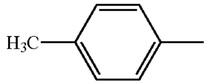 | H |
| 78 | 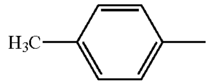 | H | Ph | Ph | H | 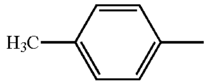 | H |
| 79 | 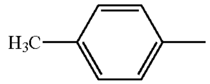 | H | Ph | H | H | 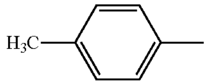 | H |
| 80 | 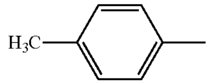 | H | H | H | H | 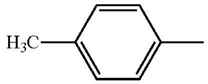 | Ph |
| 81 | 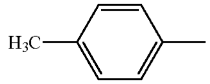 | Me | H | H | Me | 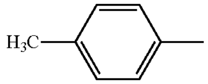 | H |
| 82 | 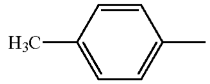 | H | Me | Me | H | 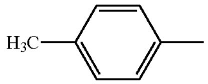 | H |
| 83 | 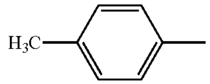 | H | H | H | H | 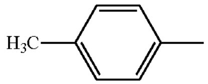 | Me |
| 84 | 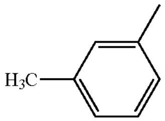 | H | H | H | H | 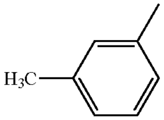 | H |
| 85 | 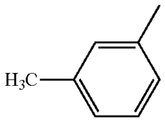 | Ph | H | H | Ph | 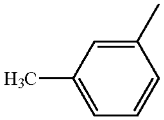 | H |

-continued
| | | | | | | | |
|---|---|---|---|---|---|---|---|
| 86 | 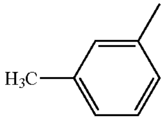 | H | Ph | Ph | H | 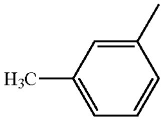 | H |
| 87 | 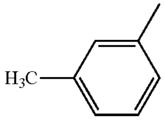 | H | Ph | H | H | 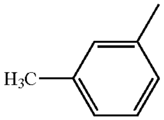 | H |
| 88 | 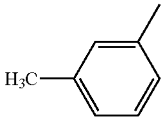 | H | H | H | H | 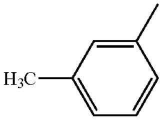 | Ph |
| 89 | 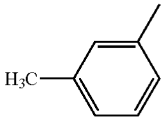 | Me | H | H | Me | 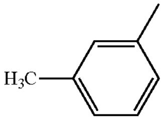 | H |
| 90 | 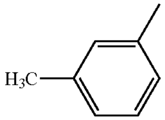 | H | Me | Me | H | 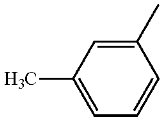 | H |
| 91 | 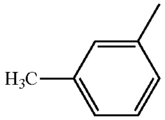 | H | H | H | H | 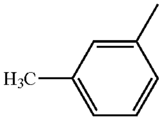 | Me |
| 92 | 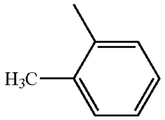 | H | H | H | H | 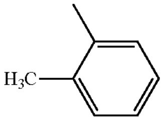 | H |
| 93 | 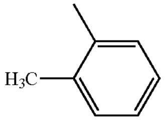 | Ph | H | H | Ph | 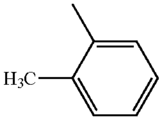 | H |

-continued
| | | | | | | | |
|---|---|---|---|---|---|---|---|
| 94 | 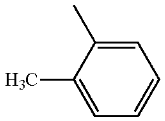 | H | Ph | Ph | H | 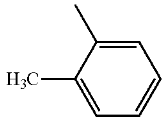 | H |
| 96 | 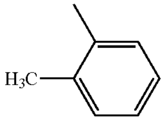 | H | Ph | H | H | 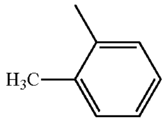 | H |
| 96 | 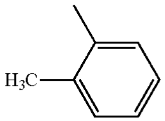 | H | H | H | H | 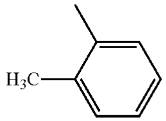 | Ph |
| 97 | 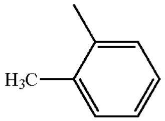 | Me | H | H | Me | 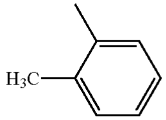 | H |
| 98 | 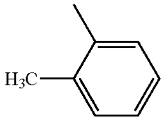 | H | Me | Me | H | 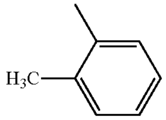 | H |
| 99 | 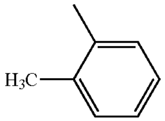 | H | H | H | H | 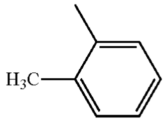 | Me |
| 100 | 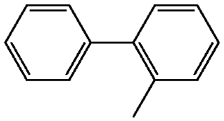 | H | H | H | H | 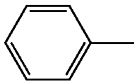 | H |

-continued
| | | | | | | | |
|---|---|---|---|---|---|---|---|
| 101 | 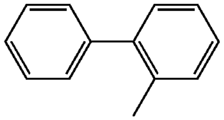 | Ph | H | H | Ph | 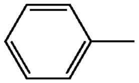 | H |
| 102 | 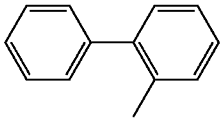 | H | Ph | Ph | H | 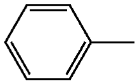 | H |
| 103 | 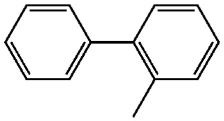 | H | Ph | H | H | 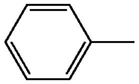 | H |
| 104 | 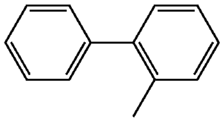 | H | H | H | H | 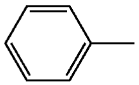 | Ph |
| 105 | 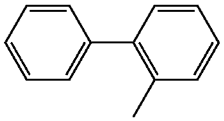 | Me | H | H | Me | 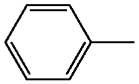 | H |
| 106 | 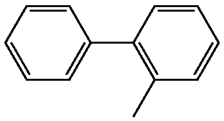 | H | Me | Me | H | 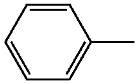 | H |
| 107 | 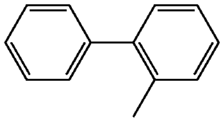 | H | H | H | H | 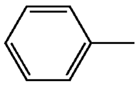 | Me |
| 108 | 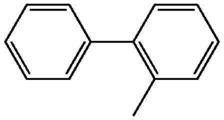 | H | H | H | H | 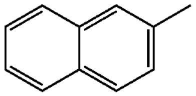 | H |

-continued
| | | | | | | | |
|---|---|---|---|---|---|---|---|
| 109 | 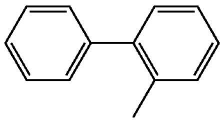 | Ph | H | H | Ph | 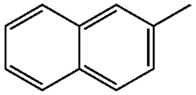 | H |
| 110 | 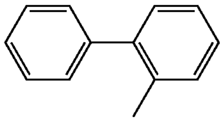 | H | Ph | Ph | H | 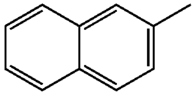 | H |
| 111 | 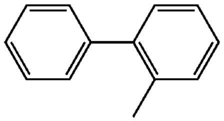 | H | Ph | H | H | 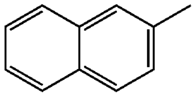 | H |
| 112 | 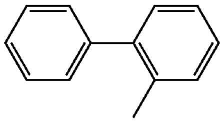 | H | H | H | H | 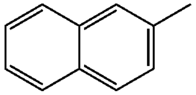 | Ph |
| 113 | 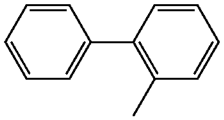 | Me | H | H | Me | 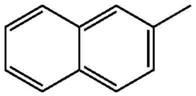 | H |
| 114 | 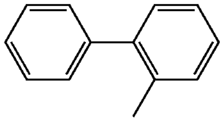 | H | Me | Me | H | 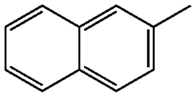 | H |
| 115 | 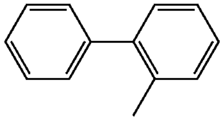 | H | H | H | H | 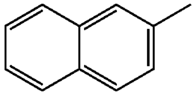 | Me |

-continued
| | | | | | | | |
|---|---|---|---|---|---|---|---|
| 116 | 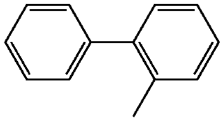 | H | H | H | H | 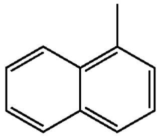 | H |
| 117 | 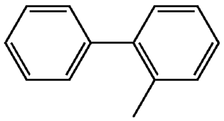 | Ph | H | H | Ph | 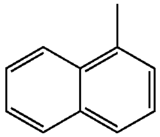 | H |
| 118 | 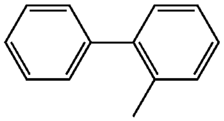 | H | Ph | Ph | H | 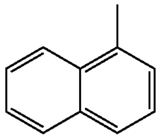 | H |
| 119 | 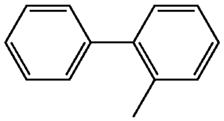 | H | Ph | H | H | 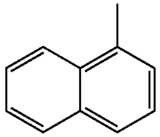 | H |
| 120 | 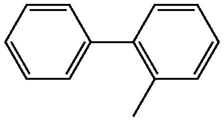 | H | H | H | H | 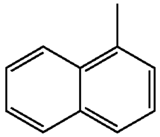 | Ph |
| 121 | 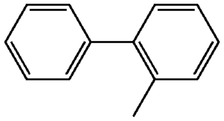 | Me | H | H | Me | 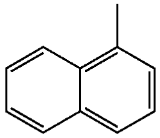 | H |
| 122 | 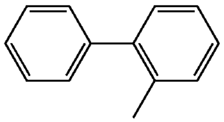 | H | Me | Me | H | 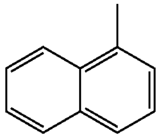 | H |

-continued
| | | | | | | | |
|---|---|---|---|---|---|---|---|
| 123 | 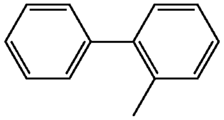 | H | H | H | H | 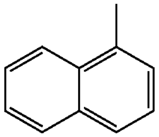 | Me |
| 124 | 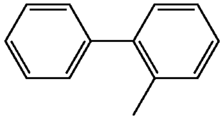 | H | H | H | H | 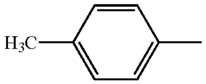 | H |
| 125 | 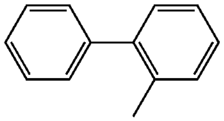 | Ph | H | H | Ph | 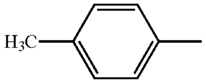 | H |
| 126 | 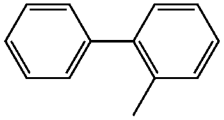 | H | Ph | Ph | H | 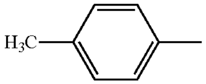 | H |
| 127 | 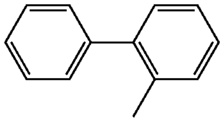 | H | Ph | H | H | 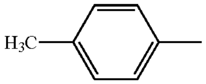 | H |
| 128 | 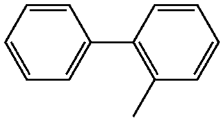 | H | H | H | H | 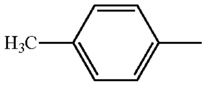 | Ph |
| 129 | 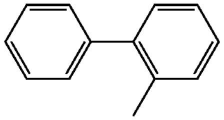 | Me | H | H | Me | 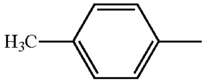 | H |

-continued
| | | | | | | | |
|---|---|---|---|---|---|---|---|
| 130 | 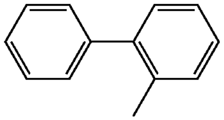 | H | Me | Me | H | 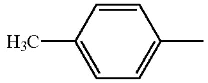 | H |
| 131 | 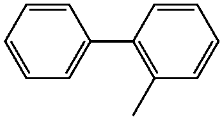 | H | H | H | H | 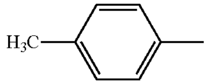 | Me |
| 132 | 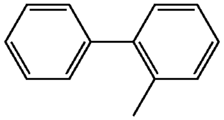 | H | H | H | H | 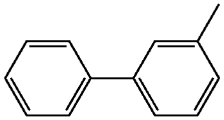 | H |
| 133 | 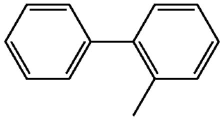 | Ph | H | H | Ph | 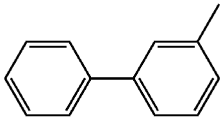 | H |
| 134 | 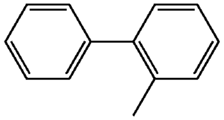 | H | Ph | Ph | H | 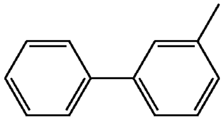 | H |
| 135 | 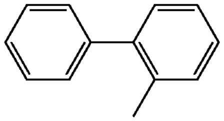 | H | Ph | H | H | 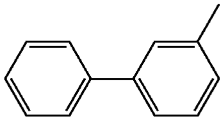 | H |
| 136 | 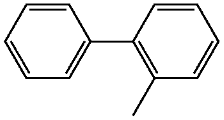 | H | H | H | H | 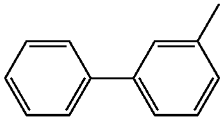 | Ph |
| 137 | 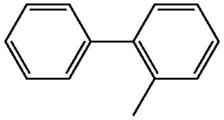 | Me | H | H | Me | 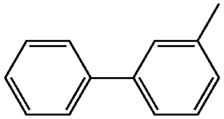 | H |

-continued
| | | | | | | | |
|---|---|---|---|---|---|---|---|
| 138 | 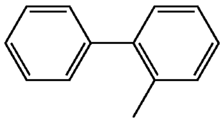 | H | Me | Me | H | 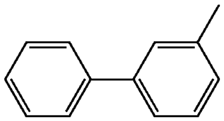 | H |
| 139 | 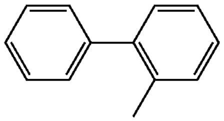 | H | H | H | H | 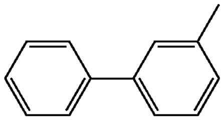 | Me |
| 140 | 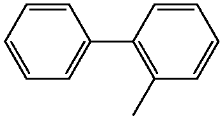 | H | H | H | H | 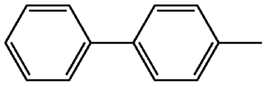 | H |
| 141 | 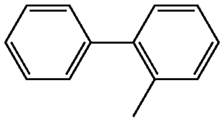 | Ph | H | H | Ph | 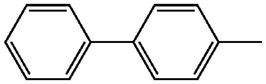 | H |
| 142 | 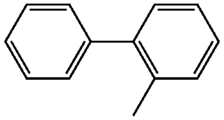 | H | Ph | Ph | H | 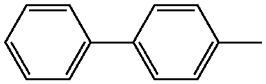 | H |

-continued
| | | | | | | | |
|---|---|---|---|---|---|---|---|
| 143 | 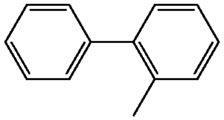 | H | Ph | H | H | 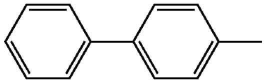 | H |
| 144 | 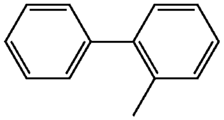 | H | H | H | H | 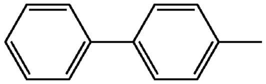 | Ph |
| 145 | 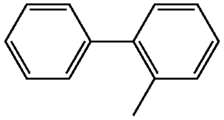 | Me | H | H | Me | 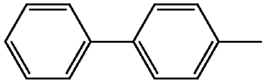 | H |
| 146 | 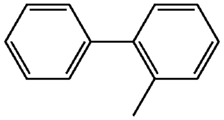 | H | Me | Me | H | 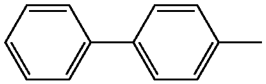 | H |
| 147 | 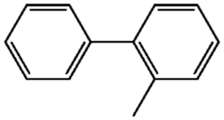 | H | H | H | H | 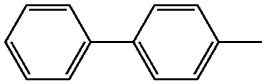 | Me |

The fluoranthene derivatives of formula (I) can be produced, for example, by the method described in J. Amer. Chem. Soc., 118, 2374 (1996). Exemplary synthesis schemes are shown below.
C67
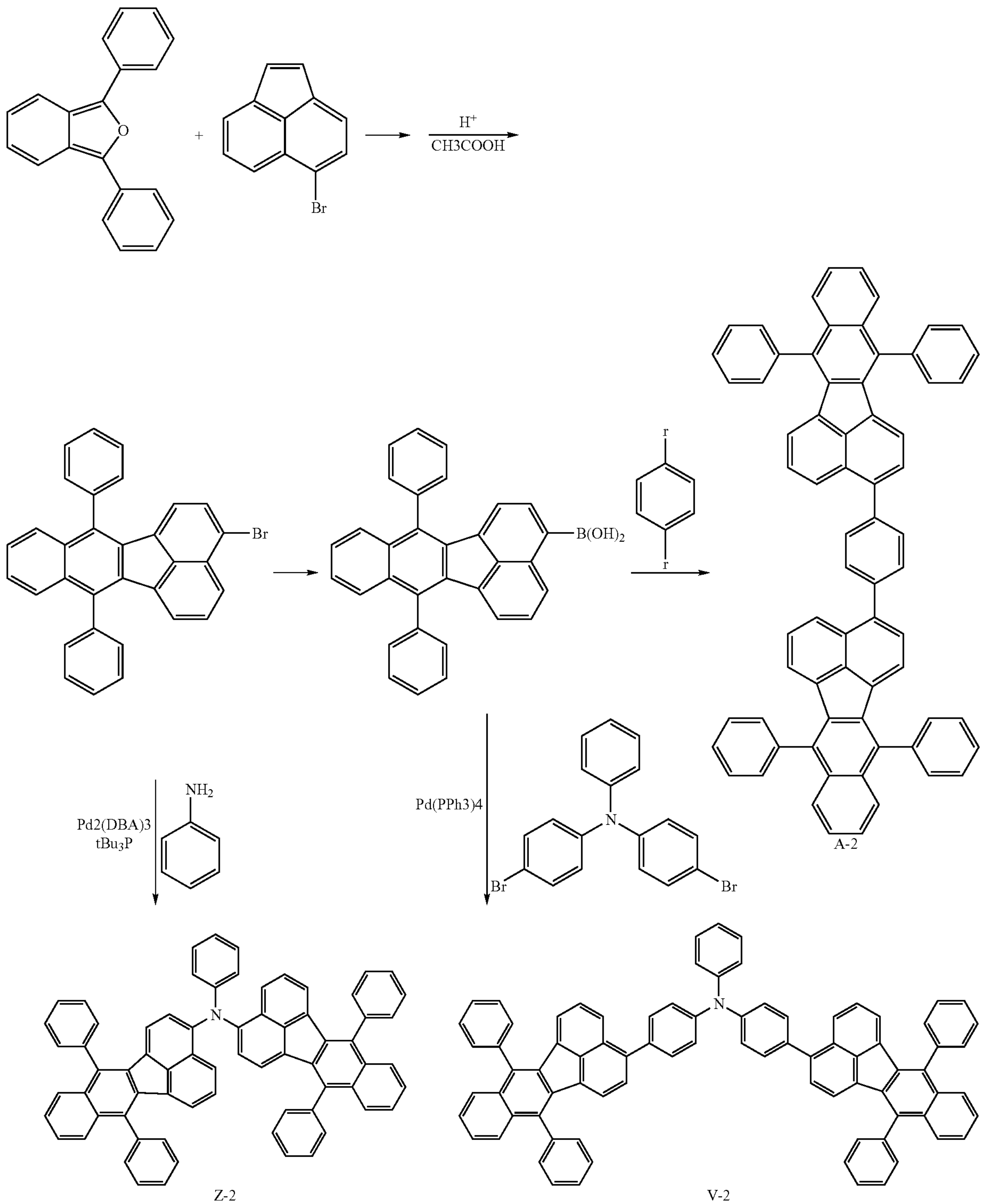
A-2
Z-2
V-2

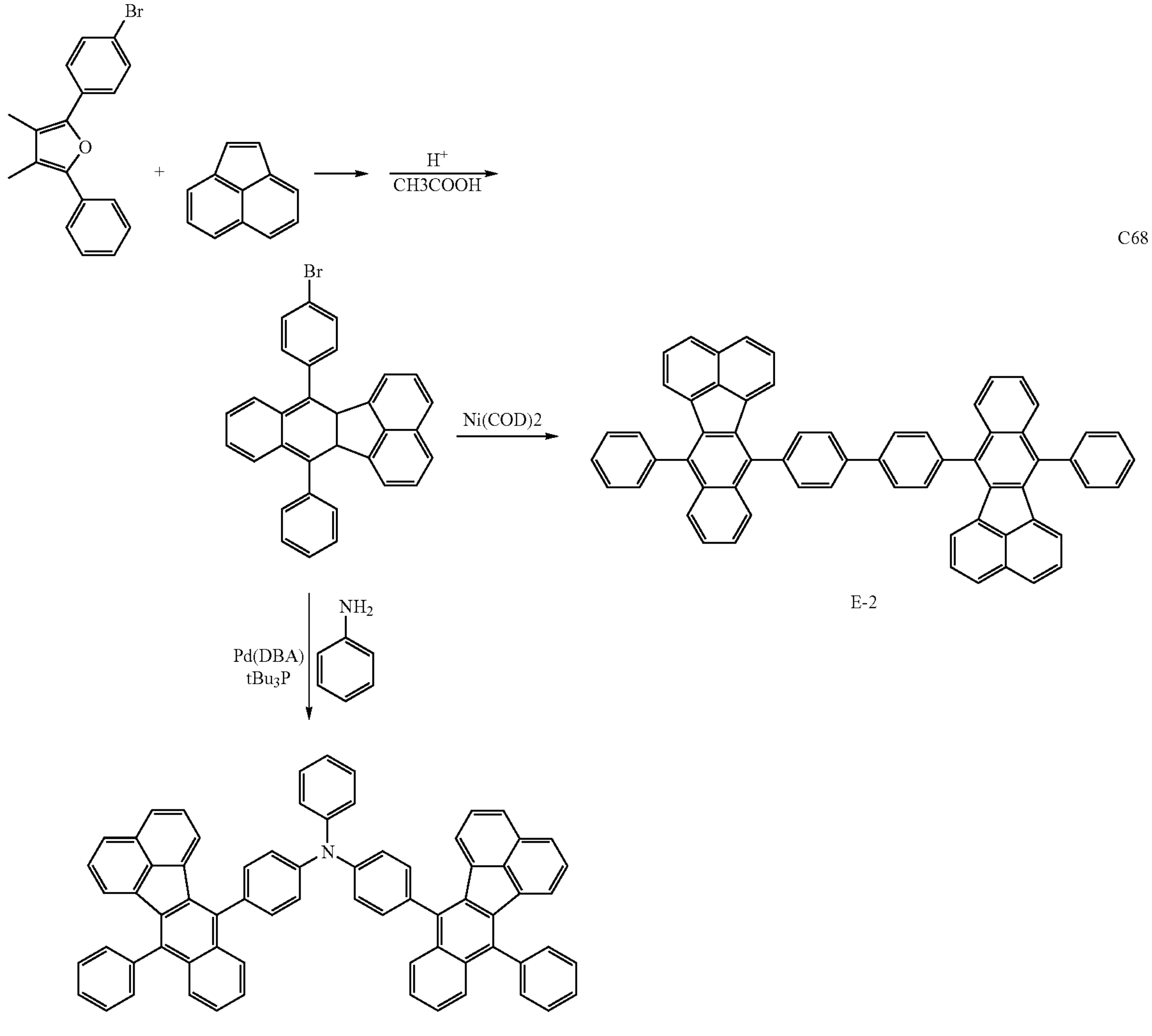

C68

E-2

X-2

The compounds of the invention have excellent properties as the fluorescent material for organic EL devices. Particularly when the inventive compounds are used as the dopant, light emission of a color close to pure blue as represented by color coordinates wherein x=0.05 to 0.20 and y=0.02 to 0.30, especially x=0.10 to 0.20 and y=0.05 to 0.20 is available.

The compounds of the invention are very stable, and exhibit properties which remain constant in the steps involved in the manufacture of organic EL devices such as evaporation and coating, and maintain such consistent properties over a long time even after the manufacture.

When the compounds of the invention are used in organic EL devices, they may serve as either the host material or the dopant. Especially when the compounds are used as the dopant, excellent color and efficiency of light emission as mentioned above are obtainable. Since the compounds of the invention have all of electron injecting and transporting properties, and hole injecting or transporting properties, they can be used as either the electron transporting material or the hole injecting or transporting material.

When a combination of the host material with the dopant is determined for an organic EL device, it is important to take into account the following points.

(1) A combination is considered on the basis of structural formula. That is, the structure of compound itself dictates emission characteristics.

(2) The dopant or light emitting material should desirably have an ionization potential equal to or lower than the ionization potential of the host material. When actuated for light emission, the dopant functions as a hole trap, with a likelihood of the dopant generating singlet excitons. Also in this case, energy exchange is likely to occur between the singlet excitons of the host and the dopant in the ground state, leading to improved emission efficiency.

(3) The dopant or light emitting material should desirably have a half-wave oxidation potential equal to or lower than the half-wave oxidation potential of the host material. When actuated for light emission, the dopant functions as a hole trap, with a likelihood of the dopant generating singlet excitons. Also in this case, energy exchange is likely to occur between the singlet excitons of the host and the dopant in the ground state, leading to improved emission efficiency.

When the compound of the invention is used in the light emitting layer, it may be serve as either the host material or the dopant, and more preferably as the dopant for blue light emission. When the compound of the invention is used as the dopant, the host material to be used in combination is preferably an anthracene material. It is also preferred to use a mix layer comprising a mixture of an electron transporting material and a hole transporting material as the host. The light emitting layer may contain one or more compounds in addition to the inventive compound. By using such a plurality of compounds in a light emitting layer or stacking light emitting layers of different compounds, the resulting light emitting layer or device can have a plurality of peak wavelengths or a wide range of light emission wavelength.

When the compounds of the invention are used as the host material, a variety of fluorescent materials for organic EL devices may be used as the dopant. Inter alia, rubrene derivatives of naphthacene series and diphenylnaphthacene derivatives used in Examples, perylene red fluorescent materials, pentacene red fluorescent materials and distyrylamine derivative materials are preferred.

When the compound of the invention is included in the hole injecting and transporting layer, it may be used as either the hole transporting material or the light emitting material. When the inventive compound is used as the hole transporting material, the dopant is selected from the aforementioned compounds.

When the compound of the invention is included in the electron injecting and transporting layer, it may be used as either the electron transporting material or the light emitting material. When the inventive compound is used as the electron transporting material, the dopant is selected from the aforementioned compounds. This electron injecting and transporting layer may also be a mix layer as mentioned above.

When the compound of the invention is used as the dopant, the dopant content is preferably up to 30% by weight, more preferably 0.1 to 20% by weight, even more preferably 0.1 to 10% by weight, and especially 0.1 to 5% by weight.

Using the compounds of the invention in organic EL devices, the following advantages are obtained.

(1) Although a monomeric system (n=1) is quite difficult to induce light emission from an anthracene host material, the compounds of the invention facilitate light emission and provide a very high luminance.

(2) The color of light emission is controllable with the linking group Y. For example, when Y is an amino group, greenish light emission is obtained. When Y is triphenylamine, pale-blue light emission is obtained. Therefore, the color of light emission is readily adjustable.

(3) Although the dimer of X joined at the position of $R_7$ or $R_8$ through a single bond is likely to undergo intramolecular polymerization or decomposition during sublimation purification or evaporation, the compounds of the invention are very stable and convenient to use.

(4) Albeit fused polycyclic aromatic hydrocarbon compounds, the compounds of the invention are well suited as the organic EL material which must transport both electrons and holes.

(5) The compounds of the invention perform well as the light emitting material and can emit light of pure blue color close to NTSC signals at an efficiency as high as 7.3 cd/A.

(6) The compounds of the invention perform well as the host material and can be used in combination with a wide variety of compounds including naphthacene derivatives, rubrene derivatives, perylene derivatives, coumarin derivatives, and styrylamine derivatives.

(7) Since the compounds of the invention have a high glass transition temperature (Tg), devices having shelf stability at elevated temperature are obtainable.

The light emitting layer containing the host material and the dopant as mentioned above has functions of injecting holes and electrons, transporting them, and recombining holes and electrons to create excitons. The use of relatively electronically neutral compounds in the light emitting layer in addition to the compounds of the invention enables easy and well-balanced injection and transportation of electrons and holes.

The host material may be used alone or in admixture of two or more. When a mixture of two or more host materials is used, the mix ratio is arbitrary. When the compound of the invention is used as the host material, it is preferably contained in an amount of 80 to 99.9%, more preferably 90 to 99.9%, even more preferably 95.0 to 99.5% by weight of the light emitting layer.

The thickness of the light emitting layer preferably ranges from the thickness corresponding to a single molecule layer to less than the thickness of an organic compound layer, for example, preferably from 1 to 85 nm, more preferably 5 to 60 nm, and most preferably 5 to 50 nm.

Preferably the mix layer is formed by a co-deposition process of evaporating the compounds from distinct sources. If both the compounds have equal or very close vapor pressure or evaporation temperature, they may be pre-mixed in a common evaporation boat, from which they are evaporated together. The mix layer is preferably a uniform mixture of both the compounds although the compounds can be present in island form. The light emitting layer is generally formed to a predetermined thickness by evaporating an organic fluorescent material or coating a dispersion thereof in a resin binder.

Anthracene Compounds

A class of organic compounds preferred as the host material in devices according to the invention are phenylanthracene derivatives of the following formula (5).

In the device of the invention, the use of the anthracene derivative of formula (5), typically formula (5-1) or (5-2), preferably as the host material, helps induce strong light emission from the dopant while controlling the interaction with the dopant. Since the anthracene derivatives are fully heat resistant and durable, devices with a longer lifetime are obtainable.

In the EL devices, the dopant concentration ensuring a color purity and maximum efficiency is about 1% by weight although dopant concentrations of about 2 or 3% by weight lead to devices which are practically acceptable albeit a drop of less than about 10%.

C 69

(5)

$(A_{101})_n$—L

In formula (5), $A_{101}$ is a monophenylanthryl or diphenylanthryl radical and may be the same or different, L is hydrogen, a single bond or a divalent linkage, and n is an integer of 1 or 2.

Of the compounds of formula (5), those compounds of the following formulas (5-1) and (5-2) are preferred.

(5-1)

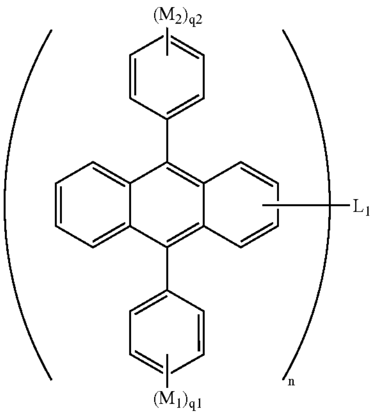

C-70

(5-2)

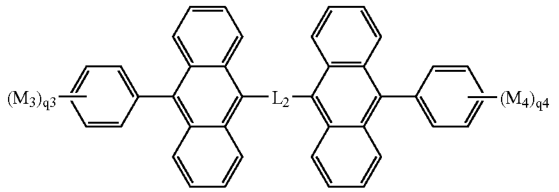

C71

Evaporated films of these compounds remain in a stable amorphous state, that is, have sufficient physical properties to produce consistent uniform light emission. The films remain stable over one year in the ambient atmosphere without crystallization.

Referring to formula (5), $A_{101}$ is a monophenylanthryl or diphenylanthryl radical and may be the same or different, and n is an integer of 1 or 2.

The monophenylanthryl or diphenylanthryl radical represented by $A_{101}$ may be substituted or unsubstituted. Examples of suitable substituents, if any, are alkyl, aryl, alkoxy, aryloxy and amino groups. These substituents may further have substituents thereon and will be described later. The position of a substituent on the monophenylanthryl or diphenylanthryl radical is not critical although the preferred substitution position is on the phenyl group bonded to the anthracene ring rather than the anthracene ring.

Preferably the phenyl group is bonded to the anthracene ring at the 9- and 10-positions.

In formula (5-1), L is hydrogen, a single bond or a divalent linkage. The divalent linkage represented by L is preferably an arylene radical which may be separated by an alkylene or analogous group. The arylene radical will be described later.

Of the phenylanthracene derivatives of formula (5), those of formulas (5-1) and (5-2) are preferred. Formula (5-1) is described in detail.

In formula (5-1), $M_1$ and $M_2$ each are alkyl, cycloalkyl, aryl, alkoxy, aryloxy, amino or heterocyclic radicals.

The alkyl radicals represented by $M_1$ and $M_2$ may be substituted or unsubstituted, straight or branched alkyl radicals, preferably of 1 to 10 carbon atoms, more preferably 1 to 4 carbon atoms. Unsubstituted alkyl radicals of 1 to 4 carbon atoms are preferred, such as, for example, methyl, ethyl, n- and i-propyl, and n-, i-, sec- and tert-butyl.

Exemplary of the cycloalkyl radicals represented by $M_1$ and $M_2$ are cyclohexyl and cyclopentyl.

The aryl radicals represented by $M_1$ and $M_2$ are preferably those aryl radicals having 6 to 20 carbon atoms which may have substituents such as phenyl and tolyl. Preferred examples of the aryl radical include phenyl, o-, m- and p-tolyl, pyrenyl, naphthyl, anthryl, biphenyl, phenylanthryl and tolylanthryl.

The alkenyl radicals represented by $M_1$ and $M_2$ are preferably those having 6 to 50 carbon atoms in total, which may be substituted or unsubstituted, with the substituted ones being preferred. Such substituents are aryl groups such as phenyl. Exemplary alkenyl radicals are triphenylvinyl, tritolylvinyl and tribiphenylvinyl.

The alkoxy radicals represented by $M_1$ and $M_2$ are preferably those having an alkyl moiety of 1 to 6 carbon atoms, for example, methoxy and ethoxy. The alkoxy radicals may have substituents.

Exemplary of the aryloxy radicals represented by $M_1$ and $M_2$ is phenoxy.

The amino radicals represented by $M_1$ and $M_2$ may be substituted or unsubstituted, with the substituted amino radicals being preferred. Such substituents are alkyl groups such as methyl and ethyl and aryl groups such as phenyl. Illustrative examples of the amino radical include diethylamino, diphenylamino and di(m-tolyl)amino radicals.

The heterocyclic radicals represented by $M_1$ and $M_2$ include bipyridyl, pyrimidyl, quinolyl, pyridyl, thienyl, furyl and oxadiazoyl radicals and may have substituents such as methyl and phenyl.

In formula (5-1), q1 and q2 each are 0 or an integer of 1 to 5, especially 0 or 1. When q1 and q2 each are an integer of 1 to 5, especially 1 or 2, $M_1$ and $M_2$ each are preferably alkyl, aryl, alkenyl, alkoxy, aryloxy or amino radicals.

In formula (5-1), $M_1$ and $M_2$ may be the same or different. Where a plurality of $M_1$ or $M_2$ are included, the $M_1$ groups or $M_2$ groups may be the same or different. Alternatively, the $M_1$ groups or $M_2$ groups bond together to form a ring such as a benzene ring. The ring formation is also a preferred embodiment.

In formula (5-1), $L_1$ is hydrogen, a single bond or an arylene radical. The arylene radicals represented by $L_1$ are preferably unsubstituted ones, for example, ordinary arylene radicals such as phenylene, biphenylene and anthrylene as well as two or more arylene radicals which are directly bonded. $L_1$ is preferably a single bond, p-phenylene or 4,4'-biphenylene.

The arylene radical represented by $L_1$ may consist of two or more arylene radicals which are connected by an alkylene radical, —O—, —S— or —NR— wherein R is an alkyl or aryl radical. Exemplary alkyl radicals are methyl and ethyl, and an exemplary aryl radical is phenyl. R is preferably an aryl radical, such as phenyl. Alternatively, R is $A_{101}$ or a phenyl radical having $A_{101}$ substituted thereon.

The alkylene radicals are preferably methylene and ethylene. Illustrative examples of the arylene radical are given below.

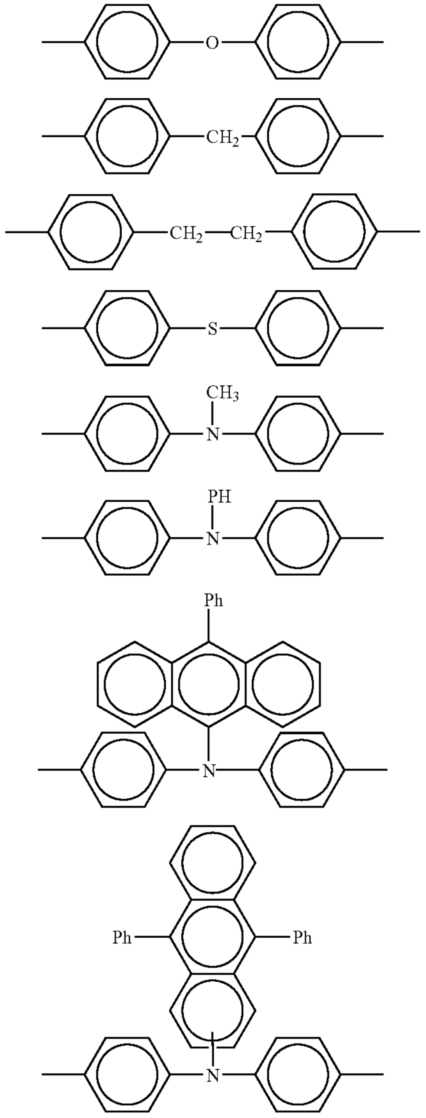

c72

Next referring to formula (5-2), $M_3$ and $M_4$ are the same as $M_1$ and $M_2$ in formula (5-1), q3 and q4 are the same as q1 and q2 in formula (5-1), and $L_2$ is the same as $L_1$ in formula (5-1). Preferred examples of these radicals are also the same.

In formula (5-2), $M_3$ and $M_4$ may be the same or different. Where a plurality of $M_3$ or $M_4$ are included, the $M_3$ groups or $M_4$ groups may be the same or different. Alternatively, the $M_3$ groups or $M_4$ groups bond together to form a ring such as a benzene ring. The ring formation is also a preferred embodiment.

Illustrative, non-limiting, examples of the compounds of formulas (5-1) and (5-2) are given below. It is noted that C41, C43, C45, C47, C49, C51, C53, and C56 are general formulas, and C42, C44, C46, C48, C50, C52, C54, C55 and C57 are illustrative examples shown by combinations of $M_{11}$ to $M_{15}$ and $M_{21}$ to $M_{25}$ or combinations of $M_{31}$ to $M_{35}$ and $M_{41}$ to $M_{45}$.

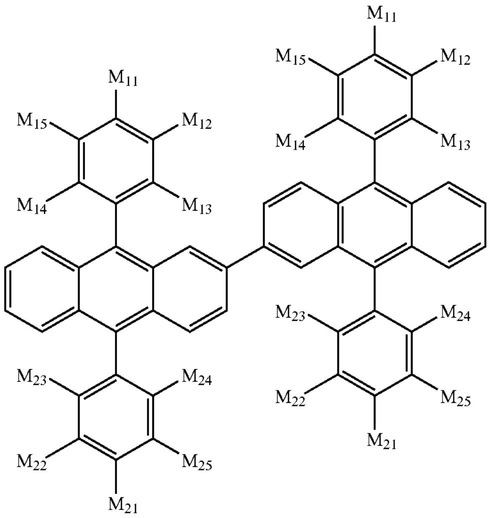

c73

C74

| Compound No. | $M_{11}$ | $M_{12}$ | $M_{13}$ | $M_{14}$ | $M_{15}$ |
|---|---|---|---|---|---|
| I-1 | H | H | H | H | H |
| I-2 | $CH_3$ | H | H | H | H |
| I-3 | t-$C_4H_9$ | H | H | H | H |
| I-4 | $OCH_3$ | H | H | H | H |
| I-5 | OPh | H | H | H | H |
| I-6 | $N(C_2H_5)_2$ | H | H | H | H |
| I-7 | $N(Ph)_2$ | H | H | H | H |
| I-8 | Ph | H | H | H | H |

-continued
| C74 | | | | | |
|---|---|---|---|---|---|
| I-9 | 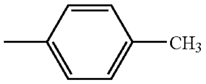 | H | H | H | H |
| I-10 | H | $CH_3$ | H | H | H |
| I-11 | H | $CH_3$ | H | $CH_3$ | H |
| I-12 | H | H | $CH_3$ | H | H |
| I-13 | H | $CH_3$ | H | H | $CH_3$ |
| I-14 | t-$C_4H_9$ | H | H | H | H |
| I-15 | 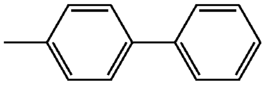 | H | H | H | H |
| I-16 | H | Ph | H | H | H |
| I-17 | H | H | Ph | H | H |
| I-18 | 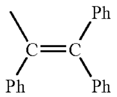 | H | H | H | H |
| I-19 | n-$C_4H_9$ | H | H | H | H |
| I-20 | 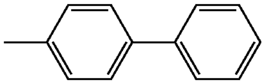 | H | H | H | H |
| I-21 | H | H | 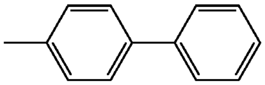 | H | H |
| I-22 | 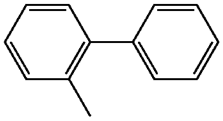 | H | H | H | H |
| I-23 | H | H | 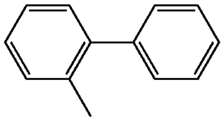 | H | H |
| I-24 | H | H | Ph | H | Ph |
| I-25 | H | H | Ph | Ph | H |
| Compound No. | $M_{21}$ | $M_{22}$ | $M_{23}$ | $M_{24}$ | $M_{25}$ |
|---|---|---|---|---|---|
| I-1 | H | H | H | H | H |
| I-2 | $CH_3$ | H | H | H | H |
| I-3 | t-$C_4H_9$ | H | H | H | H |
| I-4 | $OCH_3$ | H | H | H | H |
| I-5 | OPh | H | H | H | H |
| I-6 | $N(C_2H_5)_2$ | H | H | H | H |
| I-7 | $N(Ph)_2$ | H | H | H | H |
| I-8 | Ph | H | H | H | H |
| I-9 | 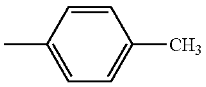 | H | H | H | H |
| I-10 | H | $CH_3$ | H | H | H |
| I-11 | H | $CH_3$ | H | $CH_3$ | H |
| I-12 | H | H | $CH_3$ | H | H |
| I-13 | H | $CH_3$ | H | H | $CH_3$ |
| I-14 | H | H | H | H | H |

-continued
| C74 | | | | | |
|---|---|---|---|---|---|
| I-15 | 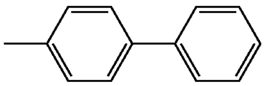 | H | H | H | H |
| I-16 | H | Ph | H | H | H |
| I-17 | H | H | Ph | H | H |
| I-18 | 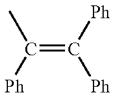 | H | H | H | H |
| I-19 | n-$C_4H_9$ | H | H | H | H |
| I-20 | 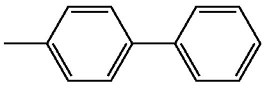 | H | H | H | H |
| I-21 | H | H | 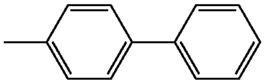 | H | H |
| I-22 | 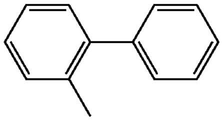 | H | H | H | H |
| I-23 | H | H | 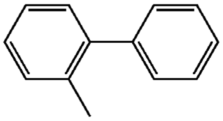 | H | H |
| I-24 | H | H | Ph | H | Ph |
| I-25 | H | H | Ph | Ph | H |
c75
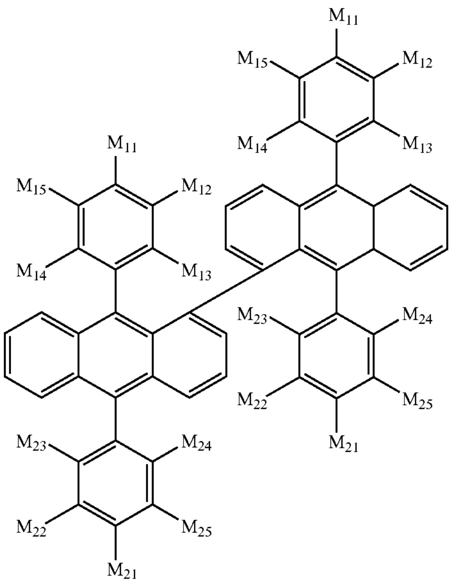

C76

| Compound No. | $M_{11}$ | $M_{12}$ | $M_{13}$ | $M_{14}$ | $M_{15}$ |
|---|---|---|---|---|---|
| II-1 | H | H | H | H | H |
| II-2 | $CH_3$ | H | H | H | H |
| II-3 | $t\text{-}C_4H_9$ | H | H | H | H |
| II-4 | $OCH_3$ | H | H | H | H |
| II-5 | OPh | H | H | H | H |
| II-6 | $N(C_2H_5)_2$ | H | H | H | H |
| II-7 | $N(Ph)_2$ | H | H | H | H |
| II-8 | Ph | H | H | H | H |
| II-9 | 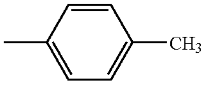 | H | H | H | H |
| II-10 | H | $CH_3$ | H | H | H |
| II-11 | H | H | $CH_3$ | H | H |
| II-12 | H | H | $CH_3$ | $CH_3$ | H |
| II-13 | H | H | $CH_3$ | H | $CH_3$ |
| II-14 | $CH_3$ | $CH_3$ | $CH_3$ | $CH_3$ | $CH_3$ |
| II-15 | $t\text{-}C_4H_9$ | H | H | H | H |
| II-16 | 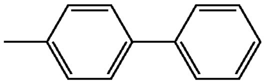 | H | H | H | H |
| II-17 | H | Ph | H | H | H |
| II-18 | H | H | Ph | H | H |
| II-19 | H | H | 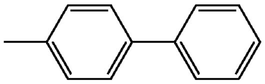 | H | H |
| II-20 | 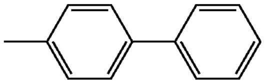 | H | H | H | H |
| II-21 | 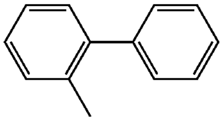 | H | H | H | H |
| II-22 | H | H | 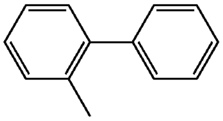 | H | H |
| II-23 | H | H | Ph | H | Ph |
| II-24 | H | H | Ph | Ph | H |

| Compound No. | $M_{21}$ | $M_{22}$ | $M_{23}$ | $M_{24}$ | $M_{25}$ |
|---|---|---|---|---|---|
| II-1 | H | H | H | H | H |
| II-2 | $CH_3$ | H | H | H | H |
| II-3 | $t\text{-}C_4H_9$ | H | H | H | H |
| II-4 | $OCH_3$ | H | H | H | H |
| II-5 | OPh | H | H | H | H |
| II-6 | $N(C_2H_5)_2$ | H | H | H | H |
| II-7 | $N(Ph)_2$ | H | H | H | H |
| II-8 | Ph | H | H | H | H |
| II-9 | 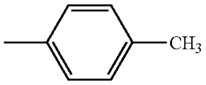 | H | H | H | H |

-continued
| | C76 | | | | |
|---|---|---|---|---|---|
| II-10 | H | $CH_3$ | H | H | H |
| II-11 | H | $CH_3$ | $CH_3$ | H | H |
| II-12 | H | H | $CH_3$ | $CH_3$ | H |
| II-13 | H | $CH_3$ | $CH_3$ | H | $CH_3$ |
| II-14 | $CH_3$ | $CH_3$ | $CH_3$ | $CH_3$ | $CH_3$ |
| II-15 | H | H | H | H | H |
| II-16 | 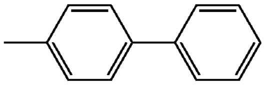 | H | H | H | H |
| II-17 | H | Ph | H | H | H |
| II-18 | H | H | Ph | H | H |
| II-19 | H | H | 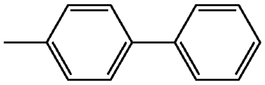 | H | H |
| II-20 | 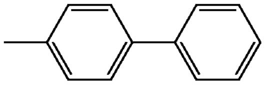 | H | H | H | H |
| II-21 | 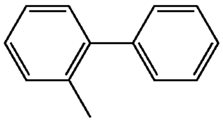 | H | H | H | H |
| II-22 | H | H | 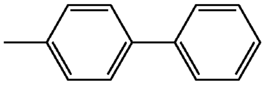 | H | H |
| II-23 | H | H | Ph | H | Ph |
| II-24 | H | H | Ph | Ph | H |
c77
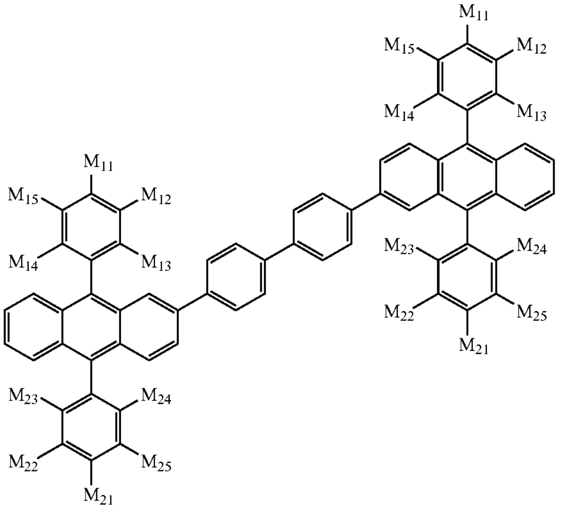

| C78 | | | | | |
|---|---|---|---|---|---|
| Compound No. | $M_{11}$ | $M_{12}$ | $M_{13}$ | $M_{14}$ | $M_{15}$ |
| III-1 | H | H | H | H | H |
| III-2 | $CH_3$ | H | H | H | H |
| III-3 | t-$C_4H_9$ | H | H | H | H |
| III-4 | $OCH_3$ | H | H | H | H |
| III-5 | OPh | H | H | H | H |
| III-6 | $N(C_2H_5)_2$ | H | H | H | H |
| III-7 | $N(Ph)_2$ | H | H | H | H |
| III-8 | Ph | H | H | H | H |
| III-9 | 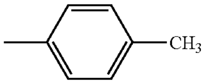 | H | H | H | H |
| III-10 | H | $CH_3$ | H | H | H |
| III-11 | H | H | $CH_3$ | H | H |
| III-12 | H | H | $CH_3$ | $CH_3$ | H |
| III-13 | H | H | $CH_3$ | H | $CH_3$ |
| III-14 | $CH_3$ | $CH_3$ | $CH_3$ | $CH_3$ | $CH_3$ |
| III-15 | H | Ph | H | H | H |
| III-16 | H | H | Ph | H | H |
| III-17 | 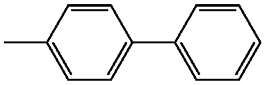 | H | H | H | H |
| III-18 | t-$C_4H_9$ | H | H | H | H |
| III-19 | 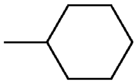 | H | H | H | H |
| III-20 | 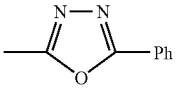 | H | H | H | H |
| III-21 | 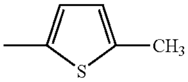 | H | H | H | H |
| III-22 | 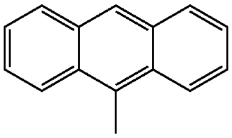 | H | H | H | H |
| III-23 | 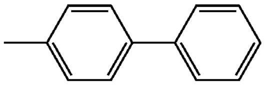 | H | H | H | H |
| III-24 | H | H | 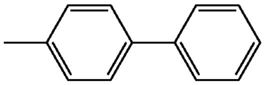 | H | H |
| III-25 | 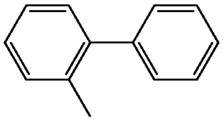 | H | H | H | H |

-continued

| | | | | | |
|---|---|---|---|---|---|
| | | C78 | | | |
| III-26 | H | H | 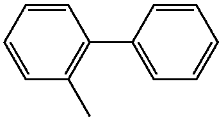 | H | H |
| III-27 | H | H | Ph | H | Ph |
| III-28 | H | H | Ph | Ph | H |
| Compound No. | $M_{21}$ | $M_{22}$ | $M_{23}$ | $M_{24}$ | $M_{25}$ |
| III-1 | H | H | H | H | H |
| III-2 | $CH_3$ | H | H | H | H |
| III-3 | t-$C_4H_9$ | H | H | H | H |
| III-4 | $OCH_3$ | H | H | H | H |
| III-5 | OPh | H | H | H | H |
| III-6 | $N(C_2H_5)_2$ | H | H | H | H |
| III-7 | $N(Ph)_2$ | H | H | H | H |
| III-8 | Ph | H | H | H | H |
| III-9 | 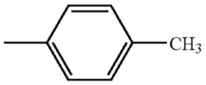 | H | H | H | H |
| III-10 | H | $CH_3$ | H | H | H |
| III-11 | H | H | $CH_3$ | H | H |
| III-12 | H | H | $CH_3$ | $CH_3$ | H |
| III-13 | H | H | $CH_3$ | H | $CH_3$ |
| III-14 | $CH_3$ | $CH_3$ | $CH_3$ | $CH_3$ | $CH_3$ |
| III-15 | H | Ph | H | H | H |
| III-16 | H | H | Ph | H | H |
| III-17 | 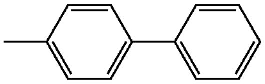 | H | H | H | H |
| III-18 | H | H | H | H | H |
| III-19 | 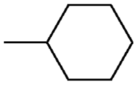 | H | H | H | H |
| III-20 | 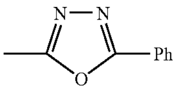 | H | H | H | H |
| III-21 | 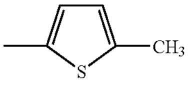 | H | H | H | H |
| III-22 | 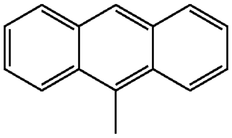 | H | H | H | H |
| III-23 | 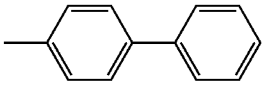 | H | H | H | H |
| III-24 | H | H | 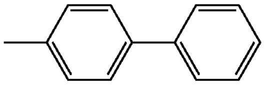 | H | H |

-continued
| C78 | | | | | |
|---|---|---|---|---|---|
| III-25 | 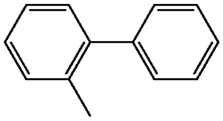 | H | H | H | H |
| III-26 | H | H | 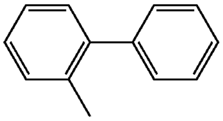 | H | H |
| III-27 | H | H | Ph | H | Ph |
| III-28 | H | H | Ph | Ph | H |
c 79
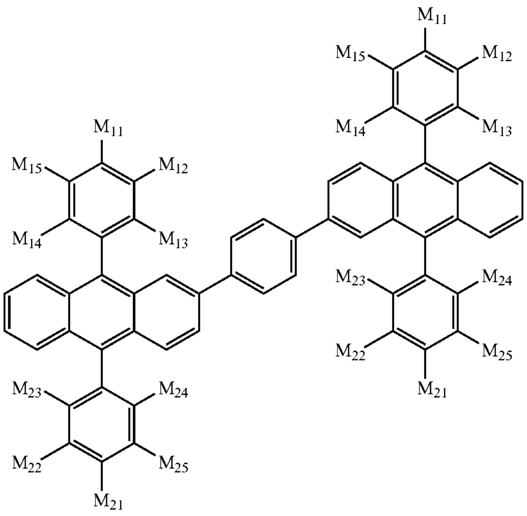
| C80 | | | | | |
|---|---|---|---|---|---|
| Compound No. | $M_{11}$ | $M_{12}$ | $M_{13}$ | $M_{14}$ | $M_{15}$ |
| IV-1 | H | H | H | H | H |
| IV-2 | $CH_3$ | H | H | H | H |
| IV-3 | $t\text{-}C_4H_9$ | H | H | H | H |
| IV-4 | $OCH_3$ | H | H | H | H |
| IV-5 | OPh | H | H | H | H |
| IV-6 | $N(C_2H_5)_2$ | H | H | H | H |
| IV-7 | $N(Ph)_2$ | H | H | H | H |
| IV-8 | Ph | H | H | H | H |
| IV-9 | 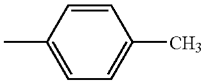 | H | H | H | H |
| IV-10 | H | $CH_3$ | H | H | H |
| IV-11 | H | H | $CH_3$ | H | H |
| IV-12 | H | H | $CH_3$ | $CH_3$ | H |

-continued

| | | | C80 | | |
|---|---|---|---|---|---|
| IV-13 | H | H | $CH_3$ | H | $CH_3$ |
| IV-14 | $CH_3$ | $CH_3$ | $CH_3$ | $CH_3$ | $CH_3$ |
| IV-15 | H | H | H | H | H |
| IV-16 | H | H | Ph | H | H |
| IV-17 | 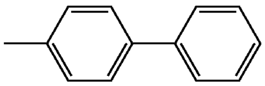 | H | H | H | H |
| IV-18 | t-$C_4H_9$ | H | H | H | H |
| IV-19 | 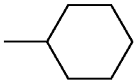 | H | H | H | H |
| IV-20 | 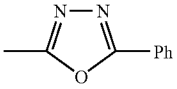 | H | H | H | H |
| IV-21 | 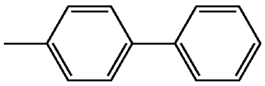 | H | H | H | H |
| IV-22 | H | H | 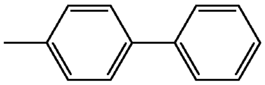 | H | H |
| IV-23 | 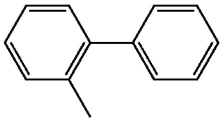 | H | H | H | H |
| IV-24 | H | H | 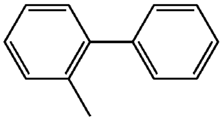 | H | H |
| IV-25 | H | H | Ph | H | Ph |
| IV-26 | H | H | Ph | Ph | H |
| Compound No. | $M_{21}$ | $M_{22}$ | $M_{23}$ | $M_{24}$ | $M_{25}$ |
| IV-1 | H | H | H | H | H |
| IV-2 | $CH_3$ | H | H | H | H |
| IV-3 | t-$C_4H_9$ | H | H | H | H |
| IV-4 | $OCH_3$ | H | H | H | H |
| IV-5 | OPh | H | H | H | H |
| IV-6 | $N(C_2H_5)_2$ | H | H | H | H |
| IV-7 | $N(Ph)_2$ | H | H | H | H |
| IV-8 | Ph | H | H | H | H |
| IV-9 | 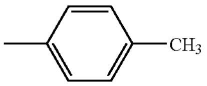 | H | H | H | H |
| IV-10 | H | $CH_3$ | H | H | H |
| IV-11 | H | H | $CH_3$ | H | H |
| IV-12 | H | H | $CH_3$ | $CH_3$ | H |
| IV-13 | H | H | $CH_3$ | H | $CH_3$ |
| IV-14 | $CH_3$ | $CH_3$ | $CH_3$ | $CH_3$ | $CH_3$ |
| IV-15 | H | H | H | H | H |
| IV-16 | H | H | Ph | H | H |

-continued
| C80 | | | | | |
|---|---|---|---|---|---|
| IV-17 | 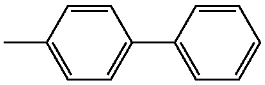 | H | H | H | H |
| IV-18 | H | H | H | H | H |
| IV-19 | 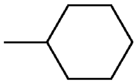 | H | H | H | H |
| IV-20 | 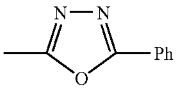 | H | H | H | H |
| IV-21 | 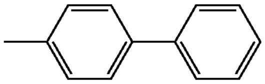 | H | H | H | H |
| IV-22 | H | H | 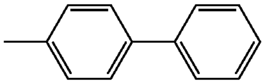 | H | H |
| IV-23 | 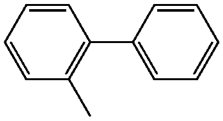 | H | H | H | H |
| IV-24 | H | H | 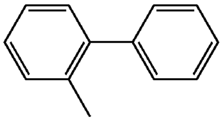 | H | H |
| IV-25 | H | H | Ph | H | Ph |
| IV-26 | H | H | Ph | Ph | H |
C 81
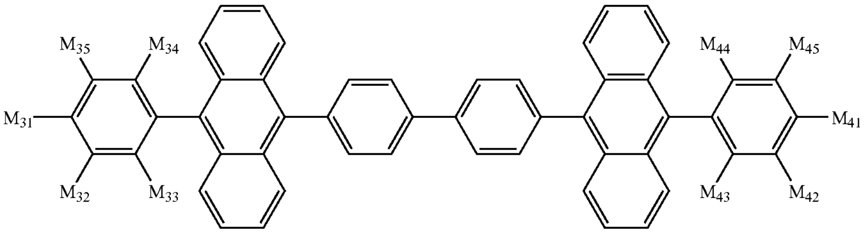
| C82 | | | | | |
|---|---|---|---|---|---|
| Com-pound No. | $M_{31}$ | $M_{32}$ | $M_{33}$ | $M_{34}$ | $M_{35}$ |
| V-1 | H | H | H | H | H |
| V-2 | $CH_3$ | H | H | H | H |
| V-3 | t-$C_4H_9$ | H | H | H | H |

-continued
| | | | C82 | | |
|---|---|---|---|---|---|
| V-4 | $OCH_3$ | H | H | H | H |
| V-5 | OPh | H | H | H | H |
| V-6 | $N(C_2H_5)_2$ | H | H | H | H |
| V-7 | $N(Ph)_2$ | H | H | H | H |
| V-8 | Ph | H | H | H | H |
| V-9 | 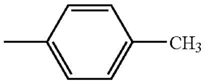 | H | H | H | H |
| V-10 | H | $CH_3$ | H | H | H |
| V-11 | H | H | $CH_3$ | H | H |
| V-12 | H | H | $CH_3$ | $CH_3$ | H |
| V-13 | H | H | $CH_3$ | H | $CH_3$ |
| V-14 | $CH_3$ | $CH_3$ | $CH_3$ | $CH_3$ | $CH_3$ |
| V-15 | H | Ph | H | H | H |
| V-16 | H | H | Ph | H | H |
| V-17 | 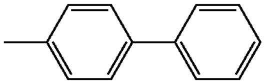 | H | H | H | H |
| V-18 | $t-C_4H_9$ | H | H | H | H |
| V-19 | 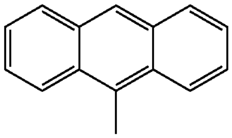 | H | H | H | H |
| V-20 | 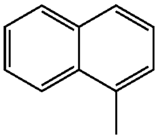 | H | H | H | H |
| V-21 | 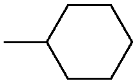 | H | H | H | H |
| V-22 | 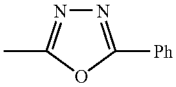 | H | H | H | H |
| V-23 | 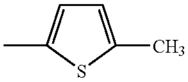 | H | H | H | H |
| V-24 | 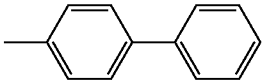 | H | H | H | H |
| V-25 | H | H | 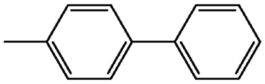 | H | H |
| V-26 | 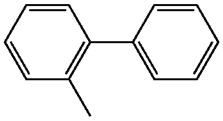 | H | H | H | H |

-continued
| | | | | | |
|---|---|---|---|---|---|
| | | C82 | | | |
| V-27 | H | H | 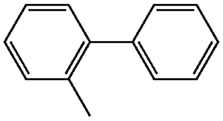 | H | H |
| V-28 | H | H | Ph | H | Ph |
| V-29 | H | H | Ph | Ph | H |
| Compound No. | $M_{41}$ | $M_{42}$ | $M_{43}$ | $M_{44}$ | $M_{45}$ |
|---|---|---|---|---|---|
| V-1 | H | H | H | H | H |
| V-2 | $CH_3$ | H | H | H | H |
| V-3 | t-$C_4H_9$ | H | H | H | H |
| V-4 | $OCH_3$ | H | H | H | H |
| V-5 | OPh | H | H | H | H |
| V-6 | $N(C_2H_5)_2$ | H | H | H | H |
| V-7 | $N(Ph)_2$ | H | H | H | H |
| V-8 | Ph | H | H | H | H |
| V-9 | 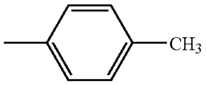 | H | H | H | H |
| V-10 | H | $CH_3$ | H | H | H |
| V-11 | H | H | $CH_3$ | H | H |
| V-12 | H | H | $CH_3$ | $CH_3$ | H |
| V-13 | H | H | $CH_3$ | H | $CH_3$ |
| V-14 | $CH_3$ | $CH_3$ | $CH_3$ | $CH_3$ | $CH_3$ |
| V-15 | H | Ph | H | H | H |
| V-16 | H | H | Ph | H | H |
| V-17 | 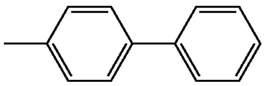 | H | H | H | H |
| V-18 | t-$C_4H_9$ | H | H | H | H |
| V-19 | 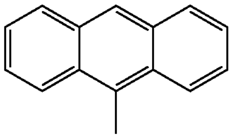 | H | H | H | H |
| V-20 | 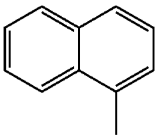 | H | H | H | H |
| V-21 | 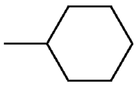 | H | H | H | H |
| V-22 | 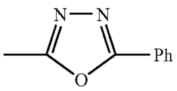 | H | H | H | H |
| V-23 | 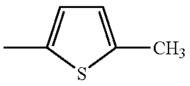 | H | H | H | H |
| V-24 | 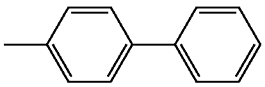 | H | H | H | H |

-continued
| C82 | | | | | |
|---|---|---|---|---|---|
| V-25 | H | H | 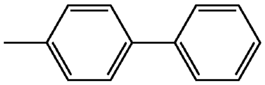 | H | H |
| V-26 | 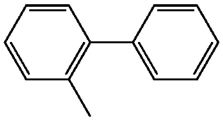 | H | H | H | H |
| V-27 | H | H | 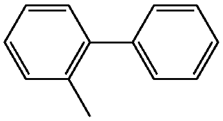 | H | H |
| V-28 | H | H | Ph | H | Ph |
| V-29 | H | H | Ph | Ph | H |
C83
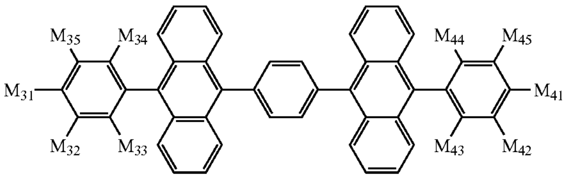
| C84 | | | | | |
|---|---|---|---|---|---|
| Compound No. | $M_{31}$ | $M_{32}$ | $M_{33}$ | $M_{34}$ | $M_{35}$ |
| VI-1 | H | H | H | H | H |
| VI-2 | $CH_3$ | H | H | H | H |
| VI-3 | t-$C_4H_9$ | H | H | H | H |
| VI-4 | $OCH_3$ | H | H | H | H |
| VI-5 | OPh | H | H | H | H |
| VI-6 | $N(C_2H_5)_2$ | H | H | H | H |
| VI-7 | $N(Ph)_2$ | H | H | H | H |
| VI-8 | Ph | H | H | H | H |
| VI-9 | 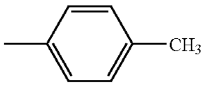 | H | H | H | H |
| VI-10 | H | $CH_3$ | H | H | H |
| VI-11 | H | H | $CH_3$ | H | H |
| VI-12 | H | H | $CH_3$ | $CH_3$ | H |
| VI-13 | H | H | $CH_3$ | H | $CH_3$ |
| VI-14 | $CH_3$ | $CH_3$ | $CH_3$ | $CH_3$ | $CH_3$ |
| VI-15 | H | Ph | H | H | H |
| VI-16 | H | H | Ph | H | H |
| VI-17 | 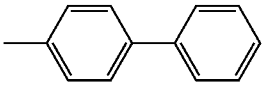 | H | H | H | H |

-continued
| | | | | | |
|---|---|---|---|---|---|
| | | C84 | | | |
| VI-18 | t-$C_4H_9$ | H | H | H | H |
| VI-19 | 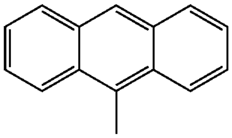 | H | H | H | H |
| VI-20 | 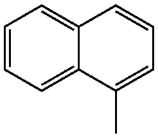 | H | H | H | H |
| VI-21 | 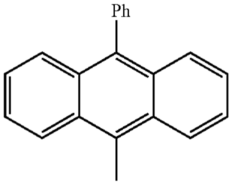 | H | H | H | H |
| VI-22 | 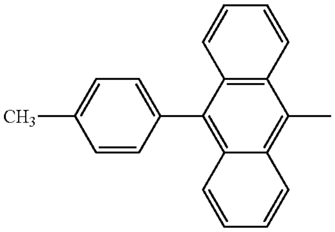 | H | H | H | H |
| VI-23 | 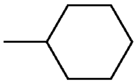 | H | H | H | H |
| VI-24 | 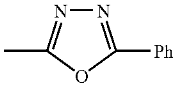 | H | H | H | H |
| VI-25 | H | H | Ph | H | Ph |
| VI-26 | H | H | Ph | Ph | H |
| VI-27 | H | H | 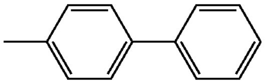 | H | H |
| VI-28 | H | H | 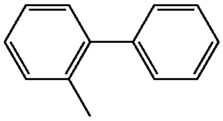 | H | H |
| Compound No. | $M_{41}$ | $M_{42}$ | $M_{43}$ | $M_{44}$ | $M_{45}$ |
|---|---|---|---|---|---|
| VI-1 | H | H | H | H | H |
| VI-2 | $CH_3$ | H | H | H | H |
| VI-3 | t-$C_4H_9$ | H | H | H | H |

-continued
| C84 | | | | | |
|---|---|---|---|---|---|
| VI-4 | $OCH_3$ | H | H | H | H |
| VI-5 | OPh | H | H | H | H |
| VI-6 | $N(C_2H_5)_2$ | H | H | H | H |
| VI-7 | $N(Ph)_2$ | H | H | H | H |
| VI-8 | Ph | H | H | H | H |
| VI-9 | 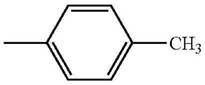 | H | H | H | H |
| VI-10 | H | $CH_3$ | H | H | H |
| VI-11 | H | H | $CH_3$ | H | H |
| VI-12 | H | H | $CH_3$ | $CH_3$ | H |
| VI-13 | H | H | $CH_3$ | H | $CH_3$ |
| VI-14 | $CH_3$ | $CH_3$ | $CH_3$ | $CH_3$ | $CH_3$ |
| VI-15 | H | Ph | H | H | H |
| VI-16 | H | H | Ph | H | H |
| VI-17 | 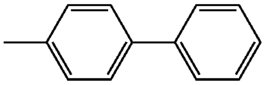 | H | H | H | H |
| VI-18 | H | H | H | H | H |
| VI-19 | 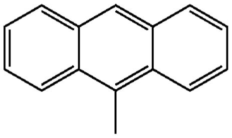 | H | H | H | H |
| VI-20 | 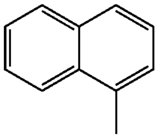 | H | H | H | H |
| VI-21 | H | H | H | H | H |
| VI-22 | $CH_3$ | H | H | H | H |
| VI-23 | 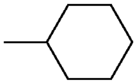 | H | H | H | H |
| VI-24 | 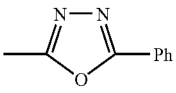 | H | H | H | H |
| VI-25 | H | H | Ph | H | Ph |
| VI-26 | H | H | Ph | Ph | H |
| VI-27 | H | H | 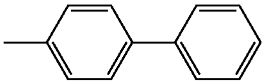 | H | H |
| VI-28 | H | H | 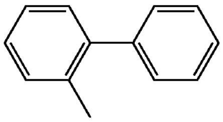 | H | H | c85

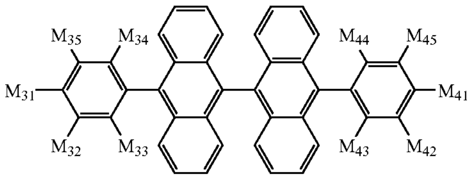

C86

| Compound No. | $M_{31}$ | $M_{32}$ | $M_{33}$ | $M_{34}$ | $M_{35}$ |
|---|---|---|---|---|---|
| VII-1 | H | H | H | H | H |
| VII-2 | $CH_3$ | H | H | H | H |
| VII-3 | t-$C_4H_9$ | H | H | H | H |
| VII-4 | $OCH_3$ | H | H | H | H |
| VII-5 | OPh | H | H | H | H |
| VII-6 | $N(C_2H_5)_2$ | H | H | H | H |
| VII-7 | $N(Ph)_2$ | H | H | H | H |
| VII-8 | Ph | H | H | H | H |
| VII-9 | 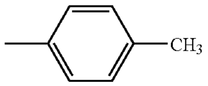 | H | H | H | H |
| VII-10 | H | H | $CH_3$ | $CH_3$ | H |
| VII-11 | H | H | $CH_3$ | H | $CH_3$ |
| VII-12 | H | $CH_3$ | H | H | H |
| VII-13 | H | H | $CH_3$ | H | H |
| VII-14 | $CH_3$ | $CH_3$ | $CH_3$ | $CH_3$ | $CH_3$ |
| VII-15 | H | H | Ph | H | Ph |
| VII-16 | H | H | Ph | Ph | H |
| VII-17 | H | H | 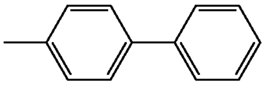 | H | H |
| VII-18 | H | H | 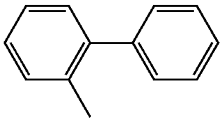 | H | H |

| Compound No. | $M_{41}$ | $M_{42}$ | $M_{43}$ | $M_{44}$ | $M_{45}$ |
|---|---|---|---|---|---|
| VII-1 | H | H | H | H | H |
| VII-2 | $CH_3$ | H | H | H | H |
| VII-3 | t-$C_4H_9$ | H | H | H | H |
| VII-4 | $OCH_3$ | H | H | H | H |
| VII-5 | OPh | H | H | H | H |
| VII-6 | $N(C_2H_5)_2$ | H | H | H | H |
| VII-7 | $N(Ph)_2$ | H | H | H | H |
| VII-8 | Ph | H | H | H | H |
| VII-9 | 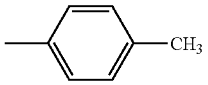 | H | H | H | H |
| VII-10 | H | H | $CH_3$ | $CH_3$ | H |
| VII-11 | H | H | $CH_3$ | H | $CH_3$ |
| VII-12 | H | $CH_3$ | H | H | H |

-continued
C86
| | | | | | |
|---|---|---|---|---|---|
| VII-13 | H | H | $CH_3$ | H | H |
| VII-14 | $CH_3$ | $CH_3$ | $CH_3$ | $CH_3$ | $CH_3$ |
| VII-15 | H | H | Ph | H | Ph |
| VII-16 | H | H | Ph | Ph | H |
| VII-17 | H | H | 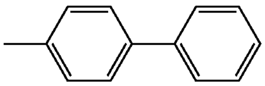 | H | H |
| VII-18 | H | H | 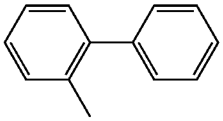 | H | H |
C87
| Compound No. | $M_{31}$ | $M_{32}$ | $M_{33}$ | $M_{34}$ | $M_{35}$ |
|---|---|---|---|---|---|
| VII-19 | H | Ph | H | H | H |
| VII-20 | H | H | Ph | H | H |
| VII-21 | 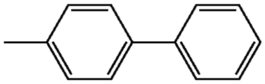 | H | H | H | H |
| VII-22 | t-$C_4H_9$ | H | H | H | H |
| VII-23 | 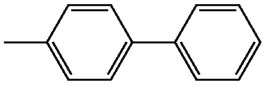 | H | H | H | H |
| VII-24 | 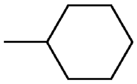 | H | H | H | H |
| VII-25 | 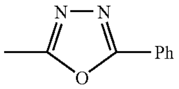 | H | H | H | H |
| VII-26 | 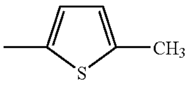 | H | H | H | H |
| VII-27 | 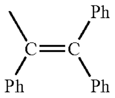 | H | H | H | H |
| VII-28 | n-$C_4H_9$ | H | H | H | H |
| VII-29 | H | H | $OCH_3$ | H | H |
| VII-30 | H | | $R_{32}$ and $R_{33}$ together form a fused benzene ring | H | H |
| VII-31 | 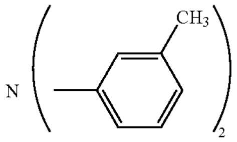 | H | H | H | H |

-continued
| | | C87 | | | |
|---|---|---|---|---|---|
| VII-32 | 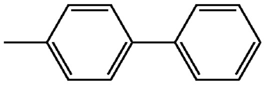 | H | H | H | H |
| VII-33 | H | H | 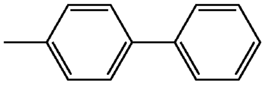 | H | H |
| VII-34 | 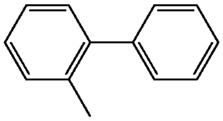 | H | H | H | H |
| VII-35 | H | H | 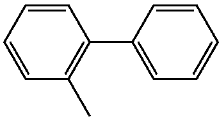 | H | H |
| VII-36 | H | H | Ph | H | Ph |
| VII-37 | H | H | Ph | Ph | H |
| Compound No. | $M_{41}$ | $M_{42}$ | $M_{43}$ | $M_{44}$ | $M_{45}$ |
|---|---|---|---|---|---|
| VII-19 | H | Ph | H | H | H |
| VII-20 | H | H | Ph | H | H |
| VII-21 | 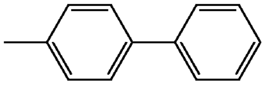 | H | H | H | H |
| VII-22 | H | H | H | H | H |
| VII-23 | 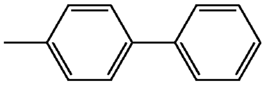 | H | H | H | H |
| VII-24 | 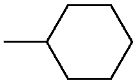 | H | H | H | H |
| VII-25 | 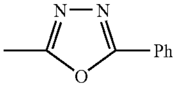 | H | H | H | H |
| VII-26 | 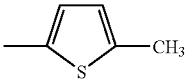 | H | H | H | H |
| VII-27 | 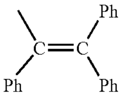 | H | H | H | H |
| VII-28 | n-$C_4H_9$ | H | H | H | H |
| VII-29 | H | H | $OCH_3$ | H | H |
| VII-30 | H | | $R_{42}$ and $R_{43}$ together form a fused benzene rig | H | H |

-continued
| C87 | | | | | |
|---|---|---|---|---|---|
| VII-31 | 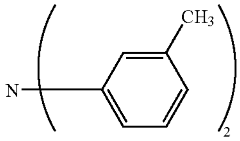 | H | H | H | H |
| VII-32 | 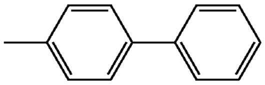 | H | H | H | H |
| VII-33 | H | H | 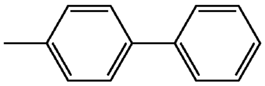 | H | H |
| VII-34 | 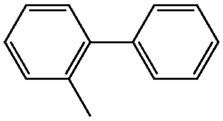 | H | H | H | H |
| VII-35 | H | H | 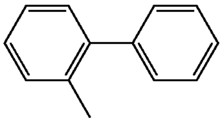 | H | H |
| VII-36 | H | H | Ph | H | Ph |
| VII-37 | H | H | Ph | Ph | H |
C88
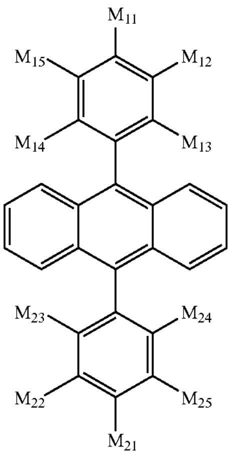
C89
| Compound No. | $M^{11} = M^{21}$ | $M^{12} = M^{22}$ | $M^{13} = M^{23}$ | $M^{14} = M^{24}$ | $M^{15} = M^{25}$ |
|---|---|---|---|---|---|
| VIII'-1 | H | H | H | H | H |
| VIII'-2 | $CH_3$ | H | H | H | H |
| VIII'-3 | H | $CH_3$ | H | H | H |
| VIII'-4 | H | H | $CH_3$ | H | H |
| VIII'-5 | Ph | H | $CH_3$ | $CH_3$ | H |

-continued
C89
| Compound No. | $M^{11} = M^{21}$ | $M^{12} = M^{22}$ | $M^{13} = M^{23}$ | $M^{14} = M^{24}$ | $M^{15} = M^{25}$ |
|---|---|---|---|---|---|
| VIII'-6 | H | Ph | H | H | H |
| VIII'-7 | H | H | Ph | H | H |
| VIII'-8 | H | H | Ph | Ph | H |
| VIII'-9 | H | H | Ph | H | Ph |
| VIII'-10 | H | H | 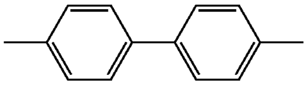 | H | H |
| VIII'-11 | 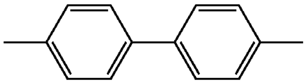 | H | H | H | H |
| VIII'-12 | H | H | 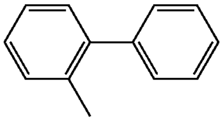 | H | H |
| VIII'-13 | 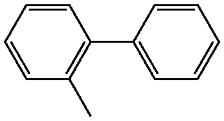 | H | H | H | H |
| VIII'-14 | $N(Ph)_2$ | H | H | H | H |
| VIII'-15 | $N(C_2H_5)_2$ | H | H | H | H |
| VIII'-16 | $OCH_3$ | H | H | H | H |
| VIII'-17 | Oph | H | H | H | H |
| VIII'-18 | 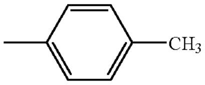 | H | H | H | H |
| VIII'-19 | 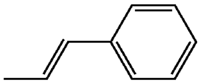 | H | H | H | H |
VIII- 1
c90
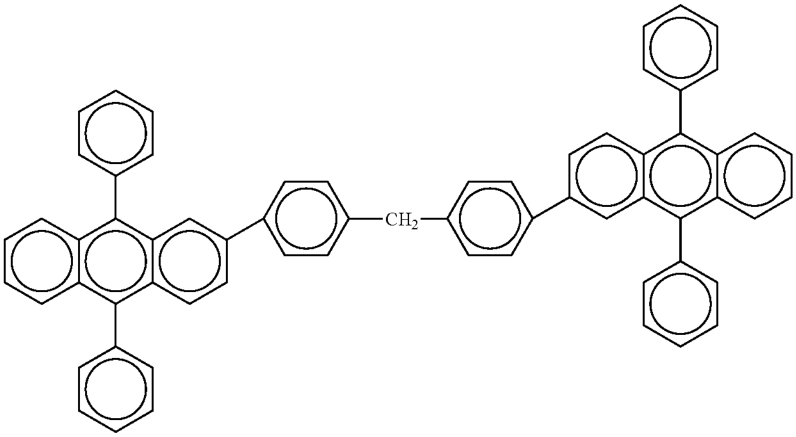

-continued
VIII- 2
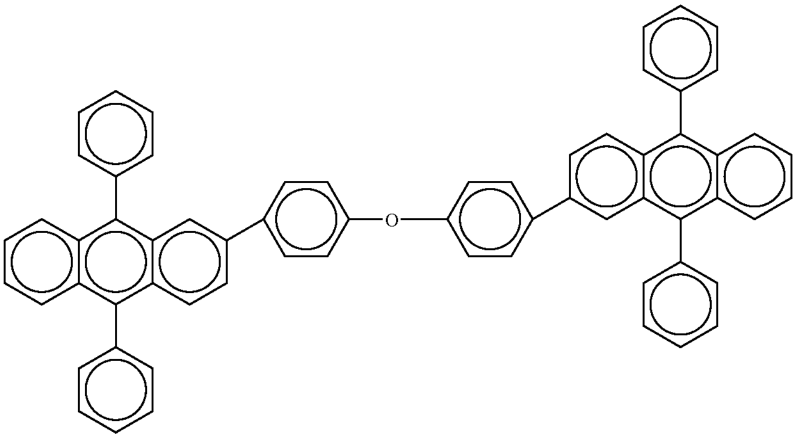
VIII- 3
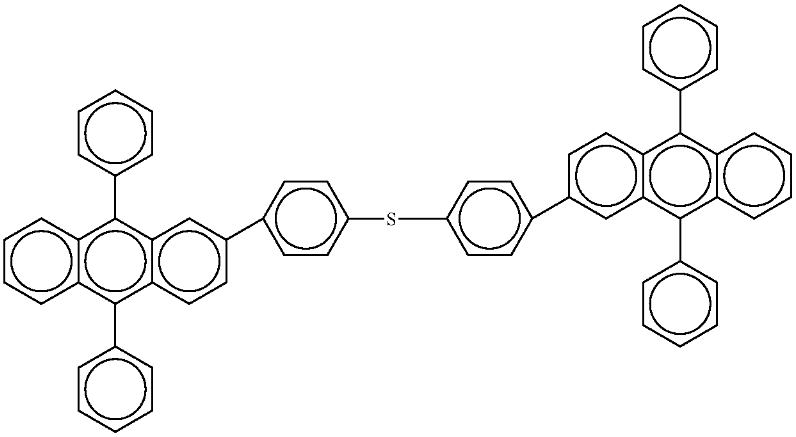
VIII- 4
c91
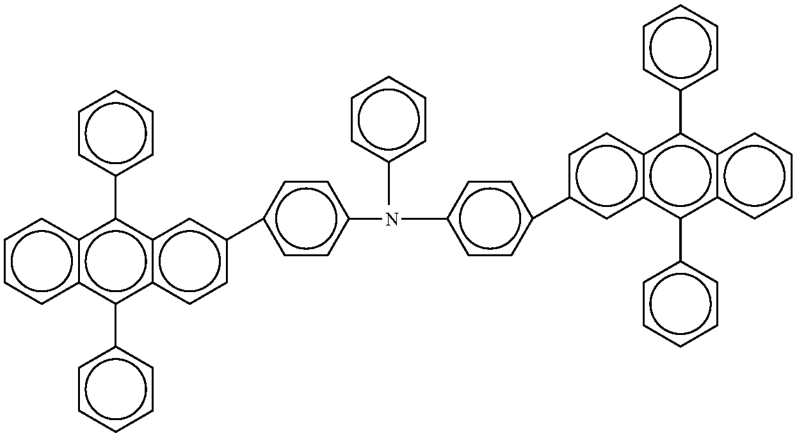

-continued
VIII- 5
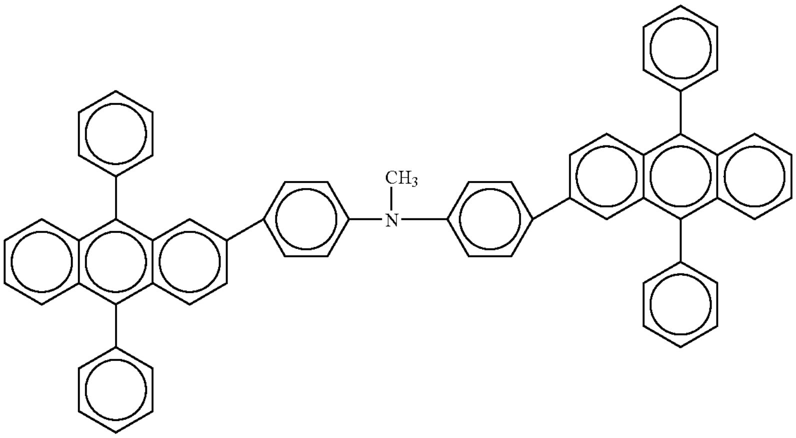
VIII- 6
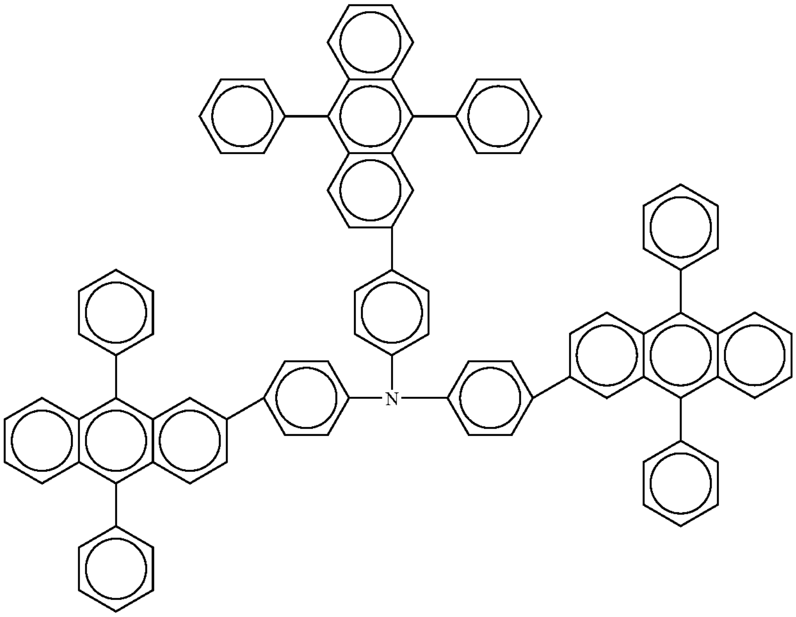
VIII- 7
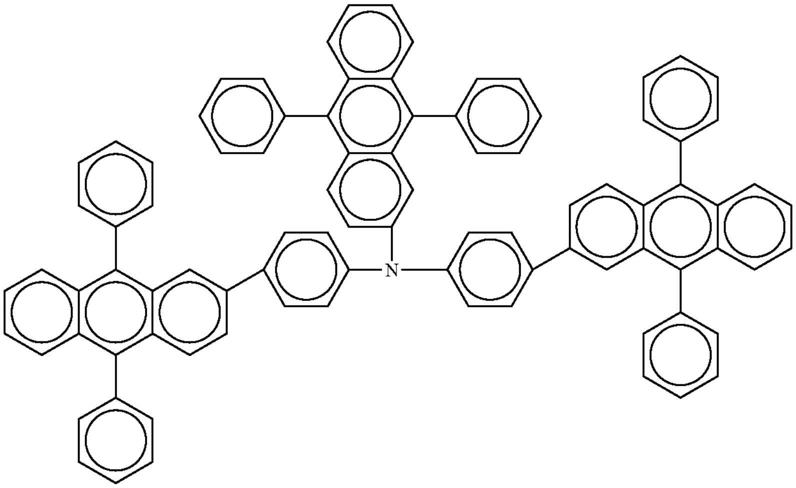

c92
IX- 1
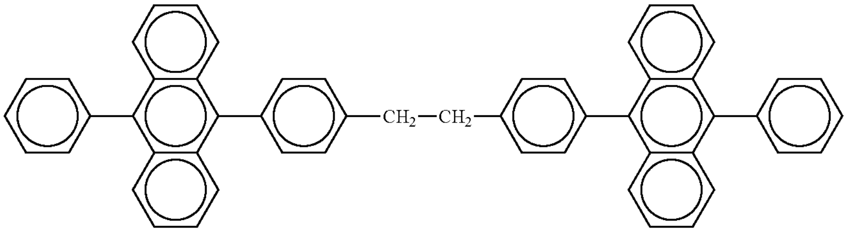
IX- 2
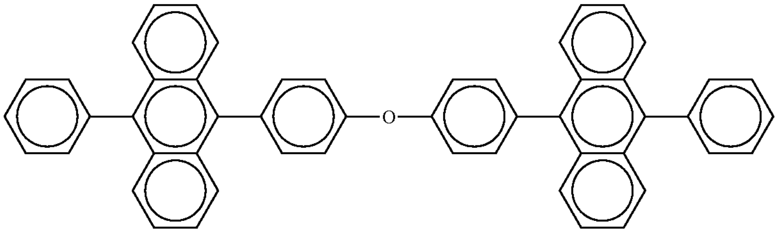
IX- 3
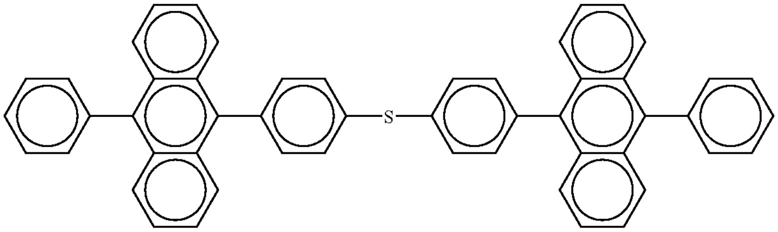
IX- 4
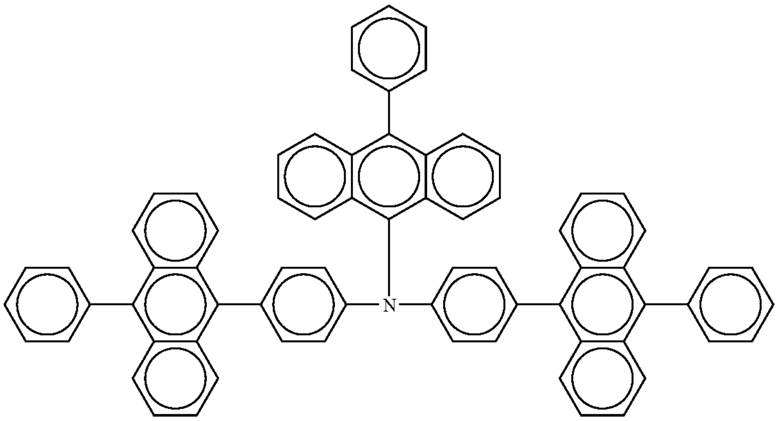
IX- 5
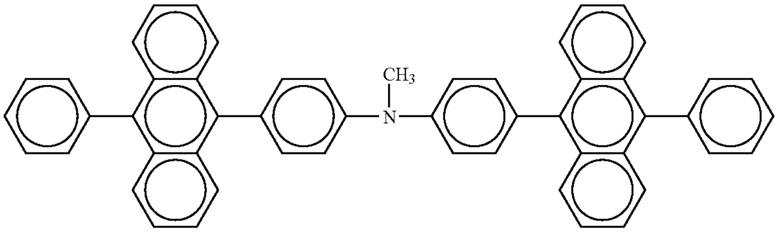

-continued

IX- 6

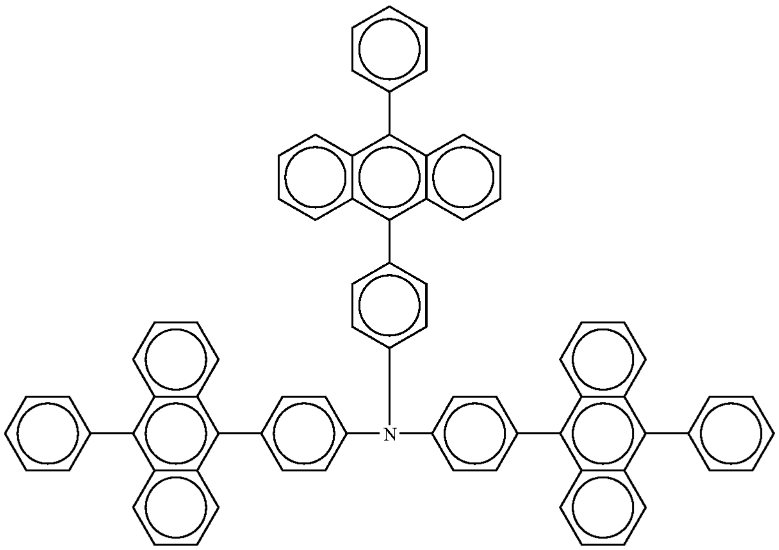

C93

IX- 7

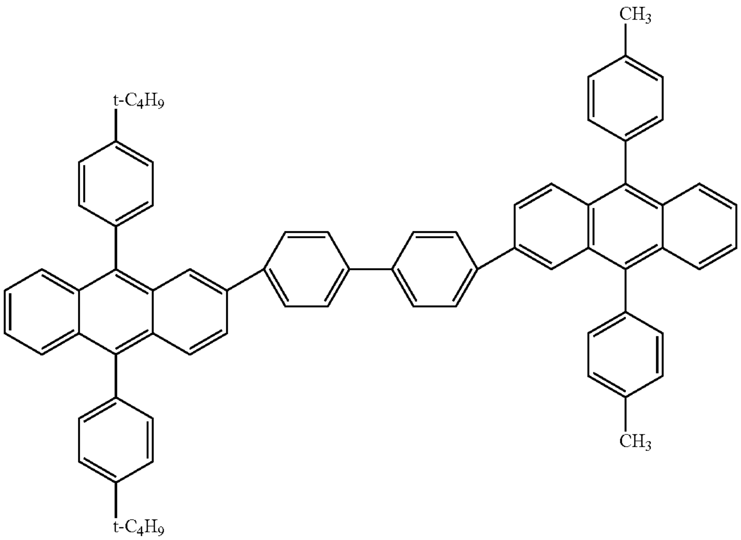

The phenylanthracene derivatives used herein can be prepared by (1) a process of coupling a halogenated diphenylanthracene compound with $Ni(cod)_2$ wherein cod represents 1,5-cyclo-octadiene, or cross-coupling a Grignard reagent of a dihalogenated aryl with a nickel complex such as $NiCl_2$(dppe) or $NiCl_2$(dppp) wherein dppe represents diphenylphosphinoethane and dppp represents diphenylphosphinopropane or (2) a cross-coupling process involving reacting anthraquinone, benzoquinone, phenylanthrone or bianthrone with a Grignard reagent of aryl or a lithiated aryl followed by reduction.

These compounds can be identified by elemental analysis, mass analysis, IR spectroscopy, $^1H$ and $^{13}C$ nuclear magnetic resonance (NMR) spectroscopy, etc.

In general, the phenylanthracene derivatives have a molecular weight of about 400 to about 2,000, preferably about 400 to about 1,000, a high melting point of about 200 to about 500° C., and a high glass transition temperature (Tg) of about 80 to about 250° C., preferably about 100 to 250° C., more preferably about 130 to 250° C., especially about 150 to 250° C. By conventional vacuum deposition or the like, they form a transparent, smooth film of quality which maintains a stable amorphous state even above room temperature and over a long period of time.

Since the phenylanthracene derivatives are relatively neutral compounds, better results are obtained on use of them in a light emitting layer. A freedom of design of the recombination/light emitting region is available by controlling the film thickness in consideration of the carrier mobility and carrier density (which is dependent on ionization potential and electron affinity) of the light emitting layer, hole injecting and transporting layer, and electron injecting and transporting layer to be combined. This enables free design of luminous color, control of the luminance and spectrum of light emission by the interference of the electrodes, and control of the space distribution of light emission.

Organic EL Device

One exemplary construction of the organic EL light emitting device fabricated using the inventive compounds has on a substrate, a hole injecting electrode, a hole injecting and transporting layer, a light emitting and electron injecting and transporting layer, and an electron injecting electrode in the described order. If desired, an auxiliary electrode and a sealing layer are provided on the electron injecting electrode.

The organic EL device of the invention is not limited to the above exemplary construction and may have various other constructions. In another exemplary construction, the light emitting layer is provided singly and an electron injecting and transporting layer is interposed between the light emitting layer and the electron injecting electrode. Also, the light emitting layer may be mixed with the hole injecting and transporting layer, if desired.

The thicknesses of the light emitting layer, hole injecting and transporting layer, and electron injecting and transporting layer are not critical and vary with a particular formation technique. Usually a single layer is about 5 to 500 nm thick, especially about 10 to 300 nm thick.

The thicknesses of the hole injecting and transporting layer and electron injecting and transporting layer are equal to or range from 1/10 to 10 times the thickness of the light emitting layer although they depend on the design of a recombination/light emitting region. When the electron or hole injecting and transporting layer is divided into an injecting layer and a transporting layer, preferably the injecting layer is at least 1 nm thick and the transporting layer is at least 1 nm thick. The upper limit of thickness is generally about 500 nm for the injecting layer and about 500 nm for the transporting layer. The same applies when two injecting and transporting layers are provided.

The hole injecting and transporting layer has functions of facilitating injection of holes from the hole injecting electrode, transporting them stably, and blocking electrons. The electron injecting and transporting layer has functions of facilitating injection of electrons from the electron injecting electrode, transporting them stably, and blocking holes. These layers are effective for increasing the number of holes and electrons injected into the light emitting layer and confining holes and electrons therein for optimizing the recombination region to improve light emission efficiency.

In the hole injecting and transporting layer, aside from the inventive compounds, there may be used various organic compounds as described, for example, in JP-A 63-295695, 2-191694, 3-792, 5-234681, 5-239455, 5-299174, 7-126225, 7-126226, and 8-100172, and EPO 650955A1. Exemplary are tetraarylbenzidine compounds (triaryldiamines or triphenyldiamines: TPD), aromatic tertiary amines, hydrazone derivatives, carbazole derivatives, triazole derivatives, imidazole derivatives, oxadiazole derivatives having an amino group, and polythiophenes. Two or more of these compounds may be used, and on such combined use, they may be formed as separate layers or mixed.

Where the hole injecting and transporting layer is formed separately as a hole injecting layer and a hole transporting layer, two or more compounds are selected in a proper combination from the compounds commonly used in hole injecting and transporting layers. In this regard, it is preferred to laminate layers in such an order that a layer of a compound having a lower ionization potential may be disposed adjacent the hole injecting electrode (ITO). It is also preferred to use a compound having good thin film forming ability at the hole injecting electrode surface. The order of lamination also applies where a plurality of hole injecting and transporting layers are provided. Such an order of lamination is effective for lowering the drive voltage and preventing current leakage and the development and growth of dark spots. Since evaporation is utilized in the manufacture of devices, films as thin as about 1 to 10 nm can be formed uniform and pinhole-free, which restrains any change in color tone of light emission and a drop of efficiency by re-absorption even if a compound having a low ionization potential and absorption in the visible range is used in the hole injecting layer. Like the light emitting layer, the hole injecting and transporting layer may be formed by evaporating the above-mentioned compounds.

In the electron injecting and transporting layer, aside from the inventive compounds, there may be used quinoline derivatives including organic metal complexes having 8-quinolinol or a derivative thereof as a ligand such as tris(8-quinolinolato)aluminum (Alq3), oxadiazole derivatives, perylene derivatives, nitrogen-containing heterocyclic aromatics such as pyridine derivatives, pyrimidine derivatives, quinoxaline derivatives and phenanthroline derivatives, diphenylquinone derivatives, and nitro-substituted fluorene derivatives. The electron injecting and transporting layer can also serve as the light emitting layer, and in such a case, the light emitting layer according to the invention is preferably employed. Like the light emitting layer, the electron injecting and transporting layer may be formed by evaporation or the like.

Where the electron injecting and transporting layer is formed separately as an electron injecting layer and an electron transporting layer, two or more compounds are selected in a proper combination from the compounds commonly used in electron injecting and transporting layers. In this regard, it is preferred to stack layers in such an order that a layer of a compound having a greater electron affinity may be disposed adjacent the electron injecting electrode. The order of stacking also applies where a plurality of electron injecting and transporting layers are provided.

In forming the hole injecting and transporting layer, the light emitting layer, and the electron injecting and transporting layer, vacuum evaporation is preferably used because homogeneous thin films are available. By utilizing vacuum evaporation, there is obtained a homogeneous thin film which is amorphous or has a crystal grain size of up to 0.1 μm. If the grain size is more than 0.1 μm, uneven light emission would take place and the drive voltage of the device must be increased with a substantial drop of hole injection efficiency.

The conditions for vacuum evaporation are not critical although a vacuum of $10^{-4}$ Pa or lower and a deposition rate of about 0.01 to 1 nm/sec are preferred. It is preferred to successively form layers in vacuum because the successive formation in vacuum can avoid adsorption of impurities on the interface between the layers, thus ensuring better performance. Also, the drive voltage of a device can be reduced and the development and growth of dark spots be restrained.

In the embodiment wherein the respective layers are formed by vacuum evaporation, where it is desired for a single layer to contain two or more compounds, preferably boats having the compounds received therein are individually temperature controlled to achieve co-deposition.

The electron injecting electrode is preferably made of metals, alloys or intermetallic compounds having a work function of up to 4 eV. With a work function of more than 4 eV, the electron injecting efficiency lowers and consequently, the light emission efficiency lowers. Examples of the metal having a work function of up to 4 eV of which the electron injecting electrode film is constructed include alkali metals such as Li, Na and K, alkaline earth metals such as Mg, Ca, Sr and Ba, rare earth metals such as La and Ce, and Al, In, Ag, Sn, Zn, and Zr. Examples of the film-forming alloy having a work function of up to 4 eV include Ag—Mg (Ag: 0.1 to 50 at %), Al—Li (Li: 0.01 to 12 at %), In—Mg (Mg: 50 to 80 at %), and Al—Ca (Ca: 0.01 to 20 at %). These materials may be present alone or in combination of two or more. Where two or more materials are combined, their mixing ratio is arbitrary. It is also acceptable that an oxide or halide of an alkali metal, alkaline earth metal or rare earth metal is thinly deposited and a supporting electrode (auxiliary electrode or wiring electrode) of aluminum etc. is used.

The electron injecting electrode may be formed by evaporation or sputtering.

The electron injecting electrode may have at least a sufficient thickness to effect electron injection, for example, a thickness of at least 0.1 nm. Although the upper limit is not critical, the electrode thickness is typically about 0.1 to about 500 nm.

The hole injecting electrode is preferably formed of such a material to such a thickness that the electrode may have a transmittance of at least 80% of emitted light. Illustratively, oxide transparent conductive thin films are preferred. For example, materials based on tin-doped indium oxide (ITO), zinc-doped indium oxide (IZO), indium oxide ($In_2O_3$), tin oxide ($SnO_2$) or zinc oxide (ZnO) are preferable. These oxides may deviate somewhat from their stoichiometry. An appropriate proportion of $SnO_2$ mixed with $In_2O_3$ is 1 to 20%, more preferably 5 to 12% by weight. An appropriate proportion of $ZnO_2$ mixed with $In_2O_3$ is 12 to 32% by weight.

The hole injecting electrode should preferably have a light transmittance of at least 80%, especially at least 90% in the light emission band, typically from 350 to 800 nm, and especially at each light emission. Since the emitted light is generally taken out through the hole injecting electrode, with a lower transmittance, the light emitted by the light emitting layer would be attenuated through the electrode, failing to provide a luminance necessary as a light emitting device. It is noted that only the side from which the emitted light exits has a transmittance of at least 80%.

The hole injecting electrode has at least a sufficient thickness to effect hole injection, preferably a thickness of 50 to 500 nm, especially 50 to 300 nm. Although the upper limit of the electrode thickness is not critical, a too thick electrode would have the risk of separation. Too thin an electrode would have problems with respect to film strength during fabrication, hole transporting ability, and resistance value.

In depositing the hole injecting electrode, a sputtering process is preferred. The sputtering process may be a high-frequency sputtering process using an RF power supply although a DC sputtering process is preferably used when the ease of control of physical properties of the hole injecting electrode being deposited and the flatness of the deposited film are taken into account.

A protective film may be formed if necessary. The protective film may be formed using an inorganic material such as $SiO_x$ or an organic material such as Teflon™. The protective film may be either transparent or opaque and have a thickness of about 50 to 1,200 nm. Apart from the reactive sputtering process mentioned above, the protective film may also be formed by an ordinary sputtering or evaporation process.

Further, a sealing layer is preferably provided on the device in order to prevent the organic layers and electrodes from oxidation. In order to prevent the ingress of moisture, the sealing layer is formed by attaching a sealing plate such as a glass plate to the substrate with an adhesive resin layer such as a commercially available low moisture absorption photo-curable adhesive, epoxy base adhesive, silicone base adhesive, or crosslinking ethylene-vinyl acetate copolymer adhesive sheet. Metal plates and plastic plates may also be used instead of the glass plate.

Transparent or translucent materials such as glass, quartz and resins are used as the substrate when the emitted light exits from the substrate side. The substrate may be provided with a color filter film, a fluorescent material-containing color conversion film or a dielectric reflecting film for controlling the color of light emission. In the case of the inversely stacked layer structure, the substrate may be either transparent or opaque. For the opaque substrate, ceramic and other materials may be used.

The color filter film used herein may be a color filter as used in liquid crystal displays and the like. The properties of a color filter may be adjusted in accordance with the light emission of the organic EL device so as to optimize the extraction efficiency and chromatic purity.

It is also preferred to use a color filter capable of cutting external light of short wavelength which is otherwise absorbed by the EL device materials and fluorescence conversion layer, because the light resistance and display contrast of the device are improved.

An optical thin film such as a dielectric multilayer film may be used instead of the color filter.

The organic EL device of the invention is constructed, as shown in FIG. 1, for example, to have on a substrate 1, a hole injecting electrode (or anode) 2, a hole injecting and transporting layer 3, a light emitting layer 4, an electron injecting and transporting layer 5, and an electron injecting electrode (or cathode) 6 in the described order. The order of lamination may be inverse to the above-described order. The hole injecting and transporting layer 3 and the electron injecting and transporting layer 5 may be omitted or either one of them may be a common layer to the light emitting layer 4. Each of these constituent layers may be adjusted optimum depending on the required function of the device.

The organic EL device of the invention is generally of the DC or pulse drive type while it can be of the AC drive type. The applied voltage is generally about 2 to 30 volts.

EXAMPLE

Examples of the present invention are given below together with Comparative Examples for further illustrating the invention.

Synthesis Example 1

Synthesis of 3-bromo-7,12-diphenylbenzo[k]fluoranthene 5 g (18.5 mmol) of diphenylisobenzofuran and 4.3 g (18.5 mmol) of 5-bromoacenaphthylene in toluene were agitated for 24 hours at the reflux temperature. The solvent was distilled off in vacuum, after which the residue was dissolved in 500 ml of acetic acid. An aqueous 40% hydrobromic acid solution, 50 $cm^3$, was added to the solution, which was heated at 80° C. for one hour. After cooling to room temperature, the precipitate was collected by filtration. This was purified by silica gel chromatography using a mixture of toluene and hexane as an extracting solvent, yielding 7 g of 3-bromo-7,12-diphenylbenzo[k]fluoranthene having a yellowish white color.

Synthesis Example 2

Synthesis of 7,12-diphenylbenzo[k]fluorantheno-3-boric acid

In 50 $cm^3$ of THF was dissolved 2.5 g of 3-bromo-7,12-diphenylbenzo[k]fluoranthene. The solution was cooled to −40° C., to which 5 $cm^3$ of a hexane solution of butyllithium (1.5 mol/l) was added, and reaction was run for 2 hours. To the solution, 1.5 g of triethyl borate was added, and reaction was run for one hour. After returning to room temperature, 15 $cm^3$ of aqueous 5N hydrochloric acid was added to the reaction solution, which was neutralized with sodium bicarbonate. After the THF was distilled off, the solids were collected by filtration. The solids were washed with distilled water and purified by reprecipitation, yielding 2 g of the boric acid.

Synthesis Example 3

Synthesis of Illustrative Compound A-2

In 50 $cm^3$ of dimethoxyethane were dissolved 2 g (4.5 mmol) of the boric acid prepared above and 0.33 g (1.4 mmol) of p-dibromobenzene. The solution was heated at 80° C., to which 50 $cm^3$ of distilled water and 10 g of sodium carbonate were admitted. Finally, 0.2 g of tetrakistriphenylphosphine palladium (0) was admitted to the solution.

After 3 hours, the precipitated end compound was recovered. It was purified by silica gel chromatography, obtaining 1 g of yellowish white crystals.

The compound thus obtained was identified by mass spectroscopy, infrared absorption spectroscopy and NMR.

Figure 2:
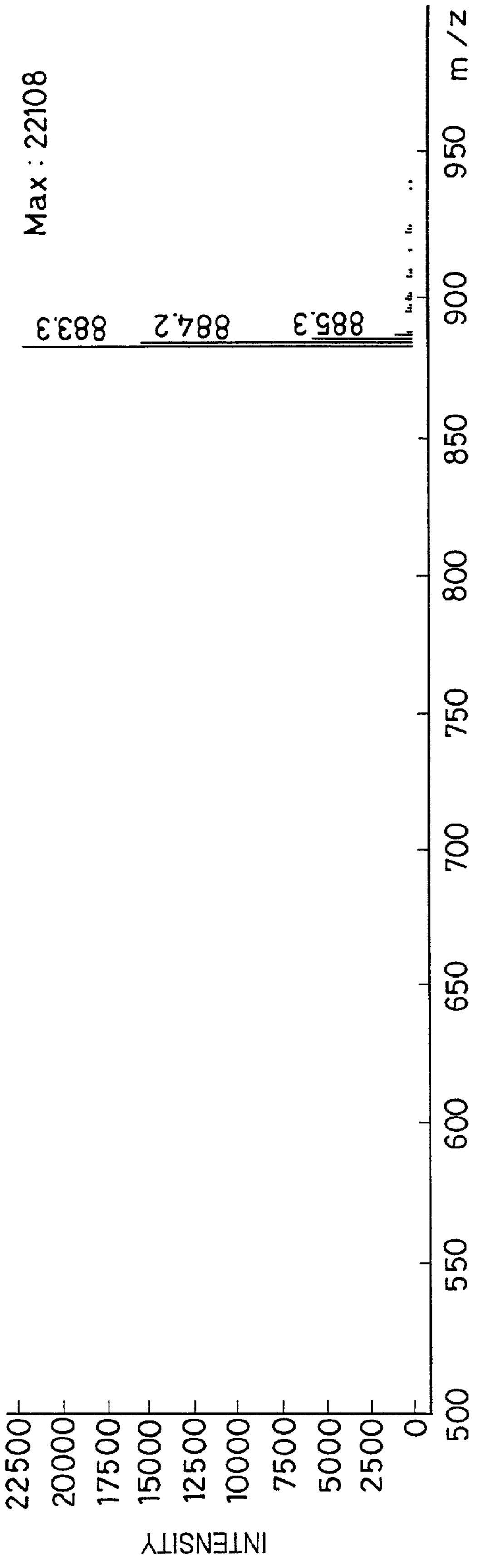
FIG. 2 is a diagram of mass spectrum.

Mass spectrum m/e=883 (M+1)+FIG. 2

Figure 3:
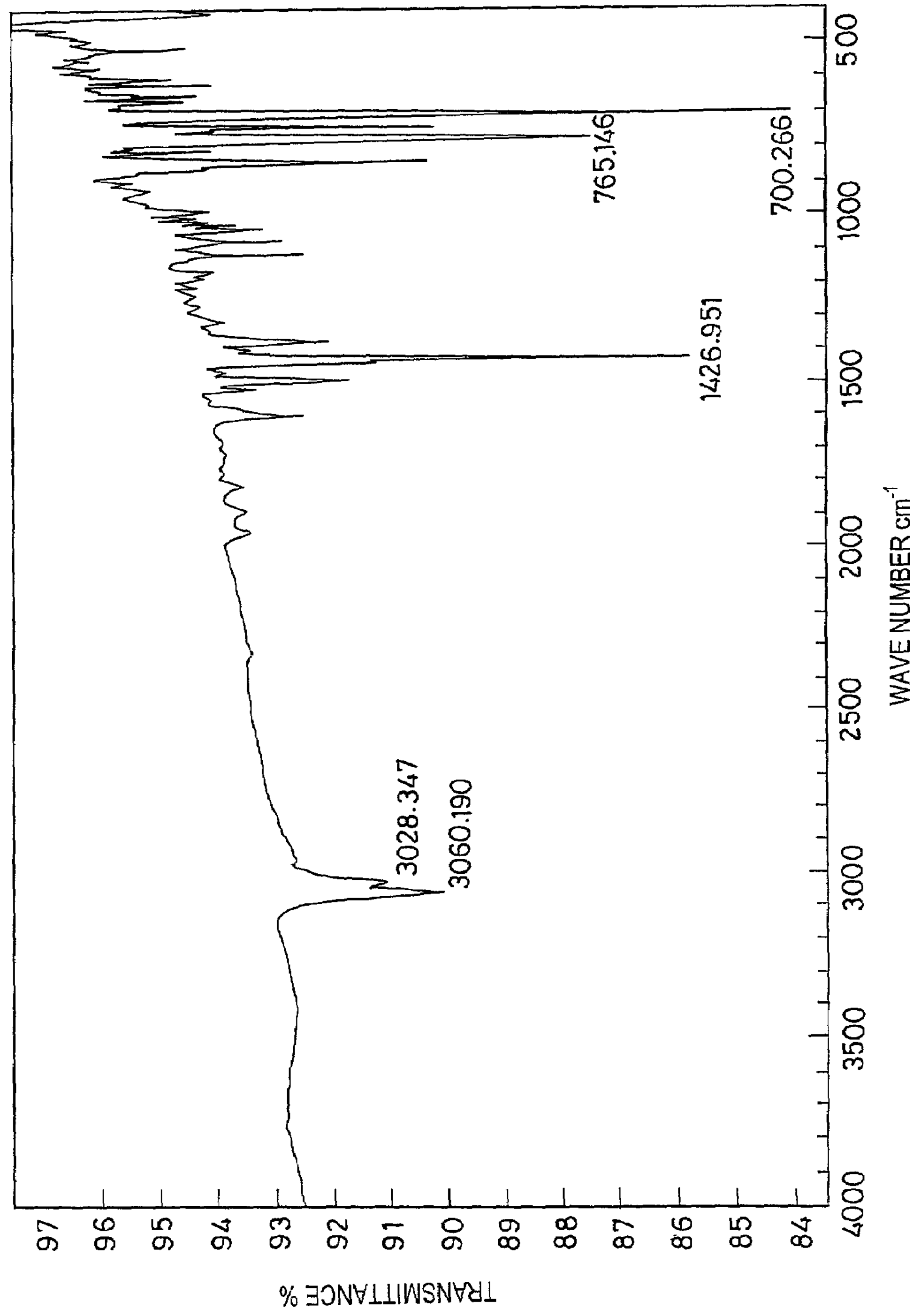
FIG. 3 is a diagram of infrared absorption spectrum.
Figure 4:
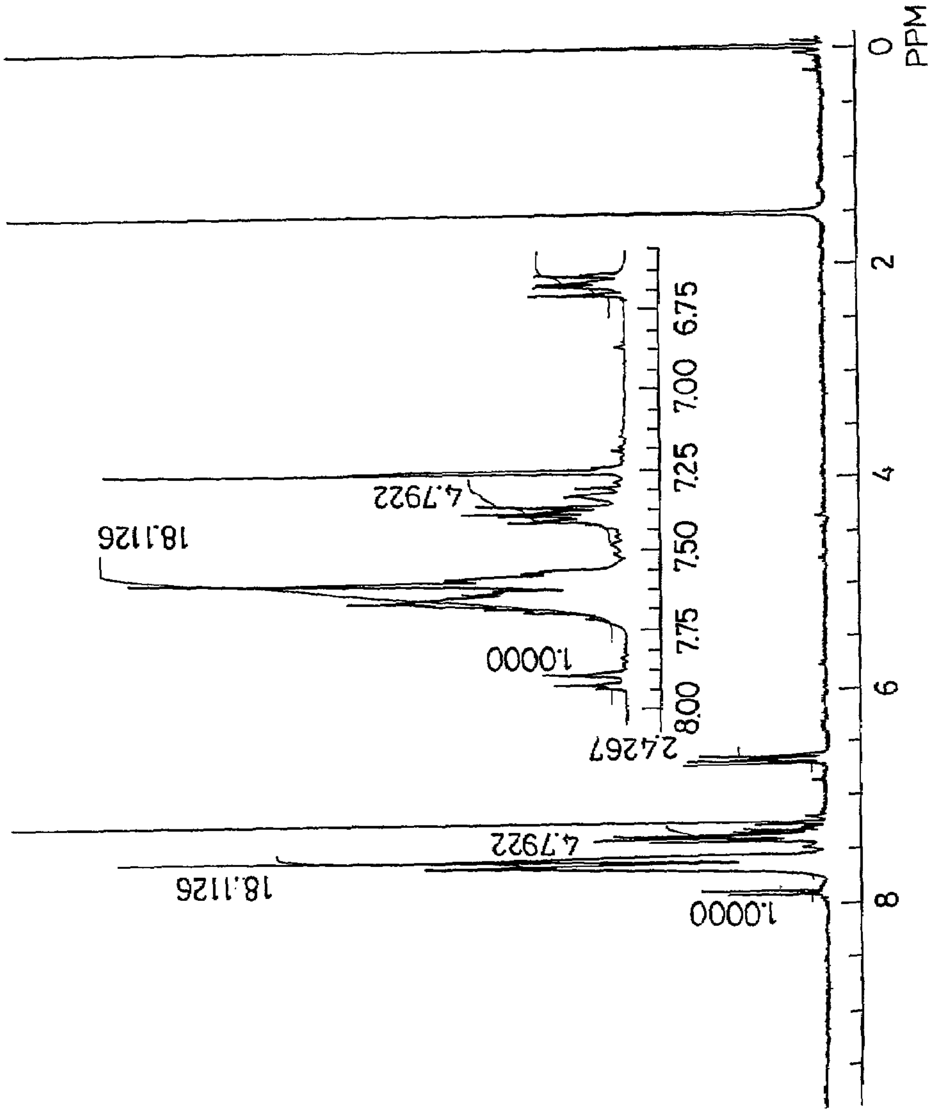
FIG. 4 is a diagram of NMR spectrum.

IR absorption spectrum FIG. 3

NMR FIG. 4

Glass transition temperature (Tg) 251° C.

Synthesis Example 4

Synthesis of Illustrative Compound V-2

In 50 $cm^3$ of dimethoxyethane were dissolved 2 g (4.5 mmol) of the boric acid prepared above and 0.56 g (1.4 mmol) of bis-p-dibromotriphenylamine. The solution was heated at 80° C., to which 50 $cm^3$ of distilled water and 10 g of sodium carbonate were admitted. Finally, 0.2 g of tetrakistriphenylphosphine palladium (0) was admitted to the solution.

After 3 hours, the precipitated end compound was recovered. It was purified by silica gel chromatography, obtaining 1 g of yellow crystals.

The compound thus obtained was identified by mass spectroscopy, infrared absorption spectroscopy and NMR.

Mass spectrum m/e=1050 (M+1)+

Synthesis of Illustrative Compound Z-2

In 50 $cm^3$ of xylene were dissolved 2 g (4.1 mmol) of 3-bromo-7,12-diphenylbenzo[k]fluoranthene synthesized above and 0.13 g (1.4 mmol) of aniline. To the solution were added 0.2 g of trisdibenzylideneacetone palladium (0) and 0.5 $cm^3$ of tri-t-butylphosphine. Reaction was run at 130° C. for 12 hours.

The precipitated end compound was recovered and purified by silica gel chromatography, obtaining 1 g of yellow crystals.

The compound thus obtained was identified by mass spectroscopy, infrared absorption spectroscopy and NMR.

Mass spectrum m/e=898 (M+1)+

Example 1

On a glass substrate, a transparent ITO electrode thin film was deposited to a thickness of 100 nm by RF sputtering and patterned. The glass substrate having the transparent ITO electrode was subjected to ultrasonic washing with neutral detergent, acetone, and ethanol, pulled up from boiling ethanol, and dried. The transparent electrode surface was further cleaned with $UV/O_3$. Thereafter, the substrate was secured by a holder in a vacuum evaporation chamber, which was evacuated to a vacuum of $1\times10^{-4}$ Pa or lower.

With the vacuum kept, N,N'-diphenyl-N,N'-bis[N-(4-methylphenyl)-N-phenyl-(4-aminophenyl)]-1,1'-biphenyl-4,4'-diamine of the structure shown below was evaporated at a deposition rate of 0.1 nm/sec. to a thickness of 100 nm, forming a hole injecting layer.

C94

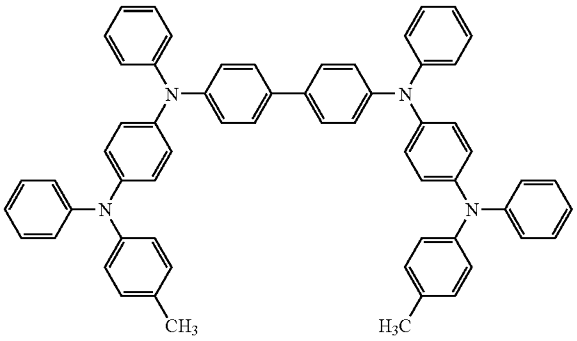

Then, N,N,N',N'-tetrakis(m-biphenyl)-1,1'-biphenyl-4,4'-diamine of the structure shown below was evaporated at a deposition rate of 0.1 nm/sec to a thickness of 10 nm, forming a hole transporting layer.

C95

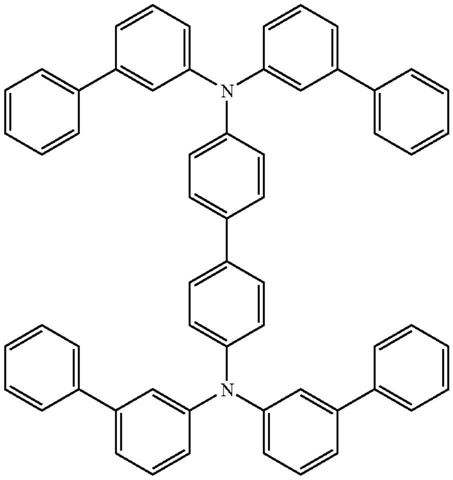

With the vacuum kept, the anthracene base host material and the inventive compound A-2 as the dopant, both of the structures shown below, were evaporated in a weight ratio of 98:2 and at an overall deposition rate of 0.1 nm/sec to a thickness of 40 nm, forming a light emitting layer.

C96

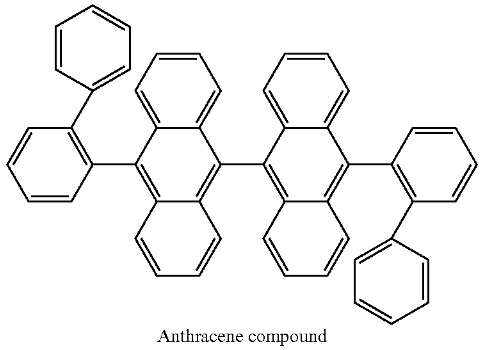

Anthracene compound

Inventive compound A-2

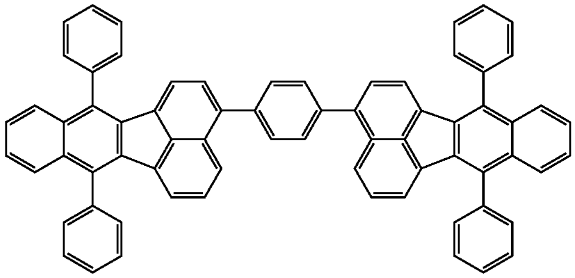

Next, with the vacuum kept, tris(8-hydroxyquinoline)-aluminum (Alq3) was evaporated at a deposition rate of 0.1 nm/sec to a thickness of 15 nm, forming an electron injecting and transporting layer.

Next, LiF was evaporated at a deposition rate of 0.1 nm/sec to a thickness of 0.5 nm, forming an electron injecting electrode. Aluminum was evaporated to a thickness of 100 nm to form a protective electrode. Final glass sealing completed an organic EL device.

Figure 5:
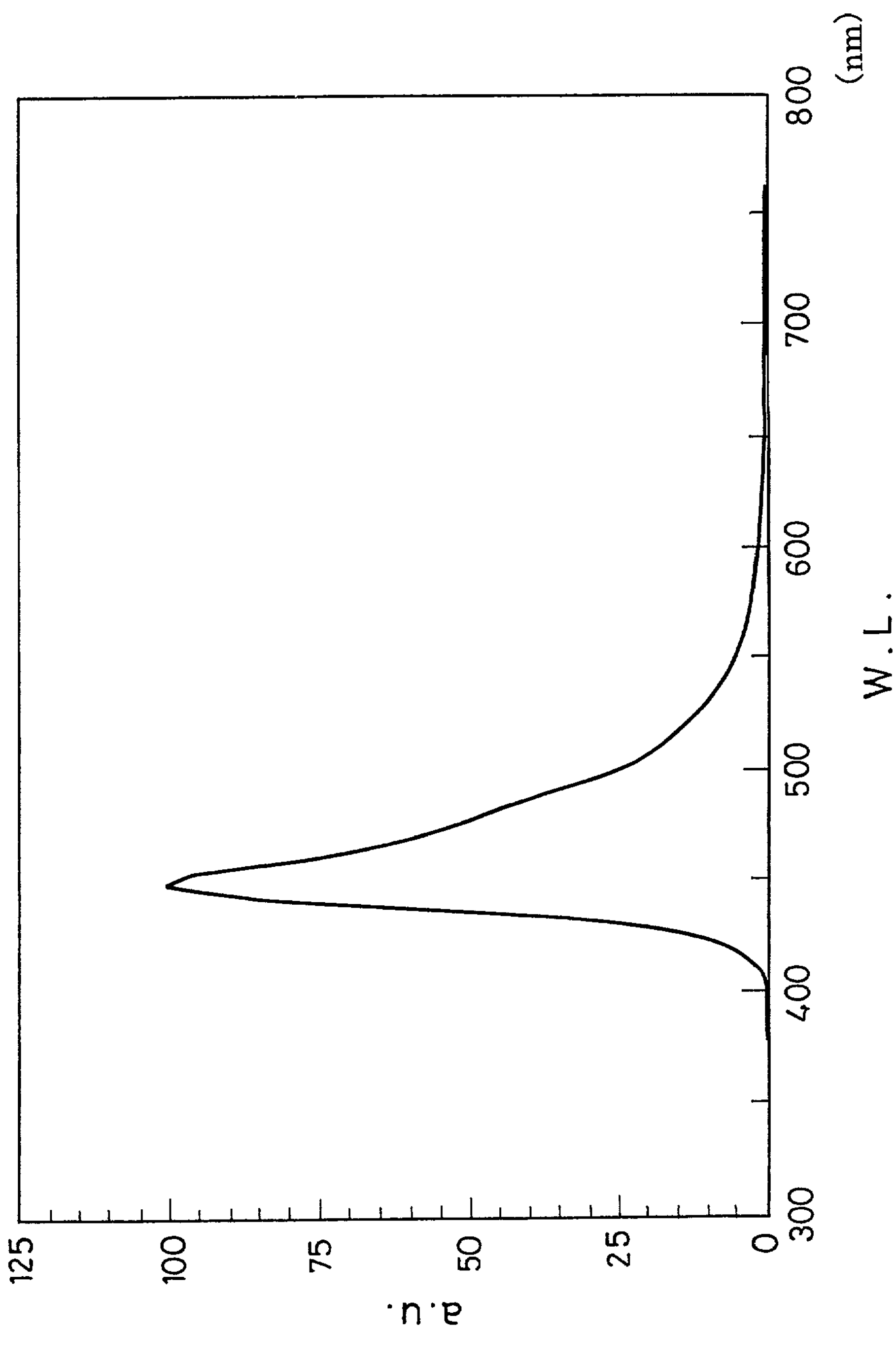
FIG. 5 is a diagram showing the light emission spectrum of the device of Example 1.

A DC voltage was applied across the organic EL device. Initially, the device was found to produce light emission to a luminance of at least 730 cd/$m^2$ when operated at a current density of 10 mA/$cm^2$ and a drive voltage of 8.6 volts. At this point, the peak wavelength was 450 nm and the chromaticity coordinates (x, y) were (0.15, 0.11). When the device was continuously driven by conducting a constant current of 10 mA/$cm^2$, it exhibited a luminance half-life period of at least 500 hours from the initial luminance of at least 730 cd/$m^2$. Therefore, the luminance (cd) multiplied by the half-life period (h) was 365,000. The spectrum of light emission is shown in FIG. 5.

Example 2

In Example 1, N,N'-diphenyl-N,N'-bis[N-(4-methylphenyl)-N-phenyl-(4-aminophenyl)]-1,1'-biphenyl-4,4'-diamine was evaporated at a deposition rate of 0.1 nm/sec. to a thickness of 50 nm, forming a hole injecting layer.

Then, N,N,N',N'-tetrakis(m-biphenyl)-1,1'-biphenyl-4,4'-diamine as the host material and the inventive compound A-2 as the dopant were evaporated in a weight ratio of 98:2 and at an overall deposition rate of 0.1 nm/sec to a thickness of 30 nm, forming a hole transporting and light emitting layer.

Next, with the vacuum kept, tris(8-hydroxyquinoline)-aluminum (Alq3) was evaporated at a deposition rate of 0.1 nm/sec to a thickness of 40 nm, forming an electron injecting and transporting layer.

Next, LiF was evaporated at a deposition rate of 0.1 nm/sec to a thickness of 0.3 nm, forming an electron injecting electrode. Aluminum was evaporated to a thickness of 200 nm to form a protective electrode. Final glass sealing completed an organic EL device.

A DC voltage was applied across the organic EL device. Initially, the device was found to produce light emission to a luminance of at least 780 cd/$m^2$ when operated at a current density of 10 mA/$cm^2$ and a drive voltage of 7.9 volts. At this point, the peak wavelength was 450 nm and the chromaticity coordinates (x, y) were (0.15, 0.11). When the device was continuously driven by conducting a constant current of 10 mA/$cm^2$, it exhibited a luminance half-life period of at least 400 hours from the initial luminance of at least 780 cd/$m^2$.

Example 3

In Example 1, N,N'-diphenyl-N,N'-bis[N-(4-methylphenyl)-N-phenyl-(4-aminophenyl)]-1,1'-biphenyl-4,4'-diamine was evaporated at a deposition rate of 0.1 nm/sec. to a thickness of 50 nm, forming a hole injecting layer.

Then, N,N,N',N'-tetrakis(m-biphenyl)-1,1'-biphenyl-4,4'-diamine was evaporated at a deposition rate of 0.1 nm/sec to a thickness of 20 nm, forming a hole transporting layer.

With the vacuum kept, the inventive compound A-2 of Example 1 as the host material and a naphthacene base compound of the structures shown below as the dopant were evaporated in a weight ratio of 98:2 and at an overall deposition rate of 0.1 nm/sec to a thickness of 40 nm, forming a light emitting layer.

C97

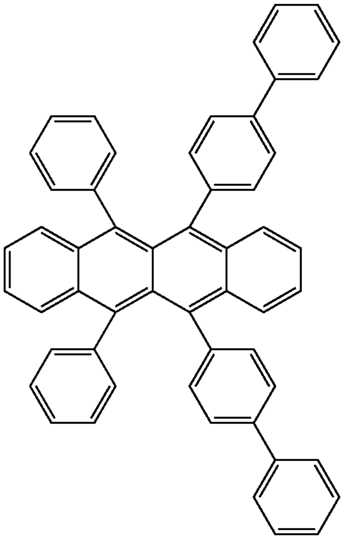

Next, with the vacuum kept, tris(8-hydroxyquinoline)-aluminum (Alq3) was evaporated at a deposition rate of 0.1 nm/sec to a thickness of 30 nm, forming an electron injecting and transporting layer.

Next, LiF was evaporated at a deposition rate of 0.1 nm/sec to a thickness of 0.3 nm, forming an electron injecting electrode. Aluminum was evaporated to a thickness of 150 nm to form a protective electrode. Final glass sealing completed an organic EL device.

A DC voltage was applied across the organic EL device. Initially, the device was found to produce light emission to a luminance of at least 900 cd/m$^2$ when operated at a current density of 10 mA/cm$^2$ and a drive voltage of 6.3 volts. At this point, the peak wavelength was 560 nm and the chromaticity coordinates (x, y) were (0.45, 0.55). When the device was continuously driven by conducting a constant current of 10 mA/cm$^2$, it exhibited a luminance half-life period of at least 3,000 hours from the initial luminance of at least 900 cd/m$^2$.

Example 4

An organic EL device was fabricated as in Example 3 except that the dopant used in the light emitting layer in Example 3 was replaced by a naphthacene base compound of the structure shown below.

C98

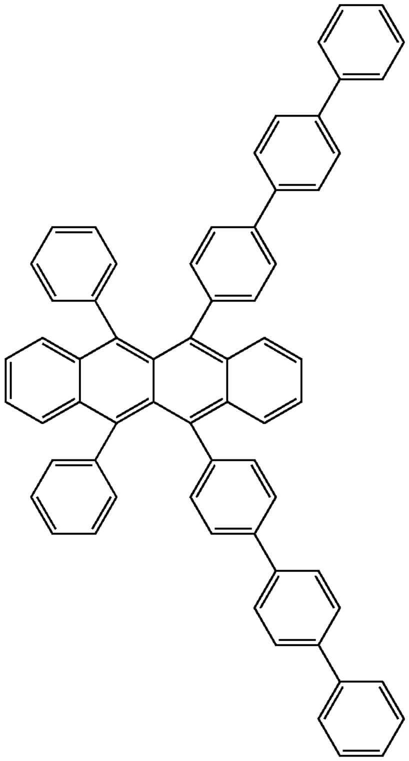

A DC voltage was applied across the organic EL device. Initially, the device was found to produce light emission to a luminance of at least 910 cd/m$^2$ when operated at a current density of 10 mA/cm$^2$ and a drive voltage of 6.3 volts. At this point, the peak wavelength was 560 nm and the chromaticity coordinates (x, y) were (0.45, 0.55). When the device was continuously driven by conducting a constant current of 10 mA/cm$^2$, it exhibited a luminance half-life period of at least 3,000 hours from the initial luminance of at least 910 cd/m$^2$.

Example 5

An organic EL device was fabricated as in Example 3 except that the dopant used in the light emitting layer in Example 3 was replaced by a compound of the structure shown below.

C99

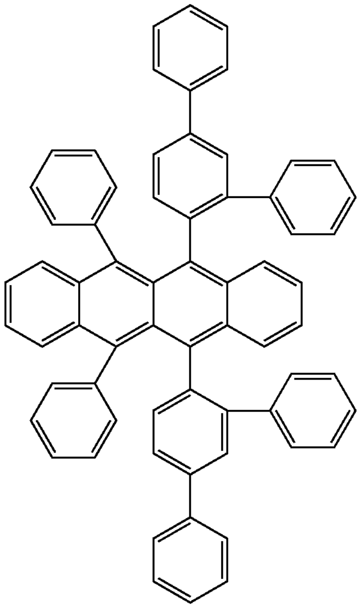

A DC voltage was applied across the organic EL device. Initially, the device was found to produce light emission to a luminance of at least 750 cd/m$^2$ when operated at a current density of 10 mA/cm$^2$ and a drive voltage of 6.5 volts. At this point, the peak wavelength was 580 nm and the chromaticity coordinates (x, y) were (0.52, 0.48). When the device was continuously driven by conducting a constant current of 10 mA/cm$^2$, it exhibited a luminance half-life period of at least 3,000 hours from the initial luminance of at least 750 cd/m$^2$.

Example 6

An organic EL device was fabricated as in Example 3 except that the dopant used in the light emitting layer in Example 3 was replaced by a compound of the structure shown below.

C100

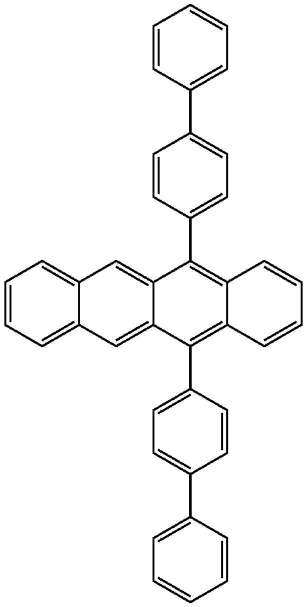

A DC voltage was applied across the organic EL device. Initially, the device was found to produce light emission to a luminance of at least 1100 cd/$m^2$ when operated at a current density of 10 mA/$cm^2$ and a drive voltage of 6.6 volts. At this point, the peak wavelength was 515 nm and the chromaticity coordinates (x, y) were (0.30, 0.65). When the device was continuously driven by conducting a constant current of 10 mA/$cm^2$, it exhibited a luminance half-life period of at least 3,000 hours from the initial luminance of at least 1100 cd/$m^2$.

Example 7

An organic EL device was fabricated as in Example 3 except that the dopant used in Example 3 was replaced by a compound of the structure shown below.

C101

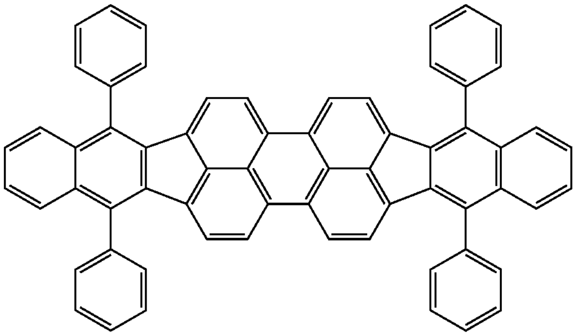

A DC voltage was applied across the organic EL device. Initially, the device was found to produce light emission to a luminance of at least 550 cd/$m^2$ when operated at a current density of 10 mA/$cm^2$ and a drive voltage of 6.5 volts. At this point, the peak wavelength was 610 nm and the chromaticity coordinates (x, y) were (0.65, 0.35). When the device was continuously driven by conducting a constant current of 10 mA/$cm^2$, it exhibited a luminance half-life period of at least 5,000 hours from the initial luminance of at least 550 cd/$m^2$.

Example 8

In Example 1, N,N'-diphenyl-N,N'-bis[N-(4-methylphenyl)-N-phenyl-(4-aminophenyl)]-1,1'-biphenyl-4,4'-diamine was evaporated at a deposition rate of 0.1 nm/sec. to a thickness of 50 nm, forming a hole injecting layer.

Then, N,N,N',N'-tetrakis(m-biphenyl)-1,1'-biphenyl-4,4'-diamine was evaporated at a deposition rate of 0.1 nm/sec to a thickness of 20 nm, forming a first hole transporting layer.

With the vacuum kept, the inventive compound A-2 of Example 1 was evaporated at a deposition rate of 0.1 nm/sec to a thickness of 10 nm, forming a second hole transporting layer.

Next, a compound of the following structure:

C102

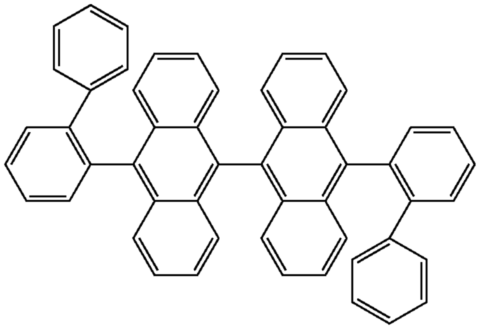

as the host material and a compound of the following structure:

C103

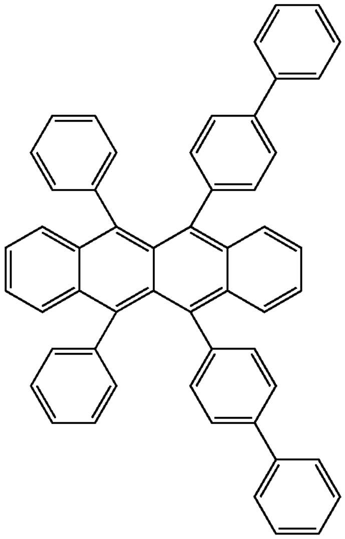

as the dopant were evaporated in a weight ratio of 98:2 and at an overall deposition rate of 0.1 nm/sec to a thickness of 40 nm, forming a light emitting layer.

Next, with the vacuum kept, tris(8-hydroxyquinoline)-aluminum (Alq3) was evaporated at a deposition rate of 0.1 nm/sec to a thickness of 30 nm, forming an electron injecting and transporting layer.

Next, LiF was evaporated at a deposition rate of 0.1 nm/sec to a thickness of 0.3 nm, forming an electron injecting electrode. Aluminum was evaporated to a thickness of 150 nm to form a protective electrode. Final glass sealing completed an organic EL device.

A DC voltage was applied across the organic EL device. Initially, the device was found to produce light emission to a luminance of at least 820 cd/$m^2$ when operated at a current density of 10 mA/$cm^2$ and a drive voltage of 6.0 volts. At this point, the peak wavelength was 556 nm and the chromaticity coordinates (x, y) were (0.45, 0.55).

Example 9

In Example 1, N,N'-diphenyl-N,N'-bis[N-(4-methylphenyl)-N-phenyl-(4-aminophenyl)]-1,1'-biphenyl-4,4'-diamine was evaporated at a deposition rate of 0.1 nm/sec. to a thickness of 90 nm, forming a hole injecting layer.

Then, N,N,N',N'-tetrakis(m-biphenyl)-1,1'-biphenyl-4,4'-diamine was evaporated at a deposition rate of 0.1 nm/sec to a thickness of 10 nm, forming a hole transporting layer.

With the vacuum kept, the inventive compound A-2 was evaporated at a deposition rate of 0.1 nm/sec to a thickness of 10 nm, forming a second hole transporting layer.

Next, the compound used in Example 8 as the host material and the inventive compound A-2 as the dopant were evaporated in a weight ratio of 98:2 and at an overall deposition rate of 0.1 nm/sec to a thickness of 40 nm, forming a light emitting layer.

Next, with the vacuum kept, tris(8-hydroxyquinoline)-aluminum (Alq3) was evaporated at a deposition rate of 0.1 nm/sec to a thickness of 15 nm, forming an electron injecting and transporting layer.

Next, LiF was evaporated at a deposition rate of 0.1 nm/sec to a thickness of 0.5 nm, forming an electron injecting electrode. Aluminum was evaporated to a thickness of 100 nm to form a protective electrode. Final glass sealing completed an organic EL device.

A DC voltage was applied across the organic EL device. Initially, the device was found to produce light emission to a luminance of at least 700 cd/$m^2$ when operated at a current density of 10 mA/$cm^2$ and a drive voltage of 8.0 volts. At this point, the peak wavelength was 450 nm and the chromaticity coordinates (x, y) were (0.15, 0.11). When the device was continuously driven by conducting a constant current of 10 mA/$cm^2$, it exhibited a luminance half-life period of at least 1,000 hours from the initial luminance of at least 700 cd/$m^2$.

Example 10

In Example 1, N,N'-diphenyl-N,N'-bis[N-(4-methylphenyl)-N-phenyl-(4-aminophenyl)]-1,1'-biphenyl-4,4'-diamine was evaporated at a deposition rate of 0.1 nm/sec. to a thickness of 10 nm, forming a hole injecting layer.

Then, N,N,N',N'-tetrakis(m-biphenyl)-1,1'-biphenyl-4,4'-diamine was evaporated at a deposition rate of 0.1 nm/sec to a thickness of 20 nm, forming a hole transporting layer.

Next, N,N,N',N'-tetrakis(m-biphenyl)-1,1-biphenyl-4,4'-diamine, the compound of Cx70 and the compound of Cx69 as the dopant were evaporated in a weight ratio of 49:49:2 and at an overall deposition rate of 0.1 nm/sec to a thickness of 15 nm, forming a first (red) light emitting layer.

Cx69

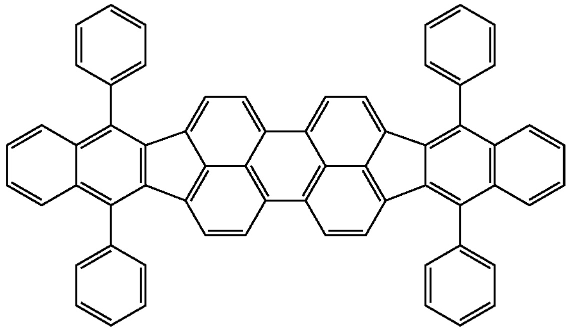

Cx70

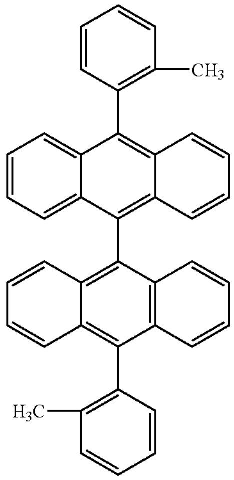

Next, N,N,N',N'-tetrakis(m-biphenyl)-1,1'-biphenyl-4,4'-diamine, the compound of Cx70 and the compound of Cx68 as the dopant were evaporated in a weight ratio of 49:49:2 and at an overall deposition rate of 0.1 nm/sec to a thickness of 20 nm, forming a second (green) light emitting layer.

Cx68

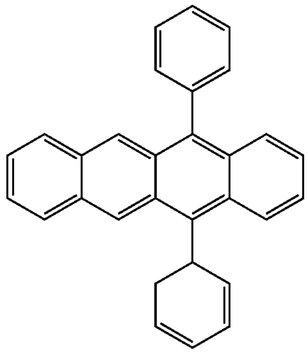

Next, N,N,N',N'-tetrakis(m-biphenyl)-1,1'-biphenyl-4,4'-diamine, the compound of Cx70, and the inventive compound A-2 as the dopant were evaporated in a weight ratio of 49:49:2 and at an overall deposition rate of 0.1 nm/sec to a thickness of 20 nm, forming a third (blue) light emitting layer.

Otherwise as in Example 1, an organic EL device was fabricated.

A DC voltage was applied across the organic EL device. Initially, the device was found to produce light emission to a luminance of at least 750 cd/$m^2$ when operated at a current density of 10 mA/$cm^2$ and a drive voltage of 8.5 volts. The overall color of light emission had chromaticity coordinates (x, y)=(0.30, 0.33), indicating a color reproduction substantially close to white.

Example 11

An organic EL device was fabricated as in Example 1 except that the dopant used in the light emitting layer in Example 1 was replaced by a compound of the structure (Type BBB-9) shown below.

c104

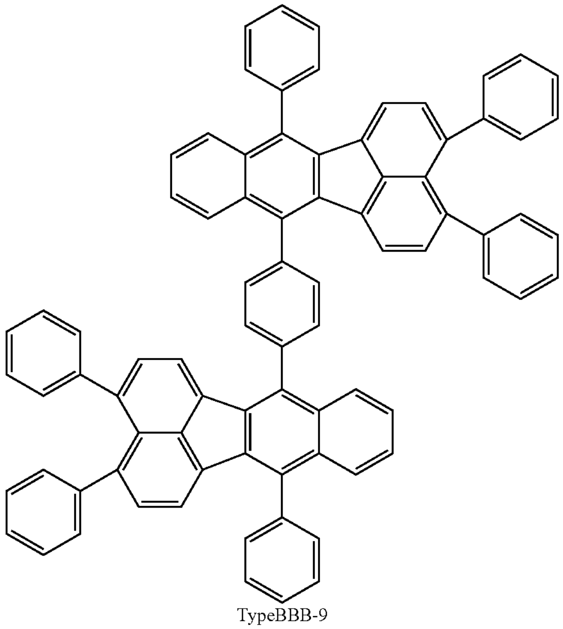

TypeBBB-9

A DC voltage was applied across the organic EL device. Initially, the device was found to produce light emission to a luminance of at least 800 cd/m$^2$ when operated at a current density of 10 mA/cm$^2$ and a drive voltage of 8.6 volts. At this point, the peak wavelength was 452 nm and the chromaticity coordinates (x, y) were (0.15, 0.11).

Figure 6:
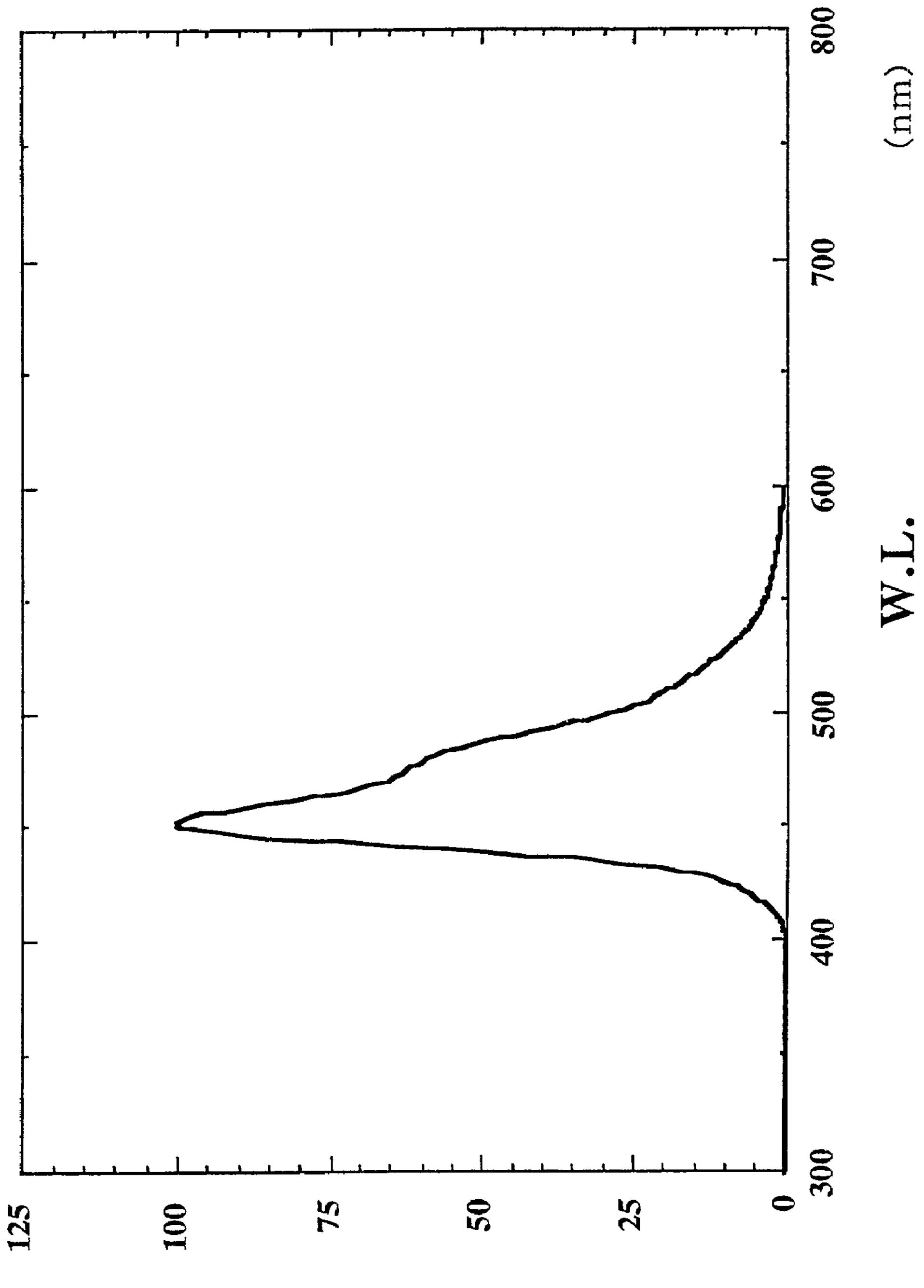
FIG. 6 is a diagram showing the light emission spectrum of the device of Example 11.

When the device was continuously driven by conducting a constant current of 10 mA/cm$^2$, it exhibited a luminance half-life period of at least 1,200 hours from the initial luminance of at least 800 cd/m$^2$. Therefore, the luminance (cd) multiplied by the half-life period (h) was 960,000. The spectrum of light emission is shown in FIG. 6.

Example 12

An organic EL device was fabricated as in Example 1 except that the dopant used in the light emitting layer in Example 1 was replaced by a compound of the structure (Type V-2) shown below.

c105

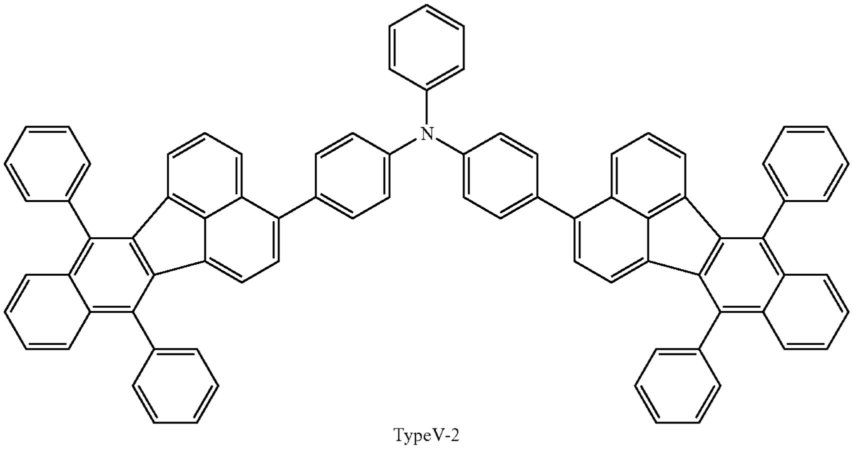

TypeV-2

A DC voltage was applied across the organic EL device. Initially, the device was found to produce light emission to a luminance of at least 900 cd/m$^2$ when operated at a current density of 10 mA/cm$^2$ and a drive voltage of 8.6 volts. At this point, the peak wavelength was 473 nm and the chromaticity coordinates (x, y) were (0.14, 0.27).

Figure 7:
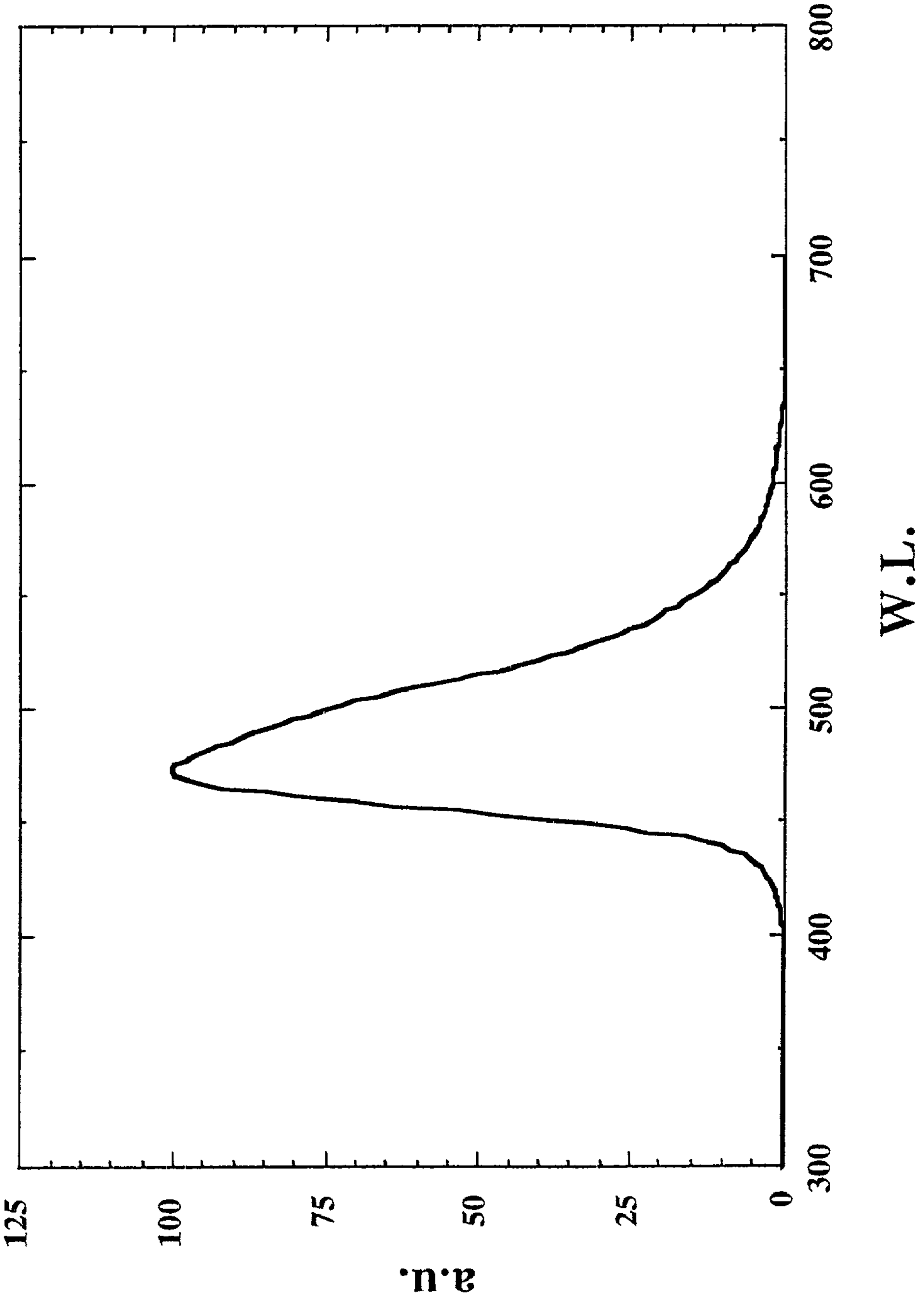
FIG. 7 is a diagram showing the light emission spectrum of the device of Example 12.

When the device was continuously driven by conducting a constant current of 50 mA/cm$^2$, it exhibited an initial luminance of at least 4500 cd/m$^2$ and a luminance half-life period of at least 500 hours. Therefore, the luminance (cd) multiplied by the half-life period (h) was 2,250,000. The spectrum of light emission is shown in FIG. 7.

Example 13

An organic EL device was fabricated as in Example 1 except that the dopant used in the light emitting layer in Example 1 was replaced by a compound of the structure (Type Z-2) shown below.

C106

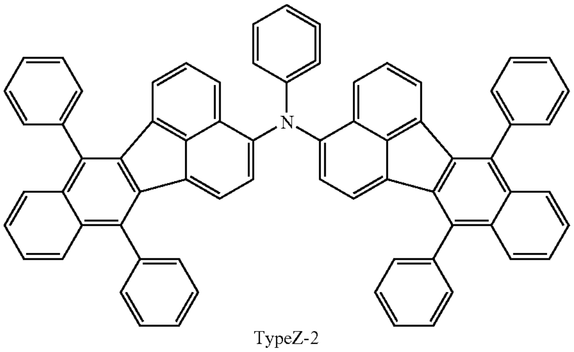

TypeZ-2

A DC voltage was applied across the organic EL device. Initially, the device was found to produce light emission to a luminance of at least 1100 cd/m$^2$ when operated at a current density of 10 $mA/cm^2$ and a drive voltage of 8.6 volts. At this point, the peak wavelength was 518 nm and the chromaticity coordinates (x, y) were (0.28, 0.61).

Figure 8:
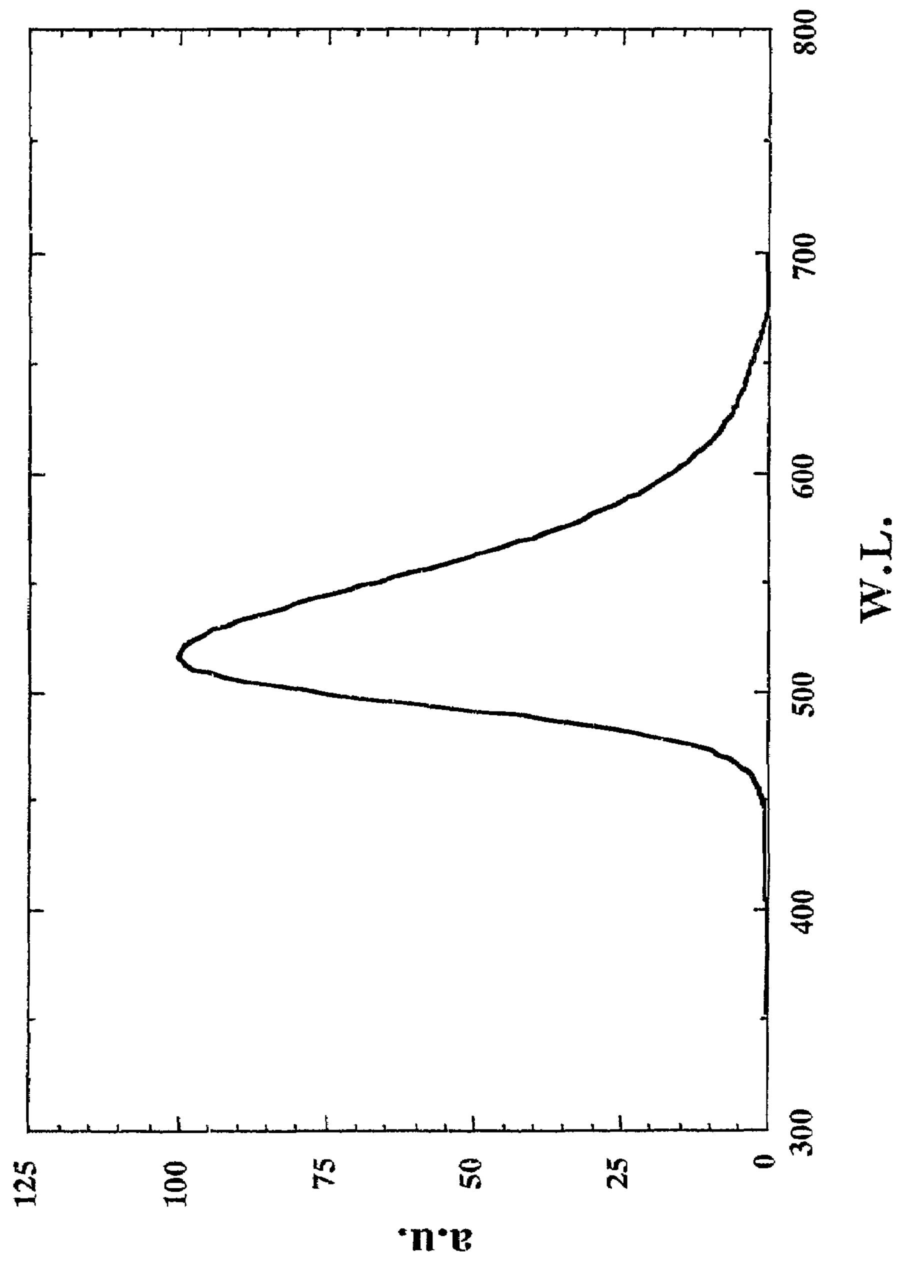
FIG. 8 is a diagram showing the light emission spectrum of the device of Example 13.

When the device was continuously driven by conducting a constant current of 50 $mA/cm^2$, it exhibited an initial luminance of at least 5500 $cd/m^2$ and a luminance half-life period of at least 500 hours. Therefore, the luminance (cd) multiplied by the half-life period (h) was 2,750,000. The spectrum of light emission is shown in FIG. 8.

Comparative Example 1

An organic EL device was fabricated as in Example 1 except that the light emitting layer was not doped with the dopant.

A DC voltage was applied across the organic EL device. Initially, the device was found to produce light emission to a luminance of up to 180 $cd/m^2$ when operated at a current density of 10 $mA/cm^2$ and a drive voltage of 6.5 volts. At this point, the peak wavelength was 440 nm and the chromaticity coordinates (x, y) were (0.16, 0.07). When the device was continuously driven by conducting a constant current of 10 $mA/cm^2$, it exhibited a luminance half-life period of up to 250 hours from the initial luminance of 180 $cd/m^2$. Therefore, the luminance (cd) multiplied by the half-life period (h) was 45,000. These data indicate that the device of Example 1 is able to emit light at a luminance at least 4 times greater than the device of Comparative Example 1 and has a life at least 8 times longer than the device of Comparative Example 1 at the same luminance.

Comparative Example 2

An organic EL device was fabricated as in Example 1 except that the dopant in the light emitting layer was replaced by a compound of the following structure.

C107

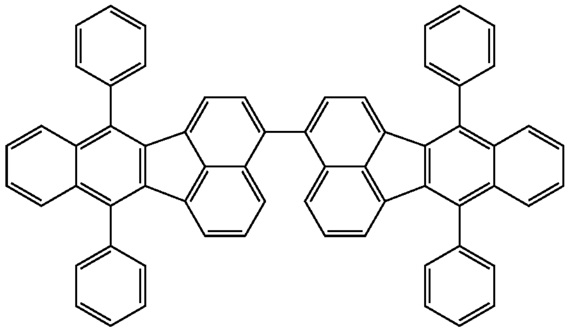

A DC voltage was applied across the organic EL device. Initially, the device was found to produce light emission to a luminance of 700 $cd/m^2$ when operated at a current density of 10 $mA/cm^2$ and a drive voltage of 6.6 volts. At this point, the peak wavelength was 465 nm and the chromaticity coordinates (x, y) were (0.20, 0.20), indicating that the color of light emission was shifted from blue toward a longer wavelength side. When the device was continuously driven by conducting a constant current of 10 $mA/cm^2$, it exhibited a luminance half-life period of 500 hours from the initial luminance of 700 $cd/m^2$.

Comparative Example 3

An organic EL device was fabricated as in Example 1 except that the dopant in the light emitting layer was replaced by a compound of the following structure.

C108

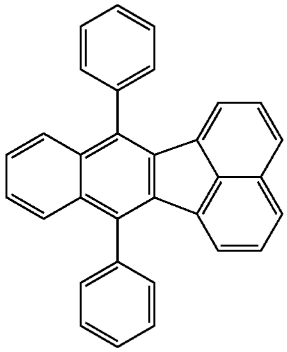

A DC voltage was applied across the organic EL device. Initially, the device was found to produce light emission to a luminance of 180 $cd/m^2$ when operated at a current density of 10 $mA/cm^2$ and a drive voltage of 6.5 volts. At this point, the peak wavelength was 440 nm and the chromaticity coordinates (x, y) were (0.16, 0.07). When the device was continuously driven by conducting a constant current of 10 $mA/cm^2$, it exhibited a luminance half-life period of 250 hours from the initial luminance of 180 $cd/m^2$.

Benefits of the Invention

According to the invention, compounds for use in organic EL devices capable of light emission to a satisfactory luminance, especially at a long wavelength, and with a high color purity, especially a color purity sufficient for use in full color displays, and having a sufficient durability to sustain such improved light emission performance over a long time are provided as well as organic EL devices using the same.

What is claimed is:

1. A compound having a basic skeleton of the following formula (1):

$$X_n\text{—}Y \quad (1)$$

wherein X is a compound of the following formula (2) and may be the same or different, Y is a linking group selected from a substituted or unsubstituted phenylene group, and n is an integer of 2, (2)

X=

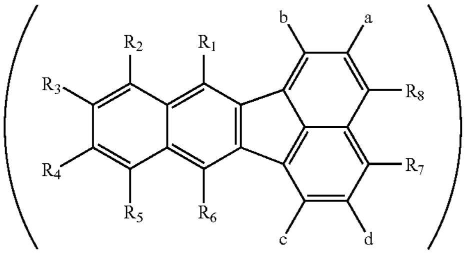

wherein $R_1$ to $R_8$ and a to d each are selected from the group consisting of hydrogen, an alkyl group, an aryl group which may be substituted, an allyl group which may be substituted, a heterocyclic group which may be substituted, an amino group, and an arylamino group which may be substituted.

2. The compound of claim 1 comprised as a dopant in an organic EL device.

3. The compound of claim 1 comprised as an electron transporting material in an organic EL device.

4. The compound of claim 1 comprised as a hole injecting or transporting material in an organic EL device.

5. The compound of claim 1, having a basic skeleton of the following formula (3a):

7. The compound of claim 1 having a basic skeleton of the following formula (3c):

(3c)

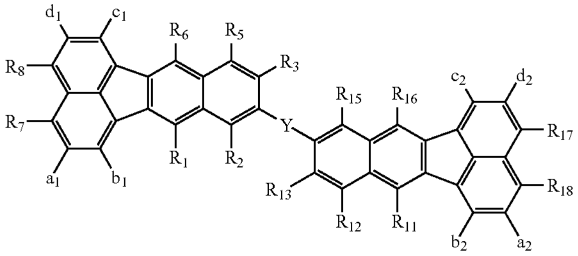

(3a)

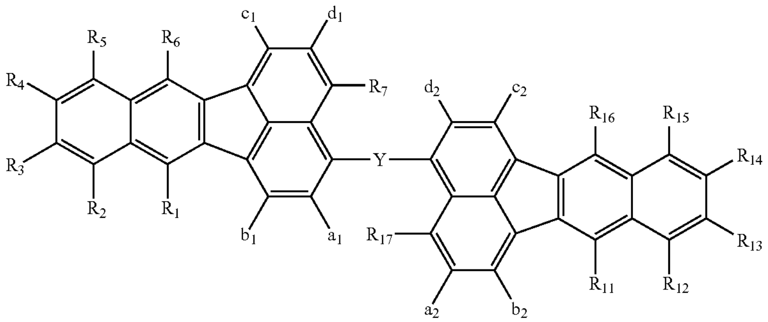

wherein $R_1$ to $R_7$, $a_1$ to $d_1$, $R_{11}$ to $R_{17}$ and $a_2$ to $d_2$ each are selected from the group consisting of hydrogen, an alkyl group, an aryl group which may be substituted, an allyl group which may be substituted, a heterocyclic group which may be substituted, an amino group, and an arylamino group which may be substituted.

6. The compound of claim 1 having a basic skeleton of the following formula (3b):

(3b)

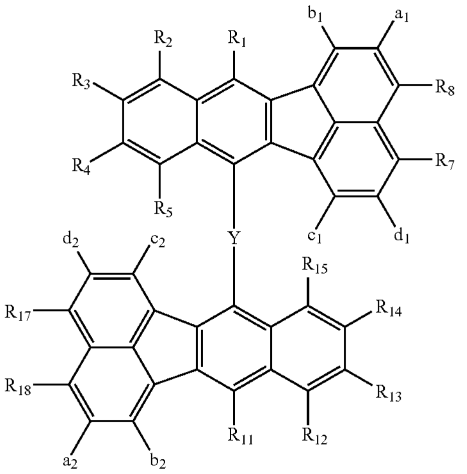

wherein $R_1$ to $R_8$, $a_1$ to $d_1$, $R_{11}$ to $R_{18}$ and $a_2$ to $d_2$ each are selected from the group consisting of hydrogen, an alkyl group, an aryl group which may be substituted, an allyl group which may be substituted, a heterocyclic group which may be substituted, an amino group, and an arylamino group which may be substituted.

wherein $R_1$ to $R_8$, $a_1$ to $d_1$, $R_{11}$ to $R_{18}$ and $a_2$ to $d_2$ each are selected from the group consisting of hydrogen, an alkyl group, an aryl group which may be substituted, an allyl group which may be substituted, a heterocyclic group which may be substituted, an amino group, and an arylamino group which may be an amino group, and an arylamino group which may be substituted.

8. The compound of claim 1, wherein, in the compound of formula (1), n=2, $R_1$ and $R_6$ are each phenyl and $R_2$ to $R_5$ and $R_7$ are each hydrogen and two of the groups $R_8$ of each of the two X groups together comprise a linking phenylene group which joins the two X groups in the compound.

9. The compound of claim 8, wherein the linking phenylene group is linked in the para position.

10. An organic EL device comprising one or more organic layers between a pair of electrodes participating in at least a light emitting function, at least one of the organic layers comprising one or more compounds according to claim 1.

11. The organic EL device of claim 10, further comprising one or more anthracene compounds.

12. The organic EL device of claim 11, wherein said one or more anthracene compounds is (are) comprised as a host material for a light emitting layer.

13. The organic EL device of claim 10, wherein said one or more compounds is (are) comprised as a dopant.

14. The organic EL device of claim 10, wherein said one or more compounds is (are) comprised in a light emitting layer.

15. The organic EL device of claim 10, wherein said one or more compounds is (are) comprised in an electron transporting layer.

16. The organic EL device of claim 10, wherein said one or more compounds is (are) comprised in a hole injecting and transporting layer.

17. The organic EL device of claim 10 exhibiting at least two maximum wavelengths of light emission ascribable to at least two light-emitting materials.

18. A compound selected from the group consisting of:

(A)

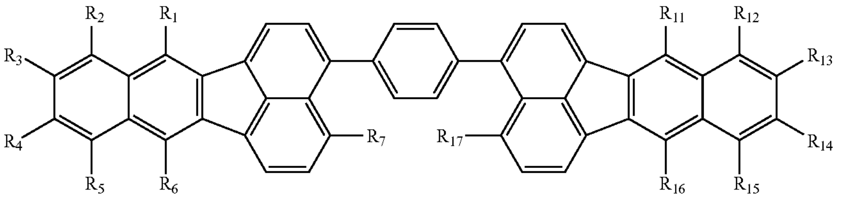

wherein for compound (A), $R_1$ to $R_7$ and $R_1$ to $R_{17}$ each are hydrogen, an alkyl group, a substituted or unsubstituted aryl group, or a heterocyclic group;

(H)

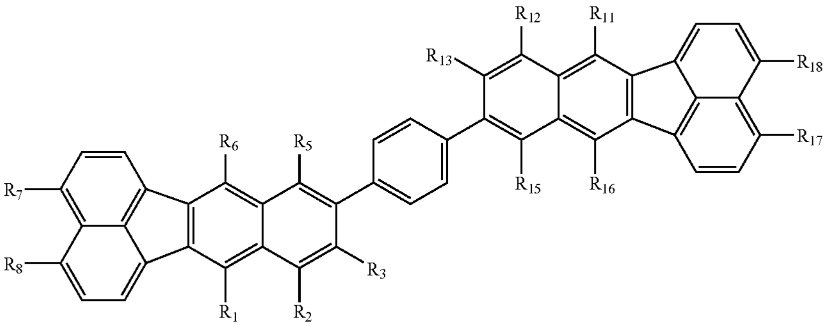

wherein for compound (H), $R_1$ to $R_3$, $R_5$ to $R_8$, $R_{11}$ to $R_{13}$, and $R_{15}$ to $R_{18}$ each are hydrogen, an alkyl group, a substituted or unsubstituted aryl group, or a heterocyclic group; and (BBB')

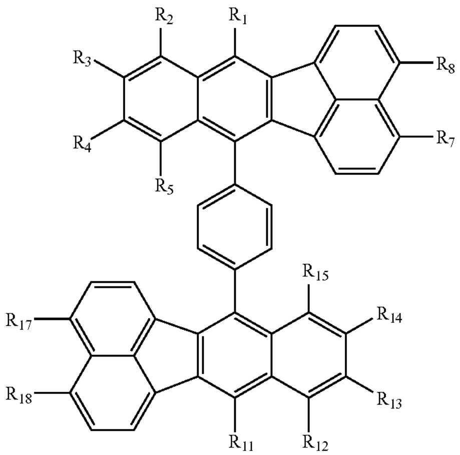

wherein for compound (BBB'), $R_1$ to $R_5$, $R_7$, $R_8$, $R_{11}$ to $R_{15}$, $R_{17}$, and $R_{18}$ each are selected from the group consisting of hydrogen, an alkyl group, an aryl group which may be substituted, an allyl group which may be substituted, a heterocyclic group which may be substituted, an amino group, and an arylamino group which may be substituted.

19. The compound of claim 18 comprised as a dopant in an organic EL device.

20. The compound of claim 18 comprised as an electron transporting material in an organic EL device.

21. The compound of claim 18 comprised as a hole injecting or transporting material in an organic EL device.

22. An organic EL device comprising one or more organic layers between a pair of electrodes participating in at least a light emitting function, at least one of the organic layers comprising one or more compounds according to claim 18.

23. The organic EL device of claim 22, further comprising one or more anthracene compounds.

24. The organic EL device of claim 23, wherein said one or more anthracene compounds is (are) comprised as a host material for a light emitting layer.

25. The organic EL device of claim 22, wherein said one or more compounds is (are) comprised as a dopant.

26. The organic EL device of claim 22, wherein said one or more compounds is (are) comprised in a light emitting layer.

27. The organic EL device of claim 22, wherein said one or more compounds is (are) comprised in an electron transporting layer.

28. The organic EL device of claim 22, wherein said one or more compounds is (are) comprised in a hole injecting and transporting layer.

29. The organic EL device of claim 22 exhibiting at least two maximum wavelengths of light emission ascribable to at least two light-emitting materials.

30. A compound represented by
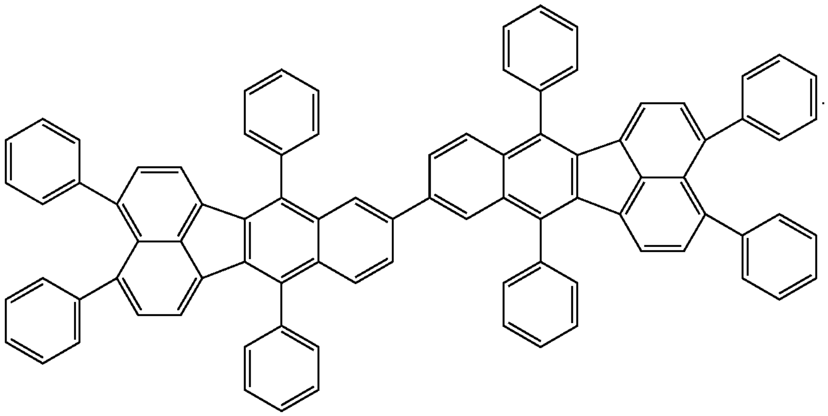
.
31. An organic EL device comprising one or more organic layers between a pair of electrodes participating in at least a light emitting function,
at least one of the organic layers comprising one or more said compound according to claim 30.
* * * * *

UNITED STATES PATENT AND TRADEMARK OFFICE

CERTIFICATE OF CORRECTION

PATENT NO. : 7,097,917 B1
APPLICATION NO. : 10/125480
DATED : August 29, 2006
INVENTOR(S) : Fujita et al.

It is certified that error appears in the above-identified patent and that said Letters Patent is hereby corrected as shown below:

On the Title page, the Terminal Disclaimer information has been omitted. It should read as follows:

Item
-- (45) **Date of Patent: *Aug. 29, 2006** --

-- (*) Notice: Subject to any disclaimer, the term of this patent is extended or adjusted under 35 U.S.C. 145(b) by 281 days.

This patent is subject to a terminal disclaimer. --

Signed and Sealed this

Thirteenth Day of January, 2009

JON W. DUDAS
*Director of the United States Patent and Trademark Office*